United States Patent
Aciro et al.

(10) Patent No.: US 9,090,653 B2
(45) Date of Patent: *Jul. 28, 2015

(54) MACROCYCLIC INHIBITORS OF FLAVIVIRIDAE VIRUSES

(71) Applicants: Gilead Sciences, Inc., Foster City, CA (US); Selcia Ltd., Ongar, Essex (GB)

(72) Inventors: Caroline Aciro, Bottisham (GB); Victoria Alexandra Steadman, Stansted (GB); Simon Neil Pettit, Colchester (GB); Karine G. Poullennec, Chelmsform (GB); Linos Lazarides, London (GB); David Kenneth Dean, Ware (GB); Neil Andrew Dunbar, Chelmsford (GB); Adrian John Highton, Chelmsford (GB); Andrew John Keats, Chelmsford (GB); Dustin Scott Siegel, Foster City, CA (US); Kapil Kumar Karki, Foster City, CA (US); Adam James Schrier, Redwood City, CA (US); Petr Jansa, San Mateo, CA (US); Richard Mackman, Millbrae, CA (US)

(73) Assignees: Gilead Sciences, Inc., Foster City, CA (US); Selcia Ltd., Ongar (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/913,184

(22) Filed: Jun. 7, 2013

(65) Prior Publication Data

US 2013/0344029 A1 Dec. 26, 2013

Related U.S. Application Data

(60) Provisional application No. 61/657,553, filed on Jun. 8, 2012.

(51) Int. Cl.
| | |
|---|---|
| *A61K 38/21* | (2006.01) |
| *C07K 5/02* | (2006.01) |
| *C07D 487/08* | (2006.01) |
| *C07D 498/08* | (2006.01) |
| *C07D 498/18* | (2006.01) |
| *C07K 5/062* | (2006.01) |
| *A61K 38/12* | (2006.01) |
| *A61K 39/29* | (2006.01) |
| *A61K 45/06* | (2006.01) |
| *C07D 471/18* | (2006.01) |
| *C07D 498/22* | (2006.01) |
| *A61K 38/55* | (2006.01) |
| *A61K 31/403* | (2006.01) |
| *A61K 31/497* | (2006.01) |
| *A61K 31/504* | (2006.01) |
| *A61K 31/7056* | (2006.01) |
| *A61K 31/7072* | (2006.01) |
| *C07K 5/078* | (2006.01) |
| *C07K 5/065* | (2006.01) |
| *A61K 38/15* | (2006.01) |

(52) U.S. Cl.
CPC ............ *C07K 5/02* (2013.01); *A61K 31/403* (2013.01); *A61K 31/497* (2013.01); *A61K 31/504* (2013.01); *A61K 31/7056* (2013.01); *A61K 31/7072* (2013.01); *A61K 38/12* (2013.01); *A61K 38/21* (2013.01); *A61K 38/55* (2013.01); *A61K 39/29* (2013.01); *A61K 45/06* (2013.01); *C07D 471/18* (2013.01); *C07D 487/08* (2013.01); *C07D 498/08* (2013.01); *C07D 498/18* (2013.01); *C07D 498/22* (2013.01); *C07K 5/0606* (2013.01); *C07K 5/06034* (2013.01); *C07K 5/06052* (2013.01); *C07K 5/06078* (2013.01); *C07K 5/06139* (2013.01); *A61K 38/15* (2013.01)

(58) Field of Classification Search
CPC .............................. A61K 38/12; A61K 38/15
See application file for complete search history.

(56) References Cited

U.S. PATENT DOCUMENTS 8,513,184 B2 * 8/2013 Appleby et al. .............. 514/1.1

FOREIGN PATENT DOCUMENTS

| WO | WO 2006/138507 A1 | 12/2006 |
| WO | WO 2012/078915 A1 | 6/2012 |

OTHER PUBLICATIONS

International Search Report from PCT/US2013/044809 issued Sep. 16, 2013 by the European Patent Office.
U.S. Appl. No. 13/942,501, filed Jul. 15, 2013, Appelby et al.
U.S. Appl. No. 13/913,259 Non-Final Rejection mailed Aug. 29, 2014.
U.S. Appl. No. 13/913,288 Non-Final Rejection mailed Aug. 28, 2014.

\* cited by examiner

*Primary Examiner* — Marcela M Cordero Garcia
*Assistant Examiner* — Kaipeen Yang
(74) *Attorney, Agent, or Firm* — Francis O. Ginah

(57) ABSTRACT

Provided are compounds of Formula I:

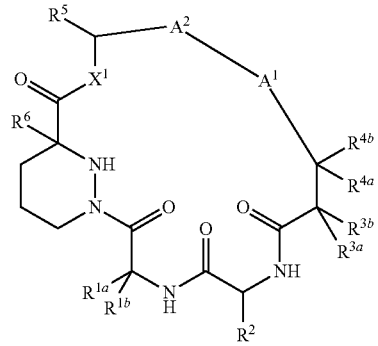

Formula I and pharmaceutically acceptable salts and esters thereof. The compounds, compositions, and methods provided are useful for the treatment of virus infections, particularly hepatitis C infections.

19 Claims, No Drawings

MACROCYCLIC INHIBITORS OF FLAVIVIRIDAE VIRUSES

CROSS-REFERENCE TO RELATED APPLICATIONS

This application claims the benefit under 35 U.S.C. §119(e) to U.S. Provisional Application Ser. No. 61/657,553, filed on Jun. 8, 2012, the entirety of which is incorporated herein by reference.

FIELD

The present application provides novel compounds inhibiting viruses, compositions containing such compounds, and therapeutic methods comprising the administration of such compounds.

BACKGROUND

RNA viruses comprising the Flaviviridae family include at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus.

The hepatitis C virus (HCV) is the leading cause of chronic liver disease worldwide (Boyer, N. et al. J. Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., J. Med. Chem. 2005, 48, 1-20; Maradpour, D., et al., Nat. Rev. Micro. 2007, 5(6), 453-463). A number of HCV treatments are reviewed by Dymock et al. in Antiviral Chemistry & Chemotherapy, 11:2; 79-95 (2000). Virologic cures of patients with chronic HCV infection are difficult to achieve because of the prodigious amount of daily virus production in chronically infected patients and the high spontaneous mutability of HCV virus (Neumann, et al., Science 1998, 282, 103-7; Fukimoto, et al., Hepatology, 1996, 24, 1351-4; Domingo, et al., Gene 1985, 40, 1-8; Martell, et al., J. Virol. 1992, 66, 3225-9.

Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. Drugs 2002, 62, 507-556) but less than half the patients given this treatment show a persistent benefit. Therefore, there is a need to develop more effective anti-HCV therapies.

The macrocycle sanglifehrin and derivatives are immunomodulatory and bind peptidyl-prolyl cis/trans isomerase (PPIase) cyclophilins in a unique manner (WO 97/02285; WO 98/07743; J. Am. Chem. Soc 2003, 125, 3849-3859; J. Org. Chem. 2000, 65, 9255-9260; Angew. Chem. Int. Ed. 1999, 38, 2443-2446). The cyclophilins are peptidyl-prolyl cis/trans isomerases (PPIase) that regulate protein folding in vivo and inhibit hepatitis C virus (Lin et al., WO2006/138507). However, none of the sanglifehrins or their derivatives has become available for human anti-viral therapy. Therefore, there is a continuing need to develop macrocyclic sanglifehrins with anti-Flaviviridae virus activity and particularly anti-HCV activity.

SUMMARY

In one embodiment, there is provided a compound represented by Formula I:

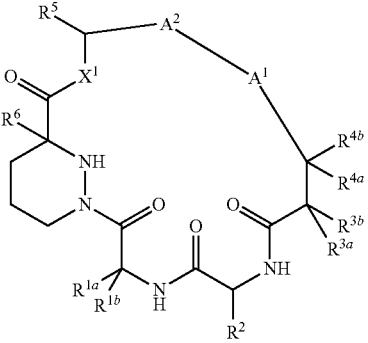

Formula I or a pharmaceutically acceptable salt, isotope, stereoisomer, mixture of stereoisomers, tautomer, ester or prodrug thereof, wherein:

$A^1$ is $(C_2-C_5)$alkylene, $(C_2-C_5)$alkenylene, $(C_2-C_5)$alkynylene, —O—$(C_2-C_4)$alkylene, —O—$(C_2-C_4)$alkenylene, arylene, aryl$(C_1-C_2)$alkylene, heterocycloalkylene or heterocycloalkyl$(C_1-C_2)$alkylene, wherein a sp$^3$ carbon atom of $A^1$ is optionally substituted with one or more $(C_1-C_4)$alkyl;

$A^2$ is arylene or heteroarylene, wherein $A^2$ is optionally substituted with halo;

$X^1$ is —O—, —NH— or —N$((C_1-C_4)$alkyl)-;

$R^{1a}$ and $R^{1b}$ are independently H, $(C_1-C_4)$alkyl, $(C_2-C_4)$alkenyl or $(C_2-C_4)$alkynyl;

$R^2$ is H, $(C_1-C_4)$alkyl, $(C_2-C_4)$alkenyl or $(C_2-C_4)$alkynyl;

$R^{3a}$ and $R^{3b}$ are independently H or $(C_1-C_8)$alkyl;

$R^{4a}$ and $R^{4b}$ are independently H, —OH, $(C_1-C_4)$alkoxy, halo$(C_1-C_4)$alkoxy or $(C_1-C_8)$alkyl;

$R^5$ is H, $(C_1-C_4)$alkyl, $(C_2-C_4)$alkenyl or $(C_2-C_4)$alkynyl, or $R^5$ forms a cyclic moiety along with —N$((C_1-C_4)$alkyl)- of $X^1$ or arylene of $A^2$; and $R^6$ is H or $(C_1-C_4)$alkyl.

In another embodiment, there is provided a pharmaceutical composition comprising a compound of Formula I r a pharmaceutically acceptable salt, isotope, stereoisomer, mixture of stereoisomers, tautomer, ester or prodrug thereof and one or more pharmaceutically acceptable carriers or excipients. In one aspect of the embodiment, the pharmaceutical composition further comprises one or more additional therapeutic agents.

In yet another embodiment, a method for treating Flaviviridae viral infection is provided comprising administering a therapeutically effective amount of a compound of Formula I r a pharmaceutically acceptable salt, isotope, stereoisomer, mixture of stereoisomers, tautomer, ester or prodrug thereof to a mammal in need thereof. In one aspect of the embodiment, the treatment results in the reduction of the in viral load or clearance of viral RNA in a patient.

In yet another embodiment, a method for treating Coronaviridae viral infection is provided comprising administering a therapeutically effective amount of a compound of Formula I r a pharmaceutically acceptable salt, isotope, stereoisomer, mixture of stereoisomers, tautomer, ester or prodrug thereof to a mammal in need thereof. In one aspect of the embodiment, the treatment results in the reduction of the in viral load or clearance of viral RNA in a patient.

DETAILED DESCRIPTION

Definitions

Unless stated otherwise, the following terms and phrases as used herein are intended to have the following meanings:

"Alkanoyl" is RC(O)—; "alkanoyloxy" is RC(O)O—; and "alkanoylamino" is RC(O)NR'—; where R is an alkyl group as defined herein, and R' is hydrogen or alkyl.

"Alkenyl" refers to a straight or branched hydrocarbyl group with at least one site of unsaturation, i.e., a carbon-carbon, $sp^2$ double bond. In some embodiments, alkenyl is a $C_2$-$C_{20}$ alkenyl group, a $C_2$-$C_{10}$ alkenyl group or a $C_2$-$C_6$ alkenyl group. Examples of alkenyl group include, but are not limited to, vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 2 to 20 carbon atoms, 2 to 10 carbon atoms, or 2 to 6 carbon atoms. Typical alkenylene radicals include, but are not limited to, 1,2-ethenylene (—CH=CH—).

"Alkoxy" is RO— where R is alkyl, as defined herein. Non-limiting examples of alkoxy groups include methoxy, ethoxy and propoxy.

"Alkyl" refers to a straight or branched chain hydrocarbyl group. In an embodiment, alkyl has from 1 to 20 carbon atoms (i.e., $C_1$-$C_{20}$ alkyl). In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Alkylene" refers to a saturated, branched or straight chain radical or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Examples of alkylene radicals include, but are not limited to, methylene (—$CH_2$—), ethylene (—$CH_2CH_2$—), propylene (—$CH_2CH_2CH_2$—) and butylene (—$CH_2CH_2CH_2CH_2$—).

"Alkynyl" refers to a hydrocarbon containing normal, secondary or tertiary carbon atoms with at least one site of unsaturation, i.e., a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne) or 2 to 6 carbon atoms (i.e., $C_2$-$C_6$ alkynyl). Examples of alkynyl groups include, but are not limited to, acetylenic (—C≡CH) and propargyl (—$CH_2$C≡CH).

"Alkylamino" refers to an amino group substituted with one or more alkyl groups. "Mono(alkyl)amino" or "(alkyl) amino" is RNH—, and "di(alkyl)amino" or "(alkyl)$_2$amino" is $R_2$N—, where each of the R groups is alkyl as defined herein and are the same or different. Examples of alkylamino groups include, but are not limited to, methylamino, ethylamino, propylamino, butylamino, dimethylamino, diethylamino and methylethylamno.

"Amino" refers to —$NH_2$.

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 2 to 20 carbon atoms, 2 to 10 carbon atoms, or 2 to 6 carbon atoms. Typical alkynylene radicals include, but are not limited to, acetylene (—C≡C—), propargylene (—$CH_2$C≡C—), and 4-pentynylene (—$CH_2CH_2CH_2$C≡C—).

"Aryl" refers to any monocyclic or bicyclic carbon ring of up to 7 atoms in each ring, wherein at least one ring is aromatic, or an aromatic ring system of 5 to 14 carbons atoms which includes a carbocyclic aromatic group fused with a 5- or 6-membered cycloalkyl group. Examples of aryl groups include, but are not limited to, phenyl, naphthyl, tetrahydronaphthyl and indanyl.

"Arylalkyl" refers to an alkyl as defined herein substituted with an aryl radical.

"Arylene" refers to an aryl as defined above having two monovalent radical centers derived by the removal of two hydrogen atoms from two different carbon atoms of a parent aryl. Typical arylene radicals include, but are not limited to, phenylene, e.g.,

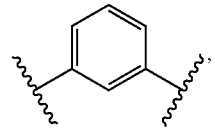 [SMILES: *c1cccc(*)c1]

and
naphthylene, e.g.,

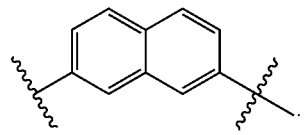 [SMILES: *c1ccc2ccc(*)cc2c1]

"Arylalkylene" refers to an arylalkyl as defined above having two monovalent radical centers derived by the removal of one hydrogen atom from the aryl radical and the other hydrogen removed from the alkyl radical of the group.

"Cycloalkyl" refers to a hydrocarbyl group containing at least one saturated or partially unsaturated ring structure, and attached via a ring carbon. Cycloalkyl groups include hydrocarbon mono-, bi-, and poly-cyclic rings, whether fused, bridged, or spiro. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

"Cycloalkylalkyl" refers to an alkyl moiety substituted with a cycloalkyl group. Examples of cycloalkylalkyl groups include cyclopropylmethyl, cyclobutylmethyl, cyclopentylethyl and cyclohexylmethyl.

"Cycloalkylene" refers to a cycloalkyl, as defined herein, having two monovalent radical centers derived by the removal of two hydrogen atoms from the same or two different carbon atoms of a parent cycloalkyl. Examples of cycloalkylene include, but are not limited to, cyclopropylene, cyclobutylene, cyclopentylene and cyclohexylene.

"Dialkylaminoalkyl" refers to an alkyl moiety substituted with a dialkylamino group, wherein dialkylamino is as defined herein.

"Ester" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof.

"Halo" refers to chloro (—Cl), bromo (—Br), fluoro (—F) or iodo (—I).

"Haloalkoxy" refers to alkoxy, as defined herein, substituted with one or more halo radicals.

"Haloalkoxyalkyl" refers to an alkyl moiety substituted with a haloalkoxy group, as defined herein.

"Haloalkyl" refers to an alkyl group, in which one or more hydrogen atoms of the alkyl group is replaced with a halogen atom. Examples of haloalkyl groups include, but are not limited to, —CF$_3$, —CHF$_2$, —CFH$_2$ and —CH$_2$CF$_3$.

"Heterocycloalkyl" refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. The heterocyclic group can be attached through a carbon atom or through a heteroatom, and when substituted, the substituent can be bonded to a carbon atom or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl and N-oxides thereof.

"Heterocycloalkylene" refers to a heterocycloalkyl, as defined above, having two monovalent radical centers derived by the removal of two hydrogen atoms from the same or two different carbon atoms of a parent heterocycloalkyl group.

"Heterocycloalkylalkylene" refers to an heterocycloalkyl as defined above having two monovalent radical centers derived by the removal of one hydrogen atom from the heterocycloalkyl radical and the other hydrogen removed from the alkyl radical of the group.

"Heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S, Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroarylalkyl" refers to an alkyl group, as defined herein, in which a hydrogen atom has been replaced with a heteroaryl group.

"Heteroarylene" refers to a heteroaryl, as defined above, having two monovalent radical centers derived by the removal of two hydrogen atoms from the same or two different carbon atoms of a parent heteroaryl group. Non-limiting examples of heteroarylene groups are:

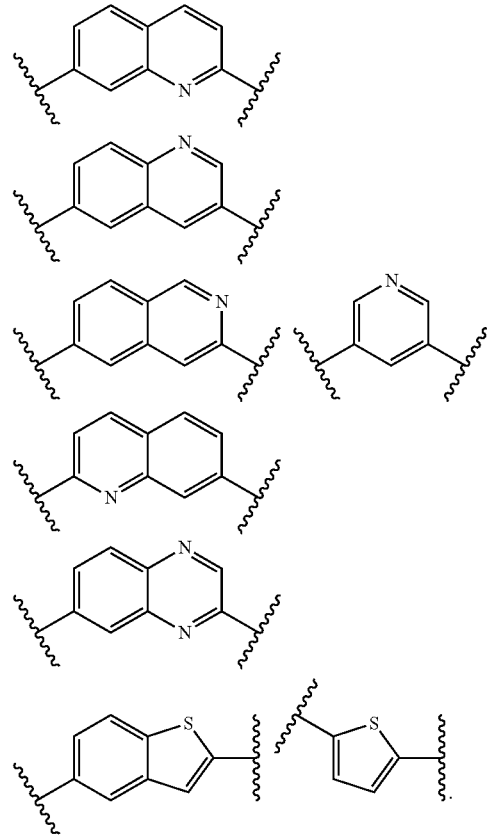

"Hydroxyalkoxy" refers to an alkoxy, as defined herein, substituted with a hydroxyl group (—OH). An example of hydroxyalkoxy is hydroxyethoxy.

"Hydroxyalkyl" refers to an alkyl group substituted with at least one hydroxy group. Examples of hydroxyalkyl groups include, but are not limited to, hydroxymethyl, hydroxyethyl, hydroxypropyl and hydroxybutyl.

"Prodrug" refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

The term "optionally substituted" refers to a moiety wherein all substituents are hydrogen or wherein one or more of the hydrogens of the moiety are replaced by non-hydrogen substituents. Multiple substitutions on the same atom are also permitted where chemically feasible (e.g., a dioxo substitution to provide —S(O)$_2$—, geminal substituents, spiro cycloalkyl or heterocycloalkyl rings, etc.). In some embodiments, "one or more" substituents is from one to three substituents.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants.

"Pharmaceutically acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically acceptable carrier" refers to a diluent, adjuvant, excipient, or carrier, or other ingredient which is pharmaceutically acceptable and with which a compound of the invention is administered.

"Pharmaceutically acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

A compound of a given formula (e.g. the compound of Formula I, which also includes Formula I-a, I-b, I-c, I-d, I-e or II) is intended to encompass the compounds of the disclosure, and the pharmaceutically acceptable salts, stereoisomers, mixture of stereoisomers or tautomers of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space. Stereoisomers include enantiomers and diastereomers.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers or "tautomers". Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure provided herein, including Formula I, I-a, I-b, I-c, I-d, I-e or II, is also intended to represent unlabeled forms as well as isotopically labeled forms of the compounds. An "isotope" may have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, I-a, I-b, I-c, I-d, I-e or II in which from 1 to n hydrogens attached to a carbon atom is/are replaced by deuterium, in which n is the number of hydrogens in the molecule. Such compounds exhibit increased resistance to metabolism and are thus useful for increasing the half life of any compound of Formula I, I-a, I-b, I-c, I-d, I-e or II when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, I-a, I-b, I-c, I-d, I-e or II.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

"Therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

Compounds

The present application provides a compound represented by Formula I:

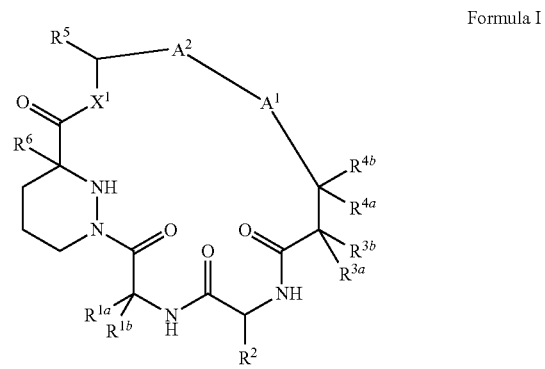

Formula I or a pharmaceutically acceptable salt, isotope, stereoisomer, mixture of stereoisomers, tautomer, ester or prodrug thereof, wherein:

$A^1$ is $(C_2$-$C_5)$alkylene, $(C_2$-$C_5)$alkenylene, $(C_2$-$C_5)$alkynylene, —O—$(C_2$-$C_4)$alkylene, —O—$(C_2$-$C_4)$alkenylene, arylene, aryl$(C_1$-$C_2)$alkylene, heterocycloalkylene or heterocycloalkyl$(C_1$-$C_2)$alkylene, wherein a sp$^3$ carbon atom of $A^1$ is optionally substituted with one or more $(C_1$-$C_4)$alkyl;

$A^2$ is arylene or heteroarylene, wherein $A^2$ is optionally substituted with halo;

$X^1$ is —O—, —NH— or —N(($C_1$-$C_4)$alkyl)-;

$R^{1a}$ and $R^{1b}$ are independently H, $(C_1$-$C_4)$alkyl, $(C_2$-$C_4)$alkenyl or $(C_2$-$C_4)$alkynyl;

$R^2$ is H, $(C_1$-$C_4)$alkyl, $(C_2$-$C_4)$alkenyl or $(C_2$-$C_4)$alkynyl;

$R^{3a}$ and $R^{4b}$ are independently H or $(C_1$-$C_8)$alkyl;

$R^{4a}$ and $R^{4b}$ are independently H, —OH, $(C_1$-$C_4)$alkoxy, halo$(C_1$-$C_4)$alkoxy or $(C_1$-$C_8)$alkyl;

$R^5$ is H, $(C_1$-$C_4)$alkyl, $(C_2$-$C_4)$alkenyl or $(C_2$-$C_4)$alkynyl, or $R^5$ forms a cyclic moiety along with —N(($C_1$-$C_4)$alkyl)- of $X^1$ or arylene of $A^2$; and $R^6$ is H or $(C_1$-$C_4)$alkyl.

In certain embodiments, provided is a compound of Formula I:

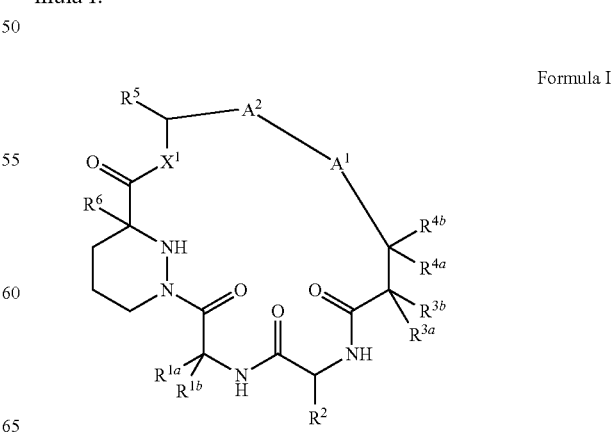

Formula I or a pharmaceutically acceptable salt, ester or prodrug thereof, wherein:

$A^1$ is $(C_1-C_5)$alkylene, $(C_2-C_5)$alkenylene, $(C_2-C_5)$alkynylene, —O—$(C_2-C_4)$alkylene, —O—$(C_2-C_4)$alkenylene, arylene, aryl$(C_1-C_2)$alkylene, heterocycloalkylene or heterocycloalkyl$(C_1-C_2)$alkylene, wherein a sp$^a$ carbon atom of $A^1$ is optionally substituted with one or more $(C_1-C_4)$alkyl;

$A^2$ is arylene or heteroarylene, wherein $A^2$ is optionally substituted with halo;

$X^1$ is —O—, —NH— or —N(($C_1-C_4$)alkyl)-;

$R^{1a}$ and $R^{1b}$ are independently H, $(C_1-C_4)$alkyl, $(C_2-C_4)$alkenyl or $(C_2-C_4)$alkynyl;

$R^2$ is H, $(C_1-C_4)$alkyl, $(C_2-C_4)$alkenyl or $(C_2-C_4)$alkynyl;

$R^{3a}$ and $R^{3b}$ are independently H or $(C_1-C_8)$alkyl;

$R^{4a}$ and $R^{4b}$ are independently H, —OH, $(C_1-C_4)$alkoxy, halo$(C_1-C_4)$alkoxy or $(C_1-C_8)$alkyl;

$R^5$ is H, $(C_1-C_4)$alkyl, $(C_2-C_4)$alkenyl or $(C_2-C_4)$alkynyl, or $R^5$ forms a cyclic moiety along with —N(($C_1-C_4$)alkyl)- of $X^1$ or arylene of $A^2$; and $R^6$ is H or $(C_1-C_4)$alkyl.

In one aspect of the embodiment, $A^1$ is ethenylene, propenylene, butenylene, ethylene, propylene, butylene, oxypropylene, oxypropenylene, pyrazolylene, phenylene or pyrimidinylene.

In another aspect of the embodiment, $A^2$ is heteroarylene such as isoquinolinylene, phenylene or halophenylene. In one aspect, $A^2$ is

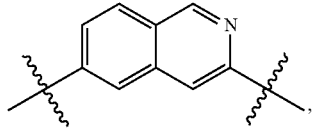

In another aspect of the embodiment, $X^1$ is —O— or —NH—; $R^{1a}$ is H; $R^{1b}$ is methyl; $R^2$ is iso-propyl; $R^5$ is methyl and $R^6$ is H or methyl.

In another aspect of the embodiment, $R^{3a}$ is H or methyl; $R^{3b}$ is H; $R^{4a}$ is H, —OH, methoxy, trifluoroethoxy; and $R^{4b}$ is H.

In another aspect of the embodiment, $A^2$ is heteroarylene; $A^1$ is $(C_2-C_5)$alkylene, $(C_2-C_5)$alkenylene or $(C_2-C_5)$alkynylene, wherein $A^1$ is optionally substituted with one or more $(C_1-C_4)$alkyl; $R^{3a}$ is H or $(C_1-C_8)$alkyl; and $R^{4a}$ is H, —OH or $(C_1-C_4)$alkoxy. In another aspect of the embodiment, $A^2$ is heteroarylene; $A^1$ is $(C_1-C_5)$alkylene, $(C_2-C_5)$alkenylene or $(C_2-C_5)$alkynylene, wherein $A^1$ is optionally substituted with one or more $(C_1-C_4)$alkyl; $R^{3a}$ is H or $(C_1-C_8)$alkyl; and $R^{4a}$ is H, —OH or $(C_1-C_4)$alkoxy. Non-limiting examples of such compounds include the following compounds and pharmaceutically acceptable salts thereof.

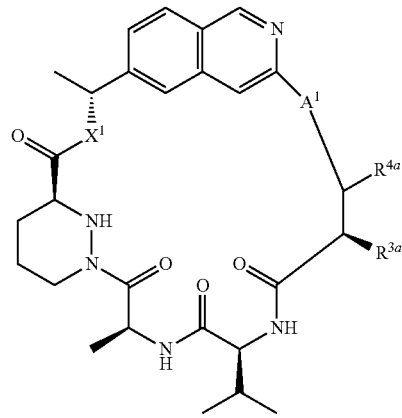

Formula (I-a)

| Compound No. | $X^1$ | $A^1$ | $R^{3a}$ | $R^{4a}$ |
|---|---|---|---|---|
| a-1 | —NH— | —CH$_2$CH$_2$— | methyl | methoxy |
| a-2 | —NH— | —CH═CH— | methyl | methoxy |
| a-3 | —O— | —CH$_2$CH$_2$— | methyl | methoxy |
| a-4 | —O— | —CH═CH— | methyl | methoxy |
| a-5 | —NH— | —CH$_2$CH$_2$— | methyl | —H |
| a-6 | —NH— | —CH═CH— | methyl | —H |
| a-7 | —O— | —CH$_2$CH$_2$— | methyl | —H |
| a-8 | —O— | —CH═CH— | methyl | —H |
| a-9 | —NH— | —CH═CHCH$_2$— | —H | —H |
| a-10 | —NH— | —CH$_2$CH$_2$CH$_2$— | —H | —H |
| a-11 | —O— | —CH═CHCH$_2$— | —H | —H |
| a-12 | —O— | —CH$_2$CH$_2$CH$_2$— | —H | —H |
| a-13 | —NH— | —CH═CHCH$_2$CH$_2$— | —H | —H |
| a-14 | —NH— | —CH$_2$CH$_2$CH$_2$CH$_2$— | —H | —H |
| a-15 | —O— | —CH═CHCH$_2$CH$_2$— | —H | —H |
| a-16 | —O— | —CH$_2$CH$_2$CH$_2$CH$_2$— | —H | —H | wherein the left bond of $A^1$ linker is attached to $A^2$.

In another aspect of the embodiment, $A^2$ is arylene; and $A^1$ is $(C_2-C_5)$alkylene, $(C_2-C_5)$alkenylene, $(C_2-C_5)$alkynylene, —O—$(C_2-C_5)$alkylene or —O—$(C_2-C_4)$alkenylene, wherein $A^1$ is optionally substituted with one or more $(C_1-C_4)$alkyl; $R^{4a}$ is H or $(C_1-C_4)$alkyl; and $R^{4a}$ is H, —OH, $(C_1-C_4)$alkoxy or halo$(C_1-C_4)$alkoxy. In another aspect of the embodiment, $A^2$ is arylene; and $A^1$ is $(C_1-C_5)$alkylene, $(C_2-C_5)$alkenylene, $(C_2-C_5)$alkynylene, —O—$(C_2-C_5)$alkylene or —O—$(C_2-C_4)$alkenylene, wherein $A^1$ is optionally substituted with one or more $(C_1-C_4)$alkyl; $R^{3a}$ is H or $(C_1-C_4)$alkyl; and $R^{4a}$ is H, —OH, $(C_1-C_4)$alkoxy or halo$(C_1-C_4)$alkoxy. Non-limiting examples of such compounds include the following compounds and pharmaceutically acceptable salts thereof.

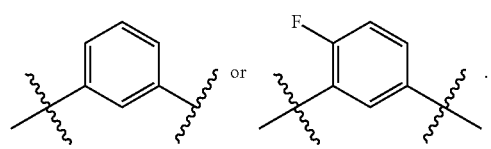

Formula (I-b)

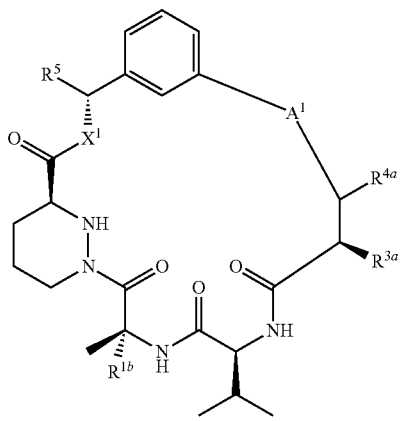

| No. | $X^1$ | $A^1$ | $R^{1b}$ | $R^{3a}$ | $R^{4a}$ | $R^5$ |
|---|---|---|---|---|---|---|
| b-1 | —NH— | —CH=CHCH$_2$CH$_2$— | —H | —H | —OH | methyl |
| b-2 | —NH— | —CH$_2$CH$_2$CH$_2$CH$_2$— | —H | —H | —OH | methyl |
| b-3 | —O— | —CH=CHCH$_2$CH$_2$— | —H | —H | —OH | methyl |
| b-4 | —O— | —CH$_2$CH$_2$CH$_2$CH$_2$— | —H | —H | —OH | methyl |
| b-5 | —NH— | —CH=CHCH$_2$CH$_2$— | —H | —H | —OCH$_2$CF$_3$ | methyl |
| b-6 | —NH— | —CH$_2$CH$_2$CH$_2$CH$_2$— | —H | —H | —OCH$_2$CF$_3$ | methyl |
| b-7 | —O— | —CH=CHCH$_2$CH$_2$— | —H | —H | —OCH$_2$CF$_3$ | methyl |
| b-8 | —O— | —CH$_2$CH$_2$CH$_2$CH$_2$— | —H | —H | —OCH$_2$CF$_3$ | methyl |
| b-9 | —NH— | —CH=CHCH$_2$C(CH$_3$)$_2$— | —H | —H | —H | methyl |
| b-10 | —O— | —CH=CHCH$_2$C(CH$_3$)$_2$— | —H | —H | —H | methyl |
| b-11 | —NH— | —OCH$_2$CH=CH— | —H | methyl | methoxy | isopropyl |
| b-12 | —O— | —OCH$_2$CH=CH— | —H | methyl | methoxy | isopropyl |
| b-13 | —NH— | —OCH$_2$CH=CH— | —H | methyl | methoxy | methyl |
| b-14 | —O— | —OCH$_2$CH=CH— | —H | methyl | methoxy | methyl |
| b-15 | —NH— | —CH=CHCH$_2$CH$_2$— | methyl | —H | —OH | methyl |
| b-16 | —NH— | —CH$_2$CH$_2$CH$_2$CH$_2$— | methyl | —H | —OH | methyl | wherein the left bond of $A^1$ linker is attached to $A^2$.

Also included are the following compounds and pharmaceutically acceptable salts thereof.

Formula (I-c)

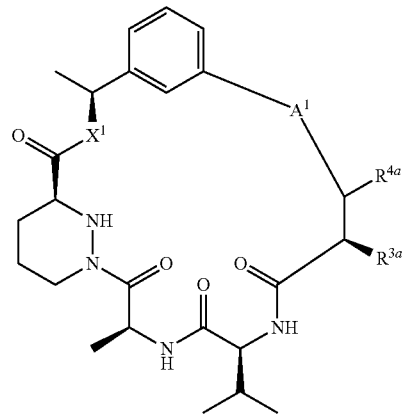

| No. | $X^1$ | $A^1$ | $R^{3a}$ | $R^{4a}$ |
|---|---|---|---|---|
| c-1 | —NH— | —CH=CHCH$_2$CH$_2$— | methyl | methoxy |
| c-2 | —NH— | —CH$_2$CH$_2$CH$_2$CH$_2$— | methyl | methoxy |
| c-3 | —O— | —CH=CHCH$_2$CH$_2$— | methyl | methoxy |
| c-4 | —O— | —CH$_2$CH$_2$CH$_2$CH$_2$— | methyl | methoxy |
| c-5 | —NH— | —CH=CHCH$_2$CH$_2$— | —H | —OH |
| c-6 | —NH— | —CH$_2$CH$_2$CH$_2$CH$_2$— | —H | —OH |
| c-7 | —O— | —CH=CHCH$_2$CH$_2$— | —H | —OH |
| c-8 | —O— | —CH$_2$CH$_2$CH$_2$CH$_2$— | —H | —OH | wherein the left bond of $A^1$ linker is attached to $A^2$.

In another aspect of the embodiment, $A^2$ is phenylene; and $A^1$ is pyrazolylene, phenylene or pyrimidinylene. Non-limiting examples of such compounds include the following compounds and pharmaceutically acceptable salts thereof.

Formula (I-d)

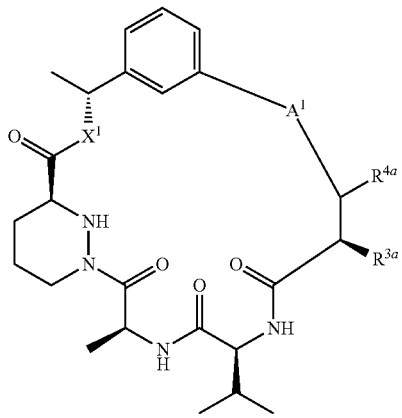

| Compound No. | $X^1$ | $A^1$ | $R^{3a}$ | $R^{4a}$ |
|---|---|---|---|---|
| d-1 | —O— | 2,5-pyridyl | —H | —H |
| d-2 | —O— | 2,5-pyridyl | —H | —H |
| d-3 | —O— | pyrazolyl | —H | —H |
| d-4 | —O— | 1,4-phenylene | —H | —H |
| d-5 | —NH— | 2,5-pyridyl | —H | —H |
| d-6 | —NH— | 2,5-pyridyl | —H | —H |
| d-7 | —NH— | pyrazolyl | —H | —H |
| d-8 | —NH— | 1,4-phenylene | —H | —H | wherein the left bond of $A^1$ linker is attached to $A^2$.

In another aspect of the embodiment, $A^2$ is halophenylene; and $A^1$ is —O—$(C_2$-$C_5)$alkylene or —O—$(C_2$-$C_4)$alkenylene. Non-limiting examples of such compounds include the following compounds and pharmaceutically acceptable salts thereof.

Formula (I-e)

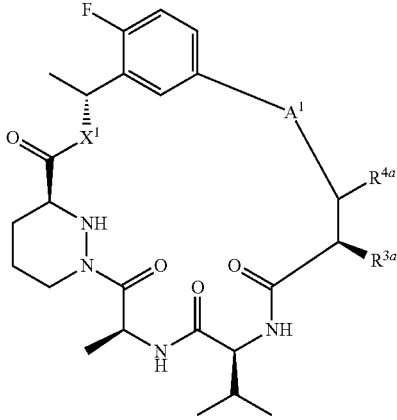

| Compound No. | $X^1$ | $A^1$ | $R^{3a}$ | $R^{4a}$ |
|---|---|---|---|---|
| e-1 | —NH— | —OCH$_2$CH=CH— | methyl | —H |
| e-2 | —O— | —OCH$_2$CH=CH— | methyl | —H |
| e-3 | —NH— | —OCH$_2$CH$_2$CH$_2$— | methyl | —H |
| e-4 | —O— | —OCH$_2$CH$_2$CH$_2$— | methyl | —H |
| e-5 | —NH— | —OCH$_2$CH=CH— | methyl | methoxy |
| e-6 | —O— | —OCH$_2$CH=CH— | methyl | methoxy |
| e-7 | —NH— | —OCH$_2$CH$_2$CH$_2$— | methyl | methoxy |
| e-8 | —O— | —OCH$_2$CH$_2$CH$_2$— | methyl | methoxy | wherein the left bond of $A^1$ linker is attached to $A^2$.

In one aspect of the embodiment, $A^1$ is $(C_2$-$C_5)$alkylene or $(C_2$-$C_5)$alkenylene; $R^5$ is methyl, or $R^5$ form

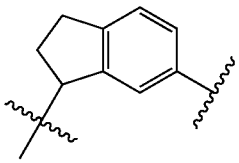 [SMILES: *c1ccc2c(c1)C(*)CC2]

along with arylene of $A^2$, or $R^5$ form

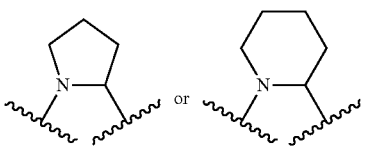 [SMILES: *C1CCCN1* ; *C1CCCCN1*]

along with —N(($C_1$-$C_4$)alkyl)- of $X^1$; and $R^6$ is H or methyl. In another aspect of the embodiment, $A^1$ is $(C_1$-$C_5)$alkylene or $(C_2$-$C_5)$alkenylene; $R^5$ is methyl, or $R^5$ form

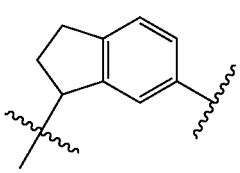 [SMILES: *c1ccc2c(c1)C(*)CC2]

along with arylene of $A^2$, or $R^5$ form
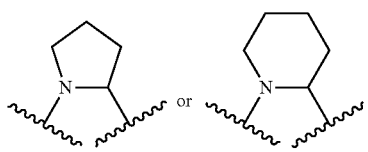 [SMILES: *C1CCCN1* ; *C1CCCCN1*]
along with —N(($C_1$-$C_4$)alkyl)- of $X^1$; and $R^6$ is H or methyl. Non-limiting examples of such compounds include the following compounds and pharmaceutically acceptable salts thereof:
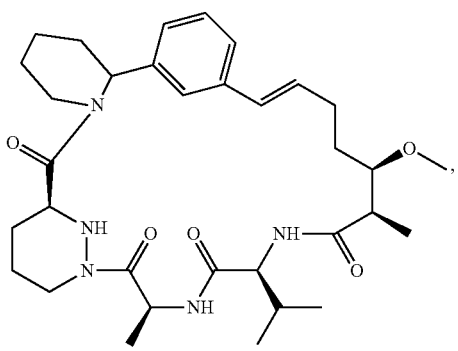
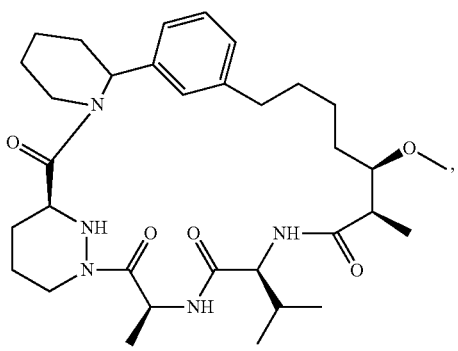
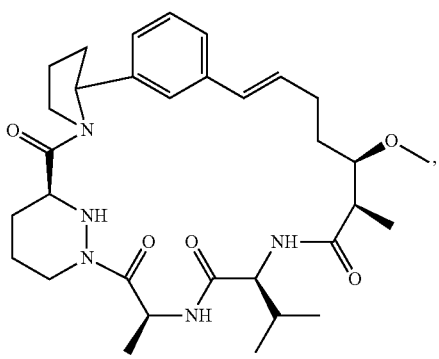
-continued
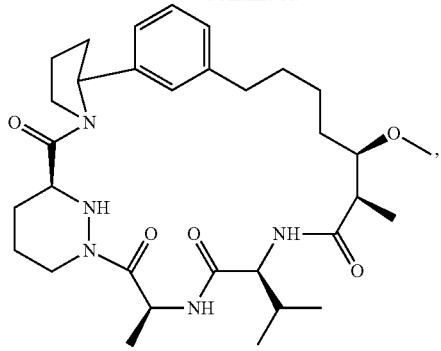
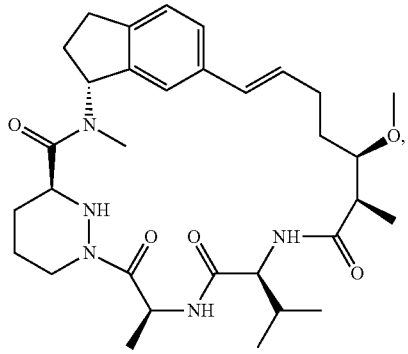
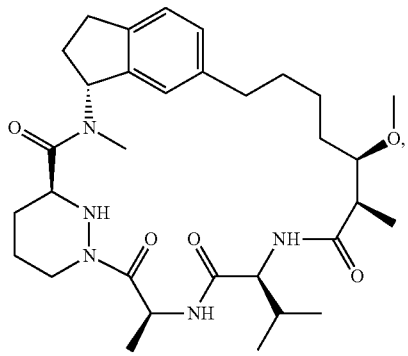
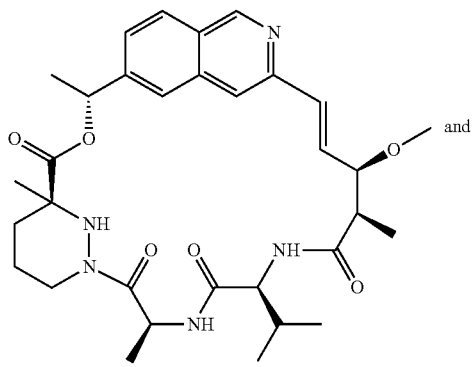
and

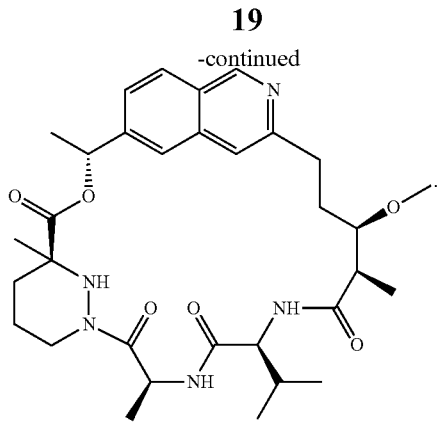

In another embodiment, there is provided a compound of Formula II:

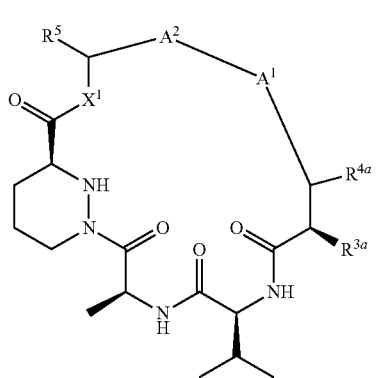

Formula II or a pharmaceutically acceptable salt, isotope, stereoisomer, mixture of stereoisomers, tautomer, ester or prodrug thereof, wherein:

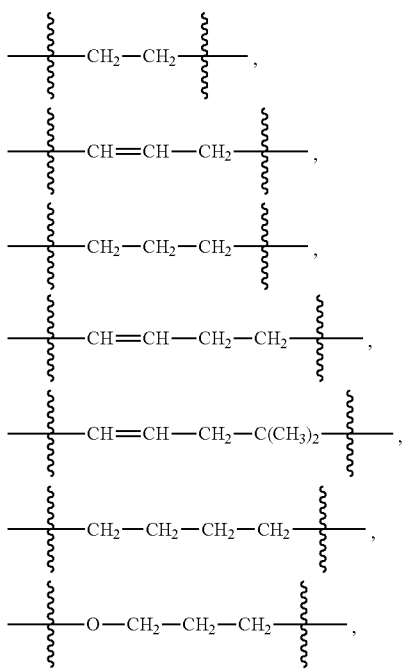

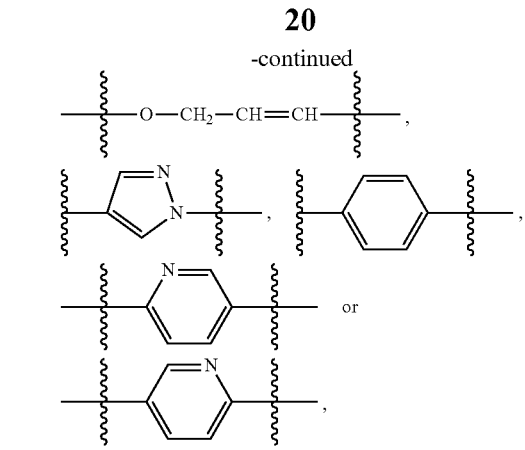

$A^1$ is ethenylene,
wherein the left bond of $A^1$ linker is attached to $A^2$;
$A^2$ is

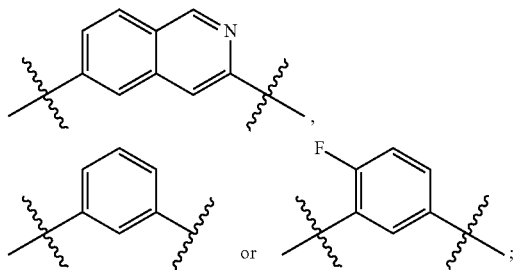

$X^1$ is —O— or —NH—;
$R^{3a}$ is H or $(C_1$-$C_4)$alkyl;
$R^{4a}$ is H, —OH, $(C_1$-$C_4)$alkoxy, halo$(C_1$-$C_4)$alkoxy or $(C_1$-$C_8)$alkyl; and
$R^5$ is H or $(C_1$-$C_4)$alkyl.

One skilled in the art will recognize that substituents and other moieties of the compounds of the generic formulae herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

Preparation of Macrocyclic Compounds

A compound of the present invention such as those of Formula I, I-a, I-b, I-c, I-d, I-e or II can be prepared according to the schemes described below, but it shall be appreciated that modifications of the illustrated process or other process can also be used. As illustrated in Scheme 1, the macrocyclic compounds M are synthesized from the five key components A-E by combining them together in sequence with the appropriate use of protecting groups ($PG^1$-$PG^8$) by one skilled in the art. The hashed lines numbered 1-5, hereby referred to as Connection 1, Connection 2, etc., respectively, are the 5 connections for combining Components A-E. The order in which the specific connections occur, can vary, and are dependent on the choice of protecting groups and chemistry required. In certain embodiments, Connections 3, 4 or 5 are used as the final macrocyclization step.

Scheme 1

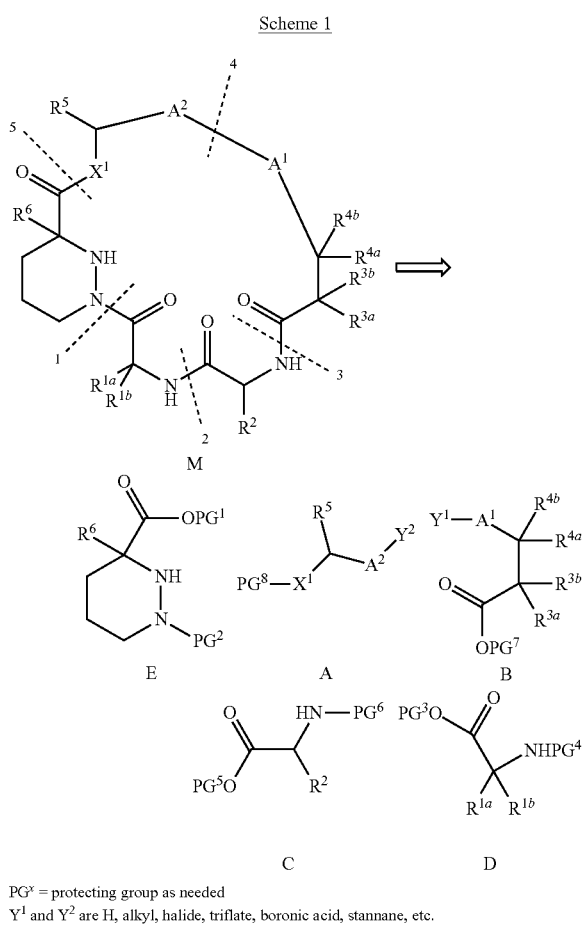

PG$^x$ = protecting group as needed
Y$^1$ and Y$^2$ are H, alkyl, halide, triflate, boronic acid, stannane, etc.

Illustratively, Connections 1 through 5 can be performed as described below:

Connections 1, 2 and 3 are amide bonds. The connections are made between the respective acid and amine using standard peptide coupling agents (EDC/HOBT, DCC, PyBOP, PyBROP, HATU, HBTU, COMO, etc.) known to one skilled in the art. The acid and amine coupling partners are combined with a coupling agent in an organic solvent, e.g., DMF, dichloromethane, acetonitrile, etc., in the presence of a base, e.g., DIPEA, triethylamine, etc., at RT or slightly elevated temperature. When any of these three steps are chosen as the final macrocyclization step, for example Connection 3, then macrolactamization conditions are preferred. Suitable macrolactamization procedures include, but are not limited to, those found in the following reference: Davies, J. S. J. Peptide Sci. 2003, 9, 471-501.

Connection 4 is typically a carbon-carbon bond or a heteroatom-carbon bond where the heteroatom is O, S or N. When Connection 4 is a carbon-carbon bond, then standard carbon-carbon bond forming procedures typically involving metal mediated cross coupling reactions are preferred. Preferably the carbon-carbon bond is formed using a Heck type coupling between an sp2 halide group and an terminal alkene, a Suzuki coupling between an sp2 halide group and a vinyl or aryl boronate, or a ring closing metathesis (RCM) between two alkenes. Stille reactions can also be performed between a vinyl stannane and an aryl or vinyl halide as described in Journal of American Chemical Society 2000, 122, 3830 Nicolaou et al. In each of the examples above the aryl or vinyl halide group can also be an aryl or vinyl triflate.

For example, when A$^2$-Y$^2$ in A contains a terminal alkene, such as —CH═CH$_2$, and A$^1$-Y$^1$ in B contains a terminal alkene, or CH$_3$—CH═CH— then a cross metathesis reaction is performed. The two components are mixed in solvent, e.g., acetonitrile, toluene and a metathesis catalyst, e.g., Grubbs I, Grubbs II or Hoyveda-Grubbs I, Hoyveda-Grubbs II is added followed by heating. If this connection is the final procedure to close the macrocyclic ring, RCM conditions are preferred (e.g., more dilute conditions to avoid dimerization). For relevant RCM conditions and examples see Journal of American Chemical Society 2003, 125, 3849 Sedrani et al and Journal of American Chemical Society 2000, 122, 3830 Nicolaou et al. A typical RCM procedure includes heating (either conventionally or by microwave) of the acyclic precursor in a solvent such as toluene, or 1,2-dichloroethane, in the presence of a RCM catalyst, e.g., Grubbs I, Grubbs II or Hoyveda-Grubbs I, Hoyveda-Grubbs II.

Alternatively, when Connection 4 is made via a Heck coupling reaction, the vinyl or aryl halide, or the triflate A and the alkene component B are mixed in a polar solvent, e.g., acetonitrile, or toluene in the presence of a Palladium(II) catalyst, e.g., Palladium(OAc)$_2$, a phosphine ligand, e.g., P(o-toluene)$_3$, P(t-butyl)$_3$, etc., and a base, e.g., triethylamine. The reaction mixture is heated either conventionally or in a microwave reactor.

Alternatively, when Connection 4 is made via a Suzuki coupling reaction, the vinyl or aryl halide, or the triflate A and the vinyl or aryl boronate B are mixed in a suitable solvent, e.g., cyclopentyl methyl ether, toluene, DMF, DME, etc., in the presence of a Palladium catalyst (e.g., Palladium(II)Cl$_2$ (p-NMe$_2$Ph)$_2$ and K$_3$PO$_4$ or tetrakis(triphenylphosphine)palladium(0) and a base, such as potassium carbonate). The reaction mixture is heated either conventionally or in a microwave reactor. It is also possible in such a coupling reaction to reverse the reactive functionalities on the two starting materials, such that A is an aryl or vinyl boronate and B contains a vinyl or aryl halide or triflate.

Alternatively, Connection 4 can be a carbon-oxygen bond and in this case typical alkylation or nucleophilic aromatic substitution conditions can be used between a hydroxyl group and an alkyl halide, or aryl (or heteroaryl) halide. The hydroxyl reagent is mixed with the alkyl or heteroaryl halide (preferably an iodide or bromide), in an inert solvent, e.g., CPME, DMF, THF, etc, in the presence base, e.g., cesium carbonate, cesium hydroxide, sodium hydride, MaHMDS, etc.; and heated.

Alternatively, Connection 4 can be a carbon-nitrogen bond and in this case typical alkylation, nucleophilic aromatic substitution or Buchwald conditions can be used between an amine group and an alkyl halide or heteroaryl halide. For example, the amine and the alkyl or heteroaryl halide are mixed and heated in an inert solvent, e.g., CPME, in the presence base, e.g., cesium carbonate, sodium hydride, etc. An alternative procedure for the carbon-nitrogen connection is to perform a reductive amination between an amine and a carbonyl compound. Typically the amine and aldehyde or ketone are mixed in an inert solvent, e.g., THF, dioxane and treated after a period of time with sodium acetoxy borohydride or alternative reducing agent.

Connection 5 is typically an amide (X$^1$═—NH or substituted N), or ester (X$^1$═O) bond. When forming the amide bond, standard coupling procedures as described for Connections 1-3 can be used. In some embodiments, this is the final step in closing the macrocycle. As such, macrolactamization types of coupling procedures are more effective. Suitable macrolactamization procedures include, but are not limited to, those found in Davies, J. S. *J. Peptide Sci.* 2003, 9, 471-501.

When forming the ester bond, standard coupling reagents (e.g., EDC, DCC, PyBOP, HATU, COMO) can be used, or when this is the final step in formation of the macrocycle, macrolactonization procedures are preferred (e.g., Shina, Yamaguchi). An exemplary method for the macrolactonization step can be found in *Journal of American Chemical Society* 2002, 124, 4257 Paquette et al or *Chemical Reviews* 2006, 106(3), 911-939. Typically, the acid and alcohol are mixed in a polar solvent, e.g., DMF, acetonitrile, etc, in the presence of the coupling agent and a base, e.g., DIPEA, DMAP.

The following general schemes provide general examples and sequences for constructing the macrocyclic compound M from the common precursors A-E.

In many cases the optimal protecting groups and their deprotection methods are as follows. For Compound E, the typical protecting group $PG^1$ for the acid is a methyl or trichloroethyl ester. The methyl and trichloroethyl esters can be removed by base, e.g., LiOH in a polar solvent, e.g., aqueous THF, etc. The trichloroethyl ester can also be removed by treatment with zinc and ammonium acetate in a polar solvent, e.g., THF. Typically, $PG^2$ and $PG^4$ are acid labile groups, e.g., BOC, and are deprotected using HCl in dioxane, or TMSOTf in dioxane, dichloromethane. Typically, $PG^3$ and $PG^5$ are ester groups, removed by treatment with alkali metal hydroxide in aqueous THF or dioxane. Typically $PG^6$ is an acid labile group, e.g., BOC, for an amine and removed as described for $PG^2$, or a silyl ether for a hydroxyl group, and can be removed by treatment with HF.pyridine of TBAF in an organic solvent, e.g., dichloromethane. Typically $PG^8$ is an amine protecting group, e.g., BOC, and is removed Scheme 2: Use of RCM method for Connection 4

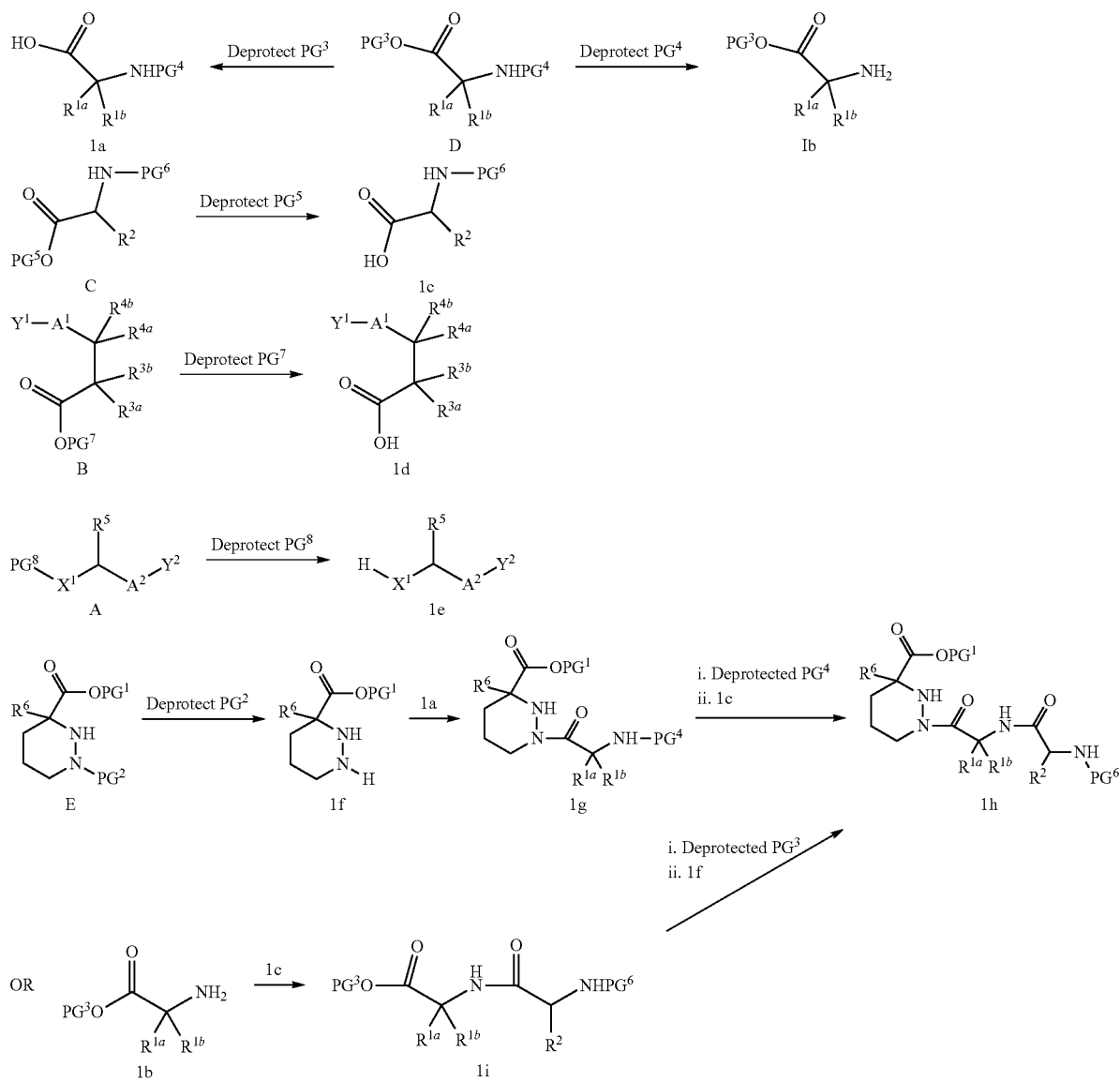

Compounds A-E can be deprotected ($PG^2$—$PG^8$) using conditions described in Greene and Wuts, Protective Groups in Organic Synthesis, John Wiley and Sons, Inc. to provide Compound 1a-1f.

as described for PG² or a silyl ether for a hydroxyl group, which can be removed as described for PG⁶, or an acetate protecting group, which can be removed with an alkali metal hydroxide in aqueous THF or dioxane.

Compound 1f is then coupled to acid 1a using the conditions described above for Connection 1 to produce compound 1g. Compound 1g is then deprotected using conditions described in Greene and Wuts and coupled to 1c to provide 1h using the conditions described above for Connection 2. An alternative sequence for generating 1h begins with coupling amine 1b to acid 1c using conditions as described for Connection 2 above, to form 1i; deprotection of the protecting group PG³ in 1i using conditions described in Greene and Wuts, and finally coupling with amine 1f using conditions described for Connection 1 above forms 1h.

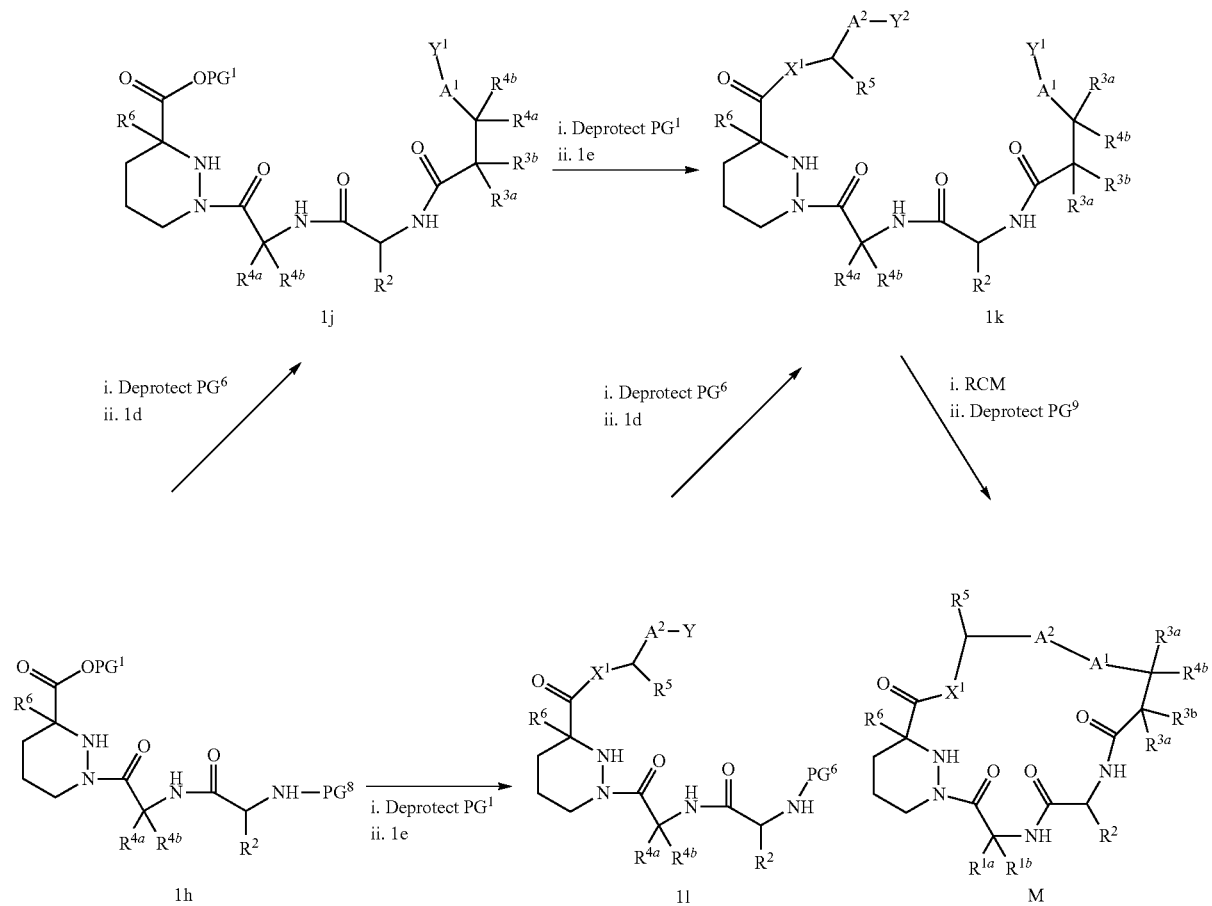

Compound 1h is deprotected at PG⁶ using conditions described in Greene and Wuts and the amine is then coupled to 1d using the conditions described above for Connection 3 to form 1j. Protecting group PG¹ in Compound 1j is then removed using conditions described in Greene and Wuts, and the acid is then coupled to 1e using conditions described for Connection 5 to form the acyclic intermediate 1k. An alternative sequence to 1k is first deprotection of PG¹ and then coupling to 1e as described for Connection 5; followed by deprotection of PG⁶ as described in Greene and Wuts, followed by coupling to 1d using the conditions described for Connection 3 to form 1k. Acyclic intermediate 1k is then subjected to the RCM as described above for Connection 4 to form the macrocycle M.

Scheme 4: Macrolactamization/Macrolactonization Connection 5

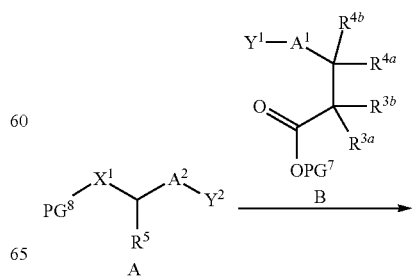

27
-continued

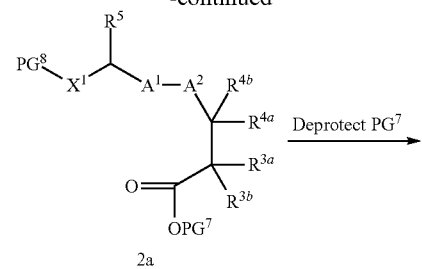

2a

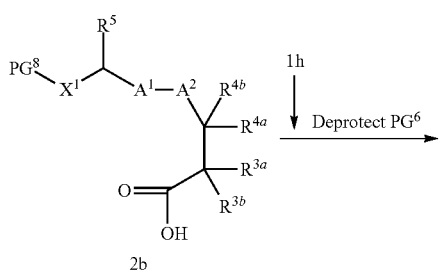

2b

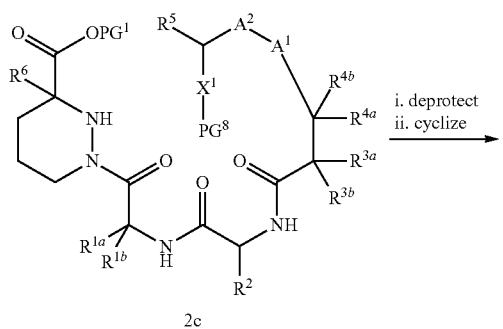

2c

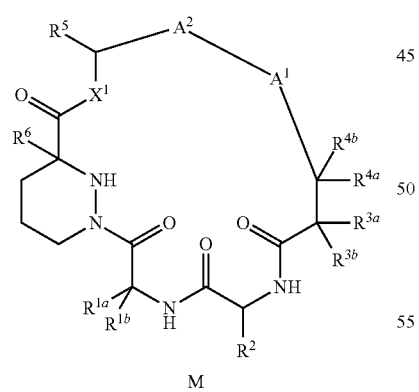

M

Compound A is coupled to Compound B using the conditions described above for Connection 4 to generate 2a. Compound 2a is then deprotected at PG⁷ as described in Greene and Wuts to generate acid 2b. Acid 2b is then coupled to the deprotected product of 1h (prepare from 1h by deprotection of PG⁶ described in Greene and Wuts) to generate the precursor 2c. Deprotection of 2c is carried out using conditions described in Greene and Wuts, and then the product is cyclized using the conditions described above for macrolactamization or macrolactonization in Connection 5, to provide Compound M.

28

Scheme 5: Macrolactamization/Macrolactonization Connection 5

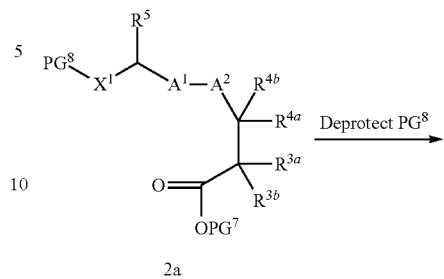

2a

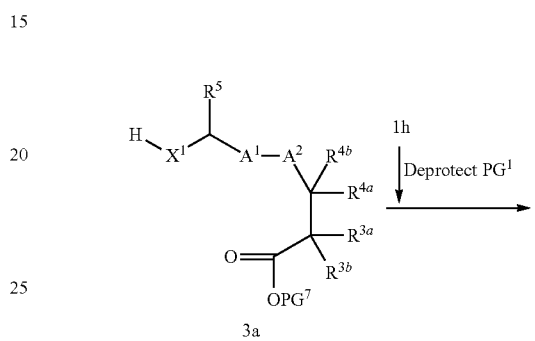

3a

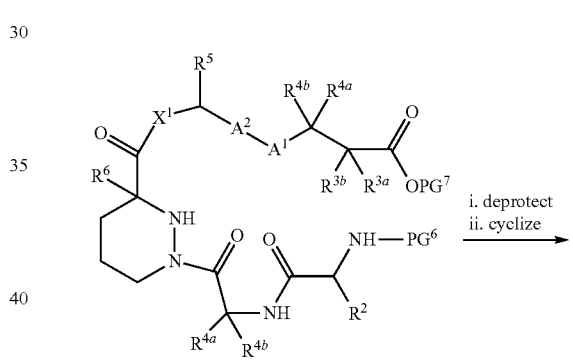

3b

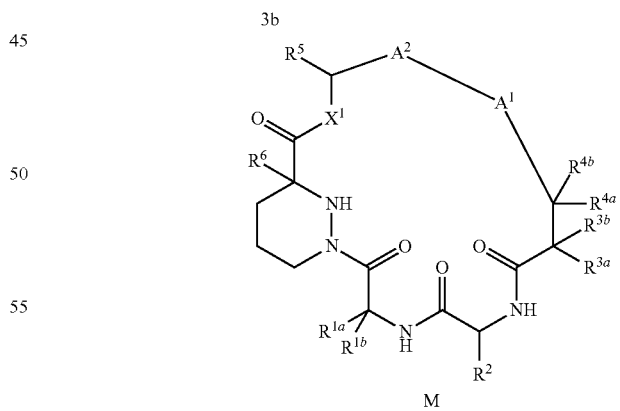

M

Compound 2a is deprotected at PG⁸ as described in Greene and Wuts and above in Connection 5 to generate 3a which is then coupled, using conditions described above for Connection 5, to the deprotected product of 1 h (prepared from 1 h by deprotection of PG¹ described in Greene and Wuts) to generate the precursor 3b. Deprotection of 3b is carried out using conditions described in Greene and Wuts, and the cyclized using the conditions described above for macrolactamization of macrolactonization in Connection 3, to provide Compound M.

Scheme 6: Further transformation of macrocyclic compounds M to M1-M5

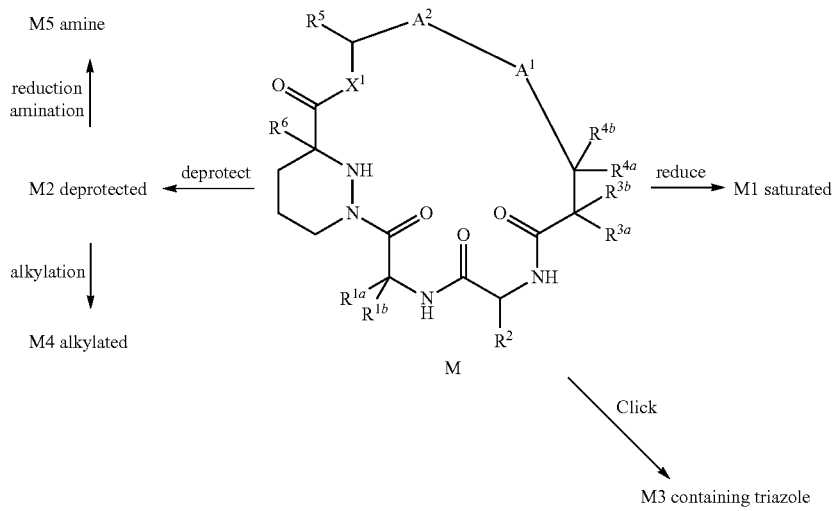

For example, when M contains a C═C as a result of RCM, Compound M is mixed in a solvent such as ethanol, methanol, etc., in the presence of palladium on carbon catalyst under an atmosphere of hydrogen gas to provide reduced Compound M1. The final macrocycle M from Schemes 4-6 often contains protecting groups on side-chains that require further removal to generate the final compound M. Protecting groups on the $R^{4a}$, $R^{4b}$, $R^{3a}$, $R^{3b}$, $A^1$, $A^2$ and/or $X^1$ are removed using conditions described in Greene and Wuts to generate Compound M2. Another transformation is click chemistry to produce triazole M3. This transformation is performed by treating the alkyne or azide in M, in solvent (e.g., DMF) with an alkyne or azide as appropriate in the presence of CuI to form M3.

Deprotected compound M2 can be further transformed after deprotection to additional macrocycle M. For example, treatment of M2 containing an —OH with an alkyl halide in the presence of a base, e.g., cesium carbonate, in a suitable solvent, e.g., DMF, acetonitrile, etc., forms alkylated product M4. M2 containing a ketone group is treated in a suitable solvent (e.g., DMF, methanol, etc.) with an amine followed by the addition of sodium acetoxyborohydride to form amine product M5.

Scheme 7: Preparation of acids or esters B

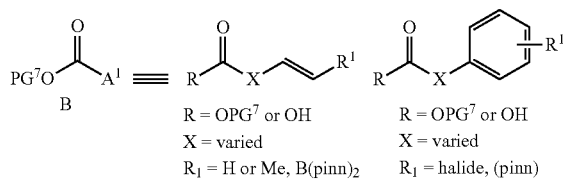

R = OPG$^7$ or OH
X = varied
R$_1$ = H or Me, B(pinn)$_2$

R = OPG$^7$ or OH
X = varied
R$_1$ = halide, (pinn)

Many B components containing an acid or ester with a terminal alkene or CH$_3$—CH═C— or vinyl/aryl boronate groups are commercially available or are described in the literature and can be used in the above schemes directly. In addition, the following schemes are examples of methods that can be used to generate additional B components.

Scheme 8: Preparation of acids or esters B

1.

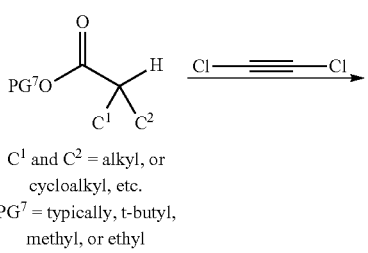

$C^1$ and $C^2$ = alkyl, or cycloalkyl, etc.
PG$^7$ = typically, t-butyl, methyl, or ethyl

2.

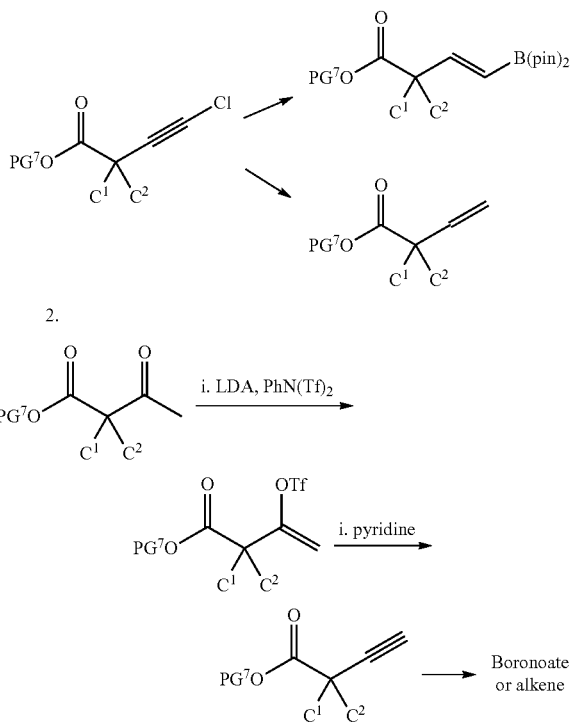

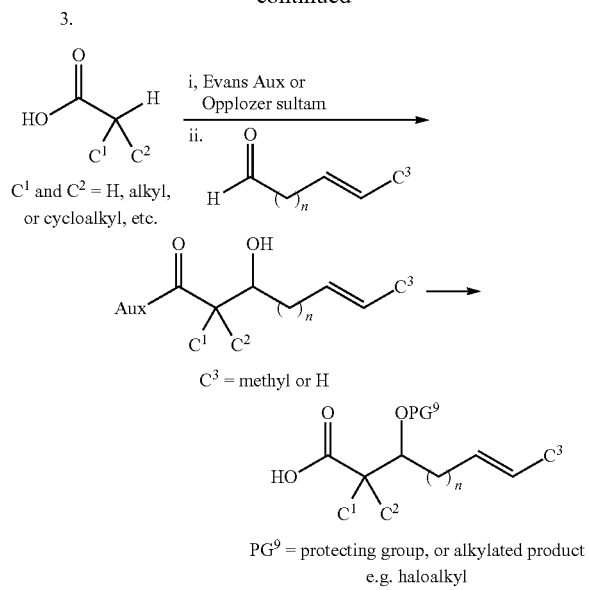
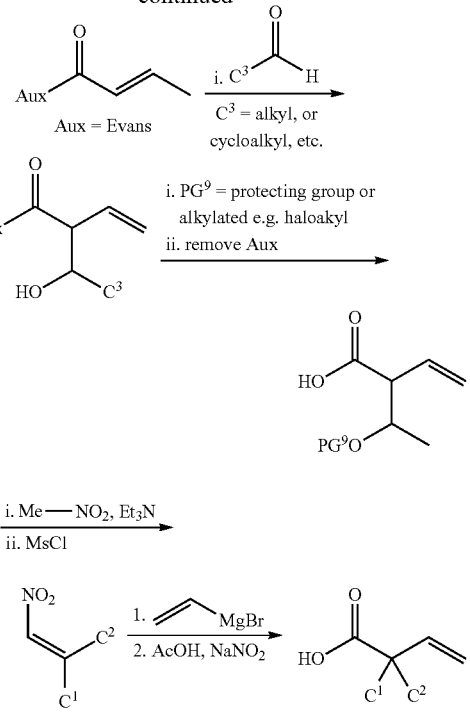

In Scheme 8, part 1, a protected acid is treated with a strong deprotonating base, e.g., LDA in an inert solvent, e.g., THF, at −78° C. and HMPA. A pre-cooled solution of dichloroacteylene (prepared by treatment of trichlorethene with potassium hydride and MeOH (catalytic) in THF) is then added to generate the chloro acetylene product. This product is then reduced, for example, by treatment with Cu in acetic acid and THF, to generate the alkyne, which is then further reduced to the alkene, for example, by treatment of an alcoholic solution of the alkyne with a poisoned palladium reducing agent (e.g., Lindlar) in the presence of hydrogen gas. Alternatively, the alkyne is treated with $Cp_2ZrHCl$ in dichloromethane in the presence of pinnacolborane to form the vinyl boronate.

In Scheme 8, part 2, a beta-keto ester with alpha substitution is converted to the vinyl triflate, for example, by treating a THF solution of the beta-keto ester with a base, e.g., LDA, in THF at −78° C., followed by addition of $PhN(Tf)_2$. The triflate product is then treated with pyridine at elevated temperature to form the alkyne. The alkyne is then treated as described above in part 1 to generate the alkene or vinyl boronate products.

In Scheme 8, part 3, a chiral aldol reaction is used. An acyl group is first attached to a chiral auxiliary, e.g., Evans, Oppolzer sultam (see *JACS* 1990, 112, p 2767), using the standard amide bond formation conditions as described above for Connection 1-3. The Oppolzer auxiliary product is treated with the aldehyde of choice, TBDMSOTf and base, e.g., triethylamine, in anhydrous solvent, e.g., dichloromethane. The Evans auxiliary is treated with base, e.g., LDA, KHMDS, DIPEA, in organic solvent, e.g., THF, at −78° C. and the aldehyde of choice in the presence of a Lewis acid, e.g., $TiCl_4$, $SnCl_4$, $BF_3OEt_2$. Protection of the resulting alcohol from the aldol reaction is performed as described in Greene and Wuts, or alternatively alkylation with an alkyl halide or Meerwein's reagent, i.e., treatment with trimethyloxonium tetrafluoroborate in an inert solvent, e.g., dichloromethane, is performed. The auxiliary is then removed using standard alkali metal hydroxide removal conditions, e.g., LiOH in THF, or LiOH and hydrogen peroxide in THF, to provide the free acids product.

In Scheme 8, part 4, an Evans auxiliary is allylated with an allyl halide as described in *Synlett* 2002, 12, 2039-2040. The product is then isomerized by treatment with RhCl$_3$ in ethanol and then the auxiliary removed by base and peroxide, e.g., LiOH and H$_2$O$_2$ in THF/Water. Alternatively the auxiliary is directly removed by LiOH and H$_2$O$_2$ in THF/Water to provide the terminal alkene.

In Scheme 8, part 5, a Horner Wadsworth Emmons reaction is used on an aldehyde (containing a terminal alkene) to generate the alpha-beta unsaturated ester, which is then selectively reduced to the ester. For example, the phosphonate is treated with base, e.g., sodium hydride, in THF at low temperature, followed by addition of the aldehyde and warming to generate the unsaturated ester. The product is reduced by treatment with magnesium powder in methanol.

In Scheme 8, part 6, an alpha-beta unsaturated acid is converted to the unsaturated Evans auxiliary (see *Organic Letters* 2007, 9, p 1635) and is treated with an aldehyde to generate the corresponding alkene product. The hydroxyl group is then protected using methods described in Greene and Wuts and then the auxiliary is removed by treatment with base and peroxide, e.g., LiOH and H$_2$O$_2$ in THF/Water. The hydroxyl can also be alkylated by as described above for aldol Scheme 8, part 3.

In Scheme 8, part 7, a ketone is transformed via the nitro olefin as described in *Angew. Chem. Int. Ed.* 2006, 45 (46), 7736. The nitro olefin is then treated with vinyl magnesium bromide in an inert solvent, e.g., THF, in the presence of a copper(I) salt, e.g., CuI and trimethylsilyl chloride. The nitro alkyl product after addition of the vinyl group is then converted to the acid by treating with sodium nitrite and acetic acid in an inert polar solvent, e.g., DMSO.

Several types of A are available commercially or described in the literature where $X^1$ is O or NH and $Y^2$ is a halide or $A^2$-$Y^2$ contains an alkene. The schemes below describe additional general methods for generating A.

Scheme 9: Preaparation of A

1. When $Y^2$ = Halogen in A

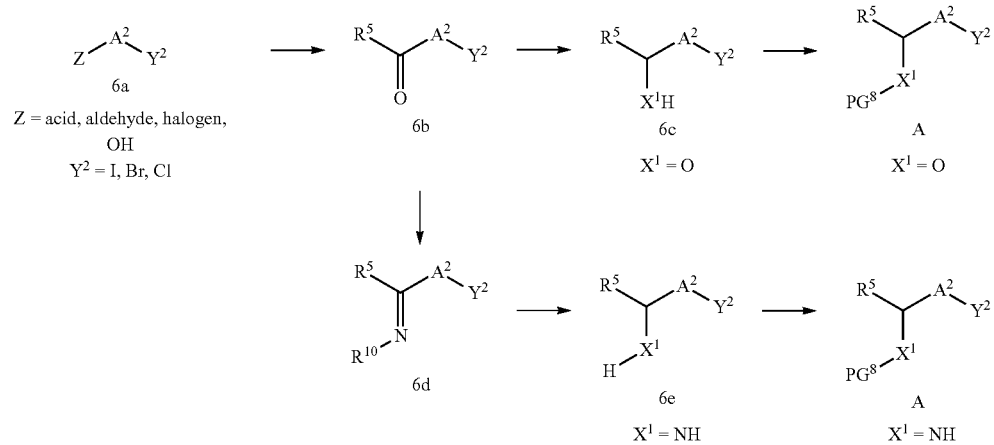

2. When $Y^2$ = H and $A^2$-$Y^2$ contains a alkene in A

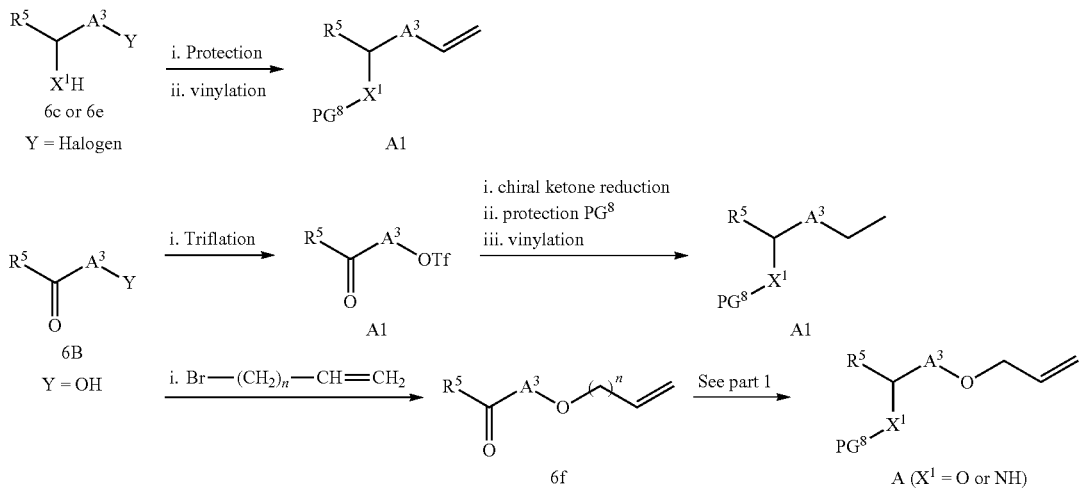

$A^3$ is aryl, heteroaryl, or biaryl, etc.

In Scheme 9, part 1 ($Y^2$ is a halogen in A); the starting Compound 6A is typically a commercially available aromatic compound, that contains halogen $Y^2$ and group Z that can be transformed to the ketone 6b. Typically Z groups are halide, acid, or aldehyde, for example.

When Z is an acid, 6a is treated with a coupling agent, e.g., HATU, EDC in the presence of a base, e.g., DIPEA and the Weinreb amine (Me-NH—OMe) to form the Weinreb amide. The amide is then treated with a nucleophile, e.g., TMS-CF$_3$ to form the CF$_3$ substituted ketone 6b or with a Grignard agent, e.g., MeMgBr in a solvent, e.g., THF, at −78° C. to form the methyl ketone 6b.

When Z is a halogen, then the initial conversion, if required, to a more reactive halogen is performed by treatment with NaI and acetyl chloride in an inert solvent, e.g., acetonitrile. The halogen is then transformed to the ketone by a Stille reaction with an ethoxyvinyl stannane. The halide is treated in an inert solvent, e.g., toluene, with the stannane and a palladium(II) catalyst, e.g., PdCl$_2$(PPh$_3$)$_2$, followed by treatment of the product with 2M HCl to afford ketone 6b. In some cases the formation of an alkyl lithium reagent from the halide group can be performed by treatment with nBuLi at −78° C. in THF and then addition of a N-methoxy-N-methyl amide to afford the ketone 6b (e.g., N-methoxy-N-methylacetamide affords the R$^5$ is methyl ketone 6b). A final method to generate the ketone 6b is through a vinyl group. 6a is treated with a vinyltrifluoroborate in the presence of a palladium catalyst, e.g., PdCl$_2$(dppf) and then the vinyl product is subsequently ozonolysed in a polar solvent, e.g., methanol at low temperature to give an aldehyde. The aldehyde is then reacted with a nucleophile, e.g., TSM-CF$_3$ or a Grignard reagent, e.g., MeMgBr to afford a secondary alcohol product. The secondary alcohol is then oxidized with Dess Martin Periodinane to give the desired ketone 6b or can be used as A itself.

Chiral alcohol (X$^1$ is O) and amine (X$^1$ is NH) A are generated using Chiral reduction methods on the ketone 6b. Chiral alcohol 6c is formed from 6b using one of the numerous chiral reduction methods available in the literature. Typically, dichloro(p-cumene)ruthenium(II) dimer and (1R,2R)-(−)-N-p-tosyl-1,2-diphenylethylenediamine are combined in water, and sodium formate and 6b is added in a water miscible solvent such as tetrahydrofuran. The reaction is then stirred at a temperature between ambient and reflux to produce 6c where X$^1$ is O. Alternatively, a chiral CBS reduction can be performed in an inert solvent, e.g., THF at low temperature to also afford the chiral alcohol 6c. Protection of the OH in 6c is performed using methods described in Greene and Wuts, typically a TBS ether or acetyl group are used to provide A (X$^1$ is O).

Alternatively, to make chiral A (X$^1$ is NH), ketone 6b is first converted to a chiral imine (R$^{10}$ is chiral group) and then reduced using a variety of methods described in the literature. For example, a chiral sulfinamide is reacted with the ketone 6b to afford a chiral sulfinimine 6d, which is then reduced with a suitable reducing agent, typically NaBH$_4$, or selectride, or a Noyori type reduction as described for the chiral alcohol above, with dichloro(p-cumene)ruthenium(II) dimer and (1R,2R)-(−)-N-p-tosyl-1,2-diphenylethylenediamine. The sulfinamide auxiliary is then removed by treatment with mineral acid, preferably HCl in a suitable organic solvent such as methanol, to afford 6e where X$^1$ is NH. Protection of the NH group can then be performed as described in Greene and Wuts to generate A (X$^1$ is NH).

In part 2 of Scheme 9, the synthesis of compound A where Y$^2$ is H and A$^2$-Y$^2$ contains —CH═CH$_2$, a precursor for metathesis and cross coupling reactions is illustrated. Exemplary methods are as follows.

Compound 6c or 6e generated in Scheme 9, part 1 is first optionally protected on X$^1$ using a suitable protecting group as described in Greene and Wuts, and then a vinyl group is introduced by a suitable cross coupling method onto the aryl or sp2 halide. For example, a transition metal mediated coupling with a vinyl stannane or vinyl tetrafluoroborate using a suitable palladium catalyst, e.g., PdCl$_2$(dppf)$_2$ or PdCl$_2$(PPh$_3$)$_2$ in a suitable organic solvent, e.g., acetonitrile, dichloromethane, etc., with either thermal or microwave heating affords alkene A.

Another typical method that can be used to introduce a vinyl group is starting from the ketone 6b where Y is OH. Initially, triflation of the alcohol is performed by treatment with Tf$_2$O in the presence of a base, e.g., pyridine. The ketone group is then reduced with a Noyori reduction, or as described above through the sulfonamide, to provide the chiral alcohol or amine. The chiral alcohol or amine is then protected as described in Greene and Wuts, and then the triflate is reacted with a vinyl cross coupling reagent, e.g., vinyl stannane in a Stille coupling, or a vinyltrifluoroborate as described above to introduce the alkene. A further example of alkene generation using 6b ketone is via introduction of an allyl group. Thus, 6b where Y is OH is treated in an inert solvent in the presence of a suitable base, e.g., alkali metal carbonate, preferably potassium carbonate with allyl bromide to form 6f. Compound 6f is then similar to ketone 6b and is therefore able to be transformed as described above in part 1 to Compound A where X$^1$ is O or NH with protecting group PG$^8$.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

The effective dose of an active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. The effective dose can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Combination Therapy

The compounds of the present invention may be combined with one or more active agents. Non-limiting examples of suitable active agents to be combined include one or more interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

More specifically, one or more compounds to be combined are selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon;

2) ribavirin and its analogs, e.g., ribavirin (Rebetol, Copegus), and taribavirin (Virami3);

3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227);

4) alpha-glucosidase 1 inhibitors, e.g., celgosivir (MX-3253), Miglitol, and UT-231B;

5) hepatoprotectants, e.g., emericasan (IDN-6556), ME-3738, GS-9450 (LB-84451), silibilin, and MitoQ;

6) nucleoside or nucleotide inhibitors of HCV NS5B polymerase, e.g., R1626, R7128 (R4048), IDX184, IDX-102, PSI-7851, BCX-4678, valopicitabine (NM-283), GS-6620 and MK-0608;

7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190;

8) HCV NS5A inhibitors, e.g., AZD-2836 (A-831), AZD-7295 (A-689), and BMS-790052;

9) TLR-7 agonists, e.g., imiquimod, 852A, GS-9524, ANA-773, ANA-975, AZD-8848 (DSP-3025), PF-04878691, and SM-360320;

10) cyclophillin inhibitors, e.g., DEBIO-025, SCY-635, and NIM811;

11) HCV IRES inhibitors, e.g., MCI-067;

12) pharmacokinetic enhancers, e.g., BAS-100, SPI-452, PF-4194477, TMC-41629, GS-9350, GS-9585, and roxythromycin;

13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOc-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib);

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride; and 18) endothelin antagonists, e.g. bosentan and ambrisentan.

In yet another embodiment, the present application provides a combination therapy comprising a composition of the present invention and a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5a inhibitors, alpha-glucosidase 1 inhibitors, cyclophilin inhibitors, hepatoprotectants, non-nucleoside inhibitors of HCV, and other drugs for treating HCV, and combinations thereof.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, Mb-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, Mb-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, reaferon, intermax alpha, r-IFN-beta, infergen+actimmune, IFN-omega with DUROS, and albuferon, 12) ribavirin analogs, e.g., rebetol, copegus, VX-497, and viramidine (taribavirin) 13) NS5a inhibitors, e.g., A-831, A-689 and BMS-790052, 14) NS5b polymerase inhibitors, e.g., NM-283, valopicitabine, R1626, PSI-6130 (R1656), IDX184, PSI-7851, HCc-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-ANA 971, NOc-205, tarvacin, EHC-18, and NIM811, 19) pharmacokinetic enhancers, e.g., BAS-100, SPI-452, PF-4194477, TMC-41629, GS-9350, GS-9585, and roxythromycin, 20)RNAse H inhibitors, e.g., ODN-93 and ODN-112, 21) other anti-HIV agents, e.g., VGc-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

In a specific aspect of this embodiment, the additional therapeutic agent is selected from ribavirin, telaprevir, boceprevir and sofosbuvir (GS-7977 (formerly PSI-7977)).

A combination therapy described herein may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Method for Treating Viral Infection

The present application provides a method for treating a Flaviviridae viral infection comprising administering a therapeutically effective amount of a compound described herein or a pharmaceutically acceptable salt, isotope, stereoisomer, mixture of stereoisomers, tautomer, ester or prodrug thereof, to a human subject in need thereof.

Also provided is a method for treating a Coronaviridae viral infection comprising administering a therapeutically effective amount of a compound described herein or a pharmaceutically acceptable salt, isotope, stereoisomer, mixture of stereoisomers, tautomer, ester or prodrug thereof, to a human subject in need thereof.

In one embodiment, the method of inhibiting or treating a disease comprises administering to an animal a composition comprising an effective amount of one or more compounds of the invention or a pharmaceutically acceptable salt, isotope, stereoisomer, mixture of stereoisomers, tautomer, ester or prodrug thereof and a pharmaceutically acceptable carrier. The composition to be administered may further contain a secondary therapeutic agent as described above.

A method of the present application is particularly suitable for use with humans, but may be used with other animals, particularly mammals, such as, for example, non-human primates, companion animals, farm animals, laboratory animals, and wild and zoo animals.

A method of the present application is particularly useful to treat diseases caused directly or indirectly by Flaviviridae virus since the compounds of the present invention have inhibitory activity against those viruses. In some embodiments, therefore, a method of the present invention is used in inhibiting or treating diseases caused by a Hepatitis C virus. In some embodiments, therefore, a method of the present invention is used in inhibiting or treating diseases caused by a Hepatitis B virus. In an aspect, such a method is applied to a patient with a disease caused by the viral infection such as dengue fever, yellow fever, hepatitis C, Japanese encephalitis, Kyasanur forest disease, Murray valley encephalitis, St. Louis encephalitis, tick-borne encephalitis or West Nile encephalitis.

In some embodiments, a sustained virologic response is achieved at about 12 weeks, at about 10 weeks, at about 8 weeks, at about 6 weeks, or at about 4 weeks, or at about 4 months, or at about 5 months, or at about 6 months, or at about 1 year, or at about 2 years.

A method of the present application is also particularly useful to treat diseases caused directly or indirectly by Coronaviridae virus since the compounds of the present invention have inhibitory activity against those viruses. In some embodiments, therefore, a method of the present invention is used in inhibiting or treating diseases caused by a SARS coronarirus. In an aspect, such a method is applied to a patient with a disease caused by the viral infection such as severe acute respiratory syndrome (SARS), cancer, inflammation, obesity, acquired immune deficiency syndrome (AIDS), or cirrhosis.

In another aspect, the compounds disclosed herein can be used for treating cancer. In yet another aspect, the compounds disclosed herein can be used for immunomodulation. In some embodiments, therefore, a method of the present invention comprises adjusting an immune response to a desired level, as in immunopotentiation, immunosuppression, or induction of immunologic tolerance.

In some embodiments, the compound is administered for about 12 weeks. In further embodiments, the compound is administered for about 12 weeks or less, for about 10 weeks or less, for about 8 weeks or less, for about 6 weeks or less, or for about 4 weeks or less. The compound may be administered once daily, twice daily, once every other day, two times a week, three times a week, four times a week, or five times a week.

In another aspect, the compounds disclosed herein can be used for treating cancer. In yet another aspect, the compounds disclosed herein can be used for immunomodulation. In some embodiments, therefore, a method of the present invention comprises adjusting an immune response to a desired level, as in immunopotentiation, immunosuppression, or induction of immunologic tolerance.

EXAMPLES

The following examples are merely illustrative, and do not limit this disclosure in any way.

LIST OF ABBREVIATIONS AND ACRONYMS

Abbreviation Meaning

° C. Degree Celsius
Ac Acetyl
app Apparent
Aq Aqueous
Boc tert-Butoxycarbonyl
Br Broad
Bu Butyl cat Catalytic
CBS Corey Bakshi Shibata
CDMT 2-chloro-4,6-dimethoxy-1,3,5-triazine
cm Centimeter
COMU (1-Cyano-2-ethoxy-2-oxoethylidenaminooxy) dimethylamino-morpholino-carbenium hexafluorophosphate
CP/Cp Cyclopentyl
CPME Cyclopentyl methyl ether
Cy/cHex Cyclohexyl
d Doublet
DBU 1,8-Diazabicyclo[5.4.0]undec-7-ene
DCC N,N'-dicyclohexylcarbodiimide
DCE Dichloroethane
DCM Dichloromethane
dd Doublet of doublets
ddd Doublet of doublet of doublet
ddt Doublet of doublet of triplet
DIAD Diisopropyl azodicarboxylate
DIPEA N,N-Diisopropylethylamine
DMAP 4-Dimethylaminopyridine
DME 1,2-dimethoxyethane
DMF Dimethylformamide
DMSO Dimethylsulfoxide
dppf 1,1'-bis(diphenylphosphino)ferrocene
dq Doublet of quartet
dt Doublet of triplet
dtd Doublet of triplet of doublet
EDC 1-Ethyl-3-(3-dimethylaminopropyl)carbodiimide
Equiv/eq Equivalents
Et Ethyl
g Grams
gen. Generation
HATU (Dimethylamino)-N,N-dimethyl(3H-[1,2,3]triazolo[4,5-b]pyridin-3-yloxy)methaniminium hexafluorophosphate
HBTU 2-(1H-benzotriazole-1-yl)-1,1,3,3-tetramethyluronium hexafluorophosphate
HMDS Hexamethyldisilazane
HMPA hexamethylphosphoramide
HOBT Hydroxybenzotriazole
HPLC High-performance liquid chromatography
hrs/h Hours
Hz Hertz
$IC_{50}$ The half maximal inhibitory concentration
Im imidazole
i-Pr/iPr Isopropyl
J Coupling constant
Kg Kilogram
LCMS Liquid chromatography—mass spectrometry
LDA Lithium diisopropylamide
M Molar
m Multiplet
m/z mass-to-charge ratio
M+ Mass peak
Me Methyl
mg Milligram
MHz Megahertz
min Minute
mL Milliliter
mM Millimolar
mm Millimeter
mmol Millimole
mol Mole
Ms Methanesulfonyl
MW Microwave
N normal
nM Nanomolar
NMM N-methylmorpholine
NMR Nuclear magnetic resonance
nPrOH n-propanol
o-Tol o-Tolyl
Ph Phenyl
pTSA p-Toluenesulfonic acid
Py/pyr Pyridine
PyAOP 7-azabenzotriazol-1-yloxy)tripyrrolidinophosphonium hexafluorophosphate
PyBop benzotriazol-1-yl-oxytripyrrolidinophosphonium hexafluorophosphate
q Quartet
Rf Retention factor
RT/rt/r.t. Room temperature
s Singlet
sat. Saturated
t Triplet
TBAF Tetra-n-butylammonium fluoride
TBDMS/TBS tert-Butyldimethylsilyl
TBDPS tert-Butyldiphenylsilyl
t-Bu tert-butyl
td Triplet of doublets
TEA Triethylamine
Tf Trifluoromethanesulfonyl
TFA Trifluoroacetic acid
THF Tetrahydrofuran
TLC Thin layer chromatography
TMEDA tetramethylethylenediamine
TMS Trimethylsilyl
Tr/tr Retention time
Ts Tosyl
tt Triplet of triplet
UV Ultraviolet
wt. weight
δ hemical shift
μL Microliter
μM Micromolar
μmol Micromole Example 1

(E)-(2R,5S,11S,14S,17R,18R)-18-Hydroxy-14-isopropyl-2,11,17-trimethyl-3,9,12,15,28-pentaazatricyclo[21.3.1.1*5,9]octacosa-1(26),21,23(27),24-tetraene-4,10,13,16-tetraone

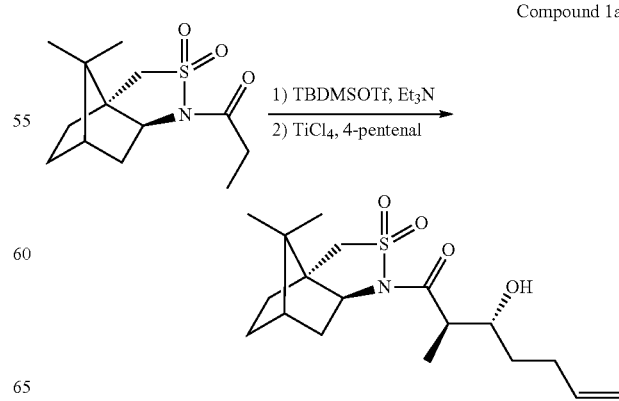

Compound 1a

A solution of 1-((1R,5S)-10,10-dimethyl-3,3-dioxo-3lambda*6*-thia-4-aza-tricyclo[5.2.1.0*1,5*]dec-4-yl)-propan-1-one (3.95 g, 14.55 mmol) in toluene (50 mL) was prepared, then evaporated to dryness. This process was repeated and the resulting white solid was dissolved in anhydrous dichloromethane (16 mL). A small quantity of calcium hydride was added before adding tert-butyldimethylsilyl trifluoromethanesulfonate (3.83 mL, 14.5 mmol) and anhydrous triethylamine (2.33 mL, 16.7 mmol). The reaction mixture was stirred at RT ("RT") under a nitrogen atmosphere for 15 hours ("h"). The resulting solution was evaporated to yield a thick paste, which was re-dissolved in anhydrous dichloromethane (15 mL) and added dropwise to a stirred solution of 4-pentenal (2.69 g, 32.0 mmol) and titanium tetrachloride (1 M in dichloromethane, 32 mL, 32 mmol) in anhydrous dichloromethane (20 mL) at −78° C., under a nitrogen atmosphere. The reaction was stirred at −78° C. for 30 minutes ("min") before diluting with saturated aqueous ammonium chloride solution (100 mL). The layers were separated and the aqueous layer was extracted with dichloromethane (2×50 mL). The combined extract was dried over sodium sulfate, filtered and evaporated to give a brown gum. This was purified by silica gel chromatography using iso-hexanes/ethyl acetate 4:1 to yield the title compound (3.09 g, 60%) as a colorless gum.

Compound 1b

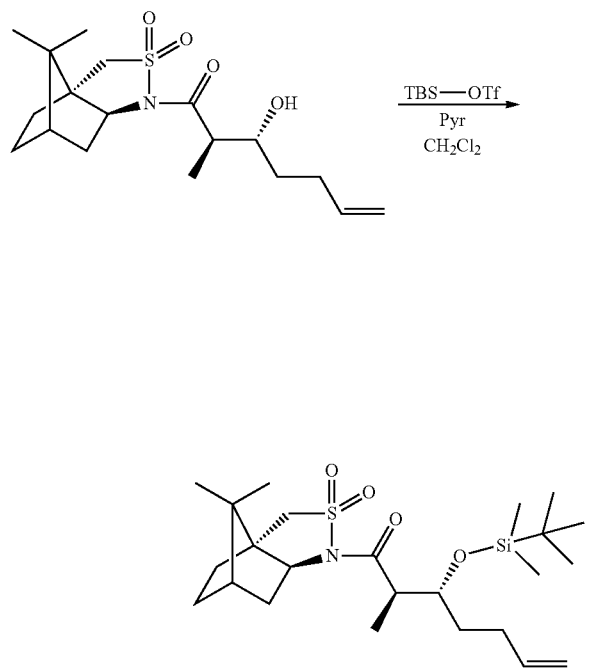

A solution of 1a (12.0 g, 0.034 mol) in anhydrous dichloromethane (520 mL) was cooled to 0° C., before adding pyridine (5.5 mL, 0.068 mol) then tert-butyldimethylsilyl trifluoromethanesulfonate (9 mL, 0.039 mol). The reaction mixture was stirred at 0° C. for 15 min then allowed to warm to RT and stirred for a further 1.5 h. The reaction mixture was washed with saturated sodium bicarbonate (400 mL). The aqueous wash was back-extracted with dichloromethane (200 mL). The organic layers were combined and washed with dilute brine (200 mL) and 2 M hydrochloric acid (200 mL). The solution was dried over sodium sulfate, filtered and evaporated to give the title product (15.29 g, 96%) as a white solid.

Compound 1c

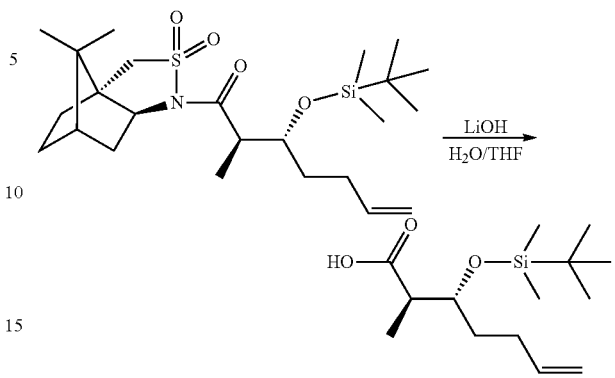

A solution of 1b (15.29 g, 0.0325 mol) in tetrahydrofuran (300 mL) was prepared and a 2 M aqueous solution of lithium hydroxide (120 mL) was added. The stirred mixture was heated to 60° C. for 15 h. The reaction was diluted with 2 M hydrochloric acid (250 mL). The layers were separated and the aqueous was extracted with ethyl acetate (2×200 mL). The organic layers were combined, dried over sodium sulfate, filtered and evaporated to give a cream solid (16.7 g). The solid was purified by silica gel chromatography using 3:7 ethyl acetate/iso-hexanes to yield the title product (7.18 g, 81%) as a colorless gum.

Compound 1d

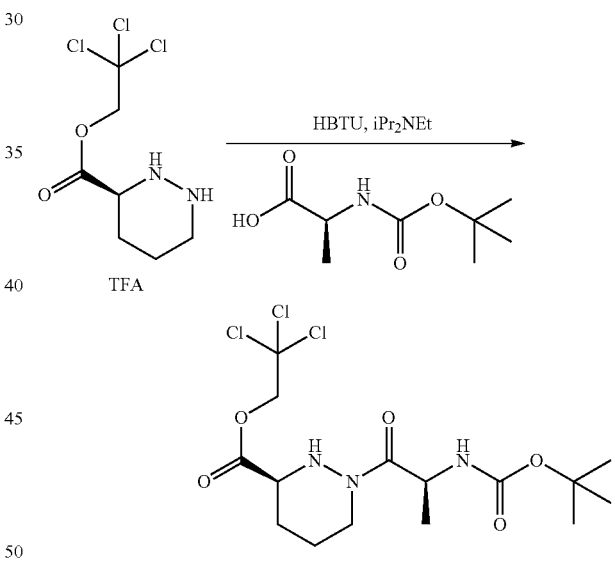

A solution of (S)-2-tert-butoxycarbonylamino-propionic acid (3.28 g, 17.32 mmol) in acetonitrile (160 mL) was cooled to 0° C. before addition of N,N-diisopropylethylamine (12 mL, 69.3 mmol) then 2-(1H-benzotriazole-1-yl)-1,1,3,3-tetramethyluronium hexafluorophosphate (6.57 g, 17.32 mmol). The reaction mixture was stirred at 0° C. for 20 min and a solution of (S)-hexahydropyridazine-3-carboxylic acid 2,2,2-trichloroethyl ester trifluoroacetic acid salt (preparation described in Angew. Chem. Int. Ed. Engl. 1999, 38, 2443, 6.49 g, 17.3 mmol) in acetonitrile (80 mL) was added. The reaction was allowed to warm to RT and was stirred for 15 h. The reaction mixture was evaporated then re-dissolved in ethyl acetate (150 mL). The solution was washed with brine (150 mL). The brine was back extracted with ethyl acetate (50 mL). The organic layers were combined, dried over sodium sulfate, filtered and evaporated to give a dark oil. The oil was purified by silica gel chromatography using iso-hexanes/ethyl acetate 1:1 to yield the title compound (6.88 g, 92%) as a colorless gum.

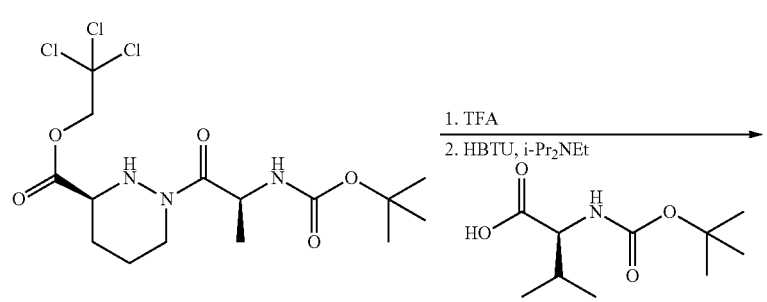

Compound 1e

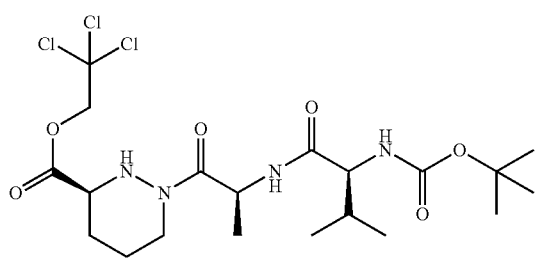

A solution of 1d (6.88 g, 15.9 mmol) in dichloromethane (200 mL) was prepared and trifluoroacetic acid (50 mL) was added. The reaction mixture was stirred at RT for 2 h. TLC showed the reaction to be complete. The solution was evaporated to give a brown oil. This was azeotroped with toluene (50 mL) and the resultant oil was dried under vacuum to give (S)-1-((S)-2-amino-propionyl)-hexahydro-pyridazine-3-carboxylic acid 2,2,2-trichloro-ethyl ester trifluoroacetic acid salt (7.8 g) as a brown gum. A solution of ((S)-1-carbamoyl-2-methylpropyl)-carbamic acid tert-butyl ester in acetonitrile (300 mL) was cooled to 0° C. before adding N,N-diisopropylethylamine (13.8 mL, 79.7 mmol) and 2-(1H-benzotriazole-1-yl)-1,1,3,3-tetramethyluronium hexafluorophosphate (6.33 g, 16.7 mmol). The reaction was stirred at 0° C. for 15 min before adding a solution of the (S)-1-((S)-2-amino-propionyl)-hexahydro-pyridazine-3-carboxylic acid 2,2,2-trichloro-ethyl ester trifluoroacetic acid salt (ca. 15.9 mmol) in acetonitrile (85 mL). The reaction was stirred at 0° C. for a further 20 min then allowed to warm to RT and stirred for 15 h. The reaction mixture was evaporated then re-dissolved in ethyl acetate (250 mL). The solution was washed with water (150 mL) then dried over sodium sulfate, filtered and evaporated to give a red oil. This was purified by silica gel chromatography using iso-hexanes/ethyl acetate 7:3 then iso-hexanes/ethyl acetate 1:1 to yield the title compound (8.2 g, 92%) as a pale orange amorphous solid.

Compound 1f

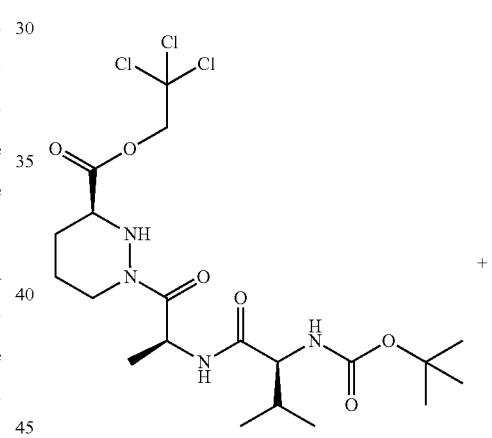

+

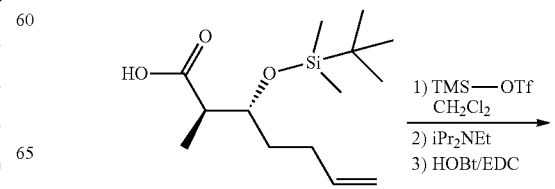

1) TMS—OTf
CH$_2$Cl$_2$
2) iPr$_2$NEt
3) HOBt/EDC

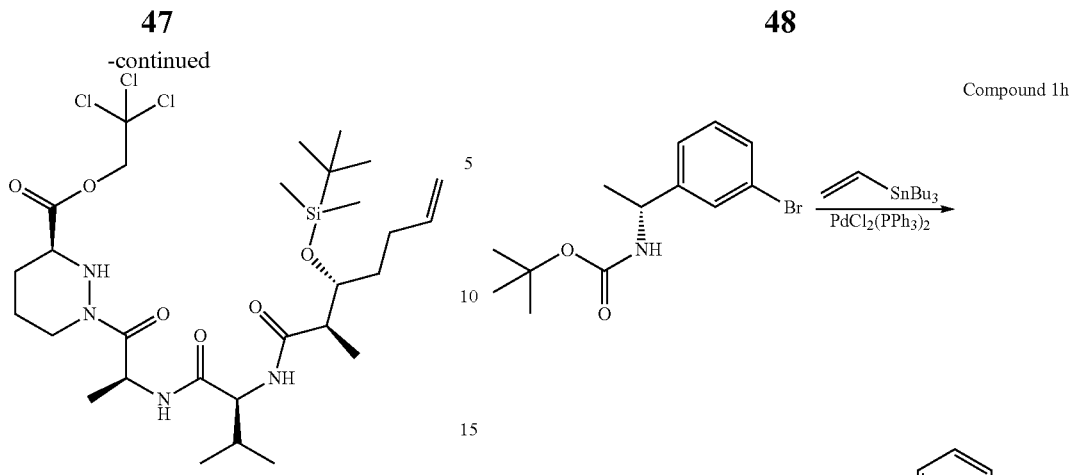

Compound 1h

A solution of 1e (10.0 g, 18.5 mmol) in anhydrous dichloromethane (200 mL) was prepared and trimethylsilyl trifluoromethanesulfonate (5 mL, 27.75 mmol) was added. The reaction mixture was stirred at RT for 2 h, then N,N-diisopropylethylamine (13.2 mL, 75.8 mmol) was added and the reaction mixture was evaporated to dryness. The residue was re-dissolved in acetonitrile (200 mL) and a solution of (2R, 3R)-3-(tert-butyl-dimethyl-silanyloxy)-2-methyl-hept-6-enoic acid (5.04 g, 18.5 mmol) in acetonitrile (60 mL) was added followed by 1-ethyl-3-(3-dimethylaminopropyl)carbodiimide (5.0 g, 26.4 mmol) and 1-hydroxybenzotriazole (4.4 g, 26.4 mmol). The reaction mixture was stirred at RT for 15 h. It was evaporated to give a thick yellow oil. The oil was purified by silica gel chromatography using 1:1 ethyl acetate/iso-hexanes then 3:2 ethyl acetate/iso-hexanes to yield the title product (8.75 g, 69%) as a white solid.

A solution of 1g (10.26 g, 0.0342 mol.) and tributyl(vinyl)tin (32.5 g, 30 mL, 0.103 mol.) in toluene (175 mL) was purged with nitrogen for 30 min before addition of bis(triphenylphosphine) palladium(II)dichloride (2.38 g, 0.0034 mol.). The stirred mixture was heated to 60° C. for 16 h before cooling to RT. The reaction mixture was filtered through hyflo-supercel then evaporated to give a dark coloured oil. The oil was purified by silica gel chromatography using iso-hexanes/ethyl acetate 19:1 to yield the title compound (6.95 g, 82%) as a yellow oil.

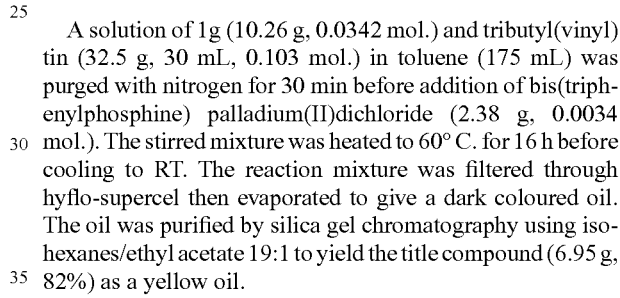

Compound 1g

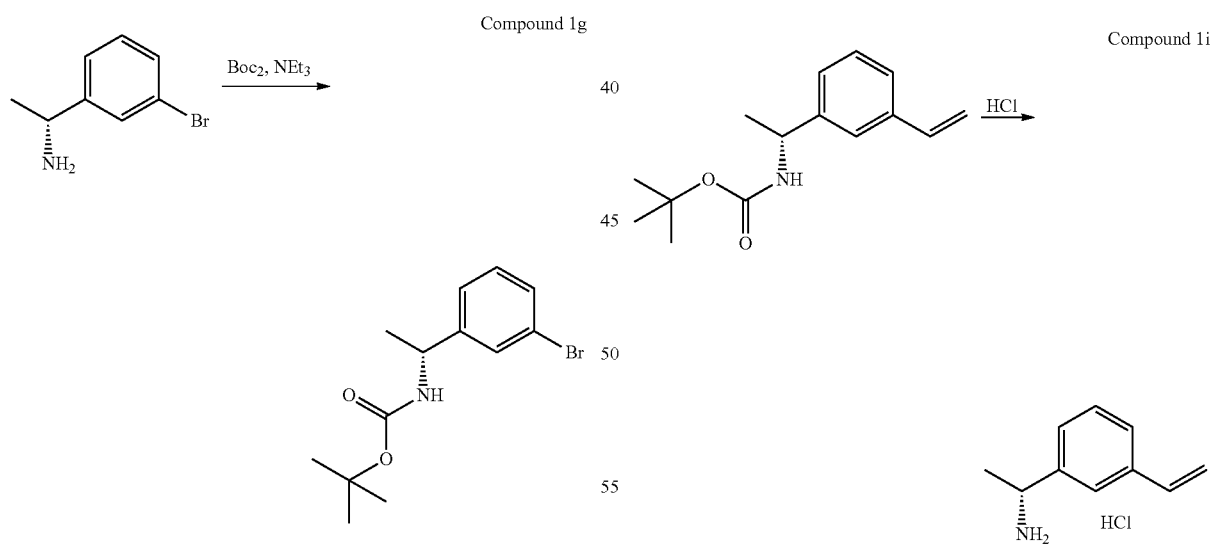

Compound 1i

A solution of (R)-bromo-α-methylbenzylamine (1.023 g, 5.112 mmol) in dichloromethane (20 mL) was subsequently treated with triethylamine (720 µL, 5.112 mmol) and di-tert-butyl dicarbonate (1.784 g, 8.179 mmol). After overnight stirring at RT, the volatiles were removed in vacuo and the residue was purified by silica gel chromatography using a 50 g Isolute cartridge eluted with a continuous gradient of iso-hexanes/diethyl ether 1:0 to 4:1 to afford the title compound (1.552 g, 100%) as a white solid.

A solution of 1h (6.95 g, 28.1 mmol.) in 1,4-dioxane (30 mL) was prepared and a solution of hydrogen chloride in 1,4 dioxane (4 M, 60 mL) was added. The reaction mixture was stirred at RT for 2 h then evaporated to dryness. The resultant solid was re-dissolved in toluene and evaporated. The solid was triturated with diethyl ether, which was removed by decanting. The solid was then dried under vacuum to give the title compound (4.96 g, 96%) as an off-white solid.

Compound 1j

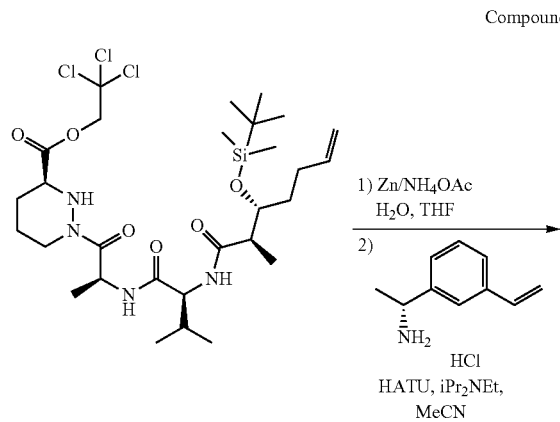

Compound 1k

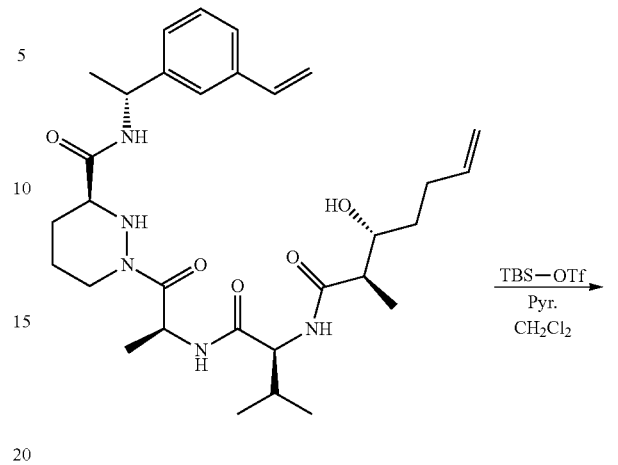

1) Zn/NH₄OAc H₂O, THF
2) (R)-1-(3-vinylphenyl)ethylamine·HCl, HATU, iPr₂NEt, MeCN TBS—OTf
Pyr.
CH₂Cl₂

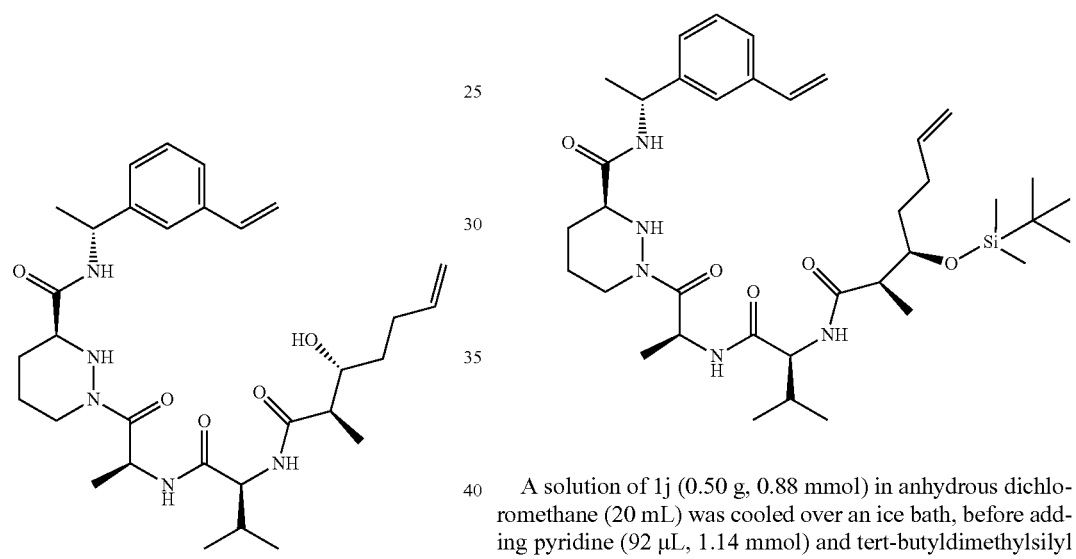

A solution of 1f (8.75 g, 12.75 mmol) in tetrahydrofuran (350 mL) was prepared and zinc powder (8.44 g, 127.5 mmol) was added followed by a 1 M aqueous solution of ammonium acetate (90 mL, 90 mmol). The reaction mixture was vigorously stirred for 16 h then filtered through hyflo-supercel. The solution was cooled over an ice bath before addition of aqueous ammonium chloride solution (350 mL). It was allowed to re-cool before acidifying to pH 1 by addition of 2 M hydrochloric acid. The layers were separated and the aqueous was extracted with ethyl acetate (2×250 mL). The organic layers were combined, dried over sodium sulfate filtered and evaporated to give a white solid. The solid was azeotroped with toluene (3×200 mL) then dried under vacuum to give a white solid (6.16 g), which was dissolved in acetonitrile (400 mL) before adding (R)-1-(3-vinyl-phenyl)-ethylamine hydrochloride (2.34 g, 12.75 mmol) followed by N,N-diisopropylethylamine (8.9 mL, 51 mmol) and 2-(1H-7-azabenzotriazol-1-yl)-1,1,3,3-tetramethyl uronium hexafluorophosphate methanaminium (6.8 g, 17.85 mmol). The reaction mixture was stirred at RT for 16 h and then evaporated to give a brown gum. The gum was purified by silica gel chromatography using ethyl acetate then 1:4 acetone/ethyl acetate to yield the title compound (5.51 g, 76%) as a cream solid.

A solution of 1j (0.50 g, 0.88 mmol) in anhydrous dichloromethane (20 mL) was cooled over an ice bath, before adding pyridine (92 µL, 1.14 mmol) and tert-butyldimethylsilyl trifluoromethanesulfonate (242 µL, 1.05 mmol). The reaction mixture was stirred at 0° C. for 15 min, then allowed to warm to RT and stirred for 1 hour. The reaction mixture was evaporated and the residue was purified by silica gel chromatography using ethyl acetate to yield the title product (477 mg, 80%) as a white solid.

Compound 1l

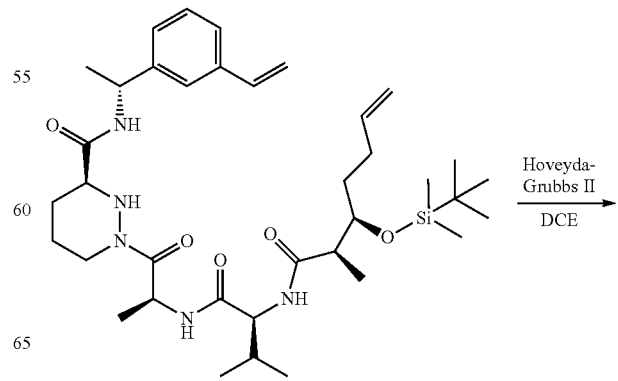

Hoveyda-Grubbs II
DCE

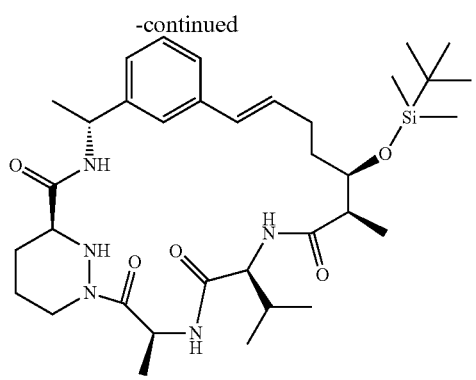

Hz, 3H), 1.36 (d, J=6.9 Hz, 3H), 1.40-1.90 (m, 7H), 1.92-2.08 (m, 1H), 2.19-2.34 (m, 2H), 2.67-2.80 (m, 1H), 3.56-3.65 (m, 1H), 3.99-4.12 (m, 1H), 4.22 (br d, J=12.2 Hz, 1H), 4.75 (d, J=11.8 Hz, 4.87-4.99 (m, 1H), 5.12-5.24 (m, 1H), 5.40 (d, J=4.5 Hz, 1H), 6.14-6.33 (m, 2H), 7.10-7.35 (m, 5H), 7.88 (d, J=8.3 Hz, 1H), 8.55 (d, J=8.3 Hz, 1H). LCMS (m/z) 542.3 [M+H], Tr=1.87 min.

Example 2

(E)-(2R,5S,11S,14S,17R,18R)-14-Isopropyl-2,11,17-trimethyl-18-(2,2,2-trifluoro-ethoxy)-3,9,12,15,28-pentaaza-tricyclo[21.3.1.1*5,9]octacosa-1(26),21,23(27),24-tetraene-4,10,13,16-tetraone Compound 2

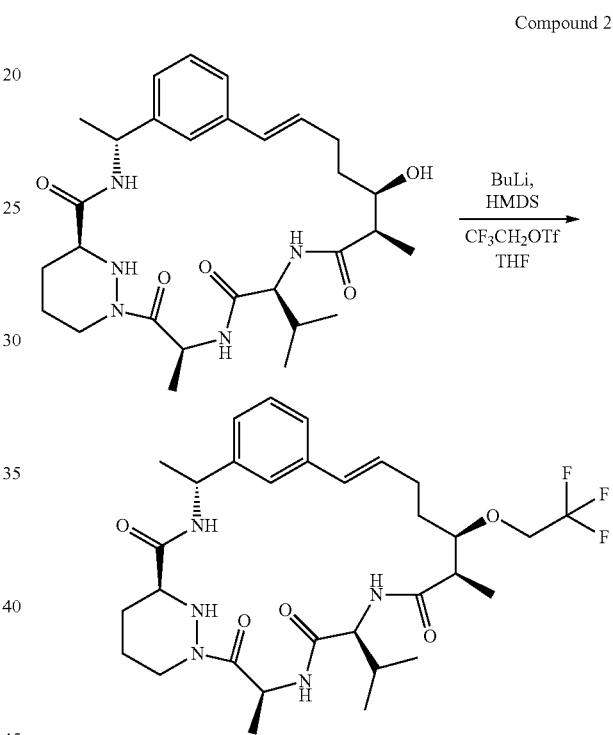

A solution of 1k (477 mg, 0.7 mmol) in 1,2-dichloroethane (250 mL) was prepared and Hoveyda-Grubbs $2^{nd}$ generation catalyst (43 mg, 0.07 mmol) was added. The stirred reaction mixture was heated to 80° C. for 1 hour. The reaction mixture was cooled to RT before adding silica gel. The mixture was stirred for 10 min then evaporated and the residue was purified by silica gel chromatography using ethyl acetate to yield the title product (198 mg, 43%) as a white solid.

Compound 1

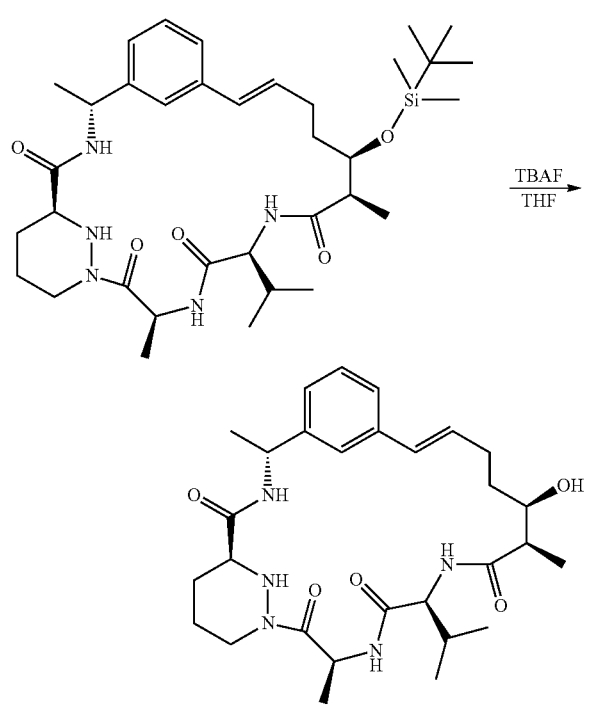

A solution of 1l (198 mg, 0.3 mmol) in tetrahydrofuran (20 mL) was cooled over an ice bath before adding a 1 M solution of tetrabutylammonium fluoride in tetrahydrofuran (1.5 mL, 1.5 mmol). The reaction was allowed to warm to RT and was stirred for 1 hour. The reaction mixture was treated with saturated aqueous sodium bicarbonate solution (20 mL) and extracted with ethyl acetate (2×20 mL). The extract was dried over sodium sulfate, filtered and evaporated. The residue was purified by silica gel chromatography using 1:9 acetone/ethyl acetate to yield the title product (150 mg, 92%) as a white solid. $^1$H NMR (300 MHz, d$_6$-DMSO) δ 0.83 (d, J=6.5 Hz, 3H), 0.85 (d, J=6.5 Hz, 3H), 1.12-1.21 (m, 4H), 1.28 (d, J=7.1

A solution of hexamethyldisilazane (235 μL, 1.13 mmol) in anhydrous tetrahydrofuran (4 mL) was cooled to −10° C. before adding a 2.5 M solution of n-butyllithium (380 μL, 0.94 mmol). The stirred mixture was warmed to 0° C. for 10 min before cooling to −78° C. A solution of Compound 1 (102 mg, 0.188 mmol) in anhydrous dimethylformamide (1.5 mL) and anhydrous tetrahydrofuran (1.5 mL) was added dropwise over 2 min followed by the addition of 2,2,2-trifluoroethyl trifluoromethanesulfonate (135 μL, 0.94 mmol). The reaction mixture was stirred at −78° C. under a nitrogen atmosphere then allowed to gradually warm to RT. The reaction mixture was quenched with the addition of a saturated aqueous solution of ammonium chloride (15 mL). The mixture was extracted with ethyl acetate (2×15 mL). The extract was dried over sodium sulfate, filtered and evaporated. The residue was purified by silica gel chromatography using 1:9 acetone/ethyl acetate to give a colorless gum (65 mg). The gum was further purified by reverse phase chromatography, using a 10 g C18 cartridge eluted with 2:3 acetonitrile/water. The partially evaporated fractions were extracted with ethyl acetate (2×15 mL). The extract was dried over sodium sulfate, filtered and evaporated to yield the title product (17 mg, 30%) as a white solid. $^1$H NMR (300 MHz, CDCl$_3$) 0.92 (d, J=6.7 Hz, 3H), 0.96 (d, J=6.9 Hz, 3H), 1.32 (d, J=7.1 Hz, 3H), 1.39 (d, J=7.1 Hz, 3H), 1.50 (d, J=6.7 Hz, 3H), 1.74-1.85 (m, 1H), 1.86-2.08 (m, 3H), 2.10-2.40 (m, 3H), 2.57-2.78 (m, 2H), 3.19-3.31 (m, 1H), 3.49 (app t, J=6.7 Hz, 1H), 3.58-3.79 (m, 4H), 3.81-4.18 (m, 2H), 4.49 (br d, J=12.3 Hz, 1H), 5.03-5.17 (m, 1H), 5.32-5.47 (m, 1H), 6.14-6.30 (m, 1H), 6.37-6.72 (m, 4H), 7.06-7.30 (m, 4H). LCMS (m/z) 624.3 [M+H], Tr=2.57 min.

Example 3

(2R,5S,11S,14S,17R,18R)-18-Hydroxy-14-isopropyl-2,11,17-trimethyl-3,9,12,15,28-pentaaza-tricyclo[21.3.1.1*5,9]octacosa-1(26),23(27),24-triene-4,10,13,16-tetraone Compound 3

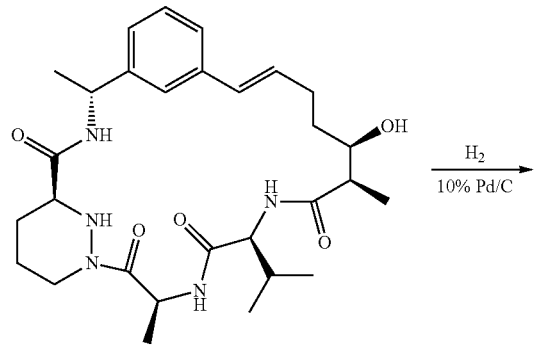

A solution of Compound 1 (100 mg, 0.184 mmol) in methanol (5 mL) was prepared and 10% palladium on carbon (5 mg) was added. The stirred mixture was placed under a hydrogen atmosphere for 1.5 h. The reaction mixture was filtered through hyflo-supercel then through a 0.2 μm filter before evaporating to give the title compound (95 mg, 95%) as a white solid. $^1$H NMR (300 MHz, CDCl$_3$) 0.93 (d, J=7.1 Hz, 3H), 0.96 (d, J=7.1 Hz, 3H), 1.32 (d, J=6.7 Hz, 3H), 1.37-2.16 (m, 12H), 1.54 (d, J=6.9 Hz, 3H), 2.34-2.46 (m, 1H), 2.52-2.75 (m, 3H), 3.16-3.27 (m, 1H), 3.43-3.62 (m, 3H), 3.74 (d, J=11.8 Hz, 1H), 3.98-4.06 (m, 1H), 4.50 (d, J=13.2 Hz, 1H), 5.11-5.36 (m, 2H), 6.39-6.50 (m, 2H), 7.70 (d, J=8.5 Hz, 1H), 7.06-7.28 (m, 4H). LCMS (m/z) 544.3 [M+H], Tr=1.91 min.

Example 4

Compound 4a

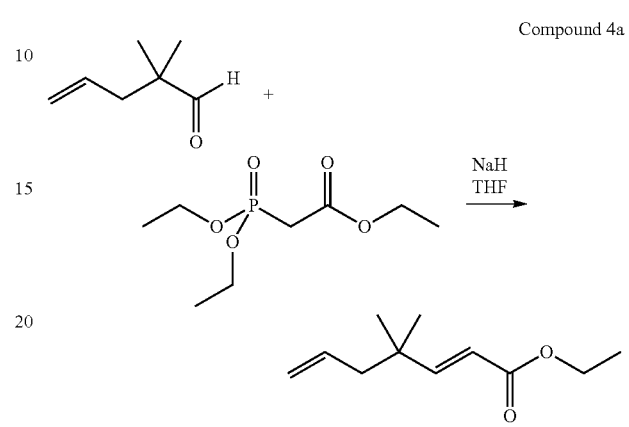

To a suspension of sodium hydride (60% in mineral oil, 783 mg, 19.6 mmol) in dry tetrahydrofuran at 0° C., under nitrogen was added dropwise triethyl phosphonoacetate (3.38 mL, 19.6 mmol). The white suspension was stirred for 1 h where it became a solution, then 2,2-dimethyl-4-pentenal (2.42 mL, 17.8 mmol) was slowly added and the resulting green/yellow solution was stirred at 0° C. and allowed to warm to RT. After 72 h ethanol (1 mL) was added to the solution, followed by water (100 mL) and the organics were extracted with diethyl ether (2×200 mL). The combined organics were washed with water (200 mL), dried over magnesium sulfate, filtered and concentrated in vacuo to give a crude residue. This was purified by silica gel chromatography, using iso-hexanes (144 mL), then iso-hexanes/diethyl ether 50:50 (72 mL), then diethyl ether (48 mL) to give the title compound (3.20 g, 99%) as an oil.

Compound 4b

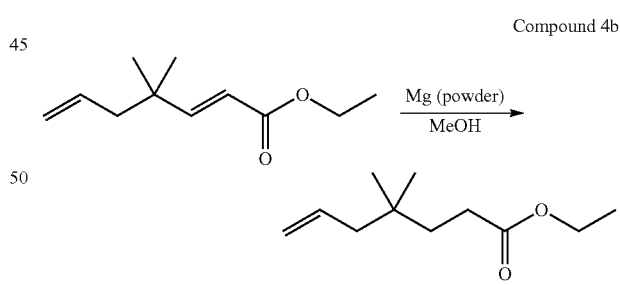

To 4a (3.20 g, 17.5 mmol) in dry methanol at RT, under nitrogen was slowly added magnesium powder (1.28 g, 52.7 mmol) while monitoring the temperature rise. After the addition was complete the mixture was stirred at RT overnight. After this time, to the reaction was added additional magnesium powder (852 mg, 35.1 mmol) and the reaction mixture stirred for 2 h. The mixture was neutralized from pH 10 to pH 7 with 2 M hydrochloric acid and then concentrated in vacuo to give a residue. The residue was suspended in ethyl acetate (300 mL) and water (500 mL) and the layers separated. The aqueous phase was then re-extracted with ethyl acetate (200 mL) and the combined organics were dried over magnesium

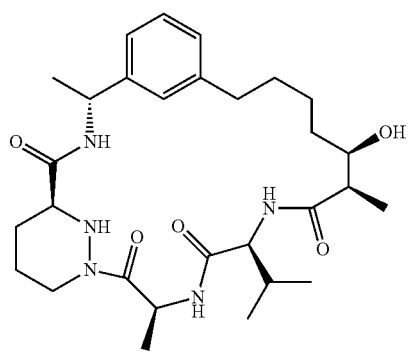

sulfate, filtered and concentrated in vacuo to give the title compound (1.96 g, 61%) as a colorless oil.

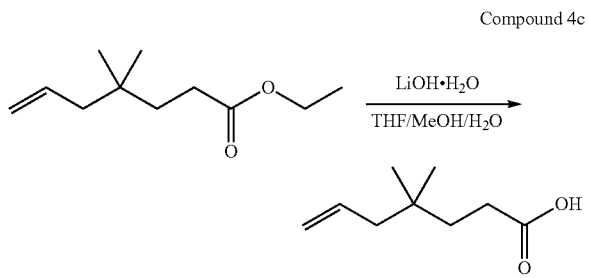

Compound 4c

To 4b (2.02 g, 11.0 mmol) in a mixture of tetrahydrofuran (35 mL), methanol (9 mL) and water (9 mL) at RT, was added lithium hydroxide monohydrate (1.38 g, 32.9 mmol) and the mixture was stirred at RT for 1 h. After this time additional lithium hydroxide monohydrate (460 mg, 11.0 mmol) was added and the reaction mixture stirred for 1 h. After this time more lithium hydroxide monohydrate (460 mg, 11.0 mmol) was added and the reaction mixture stirred for 30 min. The reaction mixture was then concentrated in vacuo and the residue diluted with water (200 mL) and the organics extracted with diethyl ether (3×50 mL). The aqueous phase was acidified from pH 14 to pH 1 with 2 M hydrochloric acid and the organics extracted with ethyl acetate (3×50 mL). The combined ethyl acetate organics were then dried over sodium sulfate, filtered and concentrated in vacuo to give the desired product (1.03 g, 60%) as an oil.

Compound 4d

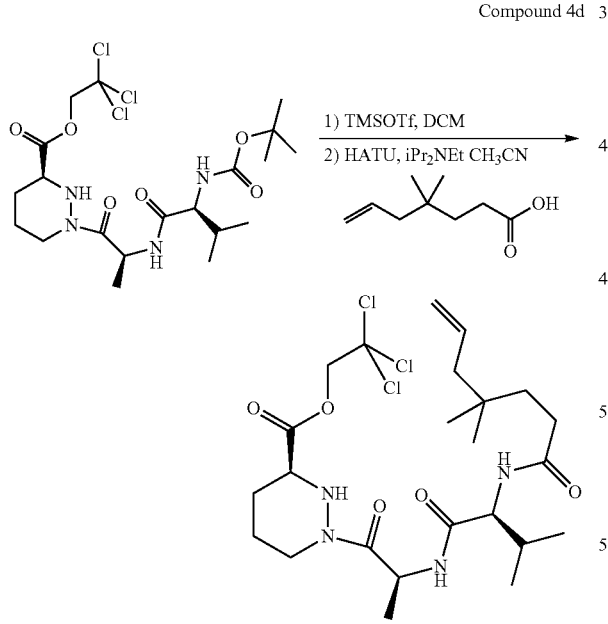

A solution of 1e (1.06 g, 2.00 mmol) in dichloromethane (10 mL) was cooled in an ice-water bath under nitrogen. Trimethylsilyl trifluoromethanesulfonate (0.591 mL, 4.00 mmol) was added dropwise, and the resulting solution was stirred for 1.5 h. The reaction was quenched with N,N-diisopropylethylamine (1.4 mL, 8.00 mmol) and the reaction mixture was concentrated in vacuo to give (S)-1-[(S)-2-((S)-2-amino-3-methyl-butyrylamino)-propionyl]-hexahydro-pyridazine-3-carboxylic acid 2,2,2-trichloro-ethyl ester a white solid which was used without further purification. To (5)-1-[(S)-2-((S)-2-amino-3-methyl-butyrylamino)-propionyl]-hexahydro-pyridazine-3-carboxylic acid 2,2,2-trichloro-ethyl ester generated in the previous step was added a solution of 4,4-dimethyl-hept-6-enoic acid (343 mg, 2.20 mmol) in acetonitrile (70 mL). To this mixture was added N,N-diisopropylethylamine (1.4 mL, 8.03 mmol) and the reaction cooled in an ice-water bath before the addition of 2-(1H-7-azabenzotriazol-1-yl)-1,1,3,3-tetramethyluronium hexafluorophosphate methanaminium (1.07 g, 2.80 mmol). The yellow solution was then stirred and allowed to warm to RT overnight. The reaction mixture was quenched with 2 M hydrochloric acid (40 mL) and concentration in vacuo. To the residue was added water (200 mL) and the organics were extracted with ethyl acetate (3×150 mL). The combined organics were then washed with brine (100 mL) and sodium hydrogen carbonate (200 mL). The organics were then dried over magnesium sulfate, filtered and concentrated in vacuo to give a crude yellow oil (2.27 g). This was purified by silica gel chromatography using iso-hexanes/ethyl acetate 90:10 (300 mL) then iso-hexanes/acetone 50:50 (300 mL) then iso-hexanes/acetone 0:100 to give the title compound (1.10 g, 97%) as a colorless oil.

Compound 4e

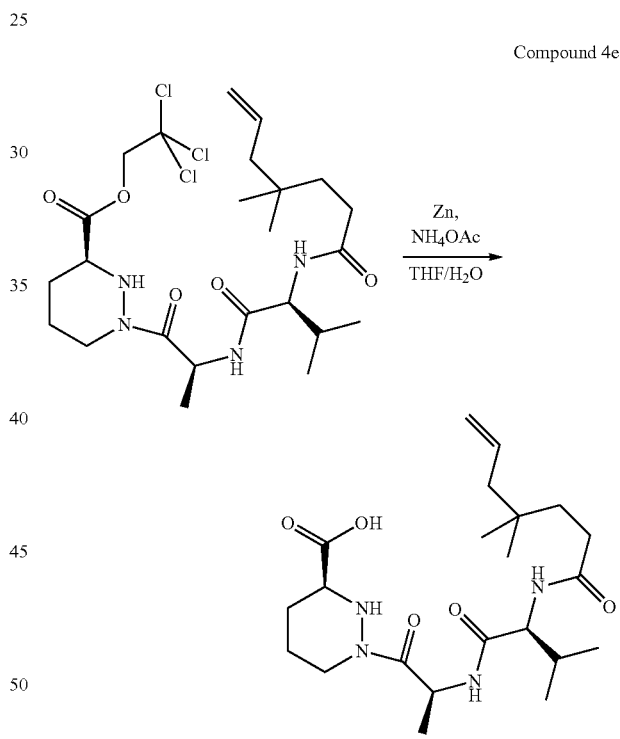

A solution of 4d (1.10 g, 1.94 mmol) in tetrahydrofuran (40 mL) was prepared and zinc powder (2.79 g, 42.6 mmol) was added followed by a solution of ammonium acetate (2.24 g, 29.0 mmol) in water (10 mL). The reaction mixture was stirred at RT for 24 h. Saturated aqueous potassium hydrogen sulphate (pH 2, 30 mL) and ethyl acetate (50 mL) were added and the suspension filtered through hyflo-supercel washing through with ethyl acetate. The layers were separated. And the aqueous phase was extracted with ethyl acetate (3×100 mL). The combined organic layers were washed with brine (250 mL), dried over sodium sulfate, filtered and evaporated to give a colorless gum. The residue was azeotroped with toluene (3×100 mL) to give the title compound (816 mg, 96%) as a white solid.

Compound 4f

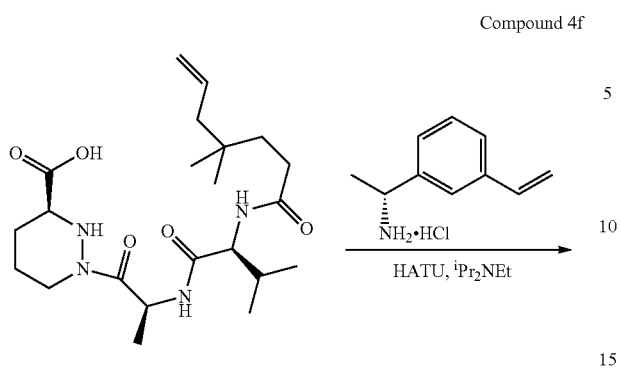

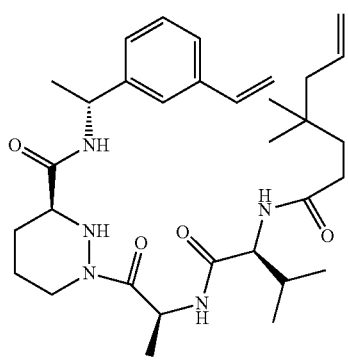

4e (439 mg, 1.00 mmol) was suspended in acetonitrile (35 mL) and (R)-1-(3-vinyl-phenyl)-ethylamine hydrochloride (202 mg, 1.10 mmol) was added followed by N,N-diisopropylethylamine (700 μL, 5.00 mmol) and the mixture cooled in an ice-water bath before addition of 2-(1H-7-azabenzotriazol-1-yl)-1,1,3,3-tetramethyluronium hexafluorophosphate methanaminium (532 mg, 1.40 mmol). The reaction mixture was stirred and allowed to warm to RT over 72 h. To the reaction mixture was added 2 M hydrochloric acid (20 mL) and the mixture concentrated in vacuo to give a residue. The aqueous layer was extracted with ethyl acetate (3×100 mL) and the combined ethyl acetate layers were washed with brine followed by sodium hydrogen carbonate (100 mL) then dried over sodium sulfate, filtered and concentrated in vacuo to give a crude residue. The residue was purified by silica gel chromatography using iso-hexanes/ethyl acetate 50:50 then neat ethyl acetate to give the title compound (402 mg, 71%).

Compound 4

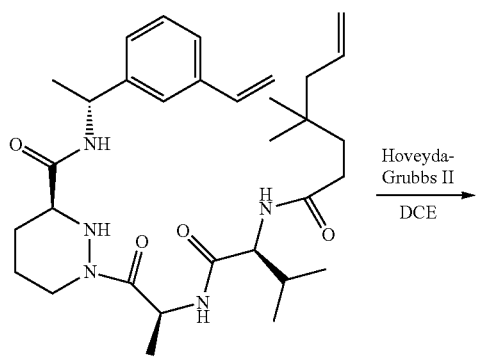

To a solution of 4f (402 mg, 0.71 mmol) in 1,2-dichloroethane (210 mL) was added Hoveyda-Grubbs $2^{nd}$ generation catalyst (45 mg, 0.07 mmol) and the reaction mixture heated at 80° C. for 1 h. After this time the mixture was allowed to cool to RT and concentrated in vacuo. The residue was purified by silica gel chromatography using a gradient of ethyl acetate to ethyl acetate/acetone 75:25. Impure product (240 mg) was collected which was further purified by silica gel chromatography using ethyl acetate. After repurification, product (43 mg) was collected containing minor impurities. The impurities were removed via trituration from diethyl ether to give the title compound (30 mg, 8%) as a white solid.
$^1$H NMR (300 MHz, CD$_3$OD) 0.89 (d, J=6.7 Hz, 3H), 0.92 (d, J=6.7 Hz, 3H), 0.96 (s, 3H), 0.97 (s, 3H), 1.35 (d, J=6.9 Hz, 3H), 1.50 (d, J=7.1 Hz, 3H), 1.59-1.83 (m, 3H), 1.85-2.00 (m, 3H), 2.09 (d, J=7.1 Hz, 2H), 2.15-2.25 (m, 1H), 2.31-2.44 (m, 1H), 2.78 (td, J=2.7, 12.7 Hz, 1H), 3.40-3.72 (m, 2H), 4.05-4.17 (m, 1H), 4.34 (br d, J=13.2 Hz, 1H), 5.05 (q, J=7.1 Hz, 1H), 5.35 (q, J=7.1 Hz, 1H), 6.19-6.32 (m, 1H), 6.37 (d, J=15.8 Hz, 1H), 7.15 (d, J=7.6 Hz, 1H), 7.21-7.29 (m, 2H), 7.37 (d, J=7.8 Hz, 1H). LCMS (m/z) 540.3 [M+H], Tr=2.41 min.

Example 5

Compound 5a

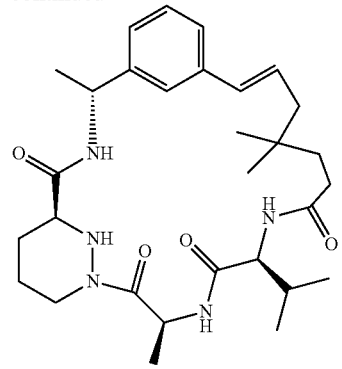

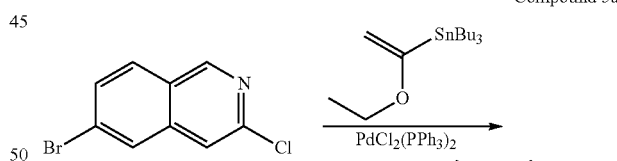

A solution of 6-bromo-3-chloro-isoquinoline (8.0 g, 33 mmol) and tributyl-(1-ethoxyvinyl)-tin (14.88 g, 14 mL, 41.2 mmol) in toluene (100 mL) was degassed with nitrogen for 30 min. Bis(triphenylphosphine)palladium(II)dichloride (1.16 g, 1.65 mmol, 5 mol %) was added and the reaction mixture was heated at 60° C. for 20 h. The reaction mixture was cooled to RT, the mixture was filtered and the filtrate was evaporated. The residue was purified by silica gel chromatography using a gradient of iso-hexanes/ethyl acetate 20:1 to 10:1 to afford the title compound (7.1 g, 92%) as a yellow solid.

Compound 5b

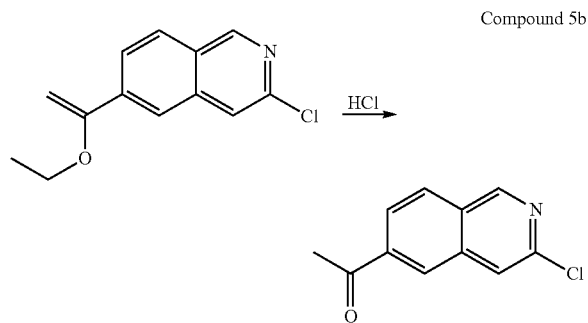

A solution of 5a (7.1 g, 30 mmol) in 1,4-dioxane (60 mL) and 2 M hydrochloric acid (30 mL) was stirred at RT for 30 min. The majority of the solvent was evaporated and the residue was partitioned between ethyl acetate and water. The organic extracts were combined, washed with water and brine, dried over sodium sulfate, filtered and evaporated. The residue was triturated with 5% ether in iso-hexanes and the resulting solid was collected and dried to afford the title compound (6.0 g, 97%) as a white solid.

Compound 5c

A solution of 5b (1.72 g, 8.3 mmol) in tetrahydrofuran (40 mL) was stirred under nitrogen. Titanium (IV) ethoxide (3.8 g, 3.45 mL, 16.6 mmol, tech. grade) was added followed by (R)-(+)-2-methyl-propanesulfinamide (1.11 g, 9.2 mmol) and the reaction mixture was stirred at 60° C. under nitrogen for 18 h. Additional (R)-(+)-2-methyl-propanesulfinimide (190 mg, 1.67 mmol) was added and the reaction mixture was stirred at 65° C. for further 2 h. The reaction mixture was cooled to RT and ethyl acetate and brine were added. The suspension was filtered through Celite and the filter pad was washed with ethyl acetate. The ethyl acetate layer was separated, washed with brine, dried over sodium sulfate, filtered and evaporated. The residue was purified by silica gel chromatography using a gradient of iso-hexanes/ethyl acetate 7:3 to 3:7 to afford the title compound (2.2 g, 86%) as a yellow solid.

Compound 5d

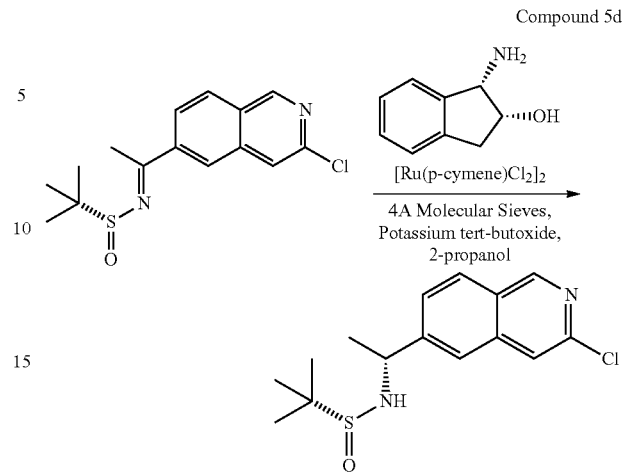

A mixture of (1S,2R)-(−)-cis-1-amino-2-indanol (60 mg, 0.4 mmol), dichloro(p-cymene)ruthenium(II) dimer (122 mg, 0.2 mmol) and powdered 4 Å molecular sieves (2 g) was suspended in anhydrous 2-propanol (9 mL) and stirred under nitrogen. The suspension was heated at 90° C. for 20 min. The reaction mixture was cooled to 40° C. and a solution of 5c (1.23 g, 4 mmol) in 2-propanol (28 mL) was added followed by a solution of potassium tert-butoxide (122 mg, 1.1 mmol) in 2-propanol (10 mL). The reaction mixture was stirred for 2 h at 40° C. and then allowed to cool. The mixture was poured directly onto a silica gel cartridge and eluted with ethyl acetate to give, after evaporation, the title compound (1.19 g, 96%) as a brown gum.

Compound 5e

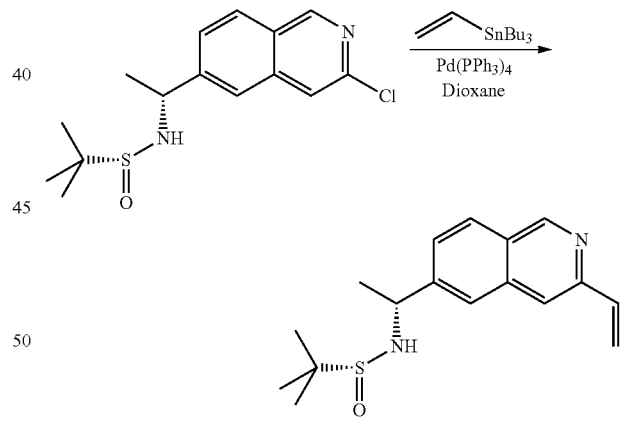

A mixture of 5d (0.66 g, 2.11 mmol), tributyl(vinyl)tin (1.85 mL, 6.35 mmol) and palladium tetrakis(triphenylphosphine) (488 mg, 0.42 mmol) in 1,4-dioxane (10.5 mL) was capped in a microwave vial. The reaction mixture was irradiated and stirred at 160° C. for 40 min in a microwave reactor. A second reaction was carried under identical scale and conditions and the reaction mixtures combined and evaporated. The residue was purified by silica gel chromatography using a gradient of 1:3 to 1:0 ethyl acetate/iso-hexanes to afford the title compound (1 g) as a brown gum. $^1$H NMR (300 MHz, CDCl$_3$) δ 1.27 (s, 9H), 1.62 (d, J=7.7 Hz, 3H), 3.53 (br s, 1H), 4.69-4.77 (m, 1H), 5.51 (dd, J=10.7, 1.3 Hz, 1H), 6.39 (dd, J=17.4, 1.3 Hz, 1H), 6.95 (dd, J=17.2, 10.7 Hz, 1H), 7.55-

7.58 (m, 2H), 7.75 (s, 1H), 7.95 (d, J=8.3 Hz, 1H), 9.20 (s, 1H). LCMS (m/z) 303.0 [M+H], Tr=1.48 min.

Compound 5f

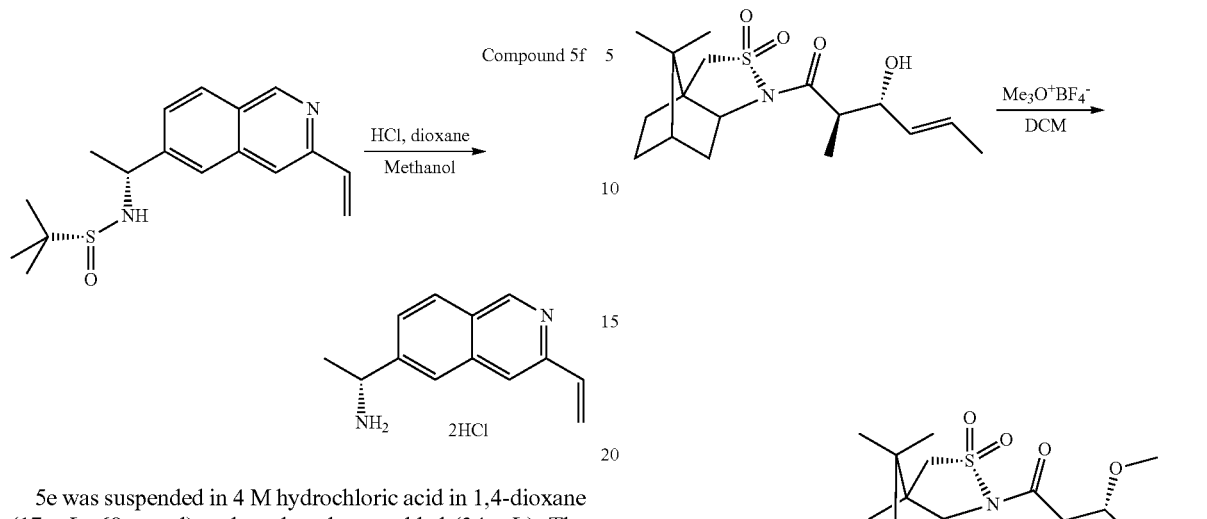

5e was suspended in 4 M hydrochloric acid in 1,4-dioxane (17 mL, 68 mmol) and methanol was added (34 mL). The reaction mixture was stirred for 90 min and then evaporated. The residue was passed through a SCX cartridge eluting with methanol and then methanolic ammonia. The basic fraction was collected and evaporated to give the title compound (530 mg, 63% over 2 steps) as a beige solid.

Compound 5g

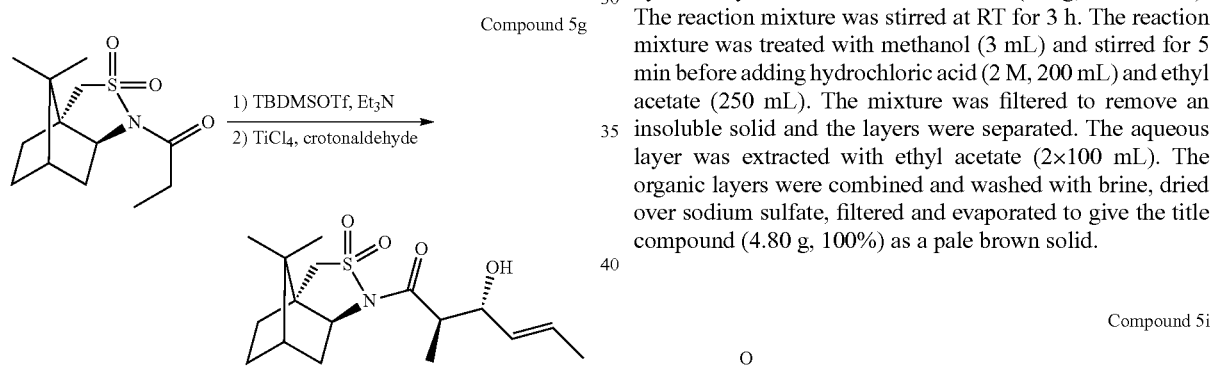

A solution of 1-((1R,5S)-10,10-dimethyl-3,3-dioxo-3lambda*6*-thia-4-aza-tricyclo[5.2.1.0*1,5*]dec-4-yl)-propan-1-one (6.0 g, 22.1 mmol) in anhydrous dichloromethane (24 mL) was prepared and tert-butyldimethylsilyl trifluoromethanesulfonate (5.0 mL, 22.1 mmol) was added, followed by anhydrous triethylamine (3.54 mL, 25.4 mmol). The reaction mixture was stirred at RT under a nitrogen atmosphere for 15 h. This gave a dark solution that was evaporated to give an oil. The oil was dissolved in anhydrous dichloromethane (22 mL) and the solution was added dropwise to a solution of crotonaldehyde (3.66 mL, 44.2 mmol) and titanium tetrachloride (1 M in dichloromethane, 44.2 mL, 44.2 mmol) in dichloromethane (22 mL) at −78° C. under a nitrogen atmosphere. The reaction mixture was stirred at −78° C. for 1 hour, before addition of ammonium chloride solution (30 mL). The stirred mixture was allowed to warm to RT before separating the layers. The aqueous layer was extracted with dichloromethane (2×25 mL). The organic layers were combined, dried over sodium sulfate, filtered and evaporated to give a brown oil. The oil was purified by silica gel chromatography using iso-hexanes/ethyl acetate 4:1 to yield the title compound (6.7 g, 89%) as a colorless solid.

Compound 5h

A solution of 5 g (4.15 g, 12.1 mmol) in anhydrous dichloromethane (80 mL) was prepared and 1,8-bis(dimethylamino)naphthalene (7.78 g, 36.3 mmol) was added followed by trimethyloxonium tetrafluoroborate (3.6 g, 24.2 mmol). The reaction mixture was stirred at RT for 3 h. The reaction mixture was treated with methanol (3 mL) and stirred for 5 min before adding hydrochloric acid (2 M, 200 mL) and ethyl acetate (250 mL). The mixture was filtered to remove an insoluble solid and the layers were separated. The aqueous layer was extracted with ethyl acetate (2×100 mL). The organic layers were combined and washed with brine, dried over sodium sulfate, filtered and evaporated to give the title compound (4.80 g, 100%) as a pale brown solid.

Compound 5i

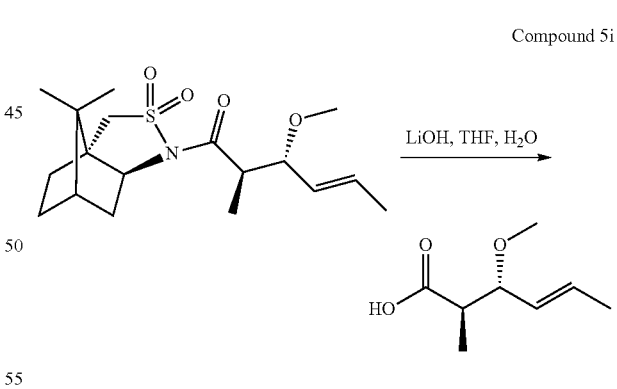

A solution of lithium hydroxide in water (2 M, 50 mL, 100 mmol) was added to a stirred solution of 5h (4.80 g, 12.1 mmol) in tetrahydrofuran (130 mL). The reaction mixture was heated to 60° C. for 15 h. The reaction mixture was cooled to RT, before partially evaporating and adding hydrochloric acid (2 M, 150 mL). The mixture was extracted with ethyl acetate (3×50 mL). The extract was dried over sodium sulfate, filtered and evaporated to give a brown oil (3.5 g). The oil was purified by silica gel chromatography using iso-hexanes/diethyl ether 1:1 to give the title compound (1.132 g, 59%) as a colorless oil.

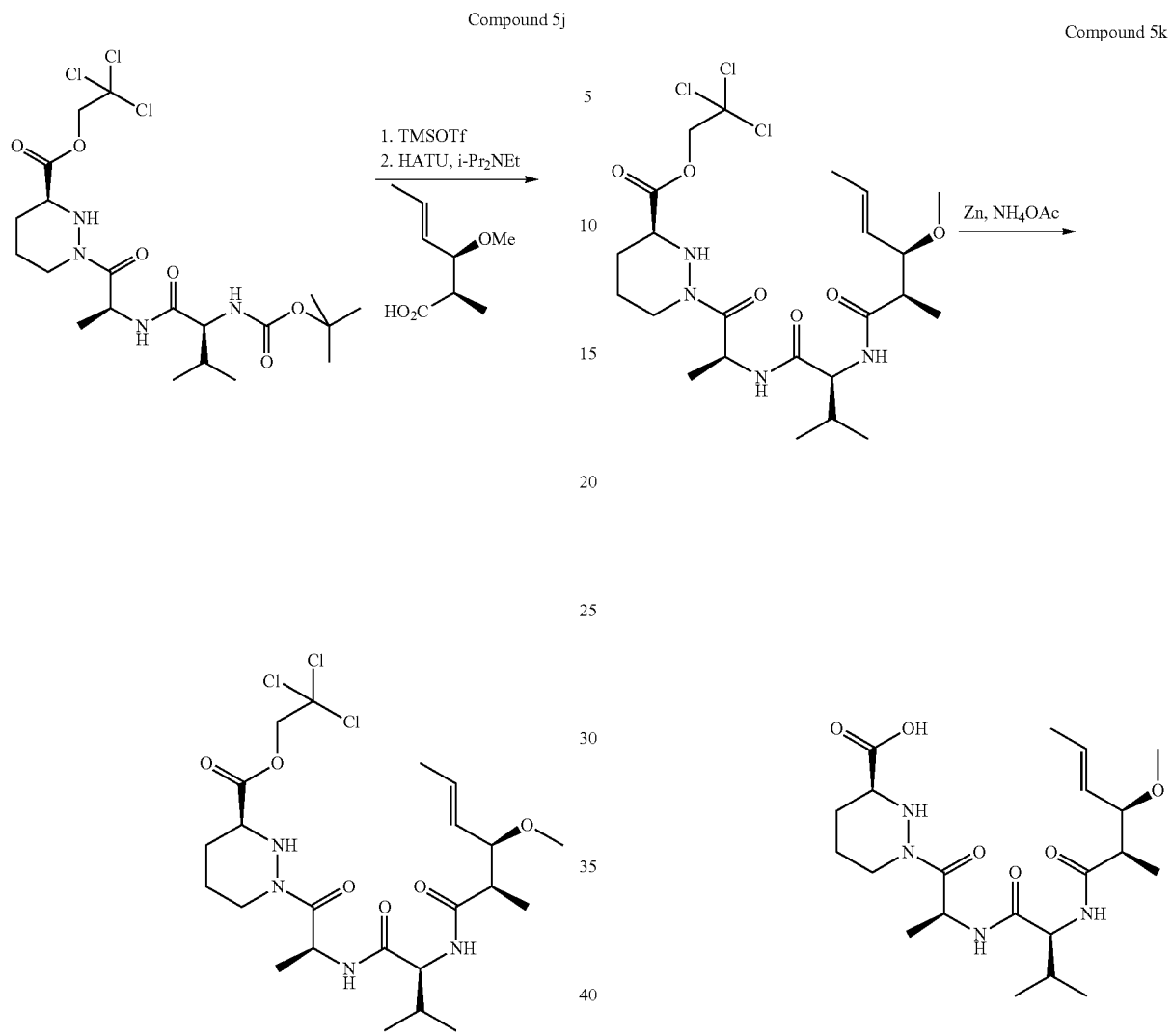

Compound 5j

Compound 5k

A cooled (0° C.) solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (2.174 g, 4.088 mmol) in anhydrous dichloromethane (50 mL) was treated with trimethylsilyl trifluoromethanesulfonate (1.2 mL, 6.814 mmol). After 1 h at 0° C., the reaction mixture was treated with N,N-diisopropylethylamine (2.4 mL, 13.628 mmol) and the volatiles were removed in vacuo to afford the corresponding amine as a yellow foam. To this amine was added 5i (539.0 mg, 3.407 mmol), N,N-diisopropylethylamine (2.4 mL, 13.628 mmol) and acetonitrile (50 mL). The reaction mixture was cooled to 0° C. and treated with 2-(1H-7-azabenzotriazol-1-yl)-1,1,3,3-tetramethyl uronium hexafluorophosphate methanaminium (1.814 g, 4.770 mmol). After overnight stirring at RT the reaction was quenched with 1 M hydrochloric acid (100 mL). The aqueous layer was extracted with ethyl acetate (2×). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:4 to afford the title compound (2.193 g, 93%) as a light yellow solid.

A solution of 5j (763.4 mg, 1.335 mmol) in tetrahydrofuran (25 mL) was subsequently treated with zinc powder (1.920 g, 29.365 mmol) and a solution of ammonium acetate (1.543 g, 20.025 mmol) in water (5 mL). After overnight stirring the reaction was filtered through Celite and quenched with 2 M hydrochloric acid. The aqueous layer was extracted with ethyl acetate (2×). The organics were combined, dried over sodium sulfate, filtered and the volatiles were removed in vacuo. Residual acetic acid was azeotroped off with toluene to provide the title compound (566.4 mg, 96%) as a light orange solid.

Compound 5l

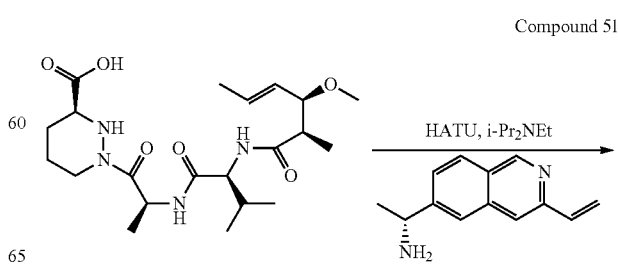

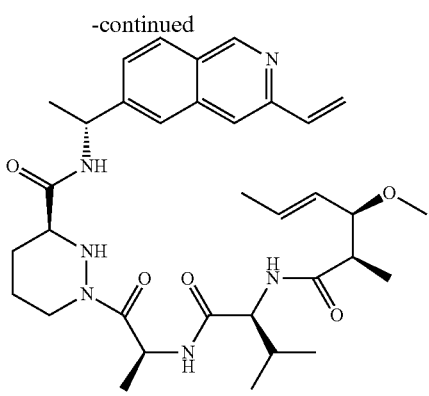

A solution of 5k (246 mg, 0.6 mmol), (R)-1-(3-vinyl-iso-quinolin-6-yl)-ethylamine dihydrochloride (162 mg, 0.6 mmol) and N,N-diisopropylethylamine (387 mg, 0.52 mL, 3 mmol) in acetonitrile (20 mL) was stirred at RT under nitrogen. 2-(1H-7-azabenzotriazol-1-yl)-1,1,3,3-tetramethyl uronium hexafluorophosphate methanaminium (320 mg, 0.84 mmol) was added and the reaction mixture was stirred at RT for 4 h. The solvent was evaporated. The residue was diluted with ethyl acetate and saturated sodium hydrogen carbonate solution. A small amount of methanol (5 mL) was added to the suspension to give two clear layers. The organic layer was separated, washed with water and brine, dried over anhydrous sodium sulfate, filtered and evaporated. The residue was purified by silica gel chromatography using methanol/dichloromethane 1:20. The residue was triturated with ether and the resulting solid was collected, washed with ether and dried to afford the title compound (238 mg, 64%) as a pale brown solid.

Compound 5

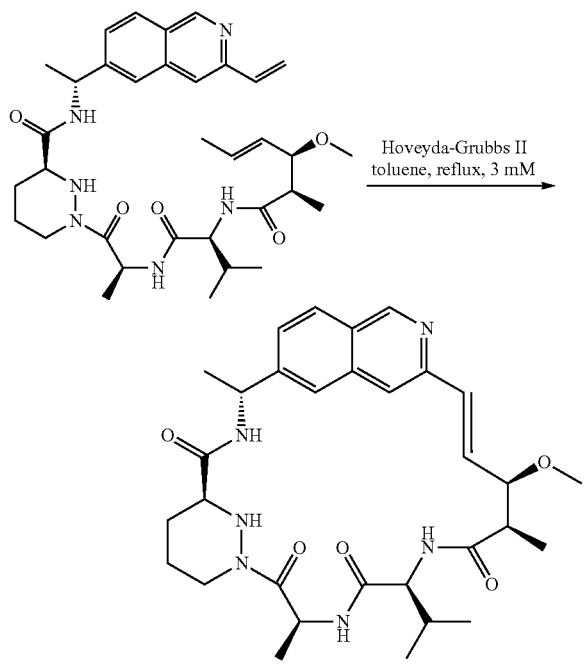

A solution of 5l (91 mg, 0.15 mmol) in toluene (45 mL) was stirred at RT under nitrogen. Hoveyda-Grubbs 2$^{nd}$ generation catalyst (10 mg, 0.015 mmol) was added and the reaction mixture was heated at reflux under nitrogen for 2 h. Additional Hoveyda-Grubbs 2$^{nd}$ generation catalyst (10 mg, 0.015 mmol) was added and the reaction mixture was heated at reflux under nitrogen for 6 h. The reaction mixture was cooled to RT, silica gel was added and the reaction mixture was evaporated. The residue was purified by silica gel chromatography using a gradient of ethyl acetate/acetone 20:1 to 5:2. The residue was triturated with ether and the resulting solid was collected, washed with ether/iso-hexanes (1:1) and dried to afford the title compound (23 mg, 26%) as a white solid. $^1$H NMR (300 MHz, CDCl$_3$) δ 0.99 (d, J=6.7 Hz, 3H), 1.04 (d, J=6.7 Hz, 3H), 1.44 (d, J=7.4 Hz, 3H), 1.53 (d, J=6.9 Hz, 3H), 1.61 (d, J=6.9 Hz, 3H), 1.68-2.20 5H), 2.62-2.74 (m, 2H), 3.35-3.43 (m, 1H), 3.44 (s, 3H), 3.72 (d, J=12.5 Hz, 1H), 3.88-3.92 (m, 2H), 4.23 (dd, J=8.9, 6.0 Hz, 1H), 4.55-4.60 (m, 1H), 5.30-5.37 (m, 1H), 5.80-5.90 (m, 1H), 6.38 (d, J=8.9 Hz, 1H), 6.43 (d, J=7.6 Hz, 1H), 6.93 (d, J=16.3 Hz, 1H), 7.24 (dd, J=16.3, 8.7 Hz, 1H), 7.45 (d, J=8.7 Hz, 1H), 7.56 (d, J=8.5 Hz, 1H), 7.69 (s, 1H), 7.93 (d, J=8.5 Hz, 1H), 9.17 (s, 1H). LCMS (m/z) 579.3 [M+H], Tr=1.40 min.

Example 6

Compound 6

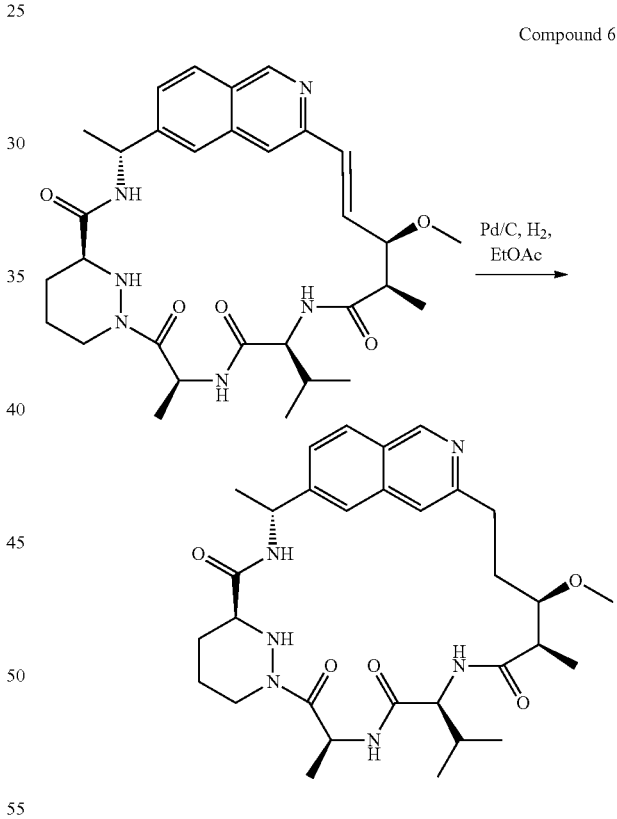

A solution of Compound 5 (11 mg, 0.019 mmol) in ethyl acetate (10 mL) containing 10% palladium on carbon (10 mg) was hydrogenated at RT and pressure for 3 h. The reaction mixture was filtered through filter aid and the filter pad was washed with ethyl acetate. The filtrate was evaporated and the residue was purified by silica gel chromatography using a gradient of ethyl acetate/acetone 10:1 to 2:1. The residue was triturated with ethyl acetate/ether (1:5) to afford the title compound (2.0 mg, 18%) as a white solid. $^1$H NMR (300 MHz, CDCl$_3$) δ 0.93 (d, J=6.7 Hz, 3H), 0.98 (d, J=6.7 Hz, 3H), 1.39 (d, J=6.9 Hz, 3H), 1.55-2.70 (m, 8H), 1.95-2.50 (m, 5H), 2.64-2.73 (m, 2H), 2.95-3.08 (m, 2H), 3.35-3.42 (m, 2H), 3.53 (s, 3H), 3.61 (d, J=12.1 Hz, 1H), 4.06-4.11 (m, 1H), 4.50-4.57 (m, 1H), 5.25-5.32 (m, 1H), 5.64-5.70 (m, 1H), 6.39 (d, J=8.3 Hz, 1H), 6.47-6.51 (m, 1H), 7.21-7.28 (m, 1H), 7.41 (d, J=8.8 Hz, 1H), 7.62 (s, 1H), 7.69 (s, 1H), 7.92 (d, J=8.8 Hz, 1H), 9.15 (s, 1H). LCMS (m/z) 581.3 [M+H], Tr=1.38 min.

Example 7

Compound 7a

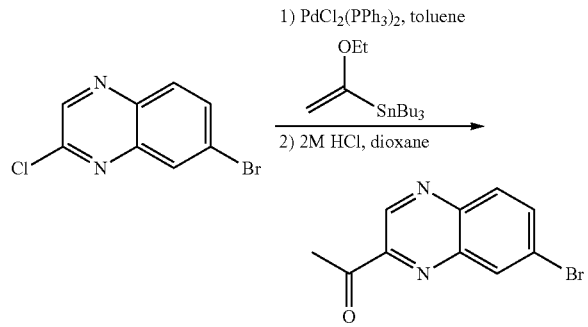

A mixture of 7-bromo-2-chloro-quinoxaline (1.46 g, 6.00 mmol) and tributyl(1-ethoxyvinyl)tin (2.71 g, 2.54 mL, 7.50 mmol) in toluene (21 mL) was degassed for 20 min. Bis(triphenylphosphine)palladium(II)dichloride (427 mg, 0.60 mmol) was added and the reaction mixture stirred under nitrogen and heated at 80° C. for 19 h before allowing to cool. The volatiles were evaporated and the residue suspended in 1,4-dioxane (15 mL), 2 M aqueous hydrochloric acid (15 mL) was added and the reaction mixture stirred for 45 min and then evaporated to remove the volatiles. The residue was diluted with water and extracted with ethyl acetate (2×) and the combined organic extracts were washed with brine, dried over magnesium sulfate, filtered and evaporated. The product was purified by chromatography using silica gel doped with 10% w/w potassium carbonate eluting using a gradient of iso-hexanes/ethyl acetate 1:0 to 9:1 to afford the title compound (836 mg, 56%) as a yellow solid.

Compound 7b

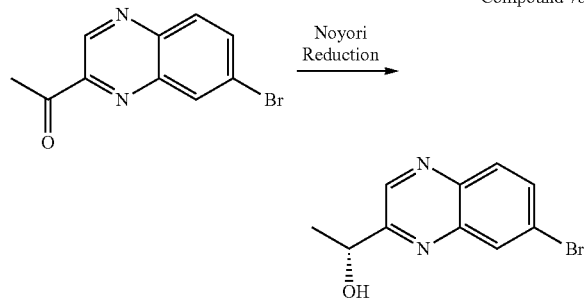

Dichloro(p-cymene)ruthenium(II)dimer (12 mg, 0.019 mmol) and (1R,2R)-(−)-N-p-tosyl-1,2-diphenylethylenediamine (17 mg, 0.045 mmol) were suspended in degassed water (7.5 mL) and the mixture was degassed with nitrogen for 15 min. The mixture was stirred at 70° C. under nitrogen for 90 min. The resulting turbid orange mixture was allowed to cool to RT. Solid 7a (948 mg, 3.78 mmol) followed by degassed tetrahydrofuran (7.5 mL) and sodium formate (1.29 g, 18.9 mmol) were added and the reaction mixture was degassed with nitrogen for 5 min. The reaction mixture was vigorously stirred at 40° C. for 3 h and allowed to cool. It was then diluted with ethyl acetate and the mixture washed with water (2×). The aqueous washes were back-extracted with ethyl acetate and the combined organics washed with brine, dried over magnesium sulfate, filtered and evaporated. The residue was purified by silica gel chromatography eluting with iso-hexanes/ethyl acetate 2:1 to afford the title compound (814 mg, 85%) as a purple solid.

Compound 7c

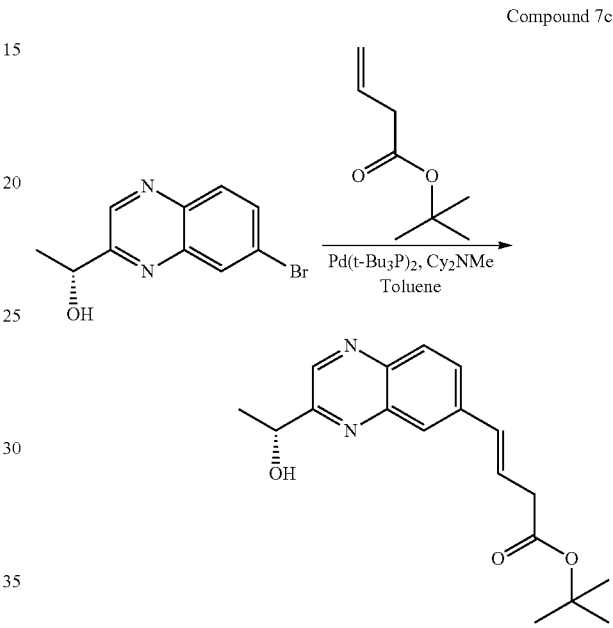

To a mixture of 7b (490 mg, 1.94 mmol), N,N-dicyclohexylmethylamine (416 mg, 457 µL, 2.13 mmol) and tert-butyl 3-butenoate (648 mg, 739 µL, 4.56 mmol) in toluene (19 mL) was added bis(tri-tert-butylphosphine)palladium(0) (41 mg, 0.080 mmol) under nitrogen and the reaction mixture stirred and heated under reflux for 5 h then allowed to cool. The mixture was evaporated and then purified by silica gel chromatography using a gradient of iso-hexanes/ethyl acetate 4:1 to 3:2 to afford the title compound (367 mg, 60%) as a yellow oil.

Compound 7d

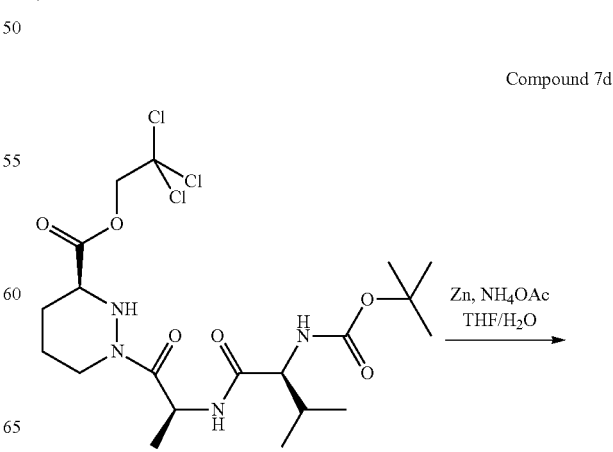

-continued

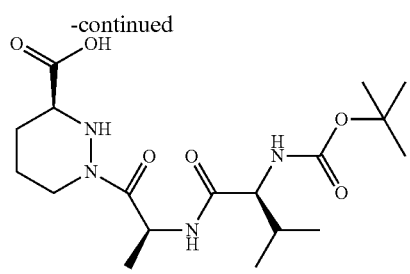

A solution of 1e (804 mg, 1.51 mmol) in tetrahydrofuran (37.7 mL) was prepared and zinc powder (2.18 g, 33.3 mmol) was added followed by a solution of ammonium acetate (1.75 g, 22.7 mmol) in water (9.4 mL). The reaction mixture was stirred at RT for 72 h. The reaction was filtered through hyflo-supercel washing through with ethyl acetate and saturated aqueous potassium hydrogen sulfate. The mixture was treated with 1 M hydrochloric acid (3 mL) and the layers were separated. The aqueous layer was extracted with ethyl acetate (2×100 mL). The organic layers were combined, washed with brine, filtered and evaporated to give a colorless gum. The residue was azeotroped with toluene (3×200 mL) to give the title compound (605 mg, quantitative yield) as a white solid.

Compound 7e

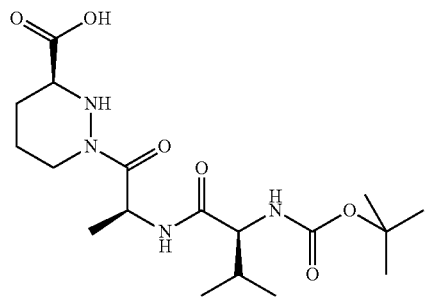
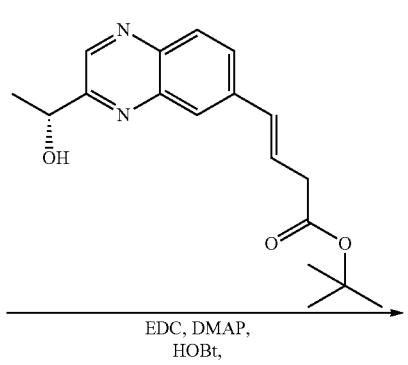

EDC, DMAP, HOBt, DCM

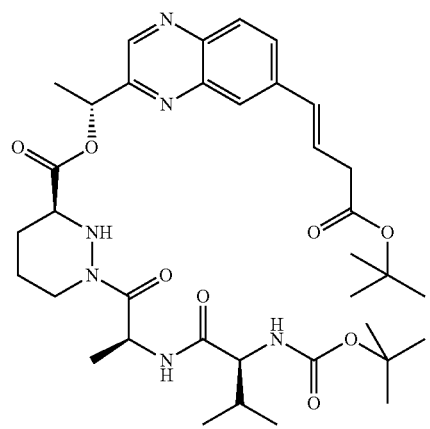

To a stirred solution of 7d (456 mg, 1.14 mmol) and (E)-4-[3-((R)-1-hydroxy-ethyl)-quinoxalin-6-yl]-but-3-enoic acid tert-butyl ester (358 mg, 1.14 mmol) in dichloromethane (22 mL) was added 1-hydroxybenzotriazole containing approx. 20% water (270 mg, 1.60 mmol) followed by 4-dimethylaminopyridine (139 mg, 1.14 mmol) and N-(3-dimethylaminopropyl)-N'-ethylcarbodiimide hydrochloride (306 mg, 1.60 mmol). The reaction was stirred for 18 h and then diluted with dichloromethane, washed with saturated ammonium chloride solution (2×), dried over sodium sulfate, filtered and evaporated. The residue was purified by silica gel chromatography using a gradient of iso-hexanes/ethyl acetate 3:1 to 0:1 to afford the title compound (335 mg, 45%) as a white foam.

Compound 7

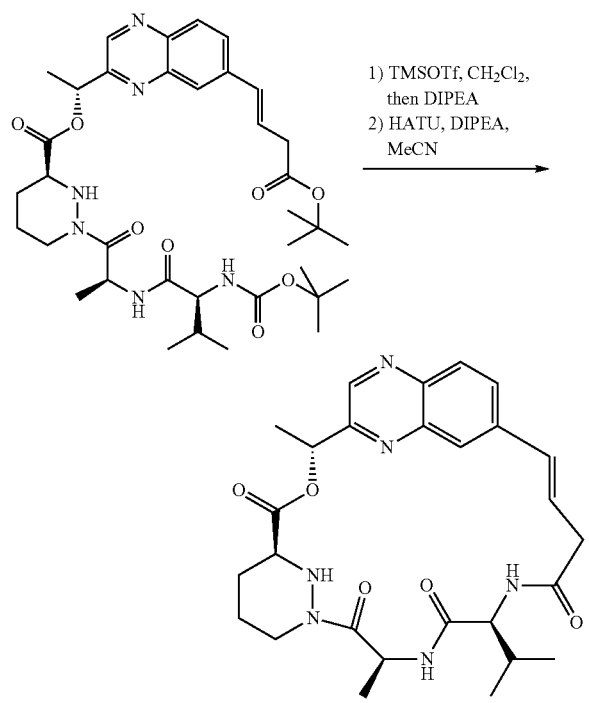

1) TMSOTf, CH$_2$Cl$_2$, then DIPEA
2) HATU, DIPEA, MeCN

To a stirred solution of 7e (309 mg, 0.444 mmol) in dichloromethane (4.5 mL) at 0° C. under nitrogen was added trimethylsilyl trifluoromethanesulfonate (346 mg, 359 µL, 1.56 mmol) and the reaction mixture was allowed to warm to RT over 2.5 h. N,N-diisopropylethylamine (164 mg, 221 µL, 1.27 mmol) was added and the reaction mixture stirred for a further 10 min, evaporated and then suspended in acetonitrile (45 mL). The stirred mixture was cooled to 0° C. and 2-(1H-7-azabenzotriazol-1-yl)-1,1,3,3-tetramethyl uronium hexafluorophosphate methanaminium (236 mg, 0.622 mmol) and N,N-diisopropylethylamine (229 mg, 309 µL, 1.77 mmol) added. After 90 min the reaction was quenched with a saturated ammonium chloride solution and the mixture evaporated to remove organic volatiles. The residue was diluted with dichloromethane and the organic layer separated and washed with saturated sodium bicarbonate (2×) and brine then dried over sodium sulfate, filtered and evaporated. The residue was purified by silica gel chromatography eluting with a gradient of ethyl acetate/acetone 1:0 to 9:1. The residue was further purified by reverse phase preparative HPLC using acetonitrile/water 3:7 to afford the title compound (7.6 mg, 3% over 2 steps) as a white solid. $^1$H NMR (300 MHz, CD$_3$OD) δ 1.00 (d, J=6.7 Hz, 3H), 1.01 (d, J=6.7 Hz, 3H), 1.62 (d, J=7.1 Hz, 3H), 1.66-1.75 (m, 2H), 1.77 (d, J=6.9 Hz, 3H), 1.91-2.05 (m, 3H), 2.72-2.82 (m, 1H), 2.98-3.08 (m, 1H), 3.38-3.41 (m, 1H), 3.78-3.84 (m, 1H), 4.25 (d, J=10.5 Hz, 1H), 4.41 (br d, J=11.3 Hz, 1H), 5.68 (q, J=7.1 Hz, 1H), 6.09 (q, J=6.9 Hz, 1H), 6.47 (d, J=16.3 Hz, 1H), 6.55-6.63 (m, 1H), 7.68 (s, 1H), 7.99 (s, 2H), 8.84 (s, 1H). LCMS (m/z) 523.2 [M+H], Tr=1.75 min.

Examples 8 and 9

Compound 8a

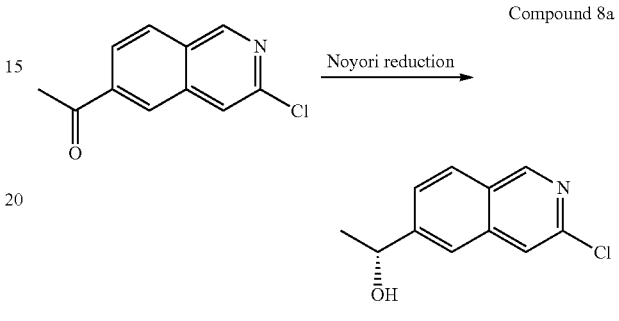

Noyori reduction

Dichloro(p-cymene)ruthenium(II)dimer (3 mg, 0.005 mmol) and (1R,2R)-(−)-N-p-tosyl-1,2-diphenylethylenediamine (4.4 mg, 0.012 mmol) were suspended in degassed water (2 mL) and the mixture was degassed with nitrogen for 15 min. The mixture was stirred at 70° C. under nitrogen for 90 min. The resulting yellow solution was cooled to RT. 1-(3-Chloro-isoquinolin-6-yl)-ethanone (206 mg, 1 mmol), sodium formate (340 mg, 5 mmol) and degassed tetrahydrofuran (1 mL) were added and the reaction mixture was degassed with nitrogen for 5 min. The reaction mixture was vigorously stirred at 40° C. for 2.5 h. The reaction mixture was cooled to RT and was extracted with ethyl acetate. The organic layer was separated, washed with water and brine, dried over sodium sulfate, filtered and evaporated. The residue was purified by silica gel chromatography using a gradient of iso-hexanes/ethyl acetate 4:1 to 2:1 to afford the title compound (193 mg, 92%) as a white solid.

Compound 8b

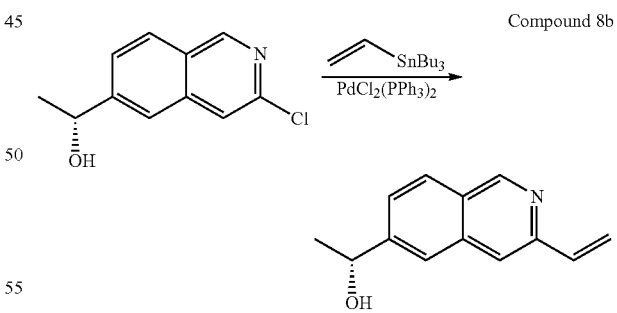

1,4-Dioxane (5 mL) was degassed with nitrogen, 8a (208 mg, 1 mmol), tributyl(vinyl)tin (951 mg, 0.9 mL, 3 mmol) and bis(triphenylphosphine)palladium(II)dichloride (70 mg, 0.1 mmol) were added and the reaction mixture was heated at 150° C. in a microwave reactor for 1 h. Additional tributyl(vinyl)tin (0.3 mL, 1 mmol) and bis(triphenylphosphine)palladium(II)dichloride (70 mg, 0.1 mmol) were added and the reaction mixture was heated at 150° C. in a microwave reactor for 1 h. The reaction mixture was cooled to RT and the mixture was filtered through filter aid and the filter pad was washed with ethyl acetate. The filtrate was evaporated and the residue was purified by silica gel chromatography using a gradient of iso-hexanes/ethyl acetate 4:1 to 2:1 followed by silica gel chromatography using iso-hexanes/ethyl acetate 3:1 to afford the title compound (100 mg, 50%) as a white solid.

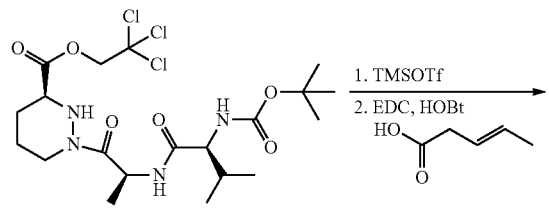

Compound 8c

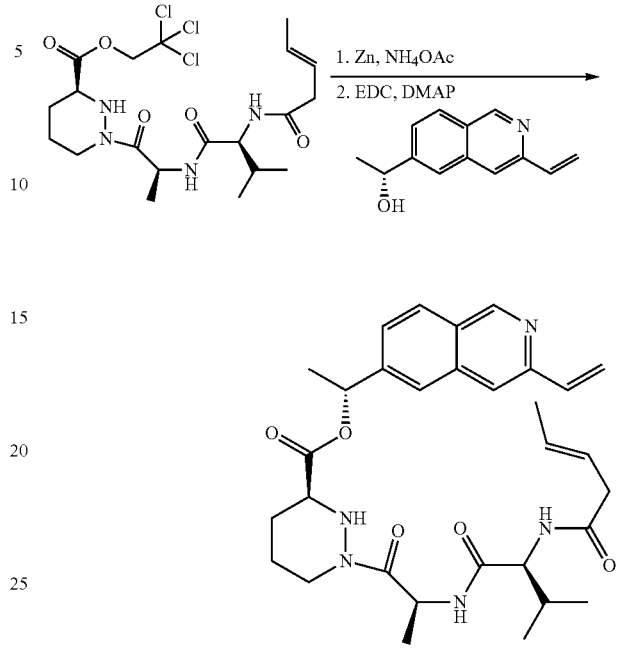

Compound 8d

A solution of 1e (10.6 g, 20 mmol) in dichloromethane (300 mL) was stirred at 0° C. under nitrogen. Trimethylsilyl trifluoromethanesulfonate (6.66 g, 5.4 mL, 30 mmol) was added dropwise and the reaction mixture was stirred at 0° C. for 1 h. Cold saturated sodium hydrogen carbonate solution (200 mL) was added and the reaction mixture was stirred at 0° C. for 15 min. The organic layer was separated, washed with saturated sodium hydrogen carbonate solution and brine, dried over sodium sulfate, filtered and evaporated to afford (S)-1-[(S)-2-((S)-2-amino-3-methyl-butyrylamino)-propionyl]-hexahydro-pyridazine-3-carboxylic acid 2,2,2-trichloro-ethyl ester (20 mmol), which was used crude in the next step. A solution of (S)-1-[(S)-2-((S)-2-amino-3-methyl-butyrylamino)-propionyl]-hexahydro-pyridazine-3-carboxylic acid 2,2,2-trichloro-ethyl ester (20 mmol) in acetonitrile (240 mL) was stirred at 0° C. under nitrogen. (E)-Pent-3-enoic acid (2.20 g, 2.2 mL, 22 mmol) and 1-hydroxybenzotriazole hydrate (3.82 g, 20 mmol, wetted with not less than 20 wt. % water) and N-(3-dimethylaminopropyl)-N'-ethylcarbodiimide hydrochloride (5.38 g, 28 mmol) was added and the reaction mixture was stirred at 0° C. for 15 min and then at RT for 20 h. The solvent was evaporated and the residue was partitioned between ethyl acetate and water. The organic extracts were combined, washed with water and brine, dried over anhydrous sodium sulfate, filtered and evaporated. The residue was purified by silica gel chromatography using iso-hexanes/ethyl acetate 3:1 to neat ethyl acetate to afford the title compound (9.0 g, 88%) as a white solid.

A solution of 8c (9.0 g, 17.5 mmol) in tetrahydrofuran (300 mL) was stirred at RT under nitrogen. Zinc powder (25.0 g, 385 mmol) was added followed by a solution of ammonium acetate (20.2 g, 263 mmol) in water (200 mL). The reaction mixture was stirred at RT under nitrogen for 18 h. The reaction mixture was filtered through Celite and the filter pad was washed with water (100 mL) and ethyl acetate (200 mL). The organic layer was separated and the solvent was evaporated to ca. 100 mL and the solution was extracted with water (100 mL). The aqueous layers were combined, saturated ammonium chloride solution (150 mL) was added and the solution was acidified to pH 1 with 2 M aqueous hydrochloric acid. The solution was extracted with ethyl acetate and the organic extracts were combined, washed with brine, dried over anhydrous magnesium sulfate, filtered and evaporated. The residue was co-evaporated with toluene (3×) to afford (S)-1-{(S)-2-[(S)-3-methyl-2-((E)-pent-3-enoylamino)-butyrylamino]-propionyl}-hexahydro-pyridazine-3-carboxylic acid (5.7 g, 85%) as a white solid which was used in the next reaction. A solution of (S)-1-{(S)-2-[(S)-3-methyl-2-((E)-pent-3-enoylamino)-butyrylamino]-propionyl}-hexahydro-pyridazine-3-carboxylic acid (5.16 g, 13.5 mmol) in dichloromethane (280 mL) and tetrahydrofuran (20 mL) was stirred at RT under nitrogen. (R)-1-(3-Vinyl-isoquinolin-6-yl)-ethanol (2.69 g, 13.5 mmol) was added followed by N-(3-dimethylaminopropyl)-N'-ethylcarbodiimide hydrochloride (3.63 g, 18.9 mmol) and 4-(dimethylamino)pyridine (1.64 g, 13.5 mmol) and the reaction mixture was stirred at RT for 6 h. Dichloromethane (200 mL) was added and the solution was washed with aqueous citric acid solution (pH 2-3). The organic layer was separated, washed with water and brine, dried over anhydrous sodium sulfate, filtered and evaporated. The residue was purified by silica gel chromatography using a gradient of iso-hexanes/ethyl acetate 3:1 to neat ethyl acetate followed by silica gel chromatography using iso-hexanes/ethyl acetate 1:8 to afford the title compound (3.91 g, 51%) as a white solid.

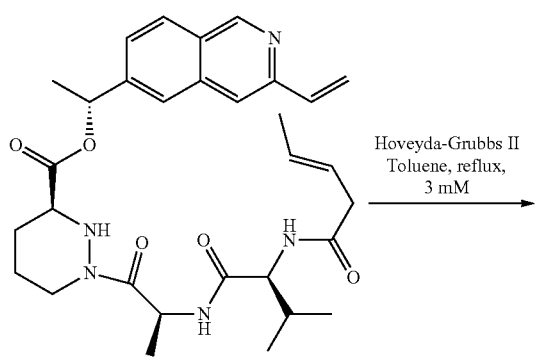

Hoveyda-Grubbs II
Toluene, reflux,
3 mM

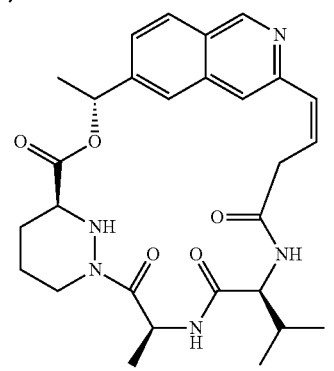

Example 8

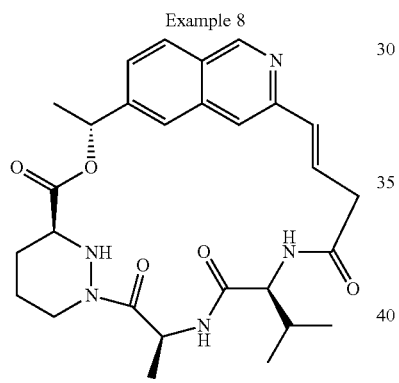

Example 9

A solution of 8d (1.13 g, 2 mmol) in toluene (600 mL) was stirred at RT under nitrogen for 15 min. Hoveyda-Grubbs $2^{nd}$ generation catalyst (125 mg, 0.2 mmol) was added and the reaction mixture was heated at reflux under nitrogen for 30 min. Additional Hoveyda-Grubbs $2^{nd}$ generation catalyst (125 mg, 0.2 mmol) was added and the reaction mixture was heated at reflux for 30 min. The reaction mixture was cooled to RT. The majority of the solvent was evaporated, silica gel was added and the solvent was evaporated. The residue was purified by silica gel chromatography using a gradient of ethyl acetate/acetone 9:1 to 3:2 followed by silica gel chromatography using ethyl acetate/methanol 40:1. The residue was triturated with ethyl acetate/ether (1:4) and the resulting solid was collected, washed with ethyl acetate/ether (1:4) and dried to afford a ~10:1 mixture of Compound 9 and Compound 8, as a pale brown solid (245 mg). A sample of the mixture was purified by reverse phase preparative HPLC to afford Compound 8 (4 mg) as a white solid. $^{1}$H NMR (300 MHz, CD$_3$OD) δ 1.01 (d, J=6.5 Hz, 3H), 1.02 (d, J=6.5 Hz, 3H), 1.37 (d, J=7.1 Hz, 3H), 1.65 (d, J=6.5 Hz, 3H), 1.70-2.15 (m, 5H), 2.95-3.05 (m, 1H), 3.70-3.76 (m, 1H), 4.03-4.10 (m, 2H), 4.12 (d, J=8.3 Hz, 1H), 5.64 (q, J=7.1 Hz, 1H), 6.10-6.20 (m, 2H), 6.98 (d, J=11.3 Hz, 1H), 7.65 (d, J=8.5 Hz, 1H), 7.93 (s, 1H), 8.05-8.10 (m, 2H), 9.21 (s, 1H). LCMS (m/z) 522.3 [M+H], Tr=1.25 min.

Compound 9, $^{1}$H NMR (300 MHz, CDCl$_3$) δ 0.97 (d, J=6.9 Hz, 3H), 0.99 (d, J=6.7 Hz, 3H), 1.53 (d, J=6.9 Hz, 3H), 1.71 (d, J=6.9 Hz, 3H), 1.75-2.70 (m, 6H), 3.20-3.40 (m, 2H), 3.63-3.77 (m, 2H), 4.23-4.29 (m, 1H), 4.53-5.57 (m, 1H), 5.65-5.76 (m, 1H), 6.04 (q, J=6.7 Hz, 1H), 6.38-6.53 (m, 3H), 6.72 (d, J=16.3 Hz, 1H), 7.39 (d, J=8.3 Hz, 1H), 7.55 (s, 1H), 7.72 (s, 1H), 7.92 (d, J=8.3 Hz, 1H), 9.13 (s, 1H). LCMS (m/z) 522.0 [M+H], Tr=1.40 min.

Example 10

Compound 10a

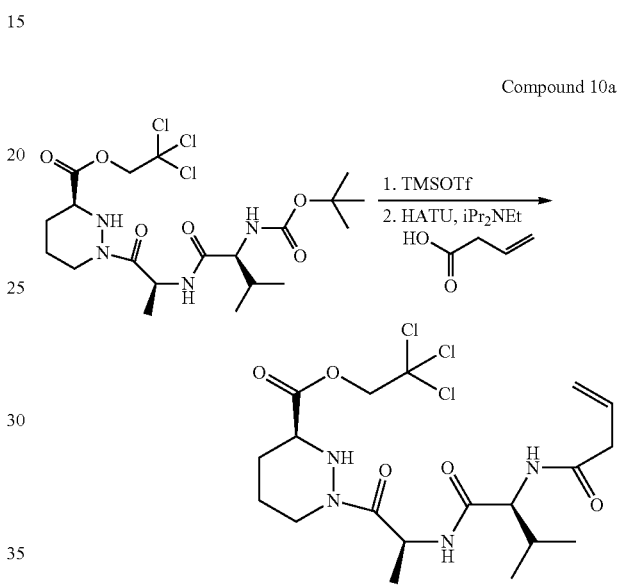

1. TMSOTf
2. HATU, iPr$_2$NEt 10a was prepared in the same manner as 4d using 3-butenoic acid instead of 4,4-dimethyl-hept-6-enoic acid in 66% yield.

Compound 10b

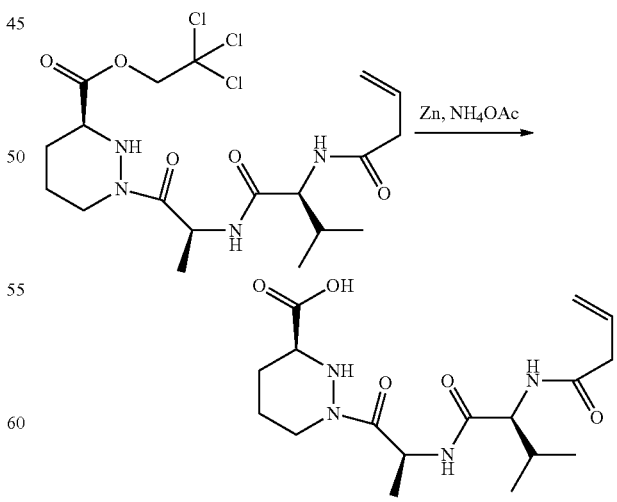

Zn, NH$_4$OAc 10b was prepared in the same manner as 4e using (S)-1-[(S)-2-((S)-2-but-3-enoylamino-3-methyl-butyrylamino)-propionyl]-hexahydro-pyridazine-3-carboxylic acid 2,2,2- trichloro-ethyl ester instead of (S)-1-{(S)-2-[(S)-2-(4,4-dimethyl-hept-6-enoyloxy)-3-methyl-butyrylamino]-propionyl}-hexahydro-pyridazine-3-carboxylic acid 2,2,2-trichloro-ethyl ester in 84% yield.

Compound 10c

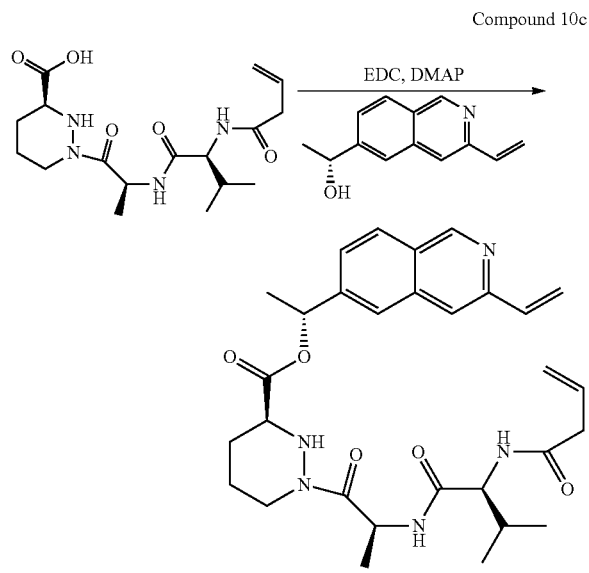

10c was prepared in the same manner as 8d using (S)-1-[(S)-2-((S)-2-but-3-enoylamino-3-methyl-butyrylamino)-propionyl]-hexahydro-pyridazine-3-carboxylic acid instead of (S)-1-{(S)-2-[(S)-3-methyl-2-((E)-pent-3-enoylamino)butyrylamino]-propionyl}-hexahydro-pyridazine-3-carboxylic acid in 84% yield.

Compound 9

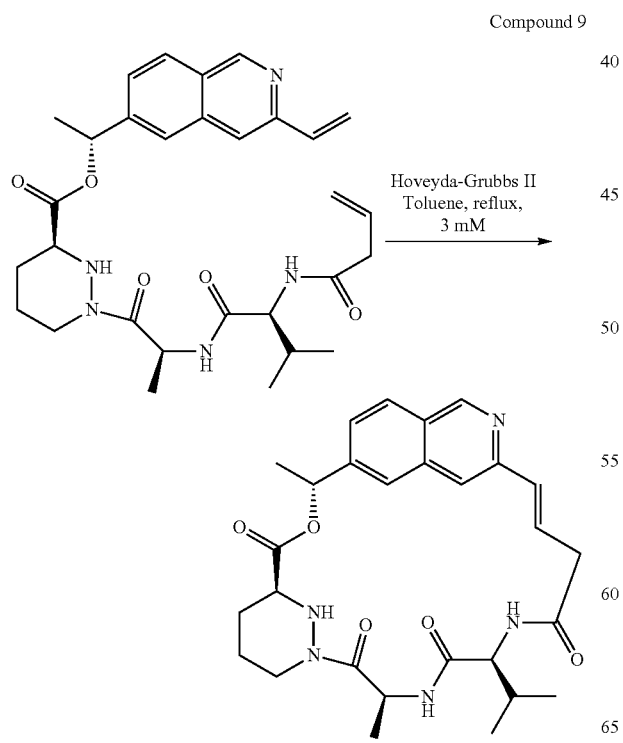

Compound 9 was prepared in the same manner as Compound 5 using (S)-1-[(S)-2-((S)-2-but-3-enoylamino-3-methyl-butyrylamino)-propionyl]-hexahydro-pyridazine-3-carboxylic acid (R)-1-(3-vinyl-isoquinolin-6-yl)-ethyl ester instead of (S)-1-{(S)-2-[(S)-2-((E)-(2R,3R)-3-methoxy-2-methyl-hex-4-enoylamino)-3-methyl-butyrylamino]-propionyl}-hexahydro-pyridazine-3-carboxylic acid [(R)-1-(3-vinyl-isoquinolin-6-yl)-ethyl]-amide in 9% yield.

Compound 10

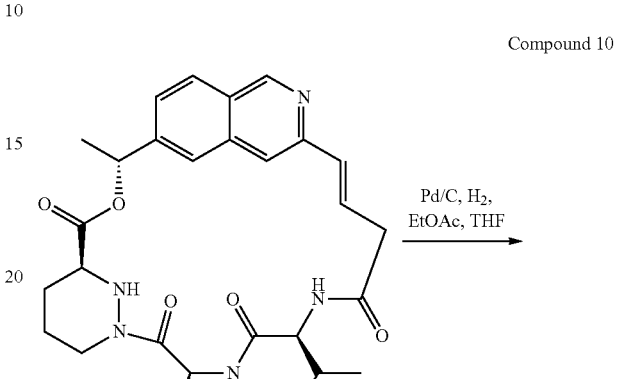

A solution of Compound 9 (16 mg, 0.03 mmol) in ethyl acetate (5 mL) and tetrahydrofuran (2 mL) containing 10% palladium on carbon (15 mg) was hydrogenated at RT and pressure for 3 h. The reaction mixture was filtered through filter aid and the filter pad was washed with ethyl acetate. The filtrate was evaporated and the residue was triturated with ether (2×2 mL) and the resulting solid was dried to afford the title compound (7.6 mg, 48%) as an off-white solid. $^1$H NMR (300 MHz, CDCl$_3$) δ 0.90 (d, J=6.7 Hz, 3H), 0.95 (d, J=6.5 Hz, 3H), 1.50 (d, J=7.1 Hz, 3H), 1.68 (d, J=6.5 Hz, 3H), 1.60-2.40 (m, 9H), 2.70-3.10 (m, 3H), 3.68-3.75 (m, 1H), 3.90 (d, J=11.8 Hz, 1H), 4.32-4.37 (m, 1H), 4.44-4.49 (m, 1H), 5.83-5.92 (m, 1H), 6.05-6.11 (m, 2H), 6.33 (d, J=7.8 Hz, 1H), 7.34 (s, 1H), 7.36 (d, J=8.3 Hz, 1H), 7.80 (s, 1H), 7.93 (d, J=8.3 Hz, 1H), 9.17 (s, 1H). LCMS (m/z) 524.3 [M+H], Tr=0.59 min.

Examples 11 and 12

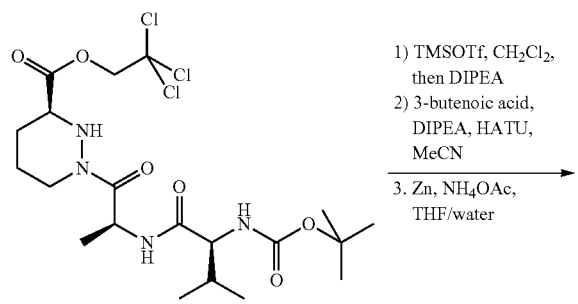

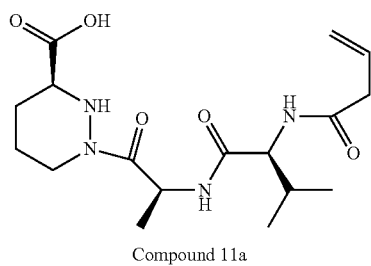

Compound 11a

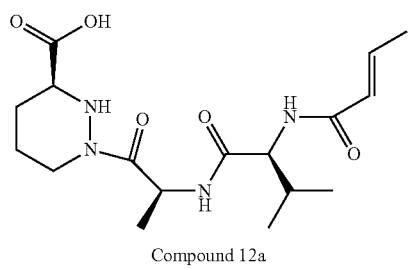

Compound 12a

To a stirred solution of 1e (10.6 g, 20.0 mmol) in dichloromethane (400 mL), at 0° C. under nitrogen, was added trimethylsilyl trifluoromethanesulfonate (6.67 g, 5.43 mL, 30.0 mmol) and the reaction mixture stirred at 0° C. for 2 h. N,N-Diisopropylethylamine (10.3 g, 13.9 mL, 80.0 mmol) was added and the mixture allowed to warm to ambient temperature. The volatiles were evaporated and the residue suspended in acetonitrile (250 mL). The stirred mixture was cooled to 0° C. under a blanket of nitrogen and then N,N-diisopropylethylamine (10.3 g, 13.9 mL, 80 mmol) and 3-butenoic acid (1.89 g, 1.86 mL, 4.40 mmol) added, followed by 2-(1H-7-azabenzotriazol-1-yl)-1,1,3,3-tetramethyl uronium hexafluorophosphate methanaminium (10.6 g, 28.0 mmol), portionwise. The reaction mixture was allowed to warm to ambient temperature and stirred for 18 h before evaporating. The residue was diluted with ethyl acetate and then washed successively with saturated sodium bicarbonate solution, water, 2 M hydrochloric acid, water then brine, dried over magnesium sulfate, filtered and evaporated. The residue was purified by silica gel chromatography using a gradient of iso-hexanes/ethyl acetate 1:1 to 0:1 to afford a ~1:1 mixture of (S)-1-[(S)-2-((S)-2-but-3-enoylamino-3-methyl-butyrylamino)-propionyl]-hexahydro-pyridazine-3-carboxylic acid 2,2,2-trichloro-ethyl ester and (S)-1-{(S)-2-[(S)-2-((E)-but-2-enoylamino)-3-methyl-butyrylamino]-propionyl}-hexahydro-pyridazine-3-carboxylic acid 2,2,2-trichloro-ethyl ester as an orange foam (7.23 g, 72%).

To a stirred solution of a mixture of (S)-1-[(S)-2-((S)-2-but-3-enoylamino-3-methyl-butyrylamino)-propionyl]-hexahydro-pyridazine-3-carboxylic acid 2,2,2-trichloro-ethyl ester and (S)-1-{(S)-2-[(S)-2-((E)-but-2-enoylamino)-3-methyl-butyrylamino]-propionyl}-hexahydro-pyridazine-3-carboxylic acid 2,2,2-trichloro-ethyl ester (~1:1, 0.99 g, 2.00 mmol) in tetrahydrofuran (40 mL) was added zinc powder (2.86 g, 44.0 mmol) and a solution of ammonium acetate (2.31 g, 30.0 mmol) in water (25 mL). The reaction mixture was allowed to warm to ambient temperature and stirred for 18 h, then diluted with ethyl acetate and the mixture filtered. From the filtrate the aqueous layer was separated and diluted with an equal amount of saturated ammonium chloride solution and then acidified to pH 1 with 2 M hydrochloric acid. The aqueous layer was extracted with ethyl acetate (2×) and the combined organic layers washed with brine, dried over magnesium sulfate, filtered and evaporated. The residue was azeotroped with toluene (3×) to give a mixture of the title compounds (~1:1, 466 mg, 63%) as a yellow foam.

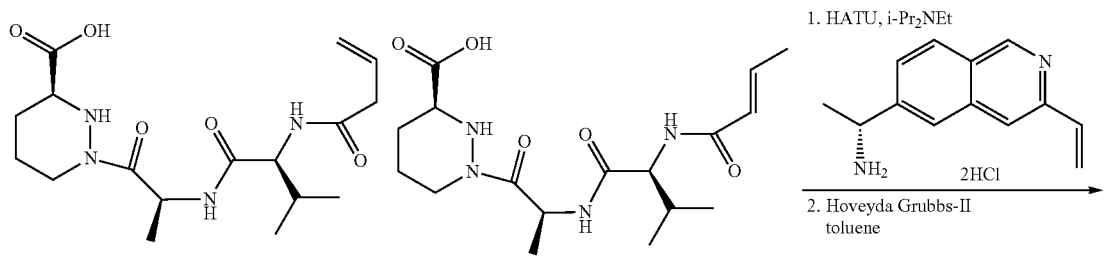

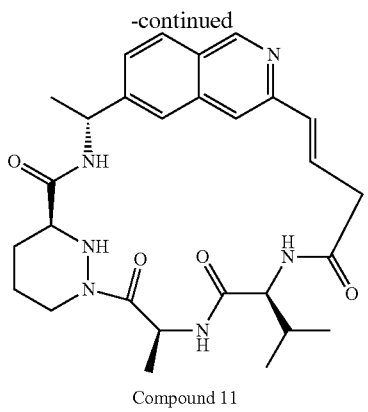
Compound 11

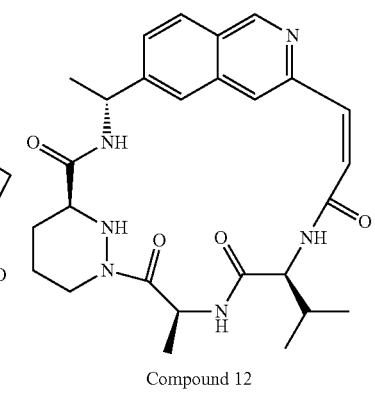
Compound 12

A mixture of 11a and 12b (~1:1, 250 mg, 0.68 mmol) in acetonitrile (20 mL) was stirred at RT under nitrogen. (R)-1-(3-vinyl-isoquinolin-6-yl)-ethylamine dihydrochloride (136 mg, 0.5 mmol) and N,N-diisopropylethylamine (323 mg, 0.44 mL, 2.5 mmol) was added followed by 2-(1H-7-azabenzotriazol-1-yl)-1,1,3,3-tetramethyl uronium hexafluorophosphate methanaminium (266 mg, 0.7 mmol) and the reaction mixture was stirred at RT for 18 h. The solvent was evaporated. The residue was diluted with ethyl acetate and the solution was washed with saturated sodium hydrogen carbonate solution, water and brine. The organic extract was dried over anhydrous magnesium sulfate, filtered and evaporated. The residue was purified by silica gel chromatography using a gradient of ethyl acetate to methanol/ethyl acetate 1:5 to afford a ~1:1 mixture of (S)-1-[(S)-2-((S)-2-but-3-enoylamino-3-methyl-butyrylamino)-propionyl]-hexahydro-pyridazine-3-carboxylic acid [(R)-1-(3-vinyl-isoquinolin-6-yl)-ethyl]-amide and (S)-1-{(S)-2-[(S)-2-((E)-but-2-enoylamino)-3-methyl-butyrylamino]-propionyl}-hexahydro-pyridazine-3-carboxylic acid [(R)-1-(3-vinyl-isoquinolin-6-yl)-ethyl]-amide as a white solid (153 mg, 56%) which was used in the next step without further purification.

A solution of a mixture of (S)-1-[(S)-2-((S)-2-but-3-enoylamino-3-methyl-butyrylamino)-propionyl]-hexahydro-pyridazine-3-carboxylic acid [(R)-1-(3-vinyl-isoquinolin-6-yl) ethyl]-amide and (S)-1-{(S)-2-[(S)-2-((E)-but-2-enoylamino)-3-methyl-butyrylamino]-propionyl}-hexahydro-pyridazine-3-carboxylic acid [(R)-1-(3-vinyl-isoquinolin-6-yl)-ethyl]-amide (~1:1, 150 mg, 0.27 mmol) in toluene (70 mL) was stirred at RT under nitrogen. Hoveyda-Grubbs $2^{nd}$ generation catalyst (17 mg, 0.027 mmol) was added and the reaction mixture was heated at reflux under nitrogen for 90 min. Additional Hoveyda-Grubbs $2^{nd}$ generation catalyst (17 mg, 0.027 mmol) was added and the reaction mixture was heated at reflux under nitrogen for 90 min. The reaction mixture was cooled to RT, silica gel was added and the solvent was evaporated. The residue was purified by silica gel chromatography using a gradient of ethyl acetate to ethyl acetate/acetone 1:1. The residue was further purified by preparative thin layer chromatography using methanol/ethyl acetate 1:4 followed by silica gel chromatography using dichloromethane/methanol 20:1 to give the title compounds. Compound 11 (1.3 mg, 1%) as a white solid: $^1$H NMR (300 MHz, CD$_3$OD) δ 1.01 (d, J=6.7 Hz, 3H), 1.02 (d, J=6.7 Hz, 3H), 1.61 (d, J=7.1 Hz, 3H), 1.66 (d, J=7.1 Hz, 3H), 1.80-2.05 (m, 5H), 2.71-2.82 (m, 1H), 2.99-3.05 (m, 1H), 3.32-3.43 (m, 1H), 3.64-3.75 (m, 1H), 4.27 (d, J=10.1 Hz, 1H), 4.40-4.53 (m, 2H), 5.12 (q, J=7.1 Hz, 1H), 5.62 (q, J=7.1 Hz, 1H), 6.47-6.56 (m, 1H), 6.62 (d, J=15.8 Hz, 1H), 7.43 (s, 1H), 7.61 (dd, J=8.5, 1.6 Hz 1H), 7.74 (s, 1H), 8.05 (d, J=8.5 Hz, 1H), 9.13 (s, 1H). LCMS (m/z) 521.3 [M+H], Tr=0.97 min.

Compound 12 (1.7 mg, 1.2%) as a white solid: $^1$H NMR (300 MHz, CD$_3$OD) δ 0.98 (d, J=6.7 Hz, 3H), 1.03 (d, J=6.7 Hz, 3H), 1.47 (d, J=7.1 Hz, 3H), 1.60 (d, J=6.9 Hz, 3H), 1.65-2.16 (m, 5H), 2.81-2.89 (m, 1H), 3.61-3.69 (m, 1H), 4.04 (d, J=6.9 Hz, 1H), 4.30-4.36 (m, 1H), 4.75 (d, J=11.6 Hz, 1H), 5.23 (q, J=7.1 Hz, 1H), 5.90 (q, J=6.9 Hz, 1H), 6.36 (d, J=13.1 Hz, 1H), 6.92 (d, J=13.1 Hz, 1H), 7.65 (d, J=8.5 Hz 1H), 7.88 (s, 1H), 8.05 (d, J=8.5 Hz 1H), 8.46 (s, 1H), 9.16 (s, 1H). LCMS (m/z) 507.2 [M+H], Tr=0.95 min.

Example 13

Compound 13a

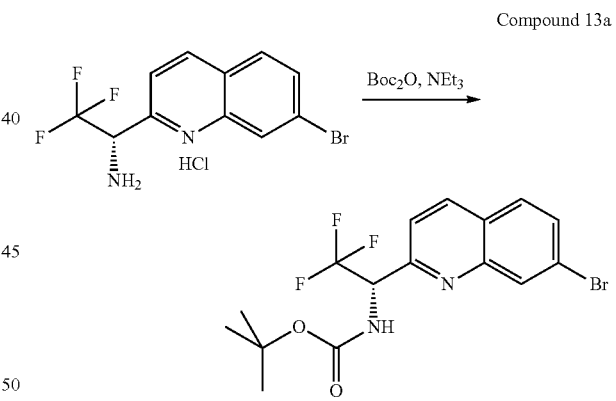

A suspension of (S)-1-(7-bromo-quinolin-2-yl)-2,2,2-trifluoro-ethylamine hydrochloride (Asiba Pharmatech, Edison, N.J., USA, 397 mg, 1.16 mmol) in dichloromethane (10 mL) was cooled using an ice bath. Triethylamine (985 μL, 3.48 mmol) was added and the reaction was stirred until a homogenous solution was observed. Di-tert-butyl dicarbonate (380 mg, 1.74 mmol) in dichloromethane (5 mL) was then added and the reaction was left to stir overnight. Di-tert-butyl dicarbonate (127 mg, 0.58 mmol) was added and the reaction was stirred for a further 6 h. Di-tert-butyl dicarbonate (253 mg, 1.16 mmol) was added along with 4 Å molecular sieves and the reaction was left to stir overnight. The reaction was washed with water and brine and the organics were dried over anhydrous sodium sulfate, filtered and concentrated. The residue was purified by silica gel chromatography using a stepwise gradient from 1:0 to 7:3 iso-hexanes/ethyl acetate to afford the title compound (343 mg, 73%) as an orange solid.

raphy using a stepwise gradient of iso-hexanes/ethyl acetate from 1:0 to 6:4. The isolated material was subjected to a second purification using the same conditions to afford the title compound (142 mg, 38%) as a pale yellow oil.

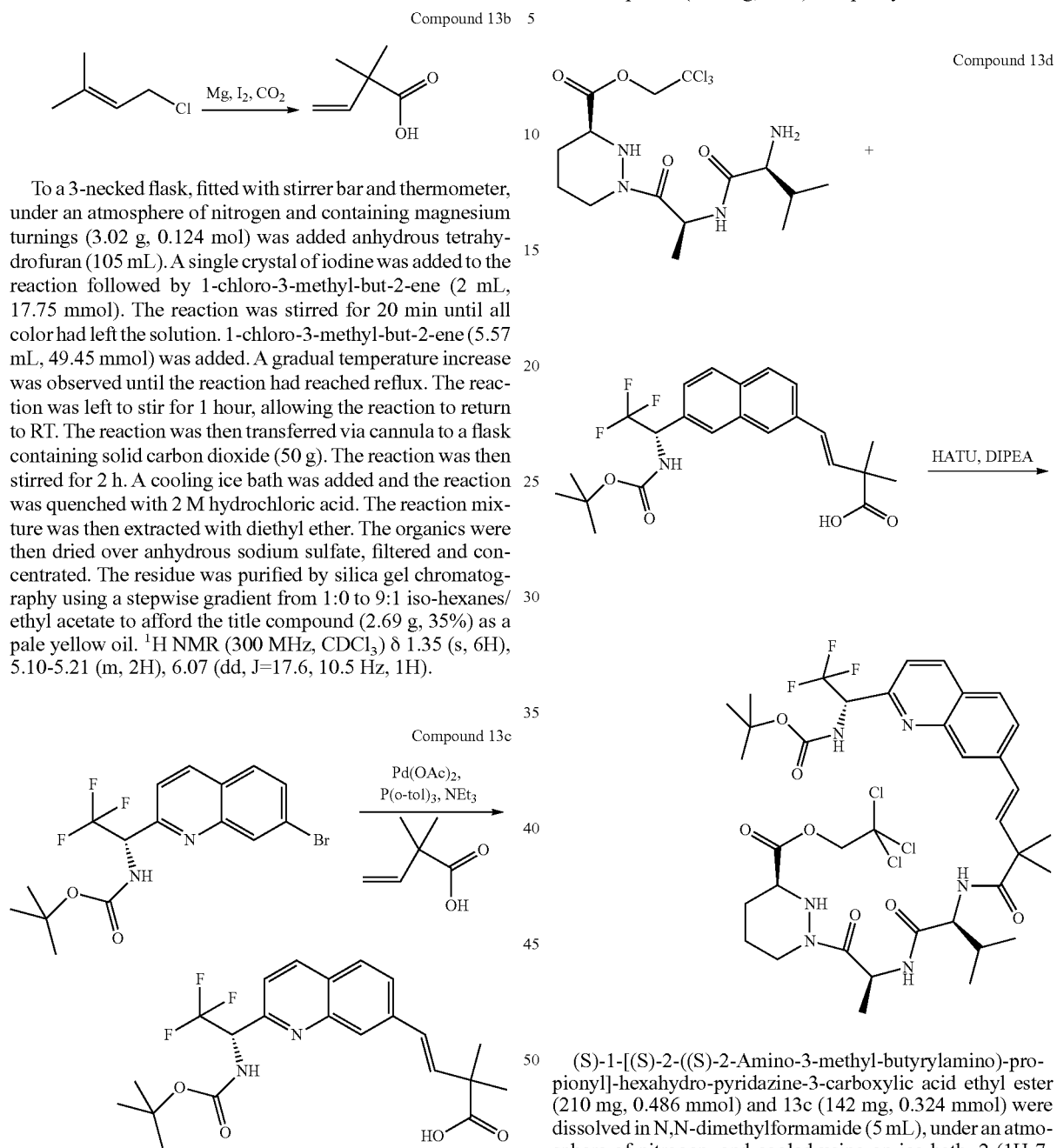

To a 3-necked flask, fitted with stirrer bar and thermometer, under an atmosphere of nitrogen and containing magnesium turnings (3.02 g, 0.124 mol) was added anhydrous tetrahydrofuran (105 mL). A single crystal of iodine was added to the reaction followed by 1-chloro-3-methyl-but-2-ene (2 mL, 17.75 mmol). The reaction was stirred for 20 min until all color had left the solution. 1-chloro-3-methyl-but-2-ene (5.57 mL, 49.45 mmol) was added. A gradual temperature increase was observed until the reaction had reached reflux. The reaction was left to stir for 1 hour, allowing the reaction to return to RT. The reaction was then transferred via cannula to a flask containing solid carbon dioxide (50 g). The reaction was then stirred for 2 h. A cooling ice bath was added and the reaction was quenched with 2 M hydrochloric acid. The reaction mixture was then extracted with diethyl ether. The organics were then dried over anhydrous sodium sulfate, filtered and concentrated. The residue was purified by silica gel chromatography using a stepwise gradient from 1:0 to 9:1 iso-hexanes/ethyl acetate to afford the title compound (2.69 g, 35%) as a pale yellow oil. $^1$H NMR (300 MHz, CDCl$_3$) δ 1.35 (s, 6H), 5.10-5.21 (m, 2H), 6.07 (dd, J=17.6, 10.5 Hz, 1H).

13a (343 mg, 0.846 mmol) and 13b (106 mg, 0.931 mmol) were placed in a microwave vessel and dissolved in acetonitrile (3 mL). Palladium(II) acetate (19 mg, 0.0846 mmol), tri(o-tolyl)phosphine (51 mg, 0.169 mmol) and triethylamine (236 µL, 1.69 mmol) were added and the vessel was sealed before being irradiated in the microwave for 30 min, using fixed hold time, on high absorption at 100° C. The solvent was removed and the residue was taken up in a mixture of water and ethyl acetate. The phases were separated and the aqueous was extracted with ethyl acetate. The combined organics were then dried over anhydrous sodium sulfate, filtered and concentrated. The residue was purified by silica gel chromatog- (S)-1-[(S)-2-((S)-2-Amino-3-methyl-butyrylamino)-propionyl]-hexahydro-pyridazine-3-carboxylic acid ethyl ester (210 mg, 0.486 mmol) and 13c (142 mg, 0.324 mmol) were dissolved in N,N-dimethylformamide (5 mL), under an atmosphere of nitrogen, and cooled using an ice bath. 2-(1H-7-azabenzotriazol-1-yl)-1,1,3,3-tetramethyl uronium hexafluorophosphate methanaminium (203 mg, 0.535 mmol) and N,N-diisopropylethylamine (423 µL, 2.43 mmol) were then added and the reaction was allowed to slowly warm to RT and left to stir overnight. The reaction was diluted with water and extracted with ethyl acetate. The combined organics were dried over anhydrous sodium sulfate, filtered and concentrated. The residue was purified by silica gel chromatography using a stepwise gradient of iso-hexanes/ethyl acetate from 1:0 to 0:1 to afford the product contaminated with residual solvent. Toluene was added and the solution was concentrated to afford the title compound (79 mg, 29%) as an orange solid.

Compound 13e

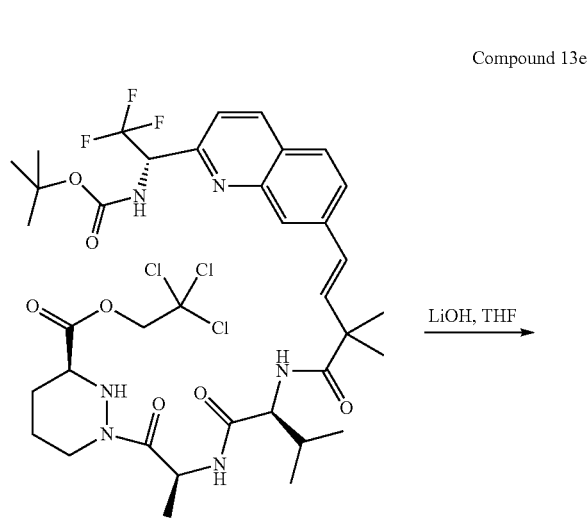

LiOH, THF 13e (66 mg, 0.0916 mmol) was dissolved in 4 M hydrochloric acid in 1,4-dioxane (2 mL) and left to stir for 30 min. The solvent was removed and the resultant solid was triturated with diethyl ether and dried to afford the title compound (50 mg, 83%) as a pale yellow solid.

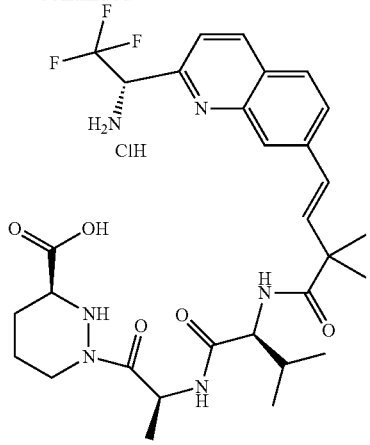

Compound 13

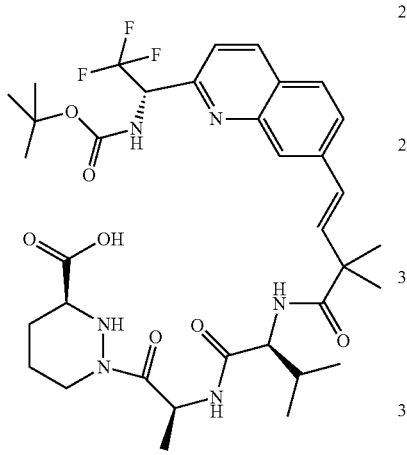

13d (79 mg, 0.0925 mmol) was dissolved in tetrahydrofuran (2 mL) and cooled using an ice bath. Methanol (1 mL) and water (1 mL) were then added followed by lithium hydroxide monohydrate (15 mg, 0.37 mmol). The reaction was then left to stir for 1 hour. 1 M hydrochloric acid was added until the solution was pH 2. The solvent was removed and the resultant solid was sequentially azeotroped with methanol, then acetonitrile and finally toluene to afford the title compound (67 mg, 100%) as a yellow solid.

HATU, DIPEA

Compound 13f

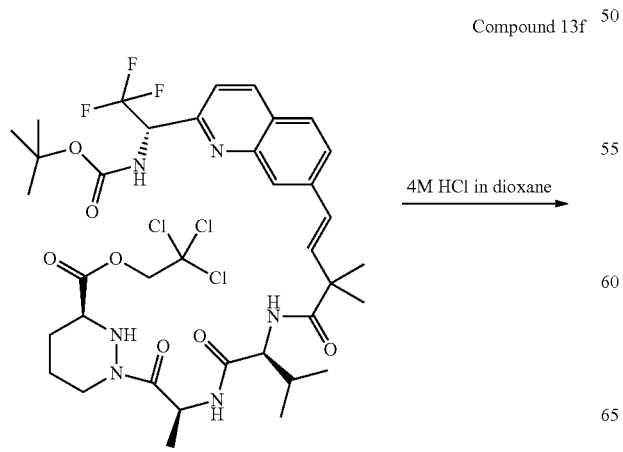

4M HCl in dioxane 13f (50 mg, 0.0761 mmol) was dissolved in dichloromethane (76 mL), under an atmosphere of nitrogen and cooled using an ice bath. 2-(1H-7-Azabenzotriazol-1-yl)-1,1,3,3-tetramethyl uronium hexafluorophosphate methanaminium (58 mg, 0.152 mmol) and N,N-diisopropylethylamine (53 µL, 0.304 mmol) were then added and the reaction was allowed to slowly warm to RT and left to stir overnight. The solvent was removed and the residue was purified by silica gel chromatography using 7:3 iso-hexanes/acetone. The residue was re-purified by silica gel chromatography using a stepwise gradient of iso-hexanes/acetone from 1:0 to 1:1. The residue was then eluted through an HPLC system fitted with a Phenomenex Gemini 10μ 110 A, 250×21.2 mm column using a continuous gradient of acetonitrile/water from 1:4 to 1:0 flow at 20 mL/min to afford the title compound (7 mg, 15%) as a solid. $^1$H NMR (300 MHz, CDCl$_3$) δ 0.86-1.08 (m, 6H), 1.25-1.54 (m, 8H), 1.57-1.81 (m, 5H), 1.88-2.00 (m, 1H), 2.37-2.80 (m, 1H), 3.32-3.65 (m, 1H), 3.69-3.97 (m, 1H), 4.22-4.39 (m, 1H), 4.50-4.68 (m, 1H), 5.74-6.05 (m, 2H), 6.22-6.39 (m, 1H), 6.44-6.54 (m, 1H), 6.63-6.76 (m, 1H), 7.45 (app t, J=8.5 Hz, 1H), 7.56 (app t, J=7.6 Hz, 1H), 7.81 (d, J=8.3 Hz, 1H), 8.19 (s, 1H), 8.76-9.09 (m, 1H). LCMS (m/z) 603.1 [M+H], Tr=2.59 min.

Example 14

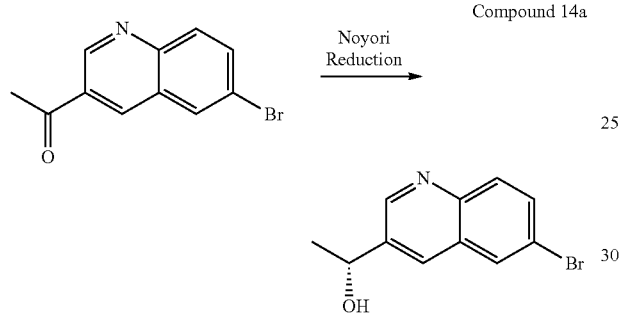

Dichloro(p-cymene)ruthenium(II)dimer (24 mg, 0.040 mmol) and (1R,2R)-(−)-N-p-tosyl-1,2-diphenylethylenediamine (35 mg, 0.096 mmol) were suspended in degassed water (16 mL) and the mixture was degassed with nitrogen for 15 min. The mixture was stirred at 70° C. under nitrogen for 90 min. The resulting turbid orange mixture was allowed to cool to RT. Solid 1-(6-bromo-quinolin-3-yl)-ethanone (prepared as in WO2011/063233, 1.92 g, 7.68 mmol) followed by degassed tetrahydrofuran (16 mL) and sodium formate (2.72 g, 40 mmol) were added and the reaction mixture was degassed with nitrogen for 5 min, further degassed tetrahydrofuran (5 mL) was added and the mixture degassed for another minute. The reaction mixture was vigorously stirred at 40° C. for 21 h and allowed to cool. It was then diluted with ethyl acetate and the mixture washed with water then brine, dried over magnesium sulfate, filtered and evaporated. The residue was purified by silica gel chromatography using a gradient of iso-hexanes/ethyl acetate 7:3 to 0:1 to afford the title compound (1.65 g, 85%) as a brown solid.

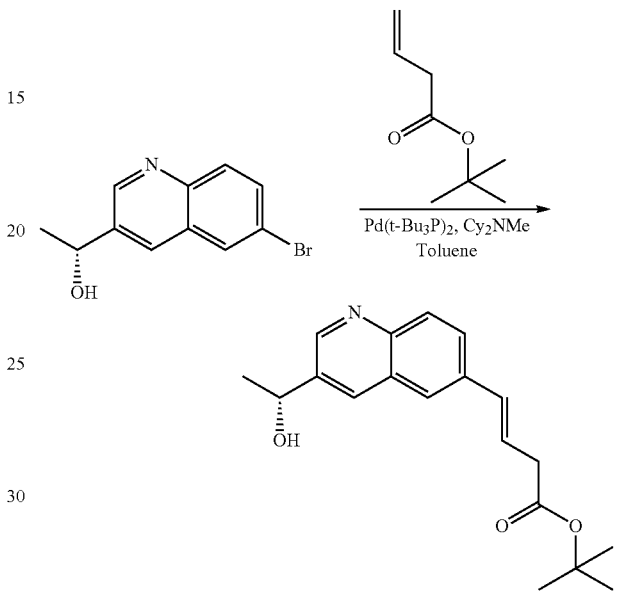

To a mixture of 14a (356 mg, 1.41 mmol), N,N-dicyclohexylmethylamine (275 mg, 301 μL, 1.41 mmol) and tert-butyl 3-butenoate (470 mg, 537 μL, 3.31 mmol) in toluene (14 mL) was added bis(tri-tert-butylphosphine)palladium(0) (30 mg, 0.058 mmol) under nitrogen and the reaction mixture stirred and heated under reflux for 90 min then allowed to cool. The mixture was evaporated and then purified by silica gel chromatography using a gradient of iso-hexanes/ethyl acetate 4:1 to 2:3 to afford the title compound as a yellow oil (144 mg, 33%).

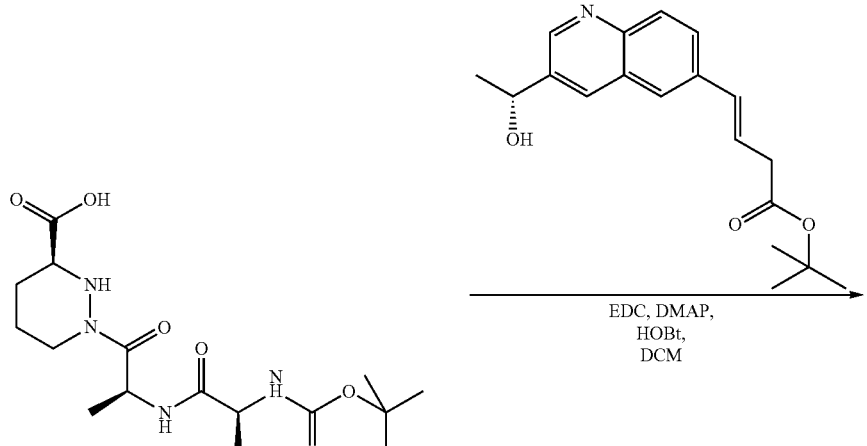

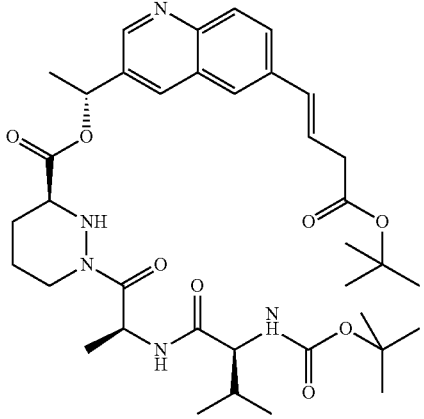

To a stirred solution of (S)-1-[(S)-2-((S)-2-tert-butoxycarbonylamino-3-methyl-butyrylamino)-propionyl]-hexahydro-pyridazine-3-carboxylic acid (189 mg, 0.473 mmol) and 14b (148 mg, 0.473 mmol) in dichloromethane (10 mL) was added 1-hydroxybenzotriazole containing approx. 20% water (89 mg, 0.662 mmol) followed by 4-dimethylaminopyridine (58 mg, 0.473 mmol) then N-(3-dimethylaminopropyl)-N'-ethylcarbodiimide hydrochloride (127 mg, 0.662 mmol). The reaction was stirred for 62 h and then diluted with dichloromethane, washed with saturated ammonium chloride solution (2×) and brine, dried over magnesium sulfate, filtered and evaporated. Purified by silica gel chromatography using a gradient of iso-hexanes/ethyl acetate 3:1 to 2:3 afforded the title compound (126 mg, 38%) as a white foam.

Compound 14

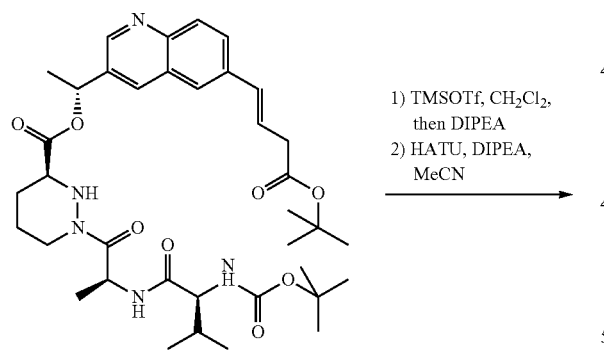

1) TMSOTf, CH$_2$Cl$_2$, then DIPEA
2) HATU, DIPEA, MeCN

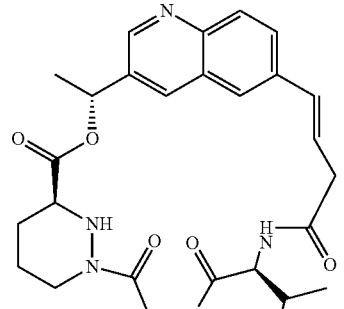

To a stirred solution of 14c (126 mg, 0.181 mmol) in dichloromethane (1.8 mL) at 0° C. under nitrogen was added trimethylsilyl trifluoromethanesulfonate (141 mg, 147 μL, 0.635 mmol) and the reaction mixture was allowed to warm to ambient temperature over 1.75 h. Further trimethylsilyl trifluoromethanesulfonate (20 mg, 21 μL, 0.091 mmol) was added and the reaction mixture was stirred for a further 15 min before the addition of N,N-diisopropylethylamine (164 mg, 221 μL, 1.27 mmol). After a further 10 min of stirring the reaction mixture was evaporated and then suspended in acetonitrile (18.1 mL). The stirred mixture was cooled to 0° C. and then 2-(1H-7-azabenzotriazol-1-yl)-1,1,3,3-tetramethyl uronium hexafluorophosphate methanaminium (96 mg, 0.253 mmol) and N,N-diisopropylethylamine (94 mg, 126 μL, 0.724 mmol) added. After 45 min the reaction was quenched with saturated ammonium chloride solution (10 mL) and the mixture evaporated to remove organic volatiles. The residue was diluted with dichloromethane and the aqueous layer separated and extracted with dichloromethane. The organic extracts were washed with saturated sodium bicarbonate, water and then brine, dried over sodium sulfate, filtered and evaporated. The residue was purified by silica gel chromatography eluting with ethyl acetate/acetone 9:1 then by preparative reverse phase HPLC using a gradient of acetonitrile/water 3:7 to 1:1 to afford the title compound (6.5 mg, 7% over 2 steps) as a white solid. $^1$H NMR (300 MHz, CD$_3$OD) δ 1.00 (d, J=6.7 Hz, 3H), 1.03 (d, J=6.7 Hz, 3H), 1.61 (d, J=7.1 Hz, 3H), 1.75 (d, J=6.7 Hz, 3H), 1.91-2.01 (m, 3H), 2.68-2.79 (m, 1H), 3.00 (dd, J=14.5, 3.6 Hz, 1H), 3.35-3.42 (m, 1H), 3.73-3.82 (m, 1H), 4.29 (d, J=9.6 Hz, 1H), 4.41 (d, J=12.9 Hz, 1H), 4.70 (d, J=12.3 Hz, 1H), 5.47 (q, J=7.3 Hz, 1H), 6.15 (q, J=6.6 Hz, 1H), 6.30-6.40 (m, 1H), 6.63 (d, J=16.1 Hz, 1H), 7.55 (s, 1H), 7.82 (dd, J=8.7, 1.5 Hz, 1H), 7.95 (d, J=8.7 Hz, 1H), 8.21 (s, 1H), 8.79 (d, J=1.8 Hz, 1H). LCMS (m/z) 522.2 [M+H], Tr=1.60 min.

Example 15

Compound 15a

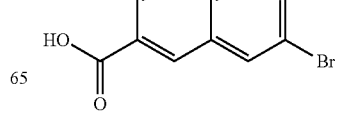

CDMT, NMM, THF
HNMeOMe

-continued

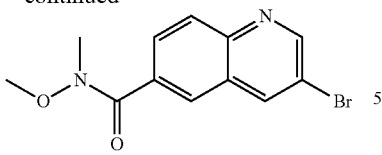

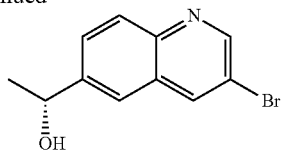

To a stirred mixture of 3-bromo-quinoline-6-carboxylic acid (prepared as in WO2011/090935, 1.94 g, 7.70 mmol) in tetrahydrofuran (77 mL) was added 2-chloro-4,6-dimethoxy-1,3,5-triazine (2.03 g, 11.5 mmol) and N-methylmorpholine (2.34 g, 2.54 mL, 23.1 mmol). The reaction mixture was stirred for 90 min and then N,O-dimethylhydroxylamine hydrochloride (751 mg, 7.70 mmol) added in one portion. The reaction mixture was stirred for a further 17 h and further N,O-dimethylhydroxylamine hydrochloride (375 mg, 3.85 mmol) was added and then after 5 h a further portion (175 mg, 1.80 mmol). The reaction mixture was stirred for a further hour and then diluted with dichloromethane, washed with water and then saturated ammonium chloride solution. The organic layer was dried over sodium sulfate, filtered and evaporated. The residue was purified by silica gel chromatography eluting with a gradient of iso-hexanes/ethyl acetate 4:1 to 7:3 to afford the title compound (1.43 g, 66%) as an off-white solid.

Dichloro(p-cymene)ruthenium(II)dimer (9 mg, 0.015 mmol) and (1R,2R)-(−)-N-p-tosyl-1,2-diphenylethylenediamine (14 mg, 0.037 mmol) were suspended in degassed water (9 mL) and the mixture was degassed with nitrogen for 15 min. The mixture was stirred at 70° C. under nitrogen for 90 min. The resulting turbid orange mixture was allowed to cool to RT. Solid 1-(3-bromo-quinolin-6-yl)-ethanone (771 mg, 3.08 mmol) and sodium formate (2.72 g, 40 mmol) followed by degassed tetrahydrofuran (4.5 mL) were added and the reaction mixture was degassed with nitrogen for 5 min. The reaction mixture was vigorously stirred at 40° C. for 3 h and allowed to cool. It was then diluted with ethyl acetate and the mixture washed with water then brine, dried over sodium sulfate, filtered and evaporated. The residue was purified by silica gel chromatography using a gradient of iso-hexanes/ethyl acetate 3:2 to 1:1 to afford the title compound (616 mg, 79%) as a grey solid.

Compound 15b

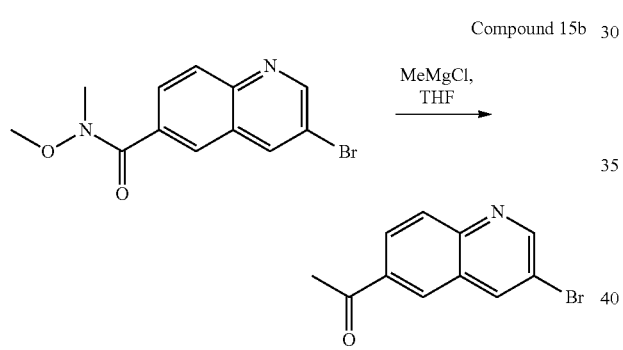

Compound 15d

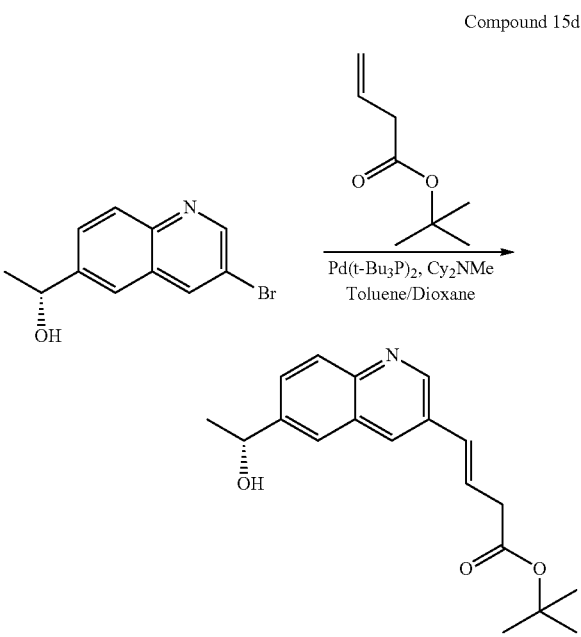

To a stirred solution of methyl magnesium chloride (3 M in tetrahydrofuran, 4.85 mL, 14.5 mmol) in tetrahydrofuran (10 mL) under nitrogen was added a solution of 15a (1.43 g, 4.85 mmol) in tetrahydrofuran (20 mL). The reaction mixture was stirred for 1 hour and then quenched with saturated ammonium chloride solution. The mixture was diluted with diethyl ether and water, the organic layer separated and washed with further water and the combined aqueous washes back-extracted with diethyl ether. The combined organic extracts were dried over magnesium sulfate, filtered and evaporated. The residue was purified by silica gel chromatography eluting with iso-hexanes/ethyl acetate 4:1 to afford the title compound as a white solid which was taken directly into the next step.

Compound 15c

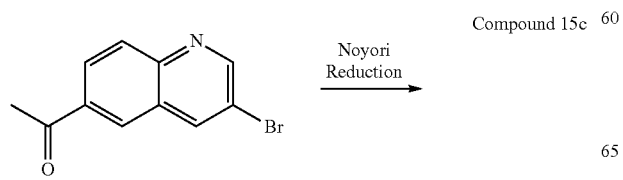

To a solution of 15c (560 mg, 2.22 mmol) in toluene (20 mL) and 1,4-dioxane (5 mL) was added N,N-dicyclohexylmethylamine (740 μL, 3.46 mmol) and tert-butyl 3-butenoate (741 mg, 844 μL, 5.22 mmol) was added bis(tri-tert-butylphosphine)palladium(0) (68 mg, 0.13 mmol) under nitrogen and the reaction mixture stirred and heated under reflux for 6 h then allowed to cool. The mixture was evaporated and then purified by silica gel chromatography using a gradient of iso-hexanes/ethyl acetate 4:1 to 0:1 to give a yellow gum. The gum was suspended in ethyl acetate and washed with saturated ammonium chloride solution (2x) followed by water then brine, dried over sodium sulfate, filtered and evaporated to afford the title compound (300 mg, 43%) as a yellow oil.

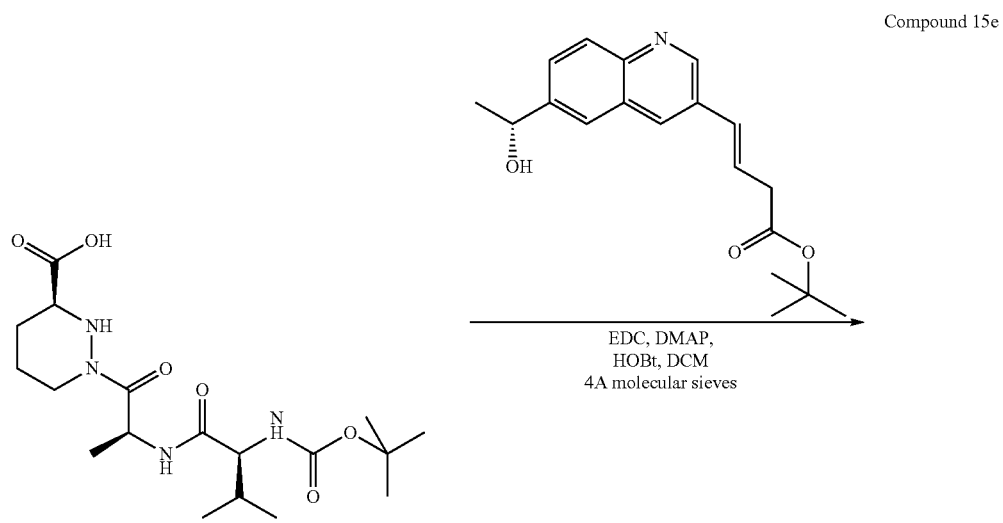

Compound 15e

EDC, DMAP,
HOBt, DCM
4A molecular sieves

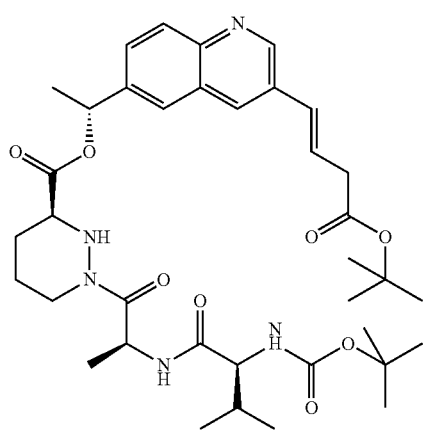

To a stirred slurry of (S)-1-[(S)-2-((S)-2-tert-butoxycarbonylamino-3-methyl-butyrylamino)-propionyl]-hexahydropyridazine-3-carboxylic acid (325 mg, 0.812 mmol), 15d (231 mg, 0.738 mmol) and powdered 4 Å molecular sieves in dichloromethane (16 mL) was added N-(3-dimethylaminopropyl)-N'-ethylcarbodiimide hydrochloride (198 mg, 1.03 mmol), 1-hydroxybenzotriazole hydrate containing approx. 20% water (174 mg, 1.03 mmol) followed by 4-dimethylaminopyridine (90 mg, 0.738 mmol). The reaction was stirred under nitrogen for 16 h and then filtered and the solid washed with dichloromethane. The filtrate was washed with saturated ammonium chloride solution (2×) and water, dried over sodium sulfate, filtered and evaporated. The residue was purified by silica gel chromatography using a gradient of isohexanes/ethyl acetate 1:1 to 0:1 to afford the title compound (307 mg, 60%) as a yellow foam.

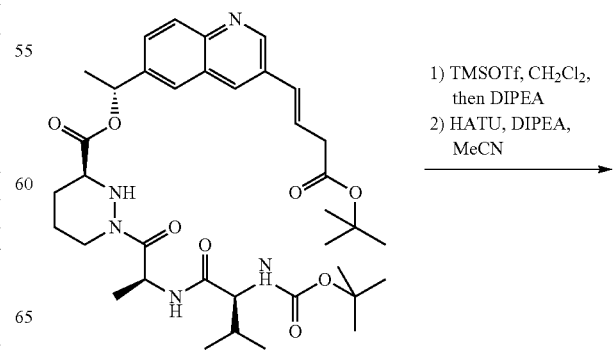

Compound 15

1) TMSOTf, CH$_2$Cl$_2$,
   then DIPEA
2) HATU, DIPEA,
   MeCN

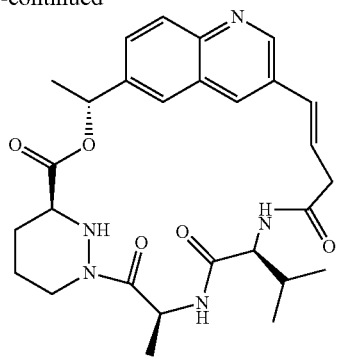

To a stirred solution of 15e (150 mg, 0.216 mmol) in dichloromethane (2 mL) at 0° C. under nitrogen was added trimethylsilyl trifluoromethanesulfonate (168 mg, 174 µL, 0.755 mmol) dropwise and the reaction mixture was allowed to warm to ambient temperature over 2.25 h. N,N-Diisopropylethylamine (195 mg, 263 µL, 1.51 mmol) was added and the reaction mixture stirred for a further 10 min, evaporated and then suspended in acetonitrile (21.6 mL). The stirred mixture was cooled to 0° C. and then 2-(1H-7-azabenzotriazol-1-yl)-1,1,3,3-tetramethyl uronium hexafluorophosphate methanaminium (115 mg, 0.320 mmol) and N,N-diisopropylethylamine (111 mg, 150 µL, 0.864 mmol) added. After 1 h the reaction was quenched with saturated ammonium chloride solution and the mixture evaporated to remove organic volatiles. The residue was diluted with dichloromethane and the organic layer separated and washed with saturated ammonium chloride (2×) and brine then dried over sodium sulfate, filtered and evaporated. The residue was purified by preparative reverse phase HPLC using a gradient of acetonitrile/water 3:7 to 11:9 to afford the title compound (4.6 mg, 4% over 2 steps) as an off-white solid. $^1$H NMR (300 MHz, CD$_3$OD) δ 1.01 (app t, J=6.7 Hz, 6H), 1.62 (d, J=7.1 Hz, 3H), 1.70 (d, J=6.7 Hz, 3H), 1.75-1.85 (m, 1H), 1.91-2.05 (m, 3H), 2.70-2.80 (m, 1H), 2.98-3.06 (m, 1H), 3.36-3.45 (m, 1H), 3.74-3.84 (m, 1H), 4.26 (d, J=10.5 Hz, 1H), 4.42 (br d, J=12.3 Hz, 4.72-4.78 (m, 1H), 5.55 (q, J=7.1 Hz, 1H), 6.09 (q, J=6.5 Hz, 1H), 6.38-6.41 (m, 1H), 6.71 (d, J=16.1 Hz, 1H), 7.68 (dd, J=8.9, 1.9 Hz, 1H), 7.88-8.01 (m, 3H), 8.86 (d, J=2.0 Hz, 1H). LCMS (m/z) 522.3 [M+H], Tr=1.64 min.

Example 16

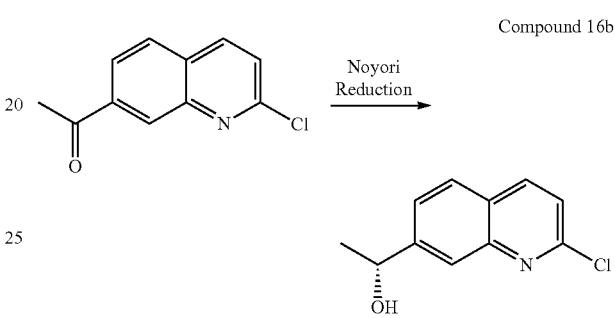

Compound 16a

A mixture of 7-bromo-2-chloro-quinoline (1.05 g, 4.32 mmol) and tributyl(1-ethoxyvinyl)tin (1.95 g, 1.83 mL, 5.40 mmol) in toluene (21 mL) was degassed for 20 min. Bis(triphenylphosphine)palladium(II)dichloride (302 mg, 0.432 mmol) was added and the reaction mixture stirred under nitrogen and heated at 80° C. for 24 h before allowing to cool. The volatiles were evaporated and the residue suspended in 1,4-dioxane (10 mL) and 2 M aqueous hydrochloric acid (5 mL) was added and the reaction mixture stirred for 30 min and then evaporated to remove organics. The residue was diluted with ethyl acetate and water and the organic layer washed with brine, dried over sodium sulfate, filtered and evaporated. The product was purified on silica gel doped with 10% w/w potassium carbonate eluting using a gradient of iso-hexanes/ethyl acetate 9:1 to 4:1 to afford the title compound (422 mg, 48%) as a yellow solid.

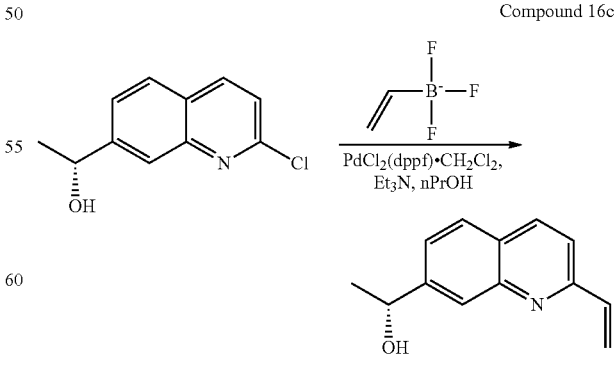

Compound 16b

Dichloro(p-cymene)ruthenium(II)dimer (8.5 mg, 0.014 mmol) and (1R,2R)-(−)-N-p-tosyl-1,2-diphenylethylenediamine (12.1 mg, 0.033 mmol) were suspended in degassed water (5.5 mL) and the mixture was degassed with nitrogen for 20 min. The mixture was stirred at 70° C. under nitrogen for 90 min. The resulting turbid orange mixture was allowed to cool to RT. Solid 16a (571 mg, 2.78 mmol) and sodium formate (945 mg, 13.9 mmol) followed by degassed tetrahydrofuran (5.5 mL) were added and the reaction mixture was degassed with nitrogen for 5 min. The reaction mixture was vigorously stirred at 40° C. for 4 h and allowed to cool. It was then diluted with ethyl acetate and the mixture washed with water and the aqueous layer back-extracted with ethyl acetate. The combined organic extracts were washed with brine, dried over sodium sulfate, filtered and evaporated. The residue was purified by silica gel chromatography using a gradient of iso-hexanes/ethyl acetate 4:1 to 7:3 to afford the title compound (413 mg, 72%) as a beige solid.

Compound 16c

To a mixture of 16b (360 mg, 1.73 mmol), potassium vinyltrifluoroborate (279 mg, 2.08 mmol) and [1,1′-bis(diphenylphosphino)ferrocene]dichloropalladium(II), complex with dichloromethane (27 mg, 0.033 mmol) in dry n-propanol (27 mL) was added triethylamine (175 mg, 241 µL, 1.73 mmol) and the system evacuated and purged with nitrogen (3×). The reaction mixture was stirred and heated at reflux for 3 h before being allowed to cool. The mixture was poured into water and extracted with diethyl ether (2×) and the combined organic extracts dried over magnesium sulfate, filtered and evaporated. The residue was purified by silica gel chromatography using a gradient of iso-hexanes/ethyl acetate 7:3 to 3:2 to afford the title compound (270 mg, 78%) as a white solid.

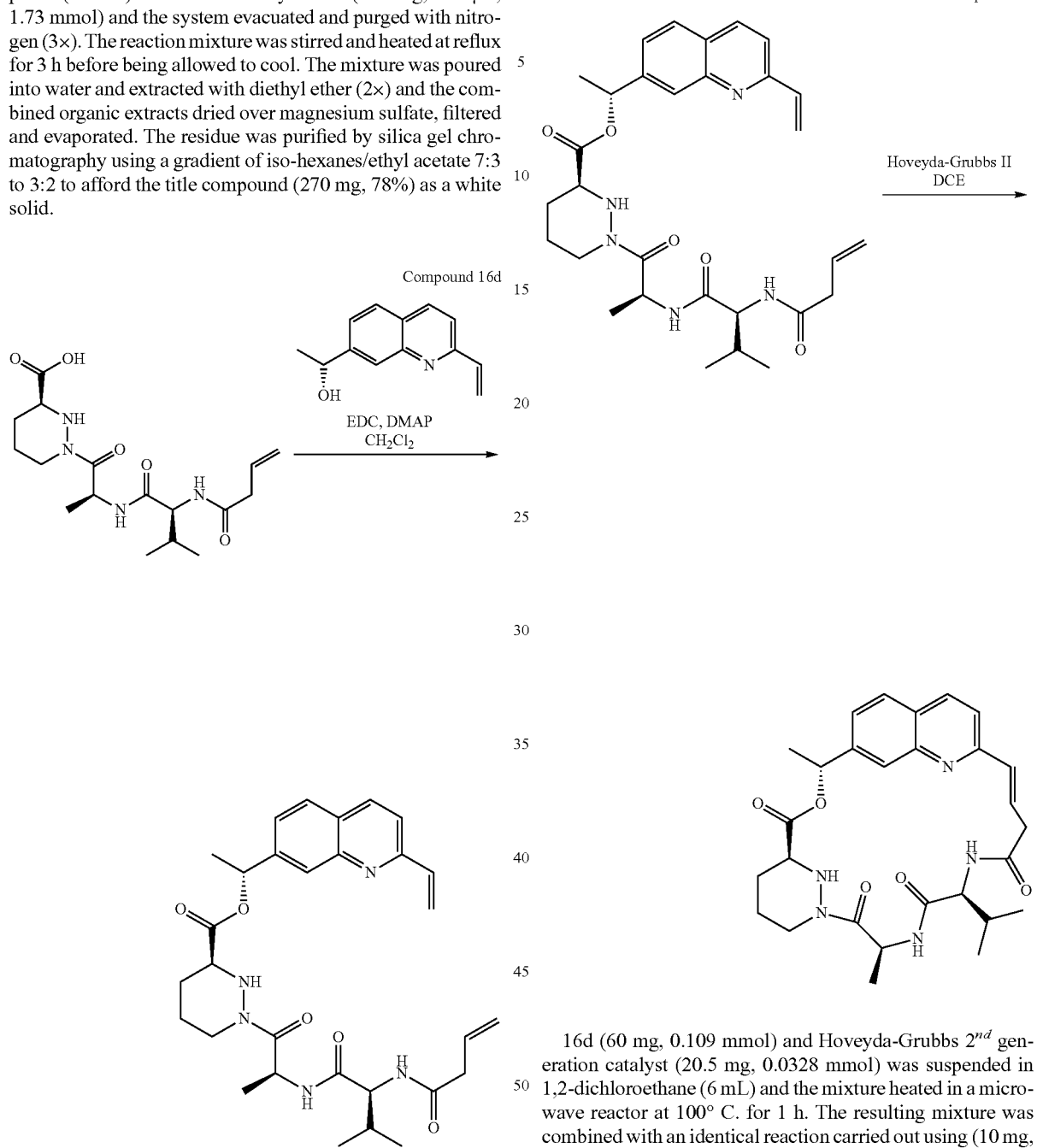

To a stirred mixture of 16c (100 mg, 0.500 mmol) and (S)-[4(S)-2-((S)-2-but-3-enoylamino-3-methyl-butyrylamino)-propionyl]-hexahydro-pyridazine-3-carboxylic acid (203 mg, 0.550 mmol) in dichloromethane (10 mL) under nitrogen was added N-(3-dimethylaminopropyl)-N'-ethyl-carbodiimide hydrochloride (134 mg, 0.700 mmol) and 4-dimethylaminopyridine (61 mg, 0.500 mmol). The reaction mixture was stirred for 16 h and then diluted with dichloromethane, washed successively with citric acid solution, water then brine, dried over sodium sulfate, filtered and evaporated. The residue was purified by silica gel chromatography using a gradient of iso-hexanes/ethyl acetate 1:1 to 0:1 to afford the title compound (103 mg, 38%) as a brown solid.

16d (60 mg, 0.109 mmol) and Hoveyda-Grubbs $2^{nd}$ generation catalyst (20.5 mg, 0.0328 mmol) was suspended in 1,2-dichloroethane (6 mL) and the mixture heated in a microwave reactor at 100° C. for 1 h. The resulting mixture was combined with an identical reaction carried out using (10 mg, 0.0182) of the (S)-[4(S)-2-((S)-2-but-3-enoylamino-3-methyl-butyrylamino)-propionyl]-hexahydro-pyridazine-3-carboxylic acid (R)-1-(2-vinyl-quinolin-7-yl)ethyl ester. The volatiles were evaporated and the residue purified by silica gel chromatography using a gradient of ethyl acetate/acetone 1:0 to 4:1 to give a brown gum. This was further purified by preparative thin layer chromatography using iso-hexanes/ethyl acetate 1:3 to afford the title compound (1.8 mg, 3%) as a white solid. $^1$H NMR (300 MHz, CDCl$_3$) δ 0.84-1.02 (m, 6H), 1.26 (app s, 3H), 1.67-1.72 (m, 3H), 1.83-1.96 (m, 1H), 2.00-2.08 (m, 1H), 2.63-2.74 (m, 1H), 3.24 (d, J=4.5 Hz, 1H), 3.50 (d, J=7.6 Hz, 1H), 4.21 (app t, J=10.3 Hz, 1H), 4.53-4.61 (m, 1H), 5.55 (app t, J=7.3 1H), 6.04-6.11 (m, 2H), 6.32 (d, J=7.8 Hz, 1H), 6.62 (d, J=16.3 Hz, 1H), 6.72-6.80 (m, 1H), 7.29-7.33 (m, 1H), 7.45 (d, J=8.5 Hz, 1H), 7.72 (d, J=8.3 Hz, 1H), 7.97-8.02 (m, 1H). LCMS (m/z) 552.2 [M+H], Tr=1.86 min.

Example 17

Compound 17a

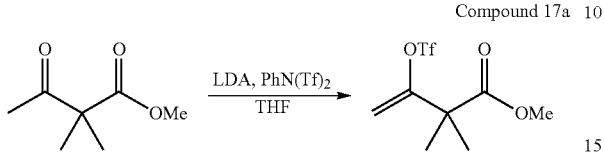

Under argon, a solution of diisopropylamine (2.51 g, 24.8 mmol) in tetrahydrofuran (150 mL) was cooled in an ice water bath. A solution of n-butyllithium in hexanes (2.5 M, 9.7 mL, 24 mmol) was added dropwise over 2 min, and the resulting solution was stirred for 10 additional min. The solution was then cooled to −78° C. in a CO$_2$:acetone bath, and methyl 2,2-dimethyl-3-oxobutanoate (3.2 g, 22 mmol) was added dropwise over 30 s. The solution was stirred for an additional 15 min, and N-phenyl-bis(trifluoromethanesulfonimide) (8.4 g, 23.5 mmol) was added as a solution in tetrahydrofuran (20 mL) via cannula over 5 min, washing with an additional portion of tetrahydrofuran (10 mL). The resulting solution was stirred for 10 min and was removed from the cold bath. After stirring an additional 1 h, the reaction mixture was concentrated in vacuo and diluted with diethyl ether (150 mL). The organic phase was washed with 1 M aqueous sodium hydroxide (1×100 mL, 1×30 mL), dried over anhydrous magnesium sulfate, filtered, and concentrated to afford the title compound (6.2 g, 100%) as an amber liquid that was used without further purification.

Compound 17b

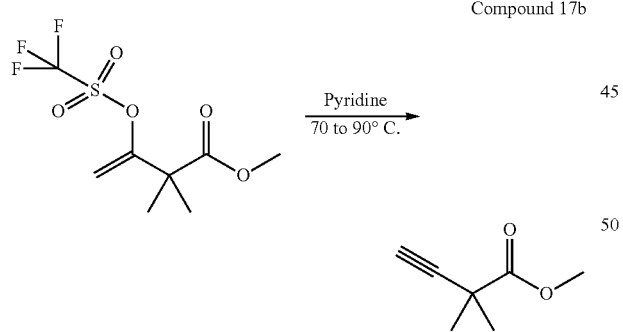

A solution of 17a (6.2 g, 22 mmol) in anhydrous pyridine (11 mL, 140 mmol) was heated to 70° C. After 18.5 h, the temperature was increased to 90° C. After stirring for a total of 72 h, the reaction mixture was partitioned between a stirred mixture of diethyl ether (100 mL) and 3 M aqueous hydrochloric acid (100 mL). The phases were separated, and the organic layer was washed with saturated aqueous sodium bicarbonate (75 mL), dried over magnesium sulfate, filtered, and concentrated to afford the title compound (2.7 g, 97%) as a slightly brown liquid that was used without further purification.

Compound 17c

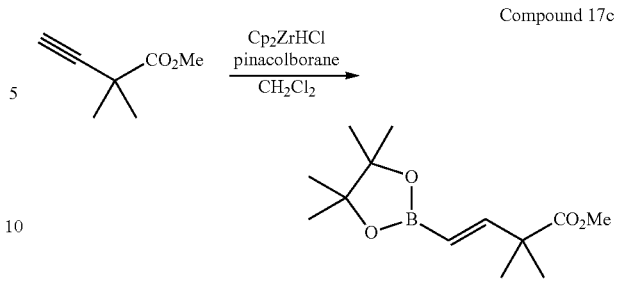

Under argon, bis(cyclopentadienyl)zirconium chloride hydride (290 mg, 1.1 mmol) was cooled in an ice water bath. A solution of 17b (1.4 g, 11.1 mmol) and pinacolborane (2.4 mL, 16.5 mmol) in dichloromethane (3 mL) was added by cannula, washing with an additional portion of dichloromethane (2 mL). The resulting mixture was removed from the cold bath and was stirred for 72 h at RT. The reaction was then diluted with ethyl acetate (50 mL), quenched with dropwise water (5 mL), and was further diluted with water (50 mL). The organic and aqueous phases were separated, and the aqueous phase was extracted with ethyl acetate (30 mL). The combined organic phases were dried over anhydrous sodium sulfate, filtered, and concentrated to afford a crude residue that was purified by silica gel chromatography (5 to 15% ethyl acetate in iso-hexanes) to afford the title compound (1.6 g, 57%) as a colorless oil that crystallized on standing at −15° C.

Compound 17d

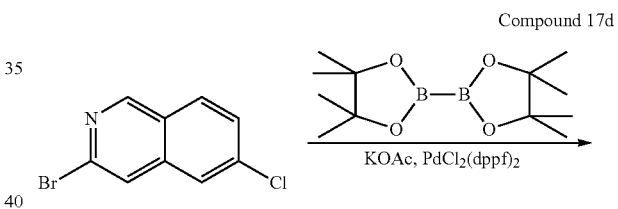

A mixture of 6-bromo-3-chloro-isoquinoline (485 mg, 2.0 mmol), bis(pinacolato)diboron (560 mg, 2.2 mmol), potassium acetate (392 mg, 4.0 mmol) and [1,1'-bis(diphenylphosphino)ferrocene]dichloropalladium(II), complex with dichloromethane (82 mg, 0.1 mmol) in 1,4-dioxane (4 mL) was heated at 160° C. in a microwave for 1 hour. The reaction mixture was filtered through Celite and the filter pad was washed with ethyl acetate. The filtrate was evaporated and the residue was purified by silica gel chromatography using a gradient of dichloromethane to dichloromethane/methanol 9:1 to afford the title compound (545 mg, 94%).

Compound 17e

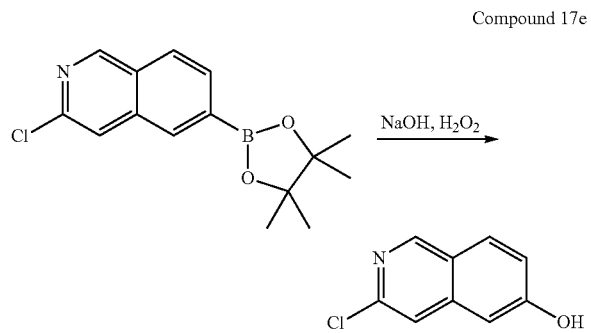

A solution of 17d (1.74 g, 6.0 mmol) in tetrahydrofuran (45 mL) was stirred at 0° C. under nitrogen. Sodium hydroxide solution (2 M, 9 mL, 18 mmol) and hydrogen peroxide (30%, 2.5 24 mmol) were added dropwise. The reaction mixture was stirred at 0° C. for 30 min. Water (30 mL) was added and the solution was acidified to pH 1 with 2 M hydrochloric acid. Sodium metabisulfite solution (1 M) was added and the mixture was extracted with ethyl acetate. The organic extracts were combined, washed with water and brine. The organic solution was filtered through a hydrophobic frit and the filtrate was evaporated to afford the title compound (662 mg, 61%) as an off-white solid.

Compound 17f

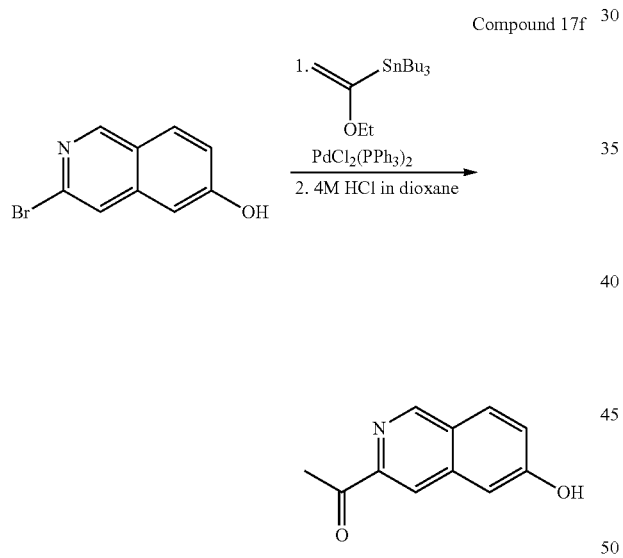

To a solution of 17e (1.25 g, 7.07 mmol) and tributyl-(1-ethoxy-vinyl)-tin (5.09 g, 4.77 mL, 14.1 mmol) in 1,4-dioxane (15 mL) was added bis(triphenylphosphine)palladium(II) dichloride (992 mg, 1.41 mmol) and the reaction mixture was heated at 160° C. in a microwave for 30 min. The reaction mixture was filtered through Celite and the filter pad was washed with ethyl acetate. The filtrate was evaporated and the residue was purified by silica gel chromatography using a gradient of iso-hexanes/ethyl acetate 9:1 to 3:1 to afford 3-(1-ethoxy-vinyl)-isoquinolin-6-ol (670 mg) as a gum which was used crude in the next step. 3-(1-Ethoxy-vinyl)-isoquinolin-6-ol (670 mg) was suspended in 1,4-dioxane (4 mL) and 4 M hydrogen chloride in 1,4-dioxane (8 mL) was added and the reaction mixture was stirred at RT for 30 min. The solvent was evaporated to afford the title compound (584 mg, 44% over 2 steps) as a white solid.

Compound 17g

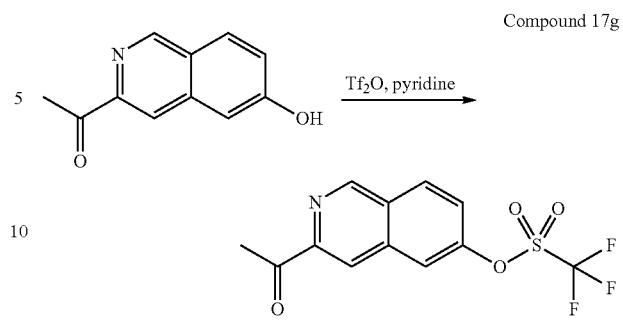

A solution of 17f (384 mg, 2.05 mmol) and pyridine (0.51 mL, 6.16 mmol) in dichloromethane (30 mL) was stirred in a salt-ice bath for 5 min. Trifluoromethanesulfonic anhydride (0.415 mL, 2.46 mmol) was added dropwise and the mixture was warmed to RT over 20 min. Additional trifluoromethanesulfonic anhydride (0.1 mL, 0.6 mmol) was added and the reaction mixture was stirred at RT for 10 min. Saturated ammonium chloride solution was added and the mixture was extracted with dichloromethane. The organic extracts were combined, dried over sodium sulfate, filtered and evaporated. The residue was purified by silica gel chromatography using iso-hexanes/ethyl acetate 19:1 to afford the title compound (300 mg, 44%) as a white solid.

Compound 17h

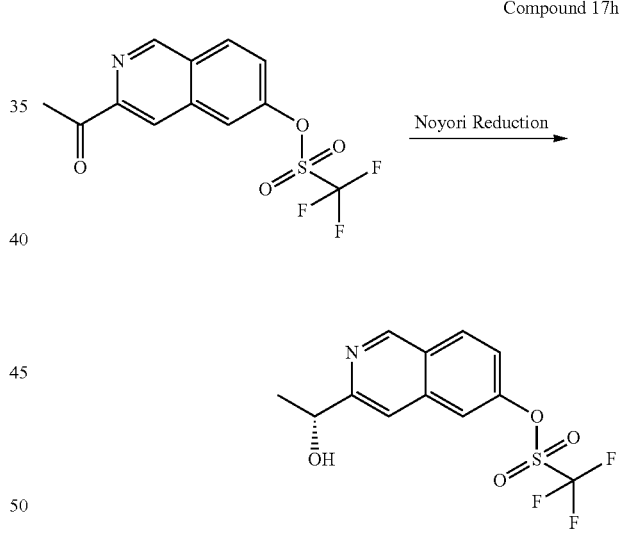

To dichloro(p-cymene)ruthenium (II)dimer (2 mg, 0.003 mmol) in water (2 mL) at RT was added (1R,2R)-(−)-N-p-tosyl-1,2-diphenylethylenediamine (3 mg, 0.008 mmol). The system was degassed for 15 min and then heated to 70° C. for 1.5 h. The reaction was cooled and a solution of 17 g (224 mg, 0.70 mmol) in degassed anhydrous tetrahydrofuran (1 mL) was added followed by sodium formate (237 mg, 3.50 mmol). The system was degassed for 2 min and then heated at 40° C. for 1 hour. After cooling to RT, water was added and the water was extracted with dichloromethane (2×). The combined organic layers were dried through a hydrophobic frit and concentrated in vacuo. The product was purified by silica gel chromatography using iso-hexanes/ethyl acetate 1:1 to afford the title compound (220 mg, 97%) as a brown oil.

Compound 17i

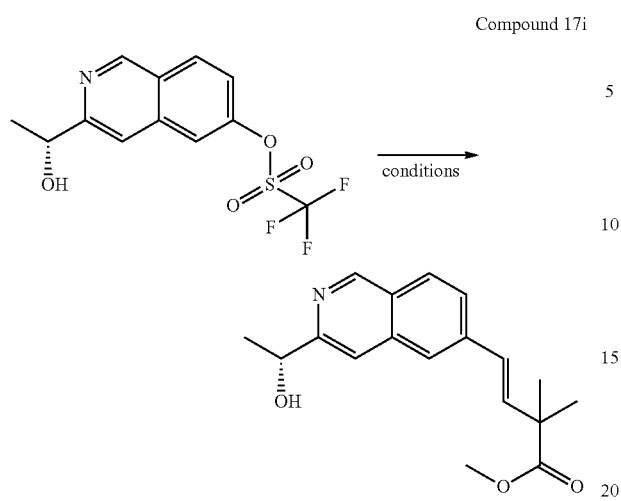

Compound 17k

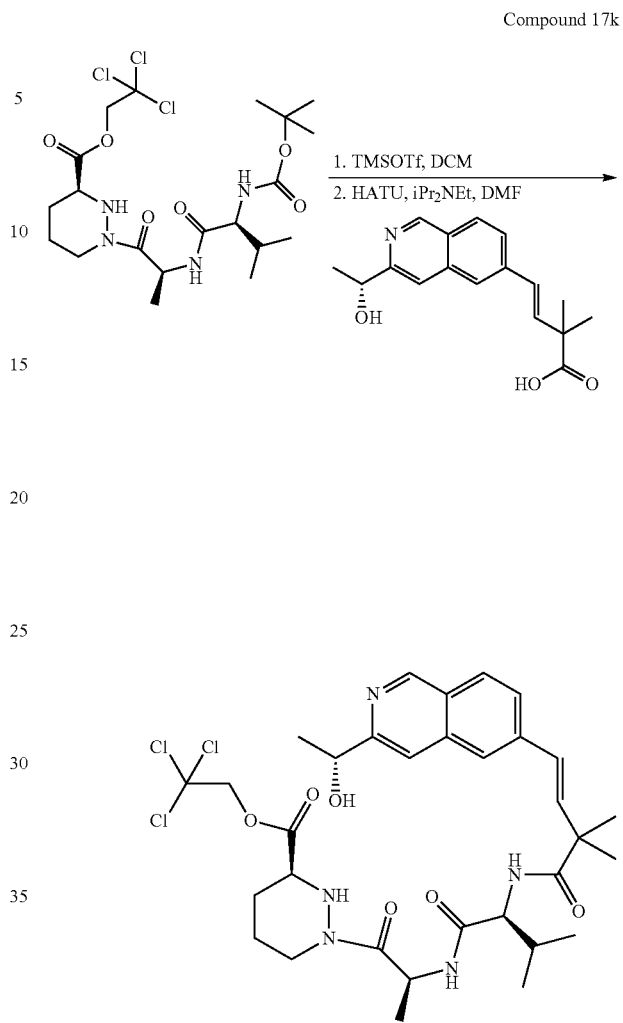

A round bottom flask was charged with 17h (100 mg, 0.31 mmol), (E)-2,2-dimethyl-4-(4,4,5,5-tetramethyl-[1,3,2]dioxaborolan-2-yl)-but-3-enoic acid methyl ester (91 mg, 0.36 mmol), bis[(dicyclohexyl)(4-dimethylaminophenyl)phosphine]palladium(II) chloride (13 mg, 0.02 mmol), potassium phosphate tribasic (198 mg, 0.93 mmol) and lithium chloride (40 mg, 0.93 mmol). The system was flushed with nitrogen and cyclopentyl methyl ether (1 mL) and water (0.5 mL) were added. The reaction was heated for 1 hour at 90° C. and then cooled to RT. Ethyl acetate was added and the solution was washed with water. The organic layer was dried over magnesium sulfate, filtered and concentrated in vacuo. The residue was purified by silica gel chromatography using iso-hexanes/ethyl acetate 1:2 to give the title compound (70 mg, 75%) as a yellow oil.

Compound 17j

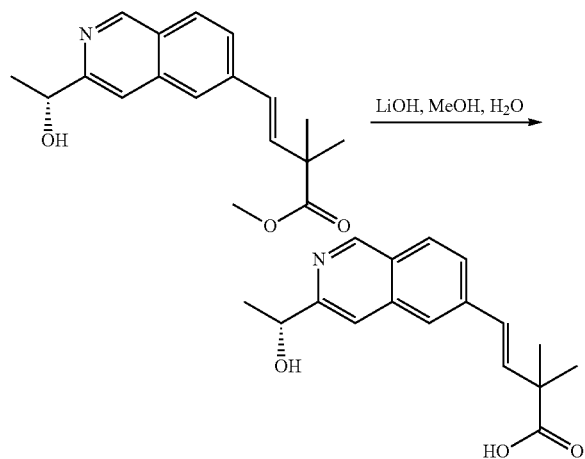

To 17i (140 mg, 0.47 mmol) in tetrahydrofuran (1 mL), methanol (0.5 mL) and water (0.5 mL) was added lithium hydroxide monohydrate (39 mg, 0.93 mmol) at RT. The reaction was stirred for 3 h and quenched by adding 2 M aqueous hydrochloric acid (0.5 mL). The reaction was concentrated in vacuo, followed by co-evaporation from methanol and then toluene. The ensuing yellow solid was used crude.

To 1e (250 mg, 0.47 mmol) in anhydrous dichloromethane (5 mL) at 0° C. and under an atmosphere of nitrogen, was added trimethylsilyl trifluoromethanesulfonate (128 µL, 0.70 mmol). The reaction mixture was stirred at 0° C. for 2 h before adding N,N-diisopropylethylamine (252 µL, 1.41 mmol) and then concentrated in vacuo, and co-evaporated with toluene to afford (S)-1-[(S)-2-((S)-2-amino-3-methyl-butyrylamino)-propionyl]-hexahydro-pyridazine-3-carboxylic acid 2,2,2-trichloro-ethyl ester as a white solid. To 17j (134 mg, 0.47 mmol) in anhydrous N,N-dimethylformamide (2 mL) at RT and under an atmosphere of nitrogen was added N,N-diisopropylethylamine (420 µL, 2.35 mmol) and 2-(1H-7-azabenzotriazol-1-yl)-1,1,3,3-tetramethyl uronium hexafluorophosphate methanaminium (250 mg, 0.66 mmol). The solution was stirred at RT for 3 min before adding a solution of (S)-1-[(S)-2-((S)-2-amino-3-methyl-butyrylamino)-propionyl] hexahydro-pyridazine-3-carboxylic acid 2,2,2-trichloro-ethyl ester in anhydrous N,N-dimethylformamide (2 mL). The reaction was stirred for 16 h. The reaction was quenched with water and extracted with ethyl acetate (2×). The combined organic layers were dried over sodium sulfate, filtered and concentrated in vacuo. The residue was purified by silica gel chromatography using iso-hexanes/acetone 1:1 to give the title compound (220 mg, 67% over 3 steps) as an off white solid.

Compound 17

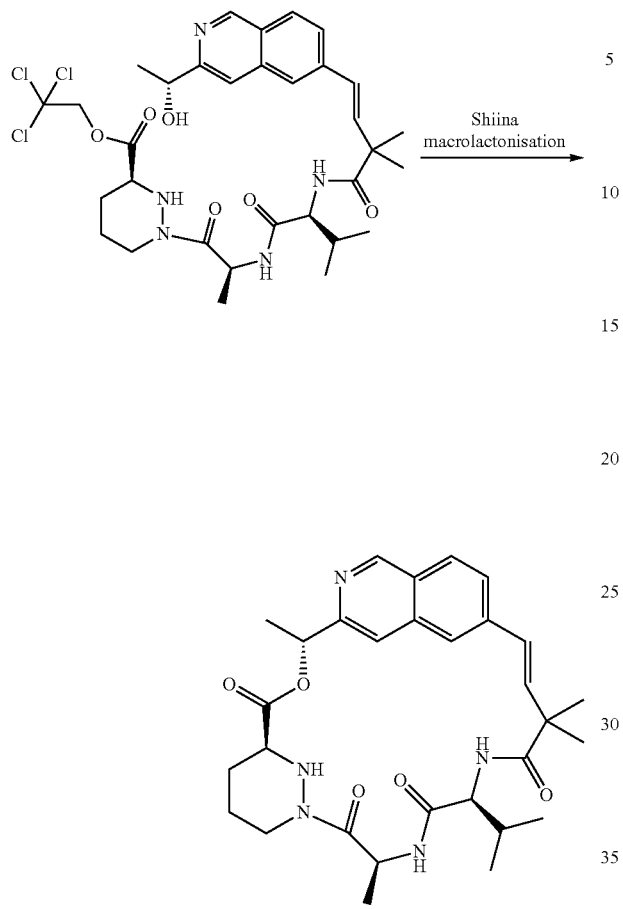

Shiina macrolactonisation →

To 17k (220 mg, 0.31 mmol) in tetrahydrofuran (3 mL), methanol (1.5 mL) and water (1.5 mL) was added lithium hydroxide monohydrate (53 mg, 1.26 mmol) at RT. The reaction was stirred for 1.25 h and quenched by adding 2 M aqueous hydrochloric acid (0.64 mL). The reaction was concentrated in vacuo, followed by co-evaporation from methanol (2×) and then acetonitrile (6×). The resulting residue was dissolved in anhydrous N,N-dimethylformamide (4 mL), and added via syringe pump over 2 h to a suspension of 2-methyl-6-nitrobenzoic anhydride (271 mg, 0.79 mmol), 4-dimethylaminopyridine (288 mg, 2.36 mmol) and powdered 4 Å molecular sieves (3 g) in 1,2-dichloroethane (103 mL) at 50° C. Following the addition the reaction was stirred at 50° C. for 3 h, cooled to RT and filtered through Celite. The filtrate was concentrated to 1/3 of its volume, diluted with dichloromethane and washed with water (2×). The organic layer was dried through a hydrophobic frit and concentrated in vacuo. The residue was purified by silica gel chromatography using iso-hexanes/acetone 1:1 to give an off white solid. The solid was triturated twice with diethyl ether and vacuum dried for 16 h to afford the title compound (65 mg, 38% over 2 steps) as a white powder. $^1$H NMR (300 MHz, CDCl$_3$) 0.93 (d, J=6.7 Hz, 3H), 0.99 (d, J=6.7 Hz, 3H), 1.41 (s, 3H), 1.51 (s, 3H), 1.61 (d, J=7.1 Hz, 3H), 1.76 (d, J=6.7 Hz, 3H), 1.76 (m, 1H), 1.78-2.03 (m, 3H), 2.07-2.17 (m, 1H), 2.62-2.76 (m, 3.62-3.79 (m, 2H), 4.21-4.31 (m, 1H), 4.52-4.62 (m, 1H), 5.82-6.01 (m, 1H), 6.13 (q, J=6.7 Hz, 1H), 6.27 (d, J=16.1 Hz, 1H), 6.30-6.41 (m, 2H), 6.64 (d, J=16.1 Hz, 1H), 7.53 (d, J=8.5 Hz, 1H), 7.71 (s, 1H), 7.82 (s, 1H), 7.90 (d, J=8.5 Hz, 1H), 9.16 (s, 1H). LCMS (m/z) 549.9 [M+H], Tr=5.21 min.

Example 18

Compound 18

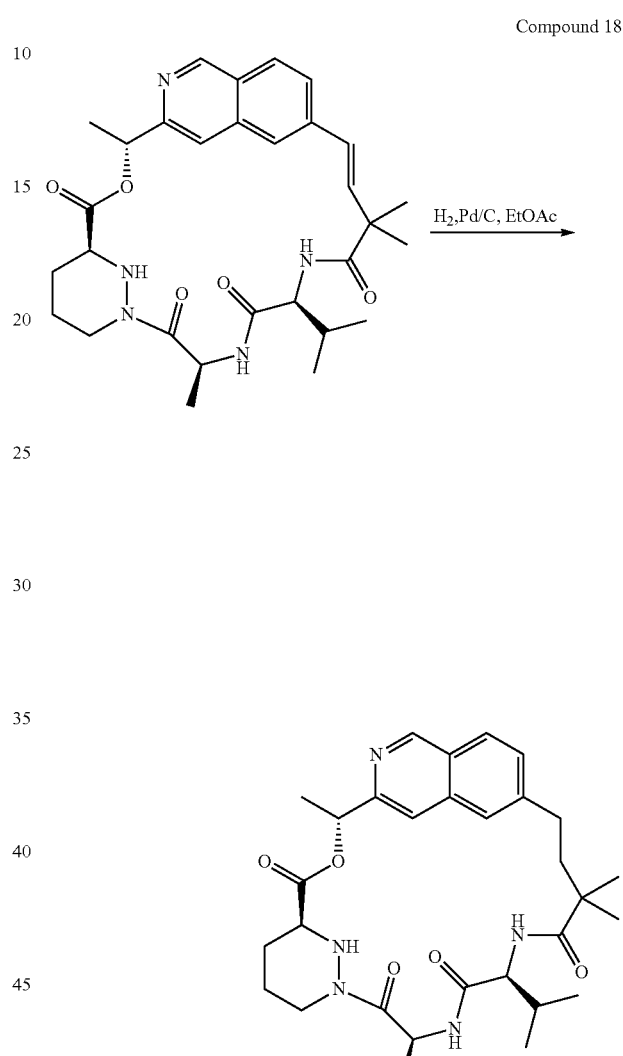

H$_2$,Pd/C, EtOAc →

To Compound 17 (40 mg, 0.073 mmol) in ethyl acetate (10 mL) was added 10% palladium on carbon (30 mg) at RT. The system was purged with hydrogen and stirred vigorously for 16 h. The suspension was filtered through Celite and the filtrate concentrated in vacuo. The residue was purified by silica gel chromatography using iso-hexanes/acetone 1:1 to afford Compound 18 (8 mg, 20%) as a white solid. $^1$H NMR (300 MHz, CDCl$_3$) 0.92 (d, J=6.5 Hz, 3H), 1.00 (d, J=6.5 Hz, 3H), 1.27 (s, 3H), 1.31 (s, 3H), 1.48 (d, J=7.1 Hz, 3H), 1.64-1.79 (m, 1H), 1.75 (d, J=6.7 Hz, 3H), 1.80-2.12 (m, 5H), 2.45 (td, J=12.7, 3.6 Hz, 1H), 2.68-2.93 (m, 2H), 3.62-3.78 (m, 2H), 3.86 (d, J=12.0 Hz, 1H), 4.37 (app t, J=8.3 Hz, 1H), 4.50-4.61 1H), 5.87-6.00 (m, 1H), 6.18 (q, J=6.7 Hz, 1H), 6.38 (d, J=8.7 Hz, 1H), 6.58 (d, J=8.3 Hz, 1H), 7.36 (d, J=8.5 Hz, 1H), 7.42 (s, 1H), 7.64 (s, 1H), 7.83 (d, J=8.5 Hz, 1H), 9.14 (s, 1H). LCMS (m/z) 552.2 [M+H], Tr=5.11 min.

Example 19

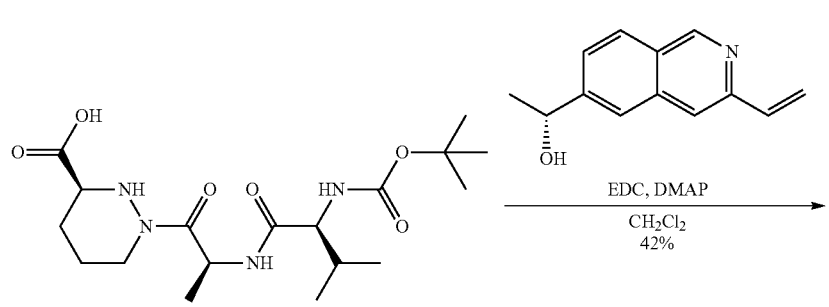

Compound 19a

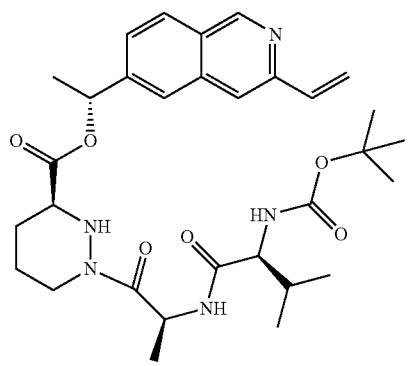

Compound 19b

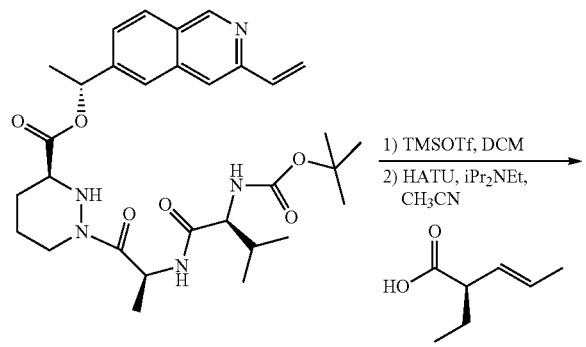

To a solution of (S)-1-[(S)-2-((S)-2-tert-butoxycarbonylamino-3-methyl-butyrylamino)-propionyl]-hexahydro-pyridazine-3-carboxylic acid (339 mg, 0.920 mmol) and (R)-1-(3-vinyl-isoquinolin-6-yl)-ethanol (183 mg, 0.920 mmol) in dichloromethane (4.6 mL) were added N-(3-dimethylaminopropyl)-N'-ethylcarbodiimide hydrochloride (211 mg, 1.10 mmol) and 4-dimethylaminopyridine (56.2 mg, 0.46 mmol) at 23° C. under an argon atmosphere. After 21 h, the reaction mixture was purified directly by silica gel flash column chromatography to afford the title compound (224 mg, 42%) as a light tan solid.

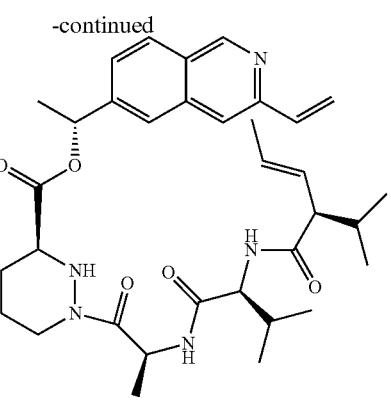

-continued

To 19a (800 mg, 1.38 mmol) in anhydrous dichloromethane (12 mL) at 0° C. and under an atmosphere of nitrogen, was added trimethylsilyl trifluoromethanesulfonate (374 µL, 2.07 mmol). The reaction mixture was stirred at 0° C. for 2 h before adding N,N-diisopropylethylamine (480 2.75 mmol) and then concentrated in vacuo to afford a white solid. To the solid was added a solution of (E)-(R)-2-ethylpent-3-enoic acid (188 mg, 1.65 mmol) in anhydrous acetonitrile (12 mL) followed by N,N-diisopropylethylamine (240 µL, 1.38 mmol) and 2-(1H-7-azabenzotriazol-1-yl)-1,1,3,3-tetramethyl uranium hexafluorophosphate methanaminium (733 mg, 1.93 mmol). The reaction was stirred at RT for 3 h and concentrated in vacuo. The residue was purified by silica gel chromatography using iso-hexanes/ethyl acetate 1:2 then 1:5 to give the title compound (250 mg, 74% over 2 steps) as a viscous yellow oil.

Compound 19

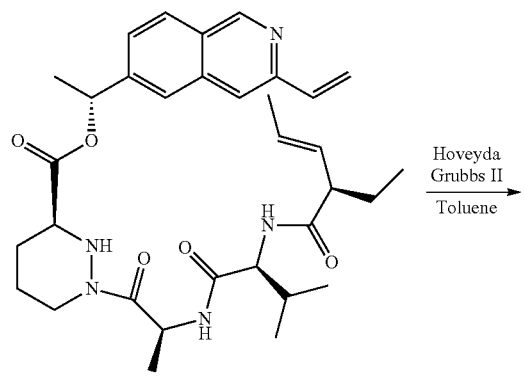

Hoveyda
Grubbs II
Toluene

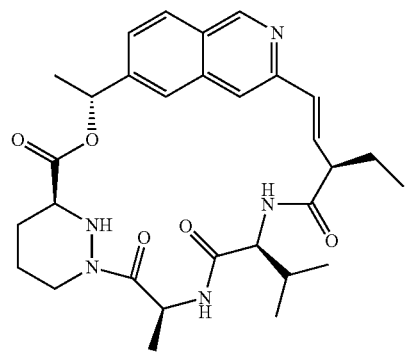

To 19b (200 mg, 0.34 mmol) in anhydrous toluene (113 mL) at 70° C. and under an atmosphere of nitrogen, was added Hoveyda-Grubbs $2^{nd}$ generation catalyst (42 mg, 0.07 mmol). The reaction was heated at 120° C. for 2 h after which an additional amount of the Hoveyda-Grubbs $2^{nd}$ generation catalyst (30 mg, 0.05 mmol) was added. Following a further 2 h at 120° C. the reaction was cooled to RT and potassium isocyanoacetate (83 mg) in methanol (2 mL) was added. The reaction was stirred for 1 hour, silica added and then concentrated in vacuo. The residue was purified by silica gel chromatography using ethyl acetate/acetone 3:1 to afford a brown solid. This was purified further by reverse phase preparative HPLC to give the title compound (2.2 mg, 1%) as a white solid. $^1$H NMR (300 MHz, CD$_3$OD) 0.97 (d, J=6.5 Hz, 3H), 1.02 (d, J=6.5 Hz, 3H), 1.11 (t, J=7.4 Hz, 3H), 1.64 (d, J=7.1 Hz, 3H), 1.70 (d, J=6.7 Hz, 3H), 1.71-2.06 (m, 7H), 2.66-2.82 (m, 1H), 3.13-3.22 (m, 1H), 3.75-3.85 (m, 1H), 4.30-4.48 (m, 2H), 5.51-5.67 (m, 1H), 6.07 (q, J=6.3 Hz, 1H), 6.48-6.57 (m, 1H), 6.61 (d, J=16.5 Hz, 1H), 7.47 (s, 1H), 7.58 (d, J=8.7 Hz, 1H), 7.89 (s, 1H), 8.07 (d, J=8.7 Hz, 1H), 9.15 (s, 1H). LCMS (m/z) 550.2 [M+H], Tr=1.67 min.

Example 20

Compound 20a

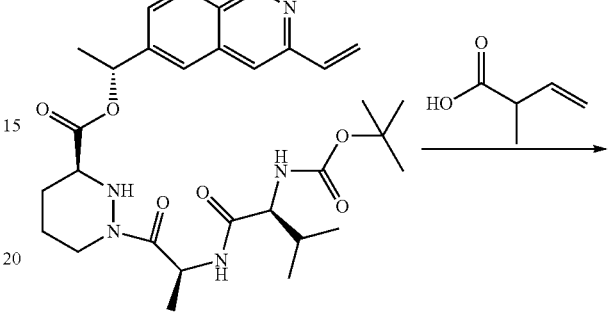

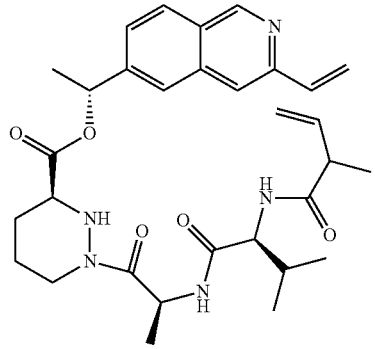

To 19a (390 mg, 0.67 mmol) in anhydrous dichloromethane (7 mL) at 0° C. and under an atmosphere of nitrogen, was added trimethylsilyl trifluoromethanesulfonate (182 μL, 1.01 mmol). The reaction mixture was stirred at 0° C. for 1 hour before quenching with a saturated aqueous solution of sodium hydrogen carbonate and extracting with ethyl acetate (2×). The organic layers were dried over sodium sulfate, filtered and concentrated in vacuo to afford a white solid. The solid was dissolved in anhydrous acetonitrile (4 mL) and 2-methyl-but-3-enoic acid (81 mg, 0.81 mmol), N-(3-dimethylaminopropyl)-N'-ethylcarbodiimide hydrochloride (184 mg, 0.94 mmol) and 1-hydroxybenzotriazole monohydrate (103 mg, 0.67 mmol) were added. The reaction was stirred at RT for 16 h and concentrated in vacuo. The residue was purified by silica gel chromatography using iso-hexanes/ethyl acetate 1:1 then 1:3 to give the title compound (259 mg, 69%) as a clear viscous oil.

Compound 20

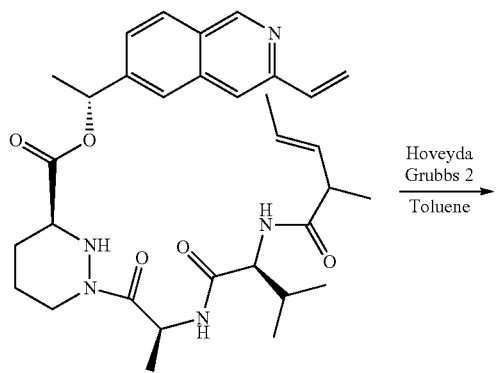

Hoveyda Grubbs 2
Toluene

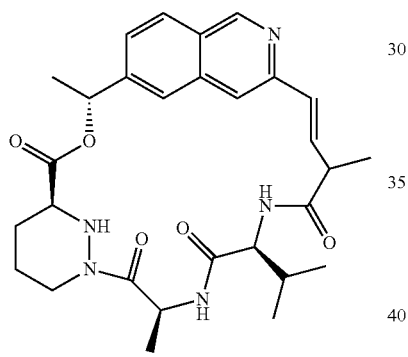

To 20a (250 mg, 0.44 mmol) in degassed anhydrous toluene (148 mL) was added 2,6-dichlorobenzoquinone (8 mg, 0.04 mmol). The mixture was heated to 105° C. and a solution of Hoveyda-Grubbs $2^{nd}$ generation catalyst (83 mg, 0.13 mmol) in anhydrous toluene (20 mL), was added via syringe pump over 2 h. An additional amount of Hoveyda-Grubbs $2^{nd}$ generation catalyst (28 mg) was added and the reaction heated to reflux for 1 h. The reaction was cooled to RT, silica gel was added and concentrated in vacuo. The residue was purified by silica gel chromatography using ethyl acetate/acetone 1:0 then 3:1 to afford an oil. This was triturated with diethyl ether and a few drops of ethyl acetate to afford a brown solid which was further purified by preparative TLC using ethyl acetate/acetone 5/1 to give the title compound (9 mg, 1%) as an off-white solid. $^1$H NMR (300 MHz, CDCl$_3$) 0.97 (d, J=6.7 Hz, 3H), 1.01 (d, J=6.7 Hz, 3H), 1.38 (d, J=6.7 Hz, 3H), 1.62 (d, J=7.1 Hz, 3H), 1.70 (d, J=6.9 Hz, 3H), 1.72-1.82 (m, 2H), 1.91-2.01 (m, 2H), 2.03-2.12 (m, 1H), 2.62-2.74 (m, 1H), 3.35 (app t, J=7.4 Hz, 1H), 3.59 (d, J=12.5 Hz, 1H), 3.65-3.77 (m, 1H), 4.26 (app t, J=8.9 Hz, 1H), 4.51-4.60 (m, 1H), 5.68-5.79 (m, 1H), 6.06 (q, J=6.7 Hz, 1H), 6.16 (d, J=9.2 Hz, 1H), 6.27 (d, J=9.2 Hz, 1H), 6.40 (dd, J=16.0, 7.8 Hz, 1H), 6.71 (d, J=16.0 Hz, 1H), 7.39 (dd, J=8.5, 1.3 Hz, 1H), 7.58 (s, 1H), 7.74 (s, 1H), 7.93 (d, J=8.5 Hz, 1H), 9.16 (s, 1H). LCMS (m/z) 536.2 [M+H], Tr=1.63 min.

Example 21

Compound 21a

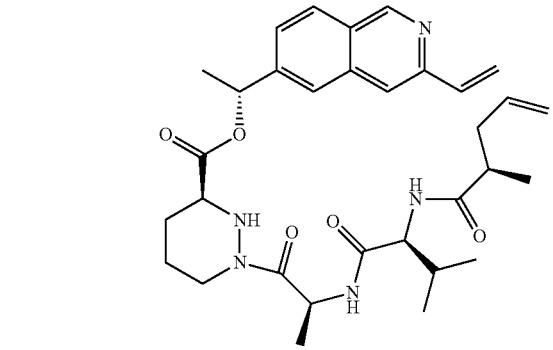

1) TMSOTf
2) HATU, iPr$_2$NEt 21a was prepared in the same manner as 20a replacing 2-methyl-but-3-enoic acid with (R)-2-methyl-pent-4-enoic acid (prepared as described in Synlett 2002, No 12, 2039-2040, 82 mg, 0.72 mmol), to afford the title compound (280 mg, 67%) as a white foam.

Compound 21

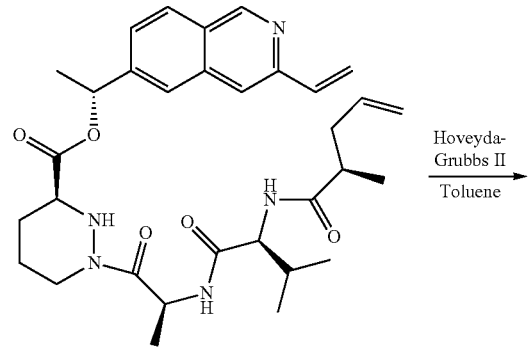

Hoveyda-Grubbs II
Toluene

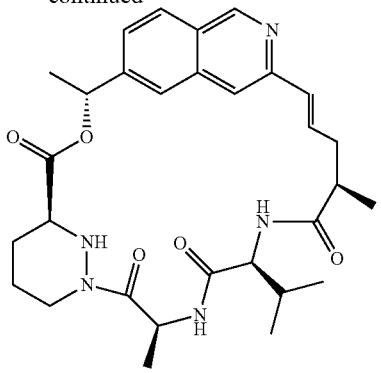

To 21a (250 mg, 0.43 mmol) in anhydrous toluene (144 mL) at RT and under an atmosphere of nitrogen, was added Hoveyda-Grubbs $2^{nd}$ generation catalyst (54 mg, 0.09 mmol). The reaction was heated at 120° C. for 2 h after which an additional amount of the Hoveyda-Grubbs $2^{nd}$ generation catalyst (25 mg, 0.04 mmol) was added. Following a further 1 h at 120° C. the reaction was cooled to RT and concentrated in vacuo. The residue was purified by silica gel chromatography using ethyl acetate/acetone 1:0 then 3:1 to afford a brown solid. This was triturated with diethyl ether/ethyl acetate 3:1 to give the title compound (50 mg, 22%) as an off-white solid. $^1$H NMR (300 MHz, CDCl$_3$) 0.91 (d, J=6.7 Hz, 3H), 0.99 (d, J=6.7 Hz, 3H), 1.29 (d, J=7.1 Hz, 3H), 1.59 (d, J=6.7 Hz, 3H), 1.67 (d, J=6.5 Hz, 3H), 1.70-1.84 (m, 1H), 1.92-2.15 (m, 4H), 2.33-2.48 (m, 1H), 2.63-2.98 (m, 3H), 3.53 (d, J=12.2 Hz, 1H), 3.60-3.72 (m, 1H), 4.42 (dd, J=6.7, 2.2 Hz, 1H), 4.52-4.61 (m, 1H), 5.62-5.74 (m, 1H), 6.11 (q, J=6.7 Hz, 1H), 6.16 (q, J=8.9 Hz, 1H), 6.42 (d, J=8.5 Hz, 1H), 6.53-6.66 (m, 1H), 6.75 (d, J=16.1 Hz, 1H), 7.37 (dd, J=8.7, 1.0 Hz, 1H), 7.80-7.96 (m, 3H), 9.16 (s, 1H). LCMS (m/z) 550.3 [M+H], Tr=1.50 min.

Example 22

Compound 22a

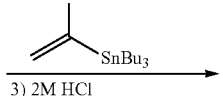

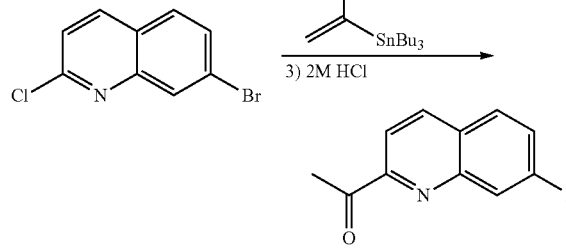

To a stirred slurry of 7-bromo-2-chloro-quinoline (8.10 g, 33.4 mmol) and sodium iodide (50.0 g, 334 mmol) in acetonitrile (27 mL) was slowly added acetyl chloride (3.56 mL, 50.0 mmol). The flask was stoppered and sealed and heated at 80° C. for 3 h before being allowed to cool. The mixture was treated sequentially with 10% w/w aqueous potassium carbonate solution (80 mL), 5% w/w aqueous sodium sulfite solution (80 mL) and saturated aqueous sodium thiosulfate solution (80 mL) and the mixture extracted with dichloromethane (2×). The combined organic extracts were dried over sodium sulfate, filtered and evaporated to give a crude 7-bromo-2-iodo-quinoline. To the quinoline was added tributyl(1-ethoxyvinyl)tin (13.6 mL, 40.1 mmol), 1,4-dioxane (67 mL) and bis(triphenylphosphine)palladium(II)dichloride (2.37 g, 3.34 mmol) and the reaction mixture heated at 100° C. for 5 h before allowing to cool. 2 M Aqueous hydrochloric acid (67 mL) was added and the reaction stirred for 1 h. The mixture was filtered and the solids washed with ethyl acetate and the filtrate evaporated to remove organics. The residue was extracted with ethyl acetate (3×) and the combined organic extracts were dried over sodium sulfate, filtered and evaporated. The product was purified on silica gel doped with 10% w/w potassium carbonate eluting with a gradient of 0 to 6% ethyl acetate in iso-hexanes to afford the title compound (5.5 g, 66%) as a white solid.

Dichloro(p-cymene)ruthenium(II)dimer (61 mg, 0.100 mmol) and (1R,2R)-(−)-N-p-tosyl-1,2-diphenylethylenediamine (88 mg, 0.012 mmol) was suspended in degassed water (40 mL) and the mixture was degassed with nitrogen for 5 min. The mixture was stirred at 70° C. under nitrogen for 90 min. The resulting turbid orange mixture was allowed to cool to RT. 22a (5.00 g, 20 mmol) in degassed tetrahydrofuran (40 mL) was added followed by sodium formate (6.8 g, 100 mmol) and the reaction mixture was degassed with nitrogen for 5 min. The reaction mixture was vigorously stirred at 40° C. for 4 h and allowed to cool. It was then diluted with ethyl acetate and water and the organic layer was separated, washed with water and brine, dried over sodium sulfate, filtered and evaporated. The residue was purified by silica gel chromatography using a gradient of 0% to 30% ethyl acetate in iso-hexanes to afford the title compound (4.96 g, 98%) as an off-white solid.

Compound 22c

To a solution of 22b (1.00 g, 3.97 mmol) and triethylamine (1.65 mL, 11.9 mmol) in anhydrous dichloromethane at 0° C., was added acetic anhydride (0.75 mL, 7.93 mmol) and 4-(dimethylamino)pyridine (24 mg, 0.197 mmol). The reaction mixture was stirred and allowed to warm to RT. After 1.5 h water (100 mL) was added and the layers separated. The aqueous phase was re-extracted with dichloromethane (2×100 mL) and the combined organics were washed with brine (100 mL), dried over magnesium sulfate, filtered and concentrated in vacuo to give a crude residue. This was purified by silica gel chromatography using iso-hexanes (66 mL) then iso-hexanes/ethyl acetate 95:5 (300 mL), then iso-hexanes/ethyl acetate 9:1 (1066 mL) to yield the title compound (1.16 g, 99%) as a colorless oil.

Compound 22d

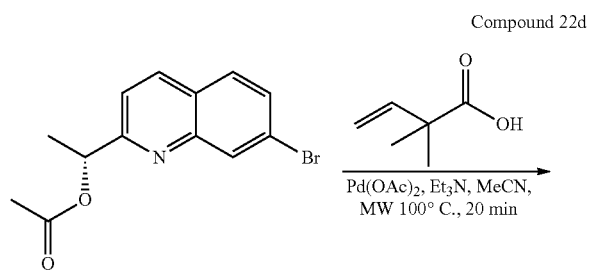

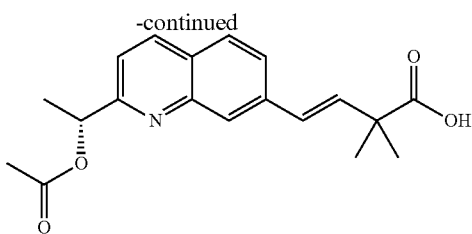

To a solution of acetic acid 22c (1.16 g, 3.95 mmol) in anhydrous acetonitrile was added palladium(II) acetate (89 mg, 0.395 mmol), 2,2-dimethyl-but-3-enoic acid (496 mg, 4.35 mmol), tri(o-tolyl)phosphine (241 mg, 0.790 mmol) and triethylamine (1.09 mL, 7.90 mmol) then the mixture was heated in the microwave at 100° C. for 20 min. The reaction mixture was concentrated in vacuo then water (200 mL) was added and the organics extracted with ethyl acetate (2×50 mL). The combined organics were dried over sodium sulfate, filtered and concentrated in vacuo to give a crude residue. This was purified by silica gel chromatography using iso-hexanes/ethyl acetate 95:5 (300 mL), then iso-hexanes/ethyl acetate 9:1 (1066 mL) then iso-hexanes/ethyl acetate 3:1 (1066 mL) to yield the title compound (792 mg, 61%) as a white solid.

Compound 22e

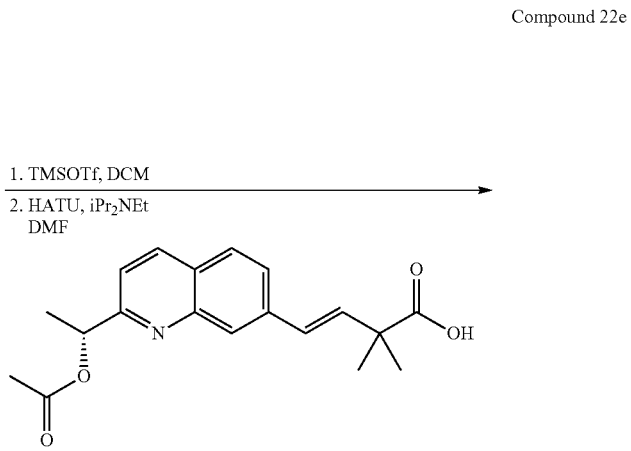

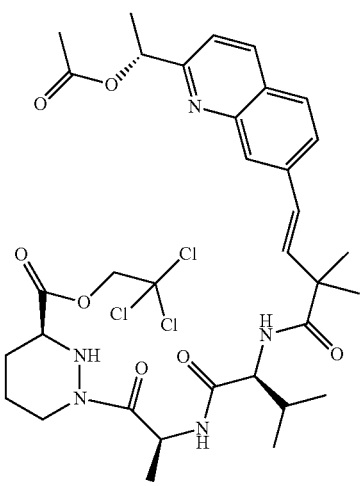

A solution of 1e (1.29 g, 2.42 mmol) in dichloromethane (12 mL) was cooled in an ice-water bath under nitrogen. Trimethylsilyl trifluoromethanesulfonate (0.715 mL, 4.84 mmol) was added dropwise, and the resulting solution was stirred for 1 h. The reaction was quenched with N,N-diisopropylethylamine (1.69 mL, 9.68 mmol) and the reaction mixture was concentrated in vacuo to give (S)-1-[(S)-2-((S)-2-amino-3-methyl-butyrylamino)-propionyl]-hexahydropyridazine-3-carboxylic acid 2,2,2-trichloro-ethyl ester as a white solid which was used without further purification. To a solution of 22d (792 mg, 2.42 mmol) in N,N-dimethylformamide (10 mL) at 0° C. under nitrogen was added N,N-diisopropylethylamine (2.11 mL, 12.1 mmol) and 2-(1H-7-azabenzotriazol-1-yl)-1,1,3,3-tetramethyl uronium hexafluorophosphate methanaminium (1.01 g, 2.66 mmol). The resulting mixture was stirred at RT for 15 min then re-cooled to 0° C. and (S)-1-[(S)-2-((S)-2-amino-3-methyl-butyrylamino)-propionyl]-hexahydro-pyridazine-3-carboxylic acid 2,2,2-trichloro-ethyl ester generated in the previous step, was added as a solution in N,N-dimethylformamide (10.7 mL). The reaction mixture was then allowed to warm to RT with stirring. After 1 h the mixture was diluted with ethyl acetate (100 mL) and water (100 mL). The phases were separated and the aqueous was extracted with ethyl acetate (100 mL). The combined organics were washed with brine (100 mL), dried over magnesium sulfate, filtered and concentrated in vacuo to give a crude residue. This was purified by silica gel chromatography using iso-hexanes/acetone 95:5 (1000 mL) then iso-hexanes/acetone 9:1 (1 L) then iso-hexanes/acetone 85:15 (1 L) then iso-hexanes/acetone 3:1 (1 L) then iso-hexanes/acetone 7:3 (1 L) to yield the title compound (1.11 g, 62%) as a colorless solid.

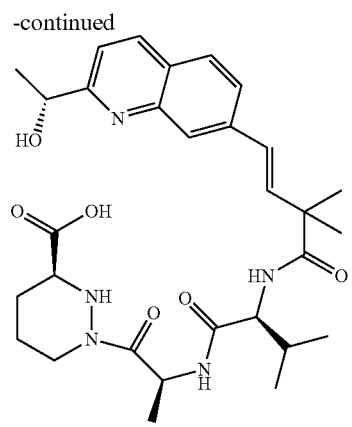

A solution of 22e (1.11 g, 1.50 mmol) in tetrahydrofuran (14.7 mL) was cooled in an ice-water bath and methanol (7.4 mL), water (7.4 mL), and lithium hydroxide monohydrate (252 mg, 6.0 mmol) were then added. The mixture was stirred for 1 h in the ice-water bath and then quenched with aqueous 1 M hydrochloric acid (6 mL, 6.0 mmol). The resulting solution was concentrated in vacuo, and the crude product was concentrated from methanol (4×250 mL) then acetonitrile (4×250 mL) and toluene (5×250 mL). The solid isolated was then left on the freeze dryer overnight to afford the title compound (853 mg, quantitative yield) as a white solid.

Compound 22

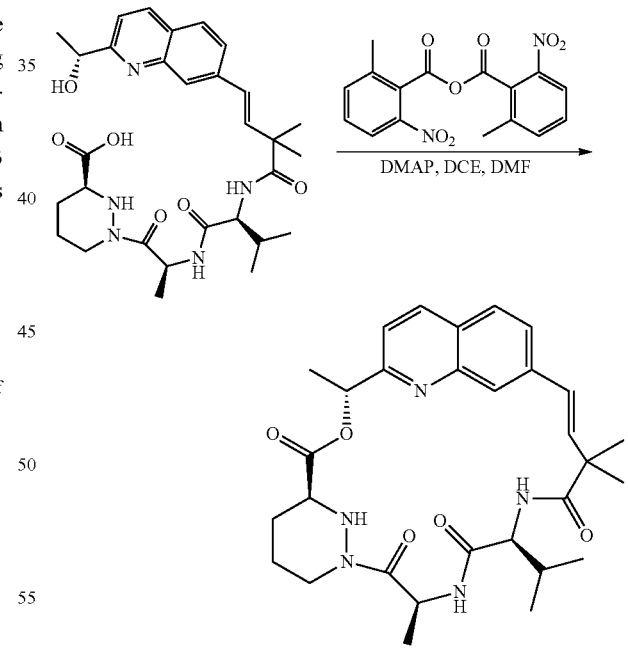

Compound 22f

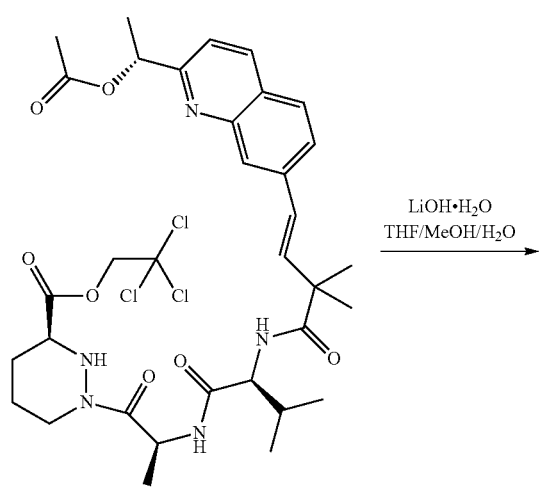

Under nitrogen, 2-methyl-6-nitrobenzoic anhydride (2.59 g, 7.51 mmol) and 4-(dimethylamino)pyridine (1.38 g, 11.3 mmol) were dissolved in 1,2-dichloroethane (500 mL) and the resulting solution was heated to 50° C. The crude seco-acid from the previous step, 22f (853 mg, 1.50 mmol) was dissolved in N,N-dimethylformamide (19 mL) and added to the reaction mixture dropwise via syringe pump over 6 h. After the addition was complete, the syringe pump was then rinsed with additional N,N-dimethylformamide (3 mL) and the reaction mixture was stirred at 50° C. for 40 min. After this time the mixture was concentrated to give a residue. This was purified by silica gel chromatography using iso-hexanes (66 mL), then iso-hexanes/acetone 4:1 (726 mL), then iso-hexanes/acetone 7:3 (726 mL), then iso-hexanes/acetone 3:2 (726 mL). This initial column gave impure product (1.10 g) which contained N,N-dimethylformamide. To this was added brine (200 mL) and the organics extracted with ethyl acetate (2×100 mL). The combined organics were dried over magnesium sulfate, filtered and concentrated in vacuo to give impure product (900 mg) which does not contain N,N-dimethylformamide. This residue was purified by a second silica gel chromatography using iso-hexanes/acetone 95:5 (6 L), then iso-hexanes/acetone 93:7 (1.5 L), then iso-hexanes/acetone 88:12 (3 L), then iso-hexanes/acetone 82:16 until all the product eluted from the column. Two batches of the desired product in 87% purity (batch A) and 77% purity (batch B) were isolated. Batch A was triturated twice with 100% diethyl ether to give the title compound (241 mg) in approximately 90-95% purity. Purification of Batch B by preparative reverse phase HPLC gave the title compound (181 mg) in approximately >95% purity. Batch A and B were combined to give the title compound (422 mg, 51%) as a white solid. $^1$H NMR (500 MHz, CD$_3$OD) 0.94 (app t, J=6.7 Hz, 6H), 1.34 (s, 3H), 1.48 (s, 3H), 1.58 (d, J=7.3 Hz, 3H), 1.62-1.75 (m, 5H), 1.82-1.91 (m, 1H), 1.92-2.03 (m, 2H), 2.66-2.78 (m, 1H), 3.78 (app d, J=8.5 Hz, 1H), 4.25-4.33 (m, 1H), 4.34-4.43 (m, 1H), 5.71 (q, J=7.3 Hz, 1H), 5.89 (q, J=6.7 Hz, 1H), 6.24 (d, J=16.0 Hz, 1H), 6.46 (d, J=16.0 Hz, 1H), 7.27 (br d, J=9.8 Hz, 1H), 7.38 (d, J=8.6 Hz, 1H), 7.60 (s, 1H), 7.75 (ABq, $\Delta\delta_{AB}$=0.03, $J_{AB}$=8.54 Hz, 2H), 8.18 (d, J=7.9 Hz, 1H). LCMS (m/z) 550.1 [M+H], Tr=2.24 min.

Example 23

Compound 23a

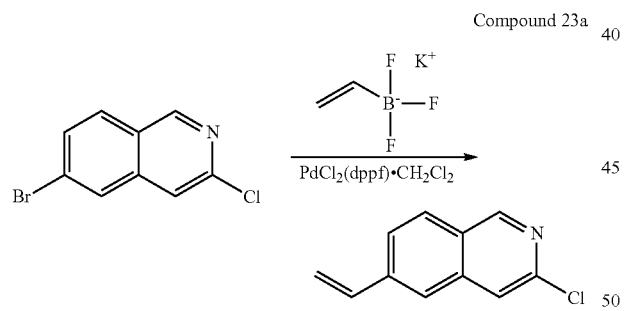

A solution of 6-bromo-3-chloro-isoquinoline (2.0 g, 8.25 mmol) in n-propanol (90 mL) was prepared and potassium vinyltrifluoroborate (1.11 g, 8.25 mmol) was added. The solution was purged with nitrogen for 10 min before addition of [1,1'-bis(diphenylphosphino)ferrocene]dichloropalladium (II), complex with dichloromethane (128 mg, 0.157 mmol) and triethylamine (1.15 mL, 8.25 mmol). The reaction mixture was then purged with nitrogen for a further 3 min before heating to reflux for 1 h. The reaction mixture was then allowed to cool to RT and water was added. The organics were then extracted with diethyl ether (3×150 mL). The combined organics were dried over magnesium sulfate, filtered and concentrated in vacuo to give a crude residue. This was purified by silica gel chromatography, using iso-hexanes/diethyl ether 9:1 to give the title compound (1.26 g, 80%) as an oil.

Compound 23b

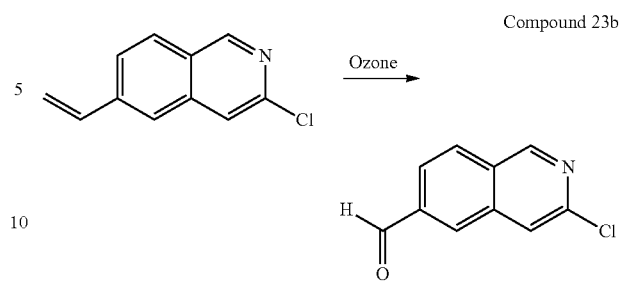

A suspension of 23a (1.24 g, 6.54 mmol) in methanol (125 mL) and dichloromethane (125 mL) was cooled to −78° C. The reaction was ozonised until a blue colour persisted (in approximately 15 min), then nitrogen was bubbled through the reaction mixture for 15 min to purge the ozone. The reaction was then treated with solid sodium bicarbonate (549 mg, 6.54 mmol) and dimethyl sulfide (1.31 mL, 1.31 mmol). The mixture was allowed to warm to RT and after 3 h the reaction mixture was concentrated in vacuo. Water (200 mL) was added to the residue and the aqueous layer extracted with dichloromethane (3×200 mL). The combined organics were dried over magnesium sulfate, filtered and concentrated in vacuo to give the title compound (1.02 g, 81%) as an oil.

Compound 23c

To a solution of 23b (1.02 g, 5.32 mmol) in tetrahydrofuran (10 mL) at 0° C. was added trimethyl(trifluoromethyl)silane solution (3.19 mL, 2 M in tetrahydrofuran, 6.38 mmol) followed by tetrabutylammonium fluoride solution (0.053 mL, 1 M in tetrahydrofuran, 0.053 mmol) and the resulting solution was stirred at 0° C. for 1.5 h. The reaction mixture was then allowed to warm to RT and 2 M hydrochloric acid (10 mL) was added and the mixture stirred for 10 min before addition of water (200 mL). The aqueous layer was then extracted with ethyl acetate (3×100 mL). The organics were combined, dried over sodium sulfate, filtered and concentrated to give the title compound (1.30 g, 93%) as a solid.

Compound 23d

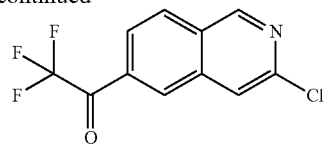

To a solution of 23c (1.30 g, 4.97 mmol) in dichloromethane (14.7 mL) at 0° C. was added Dess-Martin periodinane solution (14.7 mL, 15% in dichloromethane, 6.96 mmol) and the reaction mixture was stirred and allowed to warm to RT. 1 M Aqueous sodium metabisulfite (100 mL) was added and the reaction mixture was stirred for 15 min. To this mixture was added saturated aqueous sodium bicarbonate solution (100 mL) and the aqueous layer was extracted with dichloromethane (3×100 mL). The combined organics were washed with saturated aqueous sodium bicarbonate solution (200 mL) followed by brine (100 mL), dried over magnesium sulfate, filtered and concentrated in vacuo to give the title compound (1.0 g, 78%) as a solid.

Compound 23e

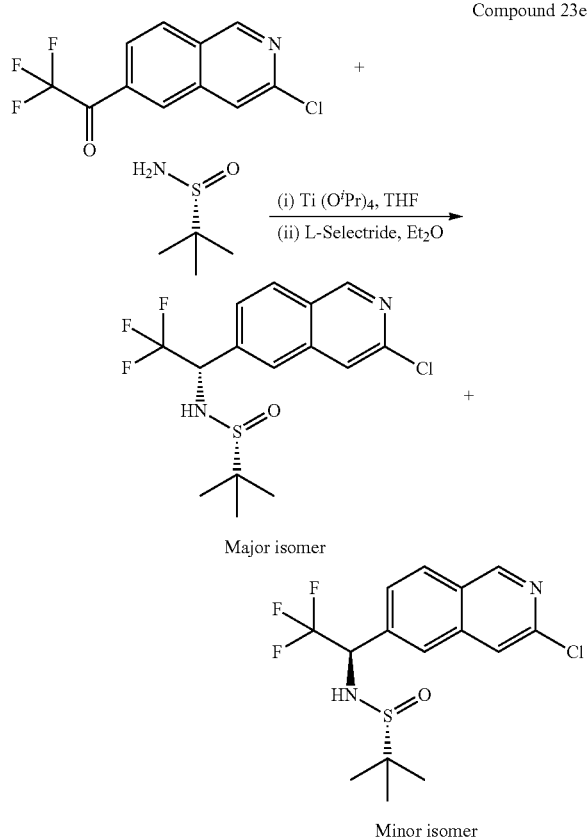

A mixture of 23d (686 mg, 2.64 mmol), (R)-2-methyl-2-propanesulfinamide (400 mg, 3.30 mmol) and titanium(IV) isopropoxide (1.95 mL, 6.60 mmol) in tetrahydrofuran (27.4 mL) was heated at reflux for 16 h then allowed to cool to RT. The reaction mixture was concentrated in vacuo and re-dissolved in diethyl ether (27.4 mL) then cooled to −78° C. To this mixture was added L-selectride® solution (7.93 mL, 1.0 M in tetrahydrofuran, 7.93 mmol) and the reaction mixture stirred at −78° C. for 1 h. Brine (30 mL) was then added and the mixture allowed to warm to RT. More brine (200 mL) and ethyl acetate (300 mL) were added and the layers separated. The aqueous phase was re-extracted with dichloromethane (500 mL). The combined organics were dried over sodium sulfate, filtered and concentrated in vacuo to give a crude residue. This was purified by silica gel chromatography, using gradient elution of dichloromethane to dichloromethane/methanol 99:1 to give the title compound (553 mg, 57% yield, 94% d.e.).

Compound 23f

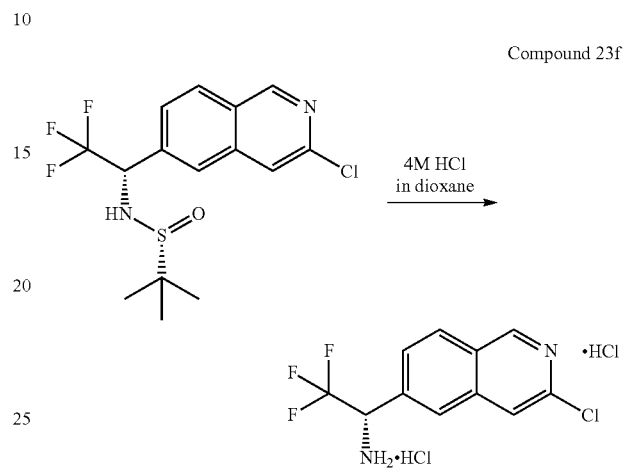

To a solution of 23e (553 mg, 1.52 mmol) in methanol (10 mL) was added 4 M hydrochloric acid solution in 1,4-dioxane (1.52 mL, 6.06 mmol) and the reaction mixture was stirred at RT for 30 min. Additional 4 M hydrochloric acid solution in 1,4-dioxane (1.52 mL, 6.06 mmol) was added and the reaction mixture stirred at RT for 30 min then concentrated in vacuo to give the title compound (507 mg, quantitative yield).

Compound 23g

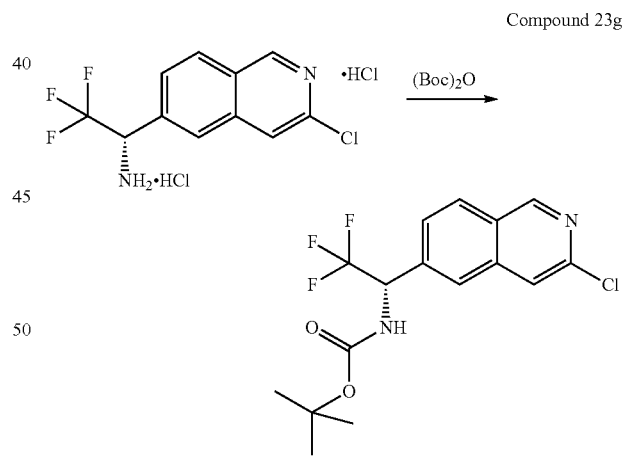

A mixture of 23f (507 mg, 1.52 mmol) and triethylamine (0.84 mL, 6.08 mmol) in dichloromethane (20 mL) was stirred at 0° C. to give a solution. Then a solution of di-tert-butyl dicarbonate (497 mg, 2.28 mmol) in dichloromethane (4 mL) was added and the reaction mixture was stirred and allowed to warm to RT over 24 h. Water (200 mL) was added and the aqueous layer extracted with dichloromethane (3×100 mL), dried over sodium sulfate, filtered and concentrated in vacuo to give a residue (816 mg). This residue was dissolved in dichloromethane (20 mL) and cooled to 0° C. then triethylamine (0.84 mL, 6.08 mmol) was added followed by a solution of di-tert-butyl dicarbonate (497 mg, 2.28 mmol) in dichloromethane (4 mL) and the reaction mixture was stirred and allowed to warm to RT over 72 h. Additional di-tert-butyl dicarbonate (162 mg, 0.74 mmol) was added and stirring continued for 30 min then water (100 mL) was added and the aqueous layer extracted with dichloromethane (2×50 mL). The combined organics were dried over sodium sulfate, filtered and concentrated in vacuo to give a crude residue. This was purified by silica gel chromatography, using gradient elution of iso-hexanes/ethyl acetate 9:1 to iso-hexanes/ethyl acetate 1:1 to give the title compound (140 mg, 25%) as an oil.

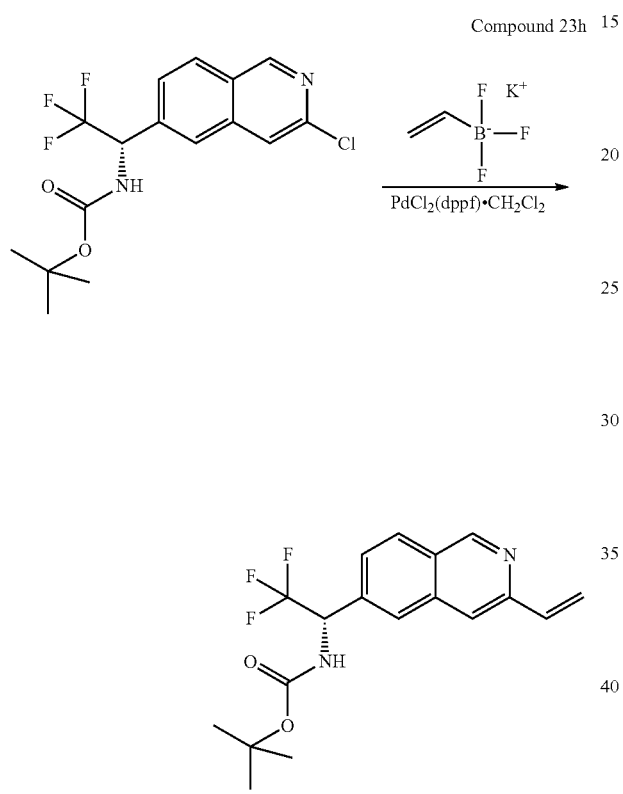

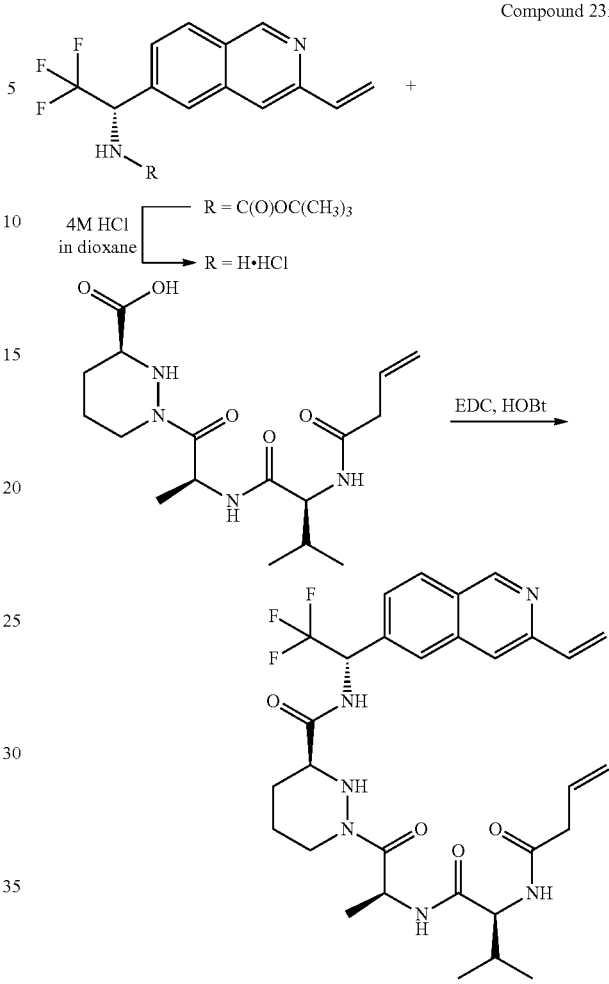

To a solution of 23 g (135 mg, 0.37 mmol) in n-propanol (6 mL) was added potassium vinyltrifluoroborate (55 mg, 0.412 mmol), [1,1'-bis(diphenylphosphino) ferrocene]dichloropalladium(II), complex with dichloromethane (5.8 mg, 0.007 mmol) and triethylamine (0.052 mL, 0.37 mmol). The suspension was evacuated and purged with nitrogen 3 times before heating to 100° C. for 2 h. After this time additional potassium vinyltrifluoroborate (100 mg, 0.748 mmol) was added and heating continued at 100° C. for 16 h. After this time, additional [1,1'-bis(diphenylphosphino)ferrocene] dichloropalladium(II), complex with dichloromethane (9 mg, 0.011 mmol) was added and the reaction mixture was heated in a microwave reactor at 150° C. for 90 min. After this time additional [1,1'-bis(diphenylphosphino)ferrocene]dichloropalladium(II), complex with dichloromethane (9 mg, 0.011 mmol) was added and the reaction mixture was heated in a microwave reactor at 150° C. for 10 min. Water (100 mL) was added to the reaction mixture and the aqueous layer was then extracted with diethyl ether (2×100 mL). The combined organics were dried over sodium sulfate, filtered and concentrated in vacuo to give the title compound (132 mg, quantitative yield).

To a solution of 23h (132 mg, 0.37 mmol) in methanol (2 mL) was added 4 M hydrochloric acid in 1,4-dioxane (0.37 mL, 0.75 mmol) and the mixture stirred at RT for 30 min. Additional 4 M hydrochloric acid in 1,4-dioxane (3.0 mL, 6.08 mmol) was added and stirring continued for 2 h then the reaction mixture was concentrated in vacuo to give a residue. The residue was then concentrated from diethyl ether (2 mL), followed by acetonitrile (10 mL) and this was repeated twice to give (S)-2,2,2-trifluoro-1-(3-vinyl-isoquinolin-6-yl)-ethylamine hydrochloric acid salt (108 mg, quantitative yield). To a suspension of (S)-2,2,2-trifluoro-1-(3-vinyl-isoquinolin-6-yl)-ethylamine hydrochloric acid salt (108 mg, 0.374 mmol) in acetonitrile (2 mL) at 0° C. under nitrogen was added (S)-1-[(S)-2-((S)-2-but-3-enoylamino-3-methyl-butyrylamino)-propionyl]-hexahydro-pyridazine-3-carboxylic acid (138 mg, 0.37 mmol), N-(3-dimethylaminopropyl)-N'-ethyl-carbodiimide hydrochloride (100 mg, 0.52 mmol) and 1-hydroxybenzotriazole hydrate (63 mg, 20 wt % in water, 0.37 mmol). The resulting suspension was stirred at 0° C. for 15 min before removing from the ice-water bath and stirring at RT for 16 h. N,N-Diisopropylethylamine (0.5 mL, 2.87 mmol) was added and the solution was stirred at RT for 2.5 h where additional (S)-1-[(S)-2-((S)-2-but-3-enoylamino-3-methyl-butyrylamino)-propionyl]-hexahydro-pyridazine-3-carboxylic acid (69 mg, 0.19 mmol) was added and stirring continued. After 1 h, N-(3-dimethylaminopropyl)-N'-ethyl-carbodiimide hydrochloride (134 mg, 0.70 mmol) was added and the reaction mixture was stirred at RT for 1 hour. After this time, the mixture was concentrated in vacuo and the residue diluted with ethyl acetate (60 mL). Water (50 mL) was added and the layers separated. The aqueous phase was re-extracted with ethyl acetate (2×10 mL) and the combined organics were then washed with ammonium chloride (2×50 mL), dried over sodium sulfate, filtered and concentrated in vacuo to give a crude residue. This was purified by silica gel chromatography, using gradient elution of iso-hexanes/ethyl acetate 9:1 to iso-hexanes/ethyl acetate 4:1 to iso-hexanes/ethyl acetate 1:1 and finally iso-hexanes/ethyl acetate 0:1. This gave the title compound (124 mg, 55%).

Compound 23

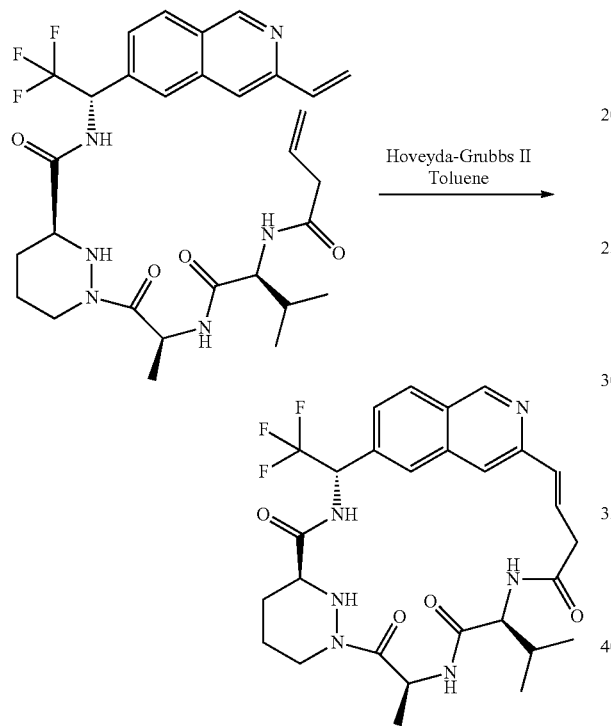

To a solution of 23i (124 mg, 0.21 mmol) in toluene (69 mL) was added Hoveyda-Grubbs $2^{nd}$ generation catalyst (13 mg, 0.02 mmol) and the reaction mixture heated at 115° C. for 1.5 h. Additional Hoveyda-Grubbs $2^{nd}$ generation catalyst (13 mg, 0.02 mmol) was added and heating continued at 120° C. for 50 min. Additional Hoveyda-Grubbs $2^{nd}$ generation catalyst (13 mg, 0.02 mmol) was added and heating continued at 120° C. for 30 min. After this time the mixture was allowed to cool to RT and concentrated in vacuo. The residue was purified by silica gel chromatography using a gradient of ethyl acetate to ethyl acetate/acetone 9:1. Impure product (28.3 mg) was collected which was further purified by preparative TLC eluting with ethyl acetate/acetone 95:5 to afford the title compound (4 mg, 3%) as a white solid. $^1$H NMR (300 MHz, CD$_3$OD) 0.99 (d, J=6.7 Hz, 3H), 1.01 (d, J=6.7 Hz, 3H), 1.29-1.39 (m, 1H), 1.69 (d, J=7.4 Hz, 3H), 1.74-2.01 (m, 5H), 2.73 (td, J=12.9, 2.9 Hz, 1H), 2.99-3.11 (m, 1H), 3.74-3.83 (m, 1H), 4.26 (d, J=10.0 Hz, 1H), 4.41 (br d, J=13.2 Hz, 1H), 5.48 (q, J=7.4 Hz, 1H), 5.84 (q, J=8.3 Hz, 1H), 6.58 (d, J=16.3 Hz, 1H), 6.62-6.71 (m, 1H), 7.47 (s, 1H), 7.76 (d, J=8.6 Hz, 1H), 7.89 (s, 1H), 8.13 (d, J=8.6 Hz, 1H), 9.22 (s, 1H). LCMS (m/z) 575.2 [M+H], Tr=1.53 min.

Example 24

Compound 24a

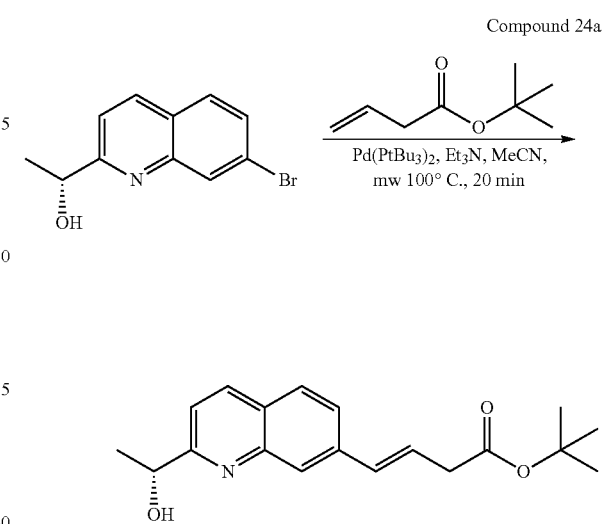

To a solution of (R)-1-(7-bromo-quinolin-2-yl)-ethanol (295 mg, 1.17 mmol) in anhydrous acetonitrile (12 mL) were added but-3-enoic acid tert-butyl ester (0.44 mL, 2.75 mmol), bis(tri-tert-butylphosphine)palladium(0) (25 mg, 0.049 mmol) and N,N-dicyclohexylmethylamine (0.39 mL, 1.83 mmol) then the mixture was heated at reflux for 2 h. The reaction mixture was concentrated in vacuo to give a crude residue. This was purified by silica gel chromatography using iso-hexanes/ethyl acetate 95:5 to yield the title compound (348 mg, 95%) as a white solid.

Compound 24b

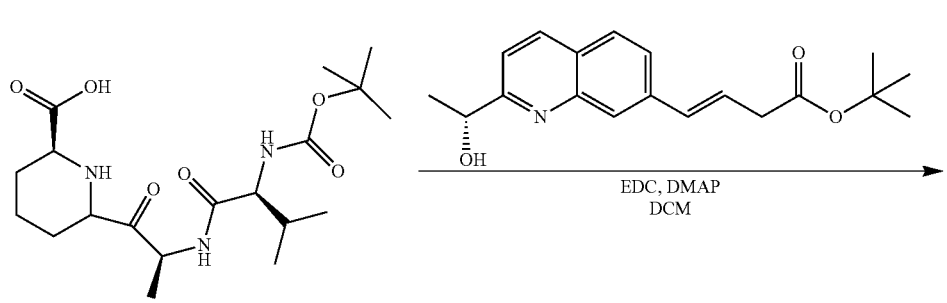

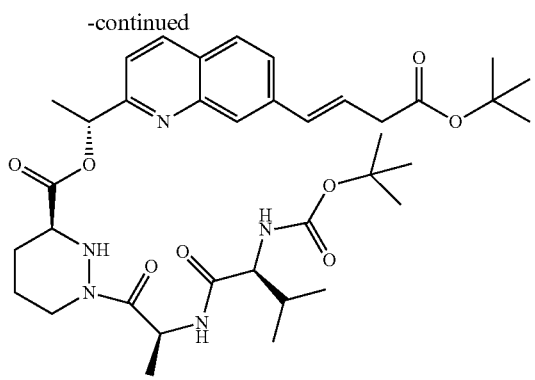

To 24a (363 mg, 1.16 mmol) and (S)-1-[(S)-2-((S)-2-tert-butoxycarbonylamino-3-methyl-butyrylamino)-propionyl]-hexahydro-pyridazine-3-carboxylic acid (505 mg, 1.26 mmol) in dichloromethane (20 mL) was added N-(3-dimethylaminopropyl)-N'-ethylcarbodiimide hydrochloride (311 mg, 1.62 mmol) and 4-dimethylaminopyridine (142 mg, 1.16 mmol). The reaction mixture was then stirred at RT for 16 h. To the mixture was added saturated aqueous ammonium chloride solution (100 mL) and the aqueous layer extracted with dichloromethane (2×50 mL). The aqueous phase was further washed with dichloromethane (20 mL) and the combined organics washed with brine (50 mL), dried over magnesium sulfate, filtered and concentrated in vacuo to give a crude residue. This was purified by silica gel chromatography using iso-hexanes/ethyl acetate 4:1 (120 mL) then iso-hexanes/ethyl acetate 7:3 (855 mL) then iso-hexanes/ethyl acetate 3:2 (540 mL) to yield the title compound (357 mg, 44%) as a white solid.

Compound 24

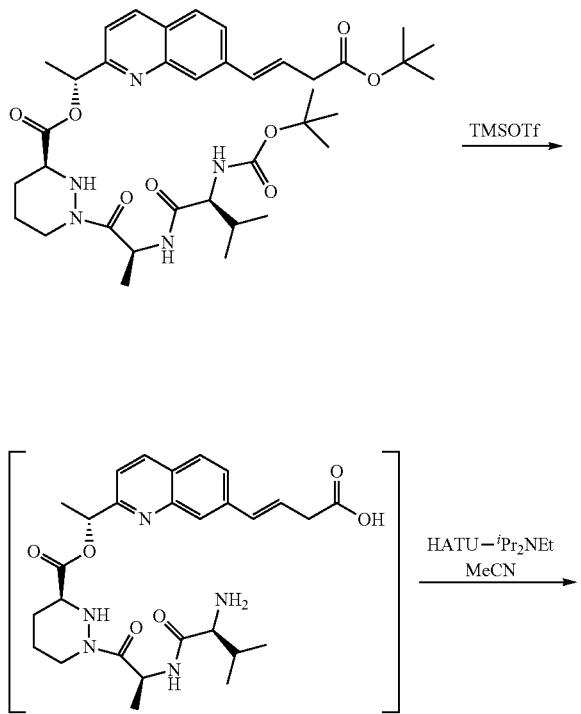

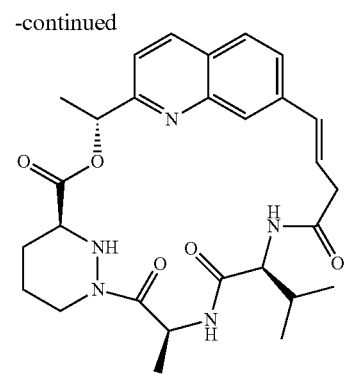

To a solution of 24b (342 mg, 0.492 mmol) in dichloromethane (2.5 mL) at 0° C. was added trimethylsilyl trifluoromethanesulfonate (0.18 mL, 0.96 mmol) and the pale yellow solution stirred at 0° C. for 2.75 h. Additional trimethylsilyl trifluoromethanesulfonate (0.073 mL, 0.45 mmol) was added and stirring continued for 1.33 h. N,N-Diisopropylethylamine (0.6 mL, 3.44 mmol) was added and the mixture stirred for 10 min then concentrated in vacuo to give intermediate (S)-1-[(S)-2-((S)-2-amino-3-methyl-butyrylamino)-propionyl]-hexahydro-pyridazine-3-carboxylic acid (R)-1-[7-((E)-3-carboxy-propenyl)-quinolin-2-yl]-ethyl ester (266 mg, 0.45 mmol). To a solution of (S)-1-[(S)-2-((S)-2-amino-3-methyl-butyrylamino)-propionyl]-hexahydro-pyridazine-3-carboxylic acid (R)-1-[7-((E)-3-carboxy-propenyl)-quinolin-2-yl]-ethyl ester (266 mg, 0.45 mmol) in acetonitrile (50 mL) at 0° C. under nitrogen was added N,N-diisopropylethylamine (0.343 mL, 1.971 mmol) and 2-(1H-7-azabenzotriazol-1-yl)-1,1,3,3-tetramethyl uronium hexafluorophosphate methanaminium (262 mg, 0.70 mmol). The mixture was stirred at 0° C. and allowed to warm to RT over 16 h. To the reaction mixture was added 2 M aqueous hydrochloric acid solution (20 mL) and the mixture concentrated in vacuo. The aqueous layer was extracted with dichloromethane/methanol 9:1 (2×100 mL). The combined organics were washed with saturated sodium hydrogen carbonate solution (2×200 mL), then brine (1×100 mL), dried over sodium sulfate, filtered and concentrated in vacuo to give a crude residue. This was purified by silica gel chromatography using gradient elution of ethyl acetate/acetone 97:3 to ethyl acetate/acetone 94:6. Collected 45 mg of impure product which was triturated with diethyl ether to give the title compound (25.4 mg, 10%) as a pale yellow solid. $^1$H NMR (300 MHz, CD$_3$OD) δ 0.99 (d, J=6.48 Hz, 3H), 1.01 (d, J=6.7 Hz, 3H), 1.64 (d, J=7.1 Hz, 3H), 1.66-1.72 (m, 1H), 1.74 (d, J=6.9 Hz, 3H), 1.85-2.08 (m, 4H), 2.75 (dd, J=2.9, 12.9 Hz, 1H), 2.97-3.07 (m, 1H), 3.35-3.40 (m, 1H), 3.79-3.88 (m, 1H), 4.23 (d, J=10.5 Hz, 1H), 4.43 (br d, J=11.2 Hz, 1H), 5.72 (q, J=7.1 Hz, 1H), 5.94 (q, J=6.9 Hz, 1H), 6.41 (d, J=16.7 Hz, 1H), 6.55 (dt, J=4.7, 16.7 Hz, 1H), 7.40 (d, J=8.5 Hz, 1H), 7.65 (s, 1H), 7.75 (dd, J=1.3, 8.7 Hz, 1H), 7.81 (d, J=8.7 Hz, 1H), 8.21 (d, J=8.5 Hz, 1H). LCMS (m/z) 522.2 [M+H], Tr=1.90 min.

Example 25

Compound 25a

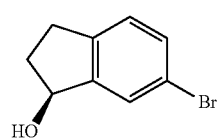
1. NEt$_3$, MsCl
2. MeNH$_2$, THF

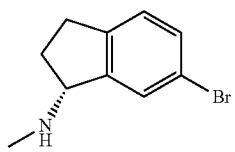

A cooled (−20° C.) solution of (S)-6-bromo-indan-1-ol (1.0462 g, 4.910 mmol, prepared as described in WO 2009/003719) in anhydrous tetrahydrofuran (20 mL) was subsequently treated with triethylamine (2.7 mL, 19.639 mmol) and methanesulfonyl chloride (760 µL, 9.820 mmol). After stirring at −30° C. for 2.5 h, a solution of methylamine (2 M in tetrahydrofuran, 25 mL, 50 mmol) was added. After stirring at RT for 22.5 h the reaction mixture was filtered. The white solid was rinsed with diethyl ether. The filtrate was evaporated to dryness to afford the title compound (1.11 g, quantitative yield) as a white solid.

Compound 25b

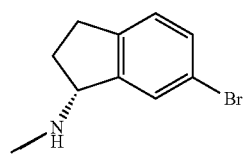
Boc$_2$O, NEt$_3$

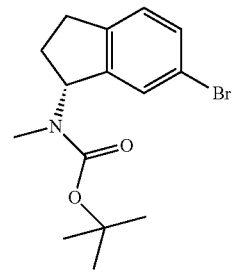

A solution of 25a (1.11 g, 4.910 mmol) was subsequently treated with di-tert-butyl dicarbonate (1.714 g, 7.856 mmol) and triethylamine (690 µL, 4.91 mmol). After stirring for 25.5 h, the volatiles were removed in vacuo and the residue was purified by silica gel chromatography using a 50 g Isolute cartridge eluted with a continuous gradient of iso-hexanes/ethyl acetate 1:0 to 9:1 to afford the title compound (1.4224 g, 89%) as a white solid as a mixture of rotamers.

Compound 25c

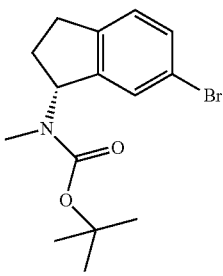
PdCl$_2$(dppf)-CH$_2$Cl$_2$
NEt$_3$, nPrOH
CH$_2$=CHBF$_3$K

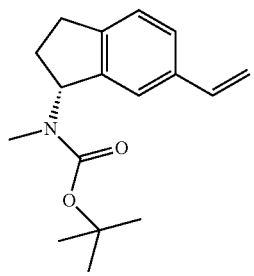

A solution of 25b (1.4224 g, 4.363 mmol), [1,1-bis(diphenylphosphino)ferrocene]dichloropalladium dichloromethane complex (71.3 mg, 0.087 mmol), potassium vinyltrifluoroborate (701.3 mg, 5.236 mmol) and triethylamine (610 µL, 4.363 mmol) in anhydrous n-propanol (40 mL) was degassed by bubbling nitrogen through for 30 min. The red suspension was then refluxed for 17.5 h. After cooling to RT, the mixture was quenched with water and the aqueous layer was extracted with diethyl ether (2×). The organics were combined, dried over sodium sulfate, filtered and the volatiles were removed in vacuo. The residue was purified by silica gel chromatography using a 50 g Isolute cartridge eluted with a continuous gradient of iso-hexanes/diethyl ether 1:0 to 4:1 to afford the title compound (977.3 mg, 82%) as a white solid as a mixture of rotamers.

Compound 25d

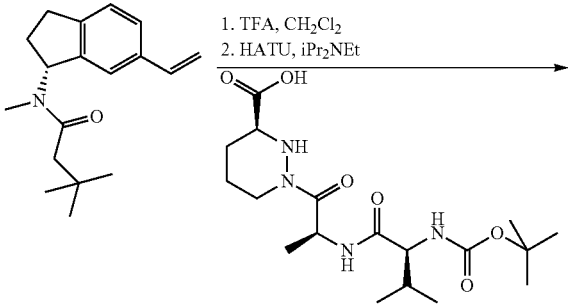
1. TFA, CH$_2$Cl$_2$
2. HATU, iPr$_2$NEt

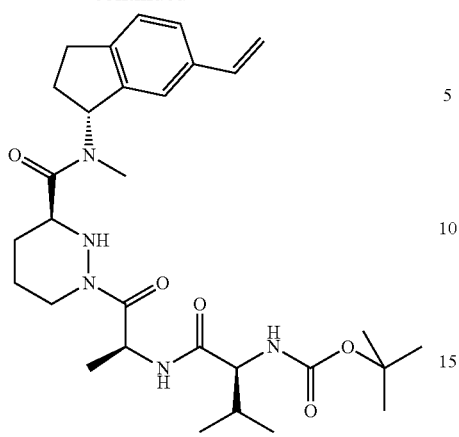

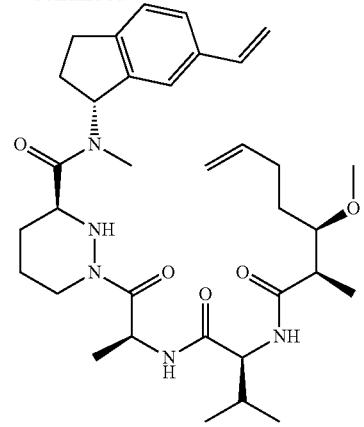

A cooled (0° C.) solution of 25c (977.3 mg, 3.575 mmol) in dichloromethane (20 mL) was treated with trifluoroacetic acid (5 mL). After stirring for 30 min at RT the volatiles were removed in vacuo and the residual trifluoroacetic acid was azeotroped off with toluene (3×) to afford the corresponding ammonium salt as a pink solid. A cooled (0° C.) solution of the crude ammonium salt, crude (S)-1-[(S)-2-((S)-2-tert-butoxycarbonylamino-3-methyl-butyrylamino)-propionyl]-hexahydro-pyridazine-3-carboxylic acid (3.932 mmol) and N,N-diisopropylethylamine (2.5 mL, 14.300 mmol) in acetonitrile (60 mL) was treated with 2-(1H-7-azabenzotriazol-1-yl)-1,1,3,3-tetramethyl uronium hexafluorophosphate methanaminium (1.903 g, 5.005 mmol). After stirring for 20 h at RT, the reaction was quenched with hydrochloric acid (1 M, 100 mL). The aqueous layer was extracted with ethyl acetate (2×). The organics were combined, dried over sodium sulfate, filtered and the volatiles were removed in vacuo. The residue was purified by silica gel chromatography using a 100 g Isolute cartridge eluted with a continuous gradient of isohexanes/ethyl acetate 1:0 to 1:2 to afford the title compound in a mixture which was dissolved in ethyl acetate and washed with aqueous potassium carbonate. The organics were dried over sodium sulfate, filtered and the volatiles were removed in vacuo to afford the title compound (798.9 mg, 36%) as a white solid as a mixture of rotamers.

Compound 25e

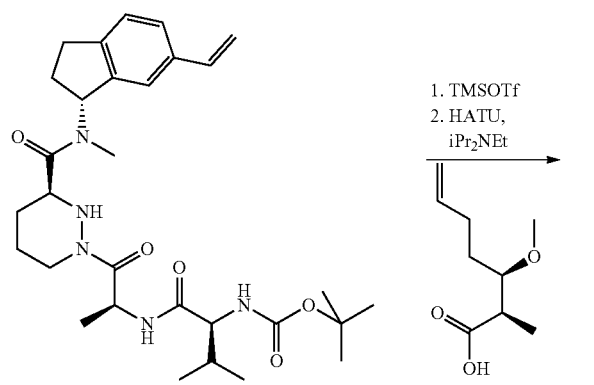

Compound 25e was prepared in the same manner as 22e using 25d instead of 1e in 27% yield as a complex mixture of rotamers.

Compound 25

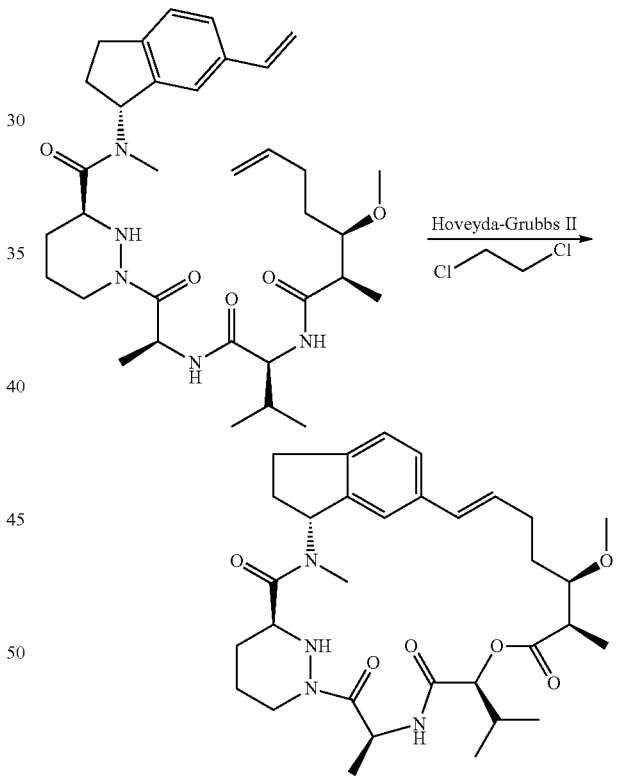

A solution of 25e (238.3 mg, 0.390 mmol) in dichloroethane (100 mL) was treated with Hoveyda-Grubbs $2^{nd}$ generation catalyst (48.9 mg, 0.078 mmol). After stirring at reflux for 1.5 h, the reaction was cooled to RT and the volatiles were removed in vacuo. The residue was purified by silica gel chromatography using a 10 g Isolute cartridge eluted by gravity with a continuous gradient of ethyl acetate/methanol 1:0 to 95:5 followed by preparative TLC eluted with ethyl acetate/methanol 97:3 (2 elutions) to provide the final compound (10.2 mg, 5%) as a white solid. $^1$H NMR (300 MHz, CD$_3$CN) δ 0.85-0.97 (m, 6H), 1.21-1.35 (m, 8H), 1.42-1.62 (m, 3H), 1.64-1.77 (m, 2H), 1.80-1.89 (m, 2H), 2.27-2.38 (m, 2H), 2.52 (dd, J=7.6, 3.1 Hz, 1H), 2.76 (s, 3H), 2.82-3.06 (m, 2H), 3.27-3.35 (m, 1H), 3.47 (s, 3H), 3.80-3.91 (m, 1H), 4.06 (dd, J=9.1, 8.2 Hz, 1H), 4.23 (d, J=11.8 Hz, 1H), 4.41 (dd, J=12.9, 3.6 Hz, 1H), 5.44 (app pentet, J=8.0 Hz, 1H), 6.10-6.30 (m, 2H), 6.43 (d, J=16.0 Hz, 1H), 6.88 (d, J=8.0 Hz, 1H), 6.96 (d, J=9.4 Hz, 1H), 7.04 (s, 1H), 7.13-7.28 (m, 2H). LCMS (m/z) 582.3 [M+H], Tr=2.57 min.

Example 26

Compound 26a

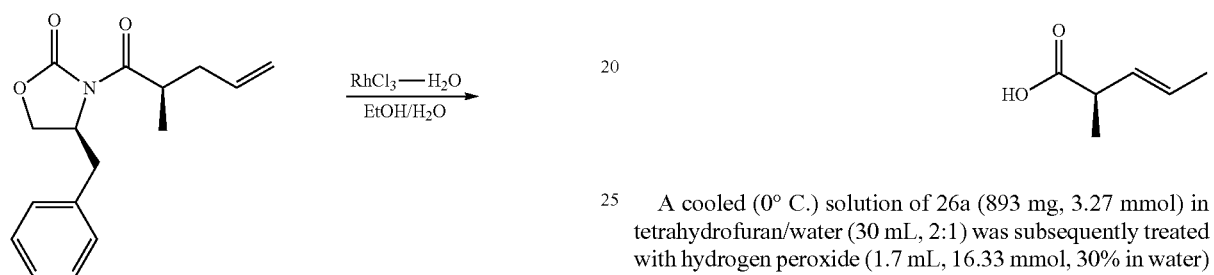

A solution of (S)-4-benzyl-3-((R)-2-methyl-pent-4-enoyl)-oxazolidin-2-one (1.65 g, 6.04 mmol, prepared as in *Synlett* 2002, 12, 2039-2040) in ethanol/water (22 mL, 10:1) was treated with rhodium(II) chloride hydrate (31.6 mg, 0.15 mmol). After stirring at 85° C. for 24 h, the reaction mixture was cooled to RT and the volatiles were removed in vacuo. The residue was purified by silica gel chromatography using a 50 g Isolute cartridge eluted with a continuous gradient of iso-hexanes/diethyl ether 1:0 to 4:1 to afford the title compound (892.7 mg, 54%) as a colorless oil.

Compound 26b

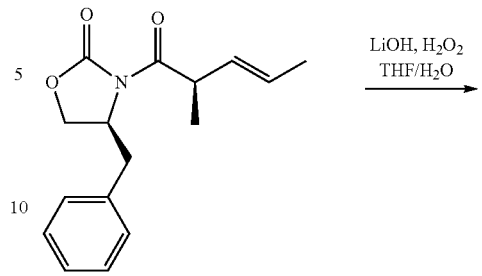

A cooled (0° C.) solution of 26a (893 mg, 3.27 mmol) in tetrahydrofuran/water (30 mL, 2:1) was subsequently treated with hydrogen peroxide (1.7 mL, 16.33 mmol, 30% in water) and lithium hydroxide hydrate (274 mg, 6.53 mmol). After stirring for 1.5 h at 0° C., the reaction was quenched with sodium metabisulfite (6.2 g, 32.66 mmol). After stirring at RT for 40 min, the mixture was acidified with hydrochloric acid (2 M) and the aqueous layer was extracted with dichloromethane (2×). The organics were combined, filtered through a phase separator and the volatiles were removed in vacuo. The residue was purified by silica gel chromatography using a 25 g Isolute cartridge eluted with a continuous gradient of iso-hexanes/ethyl acetate 1:0 to 4:1 to afford the title compound (307.1 mg, 82%) as a colorless oil.

Compound 26c

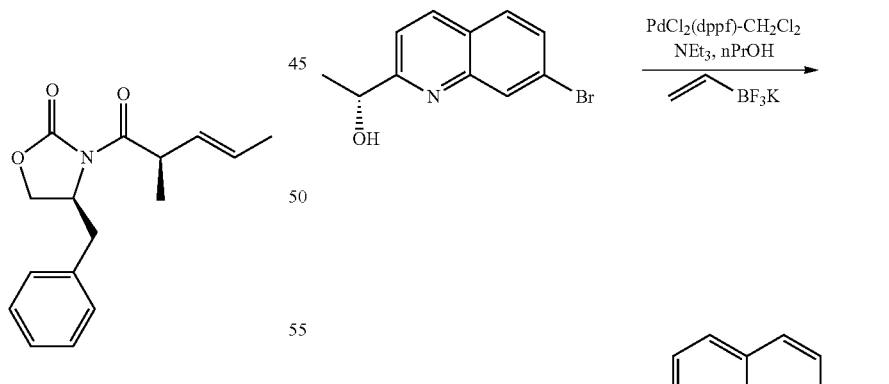

Compound 26c was prepared in the same manner as methyl-((R)-6-vinyl-indan-1-yl)-carbamic acid tert-butyl ester using (R)-1-(7-bromo-quinolin-2-yl)-ethanol instead of ((R)-6-bromo-indan-1-yl)-methyl-carbamic acid tert-butyl ester in quantitative yield.

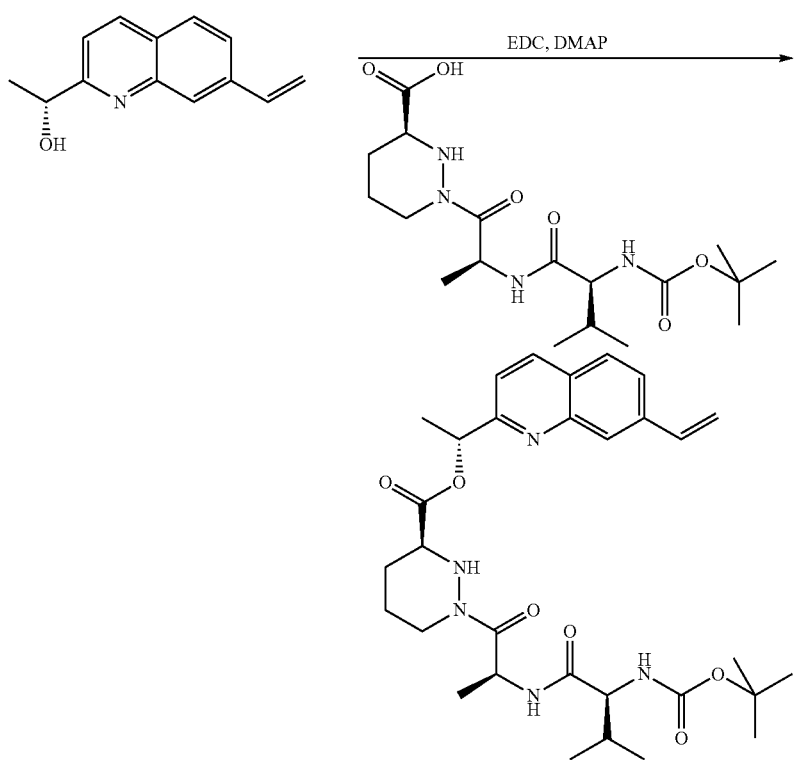

Compound 26d

A solution of (S)-1-[(S)-2-((S)-2-tert-butoxycarbonylamino-3-methyl-butyrylamino)-propionyl]-hexahydro-pyridazine-3-carboxylic acid (261.2 mg, 0.653 mmol), 26c (108.4 mg, 0.544 mmol) and 4-dimethylaminopyridine (79.7 mg, 0.653 mmol) in dichloromethane (10 mL) was treated with N-(3-dimethylaminopropyl)-N'-ethylcarbodiimide hydrochloride (166.9 mg, 0.870 mmol). After stirring at RT for 17 h, the volatiles were removed in vacuo and the residue was purified by silica gel chromatography using a 50 g Isolute cartridge eluted with a continuous gradient of iso-hexanes/ethyl acetate 1:0 to 1:4 to 0:1 to afford the title compound (139.6 mg, 44%) as a white solid.

Compound 26e

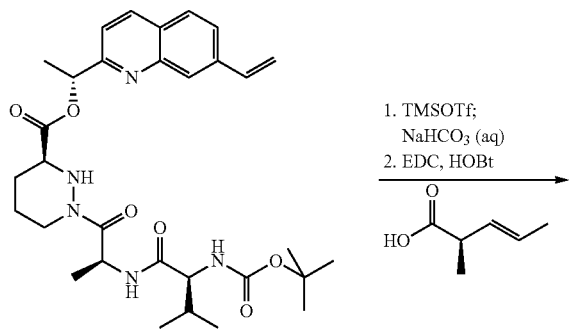

1. TMSOTf; NaHCO₃ (aq)
2. EDC, HOBt

-continued

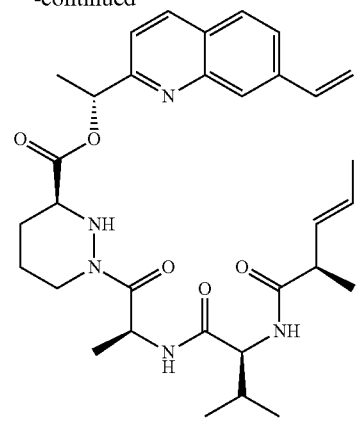

A cooled (0° C.) solution of 26d (139.6 mg, 0.240 mmol) in anhydrous dichloromethane (10 mL) was treated with trimethylsilyl methanesulfonate (90 µL, 0.480 mmol). After stirring for 1.5 h at 0° C., the reaction was quenched with saturated sodium bicarbonate. The aqueous layer was extracted with dichloromethane. The organics were combined, filtered through a phase separator and the volatiles were removed in vacuo to provide the intermediate amine. A solution of this amine, (E)-(R)-2-methyl-pent-3-enoic acid (32.9 mg, 0.288 mmol) and 1-hydroxybenzotriazole (38.9 mg, 0.288 mmol) in acetonitrile (10 mL) was treated with N-(3-dimethylaminopropyl)-N'-ethylcarbodiimide hydrochloride (64.4 mg, 0.336 mmol). After stirring at RT for 17.5 h the volatiles were removed in vacuo and the residue was purified by silica gel chromatography using a 25 g Isolute cartridge eluted with a continuous gradient of iso-hexanes/ethyl acetate 1:0 to 0:1 to afford the title compound (69.8 mg, 50%) as a colorless oil.

Compound 26

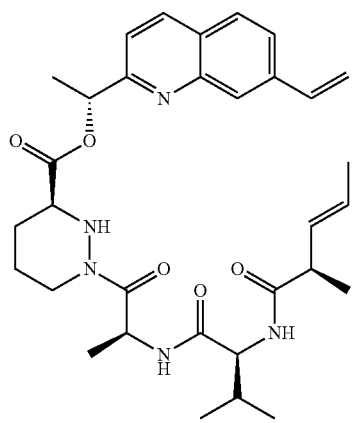

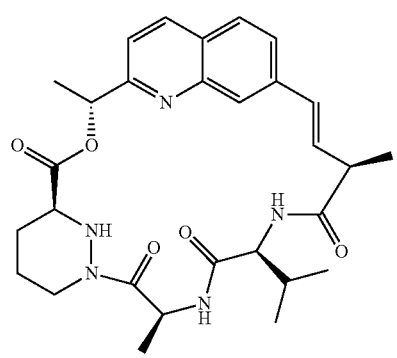

Compound 26 was prepared in the same manner as compound 25 using 26e instead of (S)-1-{(S)-2-[(S)-2-((2R,3R)-3-methoxy-2-methyl-hept-6-enoylamino)-3-methyl-butyrylamino]-propionyl}-hexahydro-pyridazine-3-carboxylic acid methyl-((R)-6-vinyl-indan-1-yl)-amide in 4% yield. $^1$H NMR (300 MHz, CD$_3$OD) δ 0.94-1.00 (m, 6H), 1.47 (d, J=7.6 Hz, 3H), 1.63 (d, J=7.1 Hz, 3H), 1.67-1.80 (m, 5H), 1.85-2.07 (m, 3H), 2.76 (td, J=12.1, 3.3 Hz, 1H), 3.79-3.86 (m, 1H), 4.28 (d, J=10.5 Hz, 1H), 4.36-4.46 (m, 1H), 5.73 (q, J=7.1 Hz, 1H), 5.93 (q, J=6.9 Hz, 1H), 6.32-6.51 (m, 2H), 7.41 (d, J=8.5 Hz, 1H), 7.65 (s, 1H), 7.77-7.85 (m, 2H), 8.21 (d, J=8.5 Hz, 1H). LCMS (m/z) 536.1 [M+H], Tr=1.80 min.

Example 27

Compound 27a

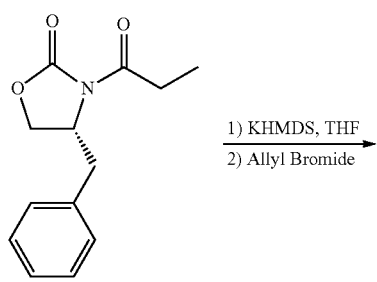

Compound 27b

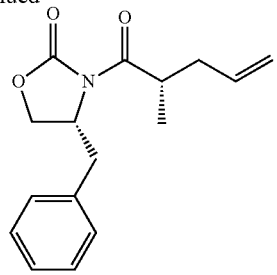

A cooled (−78° C.) solution of (of (R)-4-benzyl-3-propionyl-oxazolidin-2-one (3.00 g, 12.9 mmol) in anhydrous tetrahydrofuran (40 mL) was treated with potassium bis(trimethylsilyl)amide (19.3 mL, 19.3 mmol, 1 M in tetrahydrofuran). After stirring for 0.45 h at −78° C., the mixture was treated with allyl bromide (5.6 mL, 64.3 mmol). After stirring for 2 h at −40° C., the reaction was quenched with 2 M hydrochloric acid. The aqueous was extracted with ethyl acetate (2×50 The organics were combined, and the volatiles were removed in vacuo. The residue was purified by silica gel chromatography using a 50 g Biotage cartridge eluted with a continuous gradient of iso-hexanes/ethyl acetate 1:0 to 1:1 to afford the title compound (2.73 g, 78%) as a colorless oil.

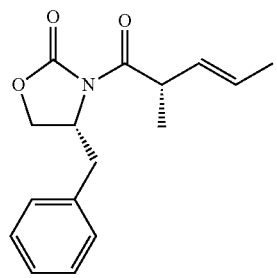

A solution of 27a (2.73 g, 9.97 mmol) in ethanol/water (22 mL, 10:1) was treated with rhodium(III)chloride hydrate (52 mg, 0.25 mmol). After stirring at 85° C. for 3 h, the reaction mixture was cooled to RT and the volatiles were removed in vacuo. The residue was purified by silica gel chromatography using a 50 g Biotage cartridge eluted with a continuous gradient of iso-hexanes/ethyl acetate 1:0 to 4:1 to afford the title compound (1.76 g, 65%) as a colorless oil.

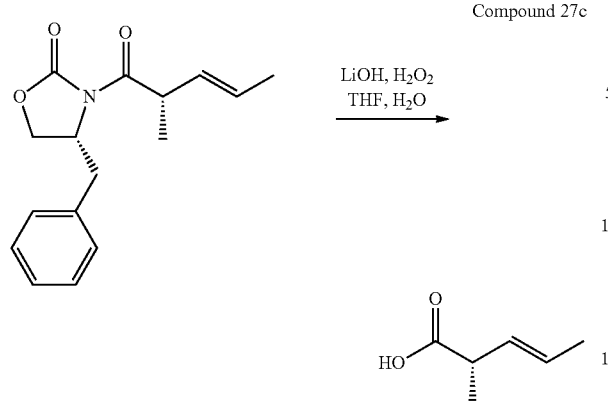

Compound 27c

LiOH, H₂O₂
THF, H₂O

Compound 27b

A cooled (0° C.) solution of 27b (1.76 g, 6.44 mmol) in tetrahydrofuran/water (60 mL, 2:1) was subsequently treated with hydrogen peroxide (3.3 mL, 32.2 mmol, 30% in water) and lithium hydroxide hydrate (534 mg, 12.9 mmol). After stirring for 2 h at 0° C., the reaction was quenched with sodium metabisulfite (12.2 g, 64.4 mmol). After stirring at RT for 1 h, the mixture was acidified with 2 M hydrochloric acid and the aqueous layer was extracted with dichloromethane (2×100 mL). The organics were combined, filtered and the volatiles were removed in vacuo. The residue was purified by silica gel chromatography using a 50 g Biotage cartridge eluted with a continuous gradient of iso-hexanes/ethyl acetate 1:0 to 4:1 to afford the title compound (463 mg, 63%) as a colorless oil.

Compound 27d

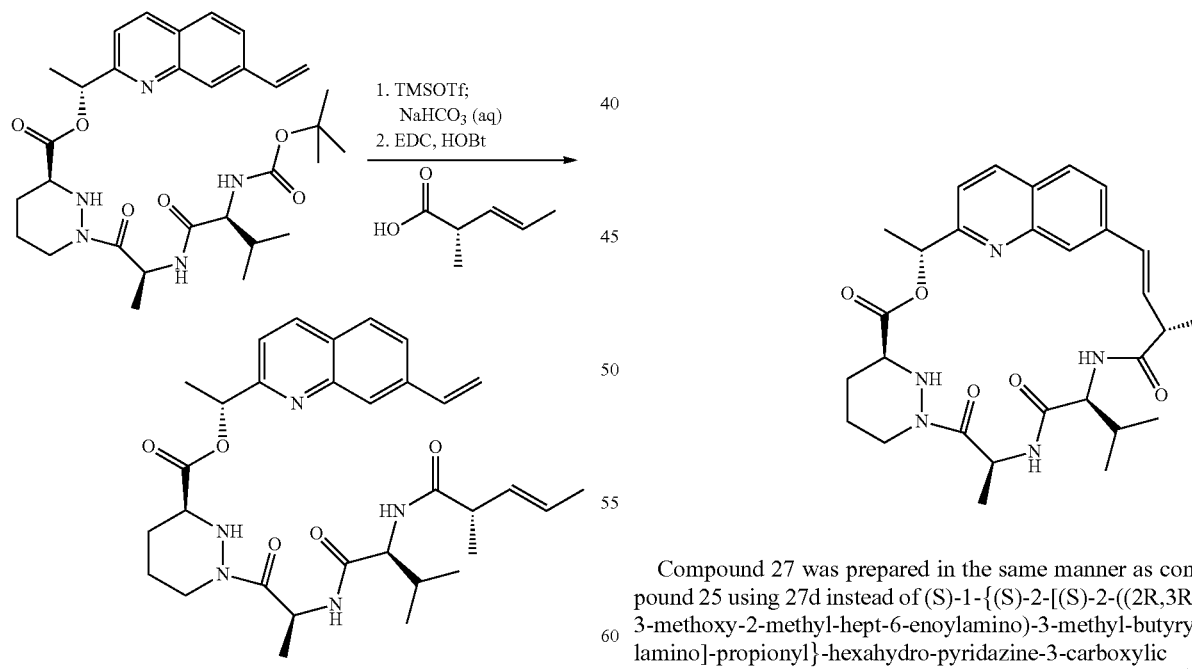

1. TMSOTf; NaHCO₃ (aq)
2. EDC, HOBt

A cooled (0° C.) solution of (S)-1-[(S)-2-((S)-2-tert-butoxycarbonylamino-3-methyl-butyrylamino)-propionyl]-hexahydro-pyridazine-3-carboxylic acid (R)-1-(7-vinyl-quinolin-2-yl)-ethyl ester (380 mg, 0.65 mmol) in anhydrous dichloromethane (10 mL) was treated with trimethylsilyl methanesulfonate (237 µL, 1.31 mmol). After stirring for 1 h at 0° C., the reaction was quenched with saturated sodium bicarbonate. The aqueous layer was extracted with dichloromethane. The organics were separated and combined, volatiles were removed in vacuo to provide the intermediate amine (305 mg). A solution of this amine, 27c (90 mg, 0.76 mmol) and 1-hydroxybenzotriazole (103 mg, 0.76 mmol) in acetonitrile (20 mL) was treated with N-(3-dimethylaminopropyl)-N'-ethylcarbodiimide hydrochloride (170 mg, 0.89 mmol). After stirring at RT for 16 h the volatiles were removed in vacuo and the residue was purified by silica gel chromatography using a 25 g Biotage cartridge eluted with a continuous gradient of iso-hexanes/ethyl acetate 1:0 to 0:1 to afford the title compound (236 mg, 65%) as a colorless oil.

Compound 27

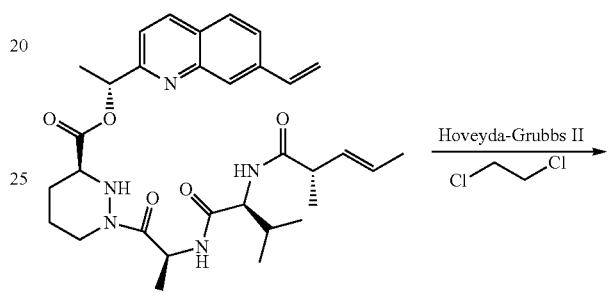

Hoveyda-Grubbs II

Compound 27 was prepared in the same manner as compound 25 using 27d instead of (S)-1-{(S)-2-[(S)-2-((2R,3R)-3-methoxy-2-methyl-hept-6-enoylamino)-3-methyl-butyrylamino]-propionyl}-hexahydro-pyridazine-3-carboxylic acid methyl-((R)-6-vinyl-indan-1-yl)-amide in 5% yield. ¹H NMR (300 MHz, CD₃OD) δ 0.85-1.00 (m, 6H), 1.30 (d, J=6.9 Hz, 3H), 1.58 (d, J=7.1 Hz, 3H), 1.62-1.80 (m, 6H), 1.83-2.07 (m, 3H), 2.70-2.82 (m, 1H), 3.38-3.48 (m, 1H), 3.76-3.84 (m, 1H), 4.20-4.28 (m, 1H), 4.36-4.47 (m, 1H), 5.62-5.74 (m, 1H). 5.93 (q, J=6.9 Hz, 1H), 6.30-6.51 (m, 2H), 7.39 (d, J=8.5

Hz, 1H), 7.63 (s, 1H), 7.70-7.80 (m, 2H), 8.13-8.22 (m, 1H). LCMS (m/z) 536.2 [M+H], Tr=2.15 min.

Example 28

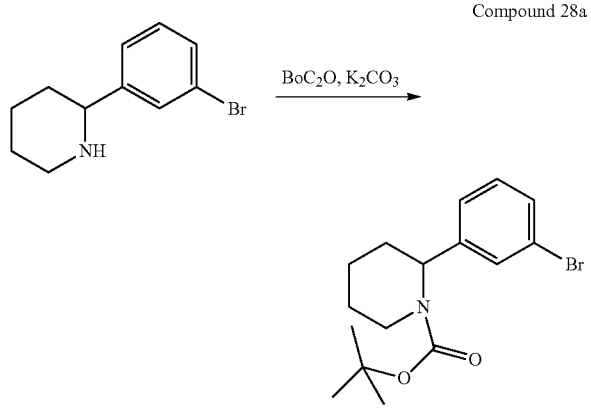

Compound 28a

Potassium carbonate (647 mg, 4.68 mmol) and di-tert-butyl dicarbonate (716 mg, 3.28 mmol) were added to 2-(3-bromo-phenyl)-piperidine (750 mg, 3.12 mmol) in dichloromethane (10 mL). After overnight stirring at RT water (20 mL) was added to the solution. The resulting biphasic solution was separated into organic and aqueous phases. The aqueous phase was back extracted with dichloromethane (20 mL). The combined organic phases were dried over anhydrous sodium sulfate, filtered and concentrated to afford the title compound (1.03 g, 97%) as a pale yellow oil.

Compound 28b

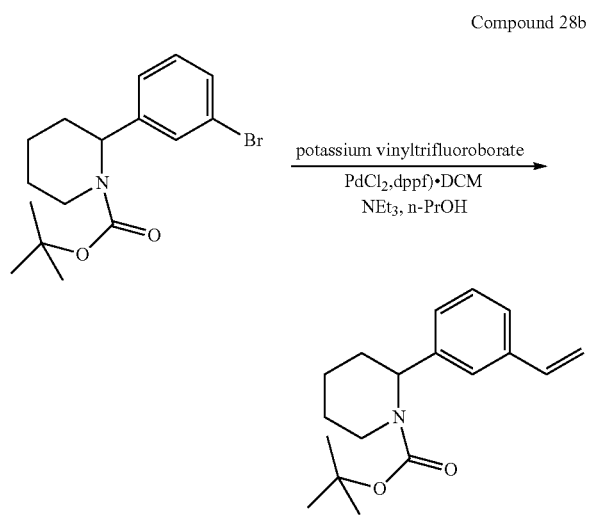

To a solution of 28a (1.03 g, 3.03 mmol) and potassium vinyltrifluoroborate (488 mg, 3.64 mmol) in n-propanol (30 mL), under an atmosphere of nitrogen was added 1,1' bis (diphenylphosphino)ferrocenedichloropalladium(II), dichloromethane adduct (49 mg, 0.06 mmol) and triethylamine (306 mg, 422 µL, 3.03 mmol). The reaction was heated to reflux and left to stir for 3 h before cooling to RT. The reaction mixture poured onto water and the resultant solution was extracted with diethyl ether (3×30 mL). The combined organics were dried over anhydrous sodium sulfate, filtered and concentrated. The resultant residue was purified by silica gel chromatography using a stepwise gradient of iso-hexanes/ethyl acetate 1:0 to 4:1 to afford the title compound (652 mg, 75%) as a pale yellow oil.

Compound 28c

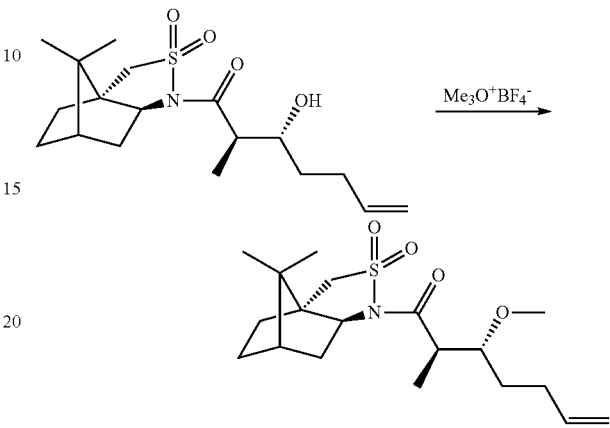

A solution of (2R,3R)-1-((1R,5S)-10,10-dimethyl-3,3-di-oxo-3lambda*6*-thia-4-aza-tricyclo[5.2.1.0*1,5*]dec-4-yl)-3-hydroxy-2-methyl-hept-6-en-1-one (250 mg, 0.703 mmol) in anhydrous dichloromethane (7 mL) was prepared and trimethyloxonium tetrafluoroborate (208 mg, 1.406 mmol) was added. The reaction mixture was stirred at RT for 15 h. The reaction mixture was treated with methanol (1 mL), then 2 M hydrochloric acid (20 mL) and saturated brine (20 mL). The mixture was extracted with ethyl acetate (3×15 mL) and the extract was dried over sodium sulfate, filtered and evaporated to give a yellow gum. The gum was purified by silica gel chromatography using iso-hexanes/ethyl acetate 4:1 to give the title compound (223 mg, 86%) as a colorless gum.

Compound 28d

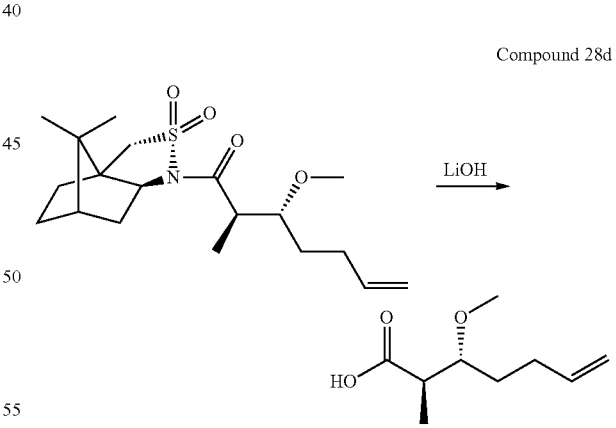

A solution of 2 M lithium hydroxide in water (5 mL, 10 mmol) was added to a stirred solution of 28c (223 mg, 0.60 mmol) in tetrahydrofuran (15 mL). The stirred mixture was heated to 60° C. for 15 h. The reaction mixture was partially evaporated before adding 2 M hydrochloric acid (20 mL). The solution was extracted with ethyl acetate (3×15 mL). The extract was dried over sodium sulfate, filtered and evaporated to give a yellow gum (209 mg). The gum was purified by silica gel chromatography using iso-hexanes/ethyl acetate 3:1 to yield the title compound (68 mg, 66%) as a yellow gum.

Compound 28e

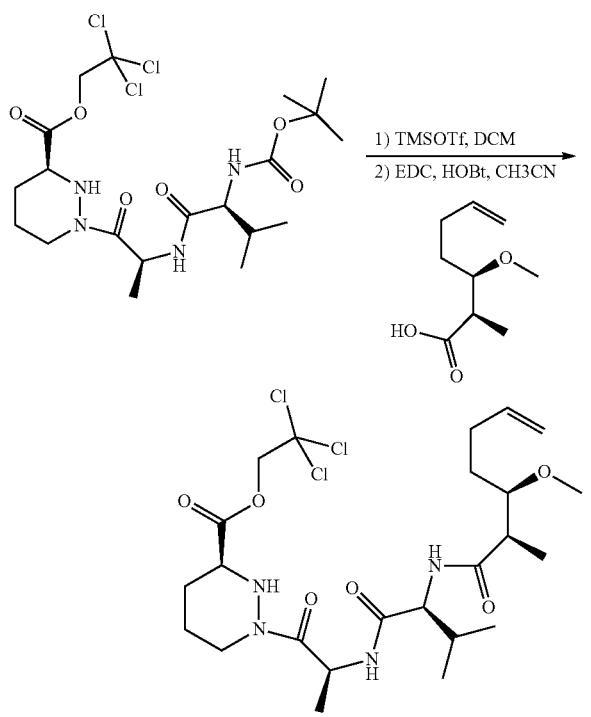

A solution of (S)-1-[(S)-2-((S)-2-tert-butoxycarbonylamino-3-methylbutyrylamino)-propionyl]-hexahydropyridazine-3-carboxylic acid 2,2,2-trichloroethyl ester (316 mg, 0.59 mmol) in anhydrous dichloromethane (10 mL) was cooled to 0° C. under a nitrogen atmosphere before adding trimethylsilyl trifluoromethanesulfonate (160 µL, 0.885 mmol). The reaction mixture was stirred at 0° C. for 2 h before adding N,N-diisopropylethylamine (413 µL, 2.36 mmol) to afford (S)-1-[(S)-2-((S)-2-amino-3-methyl-butyrylamino)-propionyl]-hexahydro-pyridazine-3-carboxylic acid 2,2,2-trichloroethyl ester. The mixture was evaporated and the residue dissolved with (2R,3R)-3-methoxy-2-methyl-hept-6-enoic acid (162 mg, 0.94 mmol.) in acetonitrile (13 mL) and N-(3-dimethylaminopropyl)-N'-ethylcarbodiimide hydrochloride (250 mg, 1.32 mmol) and 1-hydroxybenzotriazole (220 mg, 1.32 mmol) were added. The reaction was stirred at RT for 15 h then evaporated to give a yellow oil. The oil was purified by silica gel chromatography using ethyl acetate to give the title compound (425 mg, 77%) as a white solid.

Compound 28f

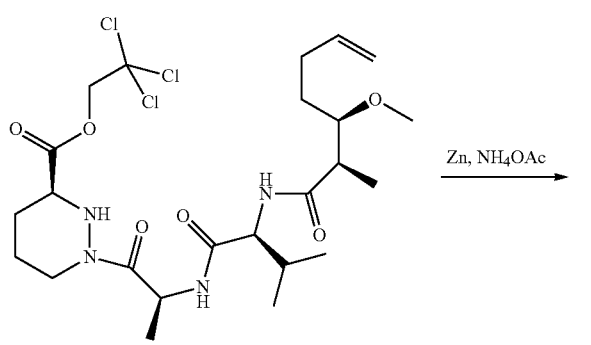

A solution of 28e (425 mg, 0.725 mmol) in tetrahydrofuran (20 mL) was prepared and zinc powder (0.48 g, 7.25 mmol) was added followed by an aqueous solution of ammonium acetate (1 M, 5 mL, 5 mmol). The reaction mixture was stirred at RT for 15 h. The reaction was filtered through hyflo-supercel washing through with ethyl acetate. The mixture was treated with hydrochloric acid (2 M, 30 mL) and the layers were separated. The aqueous layer was extracted with ethyl acetate (25 mL). The organic layers were combined, washed with brine, filtered and evaporated to give a colorless gum (299 mg) which was used directly without further purification.

Compound 28g

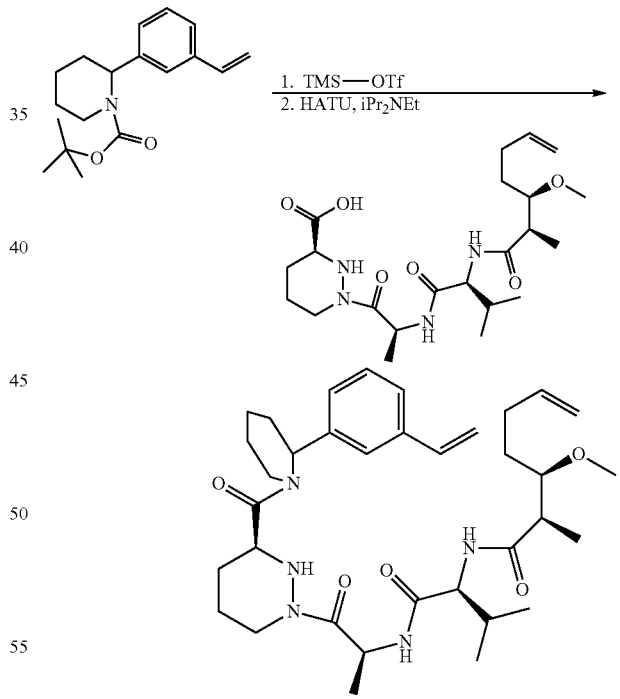

A solution of 2-(3-vinyl-phenyl)-piperidine-1-carboxylic acid tert-butyl ester (650 mg, 2.26 mmol) in dichloromethane (15 mL) was cooled to 0° C., before adding trimethylsilyl trifluoromethanesulfonate (569 µL, 3.39 mmol). The reaction mixture was stirred at 0° C. for 1 h before adding N,N-diisopropylethylamine (1.6 mL, 5.24 mmol) to afford the 2-(3-vinyl-phenyl)-piperidine as a yellow solid. The solid was redissolved, along with 28f (900 mg, 1.98 mmol) in acetonitrile (20 mL). The solution was cooled to 0° C., before adding 2-(1H-7-azabenzotriazol-1-yl)-1,1,3,3-tetramethyl uronium hexafluorophosphate methanaminium (1.05 g, 2.77 mmol) and N,N-diisopropylethylamine (1.4 mL, 7.92 mmol). The stirred reaction mixture was allowed to slowly warm to RT. After 2 h, the solvent was evaporated and the remaining residue dissolved in ethyl acetate (30 mL) and washed with water (3×30 mL). The organics were dried over anhydrous sodium sulfate, filtered and concentrated. The resultant residue was purified by silica gel chromatography using a stepwise gradient of iso-hexanes/ethyl acetate 1:0 to 0:1 to afford the title compound (1.25 g, 100%) as a yellow solid.

Compound 28

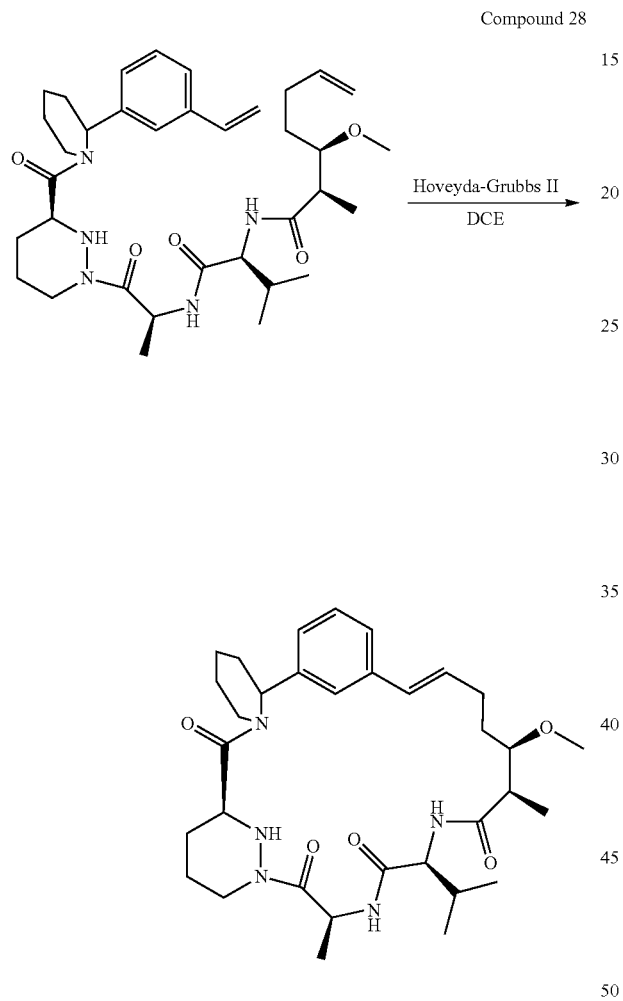

To a stirred solution of 28g (1.05 mg, 1.68 mmol) in 1,2-dichloroethane (550 mL) was added Hoveyda-Grubbs $2^{nd}$ generation catalyst (105 mg, 0.168 mmol). The solution was heated to 84° C. and was left to stir for 2.5 h. The solvent was evaporated and the remaining residue was purified by silica gel chromatography using a stepwise gradient of iso-hexanes/ethyl acetate/acetone 1:0:0 to 0:9:1. This material was then subjected to a second round of silica gel chromatography using the same gradient to afford a yellow solid. A final round of silica gel chromatography using neat ethyl acetate and eluting purely by gravity afforded the title compound (175 mg, 18%) as a white solid as a 6:4 mixture of diastereoisomers. $^1$H NMR (300 MHz, CDCl$_3$) δ 0.84 (d, J=6.9 Hz, 3H), 0.91-1.01 (m, 6H), 1.24-1.37 (m, 6H), 1.47-2.03 (m, 14H), 2.06 (s, 2H), 2.14-2.25 (m, 1H), 2.43-2.77 (m, 4H), 3.48 (s, 1H), 3.56 (s, 2H), 3.63-3.86 (m, 1H), 4.00 (app t, J=14.7 Hz, 1H), 4.12-4.17 (m, 1H), 4.53-4.65 (m, 1H), 5.45 (q, J=7.2 Hz, 1H), 6.27-6.50 (m, 2H), 6.99-7.10 (m, 2H), 7.14-7.22 (m, 1H), 7.32-7.38 (m, 1H). LCMS (m/z) 596.4 [M+H], Tr=2.51 min.

Examples 29 and 30

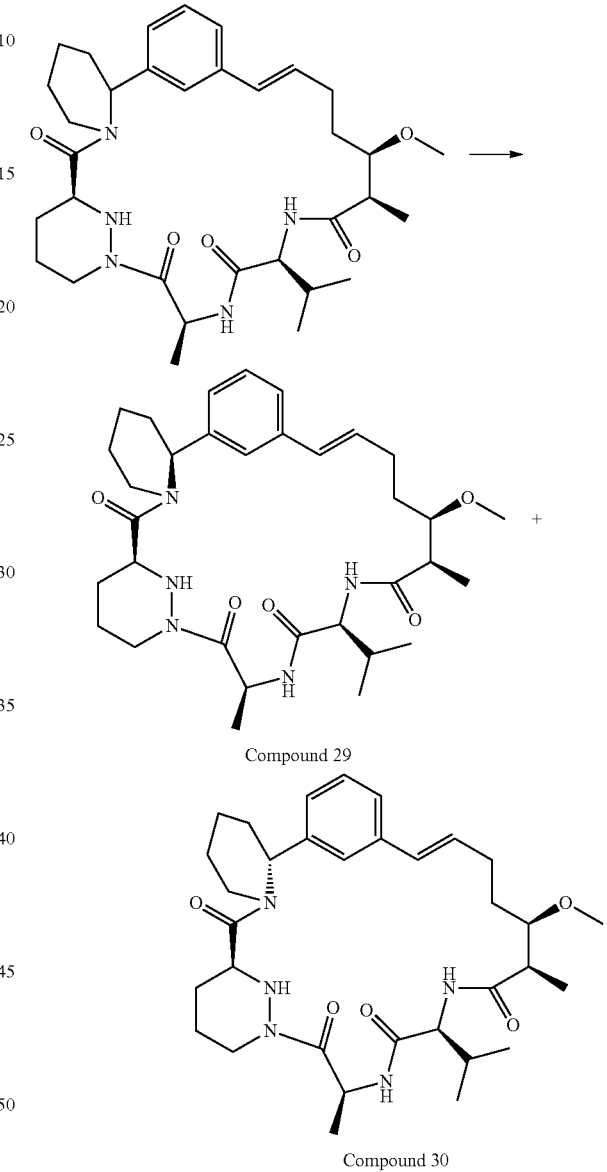

Compound 29

Compound 30

Compound 28 (155 mg, 0.26 mmol) was dissolved in a 1:1 mixture of acetonitrile/water to a concentration of 7.8 mg/mL. This solution was then eluted through a reverse phase HPLC system fitted with a Phenomenex Gemini 10µ 110 A, 250×21.2 mm column using an isocratic 2:3 acetonitrile/water flow at 20 mL/min. The mixture was resolved into the 2 separate diastereoisomers. On concentration each separate diastereoisomer yielded a white solid. The stereochemistry of each isomer was not determined. First isomer eluted, Compound 29 (15 mg, 10%). $^1$H NMR (300 MHz, CDCl$_3$) δ 0.89-1.05 (m, 8H), 1.20-1.44 (m, 10H), 1.51-1.79 (m, 3H), 1.83-1.99 (m, 4H), 2.03-2.27 (m, 3H), 2.33-2.67 (m, 3H), 2.76 (app t, J=12.3 Hz, 1H), 3.09 (app t, J=12.3 Hz, 1H), 3.22-3.38 (m, 1H), 3.47 (s, 3H), 3.54-3.62 (m, 1H), 4.17 (d, J=11.7 Hz, 1H), 4.59 (d, J=10.5 Hz, 1H), 5.39-5.53 (m, 1H), 6.01 (s, 1H), 6.09-6.23 (m, 1H), 6.30-6.55 (m, 2H), 6.99-7.23 (m, 4H). LCMS (m/z) 596.4 [M+H], Tr=2.53 min.

Second isomer eluted, Compound 30 (22 mg, 14%). $^{1}$H NMR (300 MHz, CD$_3$CN) δ 0.98-1.04 (m, 6H), 1.26-1.38 (m, 7H), 1.62-1.80 (m, 5H), 1.83-2.00 (m, 4H), 2.03-2.14 (m, 1H), 2.16-2.25 (m, 2H), 2.36-2.51 (m, 2H), 2.54-2.66 (m, 1H), 2.68-2.82 (m, 1H), 3.03-3.16 (m, 1H), 3.26-3.34 (m, 1H), 3.48 (s, 3H), 3.64-3.73 (m, 1H), 3.76-3.86 (m, 1H), 4.00 (app t, J=9.0 Hz, 1H), 4.16 (d, J=12.0 Hz, 1H), 4.55-4.66 (m, 1H), 5.41-5.53 (m, 1H), 5.97-6.06 (m, 1H), 6.10-6.22 (m, 1H), 6.35 (s, 1H), 6.38-6.49 (m, 1H), 7.00-7.11 (m, 2H), 7.14-7.23 (m, 3H). LCMS (m/z) 596.3 [M+H], Tr=2.49 min.

Example 31

Compound 31a

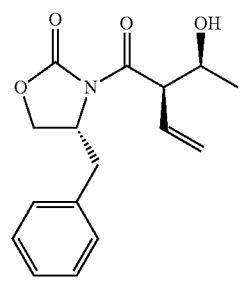

TBDMSCl, Im., DMF

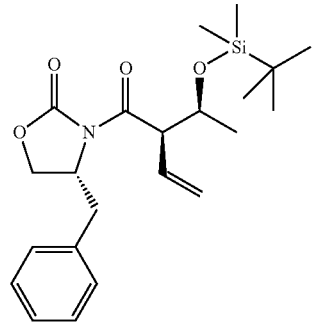

A cooled (0° C.) solution of (R)-4-benzyl-3-[(R)-2-((S)-1-hydroxy-ethyl)-but-3-enoyl]-oxazolidin-2-one (233.6 mg, 0.807 mmol, prepared as described in *Org. Lett.* 2007, 9, 1635-1638) and imidazole (241.7 mg, 3.551 mmol) in N,N-dimethylformamide (2 mL) was treated with tert-butyldimethylsilyl chloride (158.2 mg, 1.049 mmol). After stirring for 24 h at RT, the reaction was quenched with saturated ammonium chloride. The aqueous layer was extracted with diethyl ether (2×20 mL). The organics were combined, dried over sodium sulfate, filtered and the volatiles were removed in vacuo. The residue was purified by silica gel chromatography using a 25 g Isolute cartridge eluted with a continuous gradient of iso-hexanes/ethyl acetate 1:0 to 4:1 to afford the title compound (294.6 mg, 90%) as a colorless oil.

Compound 31b

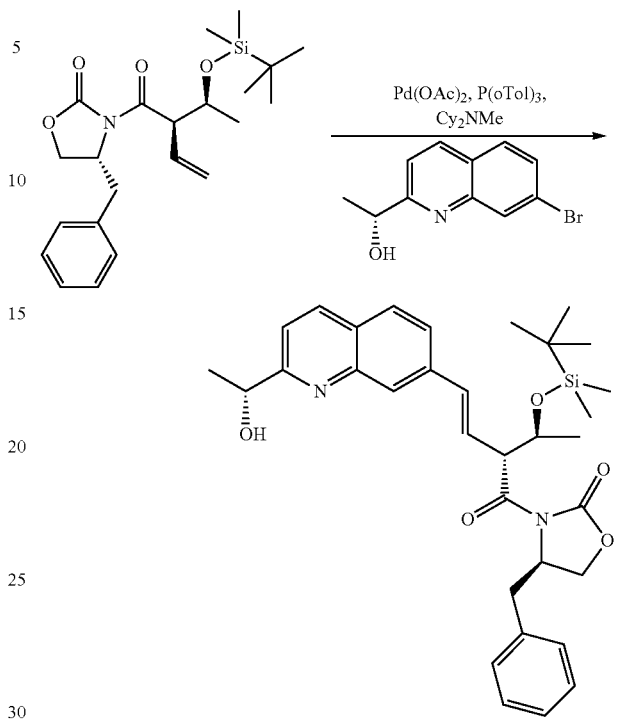

A solution of 31a (294.6 mg, 0.730 mmol), (R)-1-(7-bromo-quinolin-2-yl)-ethanol (184.0 mg, 0.730 mmol), palladium(II)acetate (32.8 mg, 0.146 mmol), tri-(o-toluoyl)phosphine (44.4 mg, 0.146 mmol) in anhydrous 1,4-dioxane (10 mL) was treated with N,N-dicylohexylmethylamine (250 μL, 1.168 mmol). After stirring at 100° C. for 5 h, the reaction was cooled to RT, diluted with dichloromethane and saturated sodium bicarbonate. The aqueous layer was extracted with dichloromethane. The organics were combined, filtered through a phase separator and the volatiles were removed in vacuo. The residue was purified by silica gel chromatography using a 25 g Isolute cartridge eluted with a continuous gradient of iso-hexanes/ethyl acetate 1:0 to 7:3 to afford the title compound (230.8 mg, 55%) as a colorless oil.

Compound 31c

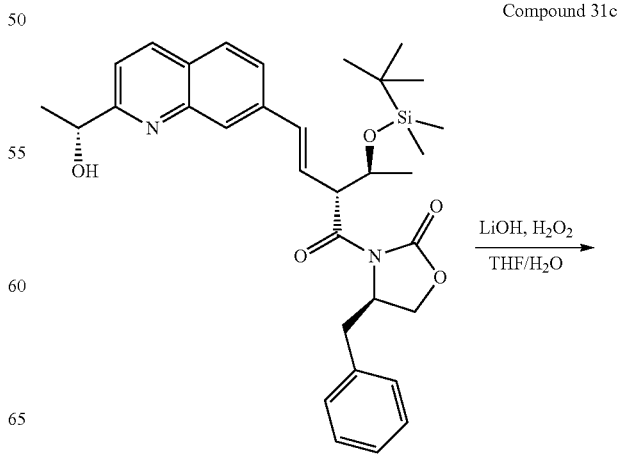

-continued

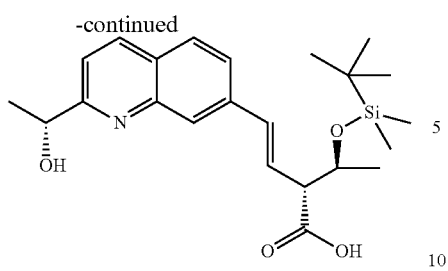

A cooled (0° C.) solution of 31b (230.8 mg, 0.401 mmol) in tetrahydrofuran/water (15 mL, 2:1) was subsequently treated with hydrogen peroxide (30% aqueous, 210 µL, 2.005 mmol) and lithium hydroxide hydrate (33.7 mg, 0.803 mmol). After stirring for 2 h at 0° C., the reaction was quenched with sodium metabisulfite (765 mg, 4.1 mmol). After stirring for 3.5 h at RT the volatiles were removed in vacuo. The mixture was then diluted with water and the pH was adjusted with potassium carbonate. The aqueous layer was washed with dichloromethane (2×20 mL) and acidified with 2 M hydrochloric acid (pH ~1) then extracted with dichloromethane (3×30 mL). All the organics were combined, dried over sodium sulfate, filtered and the volatiles were removed in vacuo. The residue was purified by silica gel chromatography using a 25 g Isolute cartridge eluted with a continuous gradient of iso-hexanes/ethyl acetate 1:0 to 0:1 to afford the title compound (69.8 mg, 42%) as a white solid.

Compound 31d was prepared in the same manner as 22e using 31c instead of (E)-4-[2-((R)-1-acetoxy-ethyl)-quinolin-7-yl]-2,2-dimethyl-but-3-enoic acid in 46% yield.

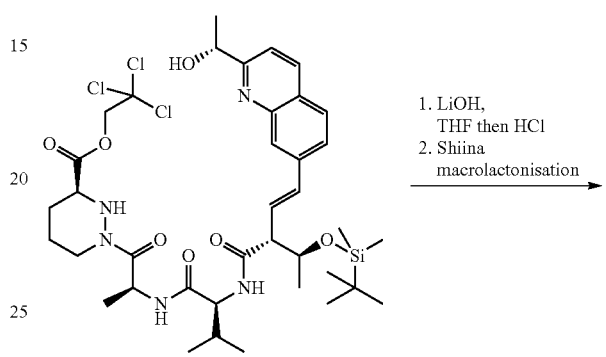

Compound 31

1. LiOH, THF then HCl
2. Shiina macrolactonisation

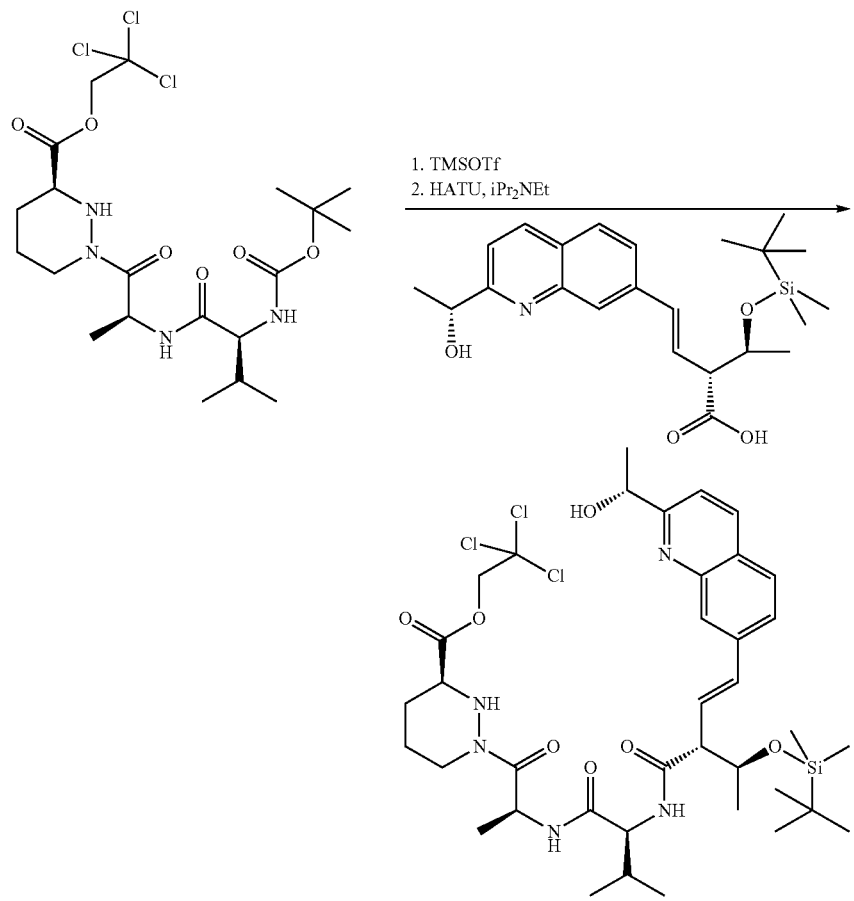

Compound 31d

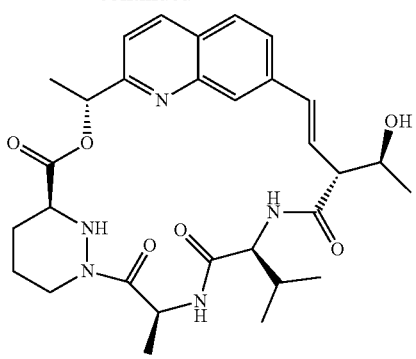

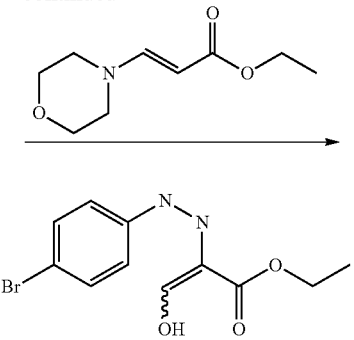

Compound 31 was prepared in the same manner as Compound 22 using 31d instead of (S)-1-[(S)-2-((S)-2-{(E)-4-[2-((R)-1-hydroxy-ethyl)-quinolin-7-yl]-2,2-dimethyl-but-3-enoylamino}-3-methyl-butyrylamino)-propionyl]-hexahydro-pyridazine-3-carboxylic acid 2,2,2-trichloro-ethyl ester in 10% yield. $^1$H NMR (300 MHz, CDCl$_3$) δ 1.00 (d, J=6.7 Hz, 3H), 1.01 (d, J=6.7 Hz, 3H), 1.22-1.44 (m, 4H), 1.64 (d, J=7.1 Hz, 3H), 1.68-1.77 (m, 4H), 1.89-2.08 (m, 3H), 2.71-2.84 (m, 1H), 3.78-3.86 (m, 1H), 4.11 (dd, J=8.2, 6.2 Hz, 1H), 4.17-4.25 (m, 2H), 4.38-4.47 (m, 1H), 5.68 (q, J=7.1 Hz, 1H), 5.94 (q, J=6.9 Hz, 1H), 6.47 (d, J=16.5 Hz, 1H), 6.69 (dd, J=16.5, 5.3 Hz, 1H), 7.40 (d, J=8.5 Hz, 1H), 7.68 (s, 1H), 7.76 (dd, J=8.7, 1.3 Hz, 1H), 7.81 (d, J=8.7 Hz, 1H), 8.21 (d, J=8.5 Hz, 1H). LCMS (m/z) 566.1 [M+H], Tr=1.65 min.

A cooled (0° C.) solution of 4-bromoaniline (2.7 g, 15.7 mmol) in water (30 mL) was subsequently treated with concentrated hydrochloric acid (3.5 mL) and sodium nitrite (1.3 g, 18.840 mmol). After 20 min at 0° C., concentrated hydrochloric acid (5.3 mL) and sodium tetrafluoroborate (6.9 g, 62.847 mmol) were added. After 40 min at 0° C., the intermediate diazonium was filtered, washed with water, methanol and diethyl ether (2.1021 g) and was used without further purification. A solution of the diazonium (7.762 mmol) in acetonitrile (50 mL) was treated with 32a (1.6614 g, 8.970 mmol). After 1 h at RT, silica gel was added. After stirring at RT for 16 h, the volatiles were removed in vacuo and the residue was purified by silica gel chromatography using a 100 g Isolute cartridge eluted with a continuous gradient of iso-hexanes/ethyl acetate 1:0 to 9:1 to afford the title compound (1.9811 g, 85%) as a highly coloured solid and as a mixture of tautomers.

Example 32

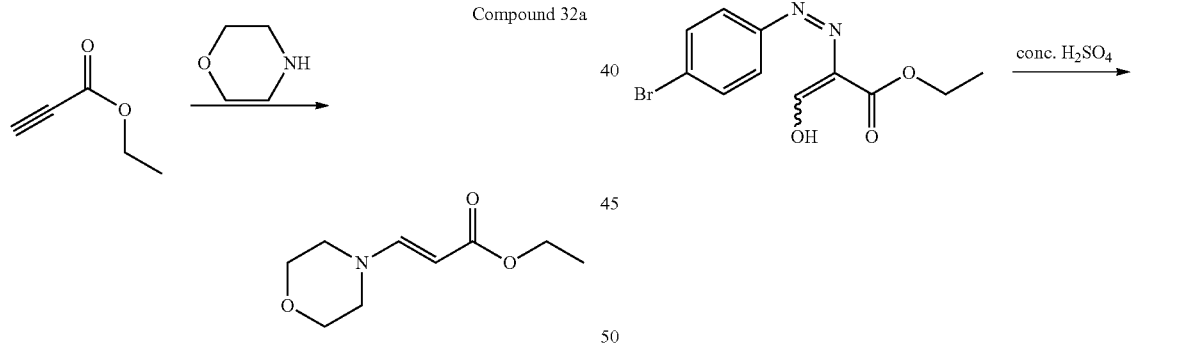

Compound 32a

To a cooled (0° C.) solution of ethyl propiolate (2 mL, 19.735 mmol) in dichloromethane (50 mL) was added dropwise morpholine (1.7 mL, 19.435 mmol). After stirring at RT for 1.5 h, the volatiles were removed in vacuo and the residue was purified by silica gel chromatography using a 50 g Isolute cartridge eluted with dichloromethane/methanol 20:1 to afford the title compound (3.5034 g, 97%) as a colorless oil.

Compound 32b

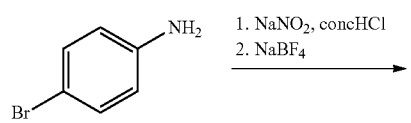

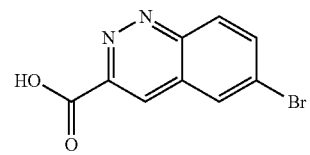

A solution of 32b (1.9811 g, 6.623 mmol) in concentrated sulphuric acid (25 mL) was heated at 100° C. for 3 h. After cooling to 0° C., the mixture was diluted with water (150 mL) and a brown solid was filtered off. The filtrate was extracted with diethyl ether (2×50 mL), dichloromethane (2×50 mL) and ethyl acetate (50 mL). The organics were combined, dried over sodium sulfate, filtered and the volatiles were removed in vacuo to provide the title compound (1.5094 g, 90%) as an orange solid that turned dark upon standing.

Compound 32d

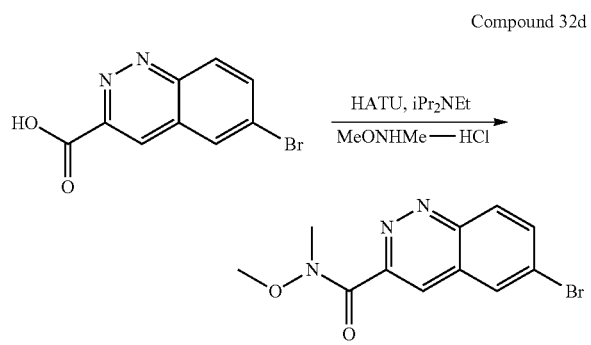

Compound 32f

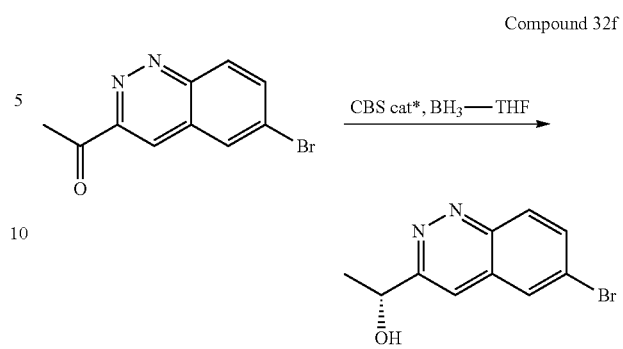

A cooled (0° C.) solution of 32c (1.5094 g, 5.964 mmol), N,O-dimethylhydroxylamine hydrochloride (755.9 mg, 7.753 mmol) and N,N-diisopropylethylamine (4.2 mL, 23.856 mmol) in acetonitrile (50 mL) was treated with 2-(1H-7-azabenzotriazol-1-yl)-1,1,3,3-tetramethyl uronium hexafluorophosphate methanaminium (3.175 g, 8.350 mmol). After stirring for 6 h at RT, the mixture was cooled to 0° C. and quenched with 1 M hydrochloric acid (60 mL). The aqueous layer was extracted with ethyl acetate (3×50 mL). The organics were combined, dried over sodium sulfate, filtered and the volatiles were removed in vacuo. The residue was purified by silica gel chromatography using a 100 g Isolute cartridge eluted with a continuous gradient of iso-hexanes/ethyl acetate 1:0 to 1:1 to afford the title compound (1.4229 g, 81%) as a bright yellow solid.

A solution of 32e (751.5 mg, 2.993 mmol) in tetrahydrofuran (30 mL) was treated with (S)-(−)-2-methyl-CBS-oxazaborolidine (3.6 mL, 3.592 mmol, 1 M in toluene). After 10 min at RT the mixture was cooled to −60° C. and treated with borane-tetrahydrofuran complex (6 mL, 5.986 mmol, 1 M in tetrahydrofuran). After 1.5 h at −55° C. to −30° C., the reaction was quenched with methanol (20 mL). After stirring at RT for 16 h, the volatiles were removed in vacuo. The residue was purified by silica gel chromatography using a 50 g Isolute cartridge eluted with a continuous gradient of iso-hexanes/ethyl acetate 1:0 to 3:2 to afford the title compound (345.0 mg, 45%) as a yellow solid.

Compound 32g

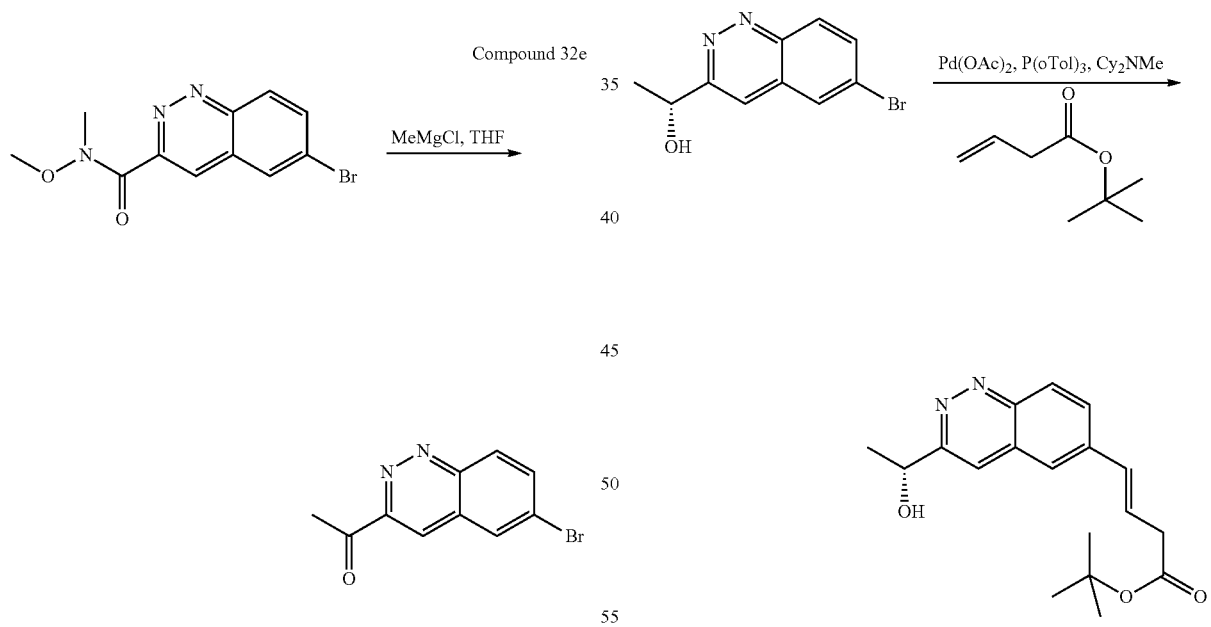

Compound 32e

A cooled (−78° C.) solution of 32d (1.4229 g, 4.805 mmol) in tetrahydrofuran (50 mL) was treated with methylmagnesium chloride (3.2 mL, 9.610 mmol, 3 M in diethyl ether). After 1 h at −78° C. and 3 h at 0° C., the reaction was quenched with saturated ammonium chloride (30 mL). The aqueous layer was extracted with ethyl acetate (3×50 mL). The organics were combined, dried over sodium sulfate, filtered and the volatiles were removed in vacuo. The residue was purified by silica gel chromatography using a 100 g Isolute cartridge eluted with a continuous gradient of iso-hexanes/ethyl acetate 1:0 to 4:1 to afford the title compound (751.5 mg, 62%) as a yellow solid.

A solution of 32f (345.0 mg, 1.363 mmol), palladium II acetate (61.2 mg, 0.273 mmol), tri-(o-toluoyl)phosphine (83.1 mg, 0.273 mmol), 3-butenoic acid tert-butyl ester (560 µL, 3.407 mmol) and N,N-dicyclohexylmethylamine (470 µL, 2.181 mmol) in anhydrous 1,4-dioxane (20 mL) was heated at 100° C. for 1.7 h. After cooling to RT the volatiles were removed in vacuo. The residue was purified by silica gel chromatography using a 50 g Isolute cartridge eluted with a continuous gradient of iso-hexanes/ethyl acetate 1:0 to 2:3 to afford the title compound (244.1 mg, 57%) as a yellow solid.

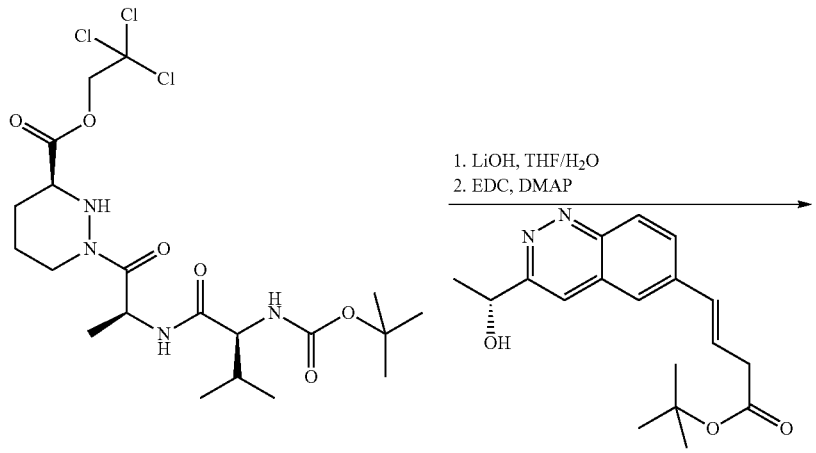

1. LiOH, THF/H₂O
2. EDC, DMAP

Compound 32h

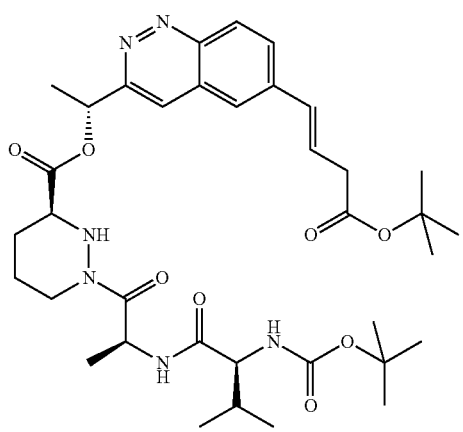

A cooled (0° C.) solution of 1e (422.0 mg, 0.793 mmol) in tetrahydrofuran/water (25 mL, 4:1) was treated with lithium hydroxide hydrate (67.0 mg, 1.587 mmol). After stirring at 0° C. for 1.5 h, the reaction was quenched with 1 M hydrochloric acid (20 mL). The aqueous layer was extracted with ethyl acetate (2×30 mL). The organics were combined, dried over sodium sulfate, filtered and the volatiles were removed in vacuo then residual trichloroethanol was azeotroped off with toluene (3×) to give the intermediate acid as a white solid which was then combined with 32 g (244.1 mg, 0.793 mmol), 4-dimethylaminopyridine (97.0 mg, 0.793 mmol), N-(3-dimethylaminopropyl)-N'-ethylcarbodiimide hydrochloride (243.3 mg, 1.269 mmol) and dichloromethane (20 mL). After stirring at RT for 16 h, the reaction was quenched with dilute hydrochloric acid. The aqueous layer was extracted with dichloromethane (30 mL). The organics were combined and filtered through a phase separator and the volatiles were removed in vacuo. The residue was purified by silica gel chromatography using a 50 g Isolute cartridge eluted with a continuous gradient of iso-hexane/sethyl acetate 1:0 to 1:2 to afford the title compound (164.4 mg, 30% over 2 steps) as a yellow glass.

Compound 32

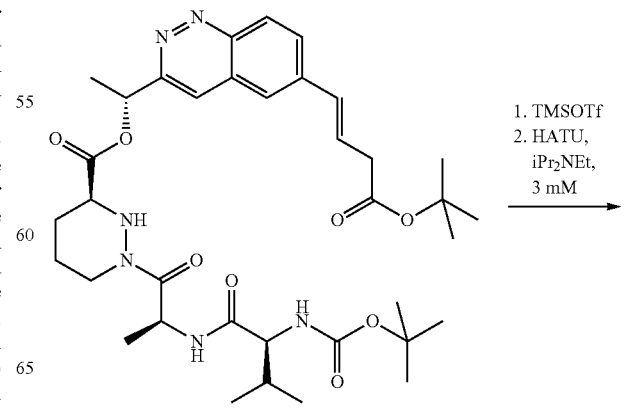

1. TMSOTf
2. HATU, iPr₂NEt, 3 mM

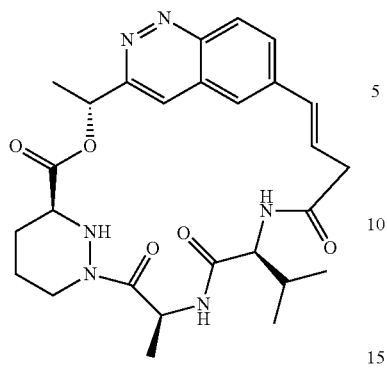

A cooled (0° C.) solution of 32h (164.4 mg, 0.236 mmol) in anhydrous dichloromethane (20 mL) was treated with trimethylsilyl methanesulfonate (170 µL, 0.944 mmol). After stirring for 1 h at 0° C., the reaction was quenched with N,N-diisopropylethylamine (330 µL, 1.888 mmol) and the volatiles were removed in vacuo. A cooled (0° C.) solution of the crude amino acid in acetonitrile (80 mL) was subsequently treated with N,N-diisopropylethylamine (330 µL, 1.888 mmol) and 2-(1H-7-azabenzotriazol-1-yl)-1,1,3,3-tetramethyl uronium hexafluorophosphate methanaminium (125.6 mg, 0.330 mmol). After stirring at RT for 2.5 h, the volatiles were removed in vacuo. The residue was purified by silica gel chromatography using a 50 g Isolute cartridge eluted with a continuous gradient of iso-hexanes/ethyl acetate 1:0 to 0:1 to afford the final compound (170.7 mg) as a mixture. Reverse phase preparative HPLC which was eluted with a gradient of water/acetonitrile 95:5 to 0:100 provided the title compound (30.6 mg, 25%) as a white solid. $^1$H NMR (300 MHz, CD$_3$OD) δ 1.00 (d, J=6.7 Hz, 3H), 1.03 (d, J=6.7 Hz, 3H), 1.61 (d, J=7.3 Hz, 3H), 1.66-2.07 (m, 8H), 2.68-2.81 (m, 1H), 2.97-3.07 (m, 1H), 3.35-3.47 (m, 1H), 3.76-3.89 (m, 1H), 4.28 (d, J=9.4 Hz, 1H), 4.37-4.47 (m, 1H), 4.53-4.67 (m, 1H), 5.52 (q, J=7.1 Hz, 1H), 6.36-6.51 (m, 2H), 6.72 (d, J=16.0 Hz, 1H), 7.61 (s, 1H), 7.97 (dd, J=8.9, 1.6 Hz, 1H), 8.06 (s, 1H), 8.38 (d, J=8.9 Hz, 1H). LCMS (m/z) 523.1 [M+H], Tr=1.65 min.

Examples 33 and 34

Compound 33a

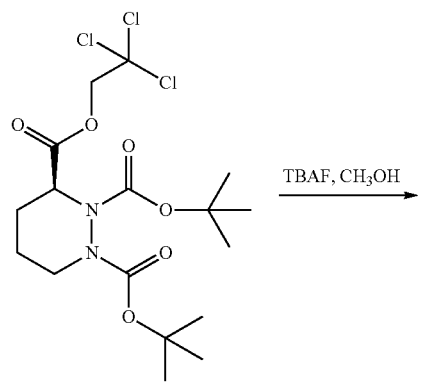

TBAF, CH$_3$OH

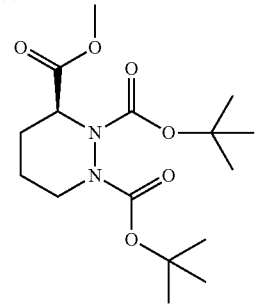

A cooled (0° C.) solution of (S)-tetrahydro-pyridazine-1,2,3-tricarboxylic acid 1,2-di-tert-butyl ester 3-(2,2,2-trichloro-ethyl) ester (5.5297 g, 11.975 mmol) in tetrahydrofuran/methanol (50 mL, 1:1) was treated with tetrabutylammonium fluoride (23.9 mL, 23.950 mmol, 1 M in tetrahydrofuran). After stirring at RT for 24 h, the volatiles were removed in vacuo. The residue was dissolved in diethyl ether and saturated sodium bicarbonate. The aqueous layer was extracted with diethyl ether (50 mL). The organics were combined, dried over sodium sulfate, filtered and the volatiles were removed in vacuo. The residue was purified by silica gel chromatography using a 100 g Isolute cartridge eluted with a continuous gradient of iso-hexanes/ethyl acetate 1:0 to 9:1 where the mixed fractions were further purified by silica gel chromatography using a 50 g Isolute cartridge eluted with a continuous gradient of iso-hexanes/ethyl acetate 1:0 to 4:1 to afford the title compound (3.9765 g, 96%) as a colorless oil and as a mixture of rotamers.

Compound 33b

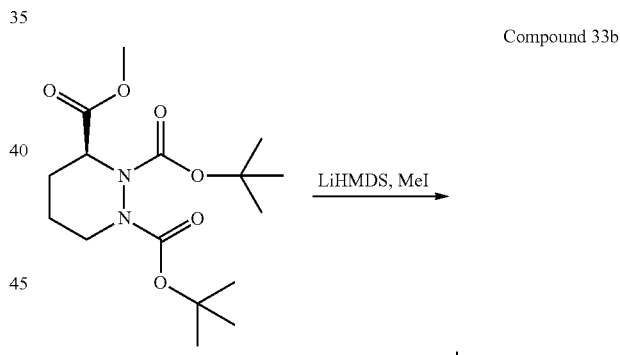

LiHMDS, MeI

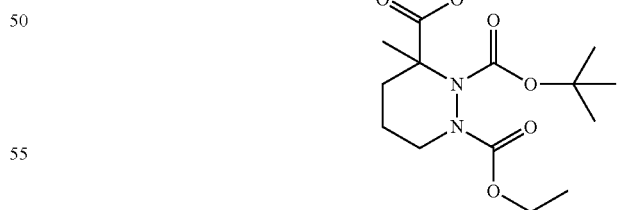

A cooled (−78° C.) solution of 33a (1.4112 g, 4.097 mmol) in anhydrous tetrahydrofuran (10 mL) was treated with lithium bis(trimethylsilyl)amide (6.2 mL, 6.146 mmol, 1 M in tetrahydrofuran). After stirring for 1.25 h at −78° C., the mixture was treated with iodomethane (640 µL, 10.242 mmol). After stirring for 1 h at −78° C., 1 h at 0° C. and 1 h at RT, the reaction was quenched with pH 7 buffer at 0° C. The aqueous was extracted with dichloromethane (2×50 mL). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 4:1 to afford the title compound (760.7 mg, 52%) as a colorless oil and as a mixture of rotamers.

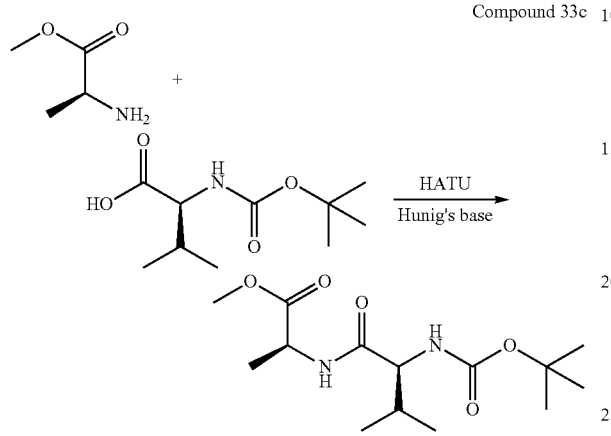

Compound 33c

A cooled (0° C.) solution of (S)-2-tert-butoxycarbonylamino-3-methyl-butyric acid (3.020 g, 13.908 mmol), (S)-2-amino-propionic acid methyl ester hydrochloride (1.9413 g, 13.908 mmol) and N,N-diisopropylethylamine (17.1 mL, 55.632 mmol) in acetonitrile (50 mL) was treated with 2-(1H-7-azabenzotriazol-1-yl)-1,1,3,3-tetramethyl uronium hexafluorophosphate methanaminium (7.403 g, 19.471 mmol). After stirring at RT for 6 h, the reaction was quenched with hydrochloric acid (1 M, 100 mL). The aqueous layer was extracted with ethyl acetate (2×100 mL). The organics were combined, dried over sodium sulfate, filtered and the volatiles were removed in vacuo. The residue was purified by silica gel chromatography using a 100 g Isolute cartridge eluted with a continuous gradient of iso-hexanes/ethyl acetate 1:0 to 3:2 to afford the title compound (4.0996 g, 97%) as a white solid.

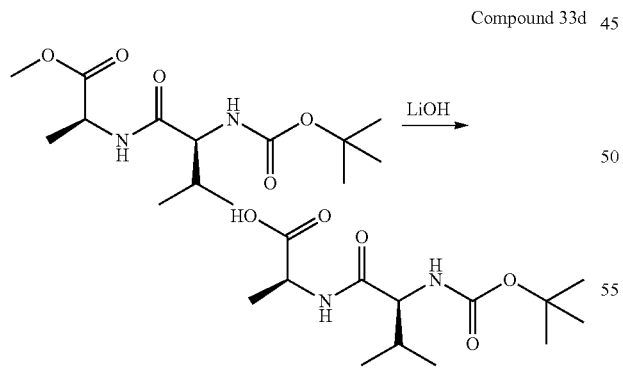

Compound 33d

A cooled (0° C.) solution of 33c (317.0 mg, 1.048 mmol) in tetrahydrofuran/water (12 mL, 5:1) was treated with lithium hydroxide hydrate (88.0 mg, 2.096 mmol). After stirring at 0° C. for 2.5 h, the reaction was quenched with hydrochloric acid (1 M, 30 mL). The aqueous layer was extracted with dichloromethane (2×30 mL). The organics were combined, filtered through a phase separator and the volatiles were removed in vacuo to provide crude acid as a white solid.

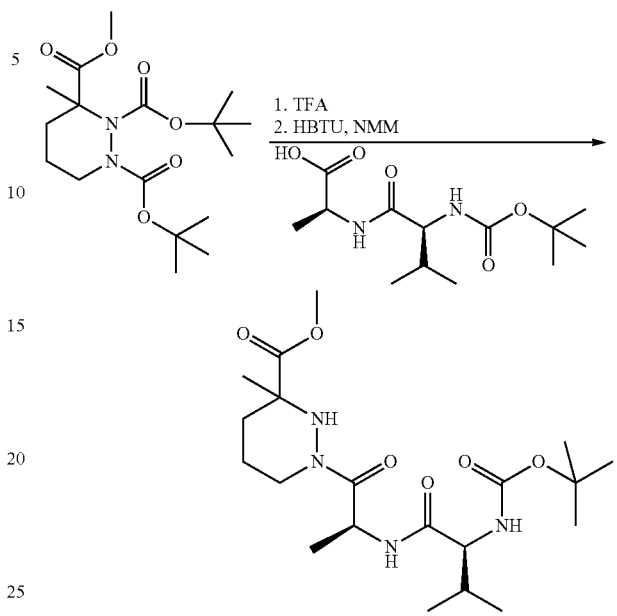

Compound 33e

A cooled (0° C.) solution of 33b (376.0 mg, 1.049 mmol) in anhydrous dichloromethane (15 mL) was treated with trifluoroacetic acid (5 mL). After stirring at 0° C. for 30 min and RT for 2 h, trifluoroacetic acid (4 mL) was added. After 1 h, the volatiles were removed in vacuo and the residual trifluoroacetic acid azeotroped off with toluene (3×) to provide the bis-trifluoroacetic acid ammonium salt as an off-white solid. A cooled (0° C.) solution of the bis-trifluoroacetic acid ammonium salt and crude (S)-2-((S)-2-tert-butoxycarbonylamino-3-methyl-butyrylamino)-propionic acid as prepared in the previous step in anhydrous dichloromethane (15 mL) was subsequently treated with N-methylmorpholine (580 µL, 5.240 mmol) and O-(benzotriazol-1-yl)-N,N,N',N'-tetramethyluronium hexafluorophosphate (596.2 mg, 1.572 mmol). After stirring for 19 h at RT, the reaction was quenched with hydrochloric acid (1 M, 30 mL). The aqueous was extracted with dichloromethane (2×30 mL). The organics were combined, washed with saturated aqueous sodium bicarbonate and filtered through a phase separator. The volatiles were removed in vacuo and the residue was purified by silica gel chromatography using a 50 g Isolute cartridge eluted with a continuous gradient of iso-hexanes/ethyl acetate 1:0 to 1:2 to afford the title compound (373.1 mg, 83% over 2 steps) as a white foam and as a mixture of diastereoisomers.

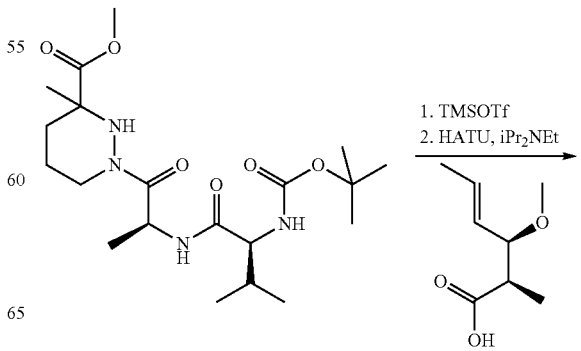

-continued

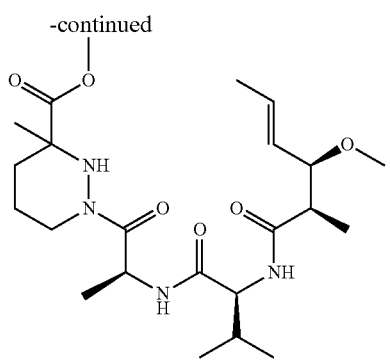

A cooled (0° C.) solution of 33e (373.1 mg, 0.871 mmol) in anhydrous dichloromethane (10 mL) was treated with trimethylsilyl methanesulfonate (310 µL, 1.741 mmol). After stirring for 1 h at 0° C., the reaction was quenched with N,N-diisopropylethylamine (610 µL, 3.484 mmol) and the volatiles were removed in vacuo. A cooled (0° C.) solution of the crude amine and (E)-(2R,3R)-3-methoxy-2-methyl-hex-4-enoic acid (137.8 mg, 0.871 mmol) in anhydrous acetonitrile (15 mL) was subsequently treated with N,N-diisopropylethylamine (610 µL, 3.484 mmol) and 2-(1H-7-azabenzotriazol-1-yl)-1,1,3,3-tetramethyl uronium hexafluorophosphate methanaminium (463.7 mg, 1.219 mmol). After stirring at RT for 18 h, the reaction was quenched with hydrochloric acid (1 M, 30 mL). The aqueous layer was extracted with ethyl acetate (2×30 mL). The organics were combined, washed with saturated sodium bicarbonate (20 mL), dried over sodium sulfate, filtered and the volatiles were removed in vacuo. The residue was purified by silica gel chromatography using a 25 g Isolute cartridge eluted with a continuous gradient of iso-hexanes/ethyl acetate 1:0 to 1:2 to 1:4 to afford the title compound (332.2 mg, 81%) as a colorless solid and as a mixture of diastereoisomers.

Compound 33g

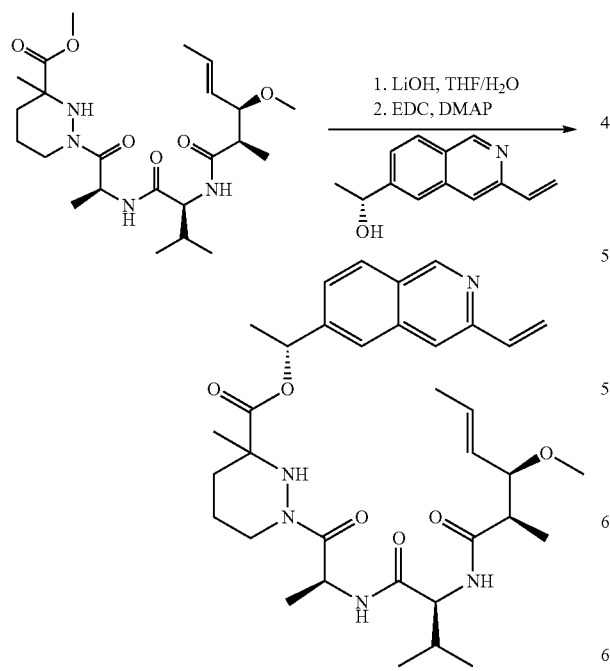

Compound 33g was prepared in the same manner as (S)-1-[(S)-2-((S)-2-tert-butoxycarbonylamino-3-methyl-butyrylamino)-propionyl]-hexahydro-pyridazine-3-carboxylic acid (R)-1-[6-((E)-3-tert-butoxycarbonyl-propenyl)-cinnolin-3-yl]-ethyl ester using 33f and (R)-1-(3-vinyl-isoquinolin-6-yl)-ethanol instead of 1e and (E)-4-[3-((R)-1-hydroxy-ethyl)-cinnolin-6-yl]-but-3-enoic acid tert-butyl ester in 30% yield over 2 steps.

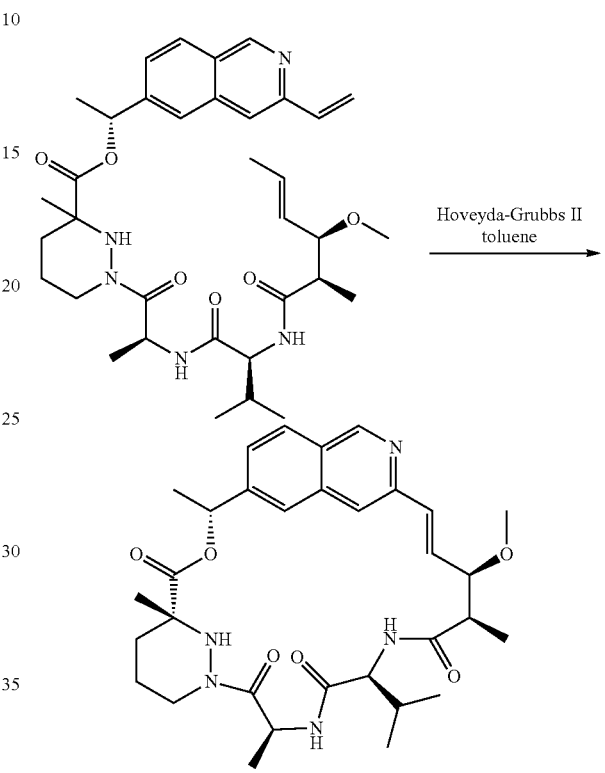

Compound 33

Compound 34

A solution of 33g (136.2 mg, 0.214 mmol) in toluene (70 mL) was degassed by bubbling $N_2$ gas through for 20 min. Hoveyda-Grubbs $2^{nd}$ generation catalyst (27 mg, 0.043 mmol) was added and the mixture was refluxed for 2.5 h. More Hoveyda-Grubbs $2^{nd}$ generation catalyst (20 mg) was added and after stirring at reflux for 1 h, the mixture was cooled to RT, the volatiles were removed in vacuo and the residue was purified by silica gel chromatography using a 25 g Isolute cartridge eluted with a continuous gradient of ethyl acetate/acetone 1:0 to 10:1 to afford both diastereoisomers in separate mixtures. Both mixtures were purified by silica gel chromatography using a 10 g Isolute cartridge eluted by gravity with a continuous gradient of ethyl acetate/acetone 1:0 to 10:1 to provide the more polar diastereoisomer (19.7 mg, 15%) as a white solid. The less polar diastereomer was further purified by preparative TLC eluted with ethyl acetate (4 elutions) and subsequent preparative TLC eluted with iso-hexanes/acetone 7:3 (2 elutions) to afford the title compound (7.6 mg, 6%) as a white solid. Relative stereochemistry was not assigned.

More polar diastereoisomer Compound 33: $^1$H NMR (300 MHz, CDCl$_3$) δ 0.83-1.07 (m, 7H), 1.41 (d, J=7.1 Hz, 3H), 1.47 (d, J=6.9 Hz, 3H), 1.50 (s, 3H), 1.70 (d, J=6.7 Hz, 3H), 1.75-1.90 (m, 2H), 1.96-2.15 (m, 3H), 2.64 (dd, J=7.6, 3.1 Hz, 1H), 2.70-2.84 (m, 1H), 3.42 (s, 3H), 3.90 (dd, J=8.7, 3.1 Hz, 1H), 4.00 (app t, J=8.0 Hz, 1H), 4.10 (s, 1H), 4.58-4.69 (m, 1H), 6.00 (dd, J=9.4, 7.1 Hz, 1H), 6.22 (q, J=6.2 Hz, 1H), 6.51 (d, J=9.8 Hz, 1H), 6.93 (s, 1H), 7.13-7.23 (m, 1H), 7.34-7.43 (m, 1H), 7.90-7.97 (m, 2H), 8.47 (s, 1H). LCMS (m/z) 594.3 [M+H], Tr=1.87 min.

Less polar diastereoisomer Compound 34: $^1$H NMR (300 MHz, CD$_3$CN) δ −0.51-−0.39 (m, 5H), −0.30 (d, J=6.9 Hz, 3H), 0.06 (d, J=7.1 Hz, 3H), 0.15 (d, J=6.9 Hz, 3H), 0.19 (s, 0.25-0.34 (m, 4H), 0.38-0.45 (m, 1H), 0.81-1.02 (m, 2H), 1.14-1.42 (m, 2H), 2.69 (dd, J=8.7, 2.9 Hz, 1H), 3.00-3.10 (m, 2H), 3.45 (s, 3H), 4.32 (app pentet, J=7.1 Hz, 1H), 4.76 (q, J=6.7 Hz, 1H), 5.53 (d, J=16.3 Hz, 1H), 5.85 (dd, J=16.1, 8.9 Hz, 1H), 6.20 (dd, J=8.5, 1.6 Hz, 6.41 (d, J=8.9 Hz, 1H), 6.65-6.75 (m, 2H), 6.91 (s, 1H), 7.11 (d, J=7.3 Hz, 1H), 7.79 (s, 1H). LCMS (m/z) 594.3 [M+H], Tr=1.83 min.

Example 35

Compound 35a

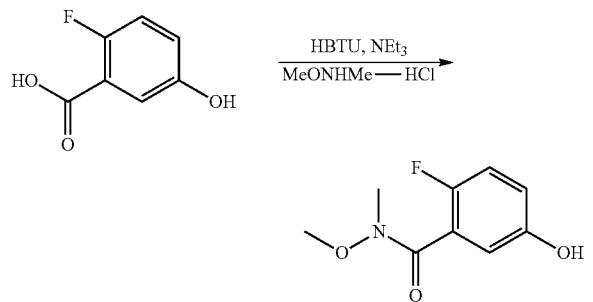

A cooled (0° C.) solution of 2-fluoro-5-hydroxy-benzoic acid (1.0051 g, 6.438 mmol), N,O-dimethylhydroxylamine hydrochloride (1.2560 g, 12.856 mmol) and triethylamine (3.6 mL, 25.752 mmol) in dichloromethane (35 mL) was treated with O-(benzotriazol-1-yl)-N,N,N'N'-tetramethyluronium hexafluorophosphate (3.663 g, 9.658 mmol). After stirring at RT for 20 h, the reaction was quenched at 0° C. with hydrochloric acid (2 M, 30 mL). The emulsion was filtered on Celite then the aqueous layer was extracted with dichloromethane (50 mL). The organics were combined, filtered through a phase separator and the volatiles were removed in vacuo. The residue was purified by silica gel chromatography using a 50 g Isolute cartridge eluted with a continuous gradient of toluene/diethyl ether 1:0 to 1:2 to afford the title compound (260.5 mg, 20%) as a colorless oil.

Compound 35b

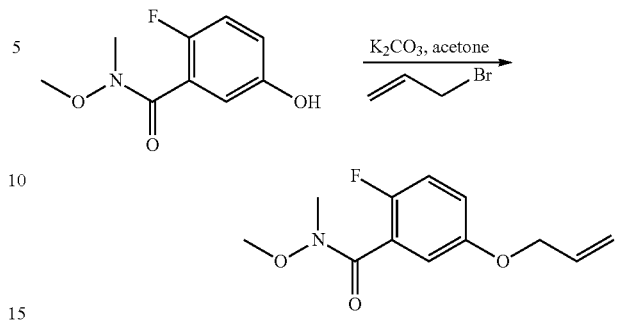

A solution of 35a (260.5 mg, 1.308 mmol) in acetone (20 mL) was subsequently treated with potassium carbonate (903.8 mg, 6.539 mmol) and allylbromide (340 μL, 3.924 mmol). After stirring at RT for 24 h, the reaction was quenched with water (20 mL). The aqueous layer was extracted with dichloromethane (2×30 mL). The organics were combined, filtered through a phase separator and the volatiles were removed in vacuo. The residue was purified by silica gel chromatography using a 25 g (solute cartridge eluted with a continuous gradient of iso-hexanes/ethyl acetate 1:0 to 3:2 to afford the title compound (289.7 mg, 92%) as a colorless oil.

Compound 35c

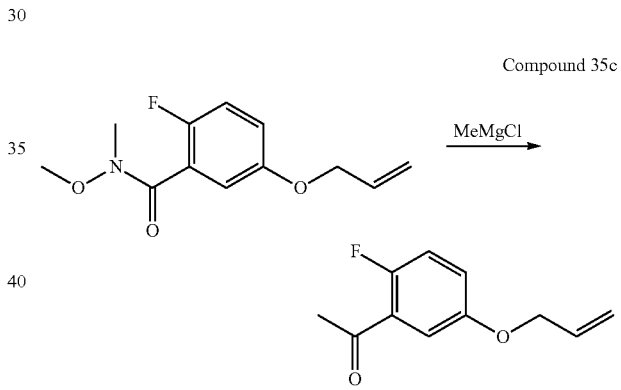

A cooled (−78° C.) solution of 35b (289.7 mg, 1.210 mmol) in tetrahydrofuran (10 mL) was treated with methylmagnesium chloride (810 μL, 2.422 mmol, 3 M in diethyl ether). After 1.25 h at −78° C., 2 h at 0° C. and 16 h at RT, methylmagnesium chloride (810 μL, 2.422 mmol, 3 M in diethyl ether) was added. After 2.5 h at −78° C. and 1.2 h at RT, the reaction was quenched with silica gel and the volatiles were removed in vacuo. The residue was purified by silica gel chromatography using a 25 g Isolute cartridge eluted with a continuous gradient of iso-hexanes/ethyl acetate 1:0 to 9:1 to afford the title compound (196.7 mg, 84%) as a colorless oil.

Compound 35d

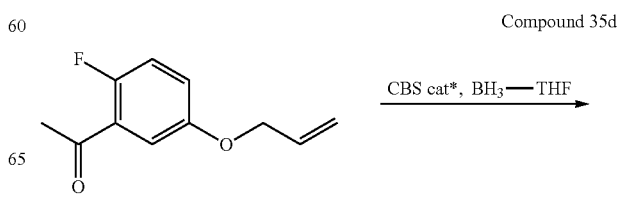

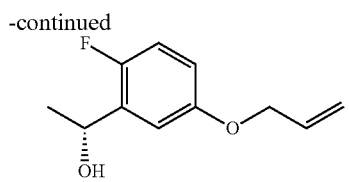

A solution of 35c (196.7 mg, 1.013 mmol) in tetrahydrofuran (15 mL) was treated with (S)-(−)-2-methyl-CBS-oxazaborolidine (1.2 mL, 1.215 mmol, 1 M in toluene). After 10 min at RT the mixture was cooled to −50° C. and treated with borane tetrahydrofuran complex (2.1 mL, 2.026 mmol, 1 M in tetrahydrofuran). After 1.5 h at −50° C. to −40° C., the reaction was quenched with methanol (6 mL). After stirring at RT for 22 h, the volatiles were removed in vacuo. The residue was purified by silica gel chromatography using a 25 g Isolute cartridge eluted with a continuous gradient of iso-hexanes/ethyl acetate 1:0 to 4:1 to afford the title compound (179.4 mg, 90%) as a white solid.

Compound 35e

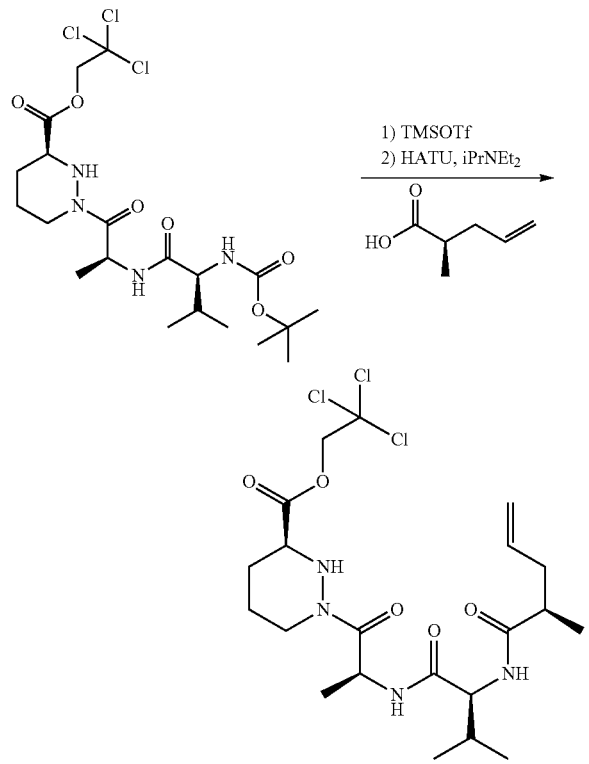

A cooled (0° C.) solution of 1e (1.9973 g, 3.755 mmol) in anhydrous dichloromethane (40 mL) was treated with trimethylsilyl trifluoromethanesulfonate (1.4 mL, 7.510 mmol). After 30 min at 0° C., the reaction mixture was treated with N,N-diisopropylethylamine (2.6 mL, 15.020 mmol) and the volatiles were removed in vacuo to afford the corresponding amine. A cooled (0° C.) solution of this amine, (E)-(2R,3R)-2-methylhex-6-enoic acid (428.6 mg, 3.755 mmol, prepared as described in *Synlett* 2002, 12, pp 2039-2040) and N,N-diisopropylethylamine (2.6 mL, 15.020 mmol) in acetonitrile (50 mL) was treated with 2-(1H-7-azabenzotriazol-1-yl)-1,1,3,3-tetramethyl uronium hexafluorophosphate methanaminium (1.999 g, 5.257 mmol). After stirring at RT for 20 h, the reaction was quenched with hydrochloric acid (1 M, 100 mL). The aqueous layer was extracted with ethyl acetate (2×50 mL). The organics were combined, washed with saturated sodium bicarbonate, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:4 to afford the title compound (1.6735 g, 84%) as a brown foam.

Compound 35f

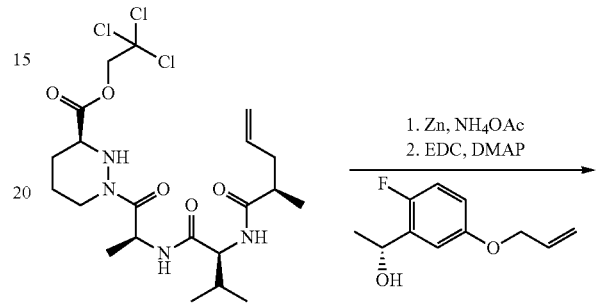

A solution of 35e (534.7 mg, 1.013 mmol) in tetrahydrofuran (20 mL) was subsequently treated with zinc powder (1.457 g, 22.286 mmol) and a solution of ammonium acetate (1.171 g, 15.195 mmol) in water (5 mL). After stirring at RT for 24 h, the mixture was filtered through Celite. The solid was rinsed with saturated potassium bisulfate and ethyl acetate. The pH of the filtrate was adjusted with 2 M hydrochloric acid then the aqueous layer was extracted with ethyl acetate (2×50 mL). The organics were combined, dried over sodium sulfate, filtered and the volatiles were removed in vacuo. Residual acetic acid was azeotroped off with toluene (3×) to provide the corresponding acid as a white solid. A solution of the crude acid, (R)-1-(5-allyloxy-2-fluoro-phenyl)-ethanol (179.4 mg, 0.914 mmol) and 4-dimethylaminopyridine (123.7 mg, 1.013 mmol) in dichloromethane (15 mL) was treated with N-(3-dimethylaminopropyl)-N'-ethylcarbodiimide hydrochloride (310.8 mg, 1.621 mmol). After stirring at RT for 20 h, the reaction was quenched at 0° C. with hydrochloric acid (2 M, 15 mL). The aqueous layer was extracted with ethyl acetate (2×). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:3 to afford the title compound (310.5 mg, 59% over 2 steps) as a white solid.

Compound 35

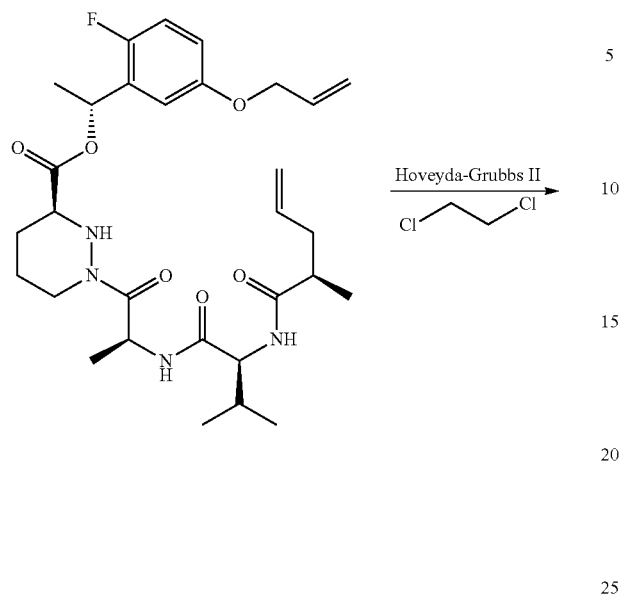

A solution of 35f (310.5 mg, 0.540 mmol) in dichloroethane (180 mL) was treated with Hoveyda-Grubbs $2^{nd}$ generation catalyst (67.7 mg, 0.108 mmol). After stirring at reflux for 2 h, the reaction was cooled to RT and the volatiles were removed in vacuo. The residue was purified by silica gel chromatography using a 50 g Isolute cartridge eluted with a continuous gradient of iso-hexanes/ethyl acetate 1:0 to 0:1 then using a 25 g Isolute cartridge eluted by gravity with a continuous gradient of iso-hexanes/ethyl acetate 1:0 to 0:1 to afford the title compound (109.9 mg) in a mixture. Purification by preparative TLC eluted with iso-hexanes/acetone 3:1 (3 elutions) followed by silica gel chromatography using a 25 g Isolute cartridge eluted with a continuous gradient of iso-hexanes/acetone 1:0 to 3:2 provided the title compound (58.7 mg, 20%) as a white solid. $^1$H NMR (300 MHz, CD$_3$CN) δ 0.85-0.97 (m, 6H), 1.17-1.22 (m, 3H), 1.28-1.39 (m, 4H), 1.44-1.63 (m, 6H), 1.70-1.82 (m, 1H), 1.83-1.92 (m, 1H), 2.30-2.45 (m, 3H), 3.62-3.73 (m, 2H), 3.89 (app t, J=8.5 Hz, 1H), 4.28 (d, J=8.0 Hz, 1H), 4.40-4.60 (m, 2H), 5.32 (app pentet, J=6.9 Hz, 1H), 5.62-5.74 (m, 1H), 5.77-5.89 (m, 1H), 6.02 (q, J=6.7 Hz, 1H), 6.40 (d, J=7.8 Hz, 1H), 6.76-6.85 (m, 2H), 7.01 (app t, J=9.4 Hz, 1H), 7.19 (br s, 1H). LCMS (m/z) 547.2 [M+H], Tr=2.39 min.

Example 36

Compound 36

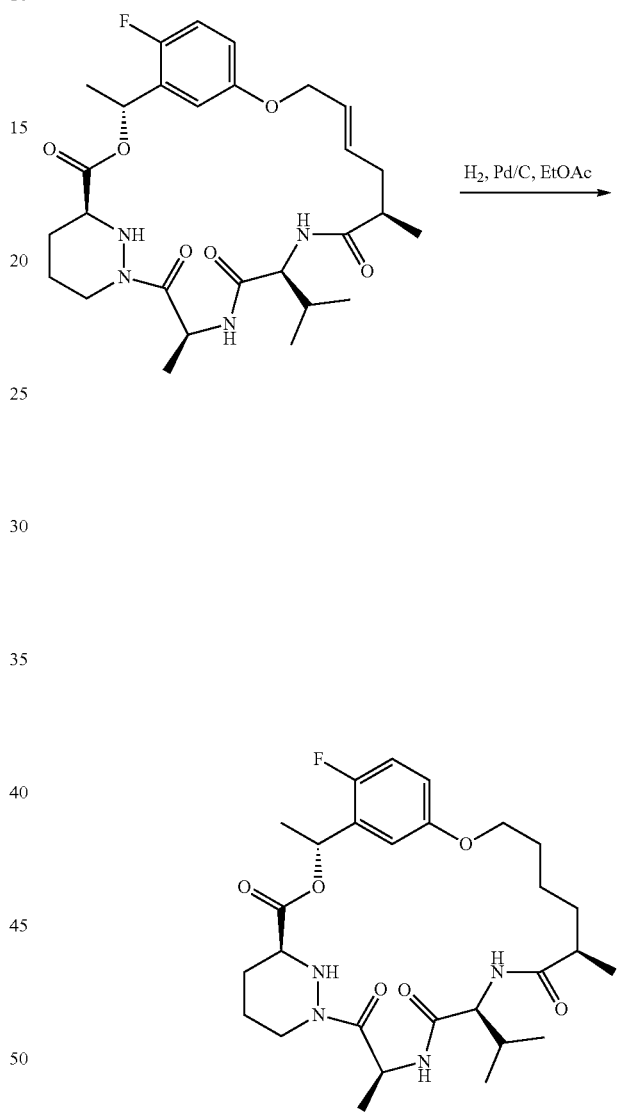

To a solution of Compound 35 (44.0 mg, 0.080 mmol) in ethyl acetate (5 mL) was added palladium on carbon (10%, 5 mg). The atmosphere was purged of oxygen. After stirring at RT under an atmosphere of hydrogen for 2.5 h, the volatiles were removed in vacuo and the residue was purified by silica gel chromatography using a 20 g Isolute cartridge eluted with a continuous gradient of iso-hexanes/acetone 1:0 to 3:2 followed by preparative TLC eluted with iso-hexanes/acetone 3:2 to afford the final compound (19.0 mg, 43%) as a white solid. $^1$H NMR (300 MHz, CDCl$_3$) δ 0.85-0.99 (m, 8H), 1.14-1.22 (m, 4H), 1.26-1.42 (m, 4H), 1.48 (d, J=6.7 1H), 1.52-1.84 (m, 8H), 2.28-2.42 (m, 1H), 3.61-3.72 (m, 1H), 3.75-4.10 (m, 4H), 4.25 (d, J=9.4 Hz, 1H), 5.26 (app pentet, J=7.1 Hz, 1H), 6.02 (q, J=6.7 Hz, 1H), 6.34 (d, J=8.5 Hz, 1H), 6.75-6.86 (m, 2H), 6.95-7.12 (m, 2H). LCMS (m/z) 549.3 [M+H], Tr=2.54 min.

Example 37

(E)-(2R,5S,11S,14S,17R,18R)-2,14-Diisopropyl-18-methoxy-11,17-dimethyl-22-oxa-3,9,12,15,28-pentaaza-tricyclo[21.3.1.1*5,9]octacosa-1(27),19,23,25-tetraene-4,10,13,16-tetraone

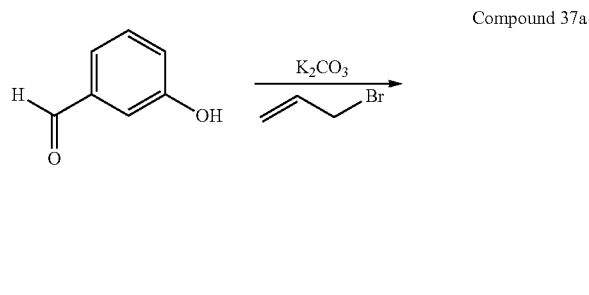

Compound 37a 37a was prepared in the same manner as 35b using 3-hydroxybenzaldehyde instead of 2-fluoro-5-hydroxy-N-methoxy-N-methyl-benzamide in 78% yield.

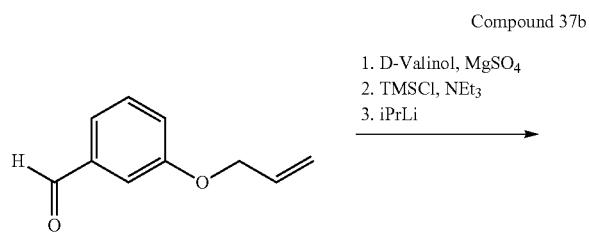

Compound 37b

1. D-Valinol, MgSO₄
2. TMSCl, NEt₃
3. iPrLi

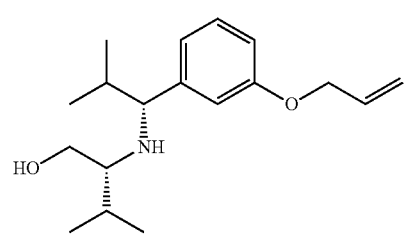

A cooled (0° C.) suspension of 37a (1.36 g, 8.434 mmol) and magnesium sulfate (5 g) in dichloromethane (40 mL) was treated with D-valinol (870.0 mg, 8.434 mmol). After stirring at 0° C. to RT for 23 h, the mixture was filtered and the volatiles were removed in vacuo. The residue was dissolved in anhydrous dichloromethane (40 mL) and was subsequently treated with triethylamine (1.3 mL, 9.277 mmol) and a solution of trimethylsilyl chloride (9.3 mL, 9.277 mmol, 1 M in dichloromethane). After stirring at RT for 24 h, the volatiles were removed in vacuo and the residue was triturated with diethyl ether/iso-hexane (100 mL, 1:1). The white solid was filtered off and the filtrate was evaporated to dryness to provide the intermediate imine. In a cooled (−40° C.) 3-neck round-bottom flask, equipped with a nitrogen line and an addition funnel was introduced anhydrous diethyl ether (25 mL) and a solution of iso-propyllithium (29 mL, 20.242 mmol, 0.7 M in pentane). To this mixture, a solution of the imine in anhydrous diethyl ether (25 mL) was added dropwise over 15 min. After stirring at −40° C. for 2.5 h, the reaction was quenched with hydrochloric acid (2 M, 50 mL) and the mixture was allowed to warm to RT. The acidic aqueous layer was basified with NaOH pellets at 0° C. and then extracted with diethyl ether (2×). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:1 to afford the title compound (470.1 mg, 19% over 3 steps) as a colorless oil.

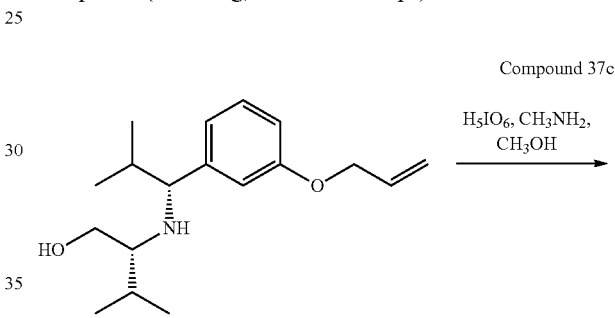

Compound 37c

H₅IO₆, CH₃NH₂, CH₃OH

A solution of 37b (470.1 mg, 1.613 mmol) in methanol (10 mL) and aqueous methylamine (3 mL, 40 wt % in water) was treated with periodic acid (1.213 g, 5.323 mmol). After stirring for 24 h at RT more aqueous methylamine (4 mL, 40 wt % in water) and periodic acid (1.213 g, 5.323 mmol) were added. After stirring for 17 h at RT the mixture was filtered over Celite and the solid rinsed with methanol. The volatiles were removed in vacuo and the residue was partitioned between water and diethyl ether. The aqueous layer was extracted with diethyl ether, the organics were combined, dried over sodium sulfate, filtered and the volatiles were removed in vacuo. The residue was purified by silica gel chromatography using a 25 g Isolute cartridge eluted with ethyl acetate to afford the title compound (191.8 mg, 58%) as a light yellow oil.

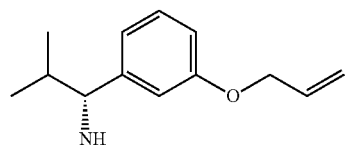 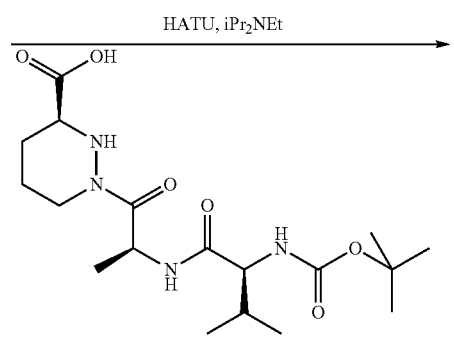

Compound 37d

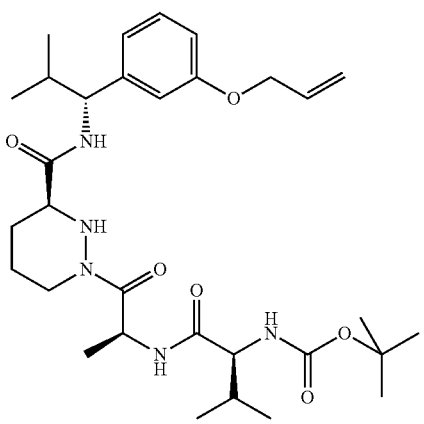

A cooled (0° C.) solution of (S)-1-[(S)-2-((S)-2-tert-butoxycarbonylamino-3-methyl-butyrylamino)-propionyl]-hexahydro-pyridazine-3-carboxylic acid (324.4 mg, 0.810 mmol), 37c (166.3 mg, 0.810 mmol) and N,N-diisopropylethylamine (560 μL, 3.240 mmol) in acetonitrile (15 mL) was treated with 2-(1H-7-azabenzotriazol-1-yl)-1,1,3,3-tetramethyl uronium hexafluorophosphate methanaminium (431.2 mg, 1.134 mmol). After stirring at RT for 20 h, the reaction was quenched with hydrochloric acid (2 M, 25 mL) at 0° C. The aqueous layer was extracted with ethyl acetate (2×). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 0:1 to afford the title compound (230.5 mg, 48%) as a solid.

Compound 37e

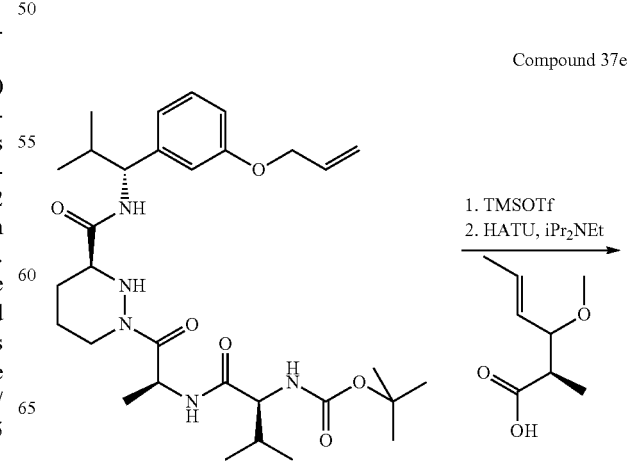

1. TMSOTf
2. HATU, iPr₂NEt

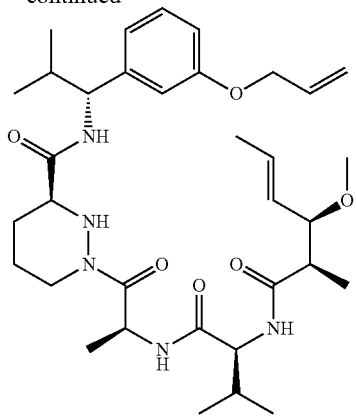

Compound 37e was prepared in the same manner as 1-{(S)-2-[(S)-2-((E)-(2R,3R)-3-methoxy-2-methyl-hex-4-enoylamino)-3-methyl-butyrylamino]-propionyl}-3-methyl-hexahydro-pyridazine-3-carboxylic acid methyl ester using 37d instead of 1-[(S)-2-((S)-2-tert-butoxycarbonylamino-3-methyl-butyrylamino)-propionyl]-3-methyl-hexahydro-pyridazine-3-carboxylic acid methyl ester in 30% yield over 2 steps.

Compound 37

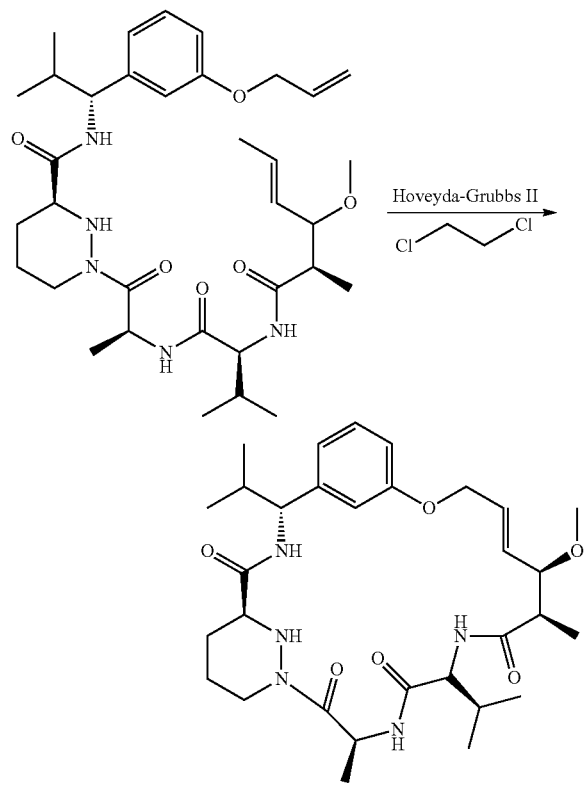

Compound 37 was prepared in the same manner as 25 using 37e instead of (S)-1-{(S)-2-[(S)-2-((2R,3R)-3-methoxy-2-methyl-hept-6-enoylamino)-3-methyl-butyrylamino]-propionyl}-hexahydro-pyridazine-3-carboxylic acid methyl-((R)-6-vinyl-indan-1-yl)-amide in 43% yield. ¹H NMR (300 MHz, d₆-DMSO) δ 0.74-0.91 (m, 12H), 1.15 (d, J=7.1 Hz, 3H), 1.28 (d, J=7.3 Hz, 3H), 1.40-1.64 (m, 3H), 1.71-1.88 (m, 3H), 1.98 (app sextet, J=6.7 Hz, 1H), 2.66-2.75 (m, 2H), 3.38-3.53 (m, 1H), 3.89 (dd, J=6.7, 2.9 Hz, 1H), 4.10 (app t, J=8.9 Hz, 1H), 4.14-4.22 (m, 1H), 4.42 (qd, J=10.0, 4.2 Hz, 1H), 4.57 (app t, J=8.2 Hz, 1H), 4.76 (d, J=11.8 Hz, 1H), 5.23 (app t, J=7.3 Hz, 1H), 5.69-5.90 (m, 2H), 6.77-6.90 (m, 3H), 7.05 (d, J=9.4 Hz, 1H), 7.16-7.24 (m, 1H), 8.01 (d, J=8.5 Hz, 1H), 8.14 (d, J=8.5 Hz, 1H). LCMS (m/z) 586.3 [M+H], Tr=2.34 min.

Example 38

Compound 38a

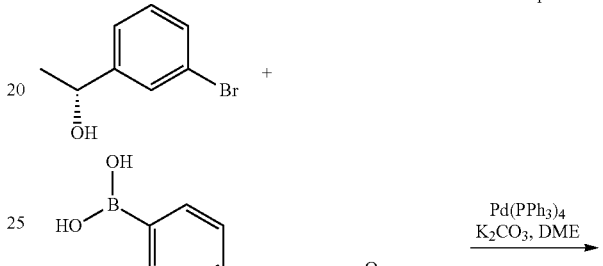

To a mixture of (R)-1-(3-bromo-phenyl)-ethanol (201 mg, 1.00 mmol), 4-(2-ethoxy-2-oxoethoxy)benzeneboronic acid (Acros Organics, 224 mg, 1.00 mmol) in 1,2-dimethoxyethane (4 mL) were added potassium carbonate (276 mg, 2.00 mmol) and water (1 mL). The mixture was stirred at RT and tetrakis(triphenylphosphine) palladium(0) (58 mg, 0.05 mmol) was added then the reaction mixture was heated at 100° C. in a microwave reactor for 30 min. The reaction mixture was then diluted with ethyl acetate and water. The layers were separated and the organics washed with water and brine, dried over magnesium sulfate, filtered and evaporated. The residue was purified by silica gel chromatography using a gradient of iso-hexanes/ethyl acetate 9:1 to 7:3 to afford the title compound (230 mg, 76%) as an oil.

Compound 38a

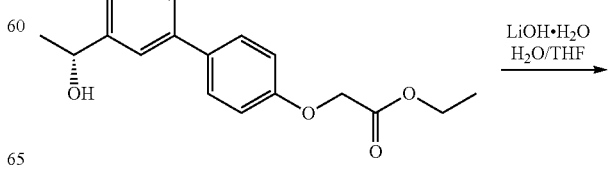

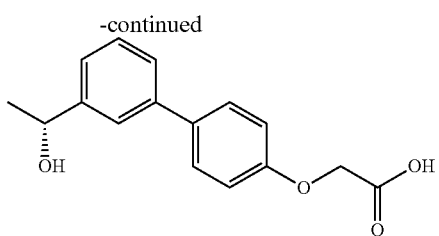

A solution of 38a (230 mg, 0.77 mmol) in tetrahydrofuran (4 mL) was stirred at 5° C. under nitrogen, a solution of lithium hydroxide monohydrate (92 mg, 1.54 mmol) was added and the reaction mixture was stirred at 5° C. for 2 h and then at RT overnight. The solution was acidified with 2 M hydrochloric acid and extracted with ethyl acetate (2×). The organic extracts were combined, washed with water and brine, dried over magnesium sulfate and evaporated to afford the title compound (175 mg, 84%) as a white solid.

stirred at 0° C. for 15 min. The organic layer was separated, washed with brine, dried over magnesium sulfate and evaporated to afford (S)-1-[(S)-2-((S)-2-amino-3-methyl-butyrylamino)-propionyl]-hexahydro-pyridazine-3-carboxylic acid 2,2,2-trichloro-ethyl ester (0.70 mmol) which was used without further purification. A solution of (S)-1-[(S)-2-((S)-2-amino-3-methyl-butyrylamino)-propionyl]-hexahydro-pyridazine-3-carboxylic acid 2,2,2-trichloro-ethyl ester (0.70 mmol) in acetonitrile (15 mL) was stirred at 0° C. under nitrogen. 38b (175 mg, 0.64 mmol) and 1-hydroxybenzotriazole hydrate (123 mg, 0.64 mmol, wetted with not less than 20 wt. % water) were added, followed by N-(3-dimethylaminopropyl)-N'-ethylcarbodiimide hydrochloride (173 mg, 0.90 mmol) and the reaction mixture was stirred at RT for 2 h. The solvent was evaporated. The residue was dissolved in ethyl acetate and the solution was washed with water (3×) followed by brine, dried over magnesium sulfate and evaporated. The residue was purified by silica gel chromatography using a gradient of iso-hexanes/ethyl acetate 1:2 to 0:1. The product was triturated with diethyl ether and dried to afford the title compound (367 mg, 83%) as a white solid.

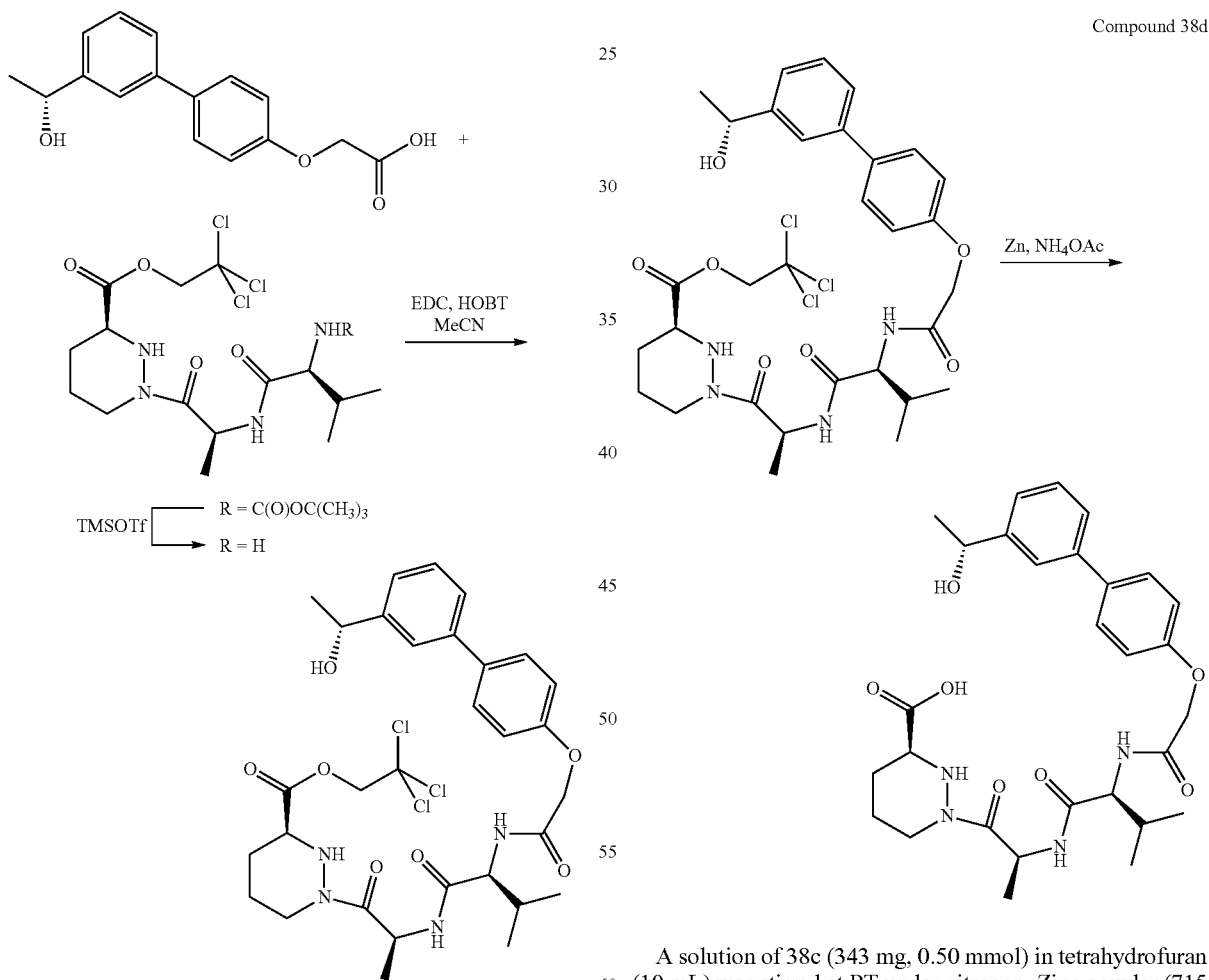

Compound 38c

Compound 38d

A solution of 1e (372 mg, 0.70 mmol) in dichloromethane (15 mL) was cooled in an ice-water bath under nitrogen. Trimethylsilyl trifluoromethanesulfonate (0.18 mL, 1.05 mmol) was added dropwise, and the resulting solution was stirred for 1 hour. Cold saturated aqueous sodium hydrogen carbonate solution (15 mL) was added and the mixture was A solution of 38c (343 mg, 0.50 mmol) in tetrahydrofuran (10 mL) was stirred at RT under nitrogen. Zinc powder (715 mg, 11 mmol) was added followed by a solution of ammonium acetate (578 mg, 7.50 mmol) in water (5 mL). The reaction mixture was stirred at RT under nitrogen for 70 h. The reaction mixture was filtered through Celite and the filter pad was washed with ethyl acetate and 2 M aqueous hydrochloric acid. The filtrate was acidified to pH 2 with 2 M aqueous hydrochloric acid, solid sodium chloride was added to saturate the aqueous layer and the mixture was extracted with ethyl acetate. The ethyl acetate extracts were combined, washed with brine, dried over magnesium sulfate and evaporated. The residue was co-evaporated with toluene (3×) to afford the title compound (237 mg, 86%) as a white powder.

Compound 38

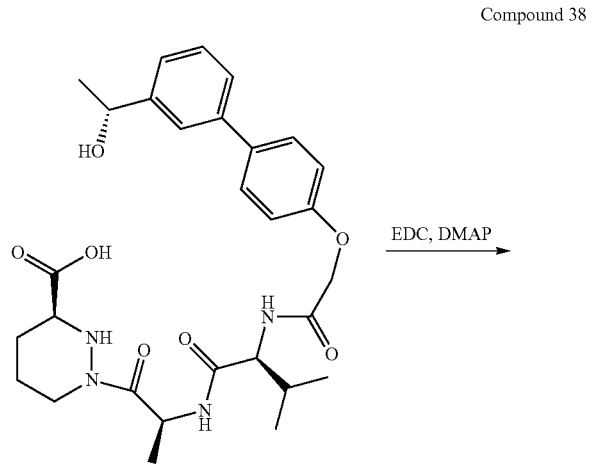

EDC, DMAP

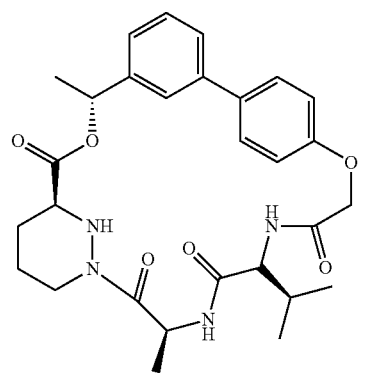

A solution of 38d (100 mg, 0.18 mmol) in dichloromethane (180 mL) was stirred at RT under nitrogen. 4-Dimethylaminopyridine (33 mg, 0.27 mmol) and N-(3-dimethylaminopropyl)-N'-ethylcarbodiimide hydrochloride (104 mg, 0.54 mmol) were added and the reaction mixture was stirred at RT for 18 h. The solvent was evaporated. The residue was purified by silica gel chromatography using a gradient of iso-hexanes/ethyl acetate 1:2 to 0:1 followed by silica gel chromatography using a gradient of ethyl acetate to ethyl acetate/acetone 4:1. The residue was co-evaporated with dichloromethane then triturated with diethyl ether to afford a solid. The solid was washed with ether and dried to afford the title compound (8 mg, 9%) as a white solid. $^1$H NMR (300 MHz, CDCl$_3$) 0.95 (d, J=6.2 Hz, 3H), 0.96 (d, J=6.5 Hz, 3H), 1.39 (d, J=7.1 Hz, 3H), 1.54-1.80 (m, 5H), 1.82-2.10 (m, 3H), 2.52-2.63 (m, 1H), 3.29-3.62 (m, 2H), 4.07 (app t, J=9.6 Hz, 1H), 4.45 (br d, J=13.6 Hz, 1H), 4.67 (ABq, Δδ$_{AB}$=0.12, J$_{AB}$=16.0 Hz, 2H), 4.88-5.01 (m, 1H), 5.93-6.00 (m, 2H), 6.57 (d, J=10.3 Hz, 1H), 6.94 (d, J=8.5 Hz, 2H), 7.15-7.53 (m, 6H). LCMS (m/z) 537.2 [M+H], Tr=2.34 min.

Example 39

Compound 39a

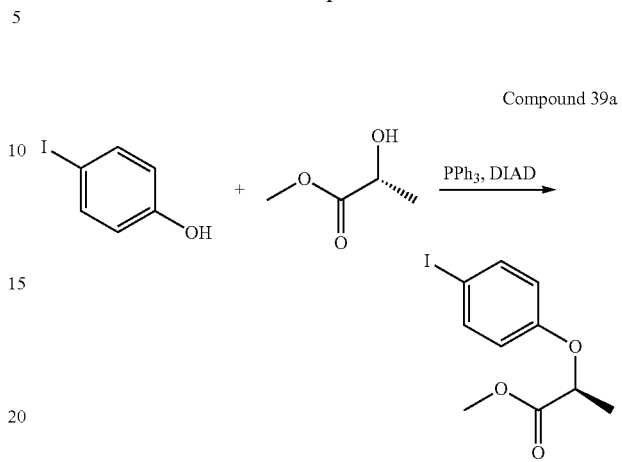

A solution of 4-iodo phenol (2.2 g, 10.0 mmol), (R)-2-hydroxy-propionic acid methyl ester (0.95 mL, 10.0 mmol) and triphenylphosphine (2.62 g, 10.0 mmol) was prepared in tetrahydrofuran (40 mL). Diisopropyl azodicarboxylate (2.0 mL, 10 mmol) was added dropwise and the reaction was stirred at −5° C. for 1 hour and then at RT for 2 h. The tetrahydrofuran was evaporated and diethyl ether/iso-hexanes (1:10, 50 mL) was added. The mixture was stirred at RT for 10 min where a precipitate formed. The filtrate was decanted off and evaporated. The residue was purified by silica gel chromatography using a gradient of iso-hexanes/ethyl acetate 20:1 to 10:1 to afford the title compound (2.02 g, 66%) as an oil.

Compound 39b

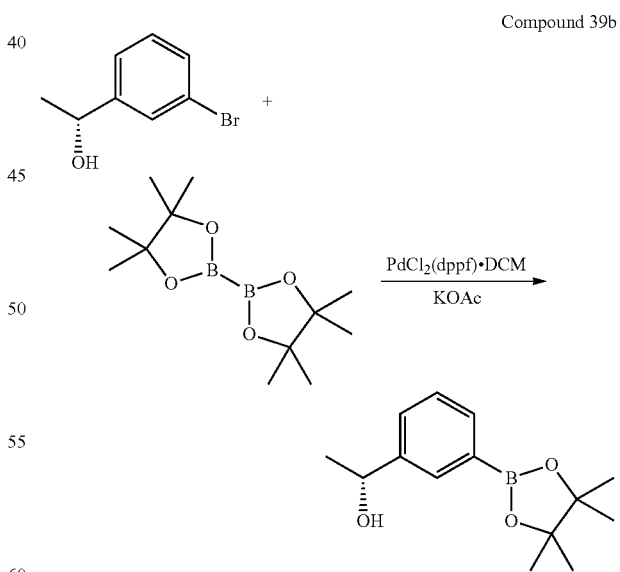

(R)-1-(3-bromophenyl)-ethanol (1.0 g, 4.97 mmol), bis(pinacolato)diboron (1.39 g, 5.47 mmol), 1,1' bis(diphenylphosphino)ferrocenedichloropalladium(II), dichloromethane adduct (203 mg, 0.249 mmol) and potassium acetate (976 mg, 9.94 mmol) were dissolved in 1,4-dioxane (10 mL) and the reaction was heated to reflux and left to stir over 3 days. The reaction was allowed to cool to RT before being filtered through a pad of Hyflo. The pad was then washed with ethyl acetate and the combined organics were then concentrated and purified by silica gel chromatography using a stepwise gradient of iso-hexanes/ethyl acetate 1:0 to 4:1 to afford the title compound (936 mg, 76%) as a pale yellow oil.

Compound 39c

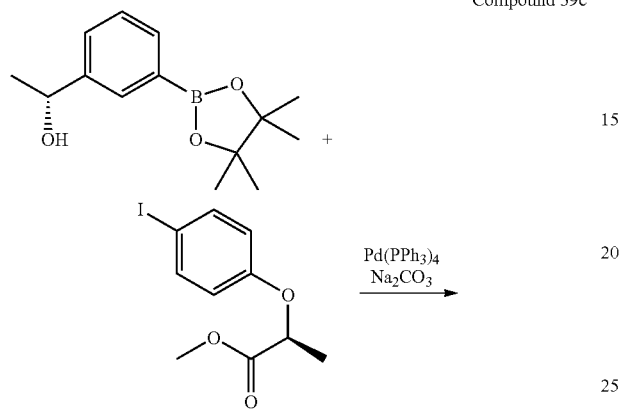

A solution of 39b (496 mg, 2.00 mmol) and 39a (612 mg, 2.00 mmol) in 1,2-dimethoxyethane (4 mL) was stirred at RT under nitrogen. A solution of 2 M aqueous sodium carbonate (4 mL) was added followed by tetrakis(triphenylphosphine)palladium(0) (116 mg, 0.1 mmol) and the reaction mixture was heated at 80° C. for 1 hour. The reaction mixture was cooled to RT, water was added and the mixture was extracted with ethyl acetate. The ethyl acetate extracts were combined, washed with brine, dried over sodium sulfate and evaporated. The residue was purified by silica gel chromatography using a gradient of iso-hexanes/ethyl acetate 17:3 to 1:1 to afford the title compound (253 mg, 42%) as a gum.

Compound 39d

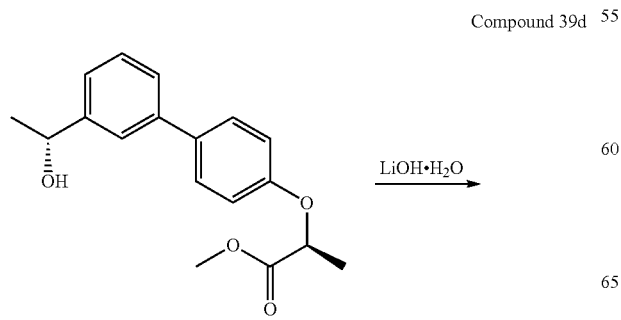

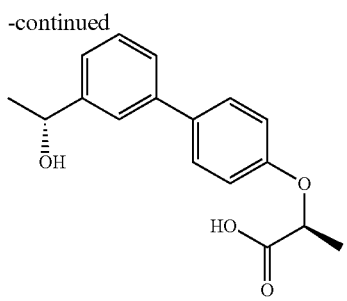

A solution of 39c (250 mg, 0.83 mmol) in tetrahydrofuran (4 mL) was stirred at 5° C. under nitrogen. A solution of lithium hydroxide monohydrate (42 mg, 1.00 mmol) in water (1 mL) was added and the reaction mixture was stirred at 5° C. for 1 hour. The reaction mixture was acidified to pH 3 with 2 M aqueous hydrochloric acid and the mixture extracted with ethyl acetate. The organic extracts were separated, washed with water and brine, dried over magnesium sulfate and evaporated to afford the title compound (224 mg, 94%) as a white foam.

Compound 39e

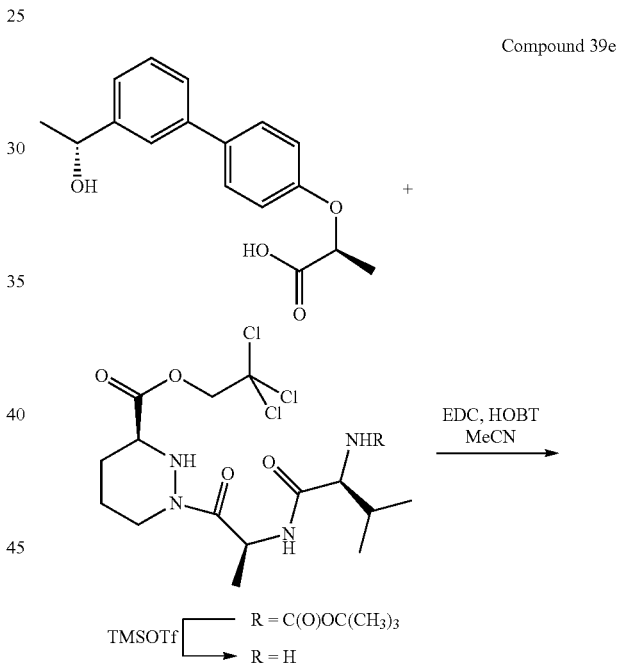

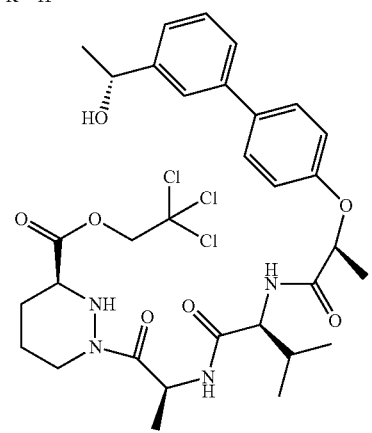

A solution of 1e (478 mg, 0.9 mmol) in dichloromethane (15 mL) was cooled in an ice-water bath under nitrogen. Trimethylsilyl trifluoromethanesulfonate (0.25 mL, 1.35 mmol) was added dropwise, and the resulting solution was stirred for 1 h. Cold saturated aqueous sodium hydrogen carbonate solution (15 mL) was added and the mixture was stirred at 0° C. for 15 min. The organic layer was separated, washed with brine, dried over magnesium sulfate and evaporated to afford (S)-1-[(S)-2-((S)-2-amino-3-methyl-butyrylamino)-propionyl]-hexahydro-pyridazine-3-carboxylic acid 2,2,2-trichloro-ethyl ester (0.9 mmol) which was used without further purification. A solution of (S)-1-[(S)-2-((S)-2-amino-3-methyl-butyrylamino)-propionyl]-hexahydro-pyridazine-3-carboxylic acid 2,2,2-trichloro-ethyl ester (0.9 mmol) in acetonitrile (15 mL) was stirred at 0° C. under nitrogen. 39d (224 mg, 0.78 mmol) and 1-hydroxybenzotriazole hydrate (184 mg, 0.96 mmol, wetted with not less than 20 wt. % water) were added, followed by N-(3-dimethylaminopropyl)-N'-ethylcarbodiimide hydrochloride (225 mg, 1.17 mmol) and the reaction mixture was stirred at RT for 2 h. The solvent was evaporated. The residue was dissolved in ethyl acetate and the solution was washed with water (3×) followed by brine, dried over magnesium sulfate and evaporated. The residue was purified by silica gel chromatography using a gradient of iso-hexanes/ethyl acetate 1:2 to 0:1 to afford the title compound (490 mg, 90%) as a gum.

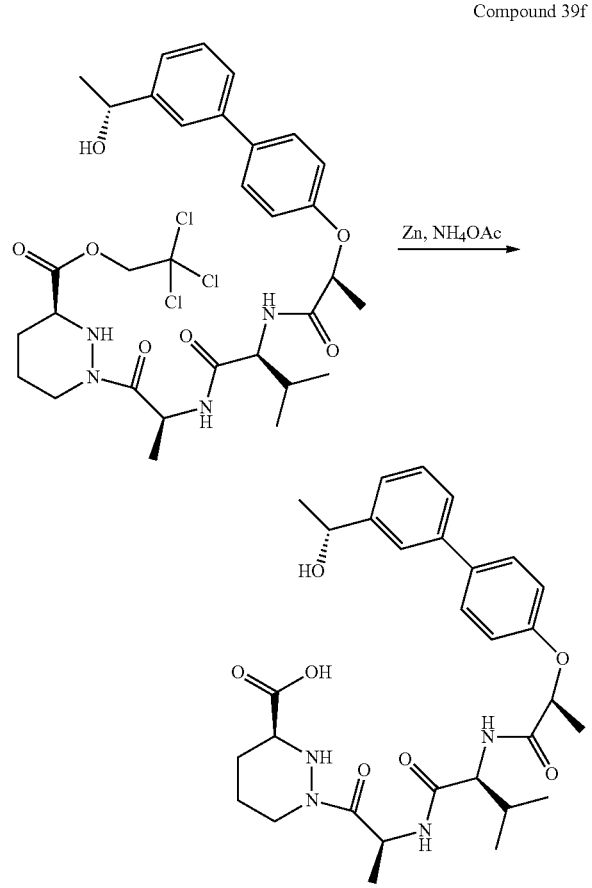

Compound 39f

A solution of 39e (490 mg, 0.70 mmol) in tetrahydrofuran (15 mL) was stirred at RT under nitrogen. Zinc powder (1.00 g, 15.40 mmol) was added followed by a solution of ammonium acetate (810 mg, 10.50 mmol) in water (8 mL). The reaction mixture was stirred at RT under nitrogen for 24 h. The reaction mixture was filtered through Celite and the filter pad was washed with ethyl acetate and 2 M aqueous hydrochloric acid. The filtrate was acidified to pH 2-3 with 2 M aqueous hydrochloric acid. Solid sodium chloride was added to saturate the aqueous layer and the mixture was extracted with ethyl acetate. The ethyl acetate extracts were combined and washed with brine. The organic extracts were passed through a hydrophobic frit and the filtrate was evaporated. The residue was co-evaporated with ethyl acetate (3×) then toluene (3×) to afford the title compound (394 mg, 98%) as a white solid.

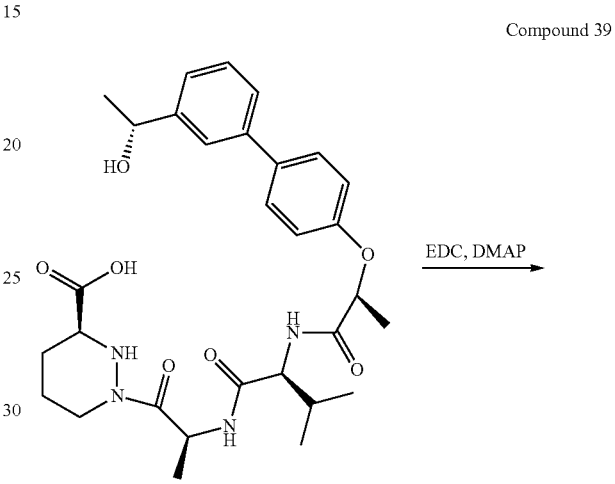

Compound 39

A solution of 39f (100 mg, 0.18 mmol) in dichloromethane (180 mL) was stirred at RT under nitrogen. 4-Dimethylaminopyridine (44 mg, 0.36 mmol) and N-(3-dimethylaminopropyl)-N'-ethylcarbodiimide hydrochloride (138 mg, 0.72 mmol) were added and the reaction mixture was stirred at RT for 4 h. The solvent was evaporated. Ethyl acetate was added to the residue and the mixture was washed with aqueous citric acid (pH 4) and brine. The organic layer was dried over magnesium sulfate and the solvent was evaporated. The residue was purified by silica gel chromatography using a gradient of iso-hexanes/ethyl acetate 3:7 to 0:1. The residue was triturated with diethyl ether/iso-hexanes 1:1 to afford the title compound (10 mg, 10%) as a white solid. $^1$H NMR (300 MHz, CD$_3$OD) 0.94 (d, J=6.7 Hz, 3H), 0.95 (d, J=6.9 Hz, 3H), 1.51 (d, J=7.1 Hz, 3H), 1.61 (d, J=6.5 Hz, 3H), 1.67 (d, J=6.9 Hz, 3H), 1.72-2.00 (m, 5H), 2.60-2.69 (m, 1H), 3.54-3.63 (m, 1H), 4.13 (d, J=10.5 Hz, 1H), 4.32 (br d, J=12.9 Hz, 1H), 4.57-4.66 (m, 2H), 4.78 (q, J=7.1 Hz, 1H), 5.92 (q, J=6.5

Hz, 1H), 6.91 (d, J=8.9 Hz, 2H), 7.22 (d, J=7.6 Hz, 1H), 7.34-7.61 (m, 5H). LCMS (m/z) 551.2 [M+H], Tr=2.51 min.

Example 40

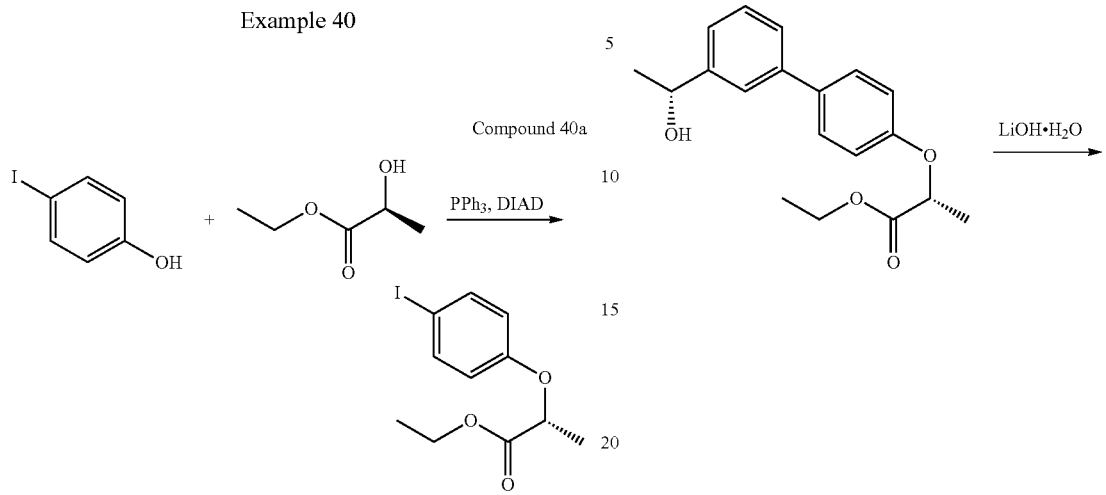

Compound 40a

Compound 40c 40a was prepared in the same manner as (S)-2-(4-iodo-phenoxy)-propionic acid methyl ester using (S)-2-hydroxy-propionic acid ethyl ester instead of (R)-2-hydroxy-propionic acid methyl ester in 28% yield.

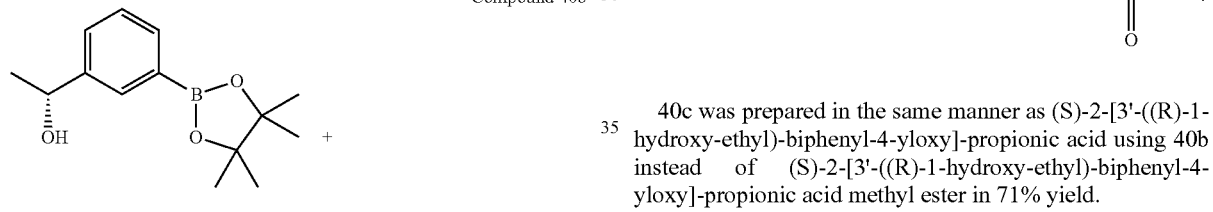

Compound 40b 40c was prepared in the same manner as (S)-2-[3'-((R)-1-hydroxy-ethyl)-biphenyl-4-yloxy]-propionic acid using 40b instead of (S)-2-[3'-((R)-1-hydroxy-ethyl)-biphenyl-4-yloxy]-propionic acid methyl ester in 71% yield.

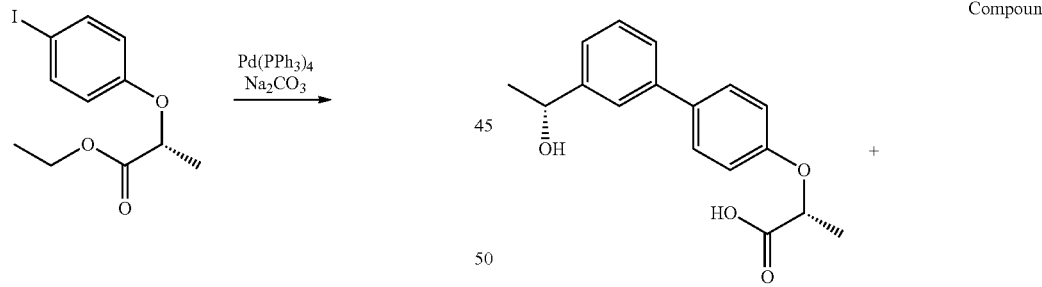

Compound 40d

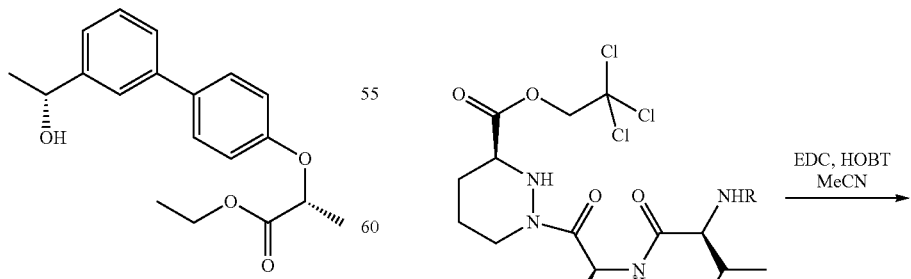

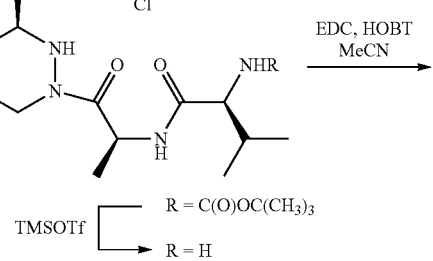

40b was prepared in the same manner as (S)-2-[3'-((R)-1-hydroxy-ethyl)-biphenyl-4-yloxy]-propionic acid methyl ester using 40a instead of (S)-2-(4-iodo-phenoxy)-propionic acid methyl ester in 54% yield.

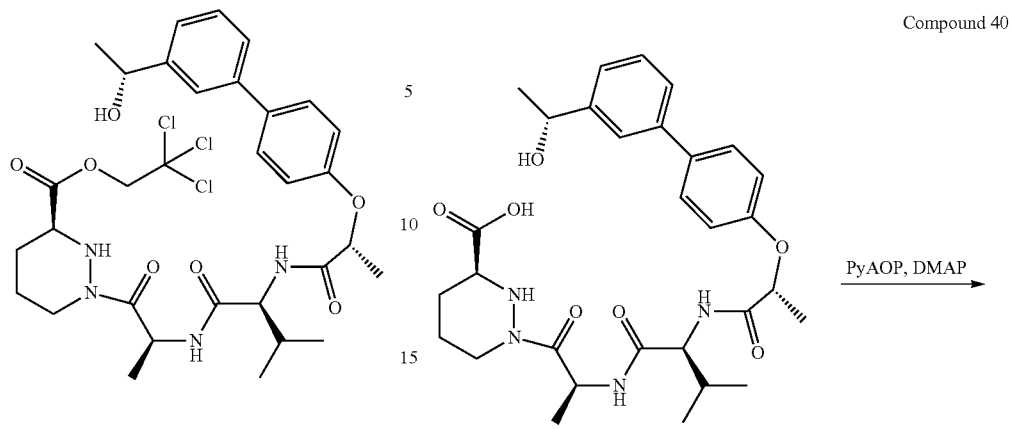

40d was prepared in the same manner as (S)-1-[(S)-2-((S)-2-{(S)-2-[3'-((R)-1-hydroxy-ethyl)-biphenyl-4-yloxy]-propionylamino}-3-methyl-butyrylamino)-propionyl]-hexahydro-pyridazine-3-carboxylic acid 2,2,2-trichloro-ethyl ester using 40c instead of (S)-2-[3'-((R)-1-hydroxy-ethyl)-biphenyl-4-yloxy]-propionic acid in 71% yield.

Compound 40e

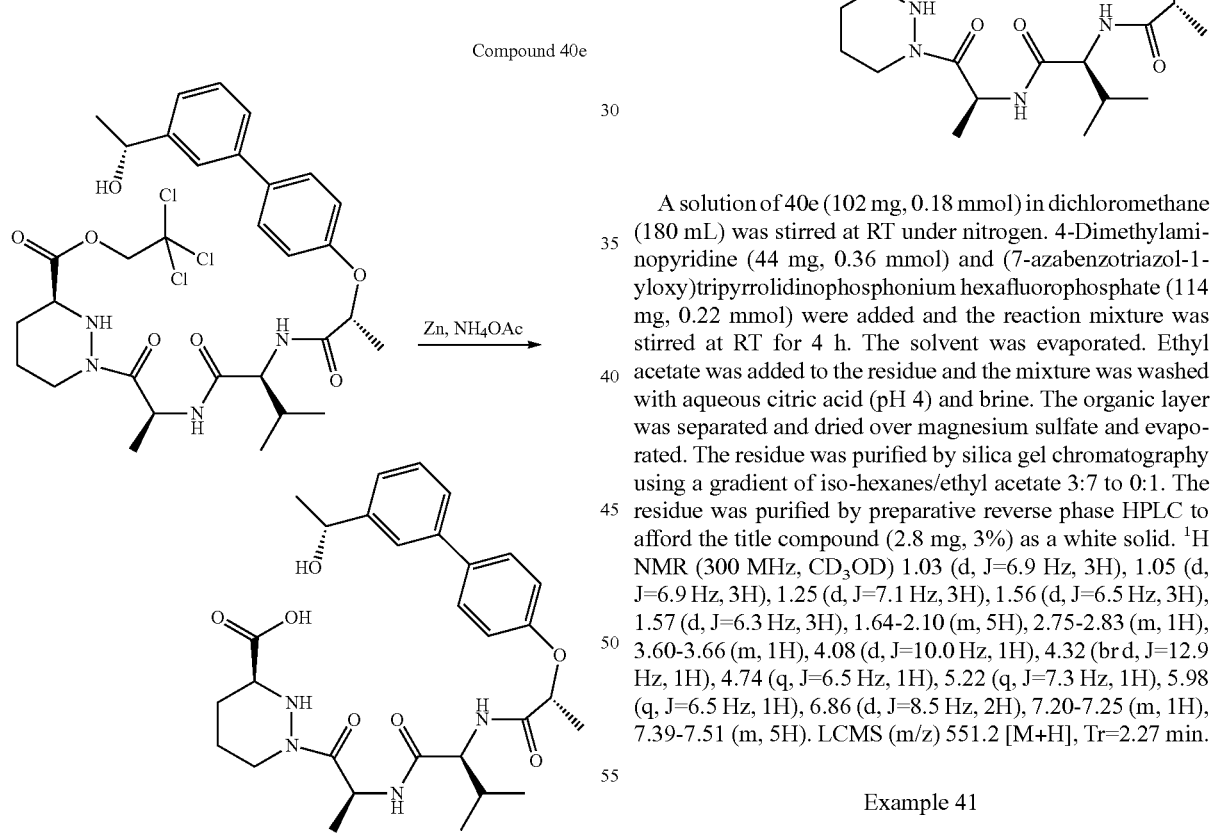

40e was prepared in the same manner as ((S)-1-[(S)-2-((S)-2-{(S)-2-[3'-((R)-1-hydroxy-ethyl)-biphenyl-4-yloxy]-propionylamino}-3-methyl-butyrylamino)-propionyl]-hexahydro-pyridazine-3-carboxylic acid using 40d instead of (S)-1-[(S)-2-((S)-2-{(S)-2-[3'-((R)-1-hydroxy-ethyl)-biphenyl-4-yloxy]-propionylamino}-3-methyl-butyrylamino)-propionyl]-hexahydro-pyridazine-3-carboxylic acid 2,2,2-trichloro-ethyl ester in 83% yield.

Compound 40

A solution of 40e (102 mg, 0.18 mmol) in dichloromethane (180 mL) was stirred at RT under nitrogen. 4-Dimethylaminopyridine (44 mg, 0.36 mmol) and (7-azabenzotriazol-1-yloxy)tripyrrolidinophosphonium hexafluorophosphate (114 mg, 0.22 mmol) were added and the reaction mixture was stirred at RT for 4 h. The solvent was evaporated. Ethyl acetate was added to the residue and the mixture was washed with aqueous citric acid (pH 4) and brine. The organic layer was separated and dried over magnesium sulfate and evaporated. The residue was purified by silica gel chromatography using a gradient of iso-hexanes/ethyl acetate 3:7 to 0:1. The residue was purified by preparative reverse phase HPLC to afford the title compound (2.8 mg, 3%) as a white solid. $^1$H NMR (300 MHz, CD$_3$OD) 1.03 (d, J=6.9 Hz, 3H), 1.05 (d, J=6.9 Hz, 3H), 1.25 (d, J=7.1 Hz, 3H), 1.56 (d, J=6.5 Hz, 3H), 1.57 (d, J=6.3 Hz, 3H), 1.64-2.10 (m, 5H), 2.75-2.83 (m, 1H), 3.60-3.66 (m, 1H), 4.08 (d, J=10.0 Hz, 1H), 4.32 (br d, J=12.9 Hz, 1H), 4.74 (q, J=6.5 Hz, 1H), 5.22 (q, J=7.3 Hz, 1H), 5.98 (q, J=6.5 Hz, 1H), 6.86 (d, J=8.5 Hz, 2H), 7.20-7.25 (m, 1H), 7.39-7.51 (m, 5H). LCMS (m/z) 551.2 [M+H], Tr=2.27 min.

Example 41

Compound 41a

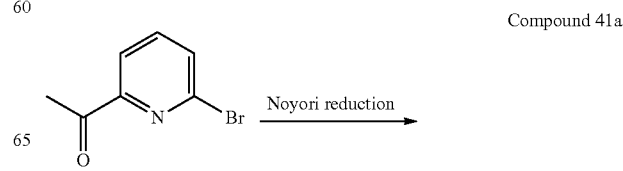

-continued

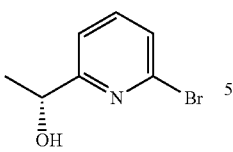

Dichloro(p-cymene)ruthenium(II)dimer (31 mg, 0.05 mmol) and (1R,2R)-(−)-N-p-tosyl-1,2-diphenylethylenediamine (44 mg, 0.12 mmol) was suspended in degassed water (20 mL) and the mixture was degassed with nitrogen for 10 min. The mixture was stirred at 70° C. under nitrogen for 90 min. The resulting yellow solution was cooled to RT. A solution of 1-(6-bromo-pyridin-2-yl)-ethanone (2.0 mg, 10 mmol) in degassed tetrahydrofuran (10 mL) and sodium formate (3.4 g, 50 mmol) was added and the reaction mixture was degassed with nitrogen for 5 min. The reaction mixture was vigorously stirred at 40° C. for 30 min. The reaction mixture was cooled to RT and was extracted with ethyl acetate. The organic extracts were combined, washed with water and brine, dried over sodium sulfate, filtered and evaporated. The residue was purified by silica gel chromatography using a gradient of iso-hexanes/ethyl acetate 3:1 to 0:1 to afford the title compound (1.78 g, 89%) as a brown oil.

Compound 41b

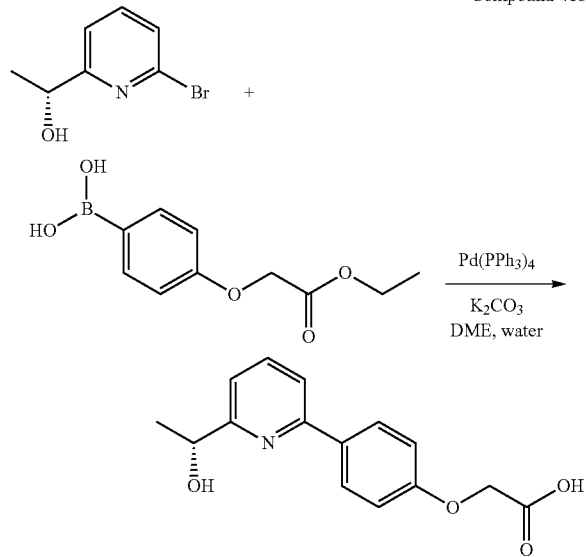

To a mixture of 41a (101 mg, 0.50 mmol), 4-(2-ethoxy-2-oxoethoxy)benzeneboronic acid (112 mg, 0.50 mmol) in 1,2-dimethoxyethane (4 mL) was added a solution of potassium carbonate (138 mg, 1.00 mmol) in water (1 mL). Tetrakis(triphenylphosphine)palladium(0) (29 mg, 0.025 mmol) was added and the reaction mixture was heated at 100° C. in a microwave reactor for 30 min. The reaction mixture was then diluted with ethyl acetate and water. 2 M Hydrochloric acid was added to adjust the pH of the reaction mixture to pH 3 and the volatiles was evaporated. Methanol was added to the residue and the mixture was filtered through a hydrophobic frit. The filtrate was evaporated and the residue was dried in vacuum to afford the title compound (143 mg, 93%) as a white solid.

Compound 41c

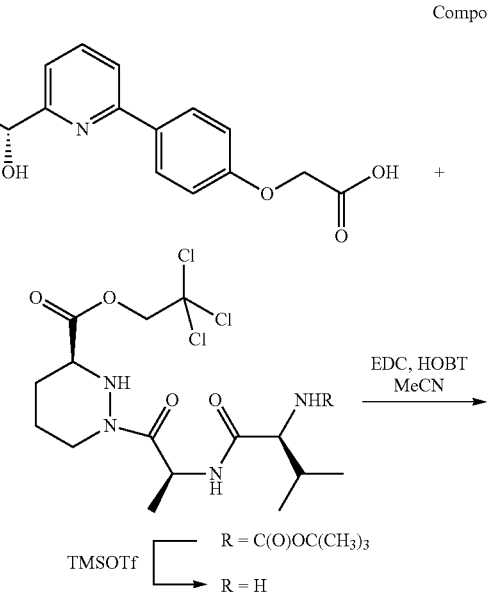

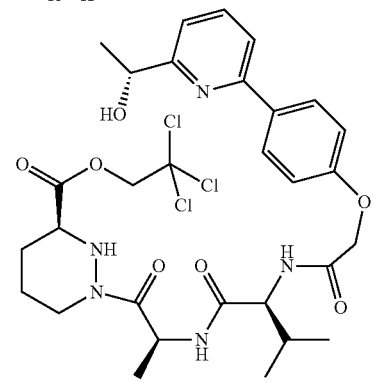

A solution of 1e (240 mg, 0.45 mmol) in dichloromethane (15 mL) was cooled in an ice-water bath under nitrogen. Trimethylsilyl trifluoromethanesulfonate (0.12 mL, 0.68 mmol) was added dropwise, and the resulting solution was stirred for 1 h. Cold saturated aqueous sodium hydrogen carbonate solution (15 mL) was added and the mixture was stirred at 0° C. for 15 min. The organic layer was separated, washed with brine, dried over magnesium sulfate and evaporated to afford (S)-1-[(S)-2-((S)-2-amino-3-methyl-butyrylamino)-propionyl]-hexahydro-pyridazine-3-carboxylic acid 2,2,2-trichloro-ethyl ester (0.45 mmol) which was used without further purification. A mixture of (S)-1-[(S)-2-((S)-2-amino-3-methyl-butyrylamino)-propionyl]-hexahydro-pyridazine-3-carboxylic acid 2,2,2-trichloro-ethyl ester (0.45 mmol), 41b (143 mg, 0.45 mmol) and N,N-diisopropylethylamine (0.16 mL, 0.9 mmol) in acetonitrile (15 mL) was stirred at RT under nitrogen. 1-Hydroxybenzotriazole hydrate (108 mg, 0.56 mmol, wetted with not less than 20 wt. % water) and N-(3-dimethylaminopropyl)-N'-ethylcarbodiimide hydrochloride (130 mg, 0.675 mmol) was added and the reaction mixture was stirred at RT for 4 h. N,N-Dimethylformamide (2 mL) was added and the reaction mixture was stirred at RT for 22 h. Additional N-(3-dimethylaminopropyl)-N'-ethylcarbodiimide hydrochloride (87 mg, 0.45 mmol) was added and the reaction mixture was stirred at RT for 6 h. The solvent was evaporated. The residue was suspended in a mixture of ethyl acetate and aqueous citric acid solution (pH 3) and the mixture was extracted with ethyl acetate. The organic extracts were combined, washed with water followed by brine. The organic layer was filtered through a hydrophobic frit and the filtrate was evaporated. The residue was purified by silica gel chromatography using ethyl acetate to afford the title compound (71 mg, 23%) as a white solid.

Compound 41

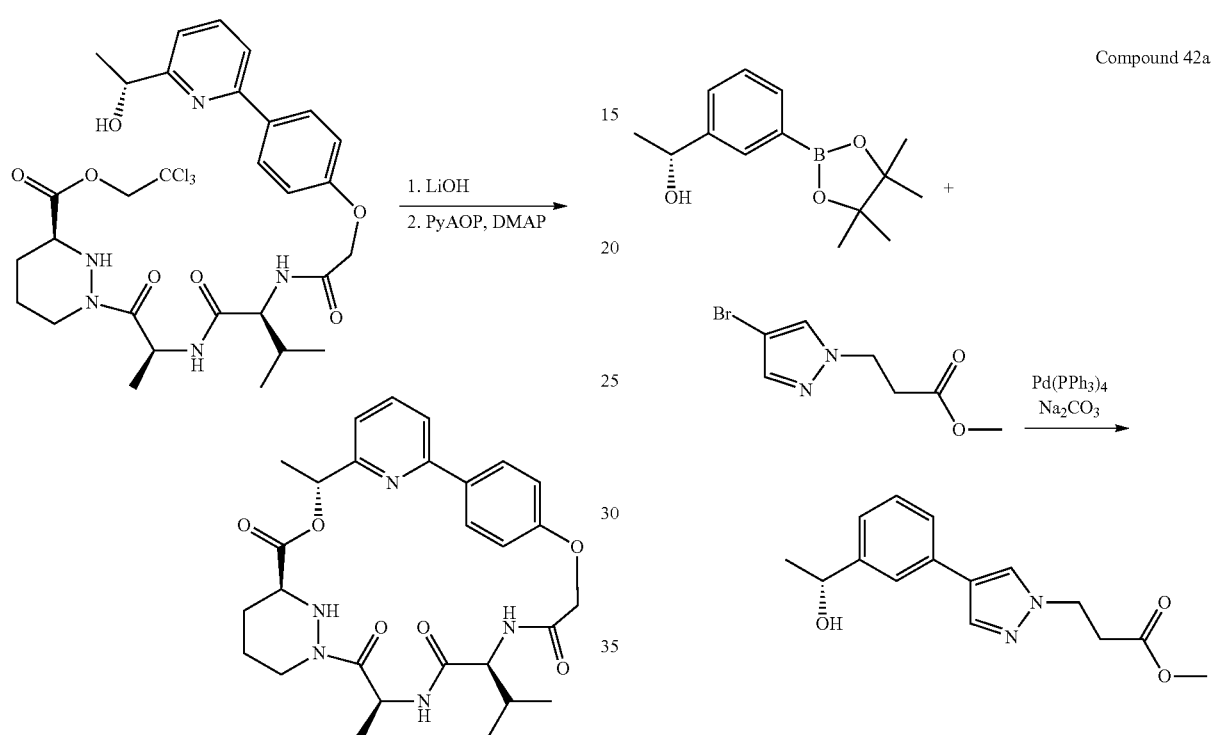

A solution of 41c (69 mg, 0.10 mmol) in tetrahydrofuran (2 mL) was stirred at 0° C. under nitrogen, a solution of lithium hydroxide monohydrate (5 mg, 0.12 mmol) in water (0.5 mL) was added and the reaction mixture was stirred at 0° C. for 1 h. The solution was acidified to pH 3 with 2 M hydrochloric acid and the solvent was evaporated. The residue was co-evaporated with toluene (3×) to afford (S)-1-{(S)-2-[(S)-2-(2-{4-[6-((R)-1-hydroxy-ethyl)-pyridin-2-yl]-phenoxy}-acetylamino)-3-methyl-butyrylamino]-propionyl}-hexahydro-pyridazine-3-carboxylic acid (58 mg, 0.1 mmol) as a white solid which was used crude in the next step. A solution of (S)-1-{(S)-2-[(S)-2-(2-{4-[6-((R)-1-hydroxy-ethyl)-pyridin-2-yl]-phenoxy}-acetylamino)-3-methyl-butyrylamino]-propionyl}-hexahydro-pyridazine-3-carboxylic acid (56 mg, 0.1 mmol) in dichloromethane (100 mL) was stirred at RT under nitrogen. 4-Dimethylaminopyridine (49 mg, 0.4 mmol) was added and the reaction mixture was for stirred for 5 min. A solution of (7-azabenzotriazol-1-yloxy) tripyrrolidinophosphonium hexafluorophosphate (78 mg, 0.15 mmol) in dichloromethane (20 mL) was added dropwise over 5 min and the reaction mixture was stirred at RT for 2 h. The solvent was evaporated and the residue was purified by silica gel chromatography using ethyl acetate. The residue was purified by preparative reverse phase HPLC to afford the title compound (14 mg, 26%) as a white solid. $^1$H NMR (300 MHz, CD$_3$OD) 0.94 (d, J=6.7 Hz, 3H), 0.98 (d, J=6.5 Hz, 3H), 1.36 (d, J=7.1 Hz, 3H), 1.68 (d, J=6.5 Hz, 3H), 1.72-2.05 (m, 5H), 2.65-2.74 (m, 1H), 3.53-3.60 (m, 1H), 4.14 (d, J=10.7 Hz, 1H), 4.30-4.38 (m, 1H), 4.66 (ABq, Δδ$_{AB}$=0.13, J$_{AB}$=15.8 Hz, 2H), 5.07 (q, J=7.1 Hz, 1H), 5.87 (q, J=6.5 Hz, 1H), 6.89 (d, J=8.9 Hz, 2H), 7.26 (br d, J=7.1 Hz, 1H), 7.71-7.78 (m, 2H), 8.06 (d, J=8.9 Hz, 2H). LCMS (m/z) 538.2 [M+H], Tr=2.07 min.

Example 42

Compound 42a

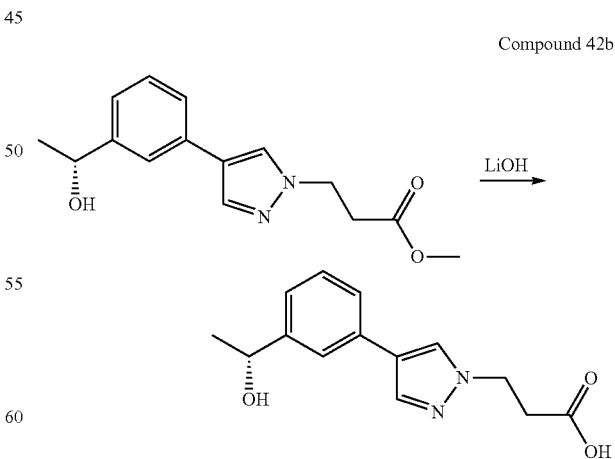

42a was prepared in the same manner as (S)-2-[3'-((R)-1-hydroxy-ethyl)-biphenyl-4-yloxy]-propionic acid methyl ester using 3-(4-bromo-pyrazol-1-yl)-propionic acid methyl ester instead of (S)-2-(4-iodo-phenoxy)-propionic acid methyl ester in 28% yield.

Compound 42b 42b was prepared in the same manner as (S)-2-[3'-((R)-1-hydroxy-ethyl)-biphenyl-4-yloxy]-propionic acid using 42a instead of (S)-2-[3'-((R)-1-hydroxy-ethyl)-biphenyl-4-yloxy]-propionic acid methyl ester in 96% yield.

Compound 42c

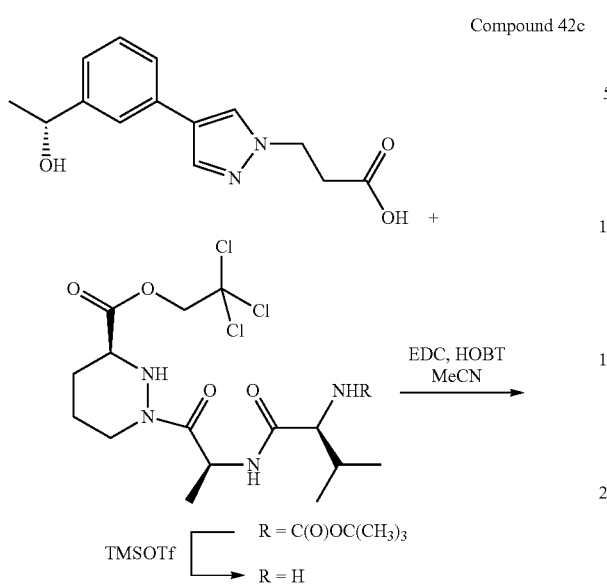

42c was prepared in the same manner as compound (S)-1-[(S)-2-((S)-2-{(S)-2-[3'-((R)-1-hydroxy-ethyl)-biphenyl-4-yloxy]-propionylamino}-3-methyl-butyrylamino)-propionyl]-hexahydro-pyridazine-3-carboxylic acid 2,2,2-trichloro-ethyl ester using 42b instead of (S)-2-[3'-((R)-1-hydroxy-ethyl)-biphenyl-4-yloxy]-propionic acid in 49% yield.

Compound 42

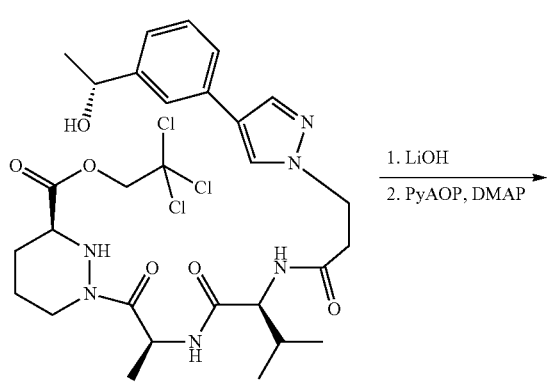

Compound 42 was prepared in the same manner as Compound 41 using 42c instead of (S)-1-{(S)-2-[(S)-2-(2-{4-[6-((R)-1-hydroxy-ethyl)-pyridin-2-yl]-phenoxy}-acetylamino)-3-methyl-butyrylamino]-propionyl}-hexahydro-pyridazine-3-carboxylic acid 2,2,2-trichloro-ethyl ester in 8% yield. $^1$H NMR (300 MHz, CD$_3$OD) 0.94 (d, J=6.7 Hz, 3H), 0.95 (d, J=6.5 Hz, 3H), 1.37 (d, J=7.1 Hz, 3H), 1.62 (d, J=6.5 Hz, 3H), 1.65-2.05 (m, 5H), 2.61-2.69 (m, 1H), 2.88-3.10 (m, 2H), 3.58-3.63 (m, 1H), 3.90-4.00 (m, 1H), 4.01 (d, J=8.5 Hz, 1H), 4.38-4.44 (m, 1H), 4.58-4.67 (m, 1H), 5.31 (q, J=7.1 Hz, 1H), 5.91 (q, J=6.5 Hz, 1H), 7.18 (d, J=7.6 Hz, 1H), 7.31 (app t, J=7.6 Hz, 1H), 7.47 (d, J=7.6 Hz, 1H), 7.58 (s, 1H), 7.77 (s, 1H), 7.95 (s, 1H). LCMS (m/z) 525.2 [M+H], Tr=4.51 min.

Example 43

Compound 43a

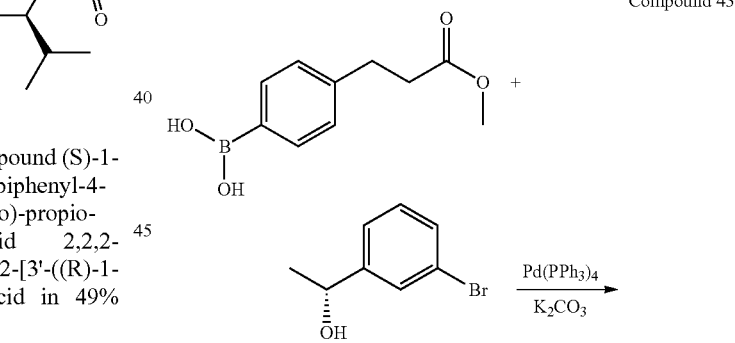

Potassium carbonate (663 mg, 4.80 mmol) and tetrakis(triphenylphosphine)palladium (0) (139 mg, 0.12 mmol) were added to a solution of (R)-1-(3-bromophenyl)-ethanol (483 mg, 2.40 mmol) and 4-(2-methoxy carbonylethyl)benzeneboronic acid (500 mg, 2.40 mmol) in 1,2-dimethoxyethane (5 mL) in a 5 mL microwave vessel. The vessel was sealed before being heated in the microwave for 20 min, using fixed hold time, on high absorption at 100° C. The reaction mixture was filtered through a pad of Hyflo and the pad was washed with ethyl acetate. The combined organics were then concentrated and the resultant brown oil was purified by silica gel chromatography using a stepwise gradient of iso-hexanes/ ethyl acetate 1:0 to 3:2 to afford the title compound (416 mg, 61%) as a yellow oil.

Compound 43b

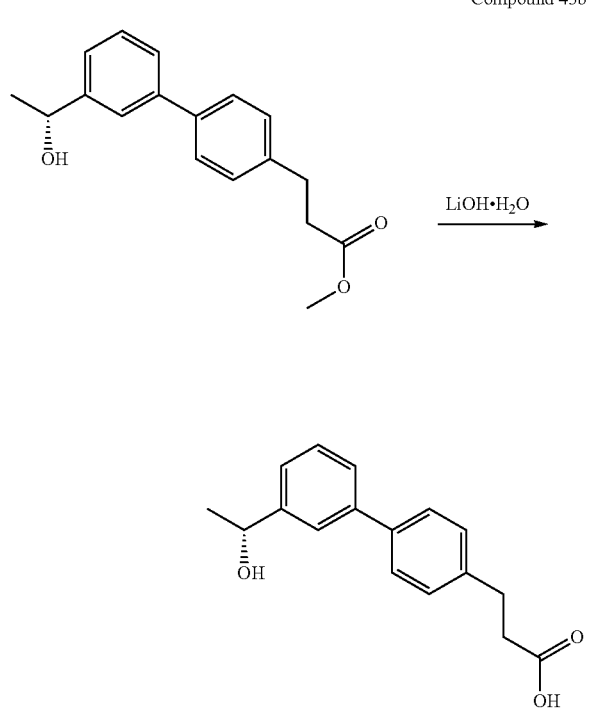

43a (416 mg, 1.46 mmol) was dissolved in a mixture of tetrahydrofuran (8 mL) and water (2 mL) and the solution was cooled using an ice bath. Lithium hydroxide monohydrate (175 mg, 2.92 mmol) was added and the solution was allowed to slowly warm to RT overnight. The solution was acidified using 2 M hydrochloric acid and then extracted with dichloromethane (2×20 mL). The combined organics were then dried over anhydrous sodium sulfate, filtered and concentrated to afford the title compound (250 mg, 89%) as a white solid.

Compound 43c

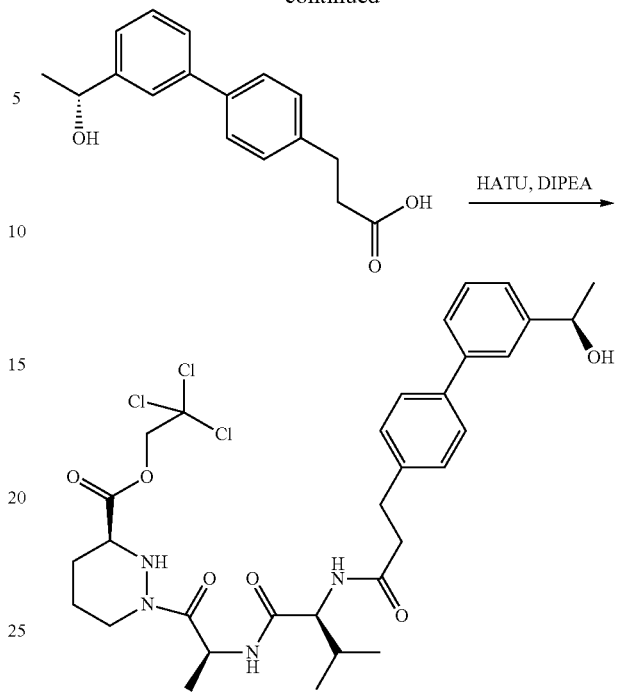

(S)-1-[(S)-2-((S)-2-Amino-3-methyl-butyrylamino)-propionyl]-hexahydro-pyridazine-3-carboxylic acid 2,2,2-trichloro-ethyl ester (669 mg, 1.55 mmol) and 43b (350 mg, 1.29 mmol) were dissolved in anhydrous acetonitrile (10 mL) and cooled using an ice bath. 2-(1H-7-Azabenzotriazol-1-yl)-1,1,3,3-tetramethyl uronium hexafluorophosphate methanaminium (688 mg, 1.81 mmol) and N,N-diisopropylethylamine (899 µL, 5.16 mmol) were then added and the reaction was allowed to slowly warm to RT and left to stir overnight. The solvent was then removed and the residue was dissolved in ethyl acetate. The solution was then washed with water (3×20 mL) and brine (20 mL), dried over anhydrous sodium sulfate, filtered and concentrated and the resultant brown oil was purified by silica gel chromatography using a stepwise gradient of iso-hexanes/ethyl acetate 1:4 to 0:1 to afford the title compound (314 mg, 36%) as a white solid.

Compound 43d

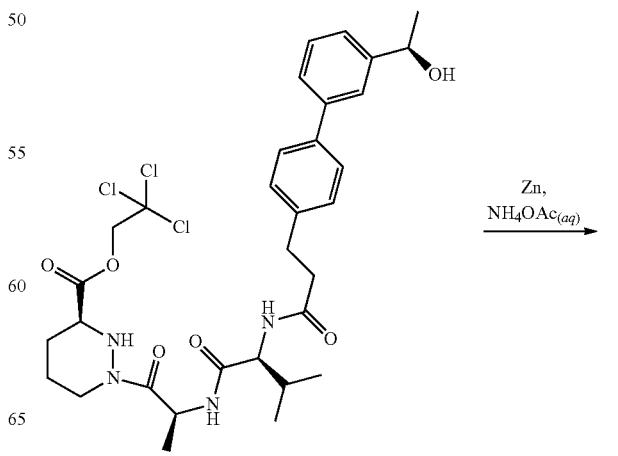

-continued

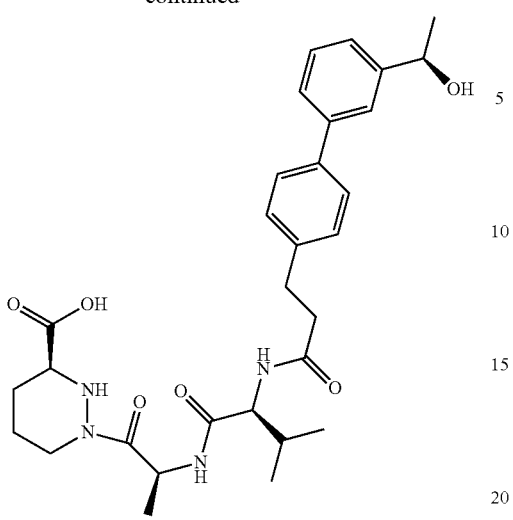

43c (314 mg, 0.459 mmol) was dissolved in tetrahydrofuran (10 mL). Zinc powder (300 mg, 4.59 mmol) was added followed by ammonium acetate (1 M in water, 3.21 mL, 3.21 mmol). The reaction was then left to stir overnight. The reaction mixture was then filtered through a pad of Hyflo. The pad was then washed with potassium hydrogen sulfate solution and ethyl acetate. The biphasic mixture was further acidified using 2 M hydrochloric acid until the solution was approximately pH 1. The phases were separated and the aqueous phase was extracted with ethyl acetate. The combined organic phases were dried over anhydrous sodium sulfate, filtered and concentrated to afford the title compound (212 mg, 84%) as a yellow solid.

Compound 43

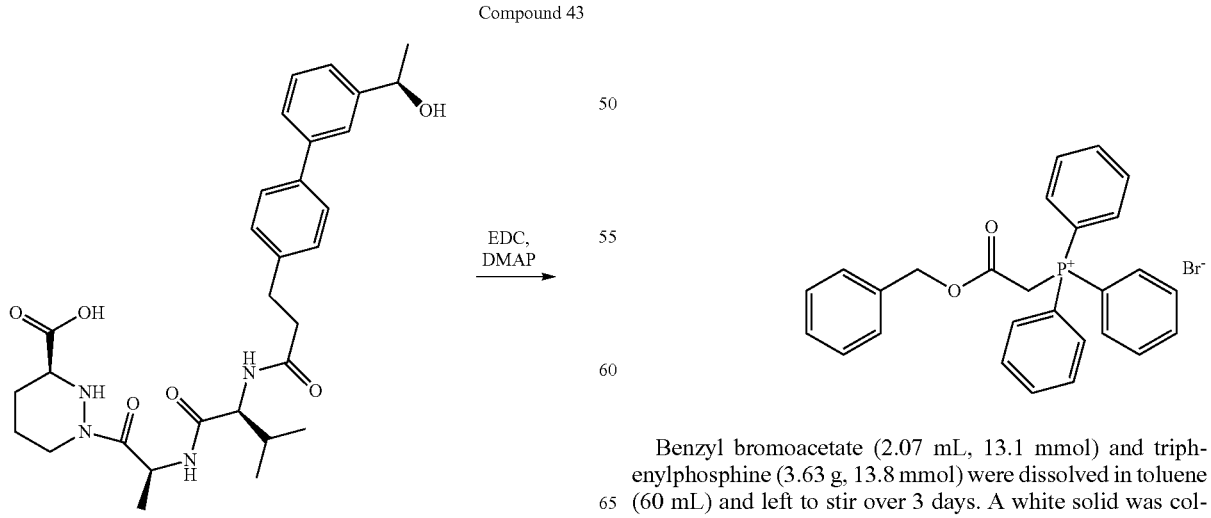

EDC, DMAP
→

-continued

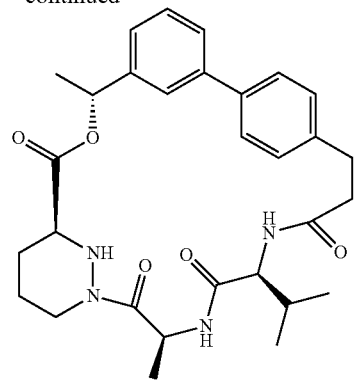

43d (100 mg, 0.181 mmol) was dissolved in dichloromethane (181 mL), under an atmosphere of nitrogen. N-(3-Dimethylaminopropyl)-N'-ethylcarbodiimide hydrochloride (142 0.724 mmol) and 4-dimethylaminopyridine (44 mg, 0.362 mmol) were added and the reaction was left to stir overnight. The solvent was removed and the residue was purified by silica gel chromatography using 100% ethyl acetate to afford the title compound (52 mg, 54%) as a white solid. $^1$H NMR (300 MHz, CDCl$_3$) δ 0.92 (d, J=6.7 Hz, 6H), 1.24-1.29 (m, 3H), 1.60-1.68 (m, 5H), 1.85-1.98 (m, 2H), 2.37-2.49 (m, 1H), 2.58-2.78 (m, 1H), 2.83-2.93 (m, 1H), 3.16-3.28 (m, 1H), 3.45 (m, 3H), 4.03-4.11 (m, 1H), 4.45-4.54 (m, 1H), 5.06-5.16 (m, 1H), 5.92-6.00 (m, 1H), 6.25 (d, J=8.5 Hz, 1H), 7.19 (s, 1H), 7.22 (s, 2H), 7.39 (app t, J=7.6 Hz, 1H), 7.48-7.56 (m, 3H), 7.62 (br s, 1H). LCMS (m/z) 535.3 [M+H], Tr=2.43 min.

Example 44

Compound 44a

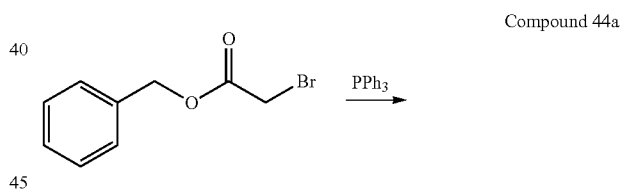

Benzyl bromoacetate (2.07 mL, 13.1 mmol) and triphenylphosphine (3.63 g, 13.8 mmol) were dissolved in toluene (60 mL) and left to stir over 3 days. A white solid was collected by filtration and washed with diethyl ether. This afforded the title compound (5.86 g, 93%) as a white solid.

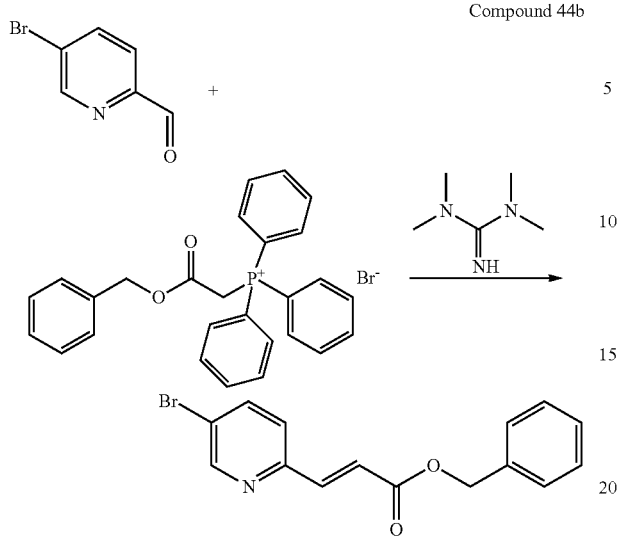

Compound 44b 5-bromo-2-pyridine carboxaldehyde (125 mg, 0.666 mmol) and 44a (655 mg, 1.33 mmol) were dissolved in dichloromethane (5 mL). 1,1,3,3-Tetramethylguanidine (251 µL, 2 mmol) was then added and the reaction was left to stir for 3.5 h. The reaction was quenched with saturated ammonium chloride solution and the phases were separated. The organic phase was then washed with brine, dried over anhydrous sodium sulfate, filtered and concentrated. The residue was then purified by silica gel chromatography using a stepwise gradient of iso-hexanes/ethyl acetate 1:0 to 4:1 to afford the title compound (186 mg, 88%) as a yellow solid.

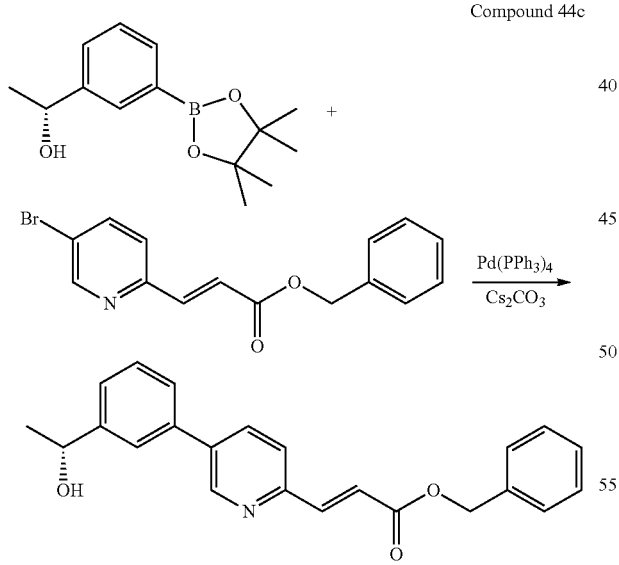

Compound 44c 44b (186 mg, 0.585 mmol), (R)-1-[3-(4,4,5,5-tetramethyl-[1,3,2]dioxaborolan-2-yl)-phenyl]-ethanol (145 mg, 0.585 mmol), cesium carbonate (476 mg, 1.46 mmol) and tetrakis(triphenylphosphine) palladium(0) (66 mg, 0.0585 mmol) were placed in a microwave vessel. 1,2-Dimethoxyethane (2 mL) and water (0.5 mL) were added and the vessel was sealed. The reaction was heated in the microwave for 30 min, using fixed hold time, on high absorption at 150° C. The reaction mixture was poured onto water and the resultant mixture was extracted with ethyl acetate. The organics were then dried over anhydrous sodium sulfate, filtered and concentrated. The residue was then purified by silica gel chromatography using a stepwise gradient of iso-hexanes/ethyl acetate 1:0 to 1:1 to afford the title compound (150 mg, 77%) as an orange gum.

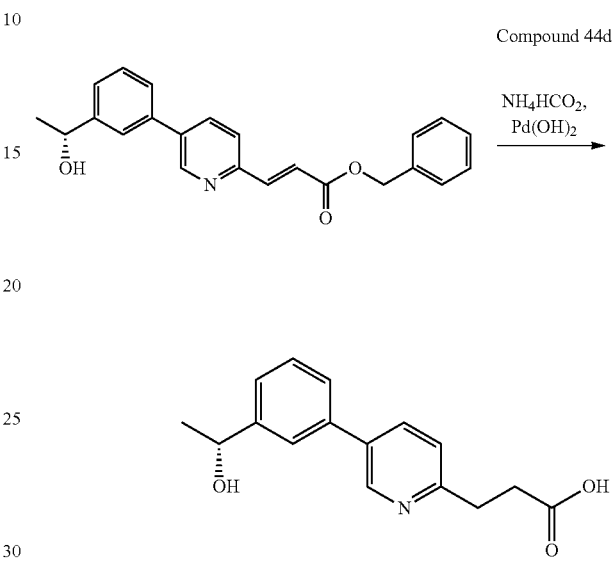

Compound 44d 44c (150 mg, 0.417 mmol) was dissolved in ethanol (5 mL). Palladium(II) hydroxide (20% on carbon, wet, 40 mg) was then added followed by ammonium formate (132 mg, 2.09 mmol). The reaction was heated to reflux and left to stir for 30 min. The reaction was allowed to cool to RT and was then filtered through a pad of Hyflo. The pad was washed with ethanol and the combined organics were concentrated to leave the title compound (105 mg, 93%) as an orange gum.

Compound 44e

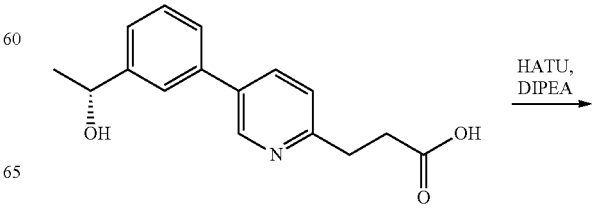

-continued

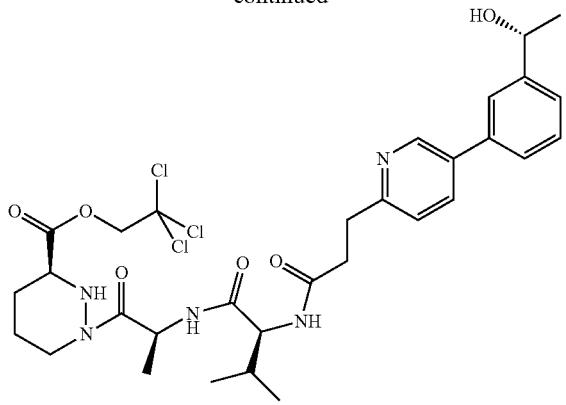

44d (105 mg, 0.387 mmol) and (S)-1-[(S)-2-((S)-2-amino-3-methyl-butyrylamino)-propionyl]-hexahydro-pyridazine-3-carboxylic acid 2,2,2-trichloro-ethyl ester (200 mg, 0.464 mmol) were dissolved in acetonitrile (5 mL) and cooled using an ice bath. 2-(1H-7-Azabenzotriazol-1-yl)-1,1,3,3-tetramethyl uronium hexafluorophosphate methanaminium (206 mg, 0.542 mmol) and N,N-diisopropylethylamine (270 µL, 1.55 mmol) were then added and the reaction was allowed to slowly warm to RT and left to stir overnight. The solvent was then removed and the residue was dissolved in ethyl acetate. The solution was then washed with water (3×20 mL) and brine (20 mL), dried over anhydrous magnesium sulfate, filtered and concentrated and the residue was purified by silica gel chromatography using a stepwise gradient of iso-hexanes/ethyl acetate/acetone 3:1:0 to 0:7:3 to afford a brown solid (110 mg). This was further purified by silica gel chromatography using a stepwise gradient of ethyl acetate/acetone 1:0 to 4:1 to afford the title compound (100 mg, 38%) as a yellow solid.

Compound 44f

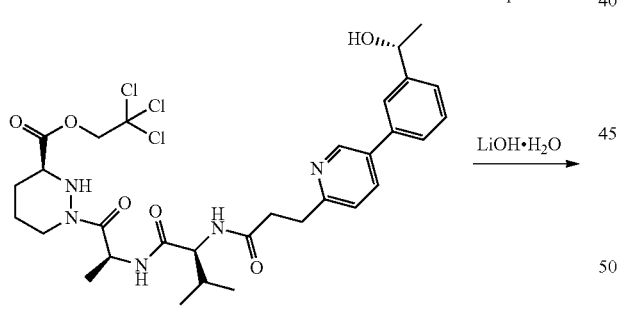

44e (100 mg, 0.146 mmol) was dissolved in a mixture of tetrahydrofuran (3 mL) and water (1 mL) and cooled using an ice bath. Lithium hydroxide monohydrate (6 mg, 0.153 mmol) was added and the reaction was stirred for 30 min. The solution was acidified to pH 1 using 2 M hydrochloric acid and evaporated to dryness. The residue was then purified by C18 chromatography using a stepwise gradient of acetonitrile/water 0:1 to 1:4 to afford the title compound (25 mg, 31%) as a white solid.

Compound 44

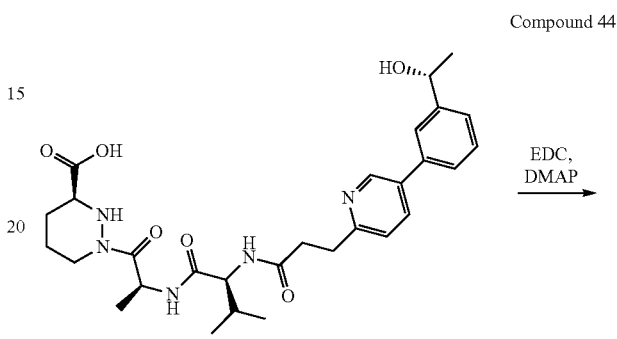

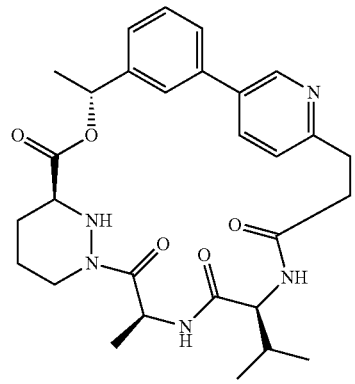

44f (25 mg, 0.045 mmol) was dissolved in dichloromethane (45 mL). N-(3-dimethylaminopropyl)-N'-ethylcarbodiimide hydrochloride (35 mg, 0.148 mmol) and 4-dimethylaminopyridine (11 mg, 0.009 mmol) were added and the reaction was left to stir for 4 h. The solvent was removed and the residue was purified by silica gel chromatography using a stepwise gradient of ethyl acetate/acetone 1:0 to 3:2 to leave a white solid (6 mg). This was then eluted through an reverse phase HPLC system fitted with a Phenomenex Gemini 10µ 110 A, 250×21.2 mm column using an isocratic 2:3 acetonitrile/water flow at 20 mL/min to afford the title compound (1.3 mg, 7%) as a white solid. $^1$H NMR (300 MHz, CDCl$_3$) δ 0.84-1.00 (m, 7H), 1.10 (d, J=6.9 Hz, 3H), 1.62-1.72 (m, 4H), 1.86-2.08 (m, 3H), 2.54-2.71 (m, 2H), 2.90-3.14 (m, 2H), 3.28-3.54 (m, 3H), 3.98 (app t, J=9.2 Hz, 1H), 4.43-4.52 (m, 1H), 5.07 (app t, J=8.0 Hz, 1H), 5.92-6.00 (m, 1H), 6.10 (d, J=8.0 Hz, 1H), 6.37 (d, J=9.1 Hz, 1H), 7.20 (d, J=8.0 Hz, 1H),

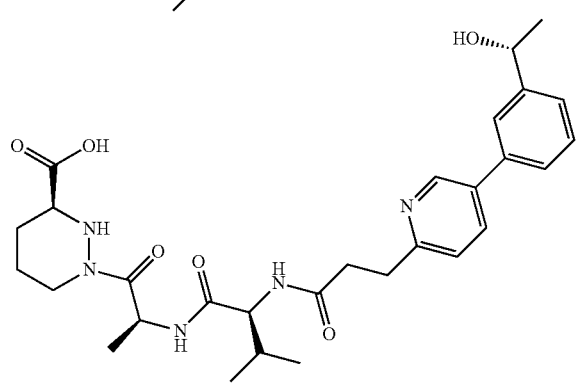

7.26-7.31 (m, 1H), 7.41-7.59 (m, 3H), 7.75 (dd, J=8.0, 2.2 Hz, 1H), 8.78 (d, J=2.4 Hz, 1H). LCMS (m/z) 536.0 [M+H], Tr=1.47 min.

Example 45

Compound 45a

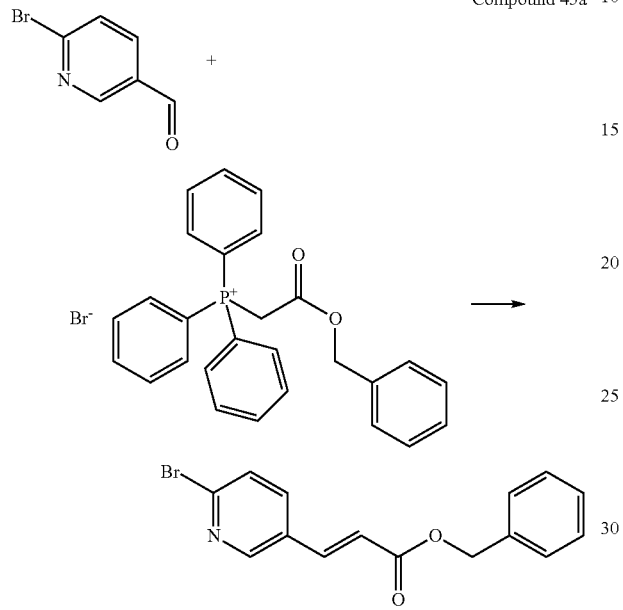

6-Bromo-3-pyridinecarboxaldehyde (500 mg, 2.69 mmol) and benzyloxycarbonylmethyl-triphenyl-phosphonium bromide (2.64 g, 5.38 mmol) were dissolved in dichloromethane (15 mL). 1,1,3,3-Tetramethylguanidine (1.01 mL, 8.03 mmol) was then added and the reaction was left to stir for 3.5 h. The reaction was quenched with saturated ammonium chloride solution and the phases were separated. The organic phase was then washed with brine, dried over anhydrous sodium sulfate, filtered and concentrated. The residue was then purified by silica gel chromatography using a stepwise gradient of iso-hexanes/ethyl acetate 1:0 to 4:1 to afford the title compound (492 mg, 57%) as a white solid.

Compound 45b

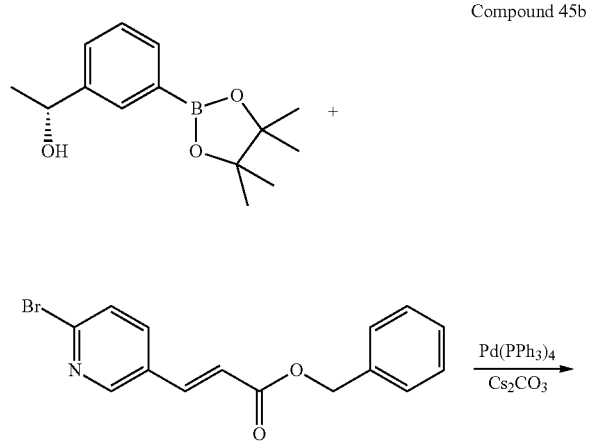

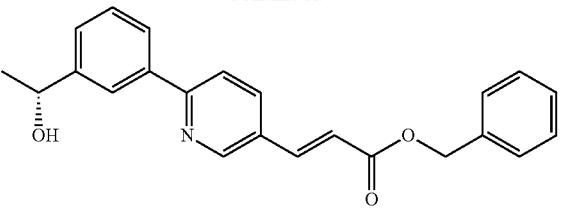

45a (382 mg, 1.54 mmol), (R)-1-[3-(4,4,5,5-tetramethyl-[1,3,2]dioxaborolan-2-yl)-phenyl]-ethanol (490 mg, 1.54 mmol), cesium carbonate (1.06 g, 3.85 mmol) and tetrakis (triphenylphosphine) palladium(0) (178 mg, 0.154 mmol) were placed in a microwave vessel. 1,2-Dimethoxyethane (4 mL) and water (1 mL) were added and the vessel was sealed. The reaction was heated in the microwave for 50 min, using fixed hold time, on high absorption at 150° C. The reaction mixture was poured onto water and the resultant mixture was extracted with ethyl acetate. The organics were then dried over anhydrous sodium sulfate, filtered and concentrated. The residue was then purified by silica gel chromatography using a stepwise gradient of iso-hexanes/ethyl acetate 1:0 to 1:1 to afford impure product. This was subjected to a second round of purification using the same conditions to afford the title compound (195 mg, 35%) as a yellow solid.

Compound 45c

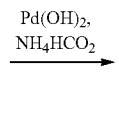

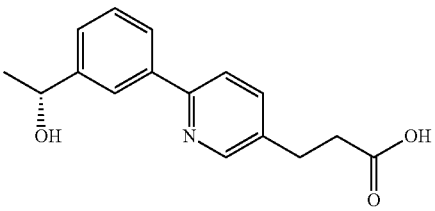

45b (195 mg, 0.543 mmol) was dissolved in ethanol (5 mL). Palladium(II) hydroxide (20% on carbon, wet, 40 mg) was then added followed by ammonium formate (172 mg, 2.72 mmol). The reaction was heated to reflux and left to stir for 30 min. The reaction was allowed to cool to RT and was then filtered through a pad of Hyflo. The pad was washed with ethanol and the combined organics were concentrated to leave the title compound (150 mg, 100%) as a pale yellow solid.

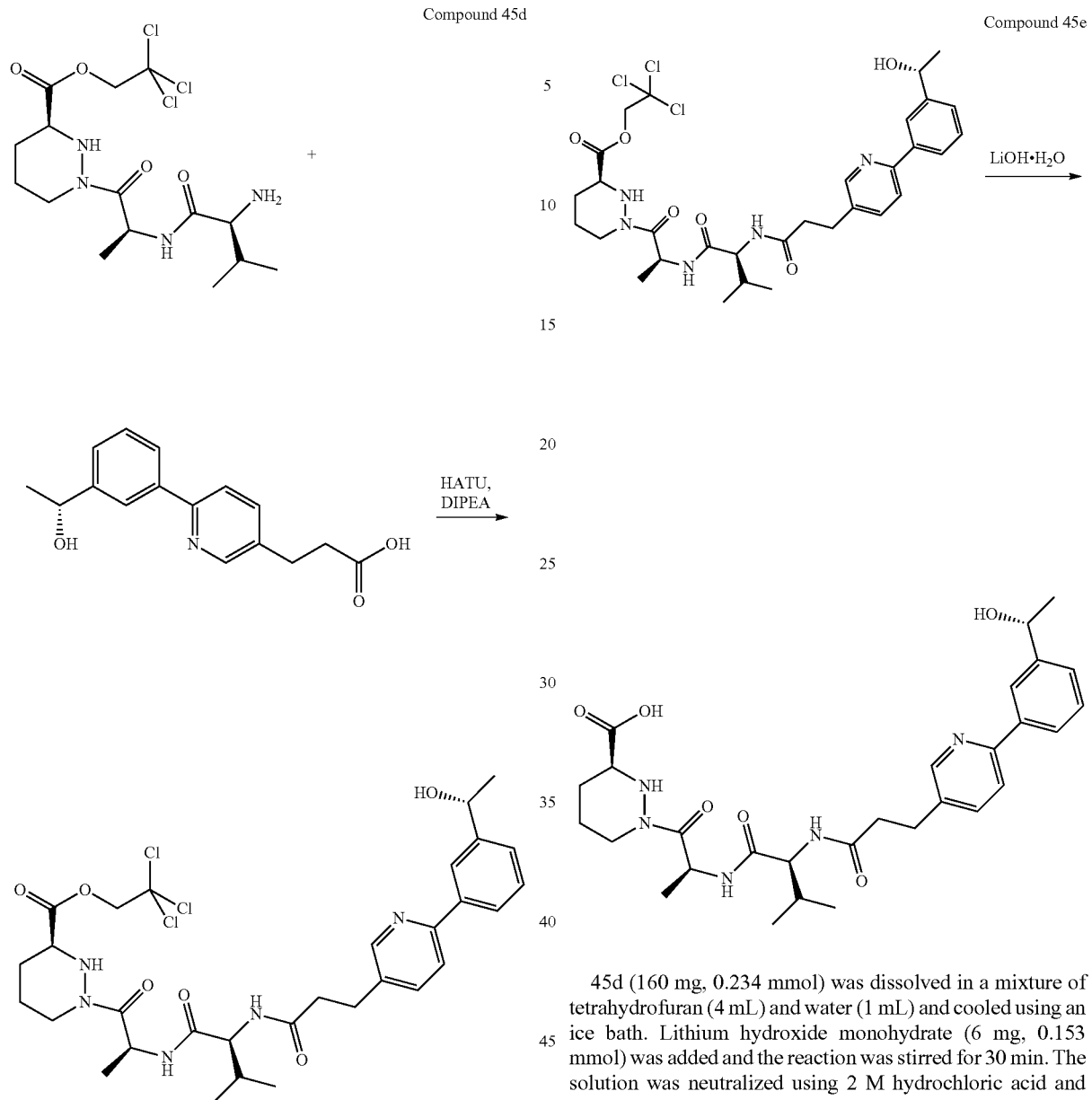

45c (150 mg, 0.553 mmol) and (S)-1-[(S)-2-((S)-2-amino-3-methyl-butyrylamino)-propionyl]-hexahydro-pyridazine-3-carboxylic acid 2,2,2-trichloro-ethyl ester (287 mg, 0.66 mmol) were dissolved in acetonitrile (5 mL) and cooled using an ice bath. 2-(1H-7-Azabenzotriazol-1-yl)-1,1,3,3-tetramethyl uronium hexafluorophosphate methanaminium (294 mg, 0.774 mmol) and N,N-diisopropylethylamine (385 µL, 2.21 mmol) were then added and the reaction was allowed to slowly warm to RT and left to stir overnight. Ethyl acetate was then poured into the reaction mixture. The resultant solution was then washed with water (3×20 mL) and brine (20 mL), dried over anhydrous sodium sulfate, filtered and concentrated and the residue was purified by silica gel chromatography using a stepwise gradient of iso-hexanes/ethyl acetate/acetone 3:1:0 to 0:7:3 to afford a solid (334 mg). This was further purified by silica gel chromatography using a stepwise gradient of ethyl acetate/acetone 1:0 to 4:1 to afford the title compound (167 mg, 44%) as a solid.

45d (160 mg, 0.234 mmol) was dissolved in a mixture of tetrahydrofuran (4 mL) and water (1 mL) and cooled using an ice bath. Lithium hydroxide monohydrate (6 mg, 0.153 mmol) was added and the reaction was stirred for 30 min. The solution was neutralized using 2 M hydrochloric acid and evaporated to dryness. The residue was then purified by C18 chromatography using a stepwise gradient of acetonitrile/water 0:1 to 1:4 to afford the title compound (21 mg, 16%) as a white solid.

Compound 45

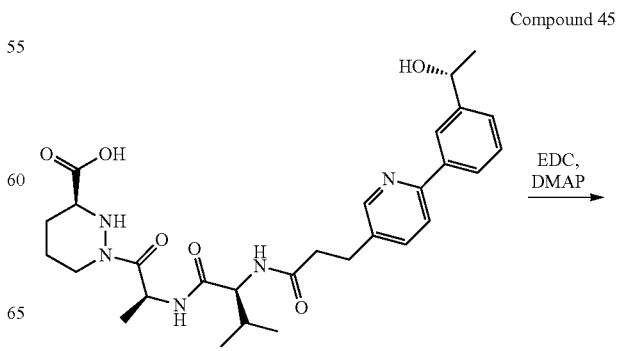

205

-continued

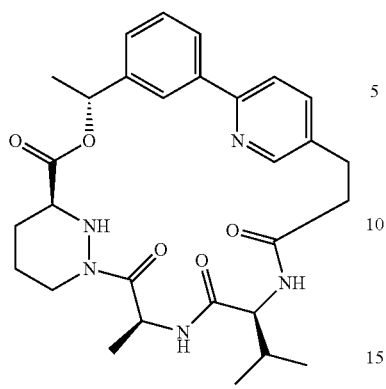

45e (21 mg, 0.0379 mmol) was dissolved in dichloromethane (38 mL). N-(3-dimethylaminopropyl)-N'-ethylcarbodiimide hydrochloride (29 mg, 0.152 mmol) and 4-dimethylaminopyridine (9 mg, 0.0758 mmol) were added and the reaction was left to stir for 4 h. The solvent was removed and the residue was purified by silica gel chromatography using 100% ethyl acetate. The resultant material was then eluted through a reverse phase HPLC system fitted with a Phenomenex Gemini 10μ. 110 A, 250×21.2 mm column using an isocratic 3:7 acetonitrile/water flow at 20 mL/min to afford the title compound (1 mg, 5%). $^1$H NMR (300 MHz, CDCl$_3$) δ 0.91 (d, J=6.5 Hz, 6H), 1.48 (d, J=7.1 Hz, 3H), 1.63-1.72 (m, 7H), 1.81-1.93 (m, 2H), 2.00-2.10 (m, 1H), 2.25-2.38 (m, 1H), 2.54-2.67 (m, 1H), 3.15-3.28 (m, 1H), 3.39-3.59 (m, 2H), 4.03 (app t, J=9.6 Hz, 1H), 4.43-4.54 (m, 1H), 5.04-5.16 (m, 1H), 5.80 (d, J=9.8 Hz, 1H), 5.94 (q, J=6.7 Hz, 1H), 7.22-7.27 (m, 1H), 7.43 (app t, J=7.8 Hz, 1H), 7.55-7.57 (m, 1H), 7.69 (d, J=8.0 Hz, 1H), 7.92 (d, J=8.3 Hz, 1H), 8.19 (br s, 1H), 8.48 (d, J=2.2 Hz, 1H). LCMS (m/z) 536.2 [M+H], Tr=1.61 min.

Example 46

206

-continued

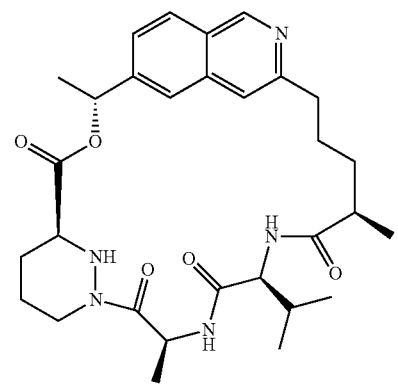

To Compound 21 (25 mg, 0.05 mmol) in ethyl acetate (5 mL) at RT was added 10% palladium on carbon (20 mg). The system was purged with hydrogen and stirred for 2 h. The reaction was filtered through Celite and concentrated in vacuo. The residue was purified by preparative TLC using ethyl acetate/acetone 5/1 to give the title compound (2.2 mg, 9%) as a white solid. $^1$H NMR (300 MHz, CDCl$_3$) 0.96 (d, J=6.7 Hz, 3H), 0.98 (d, J=6.7 Hz, 3H), 1.24 J=7.1 Hz, 3H), 1.52 (d, J=6.9 Hz, 3H), 1.67 (d, J=6.7 Hz, 3H), 1.55-2.14 (m, 10H), 2.53-2.80 (m, 2H), 2.92-3.01 (m, 2H), 3.45-3.67 (m, 1H), 4.14-4.23 (m, 1H), 4.49-4.60 (m, 1H), 5.39-5.51 (m, 1H), 5.96 (d, J=9.4 Hz, 1H), 6.06 (q, J=6.7 Hz, 1H), 6.43 (d, J=8.5 Hz, 1H), 7.39 (dd, J=8.5, 1.1 Hz, 1H), 7.56 (s, 1H), 7.75 (s, 1H), 7.93 (d, J=8.5 Hz, 1H), 9.16 (s, 1H). LCMS (m/z) =552.3 [M+H], Tr=1.25 min.

Example 47

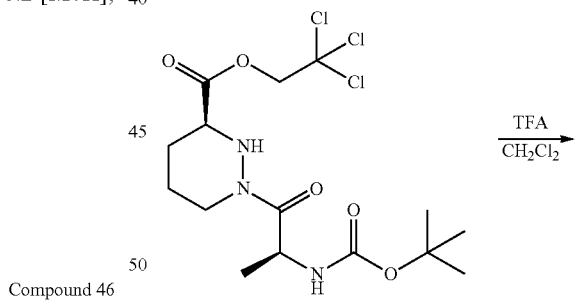

Compound 47a

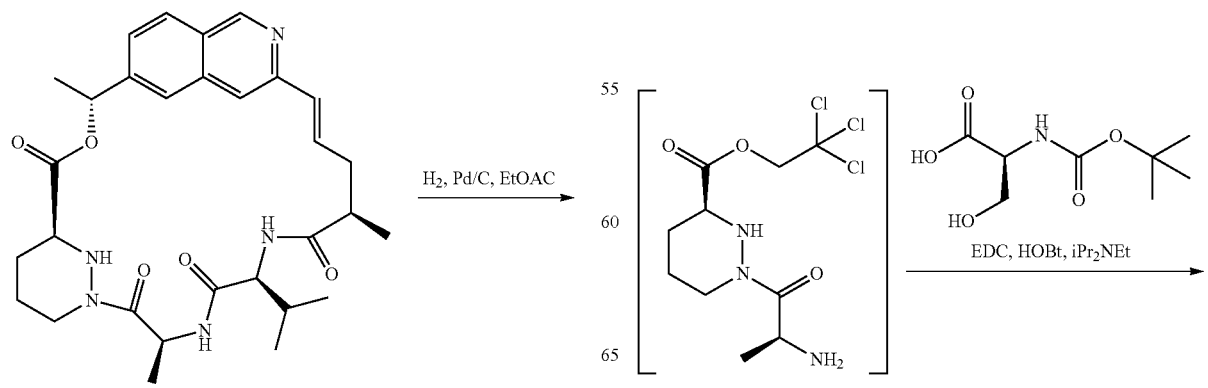

Compound 46

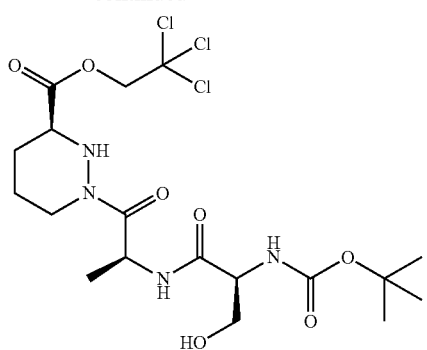

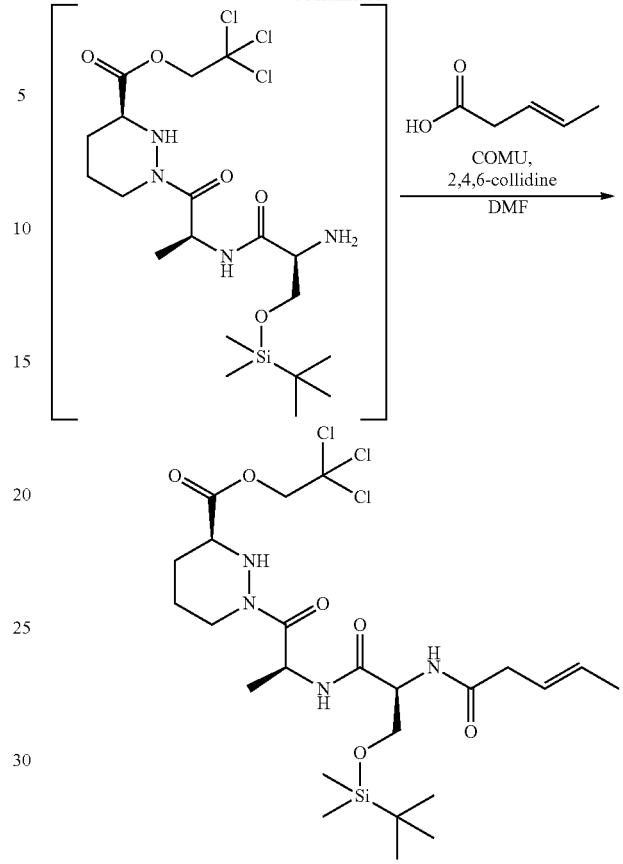

To a solution of (S)-1-((S)-2-tert-butoxycarbonylamino-propionyl)-hexahydro-pyridazine-3-carboxylic acid 2,2,2-trichloro-ethyl ester (320 mg, 0.74 mmol) in dichloromethane (8 mL) was added trifluoroacetic acid (2 mL). The reaction was stirred at RT for 105 min and was then concentrated in vacuo. The resulting crude product was dissolved in ethyl acetate (75 mL) and was washed with saturated aqueous sodium bicarbonate. The aqueous phase was extracted with ethyl acetate (2×40 mL), and the organics were dried over anhydrous sodium sulfate, filtered, and concentrated to a crude residue that was used without further purification. The residue from the previous step, 1-hydroxybenzotriazole (152 mg, 1.12 mmol) and (S)-2-tert-butoxycarbonylamino-3-hydroxy-propionic acid (154 mg, 0.75 mmol) were dissolved in dichloromethane (6 mL). N,N-Diisopropylethylamine (190 mg, 1.5 mmol) was added, and the resulting solution was cooled in an ice water bath. N-(3-Dimethylaminopropyl)-N'-ethylcarbodiimide (149 mg, 0.96 mmol) was added dropwise over 15 s. The reaction was stirred for 18 h, allowing the ice bath to slowly expire. The reaction mixture was then diluted with ethyl acetate (50 mL) and was washed with saturated aqueous sodium bicarbonate and brine. The organic phase was dried over anhydrous sodium sulfate, filtered, and concentrated to afford a crude residue that was purified by silica gel chromatography (75 to 100% ethyl acetate in iso-hexanes) to afford the title product (211 mg, 55%) as an oil.

Compound 47b

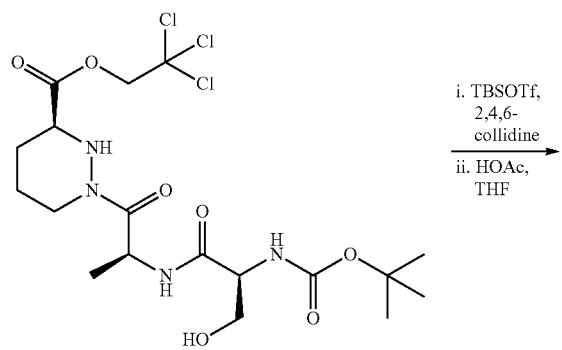

i. TBSOTf, 2,4,6-collidine
ii. HOAc, THF

To a solution of 47a (64 mg, 0.12 mmol) in dichloromethane (1 mL) was added 2,4,6-collidine (98 mg, 1.28 mmol). tert-Butyldimethylsilyl trifluoromethanesulfonate (98 mg, 0.37 mmol) was added dropwise over 20 sec. The reaction mixture was stirred for 15 h and was quenched with saturated aqueous sodium bicarbonate (1 mL). The mixture was further diluted with ethyl acetate, water, and 0.1 N aqueous hydrochloric acid to afford an acidic aqueous layer. The phases were separated, and the organics were dried over sodium sulfate, filtered, and concentrated in vacuo to afford a crude residue that was used without further purification. The crude product was dissolved in tetrahydrofuran (3 mL). Acetic acid (115 mg, 1.9 mmol) was added in one portion and the resulting solution was stirred for 3.25 h. The reaction was then diluted with ethyl acetate (25 mL) and washed with saturated aqueous sodium bicarbonate (25 mL). The phases were separated, and the aqueous phase was extracted with ethyl acetate (25 mL). The combined organic phases were washed with brine (25 mL) and dried over anhydrous sodium sulfate. The mixture was filtered, and the filtrate was concentrated in vacuo to afford crude amine which was used without further purification. The crude amine was dissolved in N,N-dimethylformamide (1.5 mL). 2,4,6-Collidine (31 mg, 0.26 mmol) and trans-3-pentenoic acid (15.3 mg, 0.152 mmol) were added, and the resulting solution was cooled in an ice water bath. (1-Cyano-2-ethoxy-2-oxoethylidenaminooxy) dimethylamino-morpholino-carbenium hexafluorophosphate (72.4 mg, 0.169 mmol) was added in one portion, and the reaction was stirred for 30 min. The reaction was then removed from the cold bath and warmed to ambient temperature. After 15 h, the reaction was diluted with ethyl acetate (35 mL), saturated aqueous sodium bicarbonate (20 mL), and brine (5 mL). The phases were separated, and the organic layer was washed with 0.1 N aqueous hydrochloric acid (25 mL) and then brine (5 mL). The acidic aqueous layer was extracted with ethyl acetate (25 mL), and the combined organic phases were then dried over anhydrous sodium sulfate, filtered, and concentrated. The resulting crude residue was purified by silica gel chromatography (50 to 80% ethyl acetate in iso-hexanes) to afford the title compound (46.9 mg, 62% over 3 steps) as a white foam.

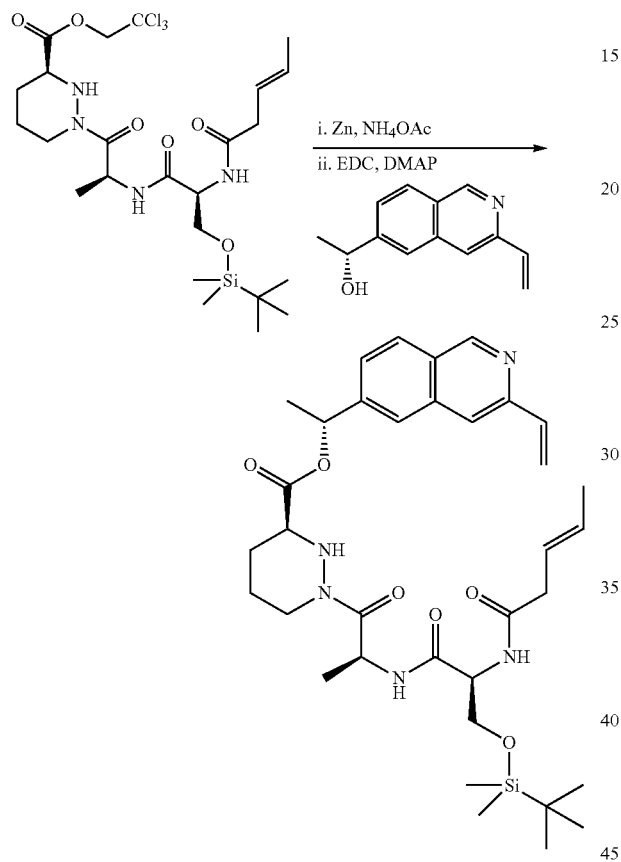

To a solution of 47b (46.9 mg, 0.0761 mmol) in tetrahydrofuran (1.5 mL) was added water (0.30 mL), ammonium acetate (96 mg, 1.2 mmol), and zinc powder (109 mg, 1.7 mmol). The reaction mixture was stirred vigorously at RT for 17.5 h, at which time the temperature was increased to 35° C. After 25.5 h, additional zinc powder (60 mg, 0.92 mmol) was added and the reaction temperature was increased to 45° C. After 39.5 h, the reaction mixture was filtered through a pad of Celite washing with water and ethyl acetate. The aqueous phase was acidified with 2 M aqueous hydrochloric acid (15 mL), and the phases were separated. The aqueous phase was extracted with ethyl acetate (2×20 mL), and the combined organic phases were dried over sodium sulfate, filtered, and concentrated to afford a white solid (34.9 mg, 95%) that was used without further purification. The crude acid (0.072 mmol) was dissolved with (R)-1-(3-vinyl-isoquinolin-6-yl)-ethanol (17.4 mg, 0.087 mmol) in dichloromethane (1.0 mL). 4-Dimethylaminopyridine (13.3 mg, 0.109 mmol) was added followed by N-(3-dimethylaminopropyl)-N'-ethylcarbodiimide hydrochloride (17 mg, 0.085 mmol). The reaction was stirred for 16.5 h, at which time it was loaded directly onto a silica gel column. Elution with 60 to 100% ethyl acetate in iso-hexanes provided the title compound (20 mg, 43%) as an amorphous residue.

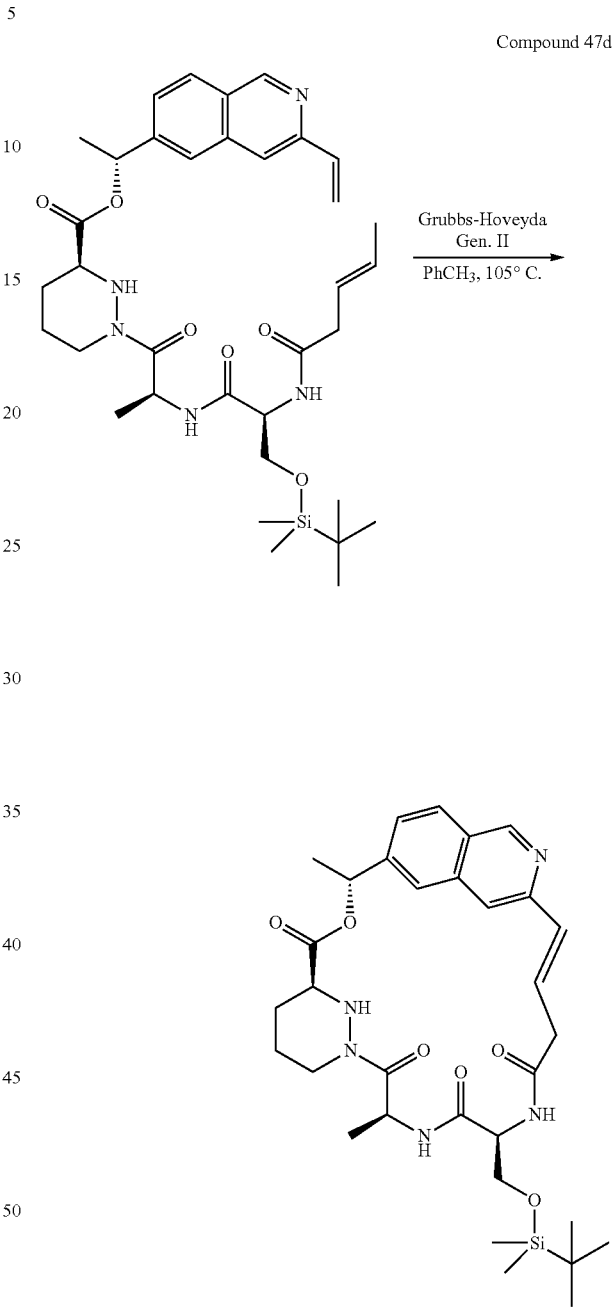

A solution of 47c (19.6 mg, 0.0294 mmol) in toluene (9.4 mL) was sparged with argon for 10 min with stirring. Hoveyda-Grubbs $2^{nd}$ generation-catalyst (2.8 mg, 0.0045 mmol) was then added as a solution in degassed toluene (0.45 mL), and the resulting solution was heated to 105° C. After 25 min, an additional portion of Hoveyda-Grubbs $2^{nd}$ generation catalyst (1.4 mg, 0.0022 mmol) was added. After 10 additional min, the reaction was cooled to ambient temperature and was concentrated in vacuo to ~4.5 mL. The solution was loaded directly onto a silica gel column which was eluted with 80 to 100% ethyl acetate in iso-hexanes to afford the title compound (6.9 mg, 38%1 as an amorphous solid.

Compound 47

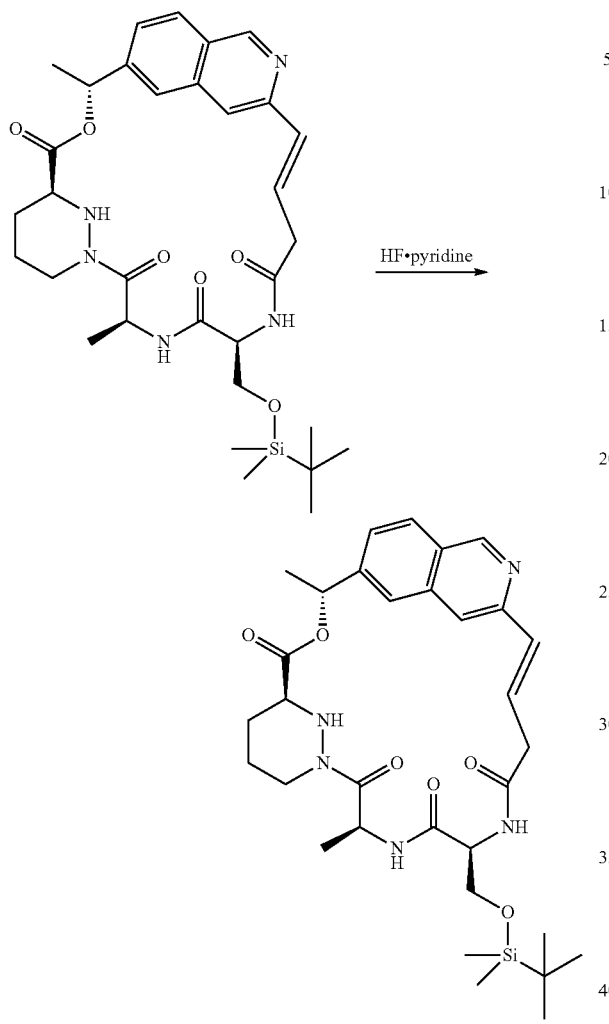

In a polypropylene vial, 47d (4.7 mg, 0.0075 mmol) was dissolved in tetrahydrofuran (0.90 mL) under argon and the resulting solution was cooled in an ice water bath. HF·pyridine (0.10 mL) was added dropwise. After 10 min, the reaction was quenched by addition to a stirred mixture of ethyl acetate (15 mL) and saturated aqueous sodium bicarbonate (15 mL). The phases were separated, and the aqueous phase was extracted with ethyl acetate (3×30 mL). The combined organic phases were dried over sodium sulfate, filtered and concentrated to afford a crude residue. In a polypropylene vial under argon, the aforementioned residue was dissolved in tetrahydrofuran (0.90 mL) and the resulting solution was cooled in an ice water bath. HF·pyridine (0.10 mL) was added dropwise, and the reaction mixture was removed from the cold bath. After 45 min, the reaction was worked up as described above to afford a crude residue. Purification by reverse-phase HPLC (5 to 100% acetonitrile in water, +0.1% trifluoroacetic acid) provided the title compound (1.6 mg, 34%) as an amorphous white solid. $^{1}$H NMR (400 MHz, CD$_3$OD) 9.54 (s, 1H), 8.38 (d, J=8.7 Hz, 1H), 8.29 (s, 1H), 8.17 (s, 1H), 7.87 (d, J=8.5 Hz, 1H), 6.90-6.75 (m, 2H), 6.18 (q, J=6.9 Hz, 1H), 5.84-5.74 (m, 1H), 4.71-4.64 (m, 1H), 4.50-4.42 (m, 1H), 3.88-3.81 (m, 2H), 3.78 (dd, J=11.3, 6.4 Hz, 1H), 3.52 (dd, J=12.9, 6.2 Hz, 1H), 3.52 (dd, J=12.9, 6.2 Hz, 1H), 2.81-2.70 (m, 1H), 2.11-2.04 (m, 1H), 1.99-1.91 (m, 1H), 1.85-1.69 (m, 2H), 1.73 (d, J=6.7 Hz, 3H), 1.60 (d, J=7.1 Hz, 3H). LCMS (m/z) 510.2 [M+H], Tr=2.19 min.

Example 48

Compound 48a

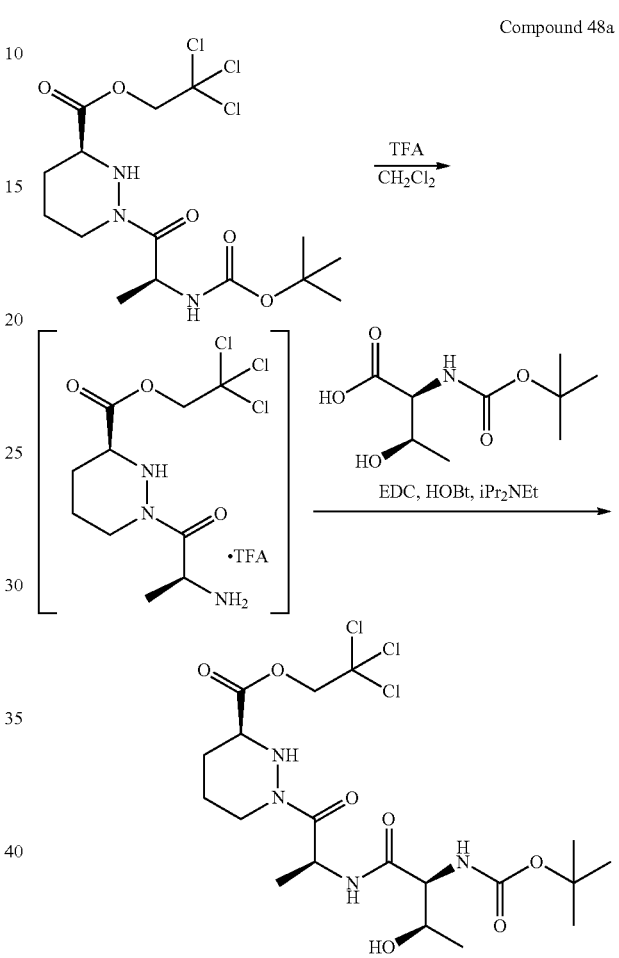

To a solution of (S)-1-((S)-2-tert-butoxycarbonylamino-propionyl)-hexahydro-pyridazine-3-carboxylic acid 2,2,2-trichloro-ethyl ester (320 mg, 0.74 mmol) in dichloromethane (8.8 mL) was added trifluoroacetic acid (2.2 mL). The reaction was stirred at RT for 45 min and was concentrated in vacuo. The resulting crude product was twice dissolved in and concentrated from anhydrous toluene (10 mL). The resulting crude residue was used without further purification. The crude residue (ca. 0.74 mmol), 1-hydroxybenzotriazole (153.8 mg, 1.1 mmol), and (2S,3R)-2-tert-butoxycarbony-lamino-3-hydroxy-butyric acid (161.2 mg, 0.735 mmol) were dissolved in dichloromethane (4 mL). N,N-Diisopropylethylamine (192 mg, 1.5 mmol) was added, and the resulting solution was cooled in an ice water bath. N-(3-Dimethylaminopropyl)-N'-ethylcarbodiimide (132 mg, 0.85 mmol) was added dropwise over 15 s. The reaction was removed from the cold bath and was stirred for 21.5 h. The reaction mixture was then diluted with ethyl acetate (50 mL) and washed with half-saturated aqueous sodium bicarbonate (30 mL). The organic phase was washed with brine, dried over anhydrous sodium sulfate, filtered, and concentrated to afford a crude residue that was purified by silica gel chromatography eluting with 65 to 90% ethyl acetate in iso-hexanes. Impure fractions were repurified by silica gel chromatography and collated with the first product to provide the title compound (230 mg, 58%).

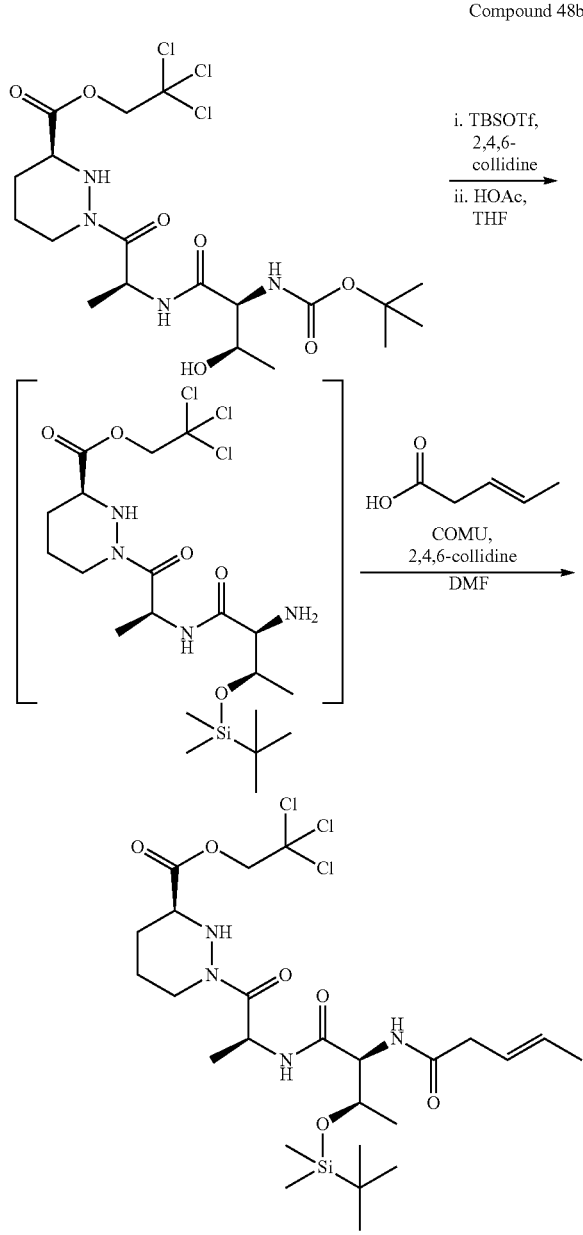

Compound 48b

To a solution of 48a (62.3 mg, 0.12 mmol) in dichloromethane (1 mL) was added 2,4,6-collidine (146 mg, 1.21 mmol). tert-Butyldimethylsilyl trifluoromethanesulfonate (94 mg, 0.36 mmol) was added dropwise over 20 s. The reaction mixture was stirred for 15 h and was quenched with saturated aqueous sodium bicarbonate (1 mL). The mixture was further diluted with ethyl acetate (2 mL) and brine (1 mL). The phases were separated, and the aqueous phase was extracted with ethyl acetate (4×1.5 mL). The combined organic phases were dried over sodium sulfate, filtered, and concentrated in vacuo to afford a crude residue that was used without further purification. The crude product was dissolved in tetrahydrofuran (3 mL). Acetic acid (104 mg, 1.6 mmol) was added in one portion and the resulting solution was stirred for 3.5 h. The reaction was then diluted with ethyl acetate (30 mL), saturated aqueous sodium bicarbonate (20 mL) and brine (10 mL). The phases were separated, and the aqueous phase was extracted with ethyl acetate (20 mL). The combined organic phases were dried over anhydrous sodium sulfate. The mixture was filtered, and the filtrate was concentrated in vacuo to afford crude intermediate amine which was used without further purification. The crude amine was dissolved in N,N-dimethylformamide (1.5 mL). 2,4,6-Collidine (28 mg, 0.23 mmol) and trans-3-pentenoic acid (14.3 mg, 0.143 mmol) were added, and the resulting solution was cooled in an ice water bath. (1-Cyano-2-ethoxy-2-oxoethylidenaminooxy)dimethylamino-morpholino-carbenium hexafluorophosphate (69 mg, 0.16 mmol) was added in one portion, and the reaction was stirred for 30 min. The reaction was then removed from the cold bath and warmed to ambient temperature. After 15 h, the reaction was diluted with ethyl acetate (25 mL), 0.1 N aqueous hydrochloric acid (30 mL), and brine (5 mL). The phases were separated, and the acidic aqueous layer was extracted with ethyl acetate (25 mL). The combined organic phases were washed with saturated aqueous sodium bicarbonate (25 mL), with brine (5 mL), dried over anhydrous sodium sulfate, filtered, and concentrated. The resulting crude residue was purified by silica gel chromatography (50 to 75% ethyl acetate in iso-hexanes) to afford the title compound (74 mg, quantitative yield over 3 steps) as a white foam.

Compound 48c

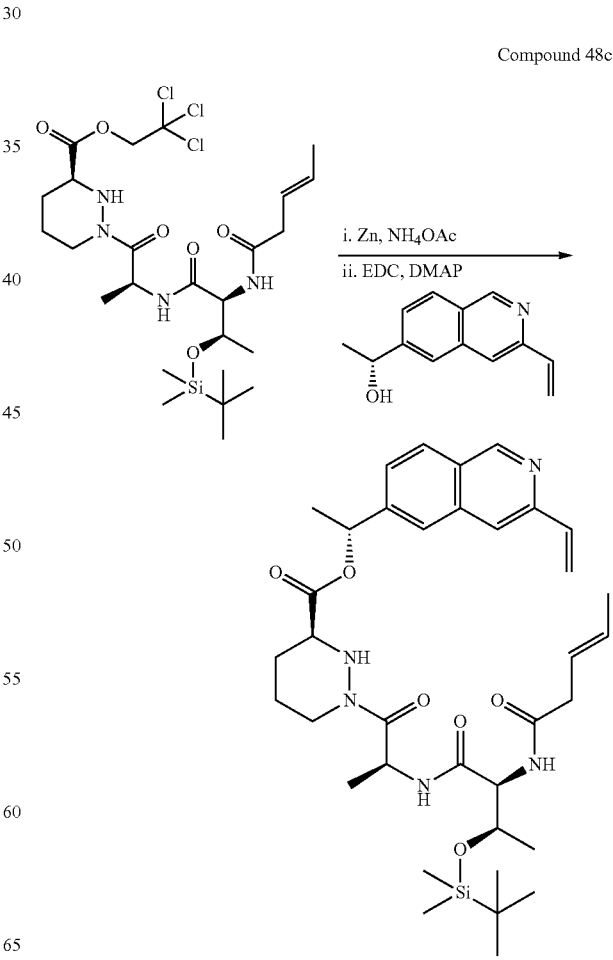

To a solution of 48b (74 mg, 0.117 mmol) in tetrahydrofuran (2.3 mL) was added water (0.47 mL), ammonium acetate (138 mg, 1.8 mmol), and zinc powder (164 mg, 2.5 mmol). The reaction mixture was stirred vigorously at RT for 17.5 h, at which time the temperature was increased to 35° C. After 25.5 h, additional zinc powder (85 mg, 1.3 mmol) was added and the reaction temperature was increased to 45° C. After 39.5 total hours, the reaction mixture was filtered through a pad of Celite, washing with water and ethyl acetate. The aqueous phase was acidified with 2 N aqueous hydrochloric acid (15 mL), and the phases were separated. The aqueous phase was extracted with ethyl acetate (2×20 mL), and the combined organic phases were dried over anhydrous sodium sulfate, filtered, and concentrated to afford an amorphous white solid (50 mg, 86%) that was used without further purification. The crude product (0.10 mmol) was dissolved along with (R)-1-(3-vinyl-isoquinolin-6-yl)-ethanol (23.9 mg, 0.12 mmol) in dichloromethane (1.0 mL). 4-Dimethylaminopyridine (15 mg, 0.12 mmol) was added followed by N-(3-dimethylaminopropyl)-N'-ethylcarbodiimide hydrochloride (17 mg, 0.019 mmol). The reaction was stirred for 16 h, at which time it was loaded directly onto a silica gel column. Elution with 50 to 85, and then to 100% ethyl acetate in iso-hexanes provided the title compound (40 mg, 58%) as a solid.

A solution of 48c (26 mg, 0.037 mmol) in toluene (12 mL) was sparged with argon for several min with stirring. Hoveyda-Grubbs 2$^{nd}$ generation catalyst (3.4 mg, 0.0054 mmol) was then added as a solution in degassed toluene (0.40 mL), and the resulting solution was heated to 105° C. After 20 min, an additional portion of Hoveyda-Grubbs 2$^{nd}$ generation catalyst (1.7 mg, 0.0027 mmol) was added as a solution in toluene (0.20 mL). After 40 additional min, the reaction was cooled to RT and was concentrated in vacuo to ~3 mL. The solution was loaded directly onto a silica gel column, which was eluted with 70 to 100% ethyl acetate in iso-hexanes to afford the title compound (10 mg, 42%) as an amorphous solid.

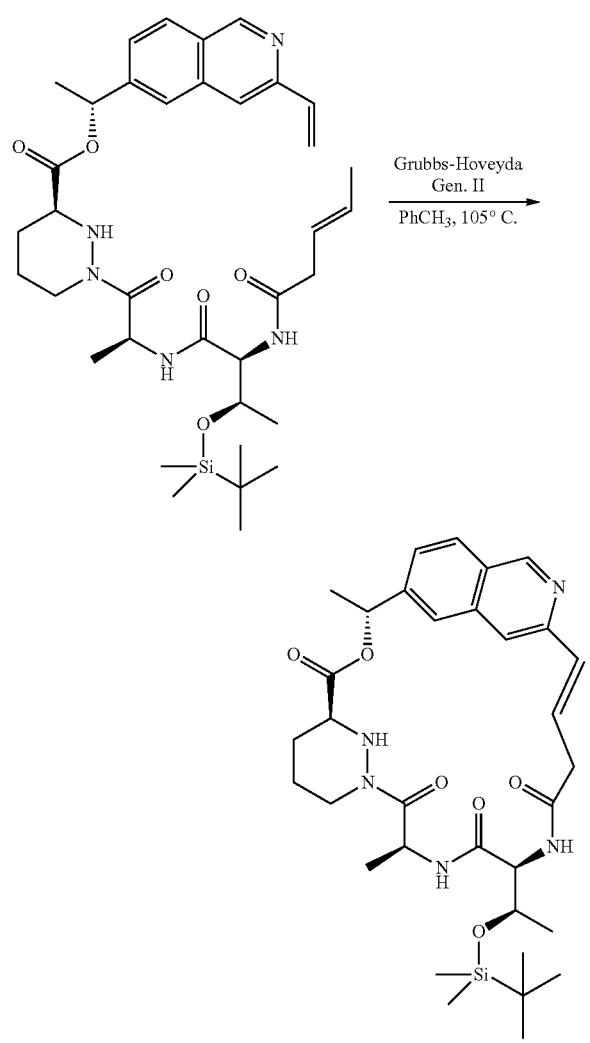

Compound 48d

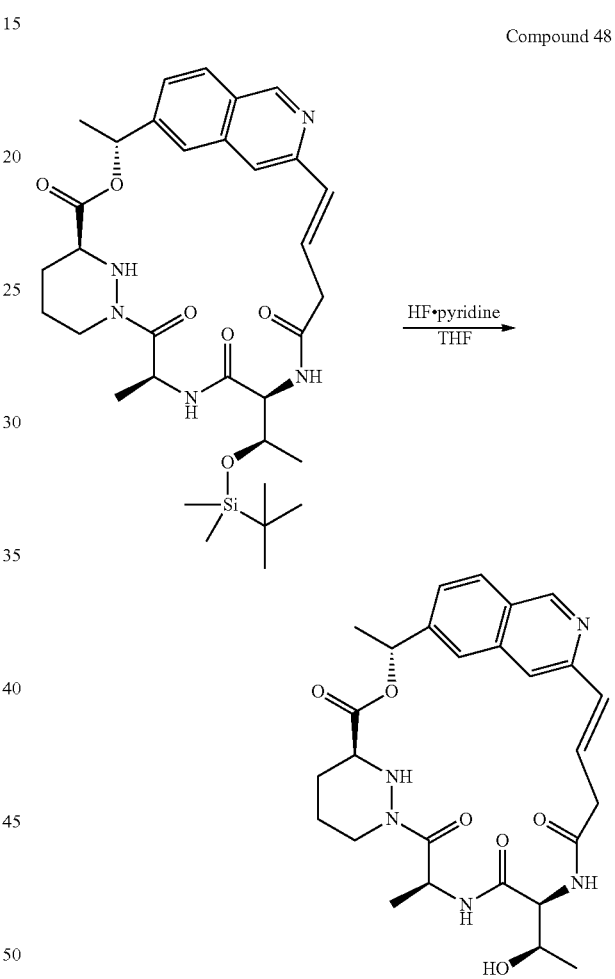

Compound 48

In a polypropylene vial under argon atmosphere, 48d (10 mg, 0.016 mmol) was dissolved in tetrahydrofuran (900 µL). HF·pyridine (~70% as HF, 100 µL) was added dropwise via syringe, and the resulting solution was stirred for 130 min. An additional aliquot of HF·pyridine (100 µL) was then added via syringe, and the resulting solution was stirred for an additional 80 min. The reaction mixture was quenched by its careful addition to a stirred mixture of ethyl acetate (50 mL) and saturated aqueous sodium bicarbonate (50 mL). The phases were separated, and the aqueous phase was extracted with ethyl acetate (2×30 mL). The combined organic phases were dried over anhydrous sodium sulfate, filtered, and concentrated to afford a crude residue that was purified by reverse phase HPLC (C18, 15 to 100% acetonitrile/water, 0.1% trifluoroacetic acid). Impure fractions from this run were repurified in the same manner to afford the title compound as the trifluoroacetic acid salt (5.0 mg, 49%) as an amorphous white solid following lyophilization. $^1$H NMR (400 MHz, CD$_3$OD) δ 9.55 (s, 1H), 8.38 (d, J=8.6 Hz, 1H), 8.22 (s, 1H), 8.15 (s, 1H), 7.87 (dd, J=8.7, 1.4 Hz, 1H), 6.86-6.75 (m, 2H), 6.15 (q, J=6.6 Hz, 1H), 5.80-5.70 (m, 1H), 4.47 (d, J=5.6 Hz, 1H), 4.45 4.38 (m, 1H), 4.09-4.01 (m, 1H), 3.83-3.78 (m, 1H), 3.55 (dd, J=13.5, 5.6 Hz, 1H), 3.11 (dd, J=13.2, 4.7 Hz, 1H), 2.78-2.67 (m, 1H), 2.09-1.99 (m, 1H), 1.96-1.89 (m, 1H), 1.82-1.64 (m, 5H), 1.60-1.54 (m, 3H), 1.25 (d, J=6.3 Hz, 3H). LCMS (m/z) 524.6 [M+H], Tr=2.15 min.

Example 49

Compound 49a

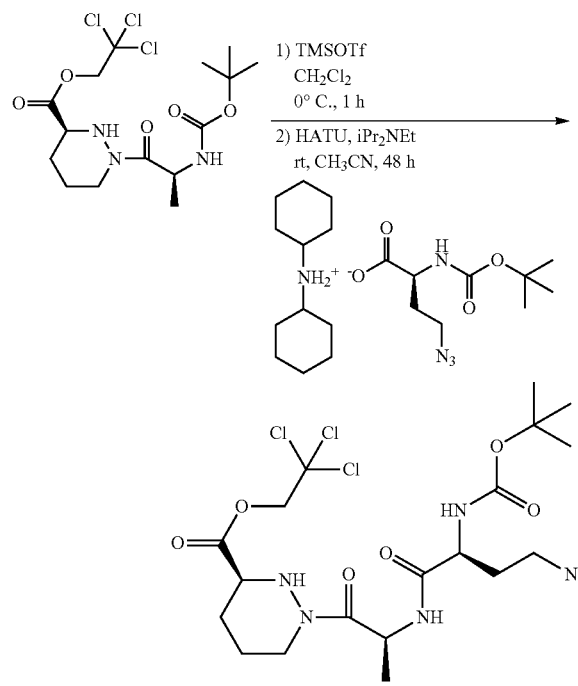

A solution of (S)-1-((S)-2-tert-butoxycarbonylamino-propionyl)-hexahydro-pyridazine-3-carboxylic acid 2,2,2-trichloro-ethyl ester (865 mg, 2 mmol) in dichloromethane (20 mL) was cooled in an ice water bath. Trimethylsilyl trifluoromethanesulfonate (667 mg, 3 mmol) was added dropwise at 0° C. under argon, and the resulting solution was stirred at RT for 30 min. The reaction mixture was evaporated to dryness and the resulting crude residue was dissolved in anhydrous acetonitrile (25 mL) under argon. The reaction mixture was stirred at 0° C., (S)-4-azido-2-(tert-butoxycarbonylamino)butanoic acid dicyclohexylamine salt (936 mg, 2.2 mmol) and N,N-diisopropylethylamine (1034 mg, 8 mmol) were added followed by 2-(1H-7-azabenzotriazol-1-yl)-1,1,3,3-tetramethyl uronium hexafluorophosphate methanaminium (1065 mg, 2.8 mmol). The reaction mixture was stirred at RT for 48 h. The solvent was evaporated, the residue was dissolved in ethyl acetate (100 mL) and the solution was washed with 20% water solution of citric acid (2×100 mL), water (100 mL) and brine (100 mL), dried over magnesium sulfate, filtered and evaporated. The residue was purified by silica gel chromatography (gradient from 0-40% ethyl acetate+methanol (4/1) in iso-hexanes) to afford the title compound (783 mg, 70%) as a white solid after evaporation. R$_f$=0.40, iso-hexanes/ethyl acetate/methanol (6/4/1).

Compound 49b

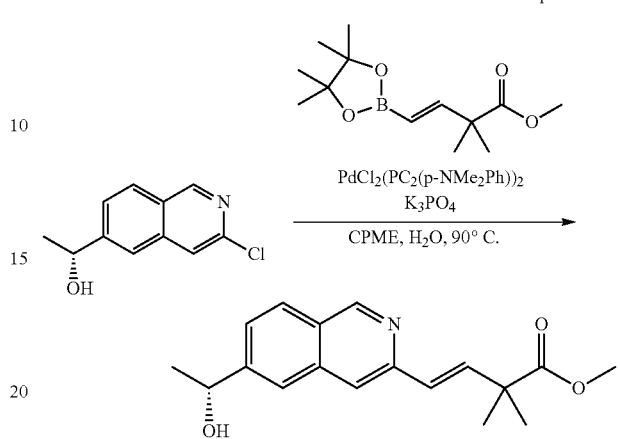

Under argon, (R)-1-(3-chloro-isoquinolin-6-yl)-ethanol (880 mg, 4.23 mmol), (E)-2,2-dimethyl-4-(4,4,5,5-tetramethyl-[1,3,2]dioxaborolan-2-yl)-but-3-enoic acid methyl ester (1.24 g, 4.88 mmol), PdCl$_2$(PCy$_2$(p-NMe$_2$Ph))$_2$(bis[(dicyclohexyl) (4-dimethylaminophenyl)phosphine]palladium (II)chloride) 173 mg, 0.21 mmol) and potassium phosphate tribasic (2.64 g, 12.4 mmol) were dissolved in cyclopentyl methyl ether (11.9 mL) and water (5.1 mL). The resulting biphasic mixture was vigorously stirred at 90° C. for 3.5 h, at which time the reaction was cooled to ambient temperature and was diluted with ethyl acetate (50 mL) and water (40 mL). The phases were separated, and the aqueous phase was extracted with ethyl acetate (2×50 mL). The combined organic phases were dried over anhydrous magnesium sulfate, filtered, and concentrated to afford a crude residue that was purified by silica gel chromatography (25 to 60% ethyl acetate in iso-hexanes) to afford the title compound (1.07 g, 85%) as a yellow oil.

Compound 49c

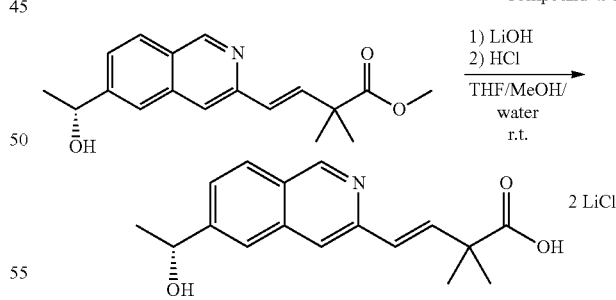

To a solution of 49b (600 mg, 2 mmol) in tetrahydrofuran (8 mL) was added methanol (4 mL), water (4 mL) and lithium hydroxide (96 mg, 4 mmol). The resulting mixture was stirred at RT for 10 h and quenched with 1 M hydrochloric acid (4.2 mL, 4.2 mmol). The resulting solution was concentrated to a crude residue which was co-distilled twice with tetrahydrofuran (20 mL), twice with anhydrous acetonitrile (20 mL) and twice with anhydrous toluene (20 mL). The resulting white solid was dried under high vacuum overnight and it was used without further purification (735 mg, quantitative yield).

Compound 49d

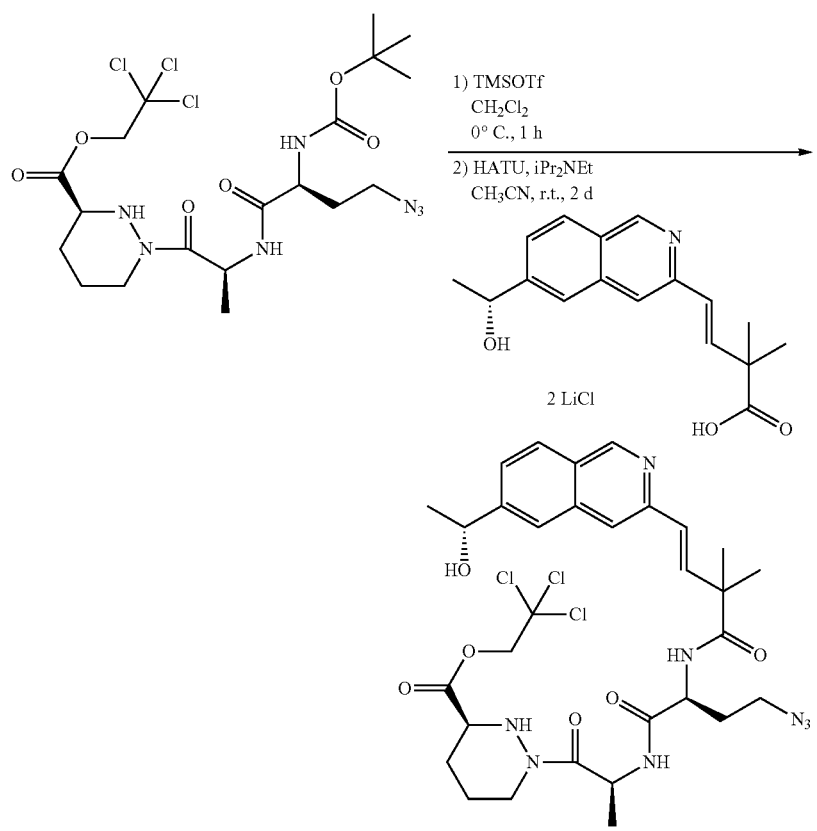

A solution of 49a (169 mg, 0.302 mmol) in dichloromethane (10 mL) was cooled in an ice water bath. Trimethylsilyl trifluoromethanesulfonate (101 mg, 0.455 mmol) was added dropwise at 0° C. under argon, and the resulting solution was stirred at RT for 30 min. The reaction mixture was evaporated to dryness and the resulting crude residue was dissolved in anhydrous acetonitrile (20 mL) under argon. Reaction mixture was stirred at 0° C., (E)-4-[6-((R)-1-hydroxy-ethyl)-isoquinolin-3-yl]-2,2-dimethyl-but-3-enoic acid (123 mg, 0.333 mmol) and N,N-diisopropylethylamine (151 mg, 1.220 mmol) were added followed by 2-(1H-7-azabenzotriazol-1-yl)-1,1,3,3-tetramethyl uronium hexafluorophosphate methanaminium (161 mg, 0.423 mmol). The reaction mixture was stirred at RT for 2 days. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-40% ethyl acetate and methanol mixture (4/1) in iso-hexanes) to afford the title compound (198 mg, 90%) as a white solid after evaporation. $R_f$=0.18, iso-hexanes/ethyl acetate/methanol (6/4/1).

Compound 49

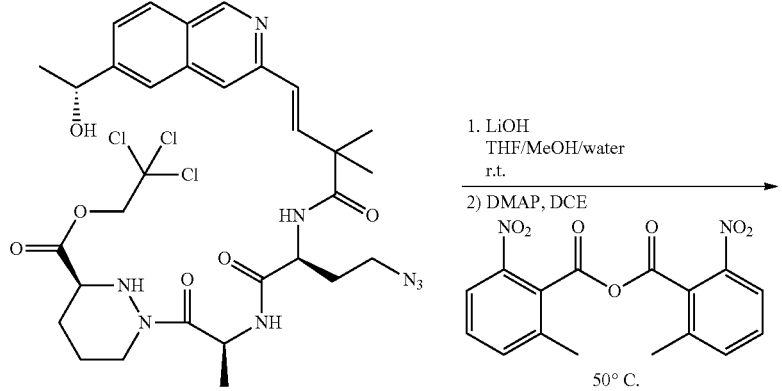

-continued

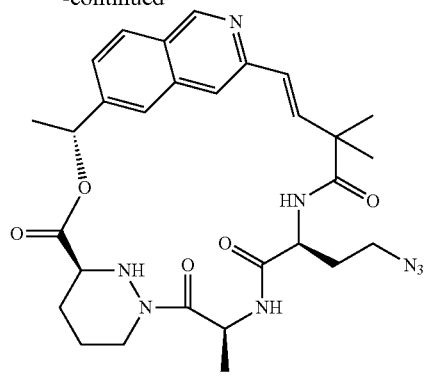

To a solution of 49d (170 mg, 0.23 mmol) in tetrahydrofuran (2 mL) was added methanol (1 mL), water (1 mL) and lithium hydroxide hydrate (7 mg, 0.28 mmol). The mixture was stirred for 2 h at ambient temperature and was quenched with aqueous 1 M hydrochloric acid (0.30 mL, 0.30 mmol). The resulting solution was concentrated to a crude residue which was co-evaporated twice with tetrahydrofuran (5 mL), twice with anhydrous acetonitrile (5 mL) and twice with anhydrous toluene (5 mL). The resulting white solid was dried under high vacuum overnight and used without further purification (151 mg, quantitative yield). Into oven-dried, argon purged flask were placed 2-methyl-6-nitrobenzoic anhydride (317 mg, 0.92 mmol), 4-dimethylaminopyridine (337 mg, 2.76 mmol) and anhydrous 1,2-dichloroethane (300 mL). The resulting solution was heated at 50° C., and the crude seco-acid was added dropwise by syringe as a solution in dry N,N-dimethylformamide (5 mL) over 12 h. An additional portion of dry N,N-dimethylformamide (2×1 ml) was used to complete the quantitative transfer. After stirring for additional 2 h at 50° C., the reaction mixture was transferred to a separatory funnel and washed with water (200 mL, 10 mL of brine was added to support the separation). The aqueous phase was extracted with dichloromethane (100 mL). Combined organic extracts were washed with brine (100 mL) and dried over magnesium sulfate, filtered and concentrated under reduced pressure. The resulting residue was dissolved in ethyl acetate (250 mL) and was washed with water (300 mL, 10 mL of brine was added to support the separation). The aqueous phase was extracted with ethyl acetate (150 mL). Combined organic extracts were washed with water (200 mL, 10 mL of brine was added to support the separation). Resulting aqueous phase was extracted with ethyl acetate (150 mL). Combined organic extracts were washed with brine (150 mL) and dried over magnesium sulfate, filtered and concentrated under reduced pressure. The residue was purified by silica gel chromatography (gradient from 0-40% ethyl acetate and methanol mixture (4/1) in iso-hexanes) to afford the title compound (76 mg, 57%) as a white solid after evaporation. $R_f$=0.51, 10% methanol in dichloromethane. $^1$H NMR (400 MHz, CD$_3$OD) δ 9.03 (s, 1H), 7.95 (d, J=8.5 Hz, 1H), 7.81 (s, 1H), 7.49 (s, 1H), 7.46 (dd, J=8.5, 1.6 Hz, 1H), 6.49 (d, J=16.1 Hz, 1H), 6.40 (d, J=16.1 Hz, 1H), 5.95 (q, J=6.6 Hz, 1H), 5.51 (q, J=7.2 Hz, 1H), 4.67 (dd, J=8.6, 6.3 Hz, 1H), 4.29 (m, 1H), 3.68 (dd, J=11.2, 2.7 Hz, 1H), 3.28 (td, J=6.8, 3.7 Hz, 2H), 2.67-2.56 (m, 1H), 1.88 (m, 2H), 1.85-1.60 (m, 4H), 1.57 (d, J=6.7 Hz, 3H), 1.54 (d, J=7.3 Hz, 3H), 1.42 (s, 3H), 1.27 (s, 3H). LCMS (m/z) 557.3 ([M+H], Tr=3.15 min.

Example 50

Compound 50

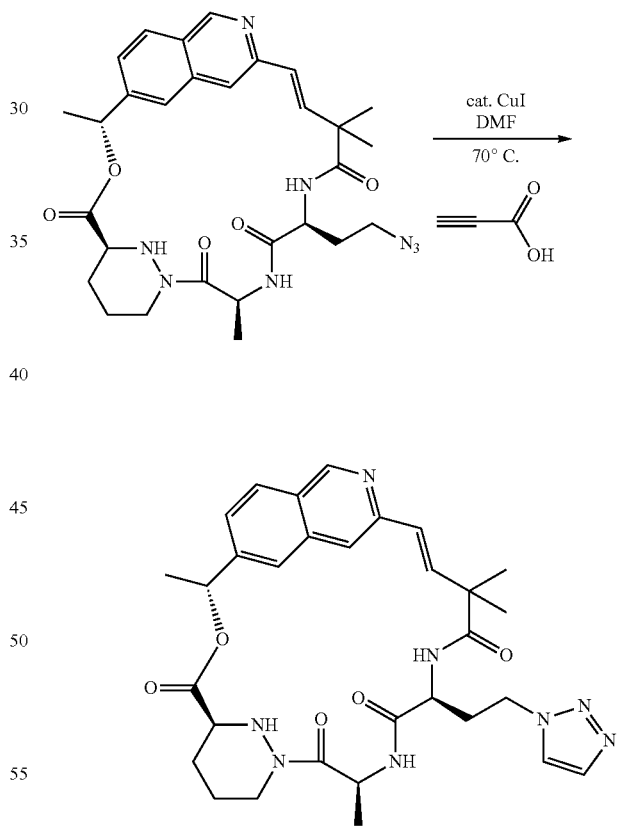

Into an oven-dried, argon purged flask, Compound 49 (20 mg, 0.034 mmol), copper(I) iodide (1 mg, 0.005 mmol) and propiolic acid (5 mg, 0.070 mmol) were added. The flask was sealed with septa and repurged with argon three times. Anhydrous N,N-dimethylformamide (5 mL) was added and the reaction mixture was repurged with argon three times. This reaction mixture was heated at 70° C. for 2 days. After evaporation of the solvent under reduced pressure, the crude residue was dissolved in ethyl acetate (10 mL) and filtered through Celite and the filter pad was washed with ethyl acetate (10 mL). After concentration under reduced pressure, the residue was purified by silica gel chromatography (gradient from 0-40% ethyl acetate and methanol mixture (4/1) in iso-hexanes) to afford the title compound (7 mg, 34%) as a white solid. $R_f$=0.36, 5% methanol in dichloromethane. $^1$H NMR (400 MHz, CD$_3$OD): δ 9.05 (s, 1H), 8.11 (br s, 1H), 8.00 (br s, 1H), 7.95 (d, J=8.8 Hz, 1H), 7.82 (s, 1H), 7.66 (s, 1H), 7.48 (d, J=10.0 Hz, 1H), 6.50 (d, J=16.2 Hz, 1H), 6.42 (d, J=16.2 Hz, 1H), 5.97 (m, 1H), 5.56 (m, 1H), 4.60 (m, 1H), 4.29 (m, 1H), 3.66 (m, 1H), 3.21 (m, 2H), 2.69-2.47 (m, 1H), 1.89 (m, 2H), 1.87-1.55 (m, 4H), 1.53 (d, J=6.7 Hz, 3H), 1.50 (d, J=7.1 Hz, 3H), 1.40 (s, 3H), 1.28 (s, 3H). LCMS (m/z) 603.1 [M+H]$^+$ Tr=2.62 min.

Example 51

Compound 51a

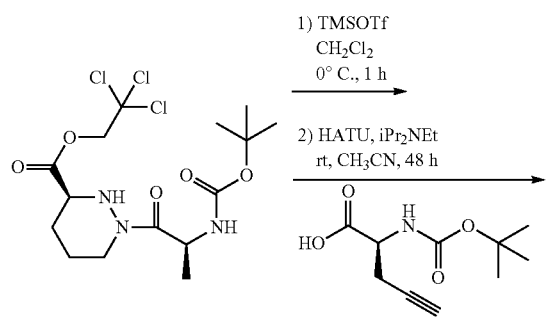

-continued

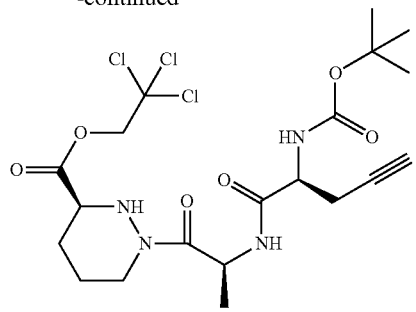

A solution of (S)-1-((S)-2-tert-butoxycarbonylamino-propionyl)-hexahydro-pyridazine-3-carboxylic acid 2,2,2-trichloro-ethyl ester (865 mg, 2 mmol) in dichloromethane (20 mL) was cooled in an ice water bath. Trimethylsilyl trifluoromethanesulfonate (667 mg, 3 mmol) was added dropwise at 0° C. under argon, and the resulting solution was stirred at RT for 30 min. The reaction mixture was evaporated to dryness and the resulting crude residue was dissolved in anhydrous acetonitrile (25 mL) under argon. Reaction mixture was stirred at 0° C., (S)-2-(tert-butoxycarbonylamino) pent-4-ynoic acid (469 mg, 2.2 mmol, source: Matrix Scientific, Catalog Number 041479) and N,N-diisopropylethylamine (1034 mg, 8 mmol) were added followed by 2-(1H-7-azabenzotriazol-1-yl)-1,1,3,3-tetramethyl uronium hexafluorophosphate methanaminium (1065 mg, 2.8 mmol). Reaction mixture was stirred at RT for 48 h. The solvent was evaporated, the residue was dissolved in ethyl acetate (100 mL) and the solution was washed with 20% water solution of citric acid (2×100 mL), water (100 mL) and brine (100 mL), dried over magnesium sulfate, filtered and evaporated. The residue was purified by silica gel chromatography (gradient from 0-40% ethyl acetate and methanol (4/1) in iso-hexanes) to afford the title compound (738 mg, 70%) as a white solid after evaporation. $R_f$=0.30, iso-hexanes/ethyl acetate/methanol (6/4/1).

Compound 51b

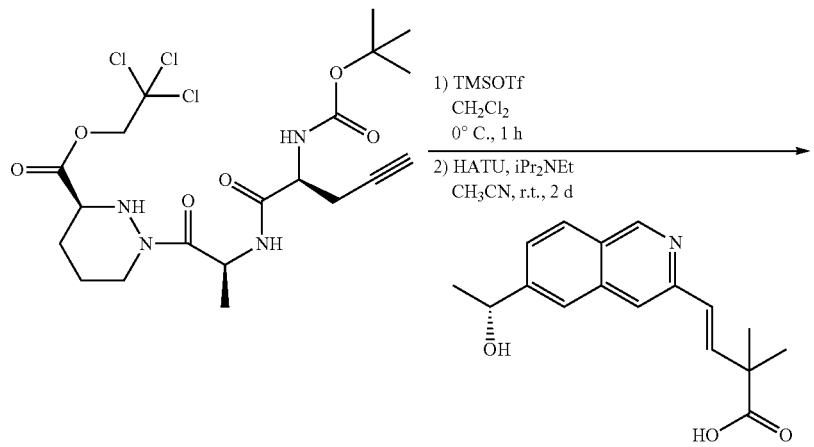

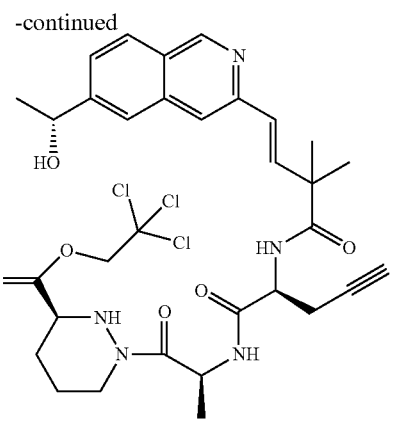

A solution of 51a (145 mg, 0.275 mmol) in dichloromethane (10 mL) was cooled in an ice water bath. Trimethylsilyl trifluoromethanesulfonate (92 mg, 0.414 mmol) was added dropwise at 0° C. under argon, and the resulting solution was stirred at RT for 30 min. The reaction mixture was evaporated to dryness and the resulting crude residue was dissolved in anhydrous acetonitrile (20 mL) under argon. The reaction mixture was stirred at 0° C., (E)-4-[6-((R)-1-hydroxy-ethyl)-isoquinolin-3-yl]-2,2-dimethyl-but-3-enoic acid (112 mg, 0.303 mmol) and N,N-diisopropylethylamine (137 mg, 1.101 mmol) were added followed by 2-(1H-7-azabenzotriazol-1-yl)-1,1,3,3-tetramethyl uronium hexafluorophosphate methanaminium (147 mg, 0.385 mmol). The reaction mixture was stirred at RT for 2 days. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-40% ethyl acetate and methanol (4/1) in iso-hexanes) to afford the title compound (163 mg, 85%) as a white solid after evaporation. $R_f$=0.29, iso-hexanes/ethyl acetate/methanol (6/4/1).

Compound 51

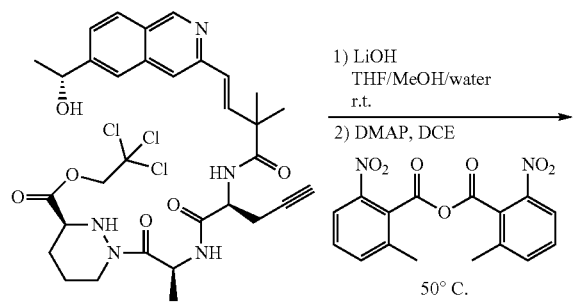

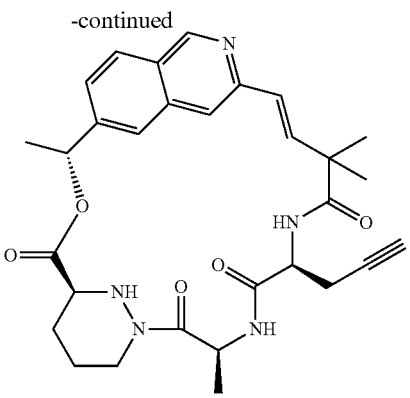

To a solution of 51b (125 mg, 0.18 mmol) in tetrahydrofuran (2 mL) was added methanol (1 mL), water (1 mL) and lithium hydroxide hydrate (5.2 mg, 0.22 mmol). The mixture was stirred for 2 h at ambient temperature and was quenched with aqueous 1 M hydrochloric acid (0.25 mL, 0.25 mmol). The resulting solution was concentrated to a crude residue which was co-evaporated twice with tetrahydrofuran (5 mL), twice with anhydrous acetonitrile (5 mL) and twice with anhydrous toluene (5 mL). The resulting white solid was dried under high vacuum overnight and it was used without further purification (113 mg, quantitative yield). Into an oven-dried, argon purged flask were placed 2-methyl-6-nitrobenzoic anhydride (248 mg, 0.72 mmol), 4-dimethylaminopyridine (264 mg, 2.16 mmol) and anhydrous 1,2-dichloroethane (200 mL). The resulting solution was heated at 50° C., and the crude seco-acid was added dropwise via syringe as a solution in anhydrous N,N-dimethylformamide (5 mL) over 12 h. An additional portion of anhydrous N,N-dimethylformamide (2×1 ml) was used to complete the quantitative transfer. After stirring for additional 2 h at 50° C., the reaction mixture was transferred to a separatory funnel and washed with water (200 mL, 10 mL of brine was added to support the separation). The aqueous phase was extracted with dichloromethane (100 mL). Combined organic extracts were washed with brine (100 mL) and dried over magnesium sulfate, filtered and concentrated under reduced pressure. The resulting residue was dissolved in ethyl acetate (250 mL) and was washed with water (300 mL, 10 mL of brine was added to support the separation). The aqueous phase was extracted with ethyl acetate (150 mL). Combined organic extracts were washed with water (200 mL, 10 mL of brine was added to support the separation). Resulting aqueous phase was extracted with ethyl acetate (150 mL). Combined organic extracts were washed with brine (150 mL) and dried over magnesium sulfate, filtered and concentrated under reduced pressure. The residue was purified by silica gel chromatography (gradient from 0-40% ethyl acetate+methanol (4/1) in iso-hexanes) to afford the title compound (56 mg, 57%) as a white solid after evaporation. $R_f$=0.53, 10% methanol in dichloromethane. $^1$H NMR (400 MHz, CD$_3$OD) δ 9.03 1H), 7.94 (d, J=8.5 Hz, 1H), 7.79 (s, 1H), 7.54 (s, 1H), 7.45 (d, J=8.5 Hz, 1H), 6.52 (d, J=16.1 Hz, 1H), 6.40 (d, J=16.1 Hz, 1H), 5.95 (q, J=6.6 Hz, 1H), 5.52 (q, J=7.2 Hz, 1H), 4.70 (dd, J=7.7, 6.7 Hz, 1H), 4.30 (m, 1H), 4.00 (q, J=7.2 Hz, 1H), 3.72-3.64 (m, 1H), 2.63 (m, 2.55-2.40 (m, 2H), 1.91 (s, 1H), 1.88 (m, 1H), 1.80 (m, 1H), 1.64 (m, 1H), 1.57 (d, J=6.7 Hz, 3H), 1.53 (d, J=7.2 Hz, 3H), 1.42 (s, 3H), 1.27 (s, 3H). LCMS (m/z) 546.2 [M+H]' Tr=3.04 min.

Example 52

Compound 52

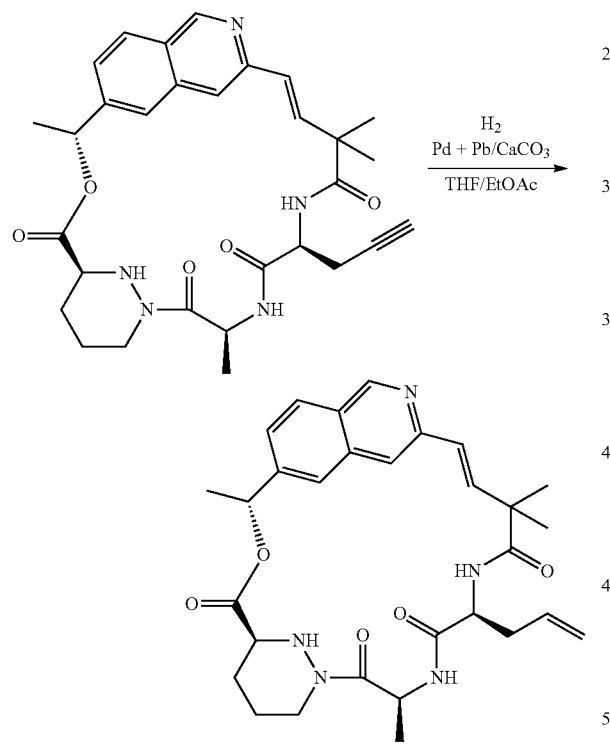

A solution of Compound 51 (10 mg, 0.018 mmol) in a mixture of ethyl acetate (4 mL) and tetrahydrofuran (4 mL) containing 5% palladium on calcium carbonate poisoned with lead-Lindlar catalyst (10 mg) was hydrogenated at RT and pressure of hydrogen for 3 h. The reaction mixture was filtered through Celite and the filter pad was washed with tetrahydrofuran (10 mL). The filtrate was evaporated to afford the title compound (10 mg, quantitative yield) as a white solid. $R_f$=0.19, iso-hexanes/ethyl acetate/methanol (6/4/1). $^1$H NMR (400 MHz, CD$_3$OD): δ 9.04 (s, 1H), 7.95 (d, J=8.4 Hz, 1H), 7.82 (s, 1H), 7.54 (s, 1H), 7.46 (d, J=8.3 Hz, 1H), 6.50 (d, J=16.1 Hz, 1H), 6.39 (d, J=16.1 Hz, 1H), 5.95 (q, J=6.4 Hz, 1H), 5.76-5.62 (m, 1H), 5.57 (q, J=7.0 Hz, 1H), 5.02 (d, J=17.0 Hz, 1H), 4.96 (d, J=10.1 Hz, 1H), 4.61-4.54 (m, 1H), 4.29 (m, 1H), 3.68n (m, 1H), 2.61 (m, 1H), 2.42-2.34 (m, 1H), 2.30-2.20 (m, 1H), 1.90 (m, 1H), 1.81 (m, 1H), 1.68-1.60 (m, 2H), 1.57 (d, J=6.6 Hz, 3H), 1.53 (d, J=7.2 Hz, 3H), 1.39 (s, 3H), 1.26 (s, 3H). LCMS (m/z) 548.3 [M+H]' Tr=2.85 min.

Example 53

Compound 53a

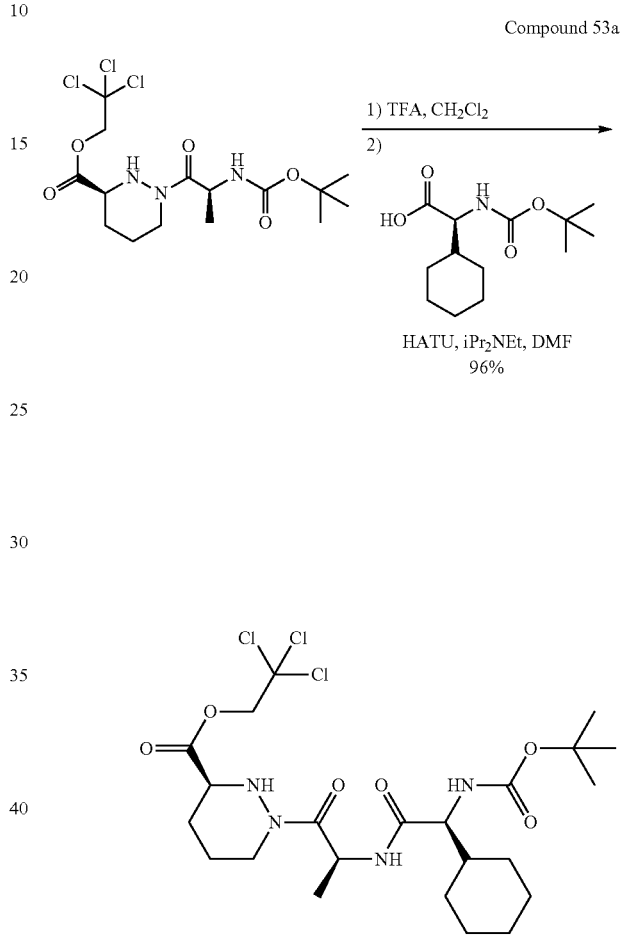

To a solution of (S)-1-((S)-2-tert-butoxycarbonylamino-propionyl)-hexahydro-pyridazine-3-carboxylic acid 2,2,2-trichloro-ethyl ester (300 mg, 0.69 mmol) in dichloromethane (1.84 mL) was slowly added trifluoroacetic acid (460 µL, 6.00 mmol) at 0° C. under an argon atmosphere. After 3 h, the reaction mixture was concentrated under reduced pressure. The crude residue was dissolved in N,N-dimethylformamide (3.45 mL) and (S)-tert-Butoxycarbonylamino-cyclohexyl-acetic acid (195 mg, 0.760 mmol), 2-(1H-7-azabenzotriazol-1-yl)-1,1,3,3-tetramethyl uronium hexafluorophosphate methanaminium (289 mg, 0.760 mmol), and N,N-diisopropylethylamine (180 µL, 1.04 mmol) were sequentially added at 23° C. under an argon atmosphere. After 18 h, the reaction mixture was diluted with ethyl acetate (300 mL), and the resulting mixture was washed with brine (4×100 mL), was dried over anhydrous sodium and was concentrated under reduced pressure. The crude residue was purified by silica gel chromatography (12 g Combiflash HP Gold Column, 0-100% ethyl acetate/iso-hexanes gradient) to afford the title compound (380 mg, 96%) as a colorless oil.

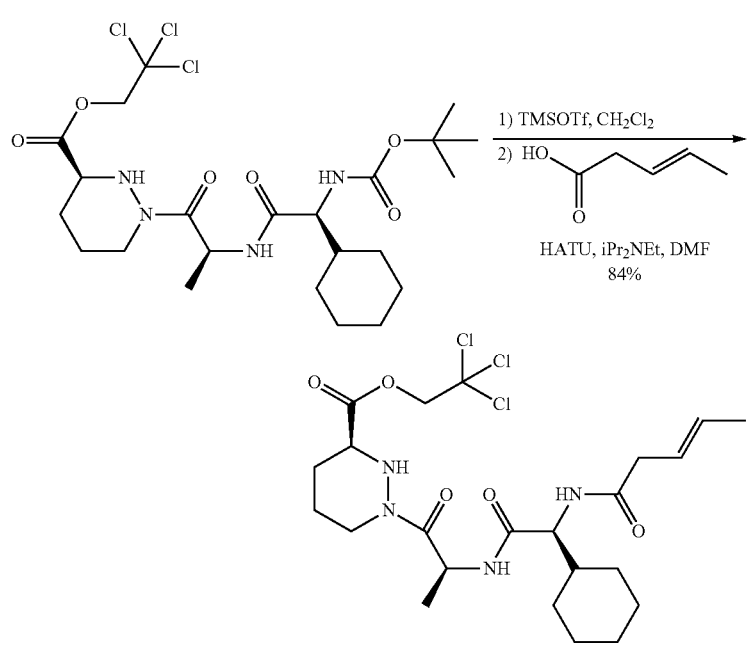

Compound 53b

To a solution of 53a (220 mg, 0.385 mmol) in dichloromethane (1.92 mL) was added trimethylsilyl trifluoromethanesulfonate (128 mg, 0.587 mmol) at 0° C. under an argon atmosphere. After 1.5 h, the reaction mixture was concentrated under reduced pressure. The resulting residue was diluted with acetonitrile (1.92 mL) and 2-(1H-7-azabenzotriazol-1-yl)-1,1,3,3-tetramethyl uronium hexafluorophosphate methanaminium (146 mg, 0.385 mmol), N,N-diisopropylethylamine (267 µL, 1.54 mmol), and (E)-pent-3-enoic acid (39.4 µL, 0.385 mmol) were sequentially added at 23° C. under an argon atmosphere. After 20 h, the reaction mixture was diluted with dichloromethane (40 mL) and the resulting mixture was washed with saturated aqueous sodium bicarbonate solution (40 mL) and with brine (2×40 mL). The organic layer was separated, was dried over anhydrous sodium sulfate, and was concentrated under reduced pressure. The crude residue was purified by silica gel flash column chromatography (12 g Combiflash HP Gold Column, 0-100% ethyl acetate/iso-hexanes gradient) to afford the title compound (180 mg, 84%) as a colorless oil. $R_f$=0.75 (ethyl acetate) $I_2$/silica stain.

Compound 53c

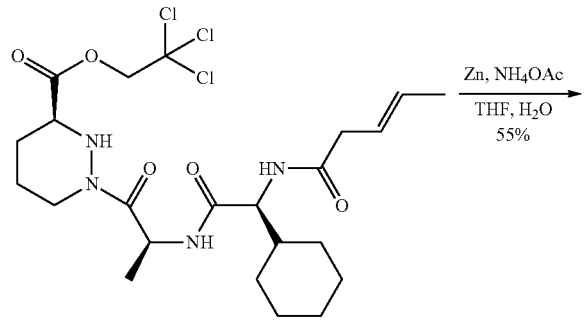

-continued

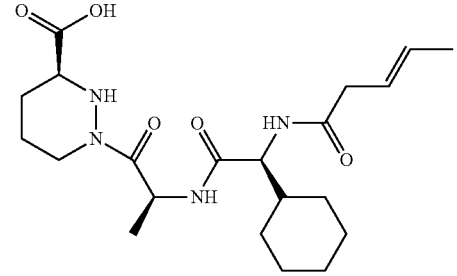

To a solution of 53b (180 mg, 0.320 mmol) in tetrahydrofuran (5.3 mL) was added zinc powder (418 mg, 6.40 mmol) followed by a solution of ammonium acetate (370 mg, 4.80 mmol) in water (3.5 mL) at 23° C. under an argon atmosphere. After 15 h, the reaction mixture was warmed to 45° C. After 2 h, the reaction mixture was allowed to cool to RT and was filtered through a pad of Celite washing with water (10 mL) and ethyl acetate (10 mL). The filtrate layers were split and the aqueous layer was diluted with brine (80 mL) and was acidified to pH 1 with 12 N aqueous hydrogen chloride solution. The aqueous layer was extracted with ethyl acetate (3×100 mL), and the combined organic extracts were dried over anhydrous sodium sulfate, and were concentrated under reduced pressure. Residual acetic acid was removed azeotropically via addition of toluene (5 mL) followed by concentration under reduced pressure (3×) to afford the title compound (74.5 mg, 55%) as a white solid.

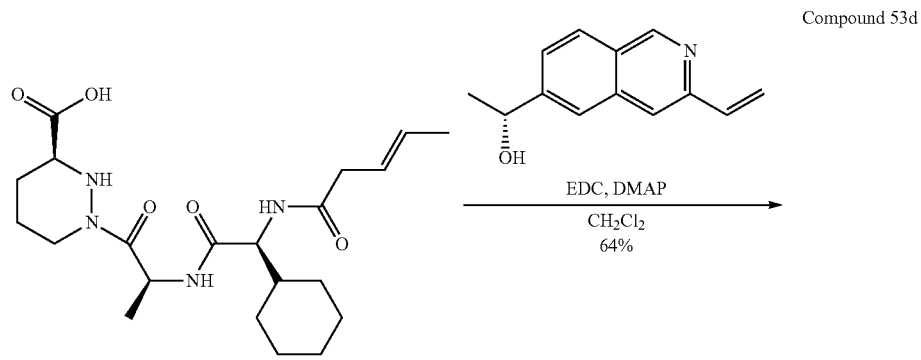

Compound 53d

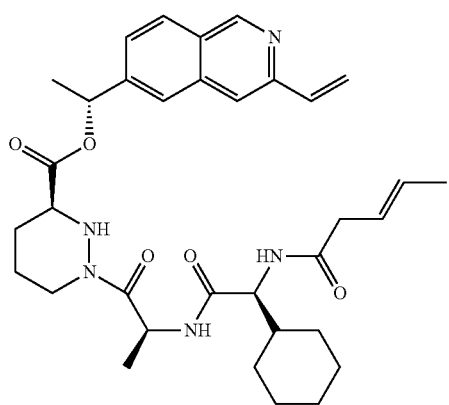

To a solution of 53c (74.5 mg, 0.176 mmol) and (R)-1-(3-vinyl-isoquinolin-6-yl)-ethanol (42.1 mg, 0.212 mmol) in dichloromethane (3.5 mL) were added N-(3-dimethylamino-propyl)-N'-ethylcarbodiimide hydrochloride (47.2 mg, 0.246 mmol) and 4-dimethylaminopyridine (11 mg, 88 μmol) at 23° C. under an argon atmosphere. After 18 h, the reaction mixture was purified directly by silica gel chromatography (12 g Combiflash HP Gold Column, 0-100% ethyl acetate/iso-hexanes gradient) to afford the title compound (67.6 mg, 64%) as a white solid.

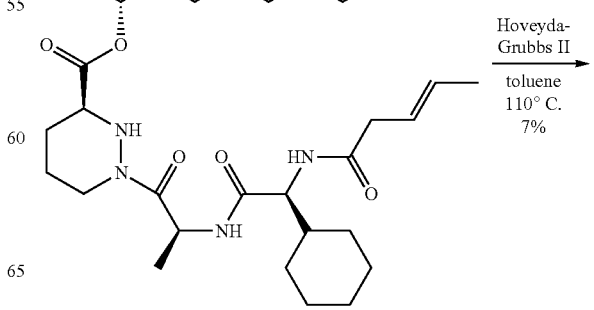

Compound 53

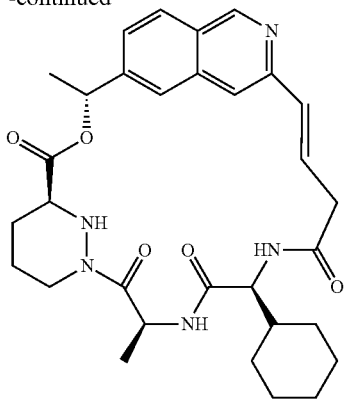

To a solution of 53d (25 mg, 41 μmol) in toluene (8.2 mL) was added the Hoveyda-Grubbs 2$^{nd}$ Generation catalyst (2.5 mg, 4.1 μmol) at 23° C. under an argon atmosphere, and the resulting mixture was heated to 110° C. After 2 h, the reaction mixture was quenched with ethyl vinyl ether (300 μL) and the resulting mixture was allowed to cool to 23° C. The reaction mixture was concentrated under reduced pressure and the crude residue was purified by silica gel chromatography (12 g Combiflash HP Gold Column, 0-100% ethyl acetate/iso-hexanes gradient). The fractions containing the desired product were combined and were repurified by preparatory HPLC to afford the title compound (1.7 mg, 7%) as a white powder as a trifluoroacetic acid salt. R$_f$=0.40 (ethyl acetate) UV. $^1$H NMR (400 MHz, CD$_3$OD) δ 9.13 (s, 1H), 8.53 (br s, 1H), 8.07 (d, J=7.6 Hz, 1H), 8.05 (d, J=8.5 Hz, 1H), 7.83 (s, 1H), 7.55 (d, J=8.3 Hz, 1H), 7.44 (s, 1H), 6.62 (d, J=16.3 Hz, 1H), 6.55-6.45 (m, 1H), 6.04 (q, J=6.5 Hz, 1H), 5.50 (q, J=6.9 Hz, 1H), 4.40 (d, J=14.1 Hz, 1H), 4.33 (d, J=9.7 Hz, 1H), 3.78 (d, J=11.0 Hz, 1H), 3.36 (app dd, J=14.7, 6.7 Hz, 1H), 2.99 (dd, J=14.5, 4.9 Hz, 1H), 2.90-2.66 (m, 4H), 2.02-1.83 (m, 4H), 1.82-1.70 (m, 3H), 1.68 (d, J=6.7 Hz, 3H), 1.65 (d, J=7.3 Hz, 3H), 1.33-1.16 (m, 4H), 1.16-0.94 (m, 2H). HPLC Tr=t$_R$ (min), 3.091 (Synergi 4u hydro-RP, 50×4.60 mm 4 micron column, 7 min, 2 ml/min, 5-100% acetonitrile/water, 0.05% trifluoroacetic acid modifier gradient). LCMS (m/z) 562.3 [M+H], Tr=2.17 min.

Example 54

Compound 54a

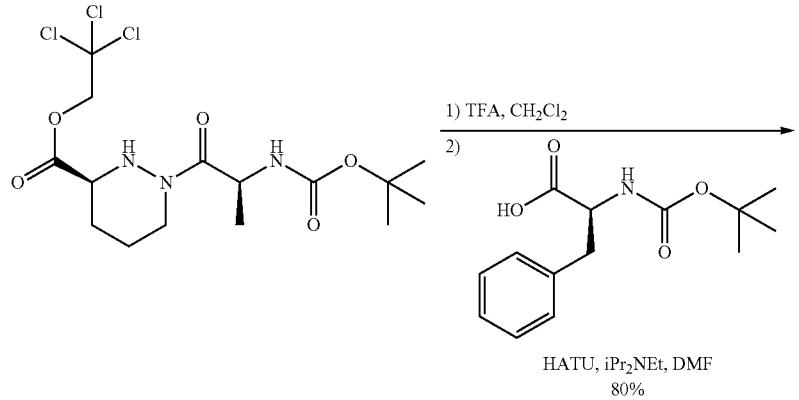

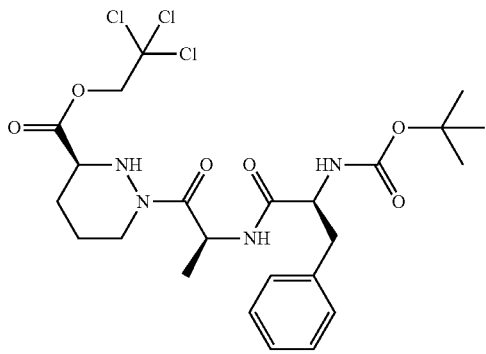

To a solution of (S)-1-((S)-2-tert-butoxycarbonylamino-propionyl)-hexahydro-pyridazine-3-carboxylic acid 2,2,2-trichloro-ethyl ester (300 mg, 0.69 mmol) in dichloromethane (1.84 mL) was slowly added trifluoroacetic acid (460 μL, 6.00 mmol) at 0° C. under an argon atmosphere. After 2 h, the reaction mixture was concentrated under reduced pressure. The crude residue was dissolved in N,N-dimethylformamide (3.45 mL) and (S)-2-tert-Butoxycarbonylamino-3-phenyl-propionic acid (201 mg, 0.760 mmol), 2-(1H-7-azabenzotriazol-1-yl)-1,1,3,3-tetramethyl uronium hexafluorophosphate methanaminium (289 mg, 0.760 mmol), and N,N-diisopropylethylamine (180 μL, 1.04 mmol) were sequentially added at 23° C. under an argon atmosphere. After 22 h, the reaction mixture was diluted with ethyl acetate (300 mL), and the resulting mixture was washed with brine (3×200 mL), was dried over anhydrous sodium and was concentrated under reduced pressure. The crude residue was purified by silica gel chromatography (24 g Combiflash HP Gold Column, 0-100% ethyl acetate/iso-hexanes gradient) to afford the title compound (319 mg, 96%) as a colorless oil. $R_f$=0.75 (ethyl acetate) $I_2$/silica stain.

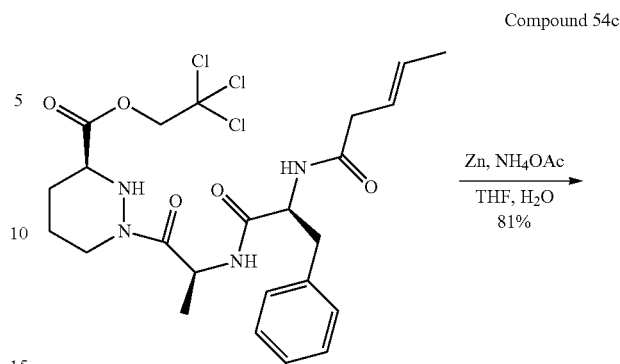

Compound 54c

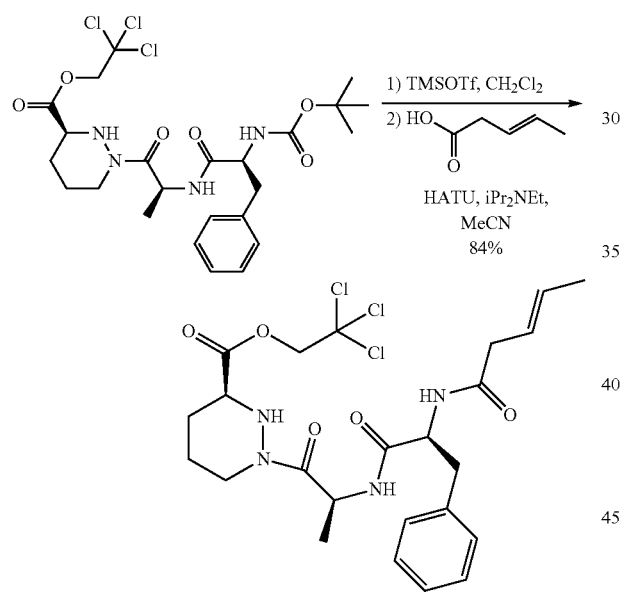

Compound 54b

To a solution of 54a (414 mg, 0.716 mmol) in dichloromethane (3.58 mL) was added trimethylsilyl trifluoromethanesulfonate (238.7 mg, 1.07 mmol) at 0° C. under an argon atmosphere. After 1 h, the reaction mixture was concentrated under reduced pressure. The resulting residue was diluted with acetonitrile (3.58 mL) and 2-(1H-7-azabenzotriazol-1-yl)-1,1,3,3-tetramethyl uronium hexafluorophosphate methanaminium (272 mg, 0.716 mmol), N,N-diisopropylethylamine (498 μL, 2.86 mmol), and (E)-pent-3-enoic acid (73.3 μL, 0.716 mmol) were sequentially added at 23° C. under an argon atmosphere. After 17 h, the reaction mixture was diluted with dichloromethane (50 mL) and the resulting mixture was washed with saturated aqueous sodium bicarbonate solution (50 mL). The organic layer was separated, was dried over anhydrous sodium sulfate, and was concentrated under reduced pressure. The crude residue was purified by silica gel chromatography to afford the title compound (386 mg, 96%) as white solid.

To a solution of 54b (443 mg, 0.789 mmol) in tetrahydrofuran (13.2 mL) was added zinc powder (1.03 g, 15.8 mmol) followed by a solution of ammonium acetate (912 mg, 11.8 mmol) in water (8.77 mL) at 23° C. under an argon atmosphere. After 17 h, the reaction mixture was warmed to 45° C. After 2 h, the reaction mixture was allowed to cool to RT and was filtered through a pad of Celite washing with water (10 mL) and ethyl acetate (10 mL). The filtrate layers were split and the aqueous layer was diluted with brine (20 mL) and was acidified to pH 2 with 12 N aqueous hydrogen chloride solution. The aqueous layer was extracted with dichloromethane (3×100 mL), and the combined organic extracts were dried over anhydrous sodium sulfate, and were concentrated under reduced pressure. Residual acetic acid was removed azeotropically via addition of toluene (5 mL) followed by concentration under reduced pressure (3×) to afford the title compound (276.2 mg, 81%) as a white solid.

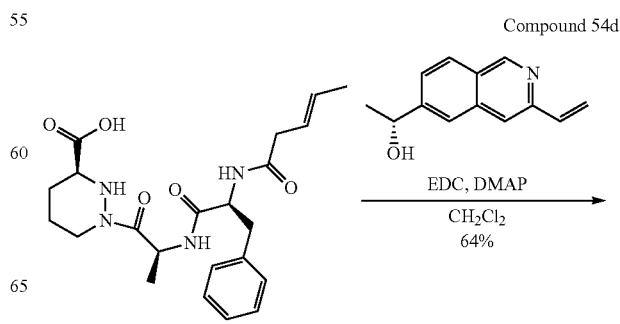

Compound 54d

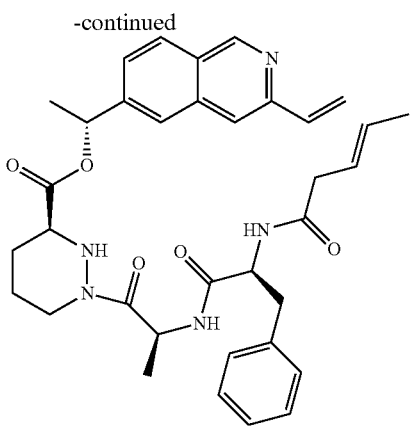

To a solution of 54c (275 mg, 0.640 mmol) and (R)-1-(3-vinyl-isoquinolin-6-yl)-ethanol (153 mg, 0.770 mmol) in dichloromethane (3.2 mL) were added N-(3-dimethylaminopropyl)-N'-ethylcarbodiimide hydrochloride (172 mg, 0.90 mmol) and 4-dimethylaminopyridine (39 mg, 32 µmol) at 23° C. under an argon atmosphere. After 23 h, the reaction mixture was purified directly by silica gel chromatography (24 g Combiflash HP Gold Column, 0-100% ethyl acetate/iso-hexanes gradient) to afford the title compound (203 mg, 52%) as a white solid.

Compound 54

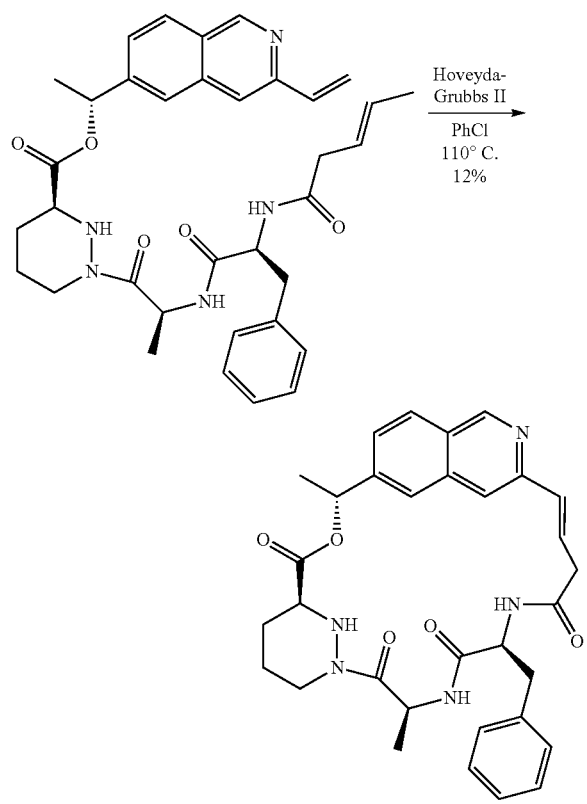

To a solution of 54d (170 mg, 278 µmol) in chlorobenzene (56 mL) was added the Hoveyda-Grubbs 2$^{nd}$ Generation catalyst (8.7 mg, 14.0 µmol) at 23° C. under an argon atmosphere, and the resulting mixture was heated to 110° C. After 3 h, the reaction mixture was quenched with ethyl vinyl ether (300 µL) and the resulting mixture was allowed to cool to 23° C. The reaction mixture was concentrated under reduced pressure and the crude residue was purified by silica gel chromatography (12 g Combiflash HP Gold Column, 0-100% ethyl acetate/iso-hexanes gradient) to afford the title compound (18.9 mg, 12%) as a tan solid. $R_f$=0.25 (ethyl acetate) UV. $^1$H NMR (400 MHz, CD$_3$OD) δ 9.12 (s, 1H), 8.05 (d, J=8.7 Hz, 1H), 7.84 (s, 1H), 7.56 (d, J=8.5 Hz, 1H), 7.53 (s, 1H), 7.32-7.12 (m, 5H), 6.66 (d, J=16.5 Hz, 1H), 6.48 (dt, J=12.8, 5.6 Hz, 1H), 6.05 (q, J=6.4 Hz, 1H), 5.53 (q, J=6.7 Hz, 1H), 4.73 (d, J=12.2 Hz, 1H), 4.43 (d, J=11.9 Hz, 1H), 3.80 (app t, J=10.2 Hz, 1H), 3.30-3.22 (m, 1H), 3.09 (dd, J=14.5, 4.9 Hz, 1H), 2.96-2.69 (m, 3H), 2.04-1.87 (m, 2H), 1.82-1.56 (m, 2H), 1.68 (d, J=6.5 Hz, 3H), 1.64 (d, J=6.9 Hz, 3H). HPLC Tr=3.060 min. LCMS (m/z) 570.5 [M+H], Tr=2.14 min.

Example 55

Compound 55a

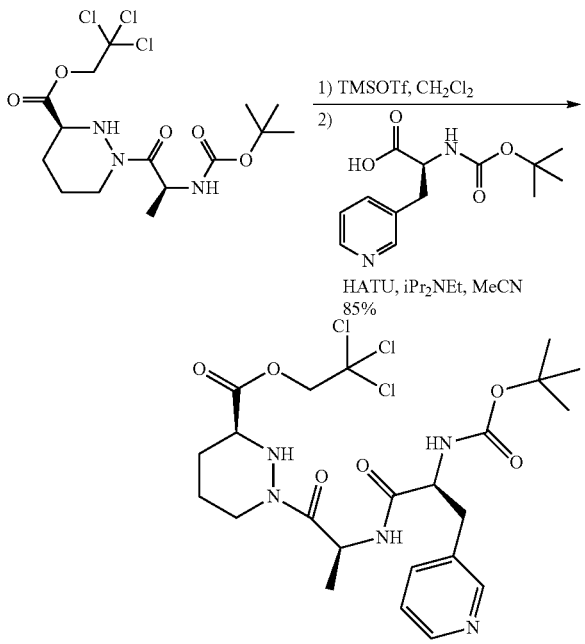

To a solution of (S)-1-((S)-2-tert-butoxycarbonylaminopropionyl)-hexahydro-pyridazine-3-carboxylic acid 2,2,2-trichloro-ethyl ester (500 mg, 0.1.16 mmol) in dichloromethane (5.8 mL) was added trimethylsilyl trifluoromethanesulfonate (386 mg, 1.74 mmol) at 0° C. under an argon atmosphere. After 1 h, the reaction mixture was concentrated under reduced pressure. The resulting residue was diluted with acetonitrile (5.8 mL) and 2-(1H-7-azabenzotriazol-1-yl)-1,1,3,3-tetramethyl uronium hexafluorophosphate methanaminium (485 mg, 1.28 mmol), N,N-diisopropylethylamine (302 µL, 1.74 mmol), N-tert-butoxycarbnyl-3-(3-pyridyl)-L-alanine (337 mg, 1.27 mmol) were sequentially added at 23° C. under an argon atmosphere. After 20 h, the reaction mixture was concentrated under reduced pressure, and the crude residue was purified by silica gel chromatography (40 g Combiflash HP Gold Column, 0-100% ethyl acetate/iso-hexanes gradient) to afford the title compound (570 mg, 85%) as light yellow oil.

Compound 55b

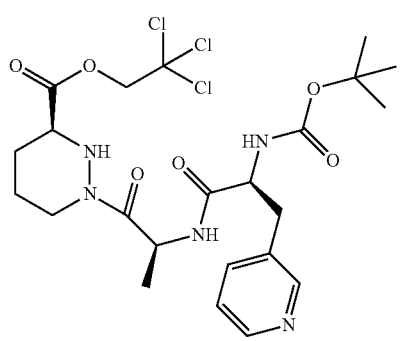

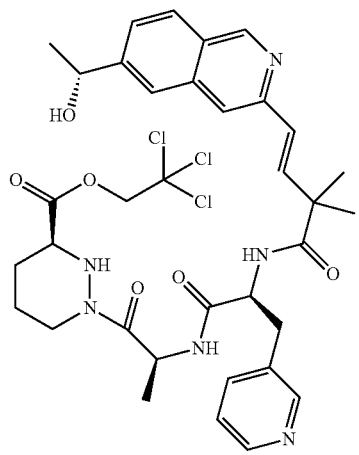

To a solution of 55b (120 mg, 0.250 mmol) in acetonitrile (1.25 mL) were sequentially added (E)-4-[6-((R)-1-hydroxyethyl)-isoquinolin-3-yl]-2,2-dimethyl-but-3-enoic acid (75 mg, 0.25 mmol), 2-(1H-7-azabenzotriazol-1-yl)-1,1,3,3-tetramethyl uronium hexafluorophosphate methanaminium (95 mg, 0.25 mmol), and N,N-diisopropylethylamine (173 µL, 1.00 mmol) at 23° C. under an argon atmosphere. N,N-Dimethylformamide (100 µL) was then added to promote solubility of the reagents. After 23 h, the reaction mixture was diluted with saturated aqueous sodium bicarbonate solution (25 mL) and brine (25 mL) and the resulting mixture was extracted with dichloromethane (2×25 mL). The combined organic extracts were dried over anhydrous sodium sulfate and were concentrated under reduced pressure. The crude residue was purified by silica gel chromatography to afford the title compound (76 mg, 41%) as a colorless solid.

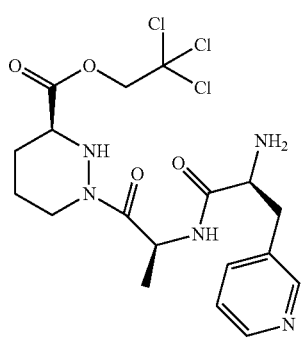

To a solution of 55a (570 mg, 0.984 mmol) in dichloromethane (5.8 mL) was added trimethylsilyl trifluoromethanesulfonate (386 mg, 1.74 mmol) at 0° C. under an argon atmosphere. After 1 h, the reaction mixture was concentrated under reduced pressure to afford the title compound (478 mg) as light yellow oil which was used without further purification.

Compound 55c

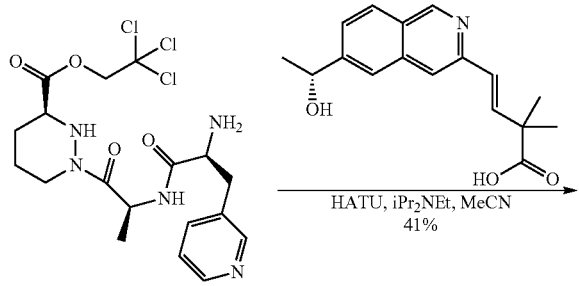

Compound 55d

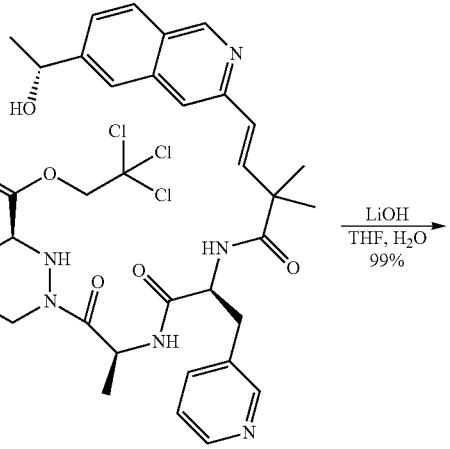

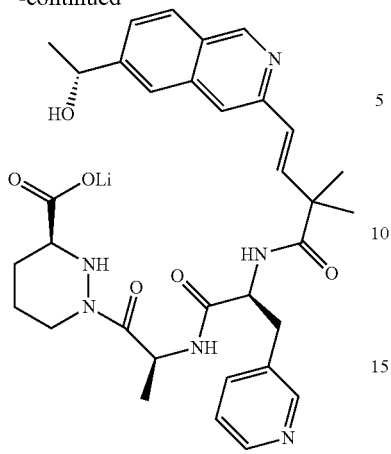

To a solution of 55c (76 mg, 0.10 mmol) in tetrahydrofuran (0.3 mL) and water (0.2 mL) was added lithium hydroxide hydrate (2.4 mg, 0.10 mmol) at 23° C. under an argon atmosphere. After 2 h, the reaction mixture was concentrated under reduced pressure to afford the title compound (61 mg, 99%) as a white solid lithium carboxylate salt.

Compound 55

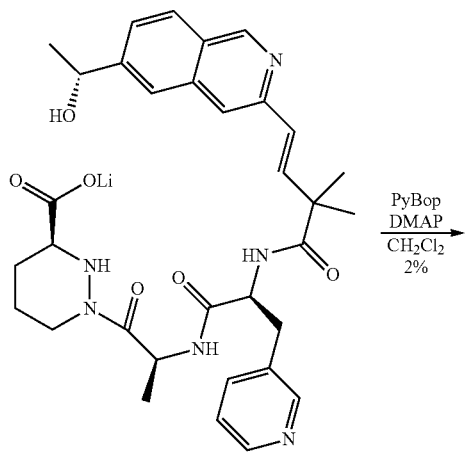

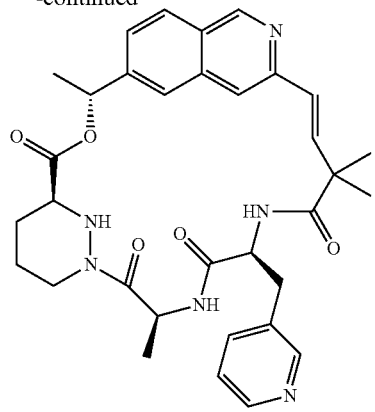

To a solution of 55d (61 mg, 0.10 mmol) in dichloromethane (50 mL) were added benzotriazol-1-yl-oxytripyrrolidinophosphonium hexafluorophosphate (208 mg, 400 μmol) and 4-dimethylaminopyridine (366 mg, 3.00 mmol) at 23° C. under an argon atmosphere. After 17 h, the reaction mixture was concentrated under reduced pressure and the crude residue was purified by silica gel chromatography (4 g Combiflash HP Gold Column, 0-20% methanol/dichloromethane gradient) to afford the title compound (1.2 mg, 2%) as a colorless solid. $R_f$=0.40 (10% methanol in dichloromethane) UV. $^1$H NMR (400 MHz, CD$_3$OD) δ 9.03 (s, 1H), 8.31 (d, J=1.6 Hz, 1H), 8.27 (dd, J=4.9, 1.5 Hz, 1H), 7.95 (d, J=8.5 Hz, 1H), 7.82 (s, 1H), 7.64 (d, J=8.0 Hz, 1H), 7.53 (s, 1H), 7.46 (dd, J=8.5, 1.5 Hz, 1H), 7.24 (dd, J=7.9, 4.9 Hz, 1H), 6.49 (d, J=16.1 Hz, 1H), 6.37 (d, J=16.1 Hz, 1H), 5.95 (q, J=6.5 Hz, 1H), 5.57 (q, J=7.3 Hz, 1H), 4.65 (d, J=12.0 Hz, 1H), 4.32 (br d, J=12.1 Hz, 1H), 3.83 (d, J=11.8 Hz, 1H), 3.73-3.65 (m, 1H), 3.00 (dd, J=14.2, 5.0 Hz, 1H), 2.83 (dd, J=13.9, 9.7 Hz, 1H), 2.64 (br t, J=11.2 Hz, 1H), 1.95-1.73 (m, 2H), 1.69-1.59 (m, 1H), 1.57 (d, J=6.7 Hz, 3H), 1.54 (d, J=7.2 Hz, 3H), 1.33 (s, 3H), 1.16 (s, 3H). HPLC Tr=4.491 min Example 56

Compound 56a

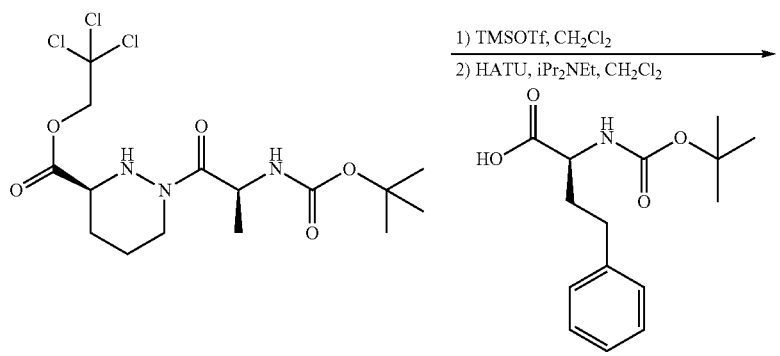

74%

Compound 56a

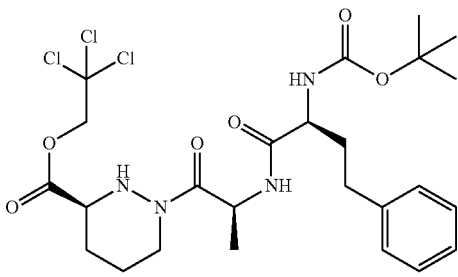

To a solution of (S)-1-((S)-2-tert-butoxycarbonylamino-propionyl)-hexahydro-pyridazine-3-carboxylic acid 2,2,2-trichloro-ethyl ester (791 mg, 1.82 mmol) in dichloromethane (10.0 mL) was slowly added trimethylsilyl trifluoromethanesulfonate (483 μL, 2.73 mmol) at 0° C. under an argon atmosphere. After 45 min, the reaction mixture was concentrated under reduced
The resulting residue was diluted with dichloromethane (10.0 mL) and 2-(1H-7-azabenzotriazol-1-yl)-1,1,3,3-tetramethyl uronium hexafluorophosphate methanaminium (761 mg, 2.00 mmol), N,N-diisopropylethylamine (1.26 mL, 7.28 mmol), and (S)-2-(tert-butoxycarbonylamino)-4-phenylbutanoic acid (Fluka, 560 mg, 2.00 mmol) were sequentially added at 23° C. under an argon atmosphere. After 18 h, the reaction mixture was concentrated under reduced pressure. The residue was pre-absorbed on silica and purified by silica gel chromatography (40 g Isco Rf Gold Column, 0-100% ethyl acetate/iso-hexanes gradient) to afford the title compound (799 mg, 74%) as a colorless oil.

To a solution of 56a (799 mg, 1.34 mmol) in dichloromethane (10.0 mL) was added trimethylsilyl trifluoromethanesulfonate (356 μL, 2.01 mmol) at 0° C. under an argon atmosphere. After 30 min, the reaction mixture was concentrated under reduced pressure. The resulting residue was diluted with acetonitrile (6.0 mL) and 2-(1H-7-azabenzotriazol-1-yl)-1,1,3,3-tetramethyl uronium hexafluorophosphate methanaminium (560 mg, 1.47 mmol), N,N-diisopropylethylamine (932 μL, 5.36 mmol), and (E)-pent-3-enoic acid (150 μL, 1.47 mmol) were sequentially added at 23° C. under an argon atmosphere. After 19 h, the reaction mixture was concentrated under reduced pressure. The residue was pre-absorbed on silica and purified by silica gel chromatography to afford the title compound (598 mg, 78%) as a colorless oil.

Compound 56b

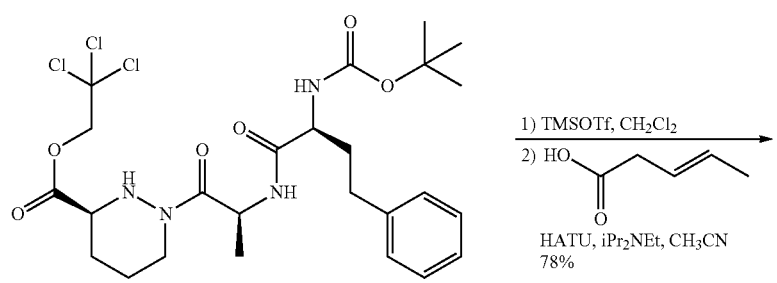

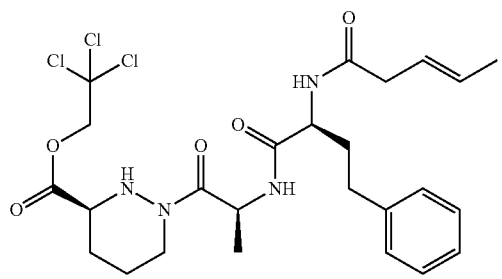

Compound 56c

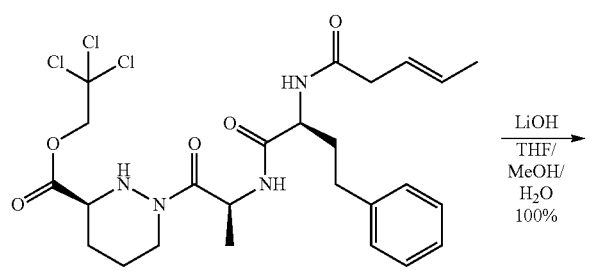

LiOH
THF/
MeOH/
H₂O
100%

To a solution of 56b (167 mg, 0.29 mmol) in tetrahydrofuran (3 mL), methanol (1 mL) and water (1 mL) was added lithium hydroxide hydrate (7.6 mg, 0.32 mmol) at 23° C. After 15 min, the reaction mixture was concentrated to dryness under reduced pressure. The residue was dissolved in water (25 mL) and washed with ethyl acetate. The organic layer was extracted with saturated aqueous sodium bicarbonate solution (25 mL). The combined aqueous layers were acidified with 1 M aqueous hydrochloric acid solution to pH ~2 and extracted with ethyl acetate (3×25 mL), and the combined organic extracts were dried over anhydrous magnesium sulfate, and were concentrated under reduced pressure to afford the title compound (129 mg, 100%) as a white solid.

Compound 56d

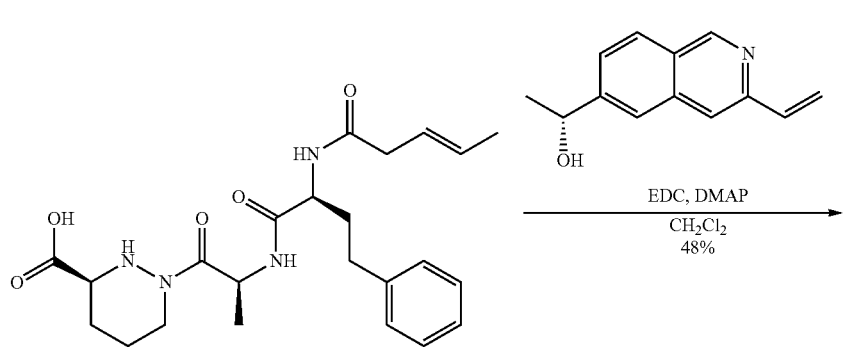

EDC, DMAP
CH₂Cl₂
48%

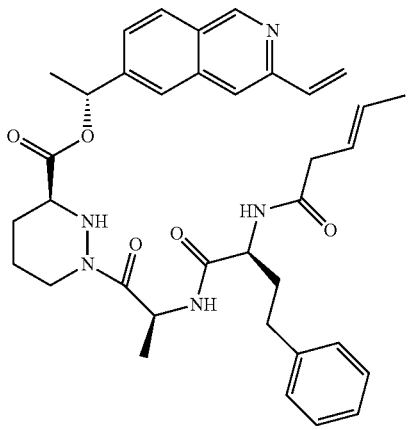

-continued

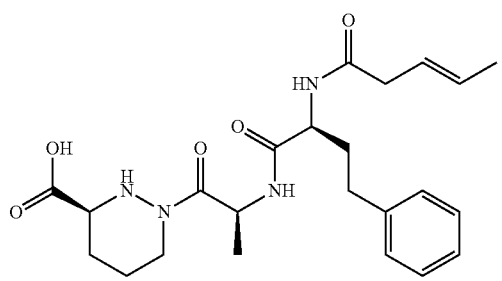

To a solution of 56c (129 mg, 0.29 mmol) and (R)-1-(3-vinyl-isoquinolin-6-yl)-ethanol (64 mg, 0.31 mmol) in dichloromethane (3.0 mL) was added N-(3-dimethylaminopropyl)-N'-ethylcarbodiimide hydrochloride (89 mg, 0.46 mmol) and 4-dimethylaminopyridine (18 mg, 0.14 mmol) at 23° C. under an argon atmosphere. After 16 h, the reaction mixture was purified directly by silica gel chromatography to afford the title compound (87 mg, 48%) as a white solid.

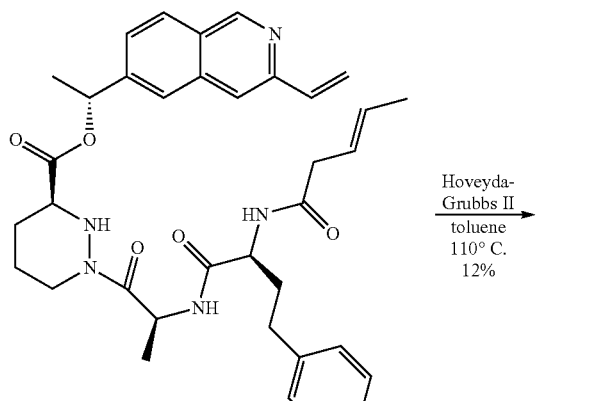

Compound 56

→ Hoveyda-Grubbs II
toluene
110° C.
12%

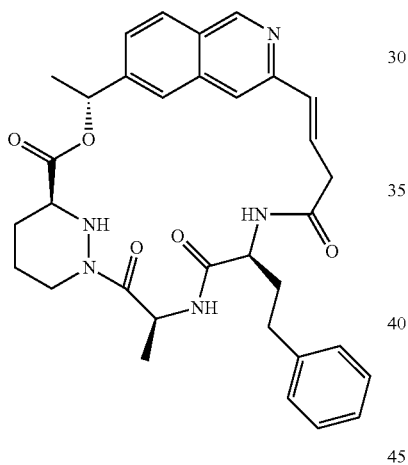

To a solution of 56d (84 mg, 0.13 mmol) in chlorobenezene (27 mL) was added the Hoveyda-Grubbs $2^{nd}$ Generation catalyst (8 mg, 13 μmol) at 23° C. under an argon atmosphere, and the resulting mixture was heated to 110° C. After 2 h, the Hoveyda-Grubbs $2^{nd}$ Generation catalyst (7.3 mg, 11 μmol) was added under argon at 110° C. The Hoveyda-Grubbs $2^{nd}$ Generation Catalyst (5 mg, 8 μmol) was then added in the interval of 30 min for three times at which point the reaction was complete. The reaction mixture was quenched with ethyl vinyl ether (1.0 μL) and the resulting mixture was allowed to cool to 23° C. The reaction mixture was concentrated under reduced pressure and the crude residue was purified by silica gel chromatography (24 g Isco Rf Gold Column, 0-100% ethyl acetate/iso-hexanes gradient for 10 min and then 100% ethyl acetate for 25 min) to afford the title compound (9.1 mg, 12%) as a pale brown solid. $R_f$=0.20 (ethyl acetate). $^1$H NMR (400 MHz, CD$_3$OD) δ 9.00 (s, 1H), 7.93 (d, J=8.5 Hz, 1H), 7.71 (s, 1H), 7.45 (dd, J=8.5, 1.5 Hz, 1H), 7.36 (s, 1H), 7.20-7.08 (m, 4H), 7.08-7.00 (m, 1H), 6.55 (d, J=15.9 Hz, 1H), 6.40 (ddd, J=15.9, 7.0, 5.1 Hz, 1H), 5.95 (q, J=6.5 Hz, 1H), 5.40 (q, J=7.2 Hz, 1H), 4.60 (d, J=12.1 Hz, 1H), 4.53 (dd, J=8.2, 6.9 Hz, 1H), 4.30 (d, J=12.5 Hz, 1H), 3.70-3.63 (m, 1H), 3.31-3.23 (m, 1H), 2.93 (ddd, J=14.0, 5.1, 1.6 1H), 2.69-2.52 (m, 3H), 2.01-1.73 (m, 4H), 1.71-1.54 (m, 2H), 1.59 (d, J=6.7 Hz, 3H), 1.46 (d, J=7.3 Hz, 3H). HPLC Tr=5.108 min. LCMS (m/z) 584.3 [M+H], Tr=2.12 min.

Example 57

Compound 57a

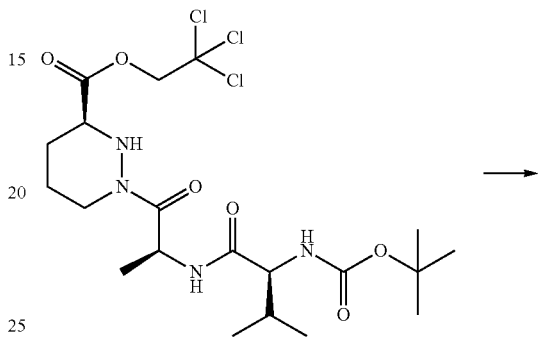

→

A solution of (S)-1-[(S)-2-((S)-2-tert-butoxycarbonylamino-3-methylbutyrylamino)-propionyl]-hexahydropyridazine-3-carboxylic acid 2,2,2-trichloroethyl ester (1.61 g, 3.03 mmol) in dichloromethane (31 mL) was cooled in an ice water bath under argon. Trimethylsilyl trifluoromethanesulfonate (1.23 g, 5.5 mmol) was added dropwise, and the resulting solution was stirred for 2 h. The reaction was quenched with N,N-diisopropylethylamine (1.2 g, 9.2 mmol) and methanol (8.5 mL). The mixture was concentrated in vacuo and was redissolved and concentrated from toluene (2×25 mL). The resulting crude residue containing (S)-1-[(S)-2-((S)-2-amino-3-methyl-butyrylamino)-propionyl]-hexahydro-pyridazine-3-carboxylic acid 2,2,2-trichloroethyl ester (1.05 g) was used without further purification.

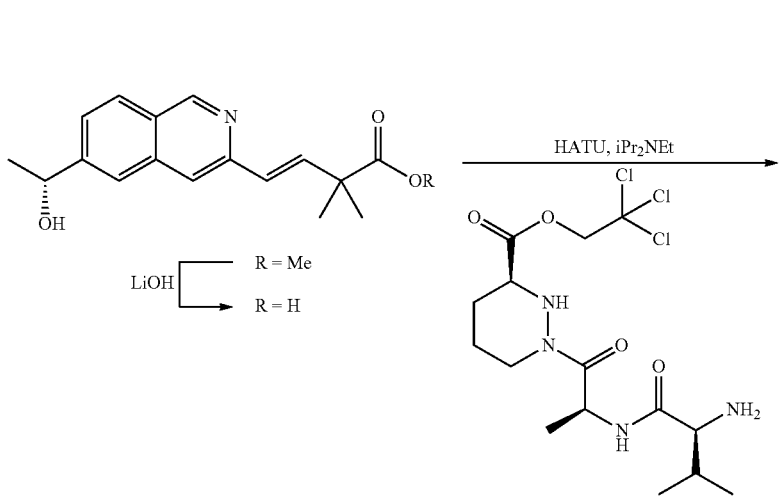
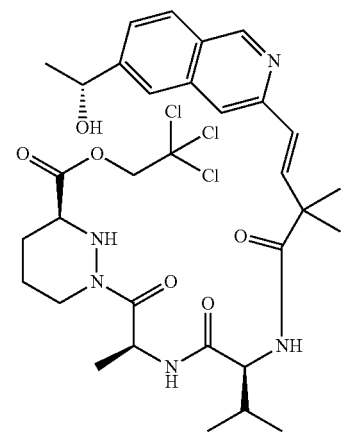

Compound 57b

To a solution of (E)-4-[6-((R)-1-hydroxy-ethyl)-isoquinolin-3-yl]-2,2-dimethyl-but-3-enoic acid methyl ester (1.05 g, 3.51 mmol) in tetrahydrofuran (8 mL) was added methanol (4 mL), water (4 mL), and lithium hydroxide hydrate (297 mg, 7.08 mmol). The resulting mixture was stirred for 6 h and was quenched with 1 M aqueous hydrochloric acid (7.2 mL, 7.2 mmol). The resulting solution was concentrated to a crude residue that was redissolved and concentrated from anhydrous methanol (50 mL) followed by toluene (50 mL). The resulting yellow solid (1.3 g, 100%) (E)-4-[6-((R)-1-hydroxy-ethyl)-isoquinolin-3-yl]-2,2-dimethyl-but-3-enoic acid was used without further purification. A portion of crude (E)-4-[6-((R)-1-hydroxy-ethyl)-isoquinolin-3-yl]-2,2-dimethyl-but-3-enoic acid (1.05 g, 2.84 mmol) was dissolved in N,N-dimethylformamide (12 mL) under argon. N,N-diisopropylethylamine (1.85 g, 14.3 mmol) was added followed by 2-(1H-7-azabenzotriazol-1-yl)-1,1,3,3-tetramethyl uronium hexafluorophosphate methanaminium (1.42 g, 3.73 mmol). The resulting mixture was stirred for 3 min, at which time crude 57a was added as a solution in N,N-dimethylformamide (8.5 mL), washing with additional N,N-dimethylformamide (2×5 mL). The reaction was stirred for 40 min and was then diluted with ethyl acetate (200 mL) and water (300 mL). The phases were separated, and the aqueous phase was extracted with ethyl acetate (200 mL). The combined organic phases were washed with water (150 mL), and the second aqueous layer was extracted with ethyl acetate (100 mL). The combined organics were dried over anhydrous sodium sulfate, filtered, and concentrated. The crude residue was purified by silica gel chromatography (35 to 60% acetone in iso-hexanes, continuous gradient) to afford the title compound (1.51 g, 71% over 2 steps) as a colorless oil. $R_F$ 0.5 (50% acetone in iso-hexanes).

Compound 57

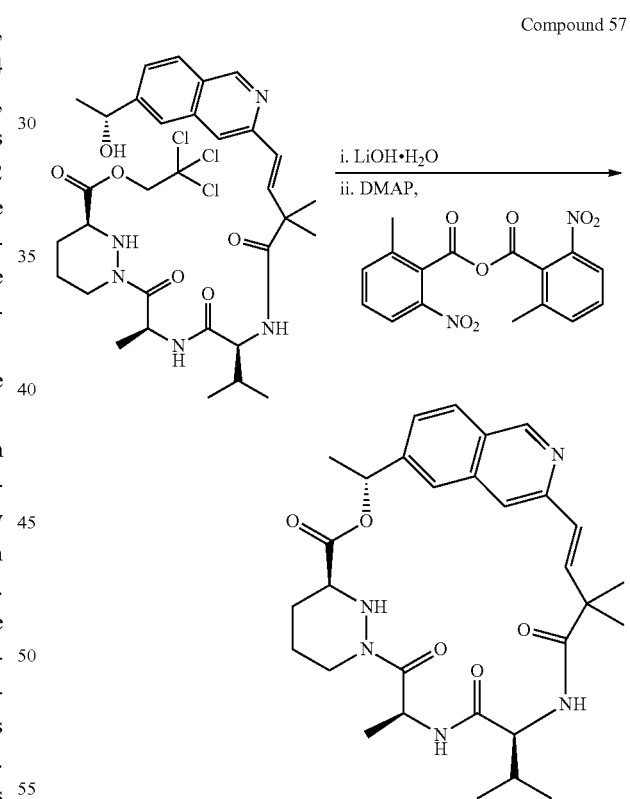

To a solution of 57b (1.50 g, 2.15 mmol) in tetrahydrofuran (20 mL) was added methanol (10 mL), water (10 mL), and lithium hydroxide hydrate (365 mg, 8.7 mmol). The mixture was stirred for 75 min at ambient temperature and was then quenched with aqueous 1 M hydrochloric acid (8.8 mL, 8.8 mmol). The resulting solution was concentrated in vacuo, and the crude product was twice dissolved and concentrated from methanol (40 mL) and suspended and concentrated from acetonitrile (6×30 mL) to afford 1.71 g of a colorless solid that was used without further purification. Under argon, 2-methyl-6-nitrobenzoic anhydride (1.85 g, 5.37 mmol) and 4-dimethylaminopyridine (1.97 g, 16.1 mmol) were dissolved in 1,2-dichloroethane (700 The resulting solution was heated to 50° C., and the crude seco-acid was added dropwise via syringe as a solution in N,N-dimethylformamide (22 mL) over 6 h. An additional wash with N,N-dimethylformamide (1.5 mL) was then added in the same manner over 15 min. After stirring an additional 1.25 h, the reaction mixture was concentrated to a final volume of 200 mL in vacuo. The solution was washed with water (250 mL), and the aqueous phase was extracted with dichloromethane (150 mL). The organic phase was dried over anhydrous magnesium sulfate, filtered, and concentrated. The resulting residue was dissolved in ethyl acetate (200 mL) and was washed with water (150 mL). The aqueous phase was extracted with ethyl acetate (150 mL). The combined organics were washed with water (100 mL), and the second aqueous phase was extracted with ethyl acetate (100 mL). The combined organics were dried over anhydrous magnesium sulfate, filtered and concentrated. The crude residue was purified by silica gel chromatography (35 to 65% acetone in iso-hexanes continuous gradient) to afford 445 mg of the pure title compound as an amorphous white solid along with 389 mg of impure product. The impure fractions were purified by recrystallization from acetone:iso-hexanes to afford an additional 173.5 mg of pure title compound (total: 618.5 mg, 52%). $R_F$ 0.5 (50% acetone in iso-hexanes). $^1$H NMR (400 MHz, CD$_3$OD) δ 9.13 (s, 1H), 8.04 (d, J=8.5 Hz, 1H), 7.89 (s, 1H), 7.55 (dd, J=8.5, 1.6 Hz, 1H), 7.53 (s, 1H), 6.73-6.34 (m, 2H), 6.03 (q, J=6.6 Hz, 1H), 5.63 (q, J=7.2 Hz, 1H), 4.67 (d, J=12.2 Hz, 1H), 4.47-4.21 (m, 2H), 3.81-3.73 (m, 1H), 2.76-2.64 (m, 1H), 2.08-1.81 (m, 3H), 1.80-1.58 (m, 8H), 1.51 (s, 3H), 1.35 (s, 3H), 0.98 (d, J=6.7 Hz, 3H), 0.93 (d, J=6.7 Hz, 3H). LCMS (m/z) 550.2 [M+H], Tr=2.74 min.

Example 58

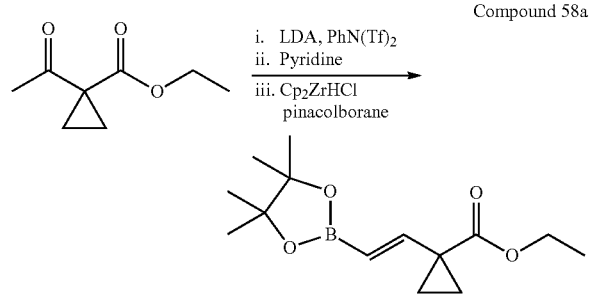

Compound 58a i. LDA, PhN(Tf)$_2$
ii. Pyridine
iii. Cp$_2$ZrHCl
pinacolborane

A solution of N,N-diisopropylamine (2.51 g, 24.8 mmol) in tetrahydrofuran (150 mL) under argon was cooled in an ice water bath. A solution of n-butyllithium in hexanes (2.5 M, 9.7 mL, 24 mmol) was added dropwise over 2 min, and the resulting solution was stirred for 15 additional minutes. The solution was then cooled to −78° C. via CO$_{2(s)}$:acetone bath, and ethyl 1-acetylcyclopropanecarboxylate (3.47 g, 22.2 mmol) was added dropwise over 2 min. The solution was stirred for an additional 20 min, and N-Phenyl-bis(trifluoromethanesulfonimide) (8.4 g, 23.5 mmol) was added as a solution in tetrahydrofuran (24 mL) via canula over 5 min, washing with additional portions of tetrahydrofuran (2×5 mL). The resulting solution was removed from the cold bath. After an additional 30 min, the reaction mixture was concentrated in vacuo and was diluted with diethyl ether (200 mL). The organic phase was washed with 1 M aqueous sodium hydroxide (1×100 mL, 1×30 mL), dried over anhydrous magnesium sulfate, filtered, and concentrated to afford 6.6 g of a crude oil that was used without further purification. A solution of the crude material from the previous step in anhydrous pyridine (11 mL) was heated to 90° C. After 16.5 h, the reaction mixture was diluted with diethyl ether (200 mL) and 3 M hydrochloric acid (100 mL) and the phases were separated. The organic phase was washed with 3 M hydrochloric acid (50 mL) and 1 M sodium hydroxide (50 mL), dried over magnesium sulfate, filtered, and concentrated to afford 2.2 g of a crude liquid that was used without further purification. To an argon-flushed vessel containing zirconocene dichloride (410 mg, 1.6 mmol) was added a solution of the crude product from the previous step (2.2 g, ca. 16 mmol) and pinacolborane (3.1 g, 24 mmol) in dichloromethane (8 mL). After 116 h, the stirred reaction mixture was diluted with ethyl acetate (50 mL) and was quenched by dropwise addition of water. The mixture was further diluted with water (50 mL), and the phases were separated. The aqueous phase was extracted with ethyl acetate (2×50 mL). The combined organic phases were dried over magnesium sulfate, filtered, and concentrated to a crude residue that was purified by silica gel chromatography (5 to 20% ethyl acetate in iso-hexanes, continuous gradient) to afford the title compound (1.26 g, 21% over 3 steps) as an oil that crystallized on standing at −15° C.

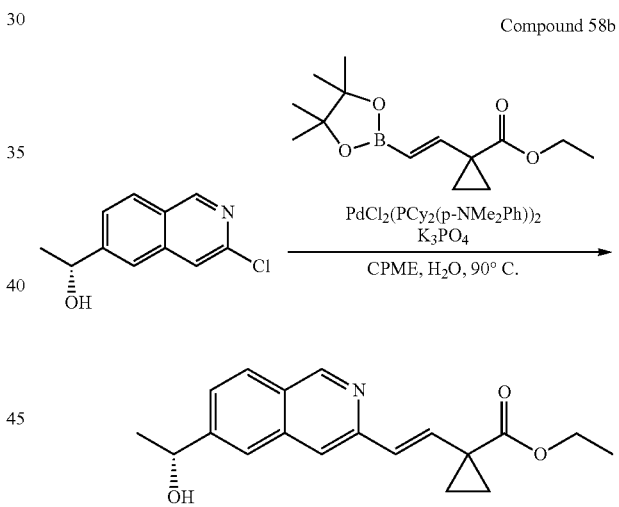

Compound 58b

PdCl$_2$(PCy$_2$(p-NMe$_2$Ph))$_2$
K$_3$PO$_4$
CPME, H$_2$O, 90° C.

To a round-bottomed flask was added (R)-1-(3-chloroisoquinolin-6-yl)ethanol (204 mg, 0.982 mmol), 58a (314 mg, 1.18 mmol), PdCl$_2$(PCy$_2$(p-NMe$_2$Ph))$_2$ (bis[(dicyclohexyl)(4-dimethylaminophenyl)phosphine]palladium(II) chloride) (40 mg, 0.049 mmol) and potassium phosphate tribasic (680 mg, 3.2 mmol). The vessel was sealed with a septum cap and was flushed with argon. Cyclopentyl methyl ether (2.8 mL) and water (1.2 mL) were added, and the resulting biphasic mixture was vigorously stirred in an oil bath pre-heated to 90° C. After 6.75 h, the reaction was cooled to ambient temperature and was diluted with ethyl acetate (50 mL) and water (40 mL). The phases were separated, and the aqueous phase was extracted with ethyl acetate (50 mL). The combined organic phases were dried over magnesium sulfate, filtered, and concentrated to afford a crude residue that was purified by silica gel chromatography (35 to 60% ethyl acetate in iso-hexanes) to afford the title compound (266 mg, 85%).

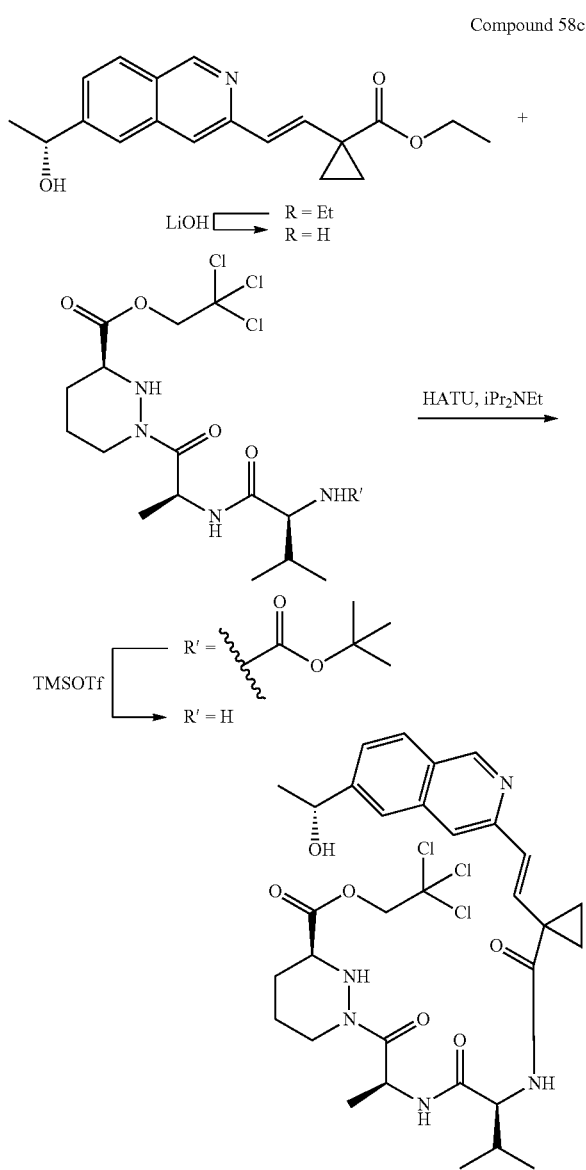

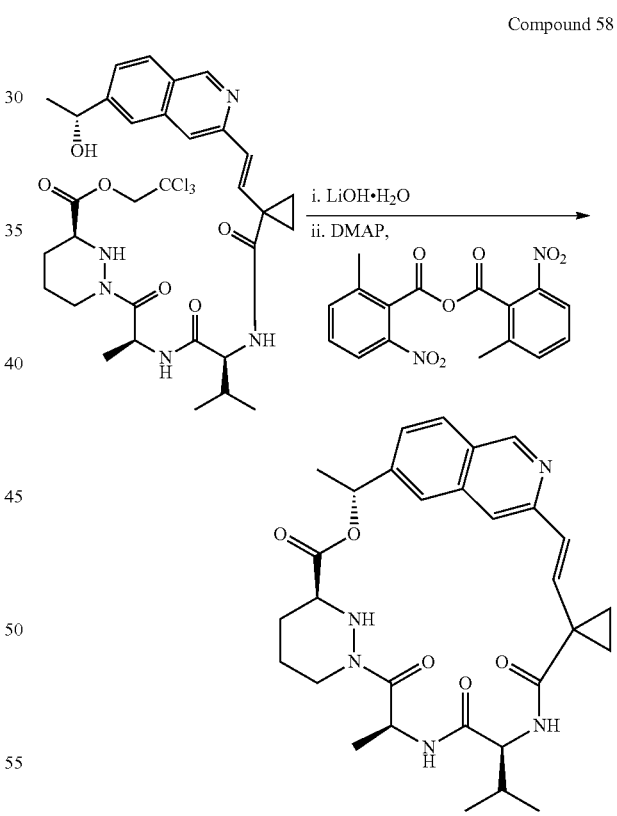

To a solution of 58b (266 mg, 0.854 mmol) in tetrahydrofuran (2 mL) was added methanol (1 mL), water (1 mL), and lithium hydroxide hydrate (70.8 mg, 1.69 mmol). The resulting mixture was stirred for 3 h and was then quenched with 1 M aqueous hydrochloric acid (1.8 mL, 1.8 mmol). Volatiles were removed in vacuo, and the resulting solid was suspended in toluene. Volatiles were removed in vacuo, and the resulting yellow solid 1-{(E)-2-[6-((R)-1-hydroxy-ethyl)-isoquinolin-3-yl]-vinyl}-cyclopropanecarboxylic acid was used without further purification. A solution of (S)-1-[(S)-2-((S)-2-tert-butoxycarbonylamino-3-methylbutyrylamino)-propionyl]-hexahydropyridazine-3-carboxylic acid 2,2,2-trichloroethyl ester (486 mg, 0.914 mmol) in dichloromethane (9.4 mL) was cooled in an ice water bath under argon. Trimethylsilyl trifluoromethanesulfonate (370 mg, 1.7 mmol) was added dropwise, and the resulting solution was stirred for 4 h. The reaction was quenched with N,N-diisopropylethylamine (360 mg, 2.7 mmol) and methanol (2.5 mL). The mixture was concentrated in vacuo and the resulting residue was redissolved and concentrated from toluene (2×15 mL). The resulting crude amine was used without further purification. To a solution of crude 1-{(E)-2-[6-((R)-1-hydroxy-ethyl)-isoquinolin-3-yl]-vinyl}-cyclopropanecarboxylic acid (ca. 0.854 mmol) in N,N-dimethylformamide (3.5 mL) under argon was added N,N-diisopropylethylamine (560 mg, 4.3 mmol) and 2-(1H-7-azabenzotriazol-1-yl)-1,1,3,3-tetramethyl uronium hexafluorophosphate methanaminium (427 mg, 1.12 mmol). The resulting mixture was stirred for 2 min, at which time crude (S)-1-[(S)-2-((S)-2-amino-3-methyl-butyrylamino)-propionyl]-hexahydro-pyridazine-3-carboxylic acid 2,2,2-trichloro-ethyl ester from the previous step was added as a solution in N,N-dimethylformamide (2.5 mL), washing with two additional portions of N,N-dimethylformamide (1.5 mL each). The reaction was stirred for 45 min and was diluted with ethyl acetate (100 mL) and water (150 mL). The phases were separated, and the aqueous phase was extracted with ethyl acetate (100 mL). The combined organic phases were washed with water (75 mL), and the second aqueous layer was extracted with ethyl acetate (75 mL). The combined organics were dried over anhydrous magnesium sulfate, filtered, and concentrated. The crude residue was purified by silica gel chromatography (35 to 60% acetone in iso-hexanes, continuous gradient) to afford title compound (467 mg, 78% over 2 steps) as a colorless oil.

To a solution of 58c (467 mg, 0.67 mmol) in tetrahydrofuran (6 mL) was added methanol (3 mL), water (3 mL), and lithium hydroxide hydrate (113 mg, 2.69 mmol). The mixture was stirred for 1.75 h at ambient temperature and was quenched with aqueous 1 M hydrochloric acid (2.8 mL, 2.8 mmol). The resulting solution was concentrated in vacuo, and the crude product was suspended and concentrated from acetonitrile (5×20 mL) to afford 530 mg of a pale yellow solid that was used without further purification. Under argon, 2-methyl-6-nitrobenzoic anhydride (283 mg, 0.82 mmol) and 4-dimethylaminopyridine (307 mg, 2.51 mmol) were dissolved in 1,2-dichloroethane (100 mL). The resulting solution was heated to 50° C., and a portion of the crude seco-acid (260 mg, ca. 0.33 mmol) was added dropwise via syringe as a solution in N,N-dimethylformamide (3.5 mL) and 1,2-dichloroethane (10 mL) over 6 h. An additional wash of N,N-dimethylformamide (1 mL) was then added in the same manner. After stirring an additional 1.25 h, the reaction mixture was concentrated to ~35 mL in vacuo. The solution was diluted with ethyl acetate (100 mL) and washed with water (100 mL). The aqueous phase was extracted with ethyl acetate (75 mL), and the combined organic phases were washed with water (50 mL). The second aqueous phase was extracted with ethyl acetate (50 mL), and the combined organics were dried over magnesium sulfate, filtered and concentrated. The crude residue was purified by silica gel chromatography (35 to 60 and then to 100% acetone in iso-hexanes) to afford 101 mg of impure product containing the title compound. This material was purified by silica gel chromatography (0 to 5% methanol in ethyl acetate) followed by reverse-phase HPLC (5 to 100% acetonitrile/water+0.1% trifluoroacetic acid) to afford the title compound as its trifluoroacetic acid salt (37 mg, 17% over 2 steps). $^1$H NMR (400 MHz, CD$_3$OD) δ 9.55 (s, 1H), 8.37 (d, J=8.6 Hz, 1H), 8.06 (s, 1H), 7.89 (s, 1H), 7.85 (d, J=8.6 Hz, 1H), 6.69 (d, J=16.4 Hz, 1H), 6.54 (d, J=16.4 Hz, 1H), 6.11 (q, J=6.7 Hz, 1H), 5.75-5.67 (m, 1H), 4.46-4.36 (m, 1H), 4.36-4.28 (m, 1H), 3.90-3.78 (m, 1H), 2.80-2.68 (m, 1H), 2.05-1.86 (m, 3H), 1.80-1.68 (m, 5H), 1.66-1.57 (m, 5H), 1.40-1.30 (m, 1H), 1.30-1.21 (m, 1H), 1.03-0.93 (m, 4H), 0.90 (d, J=6.7 Hz, 3H). LCMS (m/z) 548.4 [M+H], Tr=2.79 min.

Example 59

Compound 59a

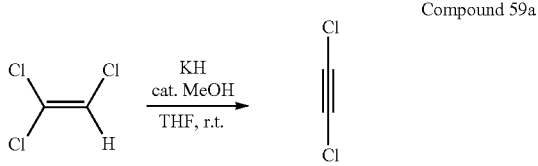

Into an oven dried, argon purged flask were placed oil-free potassium hydride (from 1740 mg of ca. 30% dispersion in mineral oil, ca. 13 mmol), anhydrous tetrahydrofuran (10 mL) and hexane (1 mL). The flask was repurged with argon and trichloroethylene (900 µL, 1.32 g, 10 mmol) was added followed by dry methanol (10 µL, 7.9 mg, 0.25 mmol). This mixture was stirred at RT for two h. After this time, hexane (10 mL) was added and the resulting solution was immediately used in the subsequent step.

Compound 59b

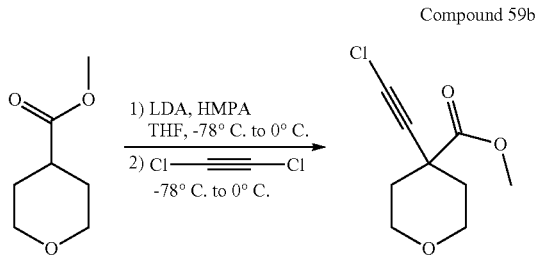

Into an oven dried, argon purged flask tetrahydrofuran (50 mL) was added and the solution was cooled with an ice bath. A 1.8 M solution of lithium diisopropylamide (7.2 mL, 13 mmol) in tetrahydrofuran/heptane/ethylbenzene was added. The resulting solution was cooled to −78° C., and treated dropwise with methyl tetrahydro-2H-pyran-4-carboxylate (1.20 mL. 1.30 g, 9 mmol) followed by hexamethylphosphoramide (1.56 mL, 1.61 g, 9 mmol). The resulting solution was warmed to 0° C., stirred for 20 min., cooled to −78° C., and treated dropwise with pre-cooled (0° C.) solution of 1,2-dichloro-ethyne (ca. 10 mmol). The reaction mixture was stirred at −78° C. for 30 min and then allowed to warm to RT. After 4 h at RT, the reaction mixture was poured into crushed ice and extracted with diethyl ether (200 mL) (5 mL of brine was added to support the separation). The organic phase was separated and washed with water (200 mL). This water phase was extracted with diethyl ether (100 mL). The combined organic fractions were washed with brine (100 mL), dried over magnesium sulfate, filtered through a 2 cm layer of silica gel (silica gel layer was washed with 50 mL of ethyl acetate), and then concentrated under reduced pressure. The crude product was subjected to silica gel chromatography (gradient from 0-15% ethyl acetate in iso-hexanes) to afford the title compound (1.22 g, 67%) as a colorless oil. R$_f$=0.48, 30% ethyl acetate in iso-hexanes, phosphomolybdic acid in ethanol.

Compound 59c

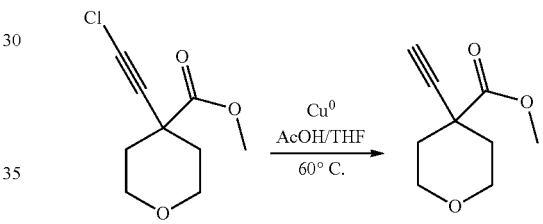

59b (1.01 g, 5 mmol) and copper powder (1.6 g, 25 mmol) were suspended in tetrahydrofuran (100 mL). Acetic acid (15 mL) was added and the reaction mixture was heated to 60° C. for 3 h. After this time, the reaction mixture was poured onto water (copper powder was filtered off with the use of the filtration paper) and extracted with diethyl ether (3×50 mL). The combined organic extracts were washed with saturated solution of ammonium chloride (3×50 mL), with saturated solution of sodium bicarbonate (2×50 mL) and with water (50 mL). This water phase was extracted with diethyl ether (50 mL). Combined organic extracts were washed with brine (50 mL) and dried over magnesium sulfate, filtered through a 2 cm layer of silica gel (silica gel layer was washed with 50 mL of ethyl acetate), and concentrated under reduced pressure. After drying under high vacuum for one day, the title compound was isolated (0.84 g, quantitative yield) as a colorless oil. R$_f$=0.37, 30% ethyl acetate in iso-hexanes, phosphomolybdic acid in ethanol.

Compound 59d

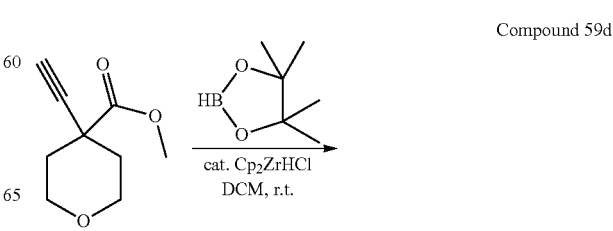

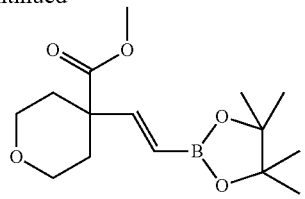

Into an oven dried, argon purged flask were placed 59c (0.84 g, 5 mmol) and dichloromethane (2 mL). This mixture was cooled to 0° C. Pinacolborane (0.96 g, 7.5 mmol) was then added dropwise via syringe. After the mixture was stirred for 1 min., it was transferred by a syringe into another oven dried, argon purged flask, immersed in an ice bath and protected from light, containing zirconocene dichloride (0.13 g, 0.5 mmol). An additional portion of dichloromethane (2 mL) was used to complete the quantitative transfer. After this the mixture was warmed to ambient temperature, it was stirred in the dark for 72 h to achieve full conversion. The reaction mixture was diluted with ethyl acetate (50 mL) and carefully quenched with water (1 ml). Water (50 mL) was added and the organic and aqueous phases were separated. The aqueous phase was extracted with ethyl acetate (3×40 mL). The combined organic phases were dried over magnesium sulfate, filtered and evaporated to afford the crude residue which was dissolved in iso-hexanes (50 mL) and extracted with 5-10% aqueous methanol (3×50 mL) and with brine (50 mL). The hexane phase was dried over magnesium sulfate. The title compound was isolated as the white crystalline compound after evaporation (1.42 g, 93%). R$_f$=0.38, 30% ethyl acetate in iso-hexanes, iodine vapor.

Compound 59e

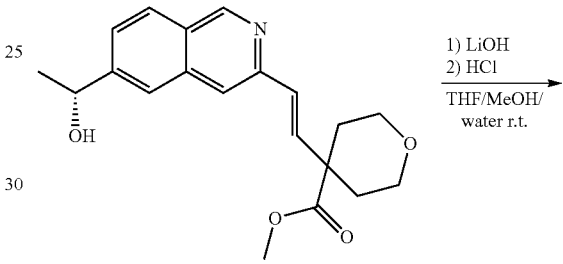

Into an oven dried, argon purged flask were placed (R)-1-(3-chloro-isoquinolin-6-yl)-ethanol (0.83 g, 4 mmol), 59d (1.40 g, 4.7 mmol), PdCl$_2$(PCy$_2$(p-NMe$_2$Ph))$_2$ (bis[(dicyclohexyl)(4-dimethylaminophenyl)phosphine]palladium(II) chloride) (173 mg, 0.21 mmol) and potassium phosphate tribasic (2.64 g, 12.4 mmol). The flask was sealed with a septum cap and was re-purged with argon. N,N-Dimethylformamide (10 mL) was added and, and the resulting reaction mixture was vigorously stirred in an oil bath pre-heated to 80° C. After 2 h, the reaction was cooled to ambient temperature and was diluted with ethyl acetate (100 mL) and water (100 mL). The phases were separated, and the aqueous phase was extracted with ethyl acetate (2×50 mL). The combined organic phases were dried over magnesium sulfate, filtered, and concentrated to afford a crude residue that was purified by silica gel chromatography (gradient from 0-40% ethyl acetate and methanol (4/1) in iso-hexanes) to afford the title compound (1.06 g, 78%) as a colorless oil after evaporation. R$_f$=0.48, iso-hexanes/ethyl acetate/methanol (6/4/1).

Compound 59f

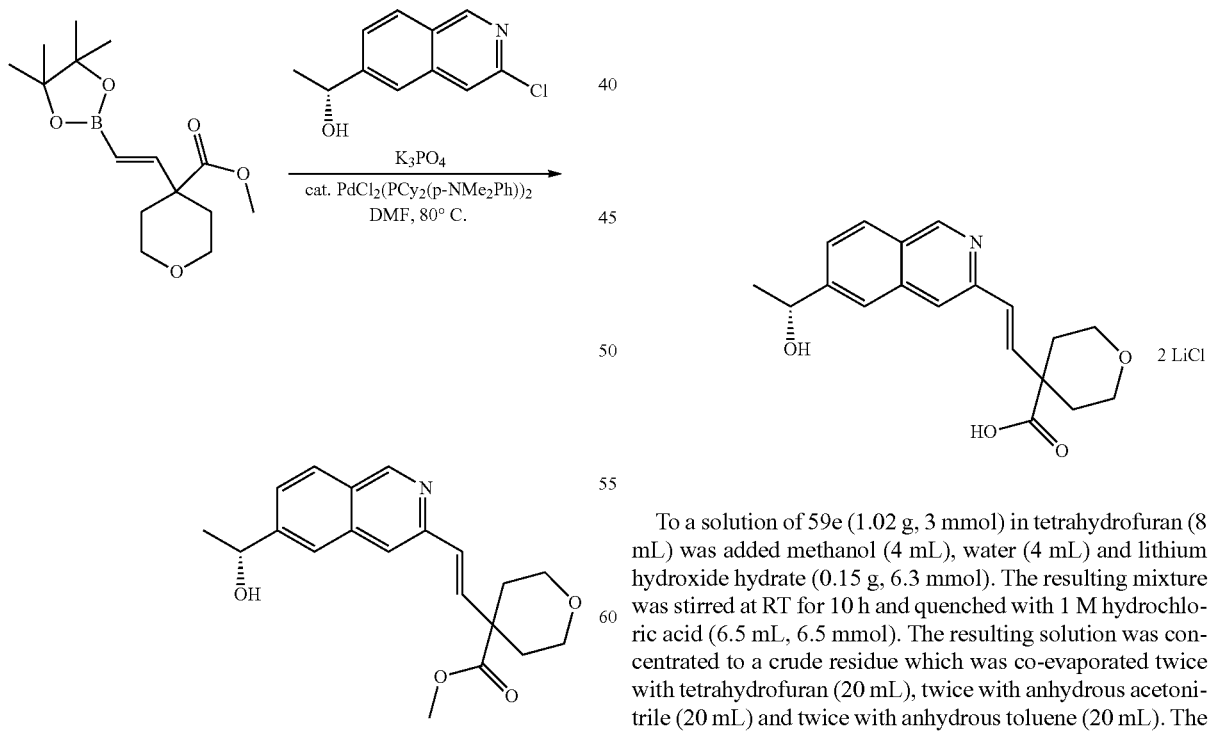

To a solution of 59e (1.02 g, 3 mmol) in tetrahydrofuran (8 mL) was added methanol (4 mL), water (4 mL) and lithium hydroxide hydrate (0.15 g, 6.3 mmol). The resulting mixture was stirred at RT for 10 h and quenched with 1 M hydrochloric acid (6.5 mL, 6.5 mmol). The resulting solution was concentrated to a crude residue which was co-evaporated twice with tetrahydrofuran (20 mL), twice with anhydrous acetonitrile (20 mL) and twice with anhydrous toluene (20 mL). The resulting white solid was dried under high vacuum overnight and used without further purification (1.24 g, quantitative yield).

Compound 59g

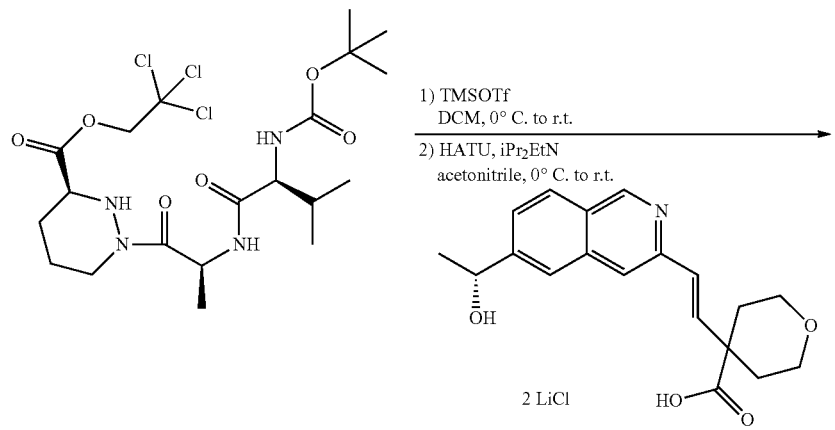

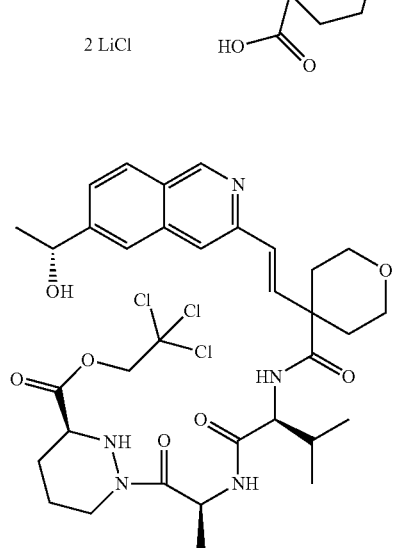

A solution of 1e (0.53 g, 1 mmol) in dichloromethane (10 mL) was cooled in an ice water bath. Trimethylsilyl trifluoromethanesulfonate (0.69 g, 1.80 mmol) was added dropwise at 0° C. under argon, and the resulting solution was stirred at RT for 30 min. The reaction mixture was evaporated to dryness and the resulting crude residue was dissolved in anhydrous acetonitrile (12 mL) under argon. The reaction mixture was stirred at 0° C., 59f (371 mg, 0.9 mmol) and N,N-diisopropylethylamine (517 mg, 4 mmol) were added followed by 2-(1H-7-azabenzotriazol-1-yl)-1,1,3,3-tetramethyl uronium hexafluorophosphate methanaminium (570 mg, 1.5 mmol). The reaction mixture was stirred at RT for 48 h. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-40% ethyl acetate and methanol (4/1) in iso-hexanes) to afford the title compound (560 mg, 84%) as a white solid after evaporation. $R_f$=0.13, iso-hexanes/ethyl acetate/methanol (6/4/1).

Compound 59

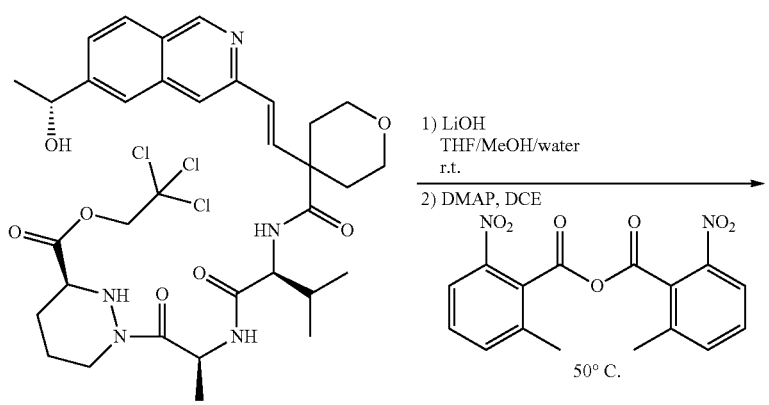

-continued

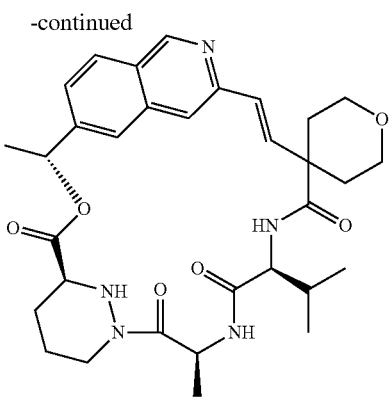

To a solution of 59g (371 mg, 0.5 mmol) in tetrahydrofuran (8 mL) was added methanol (4 mL), water (4 mL) and lithium hydroxide hydrate (36 mg, 1.5 mmol). The mixture was stirred for 2 h at ambient temperature and was quenched with aqueous 1 M hydrochloric acid (1.6 mL, 1.6 mmol). The resulting solution was concentrated to a crude residue which was co-evaporated twice with tetrahydrofuran (20 mL), twice with anhydrous acetonitrile (20 mL) and twice with anhydrous toluene (20 mL). The resulting white solid was dried under high vacuum overnight and it was used without further purification (365 mg, quantitative yield). Into oven dried, argon purged flask were placed 2-methyl-6-nitrobenzoic anhydride (258 mg, 0.75 mmol), 4-dimethylaminopyridine (275 mg, 2.25 mmol) and anhydrous 1,2-dichloroethane (150 mL). The resulting solution was heated at 50° C., and the crude seco-acid was added dropwise via syringe as a solution in dry N,N-dimethylformamide (10 mL) over 12 h. An additional portion of dry N,N-dimethylformamide (2×5 mL) was used to complete the quantitative transfer. After stirring for additional 2 h at 50° C., the reaction mixture was transferred to a separatory funnel and washed with water (100 mL, 5 mL of brine was added to support the separation). The aqueous phase was extracted with dichloromethane (50 mL). Combined organic extracts were washed with brine (50 mL) and dried over magnesium sulfate, filtered and concentrated under reduced pressure. The resulting residue was dissolved in ethyl acetate (100 mL) and was washed with water (100 mL, 5 mL of brine was added to support the separation). The aqueous phase was extracted with ethyl acetate (50 mL). Combined organic extracts were washed with water (100 mL, 5 mL of brine was added to support the separation). Resulting aqueous phase was extracted with ethyl acetate (50 mL). Combined organic extracts were washed with brine (50 mL) and dried over magnesium sulfate, filtered and concentrated under reduced pressure. The residue was purified by silica gel chromatography (gradient from 0-40% ethyl acetate and methanol (4/1) in iso-hexanes) to afford the title compound (72 mg, 24%) as a white solid after evaporation. $R_f$=0.42, 10% methanol in dichloromethane. $^1$H NMR (400 MHz, CD$_3$OD): δ 9.04 (s, 1H), 7.95 (d, J=8.5 Hz, 1H), 7.76 (s, 1H), 7.47 (dd, J=8.5, 1.5 Hz, 1H), 7.31 (s, 1H), 6.43 (m, 2H), 5.93 (q, J=6.6 Hz, 1H), 5.44-5.36 (m, 1H), 4.33-4.23 (m, 2H), 3.84 (dt, J=11.6, 4.1 Hz, 1H), 3.76-3.69 (m, 1H), 3.68-3.61 (m, 2H), 3.48 (m, 1H), 2.65-2.56 (m, 1H), 2.16-2.07 (m, 2H), 2.03-1.93 (m, 1H), 1.91-1.82 (m, 2H), 1.79e (m, 1H), 1.67-1.62 (m, 3H), 1.59 (d, J=6.6 Hz, 3H), 1.51 (d, J=7.2 Hz, 3H), 0.90 (d, J=6.7 Hz, 3H), 0.85 (d, J=6.7 Hz, 3H). LCMS (m/z) 592.3 [M+H]$^+$ Tr=3.12 min.

Example 60

Compound 60

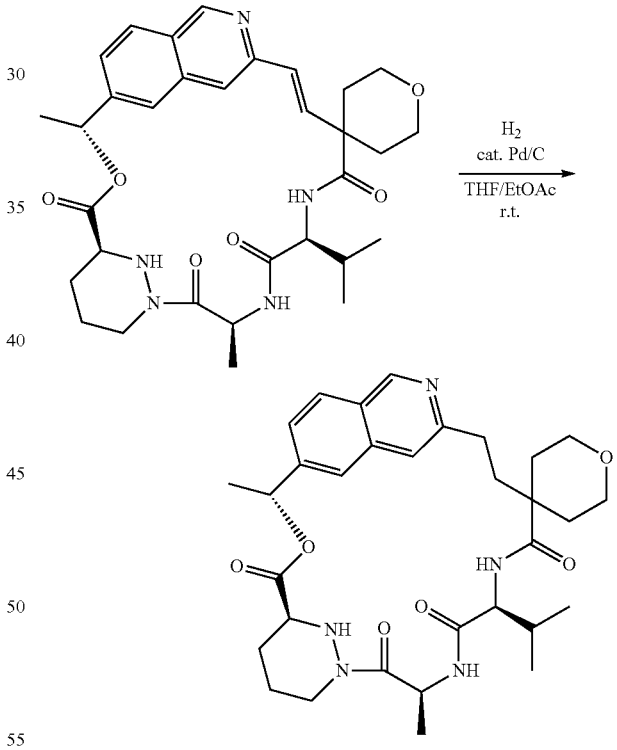

A solution of Compound 59 (10 mg, 0.017 mmol) in a mixture of ethyl acetate (4 mL) and tetrahydrofuran (4 mL) containing 10% palladium on carbon (10 mg) was hydrogenated at RT and at atmospheric pressure of hydrogen for 3 h. The reaction mixture was filtered through Celite and the filter pad was washed with tetrahydrofuran (10 mL). The filtrate was evaporated to afford the title compound (10 mg, quantitative yield) as a white solid. $R_f$=0.47, 10% methanol in dichloromethane. $^1$H NMR (400 MHz, CD$_3$OD): δ 9.02 (s, 1H), 7.94 (d, J=8.5 Hz, 1H), 7.81 1H), 7.44 (d, J=8.5 Hz, 1H), 7.20 (s, 1H), 6.02 (q, J=6.5 Hz, 1H), 5.78-5.71 (m, 1H), 5.24

(m, 1H), 4.33-4.23 (m, 2H), 3.83-3.61 (m, 6H), 3.52 (m, 1H), 2.71-2.66 (m, 1H), 2.43-2.36 (m, 2.14-2.05 (m, 2H), 2.08-1.91 (m, 1H), 1.90-1.82 (m, 2H), 1.76 (m, 1H), 1.67-1.62 (m, 2H), 1.57 (d, J=6.6 Hz, 3H), 1.54 (d, J=7.2 Hz, 3H), 0.96 (d, J=6.7 Hz, 3H), 0.88 (d, J=6.7 Hz, 3H). LCMS (m/z) 594.3 [M+H]' Tr=2.72 min.

Example 61

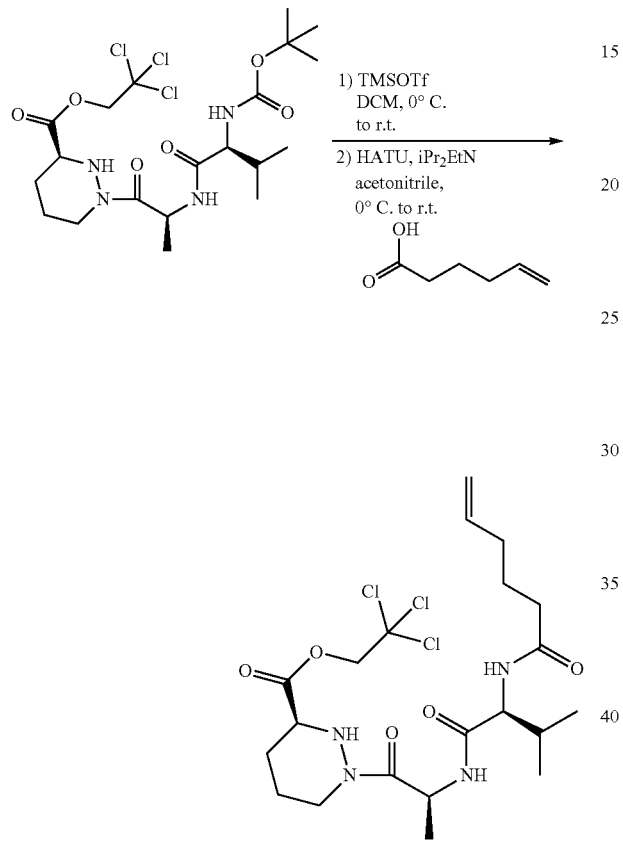

Compound 61a

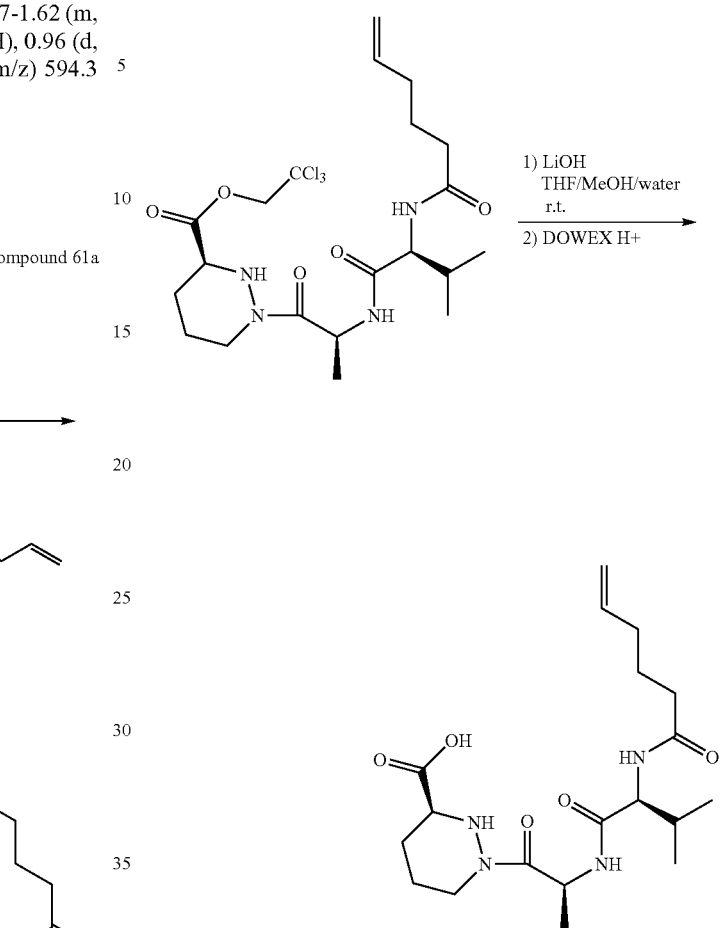

Compound 61b

A solution of 1e (1064 mg, 2 mmol) in dichloromethane (30 mL) was cooled in an ice water bath. Trimethylsilyl trifluoromethanesulfonate (666 mg, 3 mmol) was added dropwise at 0° C. under argon, and the resulting solution was stirred at RT for 30 min. The reaction mixture was evaporated to dryness and the resulting crude residue was dissolved in anhydrous acetonitrile (25 mL) under argon. The reaction mixture was stirred at 0° C., hex-5-enoic acid (251 mg, 2.2 mmol) and N,N-diisopropylethylamine (1034 mg, 8 mmol) were added followed by 2-(1H-7-azabenzotriazol-1-yl)-1,1,3,3-tetramethyl uronium hexafluorophosphate methanaminium (1065 mg, 2.8 mmol). The reaction mixture was stirred at RT for 48 h. The solvent was evaporated, the residue was dissolved in ethyl acetate (200 mL) and the solution was washed with 20% water solution of citric acid (2×150 mL), water (150 mL) and brine (150 mL), dried over magnesium sulfate, filtered and evaporated. The residue was purified by silica gel chromatography (gradient from 0-40% ethyl acetate and methanol (4/1) in iso-hexanes) to afford the title compound (864 mg, 82%) as a white solid after evaporation. $R_f$=0.35, iso-hexanes/ethyl acetate/methanol (6/4/1).

To a solution of 61a (830 mg, 1.57 mmol) in tetrahydrofuran (40 mL) were added water (10 mL) and lithium hydroxide hydrate (57 mg, 2.38 mmol). The mixture was stirred for 2 h at ambient temperature and then filtered through a 5 cm layer of DOWEX D50×8 resin in H+ cycle (resin firstly washed with water). Resin was washed with additional water (50 mL). Filtrates were collected, concentrated under reduced pressure and co-evaporated twice with toluene (10 mL). After drying under high vacuum for one day, the title compound was isolated (590 mg, 95%) as a white solid. $R_f$=0.4, 30% methanol in dichloromethane.

Compound 61c

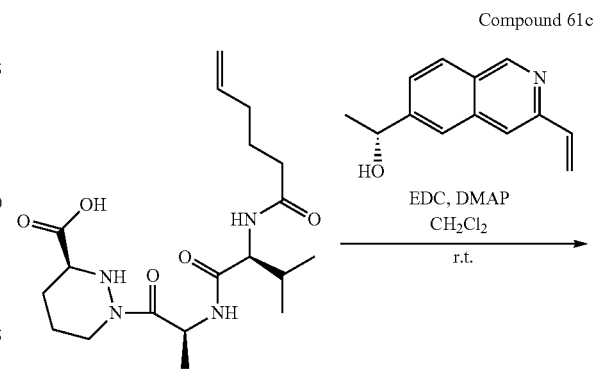

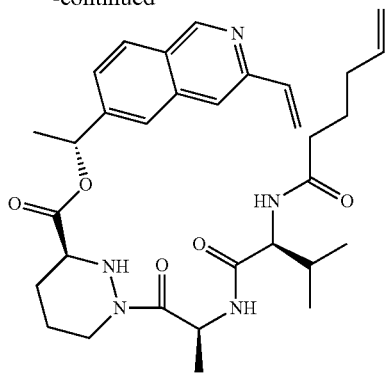

Into an oven dried, argon purged flask were added 61b (238 mg, 0.60 mmol) and (R)-1-(3-vinyl-isoquinolin-6-yl)-ethanol (120 mg, 0.6 mmol). The flask was sealed and the reaction mixture was repurged twice with argon. Anhydrous dichloromethane (10 mL) was added and the reaction mixture was repurged twice with argon. N-(3-dimethylaminopropyl)-N'-ethylcarbodiimide hydrochloride (148 mg, 0.77 mmol) was added followed by 4-dimethylaminopyridine (67 mg, 0.55 mmol). Reaction mixture was quickly repurged twice with argon and was stirred at RT for 12 h. The reaction mixture was diluted with dichloromethane (100 mL) and the solution was washed with 20% water solution of citric acid (2×150 mL), water (150 mL) and brine (150 mL), dried over magnesium sulfate, filtered and evaporated. The residue was purified by silica gel chromatography (gradient from 0-40% ethyl acetate and methanol (4/1) in iso-hexanes) to afford the title compound (307 mg, 89%) as a white solid after evaporation. $R_f$=0.29, iso-hexanes/ethyl acetate/methanol (6/4/1).

Compound 61

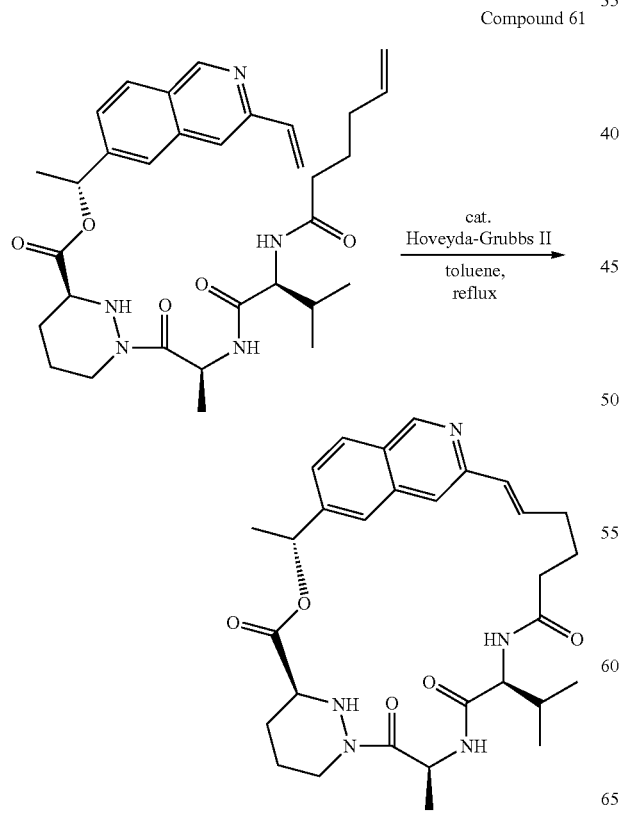

A solution of 61c (209 mg, 0.362 mmol) in toluene (150 mL) was stirred at RT under argon. Hoveyda-Grubbs $2^{nd}$ generation catalyst (23 mg, 0.036 mmol) was added and the reaction mixture was heated at reflux under argon for 30 min. Reaction mixture was cooled to RT and ethyl acetate (50 mL) was added. This solution was washed twice with aqueous solution of tris(hydroxymethyl)phosphine (372 mg, 3 mmol in 100 mL of water), with water (2×50 mL) and with brine (50 mL). The organic phase was dried over magnesium sulfate, filtered and evaporated. The residue was purified by silica gel chromatography (gradient from 0-40% ethyl acetate and methanol (4/1) in iso-hexanes) to afford the title compound (125 mg, 63%) as a white solid after evaporation. $R_f$=0.25, iso-hexanes/ethyl acetate/methanol (6/4/1). $^1$H NMR (400 MHz, CD$_3$OD): δ 9.00 (s, 1H), 7.91 (d, J=8.4 Hz, 1H), 7.77 (s, 1H), 7.41 (d, J=8.4 Hz, 1H), 7.23 (s, 1H), 6.64 (m, 1H), 6.29 (d, J=15.4 Hz, 1H), 5.97 (q, J=5.9 Hz, 1H), 5.53 (q, J=7.0 Hz, 1H), 4.37-4.18 (m, 2H), 3.65 (d, J=9.8 Hz, 1H), 2.65 (t, J=12.3 Hz, 1H), 2.36-2.18 (m, 4H), 1.98 (m, 1H), 1.94-1.73 (m, 3H), 1.71-1.57 (m, 3H), 1.55 (d, J=5.6 Hz, 6H), 0.83 (d, J=6.6 Hz, 3H), 0.78 (d, J=6.6 Hz, 3H). LCMS (m/z) 550.2 [M+H]$^+$ Tr=2.55 min.

Example 62

Compound 62

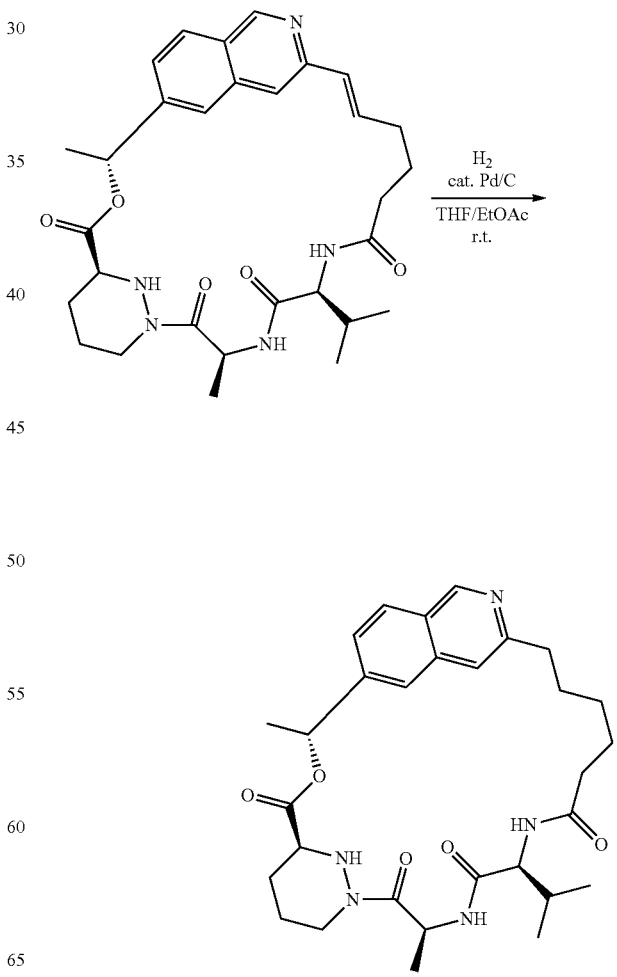

A solution of Compound 61 (10 mg, 0.018 mmol) in a mixture of ethyl acetate (4 mL) and tetrahydrofuran (4 mL) containing 10% palladium on carbon (10 mg) was hydrogenated at RT and at atmospheric pressure of hydrogen for 3 h. The reaction mixture was filtered through Celite and the filter pad was washed with tetrahydrofuran (10 mL). The filtrate was evaporated to afford the title compound (9 mg, 89%) as a white solid. $R_f$=0.16, iso-hexanes/ethyl acetate/methanol (6/4/1). $^1$H NMR (400 MHz, $CD_3OD$) δ 9.02 (s, 1H), 7.93 (d, J=8.7 Hz, 1H), 7.62 (s, 1H), 7.47 (s, 1H), 7.44 (d, J=8.7 Hz, 1H), 6.02-5.93 (m, 1H), 5.39 (m, 1H), 4.03 (m, 1H), 3.69 (m, 1H), 2.84 (m, 2H), 2.27 (s, 1H), 2.10 (m, 1H), 1.97 (m, 1H), 1.85 (m, 2H), 1.76 (m, 2H), 1.62 (m, 4H), 1.54 (d, J=5.1 Hz, 3H), 1.39 (d, J=6.6 Hz, 3H), 1.19 (m, 4H), 0.78 (d, J=5.0 Hz, 3H), 0.73 (d, J=5.8 Hz, 3H). LCMS (m/z) 552.3 [M+H]' Tr=2.10 min.

Example 63

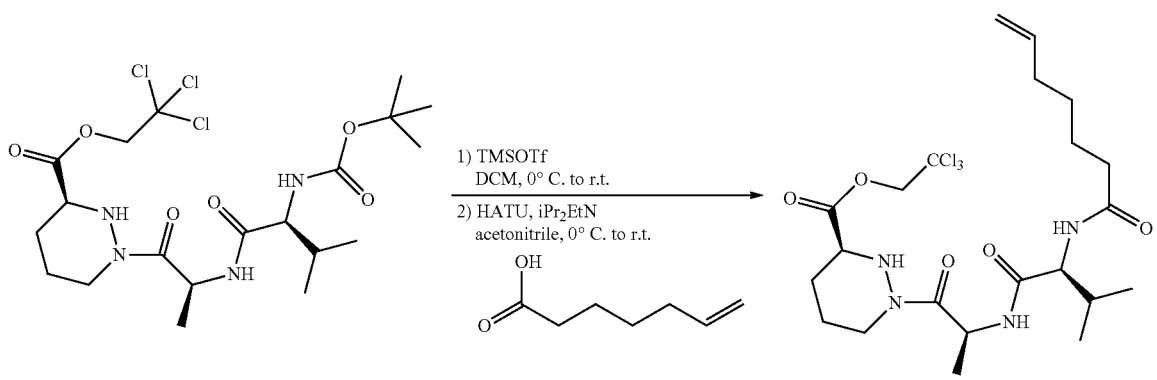

Compound 63a

A solution of 1e (1064 mg, 2 mmol) in dichloromethane (30 mL) was cooled in an ice water bath. Trimethylsilyl trifluoromethanesulfonate (666 mg, 3 mmol) was added dropwise at 0° C. under argon, and the resulting solution was stirred at RT for 30 min. The reaction mixture was evaporated to dryness and the resulting crude residue was dissolved in anhydrous acetonitrile (25 mL) under argon. The reaction mixture was stirred at 0° C., hept-6-enoic acid (281 mg, 2.2 mmol) and N,N-diisopropylethylamine (1034 mg, 8 mmol) were added followed by 2-(1H-7-azabenzotriazol-1-yl)-1,1,3,3-tetramethyl uronium hexafluorophosphate methanaminium (1065 mg, 2.8 mmol). The reaction mixture was stirred at RT for 48 h. The solvent was evaporated, the residue was dissolved in ethyl acetate (200 mL) and the solution was washed twice with 20% water solution of citric acid (2×150 mL), water (150 mL) and brine (150 mL), dried over magnesium sulfate, filtered and evaporated. The residue was purified by silica gel chromatography (gradient from 0-40% ethyl acetate+methanol (4/1) in iso-hexanes) to afford the title compound (817 mg, 75%) as a white solid after evaporation. $R_f$=0.37, iso-hexanes/ethyl acetate/methanol (6/4/1).

Compound 63b

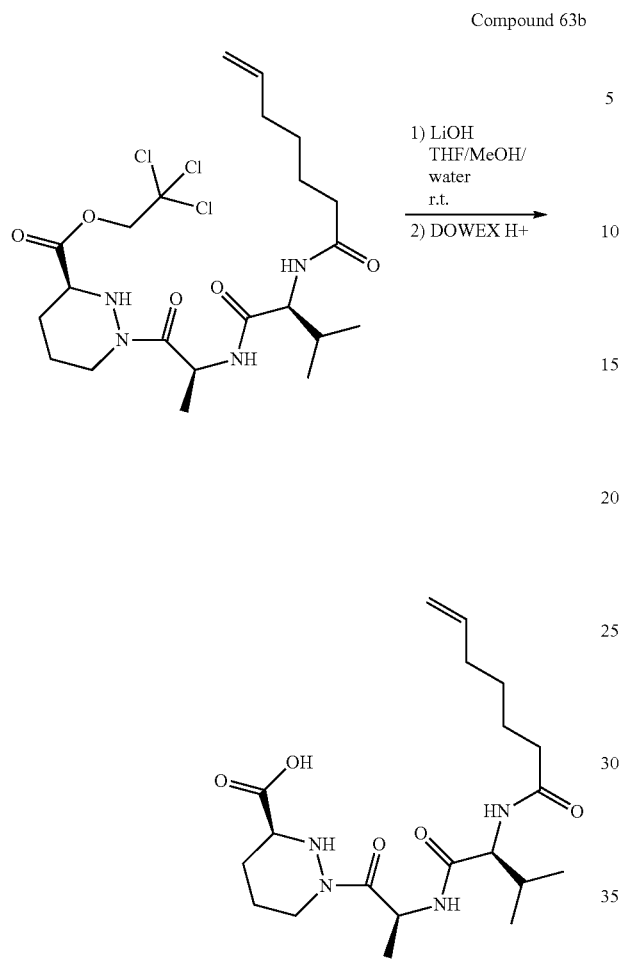

1) LiOH THF/MeOH/water r.t.
2) DOWEX H+

To a solution of 63a (790 mg, 1.46 mmol) in tetrahydrofuran (40 mL) was added water (10 mL) and lithium hydroxide hydrate (52 mg, 2.19 mmol). The mixture was stirred for 2 h at ambient temperature and then filtered through a 5 cm layer of DOWEX D50×8 resin in H+ cycle (resin firstly washed with water). Resin was washed with additional water (50 mL). The filtrates were collected, concentrated under reduced pressure and co-evaporated twice with toluene (10 mL). After drying under high vacuum for one day, the title compound was isolated (583 mg, 97%) as a white solid. $R_f$=0.4, 30% methanol in dichloromethane.

Compound 63c

EDC, DMAP
CH$_2$Cl$_2$
r.t.

Into an oven dried, argon purged flask were added 63b (276 mg, 0.67 mmol) and (R)-1-(3-vinyl-isoquinolin-6-yl)-ethanol (134 mg, 0.67 mmol). The flask was sealed and the reaction mixture was repurged twice with argon. Anhydrous dichloromethane (10 mL) was added and the reaction mixture was repurged twice with argon. N-(3-Dimethylaminopropyl)-N'-ethylcarbodiimide hydrochloride (168 mg, 0.87 mmol) was added followed by 4-dimethylaminopyridine (75 mg, 0.62 mmol). The reaction mixture was quickly repurged twice with argon and was stirred at RT for 12 h. The reaction mixture was diluted with dichloromethane (100 mL) and the solution was washed with 20% water solution of citric acid (2×150 mL), water (150 mL) and brine (150 mL), dried over magnesium sulfate, filtered and evaporated. The residue was purified by silica gel chromatography (gradient from 0-40% ethyl acetate and methanol (4/1) in iso-hexanes) to afford the title compound (316 mg, 79%) as a white solid after evaporation. $R_f$=0.30, iso-hexanes/ethyl acetate/methanol (6/4/1).

Compound 63

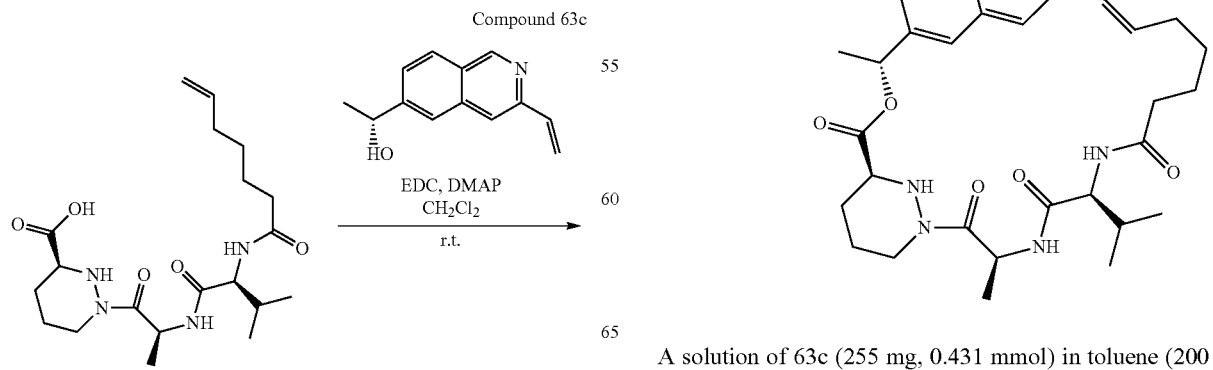

cat. Hoveyda-Grubbs II
toluene, reflux

A solution of 63c (255 mg, 0.431 mmol) in toluene (200 mL) was stirred at RT under argon. Hoveyda-Grubbs 2$^{nd}$ generation catalyst (27 mg, 0.043 mmol) was added and the reaction mixture was heated at reflux under argon for 30 min. Reaction mixture was cooled to RT and ethyl acetate (50 mL) was added. This solution was washed twice with aqueous solution of tris(hydroxymethyl)phosphine (372 mg, 3 mmol in 100 mL of water), twice with water (50 mL) and with brine (50 mL). The organic phase was dried over magnesium sulfate, filtered and evaporated. The residue was purified by silica gel chromatography (gradient from 0-40% ethyl acetate and methanol (4/1) in iso-hexanes) to afford the title compound (76 mg, 31%) as a white solid after evaporation. $R_f$=0.20, iso-hexanes/ethyl acetate/methanol (6/4/1). $^1$H NMR (400 MHz, CD$_3$OD): δ 9.01 (s, 1H), 7.93 (d, J=8.5 Hz, 1H), 7.69 (s, 1H), 7.57 (s, 1H), 7.43 (d, J=8.5 Hz, 1H), 6.55 (m, 1H), 5.95 (m, 1H), 5.43 (m, 1H), 5.23 (m, 3H), 4.32 (m, 1H), 4.20 (m, 1H), 3.67 (m, 1H), 2.69 (m, 1H), 2.30 (m, 2H), 2.13 (m, 2H), 1.96 (m, 3H), 1.83 (m, 1H), 1.64 (m, 3H), 1.56 (d, J=6.7 Hz, 3H), 1.44 (d, J=7.4 Hz, 3H), 0.92-0.72 (m, 6H). LCMS (m/z) 564.4 [M+H]' Tr=2.60 min.

Example 64

Compound 64

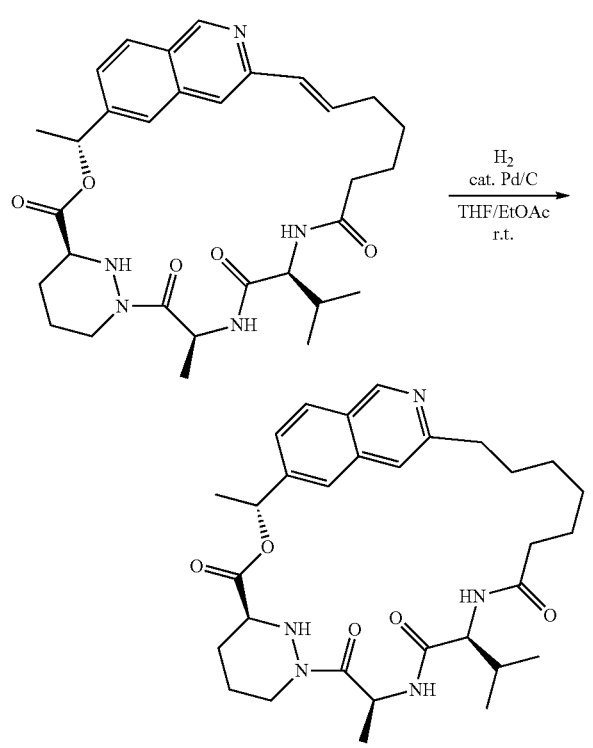

A solution of Compound 63 (15 mg, 0.027 mmol) in a mixture of ethyl acetate (4 mL) and tetrahydrofuran (4 mL) containing 10% palladium on carbon (10 mg) was hydrogenated at RT and at atmospheric pressure of hydrogen for 3 h. The reaction mixture was filtered through Celite and the filter pad was washed with tetrahydrofuran (10 mL). The filtrate was evaporated to afford the title compound (13 mg, 87%) as a white solid. $R_f$=0.11, iso-hexanes/ethyl acetate/methanol (6/4/1). $^1$H NMR (400 MHz, CD$_3$OD) δ 9.02 (s, 1H), 7.95 (d, J=8.7 Hz, 1H), 7.68 (s, 1H), 7.50 (s, 1H), 7.45 (d, J=8.7 Hz, 1H), 5.93 (q, J=6.3 Hz, 1H), 5.20 (m, 1H), 4.21 (m, 1H), 4.07 (d, J=8.0 Hz, 1H), 3.66 (m, 1H), 2.83 (m, 4H), 2.25 (m, 1H), 2.07 (m, 1H), 1.94 (m, 2H), 1.80e (m, 1H), 1.63 (m, 3H), 1.55 (d, J=6.6 Hz, 3H), 1.51-1.42 (m, 2H), 1.37 (d, J=7.0 Hz, 3H), 1.25 (m, 4H), 0.83 (d, J=6.7 Hz, 6H). LCMS (m/z) 566.3 [M+H], Tr=2.27 min.

Example 65

Compound 65a

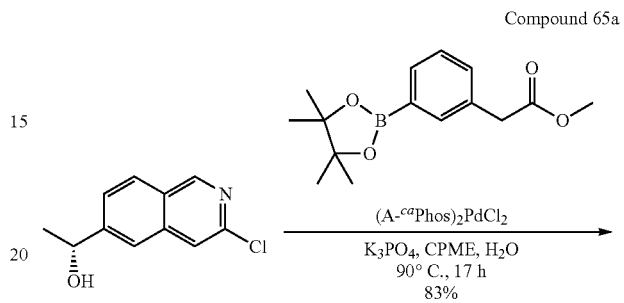

To a solution of (R)-1-(3-chloro-isoquinolin-6-yl)-ethanol (250 mg, 1.21 mmol), and potassium phosphate tribasic (770 mg, 3.63 mmol) in cyclopentyl methy ether (4.5 mL) and water (1.5 mL) preheated to 90° C. under an argon atmosphere were added 3-(2-methoxy-2-oxoethyl)phenylboronic acid, pinacol ester (Combi-Blocks, 387 mg, 1.33 mmol) and (A-$^{ca}$Phos)$_2$PdCl$_2$(49 mg, 60 μmol). After 17 h, the reaction was allowed to cool to 23° C., and was partitioned between dichloromethane (50 mL) and saturated aqueous sodium bicarbonate solution (50 mL). The phases were split and the aqueous layer was extracted with dichloromethane (50 mL). The combined organic layers were dried over anhydrous sodium sulfate, and were concentrated under reduced pressure. The crude residue was purified by silica gel chromatography (24 g Combiflash HP Gold Column, 0-100% ethyl acetate/iso-hexanes gradient) to afford the title compound (321 mg, 83%) as a faint yellow oil.

Compound 65b

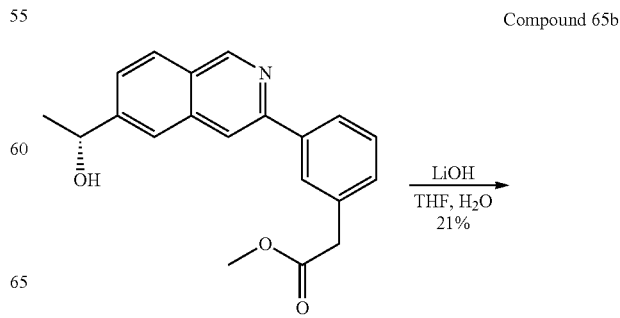

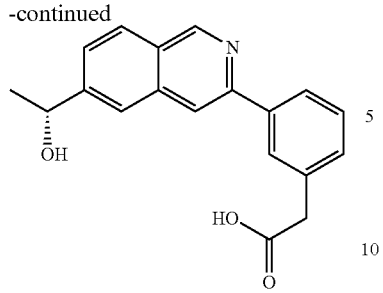

To a solution of 65a (320 mg, 1.00 mmol) in tetrahydrofuran (3 mL) and water (2 mL) was added lithium hydroxide (26 mg, 1.1 mmol) at 23° C. under an argon atmosphere. After 3 h, the reaction mixture was concentrated under reduced pressure and the crude residue was purified by silica gel chromatography (24 g Combiflash HP Gold Column, 0-20% methanol/dichloromethane gradient) to afford the title compound (64.2 mg, 21%) as a colorless oil. $R_f$=0.5 (20% methanol in dichloromethane) $I_2$/silica stain.

Compound 65c

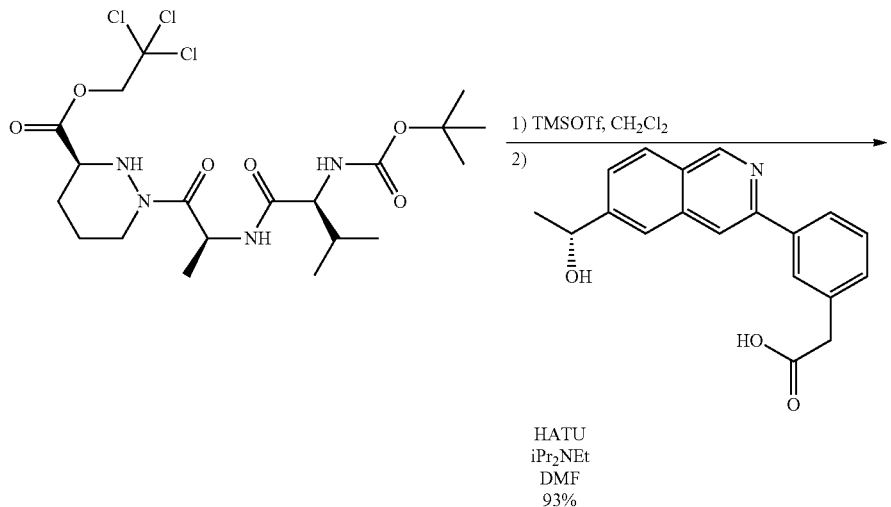

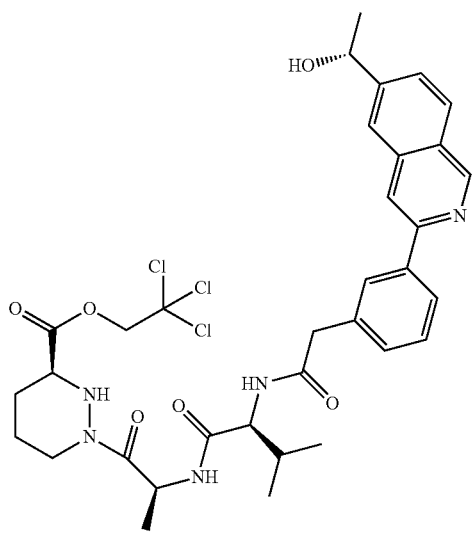

To a solution of 1e (104 mg, 0.21 mmol) in dichloromethane (1.05 mL) was added trimethylsilyl trifluoromethanesulfonate (70 mg, 1.07 mmol) at 0° C. under an argon atmosphere. After 1 h, the reaction mixture was concentrated under reduced pressure. The resulting residue was diluted with acetonitrile (1.05 mL) and 2-(1H-7-azabenzotriazol-1-yl)-1,1,3,3-tetramethyl uronium hexafluorophosphate methanaminium (79.8 mg, 0.210 mmol), N,N-diisopropylethylamine (140 µL, 0.840 mmol), and 65b (64 mg, 0.21 mmol) were sequentially added at 23° C. under an argon atmosphere. After 18 h, the reaction mixture was concentrated under reduced pressure, and the crude residue was purified by silica gel chromatography to afford the title compound (140 mg, 93%) as a faint yellow oil.

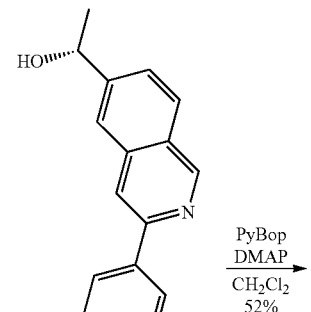

Compound 65

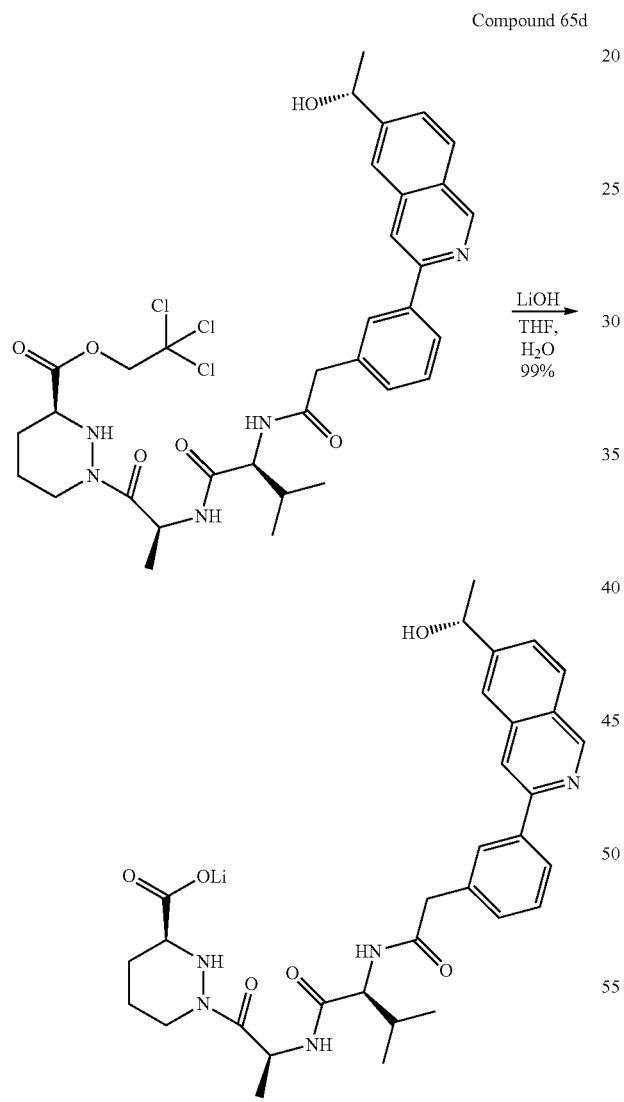

Compound 65d

To a solution of 65c (140 mg, 0.195 mmol) in tetrahydrofuran (0.9 mL) and water (0.3 mL) was added lithium hydroxide hydrate (4.6 mg, 0.195 mmol) at 23° C. under an argon atmosphere. After 3 h, the reaction mixture was concentrated under reduced pressure to afford the title compound (131 mg, 99%) as a white solid lithium carboxylate salt.

To a solution of benzotriazol-1-yl-oxytripyrrolidinophosphonium hexafluorophosphate (35.3 mg, 68 µmol) and 4-dimethylaminopyridine (62.3 mg, 510 µmol) in dichloromethane (5.7 mL) was added 65d (10 mg, 17 µmol) at 23° C. under an argon atmosphere. After 16 h, the reaction mixture was concentrated under reduced pressure and the crude residue was purified by preparative HPLC (Gemini 5u C18 110 Å column, 5-100% acetonitrile/water, 0.1% trifluoroacetic acid modifier) to afford the title compound (6.0 mg, 52%) as a white solid trifluoroacetic acid salt. $^1$H NMR (400 MHz, CD$_3$OD) δ 9.70 (s, 1H), 8.58 (s, 1H), 8.48 (d, J=8.6 Hz, 1H), 8.32 (s, 1H), 7.97-7.87 (m, 2H), 7.79 (d, J=7.9 Hz, 1H), 7.62 (app t, J=7.7 Hz, 1H), 7.53 (d, J=7.8 Hz, 1H), 6.21 (q, J=6.6 Hz, 1H), 5.84-5.71 (m, 1H), 4.45-4.29 (m, 2H), 3.96 (d, J=15.5 Hz, 1H), 3.75 (dd, J=11.1, 2.7 Hz, 1H), 3.64 (d, J=15.5 Hz, 1H), 2.74 (td, J=12.8, 3.1 Hz, 1H), 2.13-1.96 (m, 2H), 1.91 (brd, J=13.0 Hz, 1H), 1.81-1.65 (m, 2H), 1.67 (d, J=6.6

Hz, 3H), 1.62 (d, J=7.1 Hz, 3H), 1.01 (d, J=6.8 Hz, 3H), 0.94 (d, J=6.8 Hz, 3H). HPLC Tr=3.040 min. LCMS (m/z) 572.3 [M+H], Tr=2.07 min.

Example 66

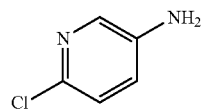

Compound 66a

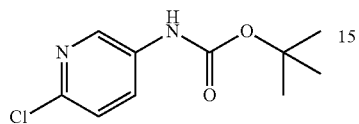

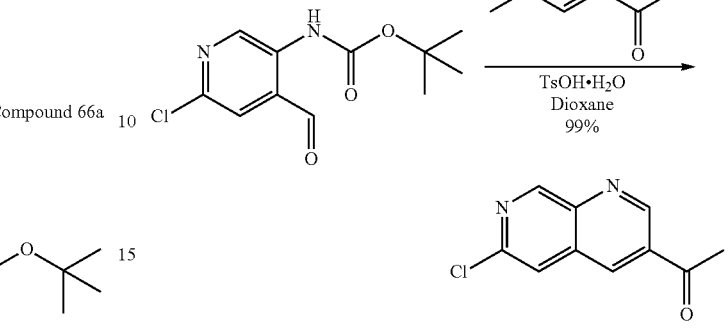

To a solution of 6-chloropyridin-3-amine (5.00 g, 38.8 mmol) in dioxane (194 mL) was added di-tert-butyl dicarbonate (10.2 g, 46.7 mmol) at 23° C. under an argon atmosphere, and the resulting mixture was heated to 100° C. After 17 h, the reaction mixture was allowed to cool to 23° C., and was diluted with water (500 mL). The resulting mixture was extracted with ethyl acetate (2×500 mL), and the combined organic extracts were dried over anhydrous sodium sulfate and were concentrated under reduced pressure. The crude residue was purified by silica gel chromatography (120 g Combiflash HP Gold Column, 0-100% ethyl acetate/iso-hexanes gradient) to afford the title compound (7.69 g, 87%) as a colorless oil.

To a solution of 66b (258 mg, 1.00 mmol) and (E)-4-(dimethylamino)but-3-en-2-one (452 mg, 4.00 mmol) in 1,4-dioxane (10 mL) was added p-toluenesulfonic acid monohydrate (761 mg, 4 mmol) at 23° C. under an argon atmosphere and the resulting mixture was heated to 80° C. After 2 h, the reaction mixture was allowed to cool to 23° C. and was partitioned between saturated aqueous sodium bicarbonate solution (200 mL) and ethyl acetate (200 mL). The layers were split and the aqueous layer was extracted with ethyl acetate (200 mL). The combined organic layers were dried over anhydrous sodium sulfate and were concentrated under reduced pressure. The crude residue was purified by silica gel chromatography to afford the title compound (107 mg, 51%) as an off-white solid.

Compound 66b

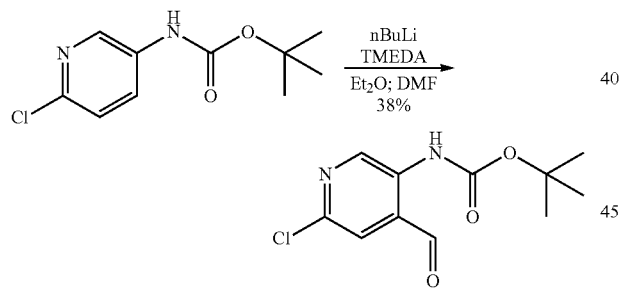

To a solution of 66a (2.00 g, 8.80 mmol) and tetramethylethylenediamine (2.70 mL, 18.0 mmol) in diethyl ether (44 mL) was added n-butyllithium (2.5 M in hexanes, 7.2 mL, 18.0 mmol) at −78° C. under an argon atmosphere. After 10 min, the resulting mixture was allowed to warm to −15° C. over a 50 min period. The reaction mixture was cooled to −78° C., and N,N-dimethylformamide (1.9 g, 26 mmol) was added via syringe. After 30 min, the reaction mixture was quenched with saturated aqueous ammonium chloride solution (20 mL) and was allowed to warm to 23° C. The resulting mixture was extracted with ethyl acetate (2×20 mL), and the combined organic layers were dried over anhydrous sodium sulfate and were concentrated under reduced pressure. The crude residue was purified by silica gel chromatography (120 g Combiflash HP Gold Column, 0-100% ethyl acetate/iso-hexanes gradient) to afford the title compound (849 mg, 38%) as colorless oil.

Dichloro(p-cymene)ruthenium(II)dimer (5 mg, 8 μmol) and (1R,2R)-(−)-N-p-tosyl-1,2-diphenylethylenediamine (7 mg, 19 μmol) were suspended in degassed water (6 mL) and the mixture was degassed with argon for 15 min. The mixture was stirred at 70° C. under argon for 90 min. The resulting yellow solution was cooled to RT. 66c (329 mg, 1.56 mmol), sodium formate (543 mg, 7.98 mmol) and degassed tetrahydrofuran (1 mL) were added and the reaction mixture was degassed for 10 min. The reaction mixture was vigorously stirred at 40° C. for 2.5 h. The reaction mixture was cooled to RT and was extracted with ethyl acetate (20 mL). The organic layer was separated, washed with water (20 mL), brine (20 mL), dried over anhydrous magnesium sulfate, and concentrated under reduced pressure. The residue was purified by silica gel chromatography to afford the title compound (180 mg, 54%) as a solid.

Compound 66e

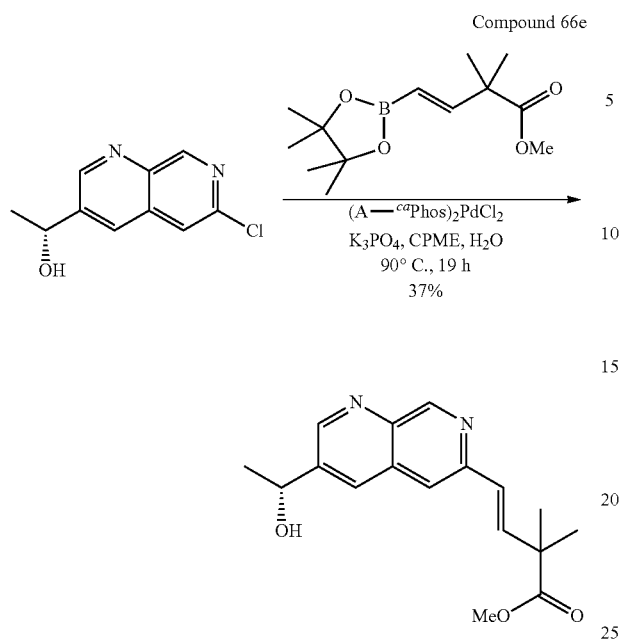

To a suspension of potassium phosphate tribasic (550 mg, 2.59 mmol) in cyclopentyl methyl ether (4.5 mL) and water (3 mL) was added 66d (180 mg, 0.89 mmol) and heated to 90° C. At this temperature, (A-$^{ca}$Phos)$_2$PdCl$_2$ (35 mg, 43 µmol) was added and stirred for 2 min. A solution of (E)-2,2-dimethyl-4-(4,4,5,5-tetramethyl-[1,3,2]dioxaborolan-2-yl)-but-3-enoic acid methyl ester (286 mg, 1.12 mmol) in cyclopentyl methyl ether (4.5 mL) was added dropwise and stirred for 19 h at 90° C. The reaction mixture was cooled to RT, diluted with ethyl acetate (40 mL) and water (20 mL). The layers were separated and the aqueous layer was extracted with ethyl acetate (2×20 mL). The combined organic layers were dried over anhydrous magnesium sulfate, concentrated and the resulting crude residue was purified via silica gel chromatography (24 g SiO$_2$ Isco Rf Gold Column, 0-100% ethyl acetate/iso-hexanes gradient) to afford the title compound (95 mg, 37%) as a pale brown solid.

Compound 66f

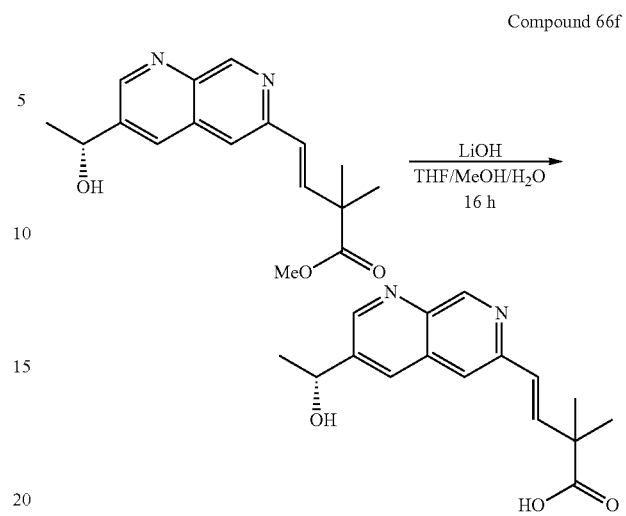

To a solution of 66e (95 mg, 0.32 mmol) in tetrahydrofuran (1.8 mL), methanol (0.6 mL) and water (0.6 mL) was added lithium hydroxide hydrate (15 mg, 0.63 mmol) at 23° C. After 16 h, the resulting mixture was concentrated under reduced pressure and residual solvents were removed azeotropically by addition of toluene (5 mL) followed by concentration under reduced pressure (2×) to afford the title compound. This was used in the subsequent amide coupling without further purification.

Compound 66g

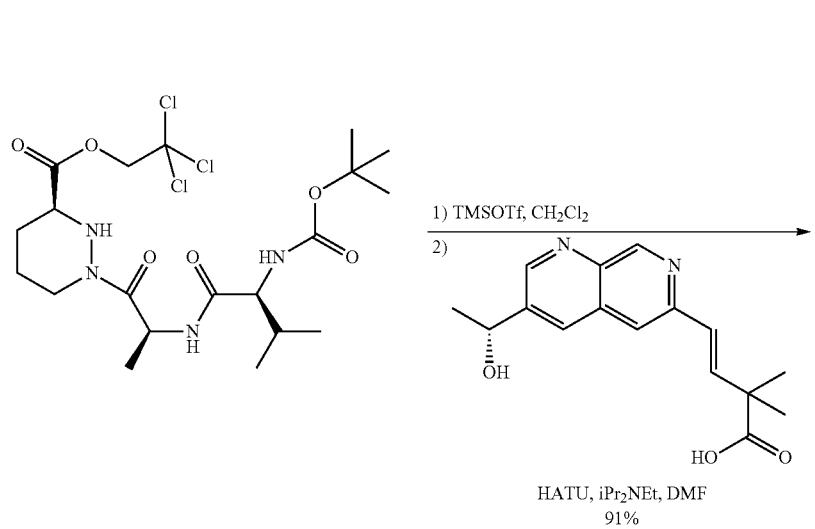

To a solution of 1e (212 mg, 0.40 mmol) in dichloromethane (3 mL) was slowly added trimethylsilyl trifluoromethanesulfonate (106 µL, 0.60 mmol) at 0° C. under an argon atmosphere. After 1 h, the resulting mixture was concentrated under reduced pressure and was used in the subsequent amide coupling without further purification. To a solution of 66f (90.5 mg, 0.32 mmol) in acetonitrile (3 mL), 2-(1H-7-azabenzotriazol-1-yl)-1,1,3,3-tetramethyl uronium hexafluorophosphate methanaminium (180 mg, 0.47 mmol), N,N-diisopropylethylamine (330 µL, 1.90 mmol) and (S)-1-[(S)-2-((S)-2-amino-3-methyl-butyrylamino)-propionyl]-hexahydro-pyridazine-3-carboxylic acid 2,2,2-trichloroethyl ester (232 mg, 0.4 mmol) in acetonitrile (2 mL) were added sequentially at 23° C. After 16 h, the resulting mixture was concentrated under reduced pressure and the residue was purified directly by silica gel chromatography to afford the title compound (201 mg, 91%) as a solid.

Compound 66h

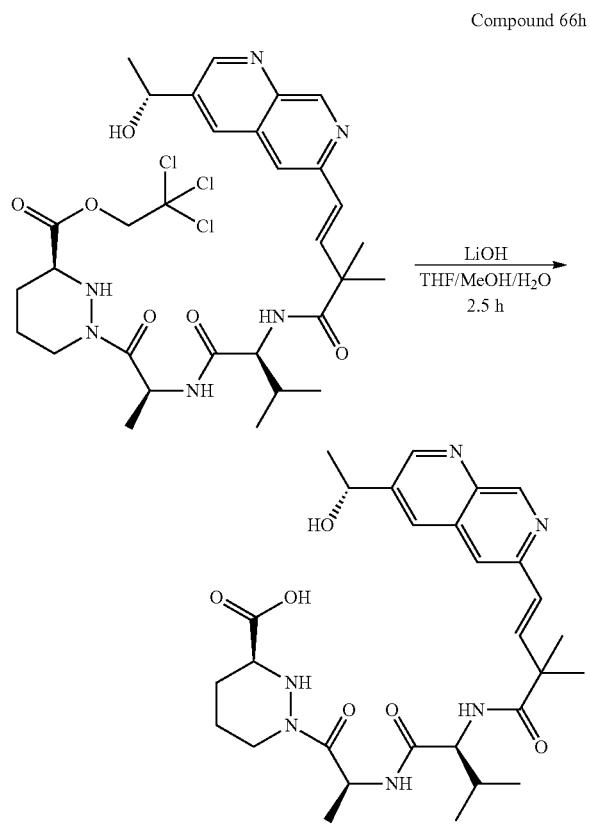

To a solution of 66g (201 mg, 0.29 mmol) in tetrahydrofuran (2 mL), methanol (0.4 mL) and water (0.4 mL) was added lithium hydroxide hydrate (14 mg, 0.57 mmol) at 23° C. After 40 min, lithium hydroxide hydrate (14 mg, 0.57 mmol) was added at 23° C. After 1 h, the resulting mixture was concentrated under reduced pressure and residual solvents were removed azeotropically by addition of toluene (2 mL) followed by concentration under reduced pressure (3×) to afford the title compound. This was used in the subsequent macrolactonization without further purification.

Compound 66

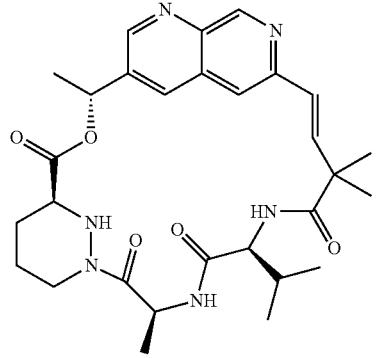

To 2-methyl-6-nitrobenzoic anhydride (43 mg, 0.12 mmol) and 4-dimethylaminopyridine (48 mh, 0.39 mmol) was added 1,2-dichloroethane (20 mL) under nitrogen atmosphere and heated to 50° C. At this temperature, 66h (28 mg, 0.049 mmol) in N,N-dimethylformamide (1 mL) was added dropwise via syringe pump over 6 h. An additional wash of N,N-dimethylformamide (0.5 mL) was then added in the same manner over 15 min. After stirring an additional 1.25 h, reaction mixture was cool to RT. It was diluted with ethyl acetate (20 mL) and washed with water (2×10 mL). The organic layer was dried over anhydrous magnesium sulfate and filtered. The solvent was removed under reduced pressure and the residue was purified by preparative HPLC (Gemini 5u C18 110 Å column, 5-100% acetonitrile/water, 0.1% trifluoroacetic acid modifier) to afford the title compound as a white powder trifluoroacetic acid salt. It was washed with saturated solution of sodium bicarbonate to remove acid impurities formed from 2-methyl-6-nitrobenzoic anhydride to afford the title compound (1.5 mg, 5%) as a white solid. $^1$H NMR (400 MHz, CD$_3$OD) δ 9.19 (s, 1H), 8.86 (d, J=2.1 Hz, 1H), 8.67 (d, J=7.5 Hz, 1H), 8.21 (s, 1H), 7.59 (s, 1H), 6.89 (d, J=9.5 Hz, 1H), 6.58 (d, J=16.1 Hz, 1H), 6.46 (d, J=16.1 Hz, 1H), 6.04 (q, J=6.4 Hz, 1H), 5.52-5.41 (m, 1H), 4.26 (d, J=14.4 Hz, 1H), 4.18 (app t, J=9.1 Hz, 1H), 3.65 (dd, J=11.4, 2.8 Hz, 1H), 2.58 (td, J=12.9, 3.2 Hz, 1H), 1.91-1.75 (m, 3H), 1.68-1.53 (m, 2H), 1.63 (d, J=6.7 Hz, 3H), 1.51 (d, J=7.3 Hz, 3H), 1.43 (s, 3H), 1.26 (s, 3H), 0.87 (d, J=6.7 Hz, 3H), 0.82 (d, J=6.7 Hz, 3H). LCMS (m/z) 551.2 [M+H], Tr=2.19 min.

Example 67

Compound 67a

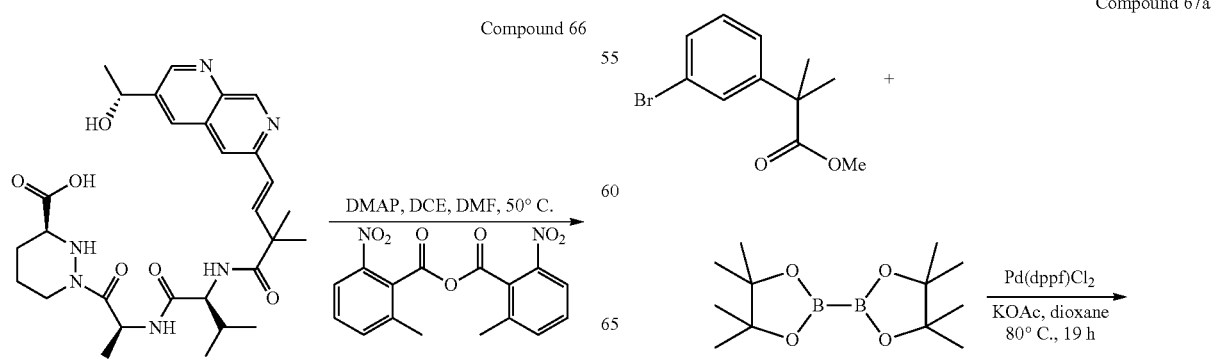

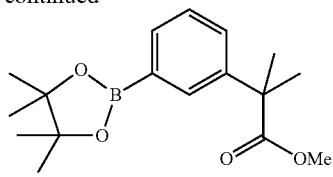

Methyl 2-(3-bromophenyl)-2-methylpropanoate (Pharmabridge, Doylestown, Pa., USA (190 mg, 0.74 mmol), 4,4,4', 4',5,5,5',5'-octamethyl-2,2'-bi(1,3,2-dioxaborolane) (206 mg, 0.81 mmol), [1,1'-bis(diphenylphosphino)ferrocene]dichloropalladium(II), complex with dichloromethane (27 mg, 0.04 mmol) and potassium acetate (217 mg, 2.22 mmol) were placed in a screw cap vial and flushed with a vacuum and argon cycle three times. Anhydrous 1,4-dioxane (4 mL) was added under argon and the resulting mixture was heated to 80° C. for 19 h. The reaction mixture was cool to RT and was diluted with ethyl acetate (20 mL). Celite (~1 g) was added and filtered through a pad of celite. Solvents were removed under reduced pressure to afford the title compound which was used directly in the subsequent reaction.

Compound 67b

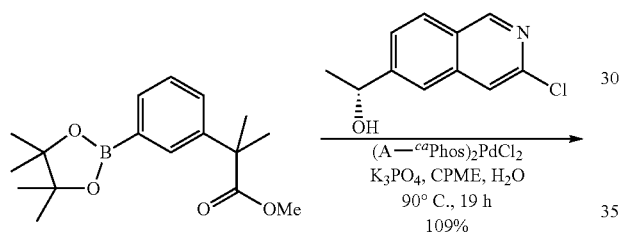

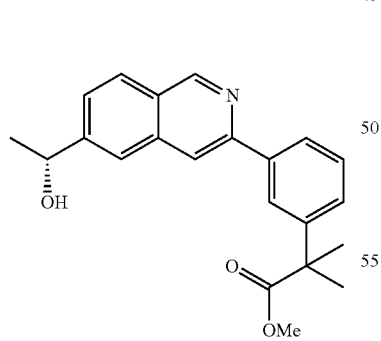

To a suspension of potassium phosphate tribasic (445 mg, 2.10 mmol) in cyclopentyl methyl ether (2.5 mL) and water (1.5 mL) was added (R)-1-(3-chloro-isoquinolin-6-yl)-ethanol (180 mg, 0.89 mmol) and the reaction mixture was heated to 90° C. At this temperature, (A-$^{ca}$Phos)$_2$PdCl$_2$(28 mg, 35 μmol) was added and the reaction mixture was stirred for 2 min. A solution of 67a (225 mg, 0.74 mmol) in cyclopentyl methyl ether (2.5 mL) was added dropwise and stirred for 19 h at 90° C. The reaction mixture was cool to RT, diluted with ethyl acetate (30 mL) and water (15 mL). The layers were separated and the aqueous layer was extracted with ethyl acetate (2×15 mL). The combined organic layers were dried over anhydrous magnesium sulfate, concentrated and the resulting crude residue was purified by silica gel column chromatography to afford the title compound (267 mg, quantitative) as a pale brown solid.

Compound 67c

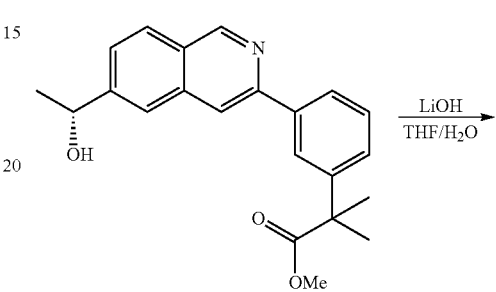

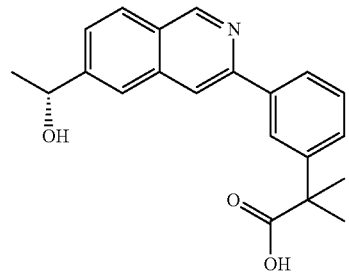

To a solution of 67b (244 mg, 0.7 mmol) in tetrahydrofuran (10 mL), and water (2.5 mL) was added lithium hydroxide hydrate (18.5 mg, 0.77 mmol) at 23° C. After 48 h, lithium hydroxide hydrate (17 mg, 0.70 mmol) was added to the reaction mixture. After 24 h, the reaction mixture was concentrated under reduced pressure and residual solvents were removed azeotropically by addition of toluene (5 mL) followed by concentration under reduced pressure (2×) to afford the title compound. This was used in the subsequent amide coupling without further purification.

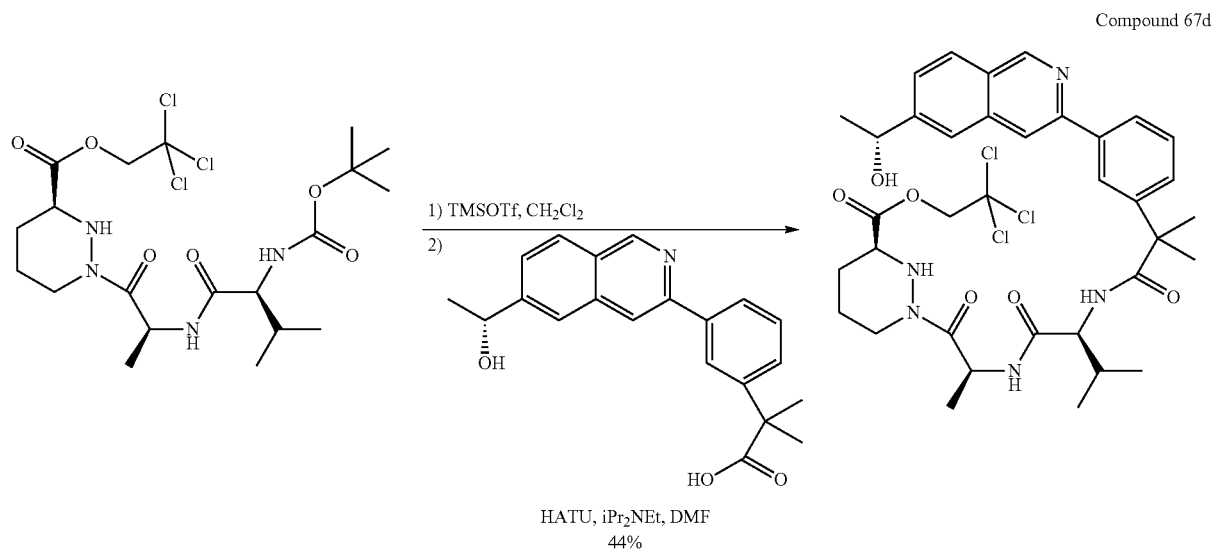

Compound 67d

To a solution of 1e (397 mg, 0.75 mmol) in dichloromethane (5 mL) was slowly added trimethylsilyl trifluoromethanesulfonate (199 μL, 1.12 mmol) at 0° C. under an argon atmosphere. After 1 h, the resulting mixture was concentrated under reduced pressure to give (S)-1-[(S)-2-((S)-2-amino-3-methyl-butyrylamino)-propionyl]-hexahydro-pyridazine-3-carboxylic acid 2,2,2-trichloro-ethyl ester as a triflate salt. This was used in the subsequent amide coupling without further purification. To a solution of 67c (234 mg, 0.7 mmol) in acetonitrile (7 mL), 2-(1H-7-azabenzotriazol-1-yl)-1,1,3,3-tetramethyl uronium hexafluorophosphate methanaminium (532 mg, 1.4 mmol), N,N-diisopropylethylamine (730 μL, 4.2 mmol) and (S)-1-[(S)-2-((S)-2-amino-3-methyl-butyrylamino)-propionyl]-hexahydro-pyridazine-3-carboxylic acid 2,2,2-trichloro-ethyl ester (435 mg, 0.75 mmol) in acetonitrile (3 mL) were added sequentially at 23° C. After 16 h, the resulting mixture was concentrated under reduced pressure and the residue was purified directly by silica gel chromatography (40 g SiO₂ Isco Rf Gold Column, 0-100% ethyl acetate/iso-hexanes gradient) to afford the title compound (230 mg, 44%) as a solid.

-continued

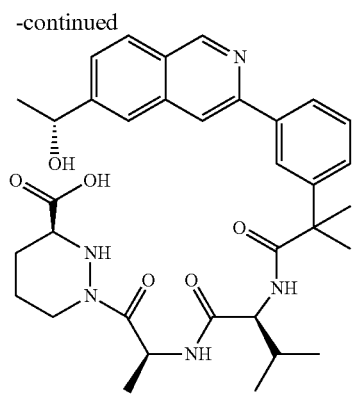

To a solution of 67d (94 mg, 0.13 mmol) in tetrahydrofuran (3 mL), and water (1 mL) was added lithium hydroxide hydrate (3.1 mg, 0.13 mmol) at 23° C. After 48 h, lithium hydroxide hydrate (17 mg, 0.70 mmol) was added to the reaction mixture. After 1 h, the reaction mixture was concentrated under reduced pressure and residual solvents were removed azeotropically by addition of toluene (5 mL) followed by concentration under reduced pressure (2×) to afford the title compound. This was used in the subsequent macrolactonization without further purification.

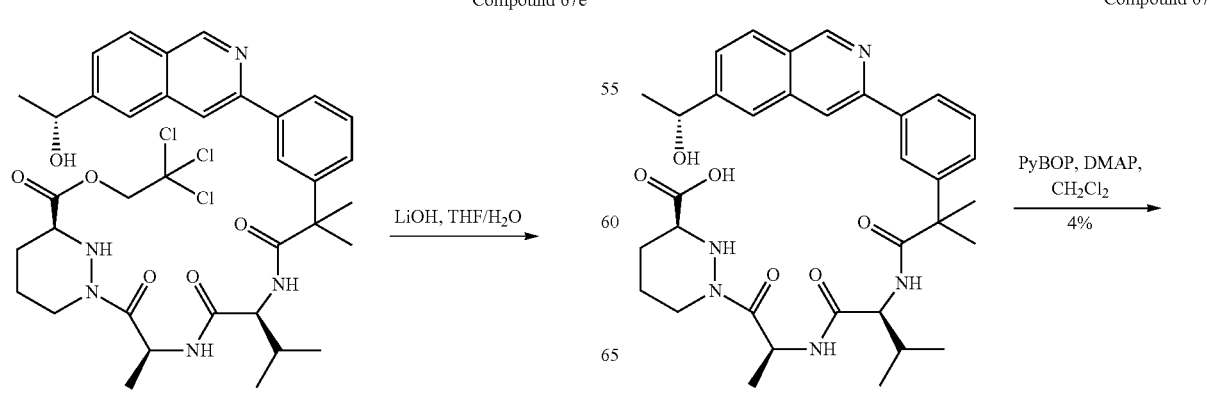

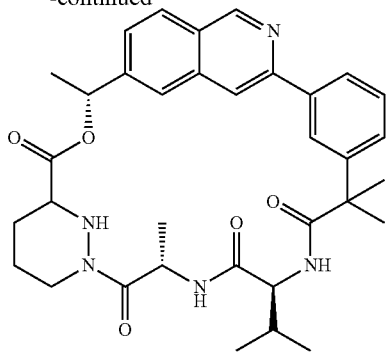

To a suspension of 67e (78 mg, 0.13 mmol) in dichloromethane (42 mL) was added benzotriazol-1-yl-oxytripyrrolidinophosphonium hexafluorophosphate (520 mg, 0.50 mmol) and 4-dimethylaminopyridine (462 mg, 4.0 mmol) at 23° C. After 24 h, the solvent was removed under reduced pressure and the residue was purified by preparative HPLC (Gemini 5u C18 110 Å column, 5-100% acetonitrile/water, 0.1% trifluoroacetic acid modifier) to afford the title compound (3.2 mg, 4%) as a white powder and as a trifluoroacetic acid salt. $^1$H NMR (400 MHz, CD$_3$OD) δ 9.65 (s, 1H), 8.69 (s, 1H), 8.49 (d, J=8.7 Hz, 1H), 8.44 (d, J=8.6 Hz, 1H), 8.34 (s, 1H), 7.90 (dd, J=8.7, 1.5 Hz, 1H), 7.83 (d, J=7.7 Hz, 1H), 7.78 (d, J=7.9 Hz, 1H), 7.74 (s, 1H), 7.69 (app t, J=7.8 Hz, 1H), 6.82 (d, J=8.6 Hz, 1H), 6.21 (q, J=6.5 Hz, 1H), 5.92-5.84 1H), 4.41-4.30 (m, 2H), 3.75 (dd, J=14.4, 6.0 Hz, 1H), 2.71 (td, J=13.0, 3.0 Hz, 1H), 2.06-1.99 (m, 1H), 1.96 (dd, J=14.2, 7.1 Hz, 1H), 1.93-1.86 (m, 1H), 1.75 (s, 3H), 1.73-1.59 (m, 2H), 1.68 (d, J=6.6 Hz, 3H), 1.63 (d, J=7.1 Hz, 3H), 1.47 (s, 3H), 0.96 (d, J=6.8 Hz, 3H), 0.84 (d, J=6.7 Hz, 3H). HPLC Tr=5.319 min. LCMS (m/z) 600.5 [M+H], Tr=2.71 min.

Examples 68 and 69

Compound 68a

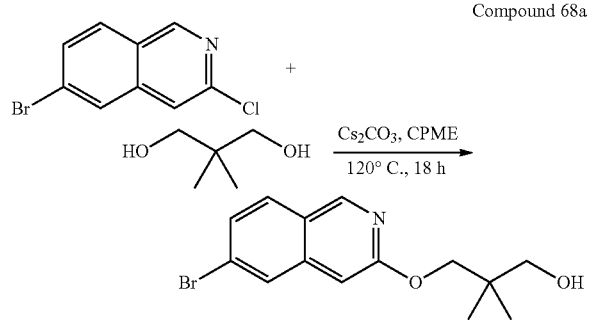

To a solution of 6-bromo-3-chloroisoquinoline (Frontier Scientific, 1.594 g, 6.57 mmol) and 2,2-dimethylpropane-1,3-diol (684 mg, 6.57 mmol) in cyclopentyl methyl ether (20 mL) was added cesium carbonate (2.354 g, 7.23 mmol) at 23° C. The reaction mixture was heated to 120° C. for 18 h. The reaction mixture was cool to RT, diluted with ethyl acetate (50 mL) and washed with water (30 mL), brine (30 mL) and the resulting organic layer was dried over anhydrous magnesium sulfate and concentrated under reduced pressure. The residue was purified by silica gel chromatography (80 g Isco Rf Gold Column, 0-100% ethyl acetate/iso-hexanes gradient) to afford the title compound (461 mg, 23%) as a white solid.

Compound 68b

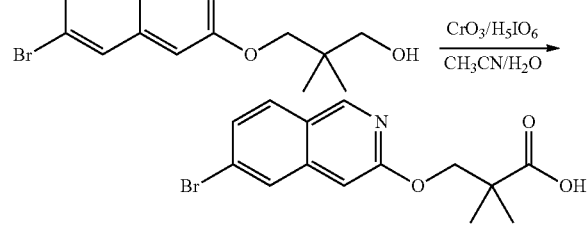

To a solution of 68a (461 mg, 1.49 mmol) in acetonitrile (10 mL) and water (2.5 mL) was added periodic acid (1.698 g, 7.45 mmol) at 23° C. The reaction mixture was cool to 0° C. and chromium trioxide (30 mg, 0.298 mmol) was added in one portion. After 2.5 hour, the reaction mixture was diluted with ethyl acetate (30 mL) and water (30 mL) and the layers were separated. The aqueous layer was extracted with ethyl acetate (30 mL) and combined organic layers were washed with brine, dried over anhydrous magnesium sulfate and concentrated under reduced pressure to afford the title compound which was used without purification (481 mg).

Compound 68c

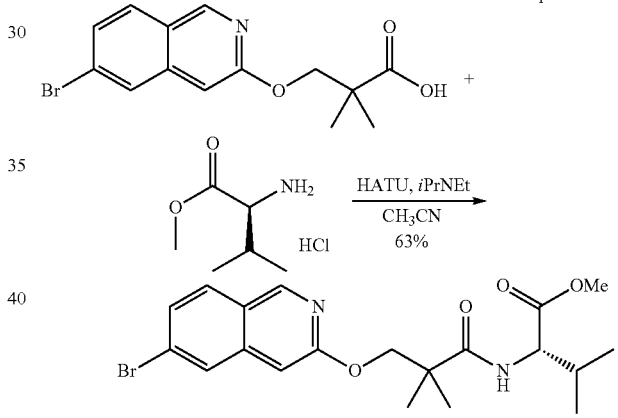

To a solution of 68b (481 mg, 1.49 mmol) in acetonitrile (10 mL), 2-(1H-7-azabenzotriazol-1-yl)-1,1,3,3-tetramethyl uronium hexafluorophosphate methanaminium (1.133 g, 2.98 mmol), N,N-diisopropylethylamine (1.55 mL, 8.94 mmol) and (S)-methyl 2-amino-3-methylbutanoate hydrochloride (749 mg, 4.47 mmol) were added sequentially at 23° C. After 16 h, the resulting mixture was concentrated under reduced pressure and the residue was purified directly by silica gel chromatography (24 g Isco Rf Gold Column, 0-100% ethyl acetate/iso-hexanes gradient) to afford the title compound (412 mg, 63% over 2 steps) as a brown oil.

Compound 68d

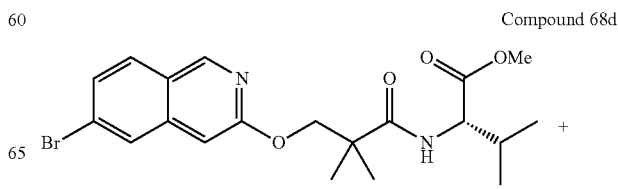

-continued

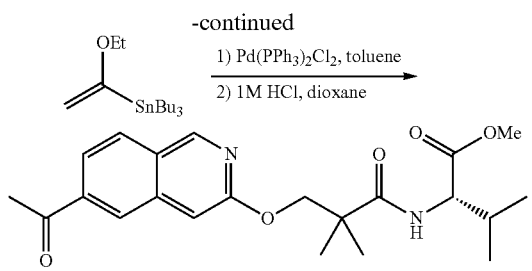

To a suspension of 68c (412 mg, 0.95 mmol) and bis(triphenylphosphine)palladium(II)dichloride in toluene (5 mL) was added tributyl(1-ethoxyvinyl)tin (962 µL, 2.85 mmol) under argon at 23° C. The reaction mixture was heated to 50° C. After 18 h, water (1 mL) was added at 50° C. After 2 h, the reaction mixture was cool to RT, diluted with ethyl acetate (15 mL) and 1 M solution of potassium fluoride (5 mL) was added. The resulting mixture was vigorously stirred at 23° C. After 2 h, the mixture was filtered through a short pad of Celite and washed with ethyl acetate (10 mL). The filtrate was washed with water (15 mL), brine (15 mL), dried over anhydrous magnesium sulfate and concentrated. This residue was dissolved in 1,4-dioxane (8 mL) and 1 M aqueous hydrochloric acid (1 mL) was added at 23° C. After 5 min, the reaction mixture was quenched with a saturated solution of sodium bicarbonate (2 mL) and concentrated to dryness. The residue was taken up in ethyl acetate (20 mL) and water (20 mL) and layers were separated. The aqueous layer was extracted with ethyl acetate (2×10 mL) and the combined organic layers were washed with brine (20 mL), dried over anhydrous magnesium sulfate and concentrated. The residue was purified by silica gel chromatography to afford the title compound (236 mg, 62%) as a brown gum.

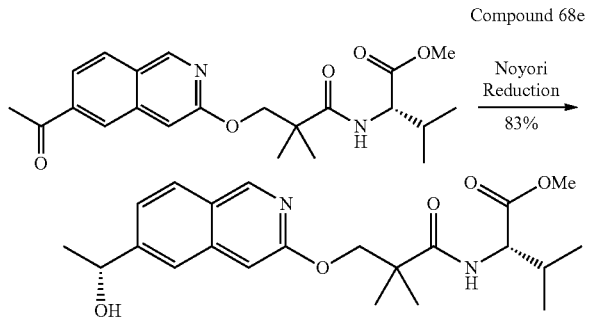

Dichloro(p-cymene)ruthenium(II)dimer (2 mg, 3 µmol) and (1R,2R)-(−)-N-p-tosyl-1,2-diphenylethylenediamine (2.6 mg, 7 µmol) were suspended in degassed water (2.5 mL) and the mixture was degassed with argon for 15 min. The mixture was stirred at 70° C. under nitrogen for 90 min. The resulting yellow solution was cooled to RT. 68d (236 mg, 0.59 mmol), sodium formate (200 mg, 2.95 mmol) and degassed tetrahydrofuran (1.25 mL) were added and the reaction mixture was degassed for 10 min. The reaction mixture was vigorously stirred at 40° C. for 3.5 h. The reaction mixture was cooled to RT and was extracted with ethyl acetate (15 mL). The organic layer was separated, washed with water (20 mL), brine (20 mL), dried over anhydrous magnesium sulfate, and concentrated under reduced pressure. The residue was purified by silica gel chromatography to afford the title compound (196 mg, 83%) as a pale brown solid.

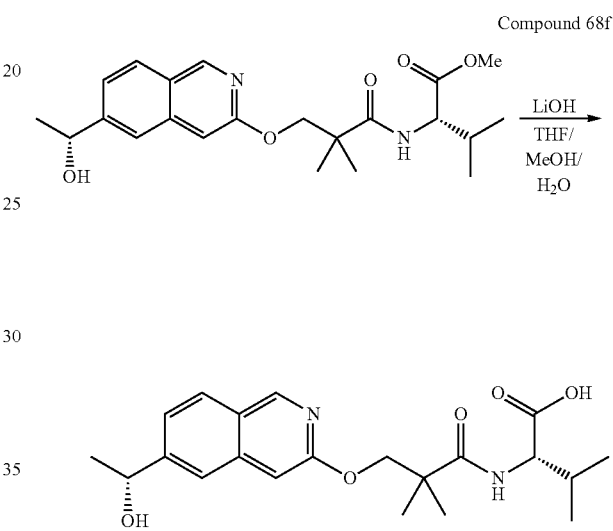

To a solution of 68e (196 mg, 0.487 mmol) in tetrahydrofuran (3 mL), methanol (1 mL) and water (1 mL) was added lithium hydroxide hydrate (23 mg, 0.97 mmol) at 23° C. After 16 h, the reaction mixture was concentrated under reduced pressure. The residue was taken up in ethyl acetate (10 mL) and water (10 mL) and acidified with 1 M aqueous hydrochloric acid solution to pH ~2. The resulting layers were separated. The aqueous layer was extracted with ethyl acetate (2×10 mL) and the combined organic layers were washed with brine, dried over anhydrous magnesium sulfate and concentrated under reduced pressure to afford the title compound which was used without purification.

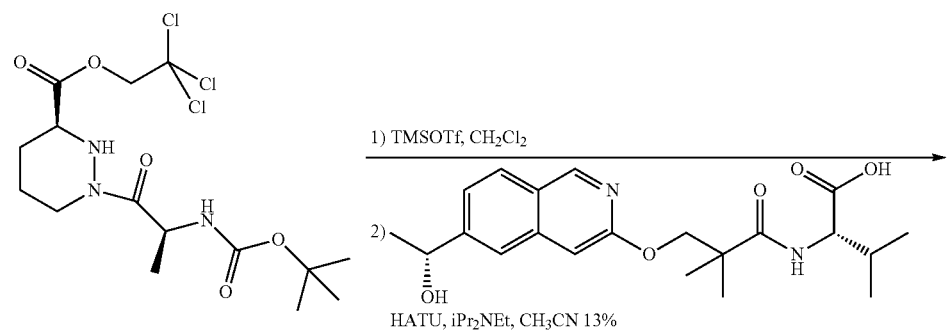

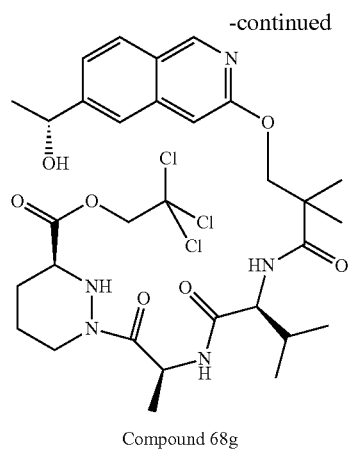

Compound 68g

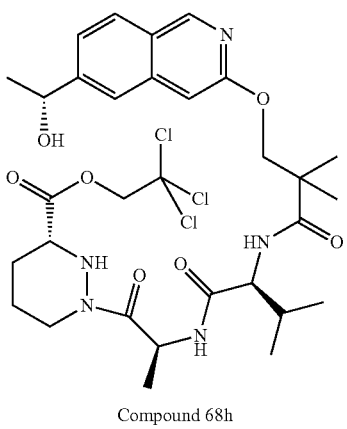

Compound 68h

To a solution of (5)-1-((S)-2-tert-butoxycarbonylamino-propionyl)-hexahydro-pyridazine-3-carboxylic acid 2,2,2-trichloro-ethyl ester (270 mg, 0.62 mmol) in dichloromethane (5 mL) was slowly added trimethylsilyl trifluoromethanesulfonate (165 μL, 0.93 mmol) at 0° C. under an argon atmosphere. After 1 hour, the reaction mixture was concentrated under reduced pressure to afford the triflate salt of (S/R)-1-((S)-2-amino-propionyl)-hexahydro-pyridazine-3-carboxylic acid 2,2,2-trichloro-ethyl ester as yellow oil which was used it without purification. To a solution of 68f (189 mg, 0.49 mmol) in acetonitrile (7 mL), 2-(1H-7-azabenzotriazol-1-yl)-1,1,3,3-tetramethyl uronium hexafluorophosphate methanaminium (278 mg, 0.73 mmol), N,N-diisopropylethylamine (730 μL, 4.2 mmol) and (S/R)-1-((S)-2-amino-propionyl)-hexahydro-pyridazine-3-carboxylic acid 2,2,2-trichloro-ethyl ester (435 mg, 0.62 mmol) in acetonitrile (3 mL) were added sequentially at 23° C. After 16 h, the resulting mixture was concentrated under reduced pressure and the residue was purified directly by silica gel chromatography (40 g SiO$_2$ Isco Rf Gold Column, 0-100% ethyl acetate/iso-hexanes gradient) to afford an inseparable diastereomeric mixture of the title compounds (43 mg, 13%) as a colorless residue.

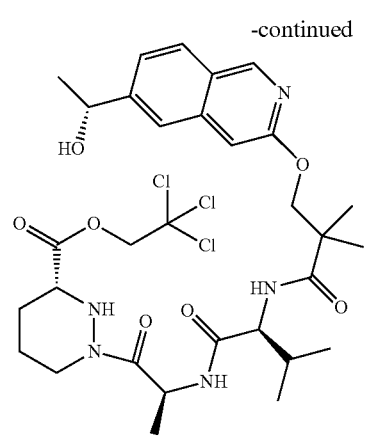

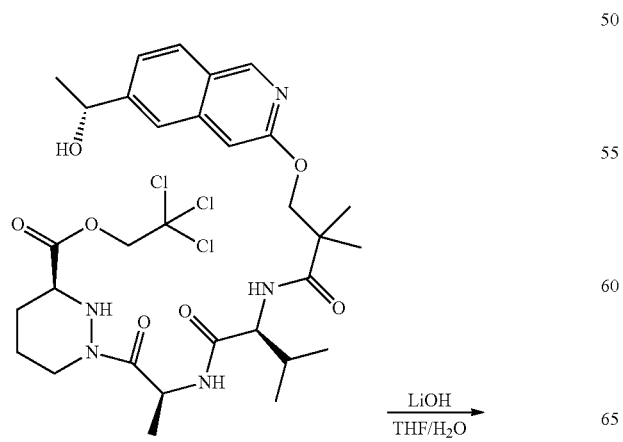

$\xrightarrow{\text{LiOH}}_{\text{THF/H}_2\text{O}}$

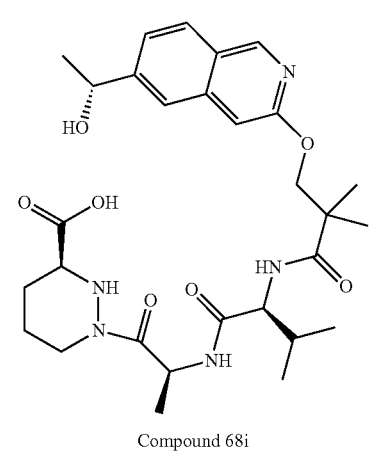

Compound 68i

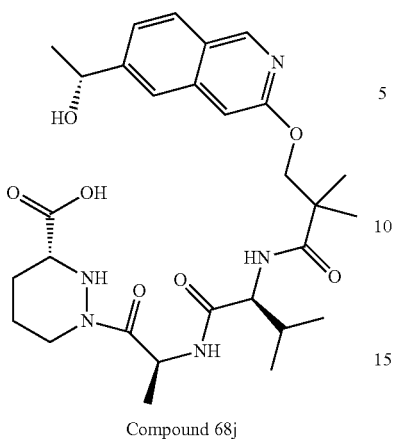

Compound 68j

To a solution of a mixture of 68g and 68h (43 mg, 61 µmol) in tetrahydrofuran (4 mL) and water (2 mL) was added lithium hydroxide hydrate (3.2 mg, 0.13 mmol) at 23° C. After 1 h, the reaction mixture was concentrated under reduced pressure and residual solvents were removed azeotropically by addition of toluene (5 mL) followed by concentration under reduced pressure (2×) to afford the title compounds as a mixture. This was used in the subsequent macrolactonization without further purification. LCMS (m/z) 572.2 [M+H], Tr=2.21 min.

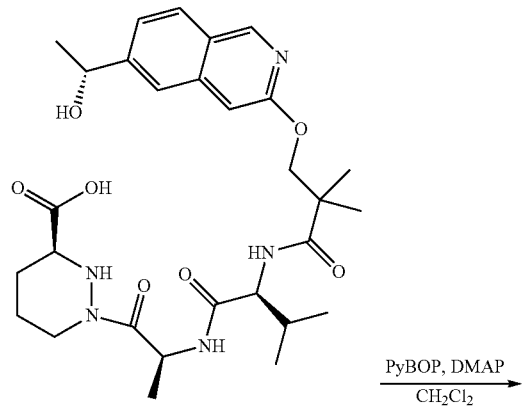

PyBOP, DMAP
CH₂Cl₂

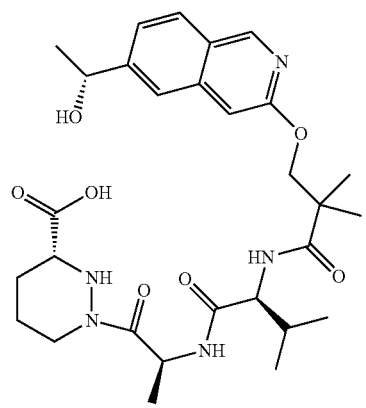

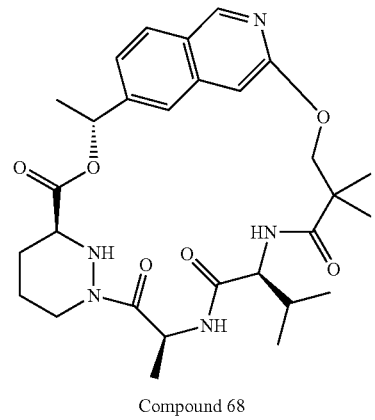

Compound 68

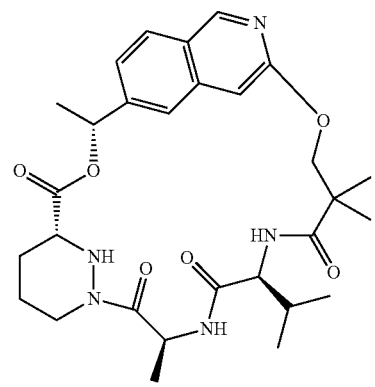

Compound 69

To a suspension of 68i and 68j (34.8 mg, 61 µmol) in dichloromethane (20 mL) was added benzotriazol-1-yl-oxytripyrrolidinophosphonium hexafluorophosphate (127 mg, 0.24 mmol) and 4-dimethylaminopyridine (224 mg, 1.83 mmol) at 23° C. After 24 h, the solvent was removed under reduced pressure and the residue was purified by preparative HPLC (Gemini 5u C18 110 Å column, 5-100% acetonitrile/water, 0.1% trifluoroacetic acid modifier) to afford both compounds (12 mg, 35%) as a ratio mixture of diastereomers. The diastereomers were separated using Chiral preparative HPLC to afford first eluting (Tr=3.73 min) Compound 68 (2.17 mg, 6%) and the second eluting (Tr=5.713 min)

Compound 69 (1.85 mg, 5%). Compound 68: $^1$H NMR (400 MHz, CD$_3$OD) δ 8.89 (s, 7.94 (d, J=8.6 Hz, 1H), 7.86 (s, 1H), 7.37 (dd, J=8.6, 1.5 Hz, 1H), 7.28 (d, J=9.2 Hz, 1H), 6.93 (s, 1H), 6.09 (q, J=6.5 Hz, 1H), 5.54 (q, J=7.2 Hz, 1H), 4.36-4.26 (m, 3H), 4.21 (d, J=9.7 Hz, 1H), 3.69 (dd, J=11.2, 2.6 Hz, 1H), 2.77 (td, J=12.9, 3.0 Hz, 1H), 2.00-1.84 (m, 2H), 1.83-1.77 (m, 1H), 1.76-1.62 (m, 2H), 1.67 (d, J=6.7 Hz, 3H), 1.47 (d, J=7.3 Hz, 3H), 1.38 (s, 3H), 1.27 (s, 3H), 0.99 (d, J=6.7 Hz, 3H), 0.95 (d, J=6.7 Hz, 3H). HPLC Tr=5.866 min. LCMS (m/z) 554.2 [M+H], Tr=2.44 min.

Compound 69: $^1$H NMR (400 MHz, CD$_3$OD) δ 8.78 (s, 1H), 7.83 (d, J=8.6 Hz, 1H), 7.74 (s, 1H), 7.24 (dd, J=8.6, 1.6 Hz, 1H), 7.03 (s, 1H), 5.93 (q, J=6.7 Hz, 1H), 5.35 (q, J=6.8 Hz, 1H), 4.31 (d, J=9.8 Hz, 1H), 4.18 (d, J=13.3 Hz, 1H), 4.02-3.97 (m, 2H), (d, J=10.0 Hz, 1H), 3.65 (dd, J=10.8, 2.8 Hz, 1H), 2.71 (td, J=12.7, 2.8 Hz, 1H), 1.98-1.89 (m, 1H), 1.87-1.77 (m, 2H), 1.73-1.64 (m, 1H), 1.57 (d, J=6.7 Hz, 3H), 1.49 (d, J=7.0 Hz, 3H), 1.40 (s, 3H), 1.13 (s, 3H), 0.89 (d, J=6.7 Hz, 3H), 0.85 (d, J=6.5 Hz, 3H) HPLC Tr=5.951 min. LCMS (m/z) 555.2 [M+H], Tr=2.49 min.

Example 70

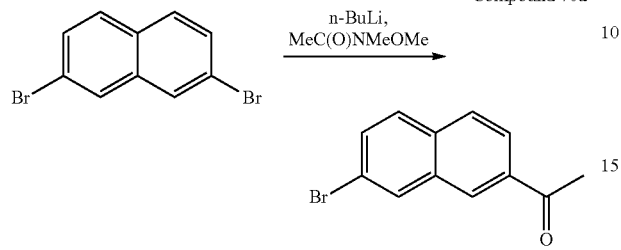

Compound 70a

To 2,7-dibromonaphthalene (1 g, 3.50 mmol) in anhydrous tetrahydrofuran (18 mL), at −78° C. and under an atmosphere of nitrogen, was added a solution of n-butyllithium (2.5 M in hexanes, 1.5 mL, 3.67 mmol) dropwise. The reaction was stirred at −78° C. for 20 min after which N-methoxy-N-methylacetamide (409 µL, 3.85 mmol) was added. After 15 min, the reaction was warmed to RT and stirred for 30 min. The reaction was quenched with 2 M hydrochloric acid and extracted twice with dichloromethane. The combined organic layers were dried through a hydrophobic frit and concentrated in vacuo. The product was purified by silica flash chromatography (iso-hexanes/ethyl acetate, 7/1) to afford the title compound (650 mg, 75%) as a colorless solid.

Compound 70b

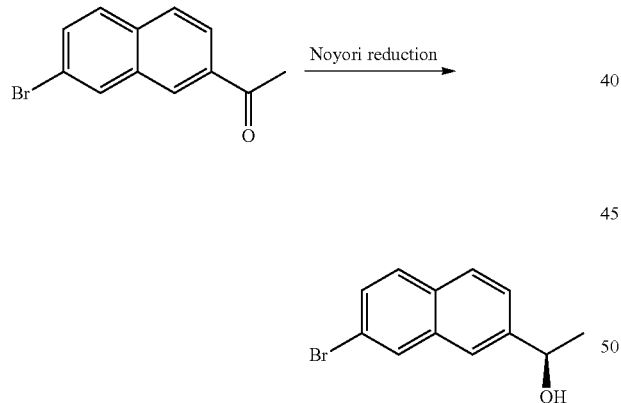

To dichloro(p-cymene)ruthenium(II)dimer (8 mg, 0.013 mmol) in water (5 mL) at RT was added (1R,2R)-(−)-N-p-tosyl-1,2-diphenylethylenediamine (11.5 mg, 0.031 mmol). The system was degassed for 15 min and then heated to 70° C. for 1.5 h. The reaction was cooled and was added a solution of 70a (650 mg, 2.61 mmol) in degassed anhydrous tetrahydrofuran (2 mL) followed by sodium formate (874 mg, 13.1 mmol). The reaction was heated at 40° C. for 3 h, cooled to RT and extracted twice with dichloromethane. The combined organic layers were dried through a hydrophobic frit and concentrated in vacuo. The product was purified by silica gel chromatography (iso-hexanes/ethyl acetate, 4/1) to afford the title compound (450 mg, 69%) as a colorless solid.

Compound 70c

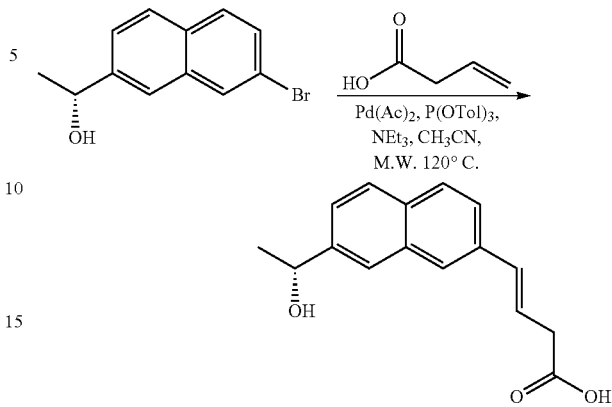

70b (42 mg, 0.17 mmol) was dissolved in acetonitrile (2 mL) in a microwave vial, to the mixture was added 3-butenoic acid (35 mg, 0.41 mmol), palladium(II) acetate (4 mg, 0.017 mmol), tri-(o-tolyl)phosphine (10 mg, 0.034 mmol) and tri-ethylamine (0.12 mL). The vial was heated at 120° in the microwave reactor for 15 mins. The reaction mixture was then filtered, the solvent was evaporated and purified with combi-flash column chromatography (Eluent methanol/dichloromethane 1:3) to afford the title compound (35 mg, 81%) as a yellow solid.

Compound 70d 70c (40 mg, 0.08 mmol) was dissolved in N,N-dimethylformamide (2 mL), to the solution was added 2-(1H-7-azabenzotriazol-1-yl)-1,1,3,3-tetramethyl uronium hexafluorophosphate methanaminium (36 mg, 0.1 mmol), the reaction mixture was stirred at RT for 10 mins. Then (S)-1-[(S)-2-((S)-2-amino-3-methylbutyrylamino)-propionyl]-hexahydro-pyridazine-3-carboxylic acid 2,2,2-trichloro-ethyl ester (0.18 mmol) in N,N-dimethylformamide (1 mL) was added to above reaction mixture followed by triethylamine (32 mg, 0.32 mmol). The reaction mixture was stirred at RT for 1 h, and then it was diluted with ethyl acetate (20 mL) and washed with brine. The aqueous layer was back extracted with ethyl acetate and the combined organic solvent was evaporated and purified with combi-flash column chromatography (Eluent methanol/dichloromethane 1:10) to afford the title compound (68 mg, 65%) as a yellow solid.

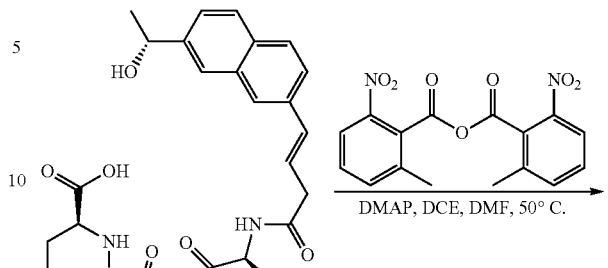

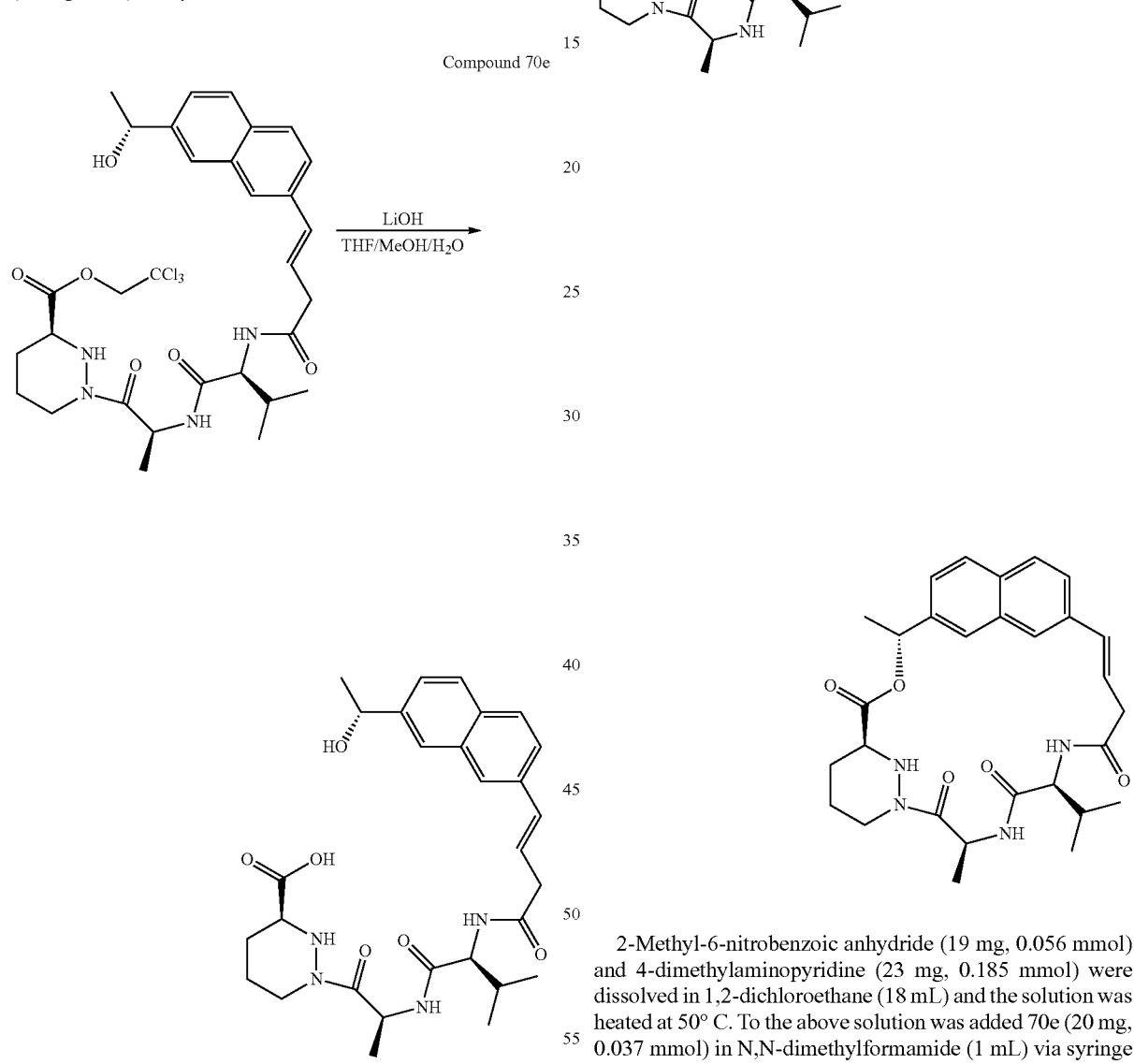

70d (55 mg, 0.08 mmol) was dissolved in the mixture of tetrahydrofuran (2 mL), methanol (1 mL) and water (1 mL). To the solution was added lithium hydroxide hydrate (4 mg, 0.16 mmol). The reaction mixture was stirred at RT for 1 h. Dichloromethane (10 mL) and water (10 mL) were added to the reaction mixture. 1 N Hydrochloric acid was added to the aqueous layer until pH reached 2, the acidic aqueous layer was extracted with dichloromethane (2×10 mL). The organic solvent was then evaporated to afford the title compound (37 mg, 84%) as a white solid.

2-Methyl-6-nitrobenzoic anhydride (19 mg, 0.056 mmol) and 4-dimethylaminopyridine (23 mg, 0.185 mmol) were dissolved in 1,2-dichloroethane (18 mL) and the solution was heated at 50° C. To the above solution was added 70e (20 mg, 0.037 mmol) in N,N-dimethylformamide (1 mL) via syringe pump in 10 h. The reaction mixture was stirred at 50° C. for 2 h after the completion of addition. The solvent was then evaporated and the residue was purified by reverse phase preparative HPLC (0-100% acetonitrile/water) to afford the title compound (4 mg, 22%) as a white solid. $^1$H NMR (400 MHz, CD$_3$OD) δ 7.79-7.72 (m, 3H), 7.52 (dd, J=1.6, 8.8 Hz, 1H), 7.41 (s, 1H), 7.33 (dd, J=8.4, 1.6 Hz, 1H), 6.48 (d, J=16.4 Hz, 1H), 6.31-6.24 (m, 1H), 6.02 (q, J=7.6 Hz, 1H), 4.64 (d, J=12.4 Hz, 1H), 4.40 (d, J=12.8 Hz, 1H), 4.30 (d, J=10.4 Hz, 1H), 3.78-3.72 (m, 1H), 3.36-3.32 (m, 2H), 2.99-2.93 (m, 1H), 2.77-2.71 (m, 1H), 1.99-1.69 (m, 5H), 1.66 (d, J=6.8 Hz, 3H), 1.58 (d, J=7.2 Hz, 3H), 0.99 (d, J=6.8 Hz, 6H). LCMS (m/z) 521.1 [M−H], Tr=3.18 min.

Example 71

Compound 71

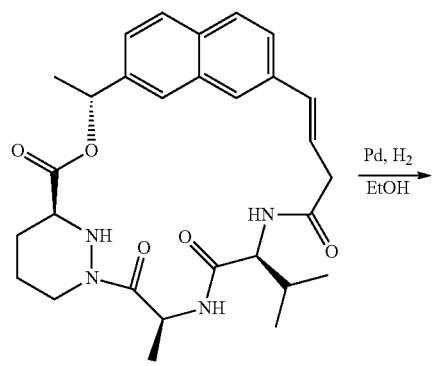

Compound 70 (5 mg, 0.01 mmol) was dissolved in ethanol (5 mL) under argon, to the solution was added Pd (10% on activated carbon, 3 mg). The reaction flask was then purged and then charged with H$_2$ using a balloon. The reaction was filtered through Celite after 2 h, the filtrate was evaporated under reduced pressure and purified by reverse phase preparative HPLC (0-100% acetonitrile/water) to afford the title compound (3.2 mg, 64%) as a white powder. $^1$H-NMR (400 MHz, CD$_3$OD) δ 8.47 (d, J=6.0 Hz, 1H), 7.97 (d, J=8.8 Hz, 1H), 7.69-7.62 (m, 3H), 7.31 (s, 1H), 7.24-7.19 (m, 2H), 5.97 (dd, J=12.8, 6.0 Hz, 1H), 5.62 (pent, J=7.2 Hz, 1H), 4.76-4.16 (m, 1H), 4.10 (app t, J=12.8 Hz, 1H), 4.05-3.69 (m, 1H), 2.85 (br s, 1H), 2.73-2.41 (m, 2H), 2.40-2.37 (m, 1H), 2.10-1.93 (m, 1H), 1.92-1.70 (m, 6H), 1.53 (d, J=6.8 Hz, 3H), 1.49 (d, J=7.6 Hz, 3H), 0.99 (d, J=6.8 Hz, 6H). LCMS (m/z) 523.140 [M+H], Tr=3.16 min.

Example 72

Compound 72

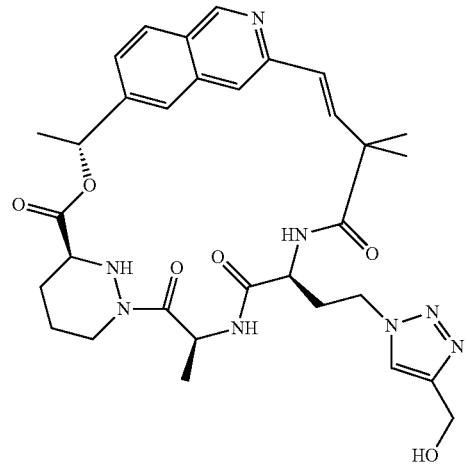

Into an oven dried, argon purged flask Compound 49 (10 mg, 0.017 mmol), copper(I) iodide (1 mg, 0.005 mmol) and prop-2-yn-1-ol (4 mg, 0.07 mmol) were added. The flask was sealed and repurged with argon three times. Anhydrous N,N-dimethylformamide (5 mL) was added and the reaction mixture was repurged with argon three times. This reaction mixture was stirred at RT for 12 h. After evaporation of the solvent under reduced pressure, the crude residue was dissolved in ethyl acetate (10 mL) and filtered through filter aid and the filter pad was washed with ethyl acetate (10 mL). After concentration under reduced pressure, the residue was purified by silica gel chromatography (gradient from 0-40% ethyl acetate and methanol (4/1) in iso-hexanes) to afford the title compound (10 mg, 93%) as a white solid after evaporation. R$_f$=0.33, 10% methanol in dichloromethane. $^1$H NMR (400 MHz, CD$_3$OD) δ 9.05 1H), 7.95 (d, J=8.6 Hz, 1H), 7.94 (s, 1H), 7.82 (s, 1H), 7.50 (s, 1H), 7.46 (d, J=8.6 Hz, 1H), 6.49 (d, J=16.0 Hz, 1H), 6.40 (d, J=16.0 Hz, 1H), 5.95 (m, 1H), 5.50 (m, 1H), 4.59-4.53 (m, 3H), 4.36 (m, 2H), 4.30 (m, 1H), 3.68 (m, 1H), 2.80 (m, 1H), 2.60 (m, 1H), 2.23 (m, 1H), 2.14 (m, 1H), 1.90-1.58 (m, 4H), 1.57 (d, J=6.6 Hz, 3H), 1.55 (d, J=7.6 Hz, 3H), 1.41 (s, 3H), 1.27 (s, 3H). LCMS (m/z) 633.4 [M+H], Tr=2.66 min.

Example 73

Compound 73a

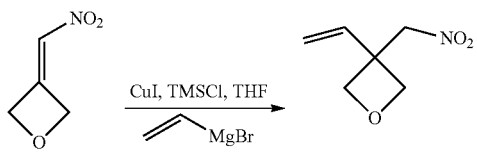

To 3-Nitromethylene-oxetane (*Angew. Chem. Int. Ed.* 2006, 45 (46), 7736, 2.5 g, 21.7 mmol) in anhydrous tetrahydrofuran (40 mL) at RT and under an atmosphere of nitrogen was added copper(I) iodide (413 mg, 2.17 mmol) and chlorotrimethylsilane (3.0 mL, 23.9 mmol). The resulting yellow solution was stirred for 5 min and cooled to between −15° C. and −11° C. with a methanol ice bath. Vinyl magnesium bromide (43.5 mL, 43.5 mmol, 1.0 M in tetrahydrofuran) was slowly added over 3 h via a syringe pump. Following the addition the reaction was quenched with a saturated aqueous solution of ammonium chloride, filtered and extracted with diethyl ether (3×). The combined organics were dried through a hydrophobic frit and concentrated in vacuo. The residue was purified by silica gel chromatography using diethyl ether to give the title compound as a yellow oil (2.0 g, 64%).

Compound 73b

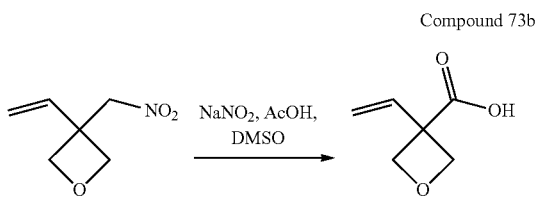

To 73a (600 mg, 4.2 mmol) in anhydrous dimethylsulfoxide (13 mL) was added acetic acid (2.4 mL, 42 mmol) and sodium nitrite (869 mg, 12.6 mmol) and the mixture heated to 35° C. for 16 h. The reaction was cooled to RT and diluted with water. The pH was adjusted to pH 3-4 with 10% aqueous hydrochloric acid and the product extracted with diethyl ether (3×) and diethyl ether/ethyl acetate (1:1). The combined organics were dried through a hydrophobic frit and concentrated in vacuo. The residue was purified by silica gel chromatography using iso-hexanes/ethyl acetate (2/1 then 1/1) to afford impure acid. This was dissolved in diethyl ether and extracted with a saturated solution of sodium carbonate. The aqueous was acidified to pH 2 with concentrated hydrochloric acid and extracted with ethyl acetate (3×). The organics were dried through a hydrophobic frit and concentrated in vacuo to give the title compound as a yellow oil (228 mg, 43%).

Compound 73c

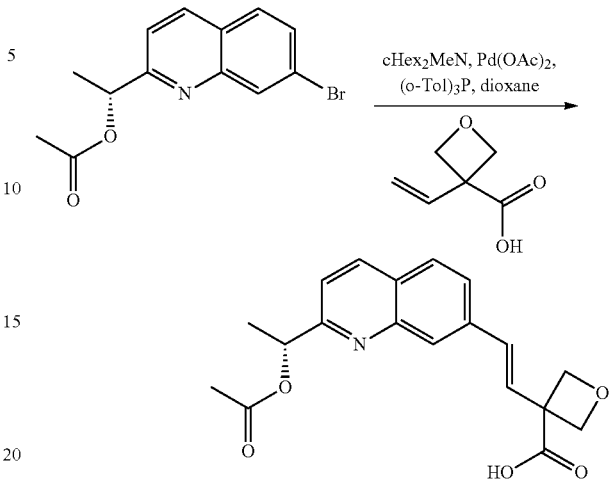

To 73b (150 mg, 1.18 mmol) in anhydrous dioxane (1 mL), was added acetic acid (R)-1-(7-bromo-quinolin-2-yl)-ethyl ester (347 mg, 1.18 mmol) followed by dicyclohexylmethylamine (0.76 mL, 3.54 mmol), palladium(II) acetate (53 mg, 0.24 mmol) and Tri(o-tolyl)phosphine (72 mg, 0.24 mmol). The mixture was heated at 100° C. for 1 hour. An additional amount of palladium(II) acetate (26 mg, 0.12 mmol) and Tri(o-tolyl)phosphine (36 mg, 0.12 mmol) was added and heating continued at 100° C. for a further 45 min. The reaction was cooled to RT and 2M HCl added until pH 3-4 was reached. The product was extracted with ethyl acetate (3×) and ethyl acetate/10% methanol (2×). The combined organics were dried through a hydrophobic frit and concentrated in vacuo to yield the title compound as a brown oil.

Compound 73d

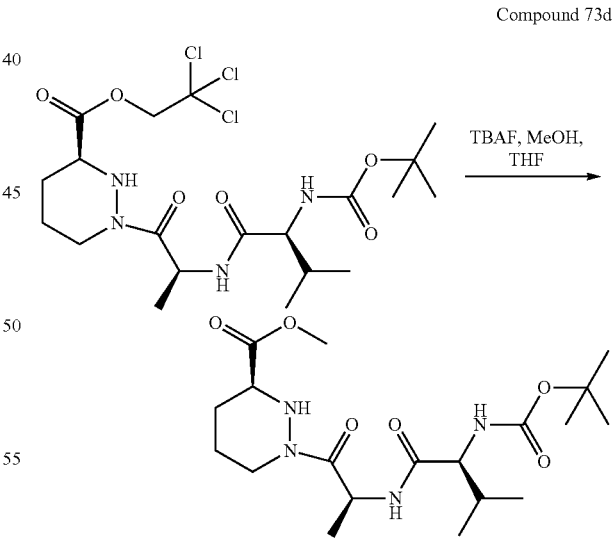

A solution of 1e (3.01 g, 5.66 mmol) in tetrahydrofuran:methanol (1:1, 60 mL) was stirred at 0° C. Tetra-n-butylammonium fluoride (1 M in tetrahydrofuran, 11.3 mL, 11.3 mmol) was added and the reaction mixture was stirred at RT for 22 h. The solvent was evaporated and the residue was purified by silica gel chromatography using iso-hexane to iso-hexane/ethyl acetate 1:1 afford the title compound (2.14 g, 91%) as a white foam.

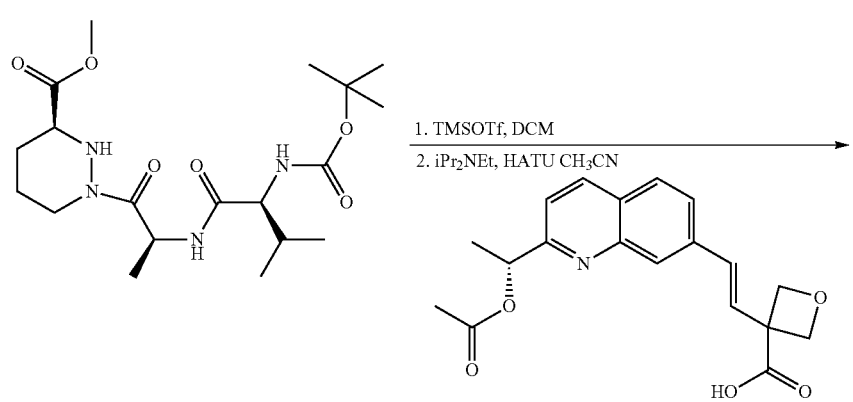

1. TMSOTf, DCM
2. iPr₂NEt, HATU CH₃CN

Compound 73e

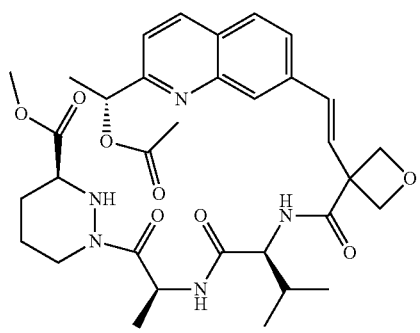

To 73d (365 mg, 0.88 mmol) in anhydrous dichloromethane (15 mL) at 0° C. and under an atmosphere of nitrogen, was added trimethylsilyl trifluoromethanesulfonate (239 µL, 1.32 mmol). The reaction mixture was stirred at 0° C. for 1 hour before adding N,N-diisopropylethylamine (613 µL, 3.52 mmol) and then concentrated in vacuo, and co-evaporated with toluene to afford (S)-1-[(S)-2-((S)-2-amino-3-methyl-butyrylamino)-propionyl]-hexahydro-pyridazine-3-carboxylic acid 2,2,2-trichloro-ethyl ester as a white solid. To 73c (300 mg, 0.88 mmol) in anhydrous acetonitrile (9 mL) at 0° C. and under an atmosphere of nitrogen was added N,N-diisopropylethylamine (766 µL, 4.4 mmol) and 2-(1H-7-azabenzotriazol-1-yl)-1,1,3,3-tetramethyl uronium hexafluorophosphate methanaminium (401 mg, 1.06 mmol). The solution was stirred at 0° C. for 3 min before adding a solution of (S)-1-[(S)-2-((S)-2-amino-3-methyl-butyrylamino)-propionyl]-hexahydro-pyridazine-3-carboxylic acid 2,2,2-trichloro-ethyl ester in anhydrous acetonitrile (2 mL). The reaction was warmed to RT stirred for 2 h. The reaction was quenched with 1M HCl and extracted with ethyl acetate (3×). The combined organic layers were dried through a hydrophobic frit and concentrated in vacuo. The residue was purified by silica gel chromatography using ethyl acetate to give the title compound as a viscous yellow oil (160 mg, 22%, 2 steps).

Compound 73

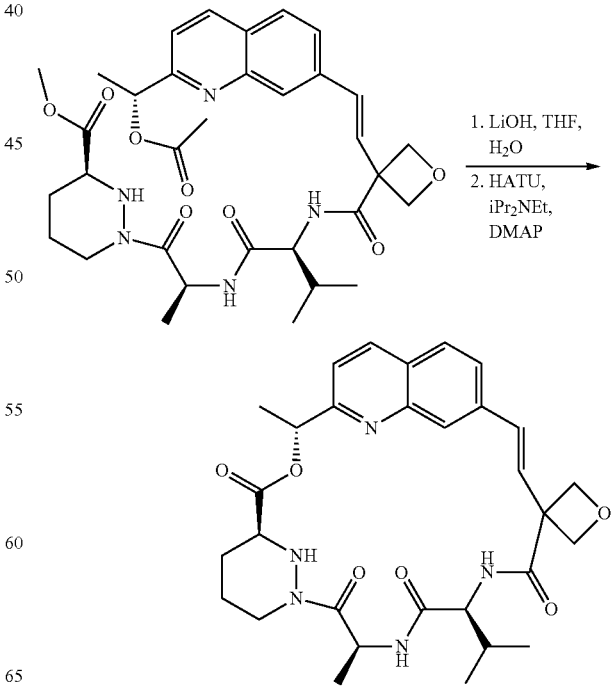

1. LiOH, THF, H₂O
2. HATU, iPr₂NEt, DMAP

To 73e (160 mg, 0.25 mmol) in tetrahydrofuran (10 mL) and water (2 mL) was added lithium hydroxide monohydrate (53 mg, 1.25 mmol) at 0° C. The reaction was stirred at 0° C. for 2 h and quenched by adding 2M aqueous hydrochloric acid (0.63 mL). The reaction was concentrated in vacuo, followed by co-evaporation from toluene/methanol (3×) and then toluene (3×) and dried on a high vacuum for 15 min. The resulting residue was dissolved in anhydrous tetrahydrofuran (83 mL) and at RT was added N,N-diisopropylethylamine (223 µL, 1.25 mmol), 2-(1H-7-azabenzotriazol-1-yl)-1,1,3,3-tetramethyl uronium hexafluorophosphate methanaminium (114 mg, 1.3 mmol) and 4-dimethylaminopyridine (3 mg, 0.03 mmol). The reaction was stirred for 24 h, diluted with ethyl acetate and washed with 1M HCl (1×) and brine (1×). The organic layer was dried through a hydrophobic frit and concentrated in vacuo. The residue was purified by silica gel chromatography using ethyl acetate/methanol 1:0 then 20/1 to give a viscous yellow oil (52 mg). This was further purified by preparative thin layer chromatography (ethyl acetate) to afford the title compound as a white solid which was triturated with diethyl ether, filtered and vacuum dried. (22 mg, 16%, 2 steps). $^1$H NMR (300 MHz, CDCl$_3$) 0.96 (d, J=6.5 Hz, 3H), 1.00 (d, J=6.5 Hz, 3H), 1.50 (d, J=7.1 Hz, 3H), 1.69 (d, J=6.9 Hz, 3H), 1.81-2.16 (m, 4H), 2.63-2.74 (m, 1H), 3.26-3.38 (m 1H), 3.70-3.83 (m, 1H), 3.98 (d, J=12.3 Hz, 1H), 4.28 (t, J=9.8 Hz, 1H), 4.33-4.43 (m, 1H), 4.57 (d, J=5.8 Hz, 1H), 4.86 (q, J=6.7 Hz, 2H), 5.13 (d, J=5.8 Hz, 1H), 5.73 (t, J=6.9 Hz, 1H), 5.96 (q, J=6.7 Hz, 1H), 6.24 (d, J=16.3 Hz, 1H), 6.61-6.73 (m, 1H), 7.00 (d, J=16.3 Hz, 1H), 7.09-7.20 (m, 1H), 7.40 J=8.5 Hz, 1H), 7.58 (s, 1H), 7.81-7.93 (m, 2H), 8.22 (d, J=8.7 Hz, 1H). LCMS (m/z)=564.2 [M+H], Tr=1.96 min.

Example 74

Compound 74

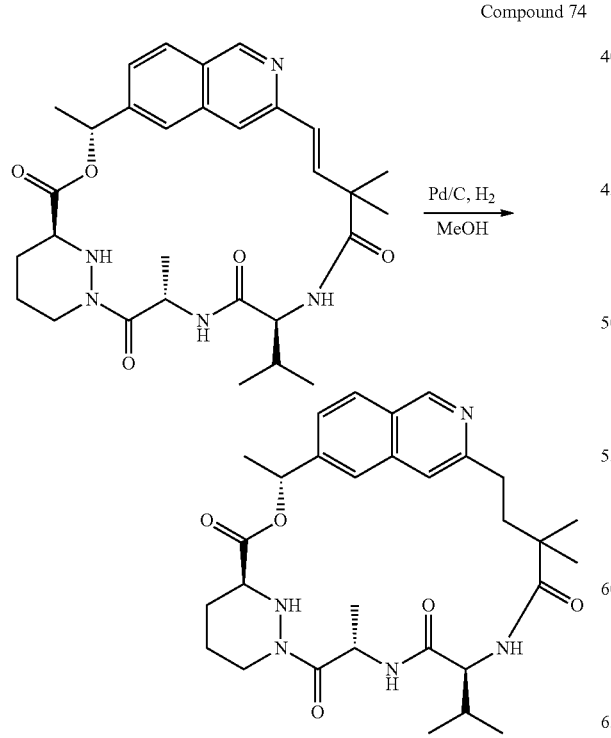

Compound 57 (20 mg, 0.036 mmol) was dissolved in methanol (5 mL) and added catalytic amount of 10% Pd on carbon. The reaction mixture was stirred under atmosphere hydrogen for 2 h. The catalyst was removed by filtration and the eluent was concentrated under reduced pressure. Purification by reverse phase preparative HPLC gave the title compound (8.4 mg, 42% yield) as a white powder. $^1$H NMR (300 MHz, CD$_3$OD): δ 9.61 (s, 1H), 8.42 (d, J=9.0 Hz, 1H), 7.99 (s, 1H), 7.89 (d, J=9.0 Hz, 1H), 7.83 (br s, 1H), 7.29 (d, J=8.7 Hz, 1H), 6.27-6.21 (m, 1H), 5.92-5.82 (m, 1H), 3.96-3.5 (m, 4H), 3.28-3.19 (m, 1H), 3.08-2.98 (m, 1H), 2.30-2.20 (m, 1H), 2.10-1.90 (m, 4H), 1.78-1.72 (m, 5H), 1.56-1.51 (m, 6H), 1.21 (s, 3H), 0.89 (d, J=7.2 Hz, 6H). LCMS (m/z): 552.3 [M+H], Tr=1.74 min.

Example 75

Compound 75a

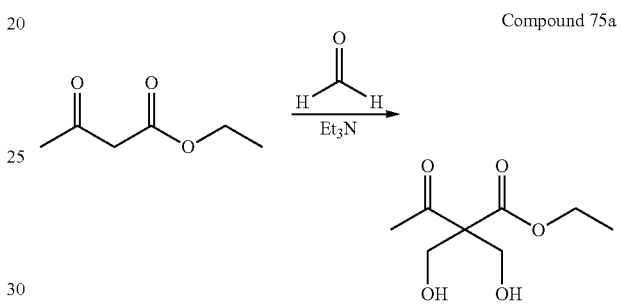

A solution of ethyl acetoacetate (20 g, 19.4 mL, 0.154 mol) in a mixture of dioxane (120 mL) and aqueous formaldehyde (37% solution in water, 57.7 mL, 0.77 mol) was stirred at RT. Triethylamine (1.0 M in tetrahydrofuran, 7.7 mL, 7.7 mmol) was added and the reaction mixture was heated at 60° C. for 20 h and then heated at 100° C. for 4 h. The reaction mixture was cooled to RT and was poured into water (1500 mL). The aqueous solution was washed with toluene. The aqueous layer was concentrated to ~50% of the initial volume and extracted with ethyl acetate. The organic extracts were combined and evaporated. The residue was purified by silica gel chromatography using a gradient of iso-hexane to iso-hexane/ethyl acetate 1:1 followed by silica gel chromatography using a gradient of iso-hexane to iso-hexane/ethyl acetate 3:2 to afford the title compound (2.33 g, 8%) as a yellow oil.

Compound 75b

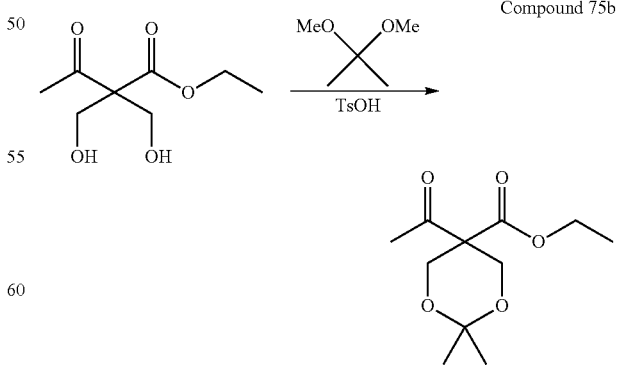

A solution of 75a (2.10 g, 11 mmol), 2,2-dimethoxypropane (13.5 mL, 110 mmol) and 4-toluenesulfonic acid hydrate (209 mg, 1.1 mmol) in acetone (8 mL) was stirred at RT for 18 h. Saturated sodium hydrogen carbonate solution was added and the mixture was extracted with ethyl acetate. The organic extracts were combined, washed with water and brine. The organic layer was filtered through a hydrophobic frit and the filtrate was evaporated. The residue was purified by silica gel chromatography using a gradient of iso-hexane/ ethyl acetate 1:5 to 3:7 to afford the title compound (1.88 g, 74%) as a colorless oil.

Compound 75c

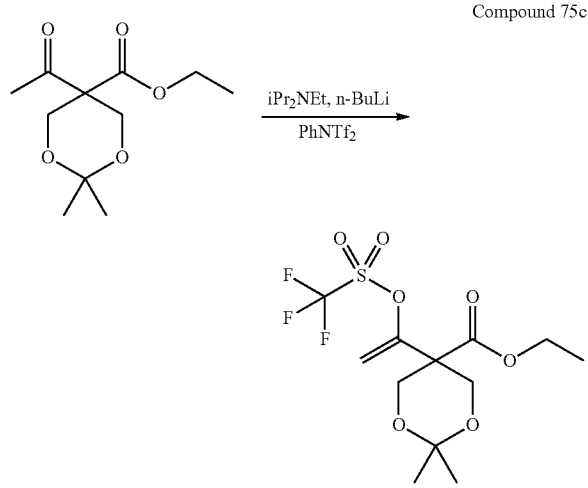

A solution of N,N-diisopropylethylamine (0.55 mL, 3.9 mmol) in tetrahydrofuran (20 mL) was stirred at −78° C. under nitrogen. n-Butyl lithium (1.6 M in hexane, 2.25 mL, 3.6 mmol) was added dropwise and the reaction mixture was warmed to 0° C. The reaction mixture was stirred at 0° C. for 5 min and then cooled to −78° C. A solution of 75b (690 mg, 3.0 mmol) in tetrahydrofuran (3 mL) was added dropwise and the reaction mixture was stirred at −78° C. for 15 min. A solution of N-phenyl-(bistrifluoromethanesulfonamide) (1.18 g, 3.3 mmol) in tetrahydrofuran (10 mL) was added dropwise over 5 min and the reaction mixture was stirred at −78° C. for 15 min. The cooling bath was removed and the reaction mixture was warmed to RT and then stirred at RT for 90 min. The solvent was evaporated and diethyl ether (30 mL) was added. The solution was cooled to 5° C. and was washed with cold 1 M sodium hydroxide solution (3×30 mL). The organic layer was separated, washed with brine, dried over anhydrous sodium sulfate, filtered and the solvent evaporated to afford the title compound (960 mg, 88%) as a yellow oil which was used directly in the next step.

Compound 75d

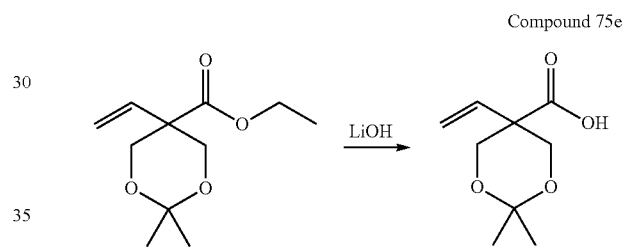

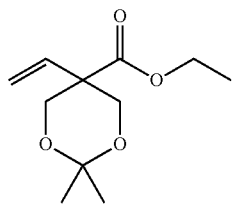

A solution of 75c (470 mg, 1.3 mmol) and tri-n-butylamine (721 mg, 0.93 mL, 3.9 mmol) in N,N-dimethylformamide (3 mL) was stirred at RT under nitrogen. Bis(triphenylphosphine)palladium(II)dichloride (45 mg, 0.065 mmol) and formic acid (120 mg, 0.1 mL, 2.6 mmol) was added and the reaction mixture was heated at 60° C. for 90 min. The reaction mixture was cooled to RT and ethyl acetate and water was added. The organic extract was separated, washed with water (×5), and brine. The organic solution was filtered through a hydrophobic frit and the filtrate was evaporated. The residue was purified by silica gel chromatography using iso-hexane/ ethyl acetate 1:9 to afford the title compound (1.88 g, 74%) as a colorless oil.

Compound 75e

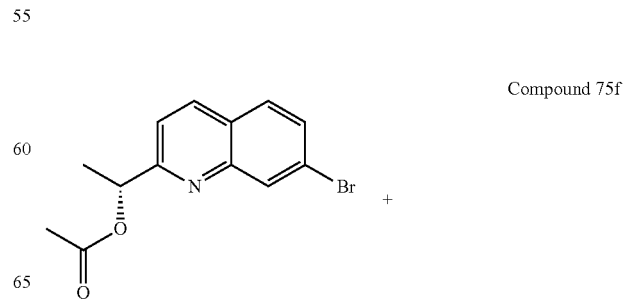

A solution of 75d (150 mg, 0.7 mmol) in tetrahydrofuran (3 mL) was stirred at 5° C. under nitrogen. A solution of lithium hydroxide monohydrate (59 mg, 1.4 mmol) in water (1 mL) was added and the reaction mixture was stirred at 5° C. for 30 min and then at RT for 5 h. Methanol (0.5 mL) was added to give a clear solution and the reaction mixture was stirred at RT for 22 h. The solvent was evaporated. Water (2 mL) was added to the residue and the solution was acidified to pH 2 with 2 M hydrochloric acid. Brine was added and the mixture was extracted with ethyl acetate. The organic extracts were combined, washed with brine. The organic extract was separated, washed with water (×5), and brine. The organic solution was filtered through a hydrophobic frit and the filtrate was evaporated to afford the title compound (117 mg, 90%) as a colorless oil.

Compound 75f

-continued

Compound 75f

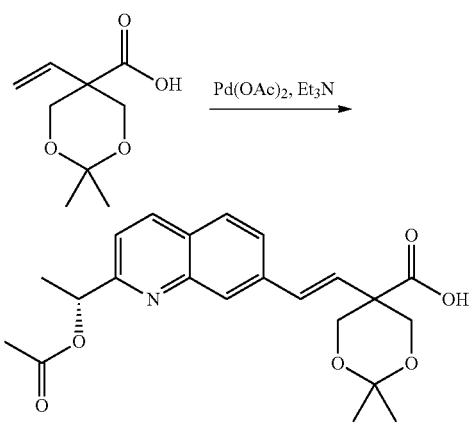

A mixture of 75e (96 mg, 0.5 mmol) and acetic acid (R)-1-(7-bromo-quinolin-2-yl)-ethyl ester (147 mg, 0.5 mmol) in acetonitrile (4 mL) was stirred at RT. Tri(o-tolyl)phosphine (46 mg, 0.15 mmol), palladium(II) acetate (17 mg, 0.075 mmol) and triethylamine (101 mg, 0.14 mL, 1.0 mmol) was added and the reaction mixture was heated in a microwave reactor at 100° C. for 20 min. The solvent was evaporated. Water and ethyl acetate was added and the mixture was acidified to pH 3-4 with 2 M hydrochloric acid. The mixture was extracted with ethyl acetate and the organic extracts were combined and washed with brine. The organic solution was filtered through a hydrophobic frit and the filtrate was evaporated. The residue was purified by silica gel chromatography using iso-hexane/ethyl acetate 1:1 to ethyl acetate to ethyl acetate/methanol 5:1. The residue was co-evaporated with ethyl acetate and then dichloromethane and dried to afford the title compound (134 mg, 67%) as a yellow gum.

Compound 75g

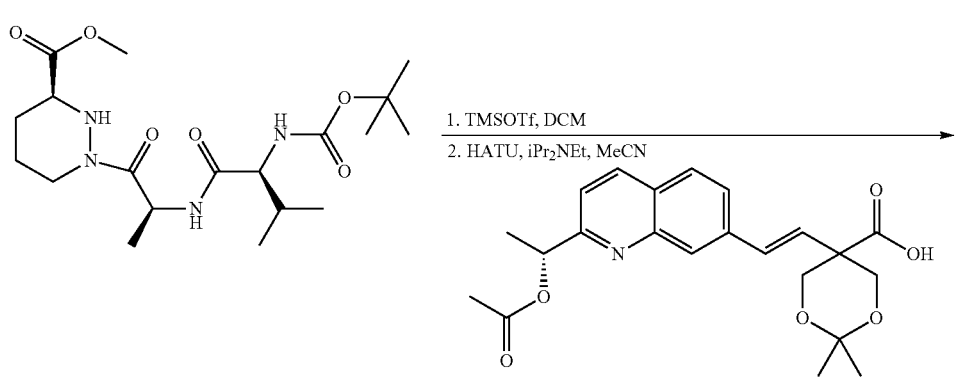

1. TMSOTf, DCM
2. HATU, iPr$_2$NEt, MeCN

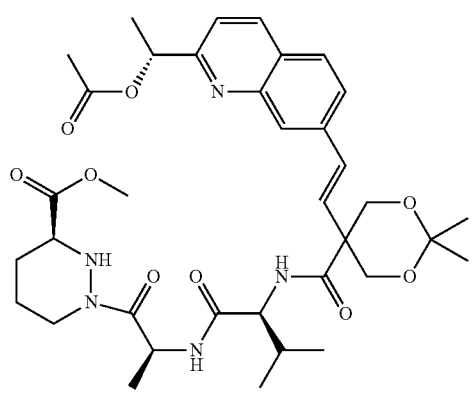

A solution of (S)-1-[(S)-2-((S)-2-tert-butoxycarbonylamino-3-methyl-butyrylamino)-propionyl]-hexahydro-pyridazine-3-carboxylic acid methyl ester (150 mg, 0.36 mmol) in dichloromethane (5 mL) was stirred at 0° C. under nitrogen. Trimethylsilyl trifluoromethanesulfonate (160 mg, 0.13 mL, 0.72 mmol) was added and the reaction mixture was stirred at 0° C. for 1 hour. N,N-Diisopropylethylamine (186 mg, 0.25 mL, 1.44 mmol) was added and the solvent was evaporated to afford (S)-1-[(S)-2-((S)-2-amino-3-methyl-butyrylamino)-propionyl]-hexahydro-pyridazine-3-carboxylic acid methyl ester (0.36 mmol) as a white solid which was used without further purification. A solution of 75f (134 mg, 0.33 mmol) in acetonitrile was stirred at 0° C. under nitrogen. A solution of (S)-1-[(S)-2-((S)-2-amino-3-methyl-butyrylamino)-propionyl]-hexahydro-pyridazine-3-carboxylic acid methyl ester (0.36 mmol) and N,N-diisopropylethylamine (129 mg, 0.17 mL, 1.0 mmol) in acetonitrile (5 mL) was added followed by 2-(1H-7-azabenzotriazol-1-yl)-1,1,3,3-tetramethyl uronium hexafluorophosphate methanaminium (175 mg, 0.46 mmol) and the reaction mixture was stirred at 0° C. for 10 min and then at RT for 1 hour. The solvent was evaporated and the residue was apportioned between ethyl acetate and water. The organic extracts were combined and washed with brine. The organic solution was filtered through a hydrophobic frit and the filtrate was evaporated. The residue was purified by silica gel chromatography using iso-hexane/ethyl acetate 1:5 to ethyl acetate to afford the title compound (165 mg, 72%) as a yellow solid.

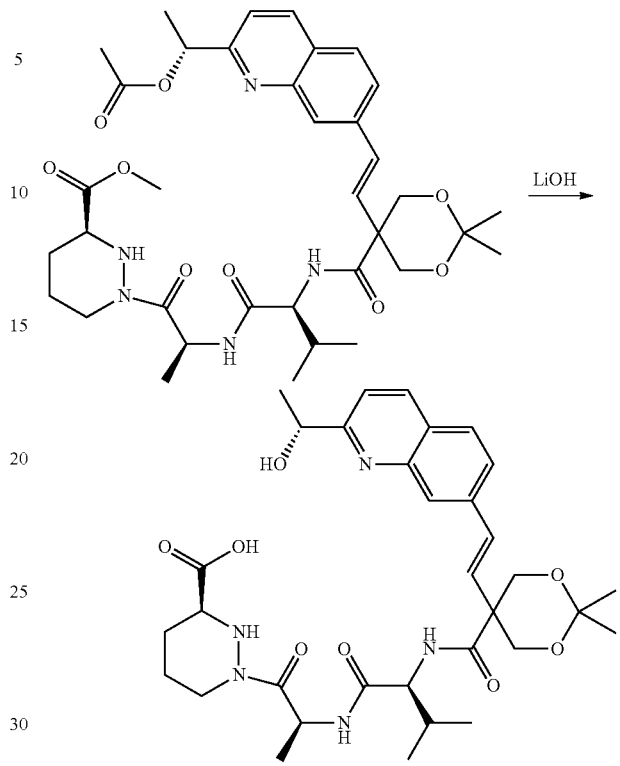

Compound 75h

A solution of 75g (35 mg, 0.05 mmol) in tetrahydrofuran (0.5 mL) was stirred at 5° C. under nitrogen. A solution of lithium hydroxide monohydrate (8.4 mg, 0.2 mmol) in water (0.5 mL) was added followed by methanol (0.5 mL) and the reaction mixture was stirred at 5° C. for 1 hour. 1 M hydrochloric acid (0.2 mL) was added and the solvent was evaporated. The residue was co-evaporated with methanol/toluene (1:1, ×2) followed by toluene (×2). The residue was triturated with diethyl ether (×3) and dried to afford the title compound (0.05 mmol) as a pale yellow solid which was used crude in the next reaction.

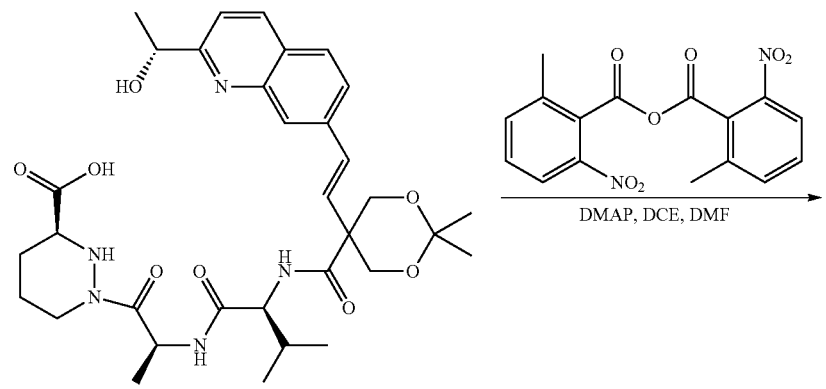

Compound 75

-continued

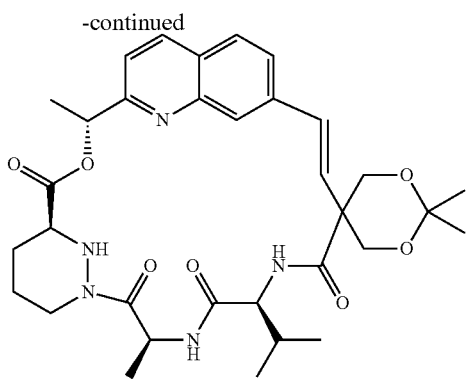

A solution of 2-methyl-6-nitrobenzoic anhydride (86 mg, 0.25 mmol) and 4-dimethylaminopyridine (46 mg, 0.38 mmol) in 1,2-dichloroethane (16 mL) was stirred at RT under nitrogen. A molecular sieves (400 mg) was added and the suspension was heated at 50° C. A solution of crude 75h (0.05 mmol) in N,N-dimethylformamide (2 mL) was added dropwise over 4 h and the reaction mixture was stirred at 50° C. for an additional 1 hour. The reaction mixture was cooled to RT and the mixture was filtered through celite. The filter pad was washed with ethyl acetate and the filtrate was evaporated. The residue was diluted with ethyl acetate and the solution was washed with brine (×3). The organic layer was separated and evaporated. The organic solution was filtered through a hydrophobic frit and the filtrate was evaporated. The residue was purified by preparative HPLC to afford the title compound (4.2 mg, 13%) as a white solid. $^1$H NMR (300 MHz, CD$_3$OD) 1.00 (d, J=6.7 Hz, 3H), 1.01 (d, J=6.6 Hz, 3H), 1.37 (s, 3H), 1.47 (s, 3H), 1.63 (d, J=7.1 Hz, 3H), 1.64-1.70 (m, 2H), 1.73 (d, J=6.9 Hz, 3H), 1.85-2.10 (m, 3H), 2.70-2.80 (m, 1H), 3.78-3.87 (m, 1H), 3.87 (d, J=11.1 Hz, 1H), 4.03-4.07 (m, 1H), 4.26-4.46 (m, 5H), 5.72 (q, J=7.1 Hz, 1H), 5.93 (q, J=6.8 Hz, 1H), 6.38 (s, 2H), 7.42 (d, J=8.5 Hz, 1H), 7.61 (br s, 1H), 7.78-7.86 (m, 2H), 8.22 (d, J=8.5 Hz, 1H). LCMS (m/z) 622.2 [M+H], Tr=2.24 min.

Example 76

Compound 76

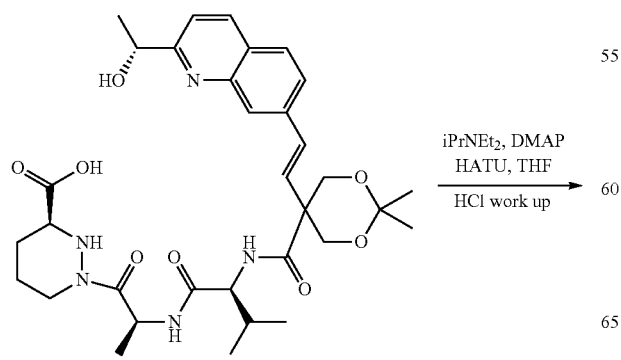

iPrNEt$_2$, DMAP
HATU, THF
─────────→
HCl work up

-continued

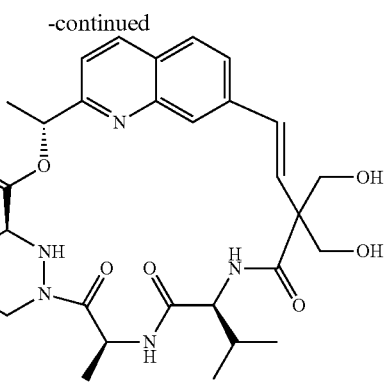

A suspension of crude 75h (200 mg, 0.25 mmol) in tetrahydrofuran (100 mL) was stirred at RT under nitrogen. N,N-diisopropylethylamine (161 mg, 0.22 mL, 1.25 mmol) and 4-dimethylaminopyridine (15 mg, 0.125 mmol) was added and the suspension was stirred for 5 min. 2-(1H-7-Azabenzotriazol-1-yl)-1,1,3,3-tetramethyl uronium hexafluorophosphate methanaminium (133 mg, 0.35 mmol) was added and the reaction mixture was stirred at RT for 2 h. Additional 2-(1H-7-azabenzotriazol-1-yl)-1,1,3,3-tetramethyl uronium hexafluorophosphate methanaminium (57 mg, 0.15 mmol) was added and the reaction mixture was stirred at RT for 1 hour. The solvent was evaporated and the residue was diluted with ethyl acetate and 2 M hydrochloric acid. The organic solution was separated and washed with water, saturated sodium hydrogen carbonate solution, and brine. The organic solution was filtered through a hydrophobic frit and the filtrate was evaporated. The residue was purified by silica gel chromatography using iso-hexane/ethyl acetate 7:3 to ethyl acetate to ethyl acetate/methanol 9:1. The residue was purified by preparative HPLC to afford the title compound (20 mg, 14%) as a white solid. $^1$H NMR (500 MHz, CD$_3$OD) 1.00 (d, J=6.5 Hz, 3H), 1.01 (d, J=6.5 Hz, 3H), 1.68 (d, J=7.1 Hz, 3H), 1.73 (d, J=6.7 Hz, 3H), 1.74-2.05 (m, 5H), 2.72-2.80 (m, 1H), 3.70 (d, J=11.1 Hz, 1H), 3.81-4.07 (m, 4H), 4.35-4.47 (m, 3H), 5.77 (q, J=7.1 Hz, 1H), 5.92 (q, J=6.8 Hz, 1H), 6.43 (s, 2H), 7.40 (d, J=8.5 Hz, 1H), 7.63 (s, 1H), 7.82 (s, 2H), 8.21 (d, J=8.5 Hz, 1H). LCMS (m/z) 582.2 [M+H], Tr=1.66 min.

Biological Examples

Inhibition of Peptidyl-Prolyl Isomerase (PPIase) Activity

The PPIase assay was based on the procedure reported by Janowski et al. (*Anal. Biochem.* 1997, 252, 299). Assay buffer (1980 L of a solution containing 35 mM HEPES pH 7.8, 50M DTT, and 0.01% NP40) was pre-equilibrated to 10° C. in a quartz cuvette equipped with an overhead stirrer. To this solution was added 10 L of compound in DMSO (final concentration: 0.5% DMSO), followed by 5 L of a 2M stock solution of cyclophilin A (final concentration: 5 nM). The reaction was initiated with the addition of 5 L of 40 mM of the tetrapeptide Succ-AAPF-pNA (100M final concentration) dissolved in a solution of 0.5M LiCl in trifluoroethanol. Upon the initiation of the reaction, the absorbance of the peptide substrate was monitored at 330 nm for five minutes using a Beckman Coulter DU800 spectrophotometer. Progress curves were fit with a single-exponential decay model to calculate rates. The $IC_{50}$ values were calculated with a four-parameter logistic fit using Graph Pad Prism software.

Cyclophilin A TR-FRET Competitive Binding Assay

Inhibitor potency was measured using a competitive binding assay with a time-resolved fluorescence resonance energy transfer (TR-FRET) readout. To a reaction buffer consisting of 35 mM HEPES pH 7.8, 100 mM NaCl, 0.01% NP-40 (Pierce), 1 mM DTT, and 1% DMSO were added the following: 5 nM of cyclophilin A modified at the N-terminus with an 8× histidine affinity tag (CypA); 150 nM of cyclosporin A modified with a linker attached to a Cy5 fluorophore (CsA-Cy5); 1 nM Eu-labeled anti-(6×His) antibody (Perkin-Elmer); and test compound at one of various concentrations. The total volume of the assay solution was 100 L. After a two-hour incubation, the TR-FRET was measured using a Perkin Elmer Envision plate reader (excitation at 340 nm, emission measured at 590 nm and 665 nm). The signal was calculated as the ratio of the emission at 665 nm to that at 590 nm. An $IC_{50}$ value was calculated using a four-parameter logistic fit.

When tested, certain compounds of this invention were found to inhibit cyclophilin binding as listed in Table 1 below. $IC_{50}$'s are presented as ranges wherein A is ≤100 nM, B is 101 to 1000 nM and C is 1001 to 10,000 nM.

Antiviral Activity

The antiviral activity of a compound can be measured using standard screening protocols: for example, cell-based Flavivirus immunodetection assay and cell-based Flavivirus cytopathic effect assay as described in U.S. Patent Publication Number US/20130022573, which is hereby incorporated by reference in its entirety.

One aspect of the invention relates to methods of inhibiting viral infections, comprising the step of treating a sample or subject suspected of needing such inhibition with a composition of the invention. The antiviral activity of a compound of the invention can be measured using standard screening protocols that are known.

The anti-HCV activity of the compounds of this invention was tested in a human hepatoma Huh-7 cell line harboring a HCV replicon. The assay comprised the following steps:

Step 1 (Compound Preparation and Serial Dilution):

Serial dilution was performed in 100% DMSO in a 384-well plate. A solution containing a compound at 225-fold concentration of the starting final serial dilution concentration was prepared in 100% DMSO and 15 µL added to the pre-specified wells in column 3 or 13 of a polypropylene 384-well plate. The rest of the 384-well plate was filled with 10 µL 100% DMSO except for columns 23 and 24, where 10 µL of 500 µM a HCV protease inhibitor (ITMN-191) in 100% DMSO was added. The HCV protease inhibitor was used a control of 100% inhibition of HCV replication. The plate was then placed on a Biomek FX Workstation to start the serial dilution. The serial dilution was performed for ten cycles of 3-fold dilution from column 3 to 12 or from column 13 to 22.

Step 2 (Cell Culture Plate Preparation and Compound Addition):

To each well of a black polypropylene 384-well plate, 90 µL of cell media containing 1600 suspended Huh-7 HCV replicon cells was added with a Biotek uFlow Workstation. A volume of 0.4 µL of the compound solution was transferred from the serial dilution plate to the cell culture plate on a Biomek FX Workstation. The DMSO concentration in the final assay condition was 0.44%. The plates were incubated for 3 days at 37° C. with 5% $CO_2$ and 85% humidity.

Step 3 (Detection of Cytotoxicity and Inhibition of Viral Replication):

a) Assessment of cytotoxicity: The media in the 384-well cell culture plate was aspirated with a Biotek EL405 plate-washer. A volume of 50 µL of a solution containing 400 nM Calcein AM in 100% PBS was added to each well of the plate with a Biotek uFlow Workstation. The plate was incubated for 30 minutes at RT before the fluorescence signal (emission 490 nm, exitation 520 nm) was measured with a Perkin Elmer Envision Plate Reader.

b) Assessment of inhibition of viral replication: The calcein-PBS solution in the 384-well cell culture plate was aspirated with a Biotek EL405 plate-washer. A volume of 20 µL of Dual-Glo luciferase buffer (Promega, Dual-Glo Luciferase Assay Reagent, cat. #E298B) was added to each well of the plate with a Biotek uFlow Workstation. The plate was incubated for 10 minutes at RT. A volume of 20 µL of a solution containing 1:100 mixture of Dual-Glo Stop & Glo substrate (Promega, Dual-Glo Luciferase Assay Reagent, cat. #E313B) and Dual-Glo Stop & Glo buffer (Promega, Dual-Glo Luciferase Assay Reagent, cat. #E314B) was then added to each well of the plate with a Biotek uFlow Workstation. The plate was incubated at RT for 10 minutes before the luminescence signal was measured with a Perkin Elmer Envision Plate Reader.

Step 4 (Calculation):

The percent cytotoxicity was determined by calcein AM conversion to fluorescent product. The average fluorescent signal from the DMSO control wells were defined as 100% nontoxic. The individual fluorescent signal from testing compound treated well was divided by the average signal from DMSO control wells and then multiplied by 100% to get the percent viability. The percent anti-HCV replication activity was determined by the luminescence signal from the testing well compared to DMSO controls wells. The background signal was determined by the average luminescence signal from the HCV protease inhibitor treated wells and was subtracted from the signal from the testing wells as well as the DMSO control wells. Following 3-fold serial dilutions, the $EC_{50}$ and $CC_{50}$ values were calculated by fitting % inhibition at each concentration to the following equation:

$$\% \text{ inhibition} = 100\%/[(EC_{50}/[I])^b + 1]$$

where b is Hill's coefficient. See, for reference, Hill, A. V., *The Possible Effects of the Aggregation of the Molecules of Hmoglobin on its Dissociation Curves*, J. Physiol. 40: iv-vii. (1910). % inhibition values at a specific concentration, for example 2 µM, can also be derived from the formula above.

When tested, certain compounds of this invention were found to inhibit viral replication as listed in Table 1. The $EC_{50}$'s are presented as a % inhibition.

TABLE 1

| Example No. | TR-FRET | Replicon 1a % inhibition at 1 µM |
|---|---|---|
| 1 | A | 32 |
| 2 | B | 63 |
| 3 | A | 44 |
| 4 | B | 58 |
| 5 | A | 80 |
| 6 | A | 86 |
| 7 | A | 94 |
| 8 | B | 37 |
| 9 | A | 98 |
| 10 | B | 28 |
| 11 | A | 6 |
| 12 | C | 0 |
| 13 | A | 87 |
| 14 | A | 94 |
| 15 | A | 99 |
| 16 | B | 94 |
| 17 | A | 100 |
| 18 | A | 94 |
| 19 | A | 97 |
| 20 | A | 99 |
| 21 | A | 93 |
| 22 | A | 100 |
| 23 | A | 99 |
| 24 | A | 99 |
| 25 | B | 71 |
| 26 | A | 99 |
| 27 | A | 100 |
| 28 | B | 56 |
| 29 | C | 28 |
| 30 | A | 73 |
| 31 | A | 98 |
| 32 | A | 71 |
| 33 | C | 14 |
| 34 | A | 92 |
| 35 | A | 94 |
| 36 | A | 73 |
| 37 | A | 76 |
| 38 | A | 98 |
| 39 | A | 98 |
| 40 | A | 96 |
| 41 | A | 96 |
| 42 | B | 16 |
| 43 | A | 97 |
| 44 | A | 78 |
| 45 | A | 80 |
| 46 | A | 90 |
| 47 | B | 9 |
| 48 | A | 40 |
| 49 | A | 85 |
| 50 | B | 12 |
| 51 | A | 83 |
| 52 | A | 98 |
| 53 | B | 89 |
| 54 | A | 98 |
| 55 | B | 76 |
| 56 | B | 47 |
| 57 | A | 100 |
| 58 | A | 99 |
| 59 | A | 100 |
| 60 | B | 65 |
| 61 | A | 72 |
| 62 | B | 25 |
| 63 | B | 80 |
| 64 | B | 35 |
| 65 | A | 92 |
| 66 | A | 80 |
| 67 | A | 97 |
| 68 | A | 91 |
| 69 | C | 19 |
| 70 | A | 95 |
| 71 | B | — |
| 72 | B | 0 |
| 73 | A | 94 |
| 74 | A | 95 |
| 75 | A | 100 |
| 76 | A | 63 |

The specific pharmacological and biochemical responses observed may vary according to and depending on the particular active compound selected or whether there are present pharmaceutical carriers, as well as the type of formulation and mode of administration and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention.

What is claimed is:

1. A compound of Formula I:

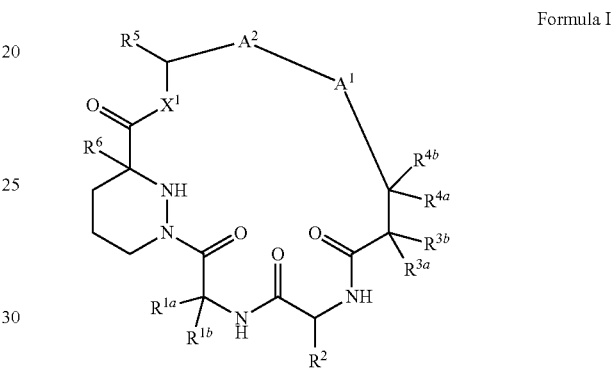

Formula I or a pharmaceutically acceptable salt, isotope, stereoisomer, mixture of stereoisomers, tautomer, ester or prodrug thereof, wherein:

$A^1$ is $(C_2-C_5)$alkylene, $(C_2-C_5)$alkenylene, $(C_2-C_5)$alkynylene, —O—$(C_2-C_4)$alkylene, —O—$(C_2-C_4)$alkenylene, arylene, aryl$(C_1-C_2)$alkylene, heterocycloalkylene or heterocycloalkyl$(C_1-C_2)$alkylene, wherein a sp$^3$ carbon atom of $A^1$ is optionally substituted with one or more $(C_1-C_4)$alkyl;

$A^2$ is arylene or heteroarylene, wherein $A^2$ is optionally substituted with halo;

$X^1$ is —O—, —NH— or —N(($C_1-C_4$)alkyl)-;

$R^{1a}$ and $R^{1b}$ are independently H, $(C_1-C_4)$alkyl, $(C_2-C_4)$alkenyl or $(C_2-C_4)$alkynyl;

$R^2$ is H, $(C_1-C_4)$alkyl, $(C_2-C_4)$alkenyl or $(C_2-C_4)$alkynyl;

$R^{3a}$ and $R^{3b}$ are independently H or $(C_1-C_8)$alkyl;

$R^{4a}$ and $R^{4b}$ are independently H, —OH, $(C_1-C_4)$alkoxy, halo$(C_1-C_4)$alkoxy or $(C_1-C_8)$alkyl;

$R^5$ is H, $(C_1-C_4)$alkyl, $(C_2-C_4)$alkenyl or $(C_2-C_4)$alkynyl, or $R^5$ forms a cyclic moiety along with —N(($C_1-C_4$)alkyl)- of $X^1$ or arylene of $A^2$; and $R^6$ is H or $(C_1-C_4)$alkyl.

2. The compound of claim 1, wherein $A^1$ is ethenylene, propenylene, butenylene, ethylene, propylene, butylene, oxypropylene, oxypropenylene, pyrazolylene, phenylene or pyrimidinylene.

3. The compound of claim 1, wherein $A^2$ is isoquinolinylene, phenylene or halophenylene.

4. The compound of claim 1, wherein
$X^1$ is —O— or —NH—; one of $R^{1a}$ and $R^{1b}$ is H and the other is methyl; $R^2$ is iso-propyl; $R^5$ is methyl and $R^6$ is H or methyl.

5. The compound of claim 1, wherein $R^{3a}$ is H or methyl; $R^{3b}$ is H; $R^{4a}$ is H, —OH, methoxy, or trifluoroethoxy; and $R^{4b}$ is H.

6. The compound of claim 1, which is a compound of Formula II:

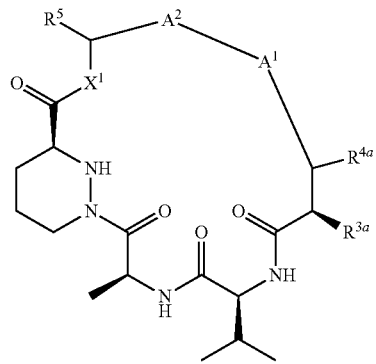

Formula II or a pharmaceutically acceptable salt, isotope, stereoisomer, mixture of stereoisomers, tautomer, ester or prodrug thereof, wherein:

$A^1$ is ethenylene,

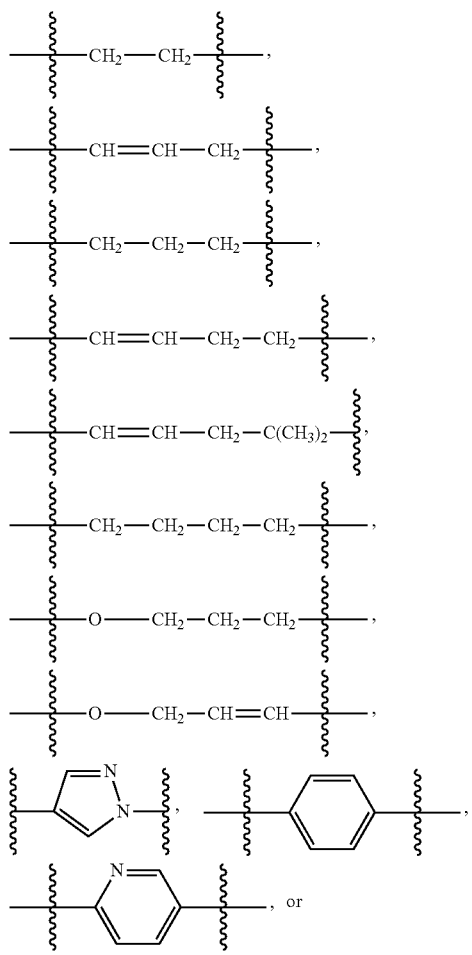

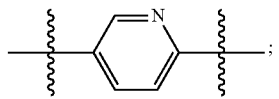

$A^2$ is

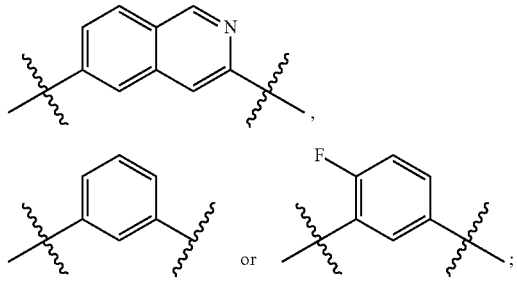 [SMILES: *c1ccc2cnc(*)cc2c1 ; *c1cccc(*)c1 ; *c1ccc(F)c(*)c1]

$X^1$ is —O— or —NH—;
$R^{3a}$ is H or $(C_1-C_4)$alkyl;
$R^{4a}$ is H, —OH, $(C_1-C_4)$alkoxy, halo$(C_1-C_4)$alkoxy or $(C_1-C_8)$alkyl; and
$R^5$ is H or $(C_1-C_4)$alkyl.

7. The compound of claim 1, wherein $A^2$ is heteroarylene; $A^1$ is $(C_2-C_5)$alkylene, $(C_2-C_5)$alkenylene, or $(C_2-C_5)$alkynylene, wherein $A^1$ is optionally substituted with one or more $(C_1-C_4)$alkyl; $R^{3a}$ is H or $(C_1-C_8)$alkyl; and $R^{4a}$ is H, —OH or $(C_1-C_4)$alkoxy.

8. The compound of claim 1, which is

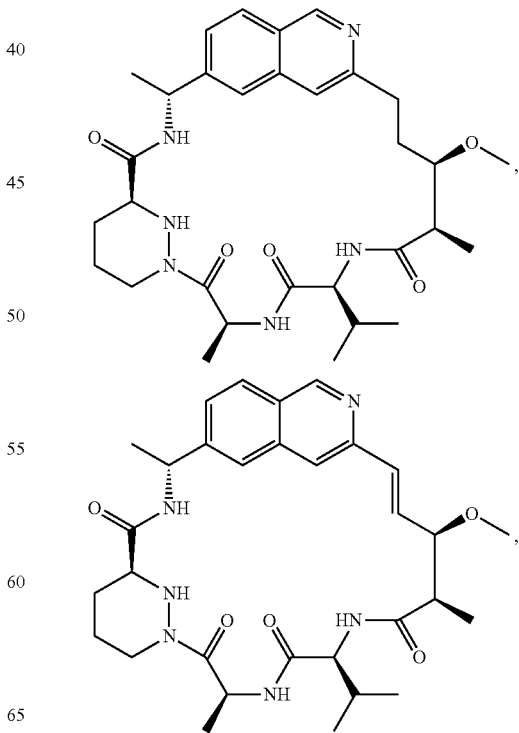

321

-continued

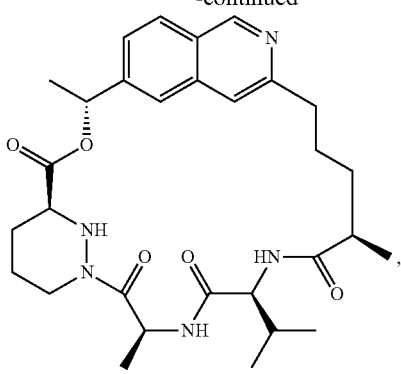

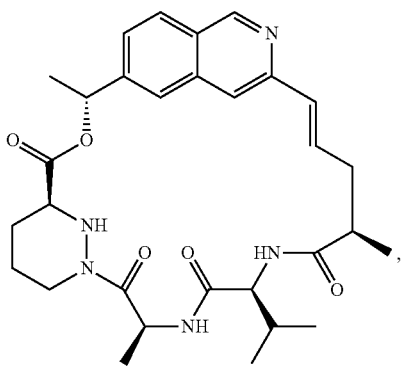

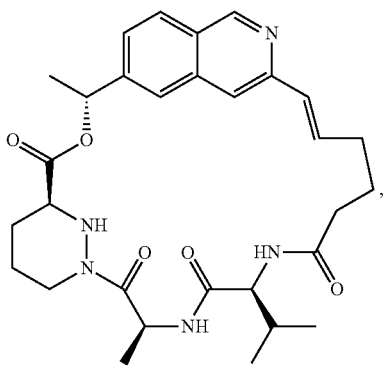

322

-continued

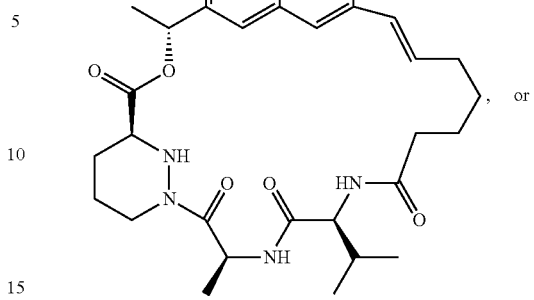

, or

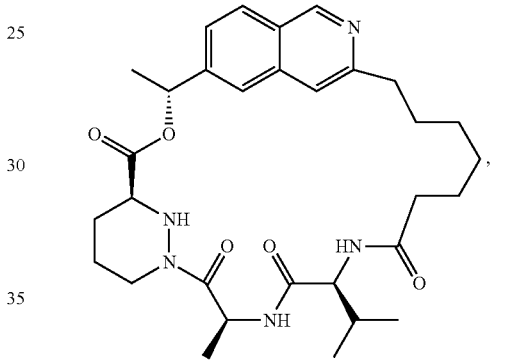

or a pharmaceutically acceptable salt, isotope, stereoisomer, mixture of stereoisomers, tautomer, ester or prodrug thereof.

9. The compound of claim 1, wherein $A^2$ is arylene; and $A^1$ is $(C_2-C_5)$alkylene, $(C_2-C_5)$alkenylene, $(C_2-C_5)$alkynylene, —O—$(C_2-C_5)$alkylene, or —O—$(C_2-C_4)$alkenylene, wherein $A^1$ is optionally substituted with one or more $(C_1-C_4)$alkyl; $R^{1a}$ is H or $(C_1-C_4)$alkyl; and $R^{4a}$ is H, —OH, $(C_1-C_4)$alkoxy or halo$(C_1-C_4)$alkoxy.

10. The compound of claim 1, which is

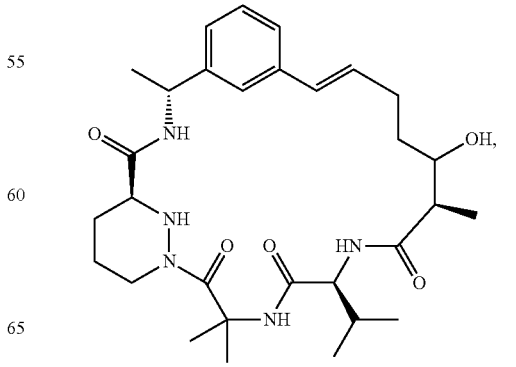

323
-continued
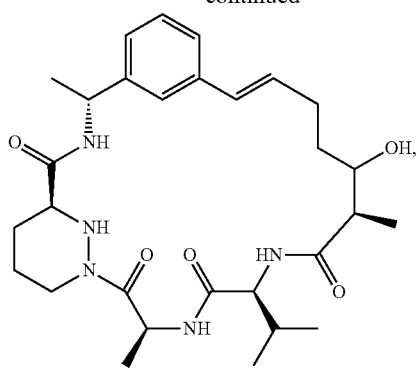
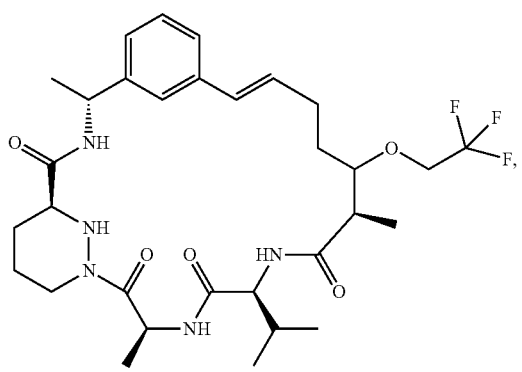
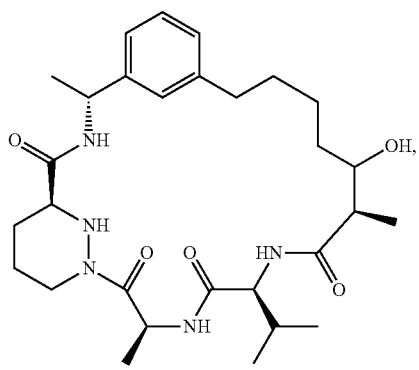
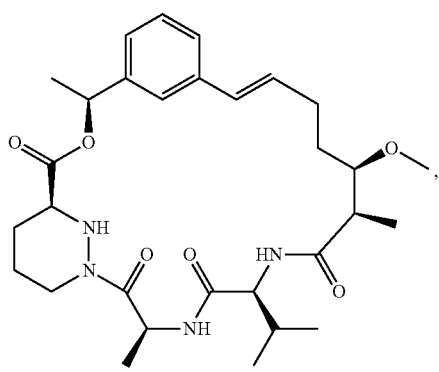
324
-continued
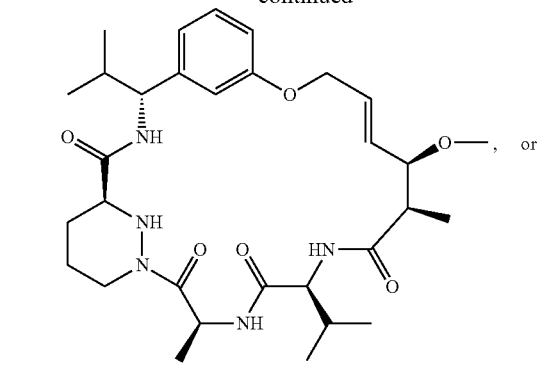, or
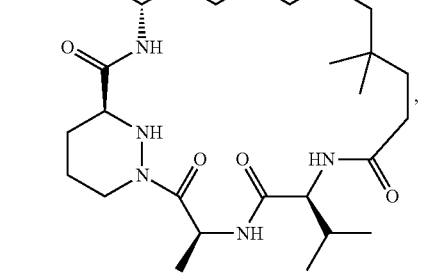
or a pharmaceutically acceptable salt, isotope, stereoisomer, mixture of stereoisomers, tautomer, ester or prodrug thereof.
11. The compound of claim 1, wherein $A^2$ is arylene; and $A^1$ is pyrazolylene, phenylene or pyrimidinylene.
12. The compound of claim 1, which is
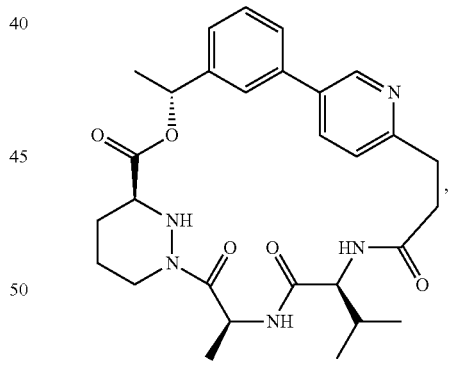
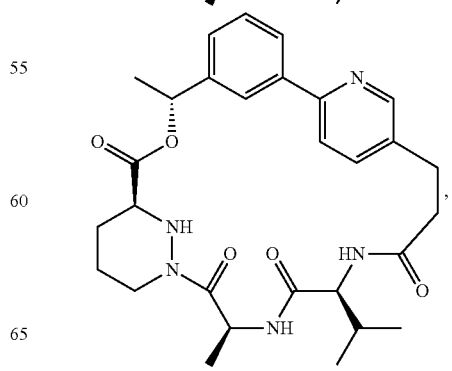

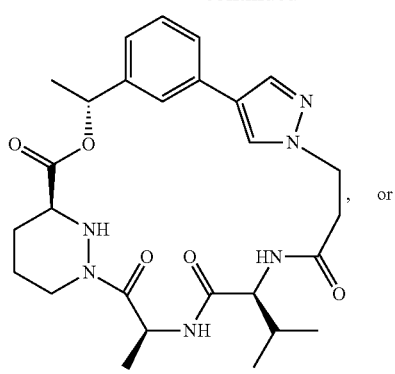

, or

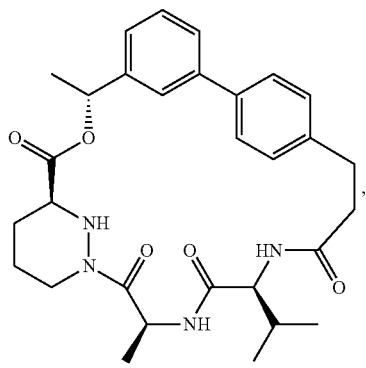

, or a pharmaceutically acceptable salt, isotope, stereoisomer, mixture of stereoisomers, tautomer, ester or prodrug thereof.

13. The compound of claim 1, wherein $A^2$ is haloarylene; and $A^1$ is —O—$(C_2$-$C_5)$alkylene or —O—$(C_2$-$C_4)$alkenylene.

14. The compound of claim 1, which is

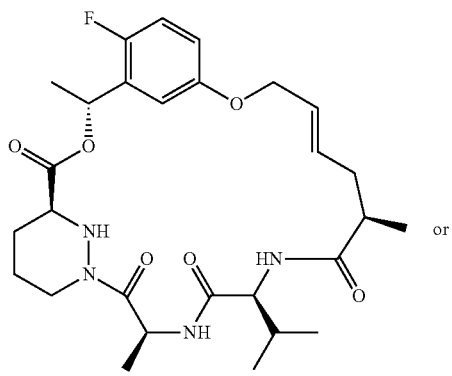

or

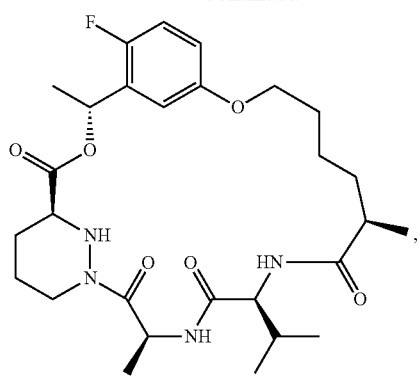

or a pharmaceutically acceptable salt, isotope, stereoisomer, mixture of stereoisomers, tautomer, ester or prodrug thereof.

15. The compound of claim 1, wherein $A^1$ is $(C_2$-$C_5)$alkylene or $(C_2$-$C_5)$alkenylene; $R^5$ is methyl, or $R^5$ forms

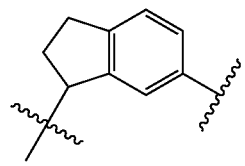 [SMILES: *c1ccc2c(c1)C(*)CC2]

along with arylene of $A^2$, or $R^5$ forms

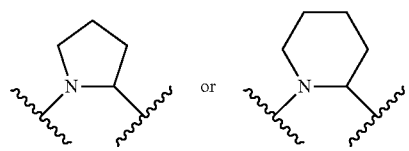 [SMILES: *C1CCCN1* ; *C1CCCCN1*]

along with —N$((C_1$-$C_4)$alkyl)- of $X^1$; and $R^6$ is H or methyl.

16. The compound of claim 1, which is

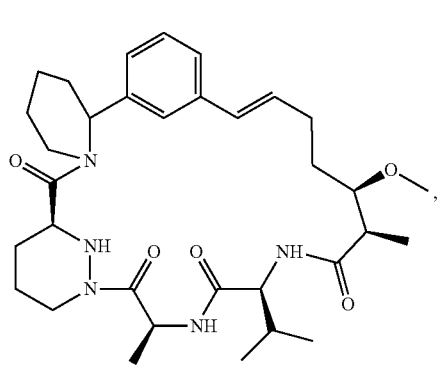

327
-continued

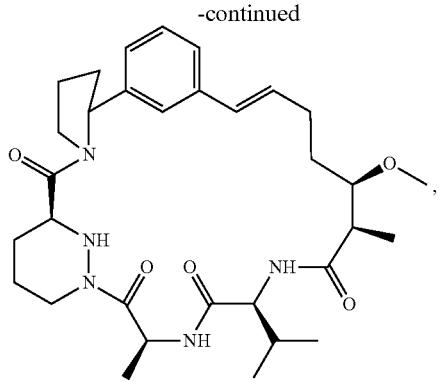
,

328
-continued

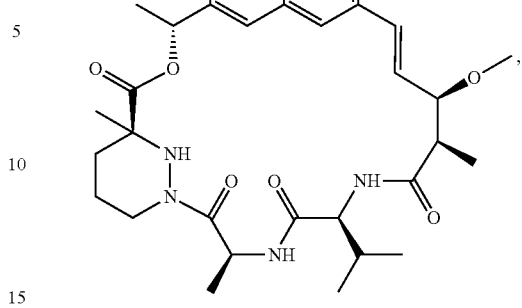
, or a pharmaceutically acceptable salt, isotope, stereoisomer, mixture of stereoisomers, tautomer, ester or prodrug thereof.

17. A pharmaceutical composition comprising a therapeutically effective amount of a compound of claim 1 or a pharmaceutically acceptable salt, isotope, stereoisomer, mixture of stereoisomers, tautomer, ester or prodrug thereof and a pharmaceutically acceptable excipient.

18. The pharmaceutical composition of claim 17, further comprising at least one additional therapeutic agent selected from the group consisting of interferons, ribavirin, HCV NS3 protease inhibitors, HCV NS5a inhibitors, nucleoside or nucleotide inhibitors of HCV NS5B polymerase, non-nucleoside inhibitors of HCV NS5B polymerase, and TLR-7 agonists; or a mixture thereof.

19. The pharmaceutical composition of claim 18, wherein the at least one addition therapeutic agent is ribavirin, telaprevir, boceprevir or sofosbuvir.

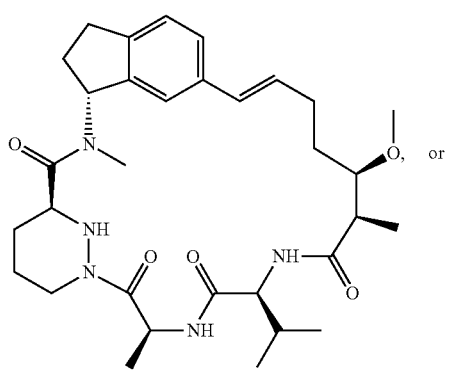 or

* * * * *